United States Patent
Freier et al.

(10) Patent No.: US 10,017,764 B2
(45) Date of Patent: Jul. 10, 2018

(54) OLIGOMERIC COMPOUNDS COMPRISING BICYCLIC NUCLEOTIDES AND USES THEREOF

(75) Inventors: Susan M. Freier, San Diego, CA (US); Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 78 days.

(21) Appl. No.: 13/984,260

(22) PCT Filed: Feb. 8, 2012

(86) PCT No.: PCT/US2012/024385
§ 371 (c)(1),
(2), (4) Date: Dec. 30, 2013

(87) PCT Pub. No.: WO2012/109395
PCT Pub. Date: Aug. 16, 2012

(65) Prior Publication Data
US 2014/0107330 A1    Apr. 17, 2014

Related U.S. Application Data

(60) Provisional application No. 61/440,828, filed on Feb. 8, 2011, provisional application No. 61/470,927, filed on Apr. 1, 2011, provisional application No. 61/522,659, filed on Aug. 11, 2011.

(51) Int. Cl.
| | |
|---|---|
| *A61K 48/00* | (2006.01) |
| *C12N 15/11* | (2006.01) |
| *C07H 21/02* | (2006.01) |
| *C07H 21/04* | (2006.01) |
| *C12N 15/113* | (2010.01) |

(52) U.S. Cl.
CPC .......... *C12N 15/113* (2013.01); *C12N 15/111* (2013.01); *C12N 2310/11* (2013.01); *C12N 2310/315* (2013.01); *C12N 2310/3231* (2013.01); *C12N 2310/341* (2013.01); *C12N 2310/346* (2013.01)

(58) Field of Classification Search
USPC ............................ 536/23.1, 24.3, 24.33, 24.5
See application file for complete search history.

(56) References Cited

U.S. PATENT DOCUMENTS

| | | | |
|---|---|---|---|
| 3,687,808 A | 8/1972 | Merigan et al. |
| 4,845,205 A | 7/1989 | Dinh et al. |
| 4,981,957 A | 1/1991 | Lebleu et al. |
| 5,118,800 A | 6/1992 | Smith et al. |
| 5,130,302 A | 7/1992 | Spielvogel et al. |
| 5,134,066 A | 7/1992 | Rogers et al. |
| 5,175,273 A | 12/1992 | Bischofberger et al. |
| 5,319,080 A | 6/1994 | Leumann |
| 5,359,044 A | 10/1994 | Cook et al. |
| 5,367,066 A | 11/1994 | Urdea et al. |
| 5,393,878 A | 2/1995 | Leumann |
| 5,432,272 A | 7/1995 | Benner |
| 5,446,137 A | 8/1995 | Maag et al. |
| 5,446,786 A | 8/1995 | Shtulman |
| 5,457,187 A | 10/1995 | Gmeiner et al. |
| 5,459,255 A | 10/1995 | Cook et al. |
| 5,484,908 A | 1/1996 | Froehler et al. |
| 5,502,177 A | 3/1996 | Matteucci et al. |
| 5,514,785 A | 5/1996 | Van Ness et al. |
| 5,519,134 A | 5/1996 | Acevedo et al. |
| 5,525,711 A | 6/1996 | Hawkins et al. |
| 5,552,540 A | 9/1996 | Haralambidis |
| 5,567,811 A | 10/1996 | Misiura et al. |
| 5,576,427 A | 11/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,091 A | 1/1997 | Switzer |
| 5,597,909 A | 1/1997 | Urdea et al. |
| 5,610,300 A | 3/1997 | Altmann et al. |
| 5,614,617 A | 3/1997 | Cook et al. |
| 5,627,053 A | 5/1997 | Usman et al. |
| 5,639,873 A | 6/1997 | Barascut et al. |
| 5,645,985 A | 7/1997 | Froehler et al. |
| 5,646,265 A | 7/1997 | McGee |
| 5,658,873 A | 8/1997 | Bertsch-Frank et al. |
| 5,670,633 A | 9/1997 | Cook et al. |
| 5,681,941 A | 10/1997 | Cook et al. |
| 5,700,920 A | 12/1997 | Altmann et al. |
| 5,750,692 A | 5/1998 | Cook et al. |
| 5,763,588 A | 6/1998 | Matteucci et al. |

(Continued)

FOREIGN PATENT DOCUMENTS

| | | |
|---|---|---|
| EP | 1015469 | 4/2005 |
| EP | 1013661 | 1/2012 |

(Continued)

OTHER PUBLICATIONS

Prakash et al. (J. Med. Chemistry, 2010 vol. 53:1636-1650).*
U.S. Appl. No. 60/746,631, filed May 5, 2006, Monia et al.
Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.
Arzumanov et al., "A structure-activity study of the inhibition of HIV-1 Tat-dependent trans-activation by mixmer 2'-O-methyl oligoribonucleotides containing locked nucleic acid (LNA), alpha-L-LNA, or 2'-thio-LNA residues" Antisense & Nucleic Acid Drug Development (2003) 13(6):435-453.
Arzumanov et al., "Inhibition of HIV-1 Tat-dependent trans activation by steric block chimeric 2'-O-methyl/LNA oligoribonucleotides" Biochemistry (2001) 40(48):14645-14654.

(Continued)

*Primary Examiner* — Terra C Gibbs
(74) *Attorney, Agent, or Firm* — McNeill Baur PLLC

(57) ABSTRACT

The present invention provides oligomeric compounds. Certain such oligomeric compounds are useful for hybridizing to a complementary nucleic acid, including but not limited, to nucleic acids in a cell. In certain embodiments, hybridization results in modulation of the amount activity or expression of the target nucleic acid in a cell.

10 Claims, No Drawings

(56) References Cited

U.S. PATENT DOCUMENTS

| | | |
|---|---|---|
| 5,792,747 A | 8/1998 | Schally et al. |
| 5,801,154 A | 9/1998 | Baracchini et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,525,191 B1 | 2/2003 | Ramasamy |
| 6,582,908 B2 | 6/2003 | Fodor et al. |
| 6,600,032 B1 | 7/2003 | Manoharan et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,098,192 B2 | 8/2006 | Karras |
| 7,399,845 B2 | 7/2008 | Seth et al. |
| 7,427,672 B2 | 9/2008 | Imanishi et al. |
| 7,741,457 B2 | 6/2010 | Seth et al. |
| 2001/0053519 A1 | 12/2001 | Fodor et al. |
| 2003/0082807 A1 | 5/2003 | Wengel |
| 2003/0087853 A1 | 5/2003 | Crooke et al. |
| 2003/0125241 A1 | 7/2003 | Wissenbach et al. |
| 2003/0207841 A1 | 11/2003 | Kaneko et al. |
| 2003/0228597 A1 | 12/2003 | Cowsert et al. |
| 2004/0014959 A1 | 1/2004 | Sorensen et al. |
| 2004/0143114 A1 | 7/2004 | Imanishi et al. |
| 2004/0171570 A1 | 9/2004 | Allerson et al. |
| 2004/0219565 A1 | 11/2004 | Kauppinen et al. |
| 2005/0053981 A1 | 3/2005 | Swayze et al. |
| 2005/0059066 A1 | 3/2005 | Swayze et al. |
| 2005/0074801 A1 | 4/2005 | Monia et al. |
| 2005/0130923 A1 | 6/2005 | Bhat et al. |
| 2005/0153921 A1 | 7/2005 | Monia et al. |
| 2007/0287831 A1 | 12/2007 | Seth et al. |
| 2008/0039618 A1 | 2/2008 | Allerson et al. |
| 2009/0203893 A1 | 8/2009 | Esau et al. |
| 2011/0112170 A1 | 5/2011 | Swayze et al. |

FOREIGN PATENT DOCUMENTS

| | | |
|---|---|---|
| WO | WO 93/24510 | 12/1993 |
| WO | WO 94/14266 | 6/1994 |
| WO | WO 94/26764 | 11/1994 |
| WO | WO 98/39352 | 9/1998 |
| WO | WO 99/14226 | 3/1999 |
| WO | WO 2000/066604 | 11/2000 |
| WO | WO 2005/021570 | 8/2003 |
| WO | WO 2004/044181 | 5/2004 |
| WO | WO 2004/046160 | 6/2004 |
| WO | WO 2004/063329 | 7/2004 |
| WO | WO 2004/069991 | 8/2004 |
| WO | WO 2004/106356 | 12/2004 |
| WO | WO 2005/023825 | 3/2005 |
| WO | WO 2005/028628 | 3/2005 |
| WO | WO 2005/061710 | 7/2005 |
| WO | WO 2005/095607 | 10/2005 |
| WO | WO 2005/121371 | 12/2005 |
| WO | WO 2006/050732 | 5/2006 |
| WO | WO 2006/050734 | 5/2006 |
| WO | WO 2007/027775 | 3/2007 |
| WO | WO 2007/027894 | 3/2007 |
| WO | WO 2007/031081 | 3/2007 |
| WO | WO 2007/089584 | 8/2007 |
| WO | WO 2007/090071 | 8/2007 |
| WO | WO 2007/131237 | 11/2007 |
| WO | WO 2007/134181 | 11/2007 |
| WO | WO 2007/146511 | 12/2007 |
| WO | WO 2008/049085 | 4/2008 |
| WO | WO 2008/101157 | 8/2008 |
| WO | WO 2008/111908 | 9/2008 |
| WO | WO 2008/113832 | 9/2008 |
| WO | WO 2008/150729 | 12/2008 |
| WO | WO 2008/154401 | 12/2008 |
| WO | WO 2009/006478 | 1/2009 |
| WO | WO 2009/023855 | 2/2009 |
| WO | WO 2009/061841 | 5/2009 |
| WO | WO 2009/061851 | 5/2009 |
| WO | WO 2009/067647 | 5/2009 |
| WO | WO 2009/100320 | 8/2009 |
| WO | WO 2009/124295 | 10/2009 |
| WO | WO 2010/036698 | 4/2010 |
| WO | WO 2010/108035 | 9/2010 |
| WO | WO 2011/017521 | 2/2011 |
| WO | WO 2011/097643 | 8/2011 |
| WO | WO 2011/097644 | 8/2011 |
| WO | WO 2012/027033 | 3/2012 |
| WO | WO 2012/109395 | 8/2012 |
| WO | WO 2012/145697 | 10/2012 |
| WO | WO 2013/022984 | 2/2013 |
| WO | WO 2013/022990 | 2/2013 |
| WO | WO 2005/023995 | 3/2015 |

OTHER PUBLICATIONS

Belikova et al., "Synthesis of Ribonucleosides and Diribonucleoside Phosphate Containing 2'-Chloro-Ethylamine and Nitrogen Mustard Residues" Tet. Lett. (1967) 37:3557-3562.

Berger et al., "Universal bases for hybridization, replication and chain termination" Nuc. Acid Res. (2000) 28:2911-2914.

Braasch et al., "Locked nucleic acid (LNA): fine-tuning the recognition of DNA and RNA" Chem. Biol. (2001) 8:1-7.

Branch et al., "A good antisense molecule is hard to find," TIBS (1998) 23:45-50.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Crooke et al., "Pharmacokinetic Properties of Several Novel Oligonucleotide Analogs in mice" J. Pharmacol. Exp. Ther. (1996) 277(2):923-937.

Elayadi et al., "Applications of PNA and LNA oligomers to chemotherapy" Curr. Opinion Invest. Drugs (2001) 2:558-561.

Englisch et al., "Chemically Modified Oligonucleotides as Probes and Inhibitors" Angewandte Chemie, International Edition (1991) 30(6): 613-629.

Fluiter et al., "On the in vitro and in vivo properties of four locked nucleic acid nucleotides incorporated into an anti-h-ras antisense oligonucleotide" Chembiochem—A European Journal of Chemical Biology (2005) 6(6):1104-1109.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

Gait et al., "Applications of Chemically synthesized RNA" in RNA: Protein Interactions, Ed. Smith, 1998, p. 1-36.

Gallo et al., "2'-C-Methyluridine phosphoramidite: a new building block for the preparation of RNA analogues carrying the 2'-hydroxyl group" Tetrahedron (2001) 57:5707-5717.

Henry et al., Antisense Drug Technology—Second Edition. CRC Press. Chapter 12, pp. 327-363.

Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.

Kierzek et al., "The influence of locked nucleic acid residues on thermodyanmic properties of 2'-O-methyl RNA/RNA heteroduplexes" Nucleic Acids Research (2005) 33(16):5082-5093.

Horie et al. "Hepatocyte-specific Pten deficiency results in steatohepatitis and hepatocellular carcinomas" J. Clincal Investigation (2004) 113(12): 1774-1783.

Koshkin et al., "LNA (Locked Nucleic Acids): Synthesis of the Adenine, Cytosine, Guanine, 5-Methylcytosine, Thymine and Uracil Biocyclonucleoside Monomers, Oligomerisation, and Unprecedented Nucleic Acid Recognition" Tetrahedron (1998) 54:3607-3630.

(56) References Cited

OTHER PUBLICATIONS

Kumar et al., "The First Analogues of LNA (Locked Nucleic Acids): Phosphorothioate-LNA and 2'-Thio-LNA" Bioorg. Med. Chem. Lett. (1998) 8:2219-2222.

Letsinger et al., "Cholesteryl-conjugated oligonucleotides: Synthesis, properties, and activity as inhibitors of replication of human immunodeficiency virus in cell culture" PNAS (1989) 86:6553-6556.

Leumann et al., "DNA Analogues: From Supramolecular Principles to Biological Properties" Bioorganic & Medicinal Chemistry (2002) 10:841-854.

Manoharan et al., "Introduction of a Lipophilic Thioether Tether in the Minor Groove of Nucleic Acids for Antisense Applications" Bioorg. Med. Chem. Lett. (1993) 3(12):2765-2770.

Manoharan et al., "Cholic Acid-Oligonucleotide Conjugates for Antisense Applications" Bioorg. Med. Chem. Lett. (1994) 4:1053-1060.

Manoharan et al., "Chemical Modifications to Improve Uptake and Bioavailability of Antisense Oligonucleotides" Arm. N.Y. Acad. Sci. (1992) 660:306.

Manoharan et al., "Lipidic Nucleic Acids" Tetrahedron Lett. (1995) 36(21):3651-3654.

Manoharan et al., "Oligonucleotide Conjugates: Alteration of the Pharmacokinetic Properties of Antisense Agents" Nucleosides & Nucleotides (1995) 14(3-5):969-973.

Mishra et al., "Improved leishmanicidal effect of phosphorotioate antisense oligonucleotides by LDL-mediated delivery" Biochim. Biophys. Acta (1995) 1264:229-237.

Morita et al., "Synthesis and Properties of 2'-O,4'-C-Ethylene-Bridged Nucleic Acids (ENA) as Effective Antisense Oligonucleotides" Bioorganic Medicinal Chemistry (2003) 11:2211-2226.

New England Biolabs 1998/99 Catalog (cover page and pp. 121 and 284).

Oberhauser et al., "Effective incorporation of 2'-O-methyl-oligoribonucleotides into liposomes and enhanced cell association through modifications with thiocholesterol" Nucl. Acids Res. (1992) 20(3):533-538.

O'Connor et al., "Nonalcoholic fatty liver (NASH syndrome)" Gastroenterologist 5(4): 316-29 abstract. Dec. 1997.

Orum et al., "Locked nucleic acids: A promising molecular family for gene-function analysis and antisense drug development" Curr. Opinion Mol. Ther. (2001) 3(3):239-243.

Prakash et al., "Antisense Oligonucleotides Containing Conformationally Constrainted 2, 4-(N-Methoxy)aminomethylene and 2,4-Aminooxymethylene and 2-O,4 C-Aminomethylene Bridged Nucleoside Analogues Show Improved Potency in Animal Models" Journal of Medicinal Chemistry (2010) 53(4):163-1650.

Reynolds et al., "Rational siRNA design for RNA interference" Nature Biotechnology (2004) 22(3):326-330.

Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.

Sanghvi et al., "Heterocyclic Base Modifications in Nucleic Acids and Their Applications in Antisense Oligonucleotides" Antisense Research and Applications (1993) pp. 273-288.

Sambrook et al., "Molecular Cloning, A Laboratory Manual" 2nd Edition, Cold Spring Harbor Laboratory Press, 1989.

Scaringe, "RNA Oligonucleotide Synthesis via 5'-Sily1-2'-Orthoester Chemistry" Methods (2001) 23:206-217.

Seth et al., "Short Antisense Oligonucleotides with Novel 2'-4' Conformationaly Restricted Nucleoside Analogues Show Improved Potency without Increased Toxicity in Animals" Journal of Medicinal Chemistry (2009) 52(1):10-13.

Shea et al., "Synthesis, hybridization properties and antiviral activity of lipid-oligodeoxynucleotide conjugates" Nucl. Acids Res. (1990) 18(13):3777-3783.

Singh et al., "LNA (locked nucleic acids): synthesis and high-affinity nucleic acid recognition" Chem. Commun. (1998) 4:455-456.

Singh et al., "Synthesis of 2'-Amino-LNA: A Novel Conformationally Restricted High-Affinity Oligonucleotide Analogue with a Handle" J. Org. Chem. (1998) 63:10035-10039.

Srivastava et al., "Five- and Six-Membered Conformationally Locked 2',4'-Carbocyclic ribo-Thymidines: Synthesis, Structure, and Biochemical Studies" J. Am. Che,. Soc. (2007) 129:8362-8379.

Straarup et al., "Short locked nucleic acid antisense oligonucleotides potently reduce apolipoprotein B mRNA and serum cholesterol in mice and non-human primates" Nucleic Acids Research (2010) 38: 7100-7111.

Suzuki et al. "Portrait of PTEN: Messages from mutant mice" Cancer Sci. (2008) vol. 99(2):209-213.

Svinarchuk et al., "Inhibition of HIV proliferation in MT-4 cells by antisense oligonucleotide conjugated to lipophilic groups" Biochimie (1993) 75:49-54.

Swayze et al., "Antisense oligonucleotides containing locked nucleic acid improve potency but cause significant hepatotoxicity in animals" Nucleic Acids Research (2006) 35(2):687-700.

Wahlestedt et al., "Potent and nontoxic antisense oligonucleoties containing locked nucleic acids" PNAS (2000) 97(10):5633-5638.

Yagi et al., "Chimeric RNA and 2'-O, 4'-C-ethylene-bridged nucleic acids have stronger activity than phosphorothioate oligodeoxynucleotides in induction of exon 19 skipping in dystrophin mRNA" Oligonucleotides (2004) 14(1):33-40.

Zamecnik et al., "Inhibition of Rous sarcoma virus replication and cell transformation by a specific oligodeoxynucleotide" PNAS (1978) 75(1):280-284.

Zhou et al., "Fine Tuning of Electrostatics around the Internucleoside Phosphate through Incorporation of Modified 2',4'-Carbocylic-LNAs and -ENAs Leads to Significant Modulation of Antisense Properties" J. Org. Chem. (2009) 74: 118-134.

International Search Report for Application No. PCT/US2012/024385 dated May 10, 2012.

Stanton et al., "Chemical Modification Study of Antisense Gapmers" Nucleic Acid Therapeutics (2012) 22(5): 344-359.

Burel et al., "Hepatotoxicity of LNA Gapmer Antisense Oligonucleotides Is Mediated by Rnase H1 Dependent but Nonspecific Preferntial Downregulation of Very Long Pre-mRNA Transcripts" Tox Expo Abstract 605 (2015).

Burdick et al., "Sequence motifs associated with hepatotoxicity of locked nucleic acid-modified antisene oligonucleotides" Nucleic Acids Research (2014) 42(8): 4882-4891.

Chattopadhyaya et al., "Conformationally-2',4'-Locked Aza-ENA and Carbocyclic ribo-Thymidine" Nucleic Acids Symposium Series No. 51 (2007), 69-70.

Drygin et al., "Sequence-dependent cytotoxicity of second-genertion oligonucleotides" Nucleic Acids Research (2004) 32(22): 6585-6594.

Filichev et al., "Enhanced inhibition of transcription start by targeting with 2'-OMe pentaribonucleotides comprising locked nucleic acids and intercalating nucleic acids." ChemBioChem (2005) 6(7): 1181-1184.

Guidotti et al., "High-level hepatitis B virus replication in transgenic mice" J. Virol. (1995) 69(10):6158-6169.

Hagedorn et al., "Hepatotoxic Potential of Therapeutic Oligonucleotides Can Be Predicted from Their Sequence and Modification Pattern" Nucleic Acid Therapeutics (2013) 23(5): 302-310.

Henry, Potential Atributes of a Platform Technology: How Bestt to Capitalize on Cumulative MOE Oligonucleotide Safety Data Presentation from Drug Information Association 50th Annual Meeting in San Diego, Jun. 15-19, 2014, pp. 1-26.

Kurreck, "Antisense technologies, improvement through novel chemical modifications" Eur. J. Biochem. (2003) 270: 1628-1644.

Kurreck et al., "Design of antisense oligonucleotides stabilized by locked nucleic acids" Nucleic Acid Research (2002) 30(9): 1911-1918.

Levin et al., "Toxicity of Antisense Oligoncleotides" Antisense Drug Technology (2001) Ch. 9, pp. 201-268.

Lima et al., "The Positional Influence of the Helical Geometry of the Heteroduplex Substrate on Human RNase H1 Catalysis" Molecular Pharmacology (2007) 71(1): 73-82.

Lima et al., "The Rnase H Mechanism" Antisense Drug Technologies, (2008) Ch. 2, pp. 47-74.

(56) References Cited

OTHER PUBLICATIONS

Mergny et al., "Analysis of Thermal Melting Curves" Oligonucleotides (2003) 13:515-537.
Nielsen et al., "The ups and downs of nucleic acid duplex stability: structure-stability studies on chemically-modified DNA:RNA duplexes" Nucleic Acids Research (1997) 25(22): 4429-4443.
Nyblom et al., "High AST/ALT ratio may indicate advanced alcoholic liver disease rather than heavy drinking" Alcohol Alcohol (2004) 39(4):336-339.
Pallen et al., "Structure and nuclease resistance of 2',4'-constrained 2'-O-methoxyethyl (cMOE) and 2'-O-ethyl (cEt) modified DNAs" ChemComm (2012) 48:8195-8197.
Seth et al., "An Exocyclic Methylene Group Acts as a Bio-isostere of the 2'-Oxygen Atom in LNA" J. Am. Chem. Soc. (2010) 132(42): 14942-14950.
Seth et al., "Conformationally Constrained Nucleoside Modifications That Increase Potency of Antisense Oligonucleotides" Pictures of poster #39 from the Oligonucleotide Therapeutics 4th Annual Meeting, 2008.
Sewell et al., "Phase 1 Trial of ISIS 104838, a 2'-Methoxyethyl Modified Antisense Oligonucleotide Targeting Target Necrosis Factor-alpha" J. Pharmacol. Exp. Ther., (2002) 303(3); 1334-1343.
Stein et al., "Physiocochemical properties of phosphorothioate oligodeoxynucleotides" Nucleic Acids Research (1988) 16(8): 3209-3221.
Tessier et al., "Hepatotoxicity of oligonucleotides: relationship between non-clinical anc clinical findings" DIA/FDA Oligonucleotide-based Therapeutics 2012, Session 5A/5C.
Tessier, "Session 10: Oligonucleotide Safety, PK, and Toxicity" 8th Annual Meeting of the Oligonucleotide Therapeutics Society, Speaker Abstracts, p. 53, Wednesday, Oct. 31, 2012.
Antisense Drug Technology, Principles, Strategies, and Applications Edited by Stanley T. Crooke, CRC Press, Boca Raton, Florida.
Opposition against European Patent No. 2092065B1 granted to Isis Pharmaceuticals, Inc. dated Oct. 3, 2012.
Response and Amendment to European application EP 07844422.1 dated Sep. 8, 2010.
European Search Report for application 11186203.3 dated Nov. 18, 2011.
European Search Report for application EP 11186113.4 dated Nov. 30, 2011.
International Search Report for Application No. PCT/US2007/081850 dated Mar. 12, 2008.
Obika et al., "Inhibition of ICAM-I gene expression by antisense 2',4'-BNA oligonucleotides" (2001) 1:145-146.
Takagi-Sato et al., "Fine-Tuning of ENA Gapmers as Antisense Oligonucleotides for Sequence-Specific Inhibitition" Oligonucleotides (2007) 17:291-301.

* cited by examiner

OLIGOMERIC COMPOUNDS COMPRISING BICYCLIC NUCLEOTIDES AND USES THEREOF

CROSS REFERENCED TO RELATED APPLICATIONS

This application is a U.S. National Phase filing under 35 U.S.C. 371 claiming priority to International Serial No. PCT/US2012/024385 filed Feb. 8, 2012, which is a non-provisional application claiming priority to U.S. Provisional Application No. 61/440,828, filed Feb. 8, 2011; U.S. Provisional Application No. 61/470,927, filed Apr. 1, 2011; and U.S. Provisional Application No. 61/522,659, filed Aug. 11, 2011; each of which is incorporated herein by reference in its entirety.

SEQUENCE LISTING

The present application is being filed along with a Sequence Listing in electronic format. The Sequence Listing is provided as a file entitled CORE0094WOSEQ.txt, created Feb. 8, 2012, which is 4 Kb in size. The information in the electronic format of the sequence listing is incorporated herein by reference in its entirety.

BACKGROUND OF THE INVENTION

Antisense compounds have been used to modulate target nucleic acids. Antisense compounds comprising a variety of chemical modifications and motifs have been reported. In certain instances, such compounds are useful as research tools, diagnostic reagents, and as therapeutic agents. In certain instances antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

Certain antisense compounds have been described previously. See for example U.S. Pat. No. 7,399,845 and published International Patent Application No. WO 2008/049085, which are hereby incorporated by reference herein in their entirety.

SUMMARY OF THE INVENTION

In certain embodiments, the present invention provides compounds comprising oligonucleotides. In certain embodiments, such oligonucleotides comprise a gapmer region. In certain embodiments, such oligonucleotides consist of a gapmer region.

The present disclosure provides the following non-limiting numbered embodiments:

Embodiment 1

A compound comprising:
a modified oligonucleotide consisting of 10 to 20 linked nucleosides, wherein the modified oligonucleotide comprises:
a 5'-wing consisting of 2 to 5 linked nucleosides;
a 3'-wing consisting of 2 to 5 linked nucleosides; and
a gap between the 5'-wing and the 3'-wing consisting of 6 to 14 linked 2'-deoxynucleosides; and
wherein at least one of the 5'-wing and the 3'-wing comprises at least one bicyclic nucleoside; at least one of the 5'-wing and the 3'-wing comprises at least one 2'-substituted nucleoside; and
wherein the nucleobase sequence of the modified oligonucleotide is complementary to the nucleobase sequence of a target nucleic acid.

Embodiment 2

The compound of embodiment 1, wherein one of the 5'-wing or the 3'-wing comprises at least one 2'-deoxynucleoside.

Embodiment 3

The compound of embodiments 1-2, wherein each of the 5'-wing and the 3'-wing comprises at least one 2'-deoxynucleoside.

Embodiment 4

The compound of embodiments 1-3, wherein the 3'-wing comprises at least one 2'-deoxynucleoside.

Embodiment 5

The compound of embodiments 1-4, wherein the 5'-wing comprises at least one 2'-deoxynucleoside.

Embodiment 6

The compound of any of embodiments 1-5, wherein the 5'-wing comprises at least one bicyclic nucleoside.

Embodiment 7

The compound of any of embodiments 1-6, wherein the 3'-wing comprises at least one bicyclic nucleoside.

Embodiment 8

The compound of any of embodiments 1-7, wherein the 5'-wing comprises at least one 2'-substituted nucleoside.

Embodiment 9

The compound of any of embodiments 1-8, wherein the 3'-wing comprises at least one 2'-substituted nucleoside.

Embodiment 10

A compound comprising:
a modified oligonucleotide consisting of 10 to 20 linked nucleosides, wherein the modified oligonucleotide comprises:
a 5'-wing consisting of 2 to 5 linked nucleosides;
a 3'-wing of 2 to 5 linked nucleosides; and
a gap between the 5' wing and the 3' wing consisting of 6 to 14 linked 2'-deoxynucleosides; and
wherein at least one of the 5'-wing and the 3'-wing comprises at least one constrained ethyl nucleoside; and at least one of the 5'-wing and the 3'-wing comprises at least one 2'-substituted nucleoside; and

3 wherein the nucleobase sequence of the modified oligonucleotide is complementary to the nucleobase sequence of a target nucleic acid.

Embodiment 11

The compound of embodiments 1-10, wherein and at least one of the 5'-wing and the 3'-wing comprises at least one 2'-deoxynucleoside.

Embodiment 12

The compound of embodiments 1-11, wherein at least one of the 5'-wing and the 3'-wing comprises both at least one constrained ethyl nucleoside and at least one 2'-substituted nucleoside.

Embodiment 13

The compound of embodiments 1-12, wherein the 5'-wing comprises at least one constrained ethyl nucleoside.

Embodiment 14

The compound of any of embodiments 10-13, wherein the 3'-wing comprises at least one constrained ethyl nucleoside.

Embodiment 15

The compound of any of embodiments 10-14, wherein the 5'-wing comprises at least one 2'-substituted nucleoside.

Embodiment 16

The compound of any of embodiments 10-15, wherein the 3'-wing comprises at least one 2'-substituted nucleoside.

Embodiment 17

The compound of any of embodiments 1-17, wherein the modified oligonucleotide has a sugar motif described by Formula I as follows:

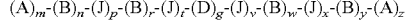

$(A)_m\text{-}(B)_n\text{-}(J)_p\text{-}(B)_r\text{-}(J)_t\text{-}(D)_g\text{-}(J)_v\text{-}(B)_w\text{-}(J)_x\text{-}(B)_y\text{-}(A)_z$ wherein:
each A is independently a 2'-substituted nucleoside;
each B is independently a bicyclic nucleoside;
each J is independently either a 2'-substituted nucleoside or a 2'-deoxynucleoside;
each D is a 2'-deoxynucleoside;
m is 0-4; n is 0-2; p is 0-2; r is 0-2; t is 0-2; v is 0-2; w is 0-4; x is 0-2; y is 0-2; z is 0-4; and g is 6-14;
provided that:
at least one of m, n, and r is other than 0;
at least one of w and y is other than 0;
the sum of m, n, p, r, and t is from 2 to 5; and
the sum of v, w, x, y, and z is from 2 to 5.

Embodiment 18

A compound comprising:
a modified oligonucleotide consisting of 10 to 20 linked nucleosides, wherein the modified oligonucleotide has a sugar motif described by Formula I as follows:

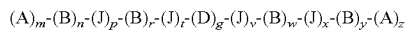

$(A)_m\text{-}(B)_n\text{-}(J)_p\text{-}(B)_r\text{-}(J)_t\text{-}(D)_g\text{-}(J)_v\text{-}(B)_w\text{-}(J)_x\text{-}(B)_y\text{-}(A)_z$

4 wherein:
each A is independently a 2'-substituted nucleoside;
each B is independently a bicyclic nucleoside;
each J is independently either a 2'-substituted nucleoside or a 2'-deoxynucleoside;
each D is a 2'-deoxynucleoside;
m is 0-4; n is 0-2; p is 0-2; r is 0-2; t is 0-2; v is 0-2; w is 0-4; x is 0-2; y is 0-2; z is 0-4; and g is 6-14;
provided that:
at least one of m, n, and r is other than 0;
at least one of w and y is other than 0;
the sum of m, n, p, r, and t is from 2 to 5; and
the sum of v, w, x, y, and z is from 2 to 5.

Embodiment 19

The compound of embodiment 17 or 18, wherein at least one bicyclic nucleoside is a constrained ethyl nucleoside.

Embodiment 20

The compound of embodiment 17 or 18, wherein each bicyclic nucleoside is a constrained ethyl nucleoside.

Embodiment 21

The compound of any of embodiments 17-19, wherein at least one bicyclic nucleoside is an LNA nucleoside.

Embodiment 22

The compound of embodiment 17 or 18, wherein each bicyclic nucleoside is an LNA nucleoside.

Embodiment 23

The compound of any of embodiments 1-22, wherein the 2'-substituent of the at least one 2'-substituted nucleoside is selected from among: $OCH_3$, F, $OCH_2F$, $OCHF_2$, $OCF_3$, $OCH_2CH_3$, $O(CH_2)_2F$, $OCH_2CHF_2$, $OCH_2CF_3$, $OCH_2\text{—}CH\text{=}CH_2$, $O(CH_2)_2\text{—}OCH_3$, $O(CH_2)_2\text{—}SCH_3$, $O(CH_2)_2\text{—}OCF_3$, $O(CH_2)_3\text{—}N(R_4)(R_5)$, $O(CH_2)_2\text{—}ON(R_4)(R_5)$, $O(CH_2)_2\text{—}O(CH_2)_2\text{—}N(R_4)(R_5)$, $OCH_2C(\text{=}O)\text{—}N(R_4)(R_5)$, $OCH_2C(\text{=}O)\text{—}N(R_6)\text{—}(CH_2)_2\text{—}N(R_4)(R_5)$ and $O(CH_2)_2\text{—}N(R_6)\text{—}C(\text{=}NR_7)[N(R_4)(R_5)]$ wherein $R_4$, $R_5$, $R_6$ and $R_7$ are each, independently, H or $C_1\text{-}C_6$ alkyl.

Embodiment 24

The compound of embodiment 23, wherein the 2'-substituent of the at least one 2'-substituted nucleoside of is selected from among: $OCH_3$, F, and $O(CH_2)_2\text{—}OCH_3$.

Embodiment 25

The compound of embodiment 24, wherein the 2'-substituent of the at least one 2'-substituted nucleoside is $O(CH_2)_2\text{—}OCH_3$.

Embodiment 26

The compound of any of embodiments 1-22, wherein the 2'-substituent of each 2'-substituted nucleoside is selected from among: $OCH_3$, F, $OCH_2F$, $OCHF_2$, $OCF_3$, $OCH_2CH_3$, $O(CH_2)_2F$, $OCH_2CHF_2$, $OCH_2CF_3$, $OCH_2\text{—}CH\text{=}CH_2$, $O(CH_2)_2\text{—}OCH_3$, $O(CH_2)_2\text{—}SCH_3$, $O(CH_2)_2\text{—}OCF_3$, $O(CH_2)_3\text{—}N(R_4)(R_5)$, $O(CH_2)_2\text{—}ON(R_4)(R_5)$, $O(CH_2)_2\text{—}N(R_4)(R_5)$, $OCH_2C(\text{=}O)\text{—}N(R_4)(R_5)$, $OCH_2C(\text{=}O)\text{—}N(R_6)\text{—}(CH_2)_2\text{—}N(R_4)(R_5)$ and $O(CH_2)_2\text{—}N$ $(R_6)$—C(=NR$_7$)[N(R$_4$)(R$_5$)] wherein R$_4$, R$_5$, R$_6$ and R$_7$ are each, independently, H or C$_1$-C$_6$ alkyl.

Embodiment 27

The compound of embodiment 26, wherein the 2'-substituent of each 2'-substituted nucleoside of is selected from among: OCH$_3$, F, and O(CH$_2$)$_2$—OCH$_3$.

Embodiment 28

The compound of embodiment 27, wherein the 2'-substituent of each 2'-substituted nucleoside is O(CH$_2$)$_2$—OCH$_3$.

Embodiment 29

The compound of any of embodiments 1-28, wherein the 5'-wing does not comprise a bicyclic nucleotide.

Embodiment 30

The compound of any of embodiments 1-29, wherein the 3'-wing does not comprise a bicyclic nucleotide.

Embodiment 31

The compound of any of embodiments 1-30, wherein the target nucleic acid is not a Huntingtin gene transcript.

Embodiment 32

The compound of any of embodiments 1-31, wherein the modified oligonucleotide has a base sequence other than:

| | |
|---|---|
| GTGCTACCCAACCTTTCTG; | (SEQ ID NO: 1) |
| CACAGTGCTACCCAACCTT; | (SEQ ID NO: 2) |
| CAGTGCTACCCAACC; | (SEQ ID NO: 3) |
| ATATCACAGTGCTACCCAA; | (SEQ ID NO: 4) |
| GATGCTGACTTGGGCCATT; | (SEQ ID NO: 5) |
| GGGATGCTGACTTGG; | (SEQ ID NO: 6) |
| TGCCAAGGGATGCTGACTT; | (SEQ ID NO: 7) |
| AATTGTCATCACCAGAAAA; | (SEQ ID NO: 8) |
| TAAATTGTCATCACC; | (SEQ ID NO: 9) |
| ACAGTAGATGAGGGAGCAG; | (SEQ ID NO: 10) |
| ACACAGTAGATGAGG; | (SEQ ID NO: 11) |
| AAGTGCACACAGTAGATGA; | (SEQ ID NO: 12) |
| AGCTGCAACCTGGCAACAA; | (SEQ ID NO: 13) |
| GCAGCTGCAACCTGG; or | (SEQ ID NO: 14) |
| GCAAGAGCAGCTGCAACCT. | (SEQ ID NO: 15) |

Embodiment 33

The compound of any of embodiments 1-31, wherein the oligonucleotide has a sugar motif other than:
E-K-K-(D)$_9$-K-K-E;
E-E-E-E-K-(D)$_9$-E-E-E-E-E;
E-K-K-K-(D)$_9$-K-K-K-E;
K-E-E-K-(D)$_9$-K-E-E-K;
K-D-D-K-(D)$_9$-K-D-D-K;
K-E-K-E-K-(D)$_9$-K-E-K-E-K;
K-D-K-D-K-(D)$_9$-K-D-K-D-K;
E-K-E-K-(D)$_9$-K-E-K-E;
E-E-E-E-E-K-(D)$_8$-E-E-E-E-E; or
E-K-E-K-E-(D)$_9$-E-K-E-K-E; wherein
K is a constrained ethyl nucleoside, E is a 2'-MOE substituted nucleoside, and D is a 2'-deoxynucleoside.

Embodiment 34

The compound of any of embodiments 1-30, wherein the 5'-wing consists of 2 linked nucleosides.

Embodiment 35

The compound of any of embodiments 1-30, wherein the 5'-wing consists of 3 linked nucleosides.

Embodiment 36

The compound of any of embodiments 1-30, wherein the 5'-wing consists of 4 linked nucleosides.

Embodiment 37

The compound of any of embodiments 1-30, wherein the 5'-wing consists of 5 linked nucleosides.

Embodiment 38

The compound of any of embodiments 1-34, wherein the 3'-wing consists of 2 linked nucleosides.

Embodiment 39

The compound of any of embodiments 1-34, wherein the 3'-wing consists of 3 linked nucleosides.

Embodiment 40

The compound of any of embodiments 1-34, wherein the 3'-wing consists of 4 linked nucleosides.

Embodiment 41

The compound of any of embodiments 1-34, wherein the 3'-wing consists of 5 linked nucleosides.

Embodiment 42

The compound of any of embodiments 1-38, wherein the gap consists of 6 linked 2'-deoxynucleosides.

Embodiment 43

The compound of any of embodiments 1-38, wherein the gap consists of 7 linked 2'-deoxynucleosides.

Embodiment 44

The compound of any of embodiments 1-38, wherein the gap consists of 8 linked 2'-deoxynucleosides.

Embodiment 45

The compound of any of embodiments 1-38, wherein the gap consists of 9 linked 2'-deoxynucleosides.

Embodiment 46

The compound of any of embodiments 1-38, wherein the gap consists of 10 linked 2'-deoxynucleosides.

Embodiment 47

The compound of any of embodiments 1-38, wherein the gap consists of 11 linked 2'-deoxynucleosides.

Embodiment 48

The compound of any of embodiments 1-38, wherein the gap consists of 12 linked 2'-deoxynucleosides.

Embodiment 49

The compound of any of embodiments 1-38, wherein the gap consists of 13 linked 2'-deoxynucleosides.

Embodiment 50

The compound of any of embodiments 1-38, wherein the gap consists of 14 linked 2'-deoxynucleosides.

Embodiment 51

The compound of any of embodiments 1-50, wherein the oligonucleotide consists of 10 linked nucleosides.

Embodiment 52

The compound of any of embodiments 1-50, wherein the oligonucleotide consists of 11 linked nucleosides.

Embodiment 53

The compound of any of embodiments 1-50, wherein the oligonucleotide consists of 12 linked nucleosides.

Embodiment 54

The compound of any of embodiments 1-50, wherein the oligonucleotide consists of 13 linked nucleosides.

Embodiment 55

The compound of any of embodiments 1-50, wherein the oligonucleotide consists of 14 linked nucleosides.

Embodiment 56

The compound of any of embodiments 1-50, wherein the oligonucleotide consists of 15 linked nucleosides.

Embodiment 57

The compound of any of embodiments 1-50, wherein the oligonucleotide consists of 16 linked nucleosides.

Embodiment 58

The compound of any of embodiments 1-50, wherein the oligonucleotide consists of 17 linked nucleosides.

Embodiment 59

The compound of any of embodiments 1-50, wherein the oligonucleotide consists of 18 linked nucleosides.

Embodiment 60

The compound of any of embodiments 1-50, wherein the oligonucleotide consists of 19 linked nucleosides.

Embodiment 61

The compound of any of embodiments 1-50, wherein the oligonucleotide consists of 20 linked nucleosides.

Embodiment 62

The compound of any of embodiments 1-50, wherein the oligonucleotide consists of 21 linked nucleosides.

Embodiment 63

The compound of any of embodiments 1-50, wherein the oligonucleotide consists of 22 linked nucleosides.

Embodiment 64

The compound of any of embodiments 1-30, wherein the gapmer motif is selected from among: 2-10-2, 2-10-3, 2-10-4, 2-10-5, 3-10-2, 3-10-3, 3-10-4, 3-10-5, 4-10-2, 4-10-3, 4-10- 4, 4-10-5, 5-10-2, 5-10-3, 5-10-4, 5-10-5, 2-9-2, 2-9-3, 2-9-4, 2-9-5, 3-9-2, 3-9-3, 3-9-4, 3-9-5, 4-9-2, 4-9-3, 4-9-4, 4-9-5, 5-9-2, 5-9-3, 5-9-4, 5-9-5, 2-8-2, 2-8-3, 2-8-4, 2-8-5, 3-8-2, 3-8-3, 3-8-4, 3-8-5, 4-8-2, 4-8-3, 4-8-4, 4-8-5, 5-8-2, 5-8-3, 5-8-4, and 5-8-5.

Embodiment 65

A compound comprising a modified oligonucleotide having a sugar motif selected from among sugar motifs 1-278 as shown in Table 4.

Embodiment 66

The compound of any of embodiments 1-65, wherein the 5'-wing has a motif selected from among the 5'-wing motifs as shown in Tables 1-3.

Embodiment 67

The compound of any of embodiments 1-66, wherein the 3'-wing has a motif selected from among the 3'-wing motifs as shown in Tables 4-6.

Embodiment 68

The compound of any of embodiments 66-67, wherein each A, each B, and each C are independently selected from among: HNA and F-HNA.

Embodiment 69

The compound of any of embodiments 1-68, wherein the 5'-wing comprises at least one F-HNA.

Embodiment 70

The compound of any of embodiments 1-69, wherein the 3'-wing comprises at least one F-HNA.

Embodiment 71

The compound of any of embodiments 1-68, wherein the 5'-wing comprises at least one modified nucleobase.

Embodiment 72

The compound of any of embodiments 1-69, wherein the 3'-wing comprises at least one modified nucleobase.

Embodiment 73

The compound of embodiment 72, wherein the modified nucleobase is 2-thio-thymidine.

Embodiment 74

The compound of any of embodiments 1-73, wherein the 5'-wing has a motif selected from among the 5'-wing motifs as shown in Tables 1-3 and the 3'-wing has a motif selected from among the 3'-wing motifs as shown in Tables 4-6.

Embodiment 75

The compound of any of embodiments 1-74, wherein the 5'-wing has an ABABA motif, wherein each A is a modified nucleoside and each B comprises a 2'-deoxynucleoside.

Embodiment 76

The compound of embodiment 75, wherein the modified nucleoside is a bicyclic nucleoside.

Embodiment 77

The compound of embodiment 76, wherein the bicyclic nucleoside is cEt.

Embodiment 78

The compound of embodiment 76, wherein the bicyclic nucleoside is LNA.

Embodiment 79

The compound of any of embodiments 75-78 wherein the 3'-wing has a motif selected from among: AA, AB, AC, BA, BB, BC, CA, CB, and CC.

Embodiment 80

The compound of embodiment 79, wherein the 3'-wing has an AA motif.

Embodiment 81

The compound of embodiment 80, wherein A is a 2'-substituted nucleoside.

Embodiment 82

The compound of embodiment 80, wherein the 2'-substituted nucleoside is selected from among: $OCH_3$, F, $OCH_2F$, $OCHF_2$, $OCF_3$, $OCH_2CH_3$, $O(CH_2)_2F$, $OCH_2CHF_2$, $OCH_2CF_3$, $OCH_2$—$CH$=$CH_2$, $O(CH_2)_2$—$OCH_3$, $O(CH_2)_2$—$SCH_3$, $O(CH_2)_2$—$OCF_3$, $O(CH_2)_3$—$N(R_4)(R_5)$, $O(CH_2)_2$—$ON(R_4)(R_5)$, $O(CH_2)_2$—$O(CH_2)_2$—$N(R_4)(R_5)$, $OCH_2C(=O)$—$N(R_4)(R_5)$, $OCH_2C(=O)$—$N(R_6)$—$(CH_2)_2$—$NR_4)(R_5)$ and $O(CH_2)_2$—$N(R_6)$—$C(=NR_7)[N(R_4)(R_5)]$ wherein $R_4$, $R_5$, $R_6$ and $R_7$ are each, independently, H or $C_1$-$C_6$ alkyl.

Embodiment 83

The compound of embodiment 82, wherein the 2'-substituent of each 2'-substituted nucleoside of is selected from among: $OCH_3$, F, and $O(CH_2)_2$—$OCH_3$.

Embodiment 84

The compound of embodiment 83, wherein the 2'-substituent of each 2'-substituted nucleoside is $O(CH_2)_2$—$OCH_3$.

Embodiment 85

The compound of any of embodiments 76-84 wherein the gap between the 5'-wing and the 3'-wing consists of 6 to 11 linked 2'-deoxynucleosides.

Embodiment 86

The compound of any of embodiments 76-84 wherein the gap between the 5'-wing and the 3'-wing consists of 7 to 10 linked 2'-deoxynucleosides.

Embodiment 87

The compound of any of embodiments 76-84 wherein the gap between the 5'-wing and the 3'-wing consists of 10 linked 2'-deoxynucleosides.

Embodiment 88

The compound of any of embodiments 75-87 having the sugar motif: K-D-K-D-K-$(D)_6$-E-E.

Embodiment 89

The compound of any of embodiments 75-87 having the sugar motif: K-D-K-D-K-$(D)_7$-E-E.

Embodiment 90

The compound of any of embodiments 75-87 having the sugar motif: K-D-K-D-K-$(D)_8$-E-E.

Embodiment 91

The compound of any of embodiments 75-87 having the sugar motif: K-D-K-D-K-$(D)_9$-E-E.

Embodiment 92

The compound of any of embodiments 75-87 having the sugar motif: K-D-K-D-K-$(D)_{10}$-E-E.

Embodiment 93

The compound of any of embodiments 75-87 having the sugar motif: K-D-K-D-K-(D)$_{11}$-E-E.

Embodiment 94

The compound of any of embodiments 75-87 having the sugar motif: K-D-K-D-K-(D)$_{12}$-E-E.

Embodiment 95

The compound of any of embodiments 75-87 having the sugar motif: K-D-K-D-K-(D)$_{13}$-E-E.

Embodiment 96

The compound of any of embodiments 75-87 having the sugar motif: K-D-K-D-K-(D)$_{14}$-E-E.

Embodiment 97

The compound of any of embodiments 75-87 having the sugar motif: K-D-K-D-K-(D)$_{15}$-E-E.

Embodiment 98

The compound of any of embodiments 1-97, wherein the 5'-wing has a BDBDB motif, wherein each B is a bicyclic nucleoside and each D comprises a 2'-deoxynucleoside.

Embodiment 99

The compound of any of embodiments 1-97, wherein the 5'-wing has a BDBDB-(D)$_{6-15}$-AA motif, wherein each B is a bicyclic nucleoside and each D comprises a 2'-deoxynucleoside.

Embodiment 100

The compound of any of embodiments 98-99, wherein B is selected from among: BNA, LNA, α-L-LNA, ENA and 2'-thio LNA.

Embodiment 101

The compound of embodiment 100, wherein B comprises BNA.

Embodiment 102

The compound of embodiment 100, wherein B comprises LNA.

Embodiment 103

The compound of embodiment 100, wherein B comprises α-L-LNA.

Embodiment 104

The compound of embodiment 100, wherein B comprises ENA.

Embodiment 105

The compound of embodiment 100, wherein B comprises 2'-thio LNA.

Embodiment 106

The compound of any of embodiments 100 to 105, wherein A comprises a 2' substituted nucleoside.

Embodiment 107

The compound of claim 106, wherein the 2' substituted nucleoside comprises MOE.

Embodiment 108

The compound of any of embodiments 1-2, wherein the compound comprises a modified oligonucleotide having sugar motif: A-B-B-(D)$_8$-B-B-A, wherein each A is an independently selected 2'-substituted nucleoside, each B is an independently selected bicyclic nucleoside, and each D is a 2'-deoxynucleoside

Embodiment 109

The compound of any of embodiments 1-2, wherein the compound comprises a modified oligonucleotide having sugar motif: A-B-B-(D)$_9$-B-B-A, wherein each A is an independently selected 2'-substituted nucleoside, each B is an independently selected bicyclic nucleoside, and each D is a 2'-deoxynucleoside

Embodiment 110

The compound of any of embodiments 1-2, wherein the compound comprises a modified oligonucleotide having sugar motif: A-B-B-(D)$_{10}$-B-B-A, wherein each A is an independently selected 2'-substituted nucleoside, each B is an independently selected bicyclic nucleoside, and each D is a 2'-deoxynucleoside

Embodiment 111

The compound of any of embodiments 1-2, wherein the compound comprises a modified oligonucleotide having sugar motif: A-A-B-(D)$_8$-B-B-A, wherein each A is an independently selected 2'-substituted nucleoside, each B is an independently selected bicyclic nucleoside, and each D is a 2'-deoxynucleoside

Embodiment 112

The compound of any of embodiments 1-2, wherein the compound comprises a modified oligonucleotide having sugar motif: A-A-B-(D)$_9$-B-B-A, wherein each A is an independently selected 2'-substituted nucleoside, each B is an independently selected bicyclic nucleoside, and each D is a 2'-deoxynucleoside

Embodiment 113

The compound of any of embodiments 1-2, wherein the compound comprises a modified oligonucleotide having sugar motif: A-A-B-(D)$_{10}$-B-B-A, wherein each A is an independently selected 2'-substituted nucleoside, each B is an independently selected bicyclic nucleoside, and each D is a 2'-deoxynucleoside

Embodiment 114

The compound of any of embodiments 1-2, wherein the compound comprises a modified oligonucleotide having sugar motif: A-D-B-(D)$_8$-B-B-A, wherein each A is an independently selected 2'-substituted nucleoside, each B is an independently selected bicyclic nucleoside, and each D is a 2'-deoxynucleoside Embodiment 115

The compound of any of embodiments 1-2, wherein the compound comprises a modified oligonucleotide having sugar motif: A-D-B-(D)$_9$-B-B-A, wherein each A is an independently selected 2'-substituted nucleoside, each B is an independently selected bicyclic nucleoside, and each D is a 2'-deoxynucleoside Embodiment 116

The compound of any of embodiments 1-2, wherein the compound comprises a modified oligonucleotide having sugar motif: A-D-B-(D)$_{10}$-B-B-A, wherein each A is an independently selected 2'-substituted nucleoside, each B is an independently selected bicyclic nucleoside, and each D is a 2'-deoxynucleoside Embodiment 117

The compound of any of embodiments 1-2, wherein the compound comprises a modified oligonucleotide having sugar motif: B-D-A-(D)$_8$-B-B-A, wherein each A is an independently selected 2'-substituted nucleoside, each B is an independently selected bicyclic nucleoside, and each D is a 2'-deoxynucleoside Embodiment 118

The compound of any of embodiments 1-2, wherein the compound comprises a modified oligonucleotide having sugar motif: B-D-A-(D)$_9$-B-B-A, wherein each A is an independently selected 2'-substituted nucleoside, each B is an independently selected bicyclic nucleoside, and each D is a 2'-deoxynucleoside Embodiment 119

The compound of any of embodiments 1-2, wherein the compound comprises a modified oligonucleotide having sugar motif: B-D-A-(D)$_{10}$-B-B-A, wherein each A is an independently selected 2'-substituted nucleoside, each B is an independently selected bicyclic nucleoside, and each D is a 2'-deoxynucleoside Embodiment 120

The compound of any of embodiments 1-2, wherein the compound comprises a modified oligonucleotide having sugar motif: B-A-A-(D)$_8$-B-B-A, wherein each A is an independently selected 2'-substituted nucleoside, each B is an independently selected bicyclic nucleoside, and each D is a 2'-deoxynucleoside Embodiment 121

The compound of any of embodiments 1-2, wherein the compound comprises a modified oligonucleotide having sugar motif: B-A-A-(D)$_9$-B-B-A, wherein each A is an independently selected 2'-substituted nucleoside, each B is an independently selected bicyclic nucleoside, and each D is a 2'-deoxynucleoside Embodiment 122

The compound of any of embodiments 1-2, wherein the compound comprises a modified oligonucleotide having sugar motif: B-A-A-(D)$_{10}$-B-B-A, wherein each A is an independently selected 2'-substituted nucleoside, each B is an independently selected bicyclic nucleoside, and each D is a 2'-deoxynucleoside Embodiment 123

The compound of any of embodiments 1-2, wherein the compound comprises a modified oligonucleotide having sugar motif: B-B-B-(D)$_3$-B-B-A, wherein each A is an independently selected 2'-substituted nucleoside, each B is an independently selected bicyclic nucleoside, and each D is a 2'-deoxynucleoside Embodiment 124

The compound of any of embodiments 1-2, wherein the compound comprises a modified oligonucleotide having sugar motif: B-B-B-(D)$_9$-B-B-A, wherein each A is an independently selected 2'-substituted nucleoside, each B is an independently selected bicyclic nucleoside, and each D is a 2'-deoxynucleoside Embodiment 125

The compound of any of embodiments 1-2, wherein the compound comprises a modified oligonucleotide having sugar motif: B-B-B-(D)$_{10}$-B-B-A, wherein each A is an independently selected 2'-substituted nucleoside, each B is an independently selected bicyclic nucleoside, and each D is a 2'-deoxynucleoside Embodiment 126

The compound of any of embodiments 1-2, wherein the compound comprises a modified oligonucleotide having sugar motif: A-A-A-(D)$_8$-B-B-A, wherein each A is an independently selected 2'-substituted nucleoside, each B is an independently selected bicyclic nucleoside, and each D is a 2'-deoxynucleoside Embodiment 127

The compound of any of embodiments 1-2, wherein the compound comprises a modified oligonucleotide having sugar motif: A-A-A-(D)$_9$-B-B-A, wherein each A is an independently selected 2'-substituted nucleoside, each B is an independently selected bicyclic nucleoside, and each D is a 2'-deoxynucleoside Embodiment 128

The compound of any of embodiments 1-2, wherein the compound comprises a modified oligonucleotide having sugar motif: A-A-A-(D)$_{10}$-B-B-A, wherein each A is an independently selected 2'-substituted nucleoside, each B is an independently selected bicyclic nucleoside, and each D is a 2'-deoxynucleoside Embodiment 129

The compound of any of embodiments 1-2, wherein the compound comprises a modified oligonucleotide having sugar motif: B-B-B-(D)$_8$-B-B-B, wherein each B is an independently selected bicyclic nucleoside, and each D is a 2'-deoxynucleoside Embodiment 130

The compound of any of embodiments 1-2, wherein the compound comprises a modified oligonucleotide having sugar motif: B-B-B-(D)$_9$-B-B-B, wherein each B is an independently selected bicyclic nucleoside, and each D is a 2'-deoxynucleoside Embodiment 131

The compound of any of embodiments 1-2, wherein the compound comprises a modified oligonucleotide having sugar motif: B-B-B-(D)$_{10}$-B-B-B, wherein each B is an independently selected bicyclic nucleoside, and each D is a 2'-deoxynucleoside Embodiment 132

The compound of any of embodiments 1-2, wherein the compound comprises a modified oligonucleotide having sugar motif: A-A-A-(D)$_8$-B-B-B, wherein each A is an independently selected 2'-substituted nucleoside, each B is an independently selected bicyclic nucleoside, and each D is a 2'-deoxynucleoside Embodiment 133

The compound of any of embodiments 1-2, wherein the compound comprises a modified oligonucleotide having sugar motif: A-A-A-(D)$_9$-B-B-B, wherein each A is an independently selected 2'-substituted nucleoside, each B is an independently selected bicyclic nucleoside, and each D is a 2'-deoxynucleoside Embodiment 134

The compound of any of embodiments 1-2, wherein the compound comprises a modified oligonucleotide having sugar motif: A-A-A-(D)$_{10}$-B-B-B, wherein each A is an independently selected 2'-substituted nucleoside, each B is an independently selected bicyclic nucleoside, and each D is a 2'-deoxynucleoside Embodiment 135

The compound of any of embodiments 1-2, wherein the compound comprises a modified oligonucleotide having sugar motif: A-D-D-B-(D)$_8$-B-B-A, wherein each A is an independently selected 2'-substituted nucleoside, each B is an independently selected bicyclic nucleoside, and each D is a 2'-deoxynucleoside Embodiment 136

The compound of any of embodiments 1-2, wherein the compound comprises a modified oligonucleotide having sugar motif: A-D-D-B-(D)$_9$-B-B-A, wherein each A is an independently selected 2'-substituted nucleoside, each B is an independently selected bicyclic nucleoside, and each D is a 2'-deoxynucleoside Embodiment 137

The compound of any of embodiments 1-2, wherein the compound comprises a modified oligonucleotide having sugar motif: A-D-D-B-(D)$_{10}$-B-B-A, wherein each A is an independently selected 2'-substituted nucleoside, each B is an independently selected bicyclic nucleoside, and each D is a 2'-deoxynucleoside Embodiment 138

The compound of any of embodiments 1-2, wherein the compound comprises a modified oligonucleotide having sugar motif: B-D-D-A-(D)$_8$-B-B-A, wherein each A is an independently selected 2'-substituted nucleoside, each B is an independently selected bicyclic nucleoside, and each D is a 2'-deoxynucleoside Embodiment 139

The compound of any of embodiments 1-2, wherein the compound comprises a modified oligonucleotide having sugar motif: B-D-D-A-(D)$_9$-B-B-A, wherein each A is an independently selected 2'-substituted nucleoside, each B is an independently selected bicyclic nucleoside, and each D is a 2'-deoxynucleoside Embodiment 140

The compound of any of embodiments 1-2, wherein the compound comprises a modified oligonucleotide having sugar motif: B-D-D-A-(D)$_{10}$-B-B-A, wherein each A is an independently selected 2'-substituted nucleoside, each B is an independently selected bicyclic nucleoside, and each D is a 2'-deoxynucleoside Embodiment 141

The compound of any of embodiments 1-2, wherein the compound comprises a modified oligonucleotide having sugar motif: A-A-A-B-(D)$_8$-B-B-A, wherein each A is an independently selected 2'-substituted nucleoside, each B is an independently selected bicyclic nucleoside, and each D is a 2'-deoxynucleoside Embodiment 142

The compound of any of embodiments 1-2, wherein the compound comprises a modified oligonucleotide having sugar motif: A-A-A-B-(D)$_9$-B-B-A, wherein each A is an independently selected 2'-substituted nucleoside, each B is an independently selected bicyclic nucleoside, and each D is a 2'-deoxynucleoside Embodiment 143

The compound of any of embodiments 1-2, wherein the compound comprises a modified oligonucleotide having sugar motif: A-A-A-B-(D)$_{10}$-B-B-A, wherein each A is an independently selected 2'-substituted nucleoside, each B is an independently selected bicyclic nucleoside, and each D is a 2'-deoxynucleoside Embodiment 144

The compound of any of embodiments 1-2, wherein the compound comprises a modified oligonucleotide having sugar motif: B-A-A-A-(D)$_8$-B-B-A, wherein each A is an independently selected 2'-substituted nucleoside, each B is an independently selected bicyclic nucleoside, and each D is a 2'-deoxynucleoside

Embodiment 145

The compound of any of embodiments 1-2, wherein the compound comprises a modified oligonucleotide having sugar motif: B-A-A-A-$(D)_9$-B-B-A, wherein each A is an independently selected 2'-substituted nucleoside, each B is an independently selected bicyclic nucleoside, and each D is a 2'-deoxynucleoside

Embodiment 146

The compound of any of embodiments 1-2, wherein the compound comprises a modified oligonucleotide having sugar motif: B-A-A-A-$(D)_{10}$-B-B-A, wherein each A is an independently selected 2'-substituted nucleoside, each B is an independently selected bicyclic nucleoside, and each D is a 2'-deoxynucleoside

Embodiment 147

The compound of any of embodiments 1-2, wherein the compound comprises a modified oligonucleotide having sugar motif: A-A-A-A-$(D)_8$-B-B-A, wherein each A is an independently selected 2'-substituted nucleoside, each B is an independently selected bicyclic nucleoside, and each D is a 2'-deoxynucleoside

Embodiment 148

The compound of any of embodiments 1-2, wherein the compound comprises a modified oligonucleotide having sugar motif: A-A-A-A-$(D)_9$-B-B-A, wherein each A is an independently selected 2'-substituted nucleoside, each B is an independently selected bicyclic nucleoside, and each D is a 2'-deoxynucleoside

Embodiment 149

The compound of any of embodiments 1-2, wherein the compound comprises a modified oligonucleotide having sugar motif: A-A-A-A-$(D)_{10}$-B-B-A, wherein each A is an independently selected 2'-substituted nucleoside, each B is an independently selected bicyclic nucleoside, and each D is a 2'-deoxynucleoside

Embodiment 150

The compound of any of embodiments 1-2, wherein the compound comprises a modified oligonucleotide having sugar motif: B-A-A-A-$(D)_8$-B-B-B, wherein each A is an independently selected 2'-substituted nucleoside, each B is an independently selected bicyclic nucleoside, and each D is a 2'-deoxynucleoside

Embodiment 151

The compound of any of embodiments 1-2, wherein the compound comprises a modified oligonucleotide having sugar motif: B-A-A-A-$(D)_9$-B-B-B, wherein each A is an independently selected 2'-substituted nucleoside, each B is an independently selected bicyclic nucleoside, and each D is a 2'-deoxynucleoside

Embodiment 152

The compound of any of embodiments 1-2, wherein the compound comprises a modified oligonucleotide having sugar motif: B-A-A-A-$(D)_{10}$-B-B-B, wherein each A is an independently selected 2'-substituted nucleoside, each B is an independently selected bicyclic nucleoside, and each D is a 2'-deoxynucleoside

Embodiment 153

The compound of any of embodiments 1-2, wherein the compound comprises a modified oligonucleotide having sugar motif: B-D-D-B-$(D)_8$-B-B-A, wherein each A is an independently selected 2'-substituted nucleoside, each B is an independently selected bicyclic nucleoside, and each D is a 2'-deoxynucleoside

Embodiment 154

The compound of any of embodiments 1-2, wherein the compound comprises a modified oligonucleotide having sugar motif: B-D-D-B-$(D)_9$-B-B-A, wherein each A is an independently selected 2'-substituted nucleoside, each B is an independently selected bicyclic nucleoside, and each D is a 2'-deoxynucleoside

Embodiment 155

The compound of any of embodiments 1-2, wherein the compound comprises a modified oligonucleotide having sugar motif: B-D-D-B-$(D)_{10}$-B-B-A, wherein each A is an independently selected 2'-substituted nucleoside, each B is an independently selected bicyclic nucleoside, and each D is a 2'-deoxynucleoside

Embodiment 156

The compound of any of embodiments 1-2, wherein the compound comprises a modified oligonucleotide having sugar motif: A-A-A-A-$(D)_8$-B-B-B, wherein each A is an independently selected 2'-substituted nucleoside, each B is an independently selected bicyclic nucleoside, and each D is a 2'-deoxynucleoside

Embodiment 157

The compound of any of embodiments 1-2, wherein the compound comprises a modified oligonucleotide having sugar motif: A-A-A-A-$(D)_9$-B-B-B, wherein each A is an independently selected 2'-substituted nucleoside, each B is an independently selected bicyclic nucleoside, and each D is a 2'-deoxynucleoside

Embodiment 158

The compound of any of embodiments 1-2, wherein the compound comprises a modified oligonucleotide having sugar motif: A-A-A-A-$(D)_{10}$-B-B-B, wherein each A is an independently selected 2'-substituted nucleoside, each B is an independently selected bicyclic nucleoside, and each D is a 2'-deoxynucleoside

Embodiment 159

The compound of any of embodiments 1-2, wherein the compound comprises a modified oligonucleotide having sugar motif: B-B-B-B-$(D)_8$-B-B-B, wherein each B is an independently selected bicyclic nucleoside, and each D is a 2'-deoxynucleoside

Embodiment 160

The compound of any of embodiments 1-2, wherein the compound comprises a modified oligonucleotide having sugar motif: B-B-B-B-(D)$_9$-B-B-B, each B is an independently selected bicyclic nucleoside, and each D is a 2'-deoxynucleoside

Embodiment 161

The compound of any of embodiments 1-2, wherein the compound comprises a modified oligonucleotide having sugar motif: B-B-B-B-(D)$_{10}$-B-B-B, wherein each B is an independently selected bicyclic nucleoside, and each D is a 2'-deoxynucleoside

Embodiment 162

The compound of any of embodiments 1-2, wherein the compound comprises a modified oligonucleotide having sugar motif: A-A-A-A-A-(D)$_8$-B-B-A, wherein each A is an independently selected 2'-substituted nucleoside, each B is an independently selected bicyclic nucleoside, and each D is a 2'-deoxynucleoside

Embodiment 163

The compound of any of embodiments 1-2, wherein the compound comprises a modified oligonucleotide having sugar motif: A-A-A-A-A-(D)$_9$-B-B-A, wherein each A is an independently selected 2'-substituted nucleoside, each B is an independently selected bicyclic nucleoside, and each D is a 2'-deoxynucleoside

Embodiment 164

The compound of any of embodiments 1-2, wherein the compound comprises a modified oligonucleotide having sugar motif: A-A-A-A-A-(D)$_{10}$-B-B-A, wherein each A is an independently selected 2'-substituted nucleoside, each B is an independently selected bicyclic nucleoside, and each D is a 2'-deoxynucleoside

Embodiment 165

The compound of any of embodiments 1-2, wherein the compound comprises a modified oligonucleotide having sugar motif: A-A-A-A-A-(D)$_8$-B-B-B, wherein each A is an independently selected 2'-substituted nucleoside, each B is an independently selected bicyclic nucleoside, and each D is a 2'-deoxynucleoside

Embodiment 166

The compound of any of embodiments 1-2, wherein the compound comprises a modified oligonucleotide having sugar motif: A-A-A-A-A-(D)$_9$-B-B-B, wherein each A is an independently selected 2'-substituted nucleoside, each B is an independently selected bicyclic nucleoside, and each D is a 2'-deoxynucleoside

Embodiment 167

The compound of any of embodiments 1-2, wherein the compound comprises a modified oligonucleotide having sugar motif: A-A-A-A-A-(D)$_{10}$-B-B-B, wherein each A is an independently selected 2'-substituted nucleoside, each B is an independently selected bicyclic nucleoside, and each D is a 2'-deoxynucleoside

Embodiment 168

The compound of any of embodiments 1-2, wherein the compound comprises a modified oligonucleotide having sugar motif: A-D-A-D-B-(D)$_8$-B-B-A, wherein each A is an independently selected 2'-substituted nucleoside, each B is an independently selected bicyclic nucleoside, and each D is a 2'-deoxynucleoside

Embodiment 169

The compound of any of embodiments 1-2, wherein the compound comprises a modified oligonucleotide having sugar motif: A-D-A-D-B-(D)$_9$-B-B-A, wherein each A is an independently selected 2'-substituted nucleoside, each B is an independently selected bicyclic nucleoside, and each D is a 2'-deoxynucleoside

Embodiment 170

The compound of any of embodiments 1-2, wherein the compound comprises a modified oligonucleotide having sugar motif: A-D-A-D-B-(D)$_{10}$-B-B-A, wherein each A is an independently selected 2'-substituted nucleoside, each B is an independently selected bicyclic nucleoside, and each D is a 2'-deoxynucleoside

Embodiment 171

The compound of any of embodiments 1-2, wherein the compound comprises a modified oligonucleotide having sugar motif: A-D-B-D-A-(D)$_8$-B-B-A, wherein each A is an independently selected 2'-substituted nucleoside, each B is an independently selected bicyclic nucleoside, and each D is a 2'-deoxynucleoside

Embodiment 172

The compound of any of embodiments 1-2, wherein the compound comprises a modified oligonucleotide having sugar motif: A-D-B-D-A-(D)$_9$-B-B-A, wherein each A is an independently selected 2'-substituted nucleoside, each B is an independently selected bicyclic nucleoside, and each D is a 2'-deoxynucleoside

Embodiment 173

The compound of any of embodiments 1-2, wherein the compound comprises a modified oligonucleotide having sugar motif: A-D-B-D-A-(D)$_{10}$-B-B-A, wherein each A is an independently selected 2'-substituted nucleoside, each B is an independently selected bicyclic nucleoside, and each D is a 2'-deoxynucleoside

Embodiment 174

The compound of any of embodiments 1-2, wherein the compound comprises a modified oligonucleotide having sugar motif: B-D-A-D-A-(D)$_8$-B-B-A, wherein each A is an independently selected 2'-substituted nucleoside, each B is an independently selected bicyclic nucleoside, and each D is a 2'-deoxynucleoside

Embodiment 175

The compound of any of embodiments 1-2, wherein the compound comprises a modified oligonucleotide having sugar motif: B-D-A-D-A-(D)$_9$-B-B-A, wherein each A is an independently selected 2'-substituted nucleoside, each B is an independently selected bicyclic nucleoside, and each D is a 2'-deoxynucleoside

Embodiment 176

The compound of any of embodiments 1-2, wherein the compound comprises a modified oligonucleotide having sugar motif: B-D-A-D-A-(D)$_{10}$-B-B-A, wherein each A is an independently selected 2'-substituted nucleoside, each B is an independently selected bicyclic nucleoside, and each D is a 2'-deoxynucleoside

Embodiment 177

The compound of any of embodiments 1-2, wherein the compound comprises a modified oligonucleotide having sugar motif: A-A-A-A-B-(D)$_8$-B-B-A, wherein each A is an independently selected 2'-substituted nucleoside, each B is an independently selected bicyclic nucleoside, and each D is a 2'-deoxynucleoside

Embodiment 178

The compound of any of embodiments 1-2, wherein the compound comprises a modified oligonucleotide having sugar motif: A-A-A-A-B-(D)$_9$-B-B-A, wherein each A is an independently selected 2'-substituted nucleoside, each B is an independently selected bicyclic nucleoside, and each D is a 2'-deoxynucleoside

Embodiment 179

The compound of any of embodiments 1-2, wherein the compound comprises a modified oligonucleotide having sugar motif: A-A-A-A-B-(D)$_{10}$-B-B-A, wherein each A is an independently selected 2'-substituted nucleoside, each B is an independently selected bicyclic nucleoside, and each D is a 2'-deoxynucleoside

Embodiment 180

The compound of any of embodiments 1-2, wherein the compound comprises a modified oligonucleotide having sugar motif: A-A-B-A-A-(D)$_8$-B-B-A, wherein each A is an independently selected 2'-substituted nucleoside, each B is an independently selected bicyclic nucleoside, and each D is a 2'-deoxynucleoside

Embodiment 181

The compound of any of embodiments 1-2, wherein the compound comprises a modified oligonucleotide having sugar motif: A-A-B-A-A-(D)$_9$-B-B-A, wherein each A is an independently selected 2'-substituted nucleoside, each B is an independently selected bicyclic nucleoside, and each D is a 2'-deoxynucleoside

Embodiment 182

The compound of any of embodiments 1-2, wherein the compound comprises a modified oligonucleotide having sugar motif: A-A-B-A-A-(D)$_{10}$-B-B-A, wherein each A is an independently selected 2'-substituted nucleoside, each B is an independently selected bicyclic nucleoside, and each D is a 2'-deoxynucleoside

Embodiment 183

The compound of any of embodiments 1-2, wherein the compound comprises a modified oligonucleotide having sugar motif: B-A-A-A-A-(D)$_8$-B-B-A, wherein each A is an independently selected 2'-substituted nucleoside, each B is an independently selected bicyclic nucleoside, and each D is a 2'-deoxynucleoside

Embodiment 184

The compound of any of embodiments 1-2, wherein the compound comprises a modified oligonucleotide having sugar motif: B-A-A-A-A-(D)$_9$-B-B-A, wherein each A is an independently selected 2'-substituted nucleoside, each B is an independently selected bicyclic nucleoside, and each D is a 2'-deoxynucleoside

Embodiment 185

The compound of any of embodiments 1-2, wherein the compound comprises a modified oligonucleotide having sugar motif: B-A-A-A-A-(D)$_{10}$-B-B-A, wherein each A is an independently selected 2'-substituted nucleoside, each B is an independently selected bicyclic nucleoside, and each D is a 2'-deoxynucleoside

Embodiment 186

The compound of any of embodiments 89-185, wherein at least one bicyclic nucleoside is a constrained ethyl nucleoside.

Embodiment 187

The compound of any of embodiments 89-185, wherein each bicyclic nucleoside is a constrained ethyl nucleoside.

Embodiment 188

The compound of any of embodiments, 89-185, wherein at least one bicyclic nucleoside is selected from among: BNA, LNA, α-L-LNA, ENA and 2'-thio LNA.

Embodiment 189

The compound of any of embodiments, 89-185, wherein at least one bicyclic nucleoside is an LNA nucleoside.

Embodiment 190

The compound of any of embodiments 89-185, wherein each bicyclic nucleoside is an LNA nucleoside.

Embodiment 191

The compound of any of embodiments 89-185, wherein the 2'-substituent of the at least one 2'-substituted nucleoside is selected from among: OCH$_3$, F, OCH$_2$F, OCHF$_2$, OCF$_3$, OCH$_2$CH$_3$, O(CH$_2$)$_2$F, OCH$_2$CHF$_2$, OCH$_2$CF$_3$, OCH$_2$—CH═CH$_2$, O(CH$_2$)$_2$—OCH$_3$, O(CH$_2$)$_2$—SCH$_3$, O(CH$_2$)$_2$—OCF$_3$, O(CH$_2$)$_3$—N(R$_4$)(R$_5$), O(CH$_2$)$_2$—ON $(R_4)(R_5)$, $O(CH_2)_2$—$O(CH_2)_2$—$N(R_4)(R_5)$, $OCH_2C(=O)$—$N(R_4)(R_5)$, $OCH_2C(=O)$—$N(R_6)$—$(CH_2)_2$—$N(R_4)(R_5)$ and $O(CH_2)_2$—$N(R_6)$—$C(=NR_7)[N(R_4)(R_5)]$ wherein $R_4$, $R_5$, $R_6$ and $R_7$ are each, independently, H or $C_1$-$C_6$ alkyl.

Embodiment 192

The compound of embodiment 191, wherein the 2'-substituent of the at least one 2'-substituted nucleoside of is selected from among: $OCH_3$, F, and $O(CH_2)_2$—$OCH_3$.

Embodiment 193

The compound of embodiment 192, wherein the 2'-substituent of the at least one 2'-substituted nucleoside is $O(CH_2)_2$—$OCH_3$.

Embodiment 194

The compound of any of embodiments 89-185, wherein the 2'-substituent of each 2'-substituted nucleoside is selected from among: $OCH_3$, F, $OCH_2F$, $OCHF_2$, $OCF_3$, $OCH_2CH_3$, $O(CH_2)_2F$, $OCH_2CHF_2$, $OCH_2CF_3$, $OCH_2$—$CH=CH_2$, $O(CH_2)_2$—$OCH_3$, $O(CH_2)_2$—$SCH_3$, $O(CH_2)_2$—$OCF_3$, $O(CH_2)_3$—$N(R_4)(R_5)$, $O(CH_2)_2$—$ON(R_4)(R_5)$, $O(CH_2)_2$—$O(CH_2)_2$—$N(R_4)(R_5)$, $OCH_2C(=O)$—$N(R_4)(R_5)$, $OCH_2C(=O)$—$N(R_6)$—$(CH_2)_2$—$N(R_4)(R_5)$ and $O(CH_2)_2$—$N(R_6)$—$C(=NR_7)[N(R_4)(R_5)]$ wherein $R_4$, $R_5$, $R_6$ and $R_7$ are each, independently, H or $C_1$-$C_6$ alkyl.

Embodiment 195

The compound of embodiment 194, wherein the 2'-substituent of each 2'-substituted nucleoside of is selected from among: $OCH_3$, F, and $O(CH_2)_2$—$OCH_3$

Embodiment 196

The compound of embodiment 195, wherein the 2'-substituent of each 2'-substituted nucleoside is $O(CH_2)_2$—$OCH_3$.

Embodiment 197

The compound of any of embodiments 1-196, wherein the oligonucleotide comprises at least one modified internucleoside linkage.

Embodiment 198

The compound of embodiment 197, wherein each internucleoside linkage is a modified internucleoside linkage.

Embodiment 199

The compound of embodiment 197 or 198, wherein the modified internucleoside linkage is a phosphorothioate linkage.

Embodiment 200

The compound of embodiment 197 or 198, wherein the modified internucleoside linkage is a methylphosphonate.

Embodiment 201

The compound of any of embodiments 1-200 comprising a conjugate.

Embodiment 202

The compound of any of embodiments 1-201 comprising at least one 5-methyl cytosine nucleobase.

Embodiment 203

The compound of any of embodiments 1-202 comprising at least one modified nucleobase.

Embodiment 204

The compound of any of embodiments 1-203, wherein the compound is an antisense compound.

Embodiment 205

The compound of embodiment 204, wherein the compound is capable of inhibiting expression of the target nucleic acid in a cell.

Embodiment 206

The compound of embodiment 205, wherein the compound is capable of inhibiting expression of the target nucleic acid in a cell by at least 50%.

Embodiment 207

The compound of embodiment 205, wherein the compound is capable of inhibiting expression of the target nucleic acid in a cell by at least 80%.

Embodiment 208

The compound of any of embodiments 205-207, wherein the cell is in an animal.

Embodiment 209

The compound of embodiment 208, wherein the animal is a human.

Embodiment 210

The compound of any of embodiments 1 to 209, wherein bicyclic nucleoside is selected from among: BNA, LNA, α-L-LNA, ENA and 2'-thio LNA.

Embodiment 211

A compound of any of embodiments 1-210, comprising not more than 6 bicyclic nucleosides.

Embodiment 212

A compound of any of embodiments 1-210, comprising not more than 5 bicyclic nucleosides.

Embodiment 213

A compound of any of embodiments 1-210, comprising not more than 4 bicyclic nucleosides.

Embodiment 214

A compound of any of embodiments 1-210, comprising not more than 3 bicyclic nucleosides.

Embodiment 215

A compound of any of embodiments 1-210, comprising not more than 2 bicyclic nucleosides.

Embodiment 216

A compound of any of embodiments 1-210, comprising not more than 1 bicyclic nucleoside.

Embodiment 217

The compound of any of embodiments 211-216, wherein the bicyclic nucleoside comprises cEt.

Embodiment 218

The compound of any of embodiments 211-216, wherein the bicyclic nucleoside comprises LNA.

Embodiment 219

A pharmaceutical composition comprising the compound according to any of embodiments 1-218 and a pharmaceutically acceptable diluent.

Embodiment 220

A method of modulating expression of a target nucleic acid in a cell comprising contacting the cell with a compound according to any of embodiments 1-218.

Embodiment 221

A method of modulating expression of a target nucleic acid in an animal comprising administering to the animal the pharmaceutical composition according to embodiment 220.

Embodiment 222

A method of manufacturing a compound according to any of embodiments 1-219 comprising forming chemical bonds.

Embodiment 223

The method of embodiment 222, wherein said chemical bonds are internucleoside linkages.

Embodiment 224

The method embodiment 222 or 223, wherein the method is performed under conditions suitable for the preparation of products for administration to humans.

Embodiment 225

A method of manufacturing the pharmaceutical composition according to embodiment 224 comprising combining the compound according to any of embodiments 1-219 and the pharmaceutically acceptable diluent.

Embodiment 226

The method embodiment 225, wherein the method is performed under conditions suitable for the preparation of products for administration to humans.

Embodiment 227

A compound comprising a modified oligonucleotide having a sugar motif selected from among sugar motifs 279-615 as shown in Table 4.

Embodiment 228

A compound comprising:
a modified oligonucleotide consisting of 10 to 20 linked nucleosides, wherein the modified oligonucleotide comprises:
a 5'-wing consisting of 2 to 5 linked nucleosides;
a 3'-wing consisting of 2 to 5 linked nucleosides; and
a gap between the 5'-wing and the 3'-wing consisting of 6 to 14 linked 2'-deoxynucleosides; and
wherein the 5'-wing has a sugar modification motif selected from among the motifs in Table 1.

Embodiment 229

A compound comprising:
a modified oligonucleotide consisting of 10 to 20 linked nucleosides, wherein the modified oligonucleotide comprises:
a 5'-wing consisting of 2 to 5 linked nucleosides;
a 3'-wing consisting of 2 to 5 linked nucleosides; and
a gap between the 5'-wing and the 3'-wing consisting of 6 to 14 linked 2'-deoxynucleosides; and
wherein the 3'-wing has a sugar modification motif selected from among the motifs in Table 2.

Embodiment 230

A compound comprising:
a modified oligonucleotide consisting of 10 to 20 linked nucleosides, wherein the modified oligonucleotide comprises:
a 5'-wing consisting of 2 to 5 linked nucleosides;
a 3'-wing consisting of 2 to 5 linked nucleosides; and
a gap between the 5'-wing and the 3'-wing consisting of 6 to 14 linked 2'-deoxynucleosides; and
wherein the 5'-wing has a sugar modification motif selected from among the motifs in Table 1 and the 3'-wing has a sugar modification motif selected from among the motifs in Table 2.

Embodiment 231

A compound of any of embodiments 1-16, wherein the modified oligonucleotide has a sugar motif described by Formula II as follows:

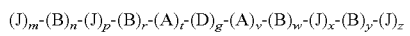

$$(J)_m\text{-}(B)_n\text{-}(J)_p\text{-}(B)_r\text{-}(A)_t\text{-}(D)_g\text{-}(A)_v\text{-}(B)_w\text{-}(J)_x\text{-}(B)_y\text{-}(J)_z$$

wherein:
each A is independently a 2'-substituted nucleoside;
each B is independently a bicyclic nucleoside;
each J is independently either a 2'-substituted nucleoside or a 2'-deoxynucleoside;

each D is a 2'-deoxynucleoside;
m is 0-4; n is 0-2; p is 0-2; r is 0-2; t is 0-2; v is 0-2; w is 0-4; x is 0-2; y is 0-2; z is 0-4; g is 6-14;
provided that:
at least one of m, n, and r is other than 0;
at least one of w and y is other than 0;
the sum of m, n, p, r, and t is from 1 to 5; and
the sum of v, w, x, y, and z is from 1 to 5.

Embodiment 232

A compound comprising:
a modified oligonucleotide consisting of 10 to 20 linked nucleosides, wherein the modified oligonucleotide has a sugar motif described by Formula II as follows:

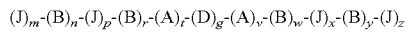

wherein:
each A is independently a 2'-substituted nucleoside;
each B is independently a bicyclic nucleoside;
each J is independently either a 2'-substituted nucleoside or a 2'-deoxynucleoside;
each D is a 2'-deoxynucleoside;
m is 0-4; n is 0-2; p is 0-2; r is 0-2; t is 0-2; v is 0-2; w is 0-4; x is 0-2; y is 0-2; z is 0-4; g is 6-14;
provided that:
at least one of m, n, and r is other than 0;
at least one of w and y is other than 0;
the sum of m, n, p, r, and t is from 1 to 5; and
the sum of v, w, x, y, and z is from 1 to 5.

Embodiment 233

The compound of embodiment 231 or 232, wherein at least one bicyclic nucleoside is a constrained ethyl nucleoside.

Embodiment 234

The compound of embodiment 233, wherein each bicyclic nucleoside is a constrained ethyl nucleoside.

Embodiment 235

The compound of any of embodiments 231-232, wherein at least one bicyclic nucleoside is an LNA nucleoside.

Embodiment 236

The compound of embodiments 228-232, wherein each bicyclic nucleoside is an LNA nucleoside.

Embodiment 237

A method of treating a disease or condition.

Embodiment 238

Use of a compound of any of embodiments 1 to 237 for the preparation of a medicament for the treatment of a disease or condition.

In certain embodiments, including but not limited to any of the above numbered embodiments, compounds including oligonucleotides described herein are capable of modulating expression of a target mRNA. In certain embodiments, the target mRNA is associated with a disease or disorder, or encodes a protein that is associated with a disease or disorder. In certain embodiments, the compounds or oligonucleotides provided herein modulate the expression of function of such mRNA to alleviate one or more symptom of the disease or disorder.

In certain embodiments, compounds including oligonucleotides describe herein are useful in vitro. In certain embodiments such compounds are used in diagnostics and/or for target validation experiments.

DETAILED DESCRIPTION OF THE INVENTION

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. In reference to an oligonucleotide, chemical modification does not include differences only in nucleobase sequence. Chemical modifications of oligonucleotides include nucleoside modifications (including sugar moiety modifications and nucleobase modifications) and internucleoside linkage modifications.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein the term "sugar surrogate" means a structure that does not comprise a furanosyl and that is capable of replacing the naturally occurring sugar moiety of a nucleoside, such that the resulting nucleoside is capable of (1) incorporation into an oligonucleotide and (2) hybridization to a complementary nucleoside. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein, "heterocyclic base" or "heterocyclic nucleobase" means a nucleobase comprising a heterocyclic structure.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2' bridge.

As used herein, "locked nucleic acid nucleoside" or "LNA" means a nucleoside comprising a bicyclic sugar moiety comprising a 4'-CH$_2$—O-2' bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero.

Thus, if a test for detection or measuring results in a finding of no activity (activity of zero), the step of detecting or measuring the activity has nevertheless been performed.

As used herein, "detectable and/or measurable activity" means a measurable activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "single nucleotide polymorphism" or "SNP" means a single nucleotide variation between the genomes of individuals of the same species. In some cases, a SNP may be a single nucleotide deletion or insertion.

As used herein, "mRNA" means an RNA molecule that encodes a protein.

As used herein, "pre-mRNA" means an RNA transcript that has not been fully processed into mRNA. Pre-RNA includes one or more intron.

As used herein, "object RNA" means an RNA molecule other than a target RNA, the amount, activity, splicing, and/or function of which is modulated, either directly or indirectly, by a target nucleic acid. In certain embodiments, a target nucleic acid modulates splicing of an object RNA. In certain such embodiments, an antisense compound modulates the amount or activity of the target nucleic acid, resulting in a change in the splicing of an object RNA and ultimately resulting in a change in the activity or function of the object RNA.

As used herein, "microRNA" means a naturally occurring, small, non-coding RNA that represses gene expression of at least one mRNA. In certain embodiments, a microRNA represses gene expression by binding to a target site within a 3' untranslated region of an mRNA. In certain embodiments, a microRNA has a nucleobase sequence as set forth in miRBase, a database of published microRNA sequences found at http://microrna.sanger.ac.uk/sequences/. In certain embodiments, a microRNA has a nucleobase sequence as set forth in miRBase version 12.0 released September 2008, which is herein incorporated by reference in its entirety.

As used herein, "microRNA mimic" means an oligomeric compound having a sequence that is at least partially identical to that of a microRNA. In certain embodiments, a microRNA mimic comprises the microRNA seed region of a microRNA. In certain embodiments, a microRNA mimic modulates translation of more than one target nucleic acids. In certain embodiments, a microRNA mimic is double-stranded.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "separate regions" means portions of an oligonucleotide wherein the chemical modifications or the motif of chemical modifications of any neighboring portions include at least one difference to allow the separate regions to be distinguished from one another.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)R$_{aa}$), carboxyl (—C(O)O—R$_{aa}$), aliphatic groups, alicyclic groups, alkoxy, substituted oxy (—O—R$_{aa}$), aryl, aralkyl, heterocyclic radical, heteroaryl, heteroarylalkyl, amino (—N(R$_{bb}$)(R$_{cc}$)), imino(=NR$_{bb}$), amido (—C(O)N(R$_{bb}$)(R$_{cc}$) or —N(R$_{bb}$)C(O)R$_{aa}$), azido (—N$_3$), nitro (—NO$_2$), cyano (—CN), carbamido (—OC(O)N(R$_{bb}$)(R$_{cc}$) or —N(R$_{bb}$)C(O)OR$_{aa}$), ureido (—N(R$_{bb}$)C(O)N(R$_{bb}$)(R$_{cc}$)), thioureido (—N(R$_{bb}$)C(S)N(R$_{bb}$)—(R$_{cc}$)), guanidinyl (—N(R$_{bb}$)C(=NR$_{bb}$)N(R$_{bb}$)(R$_{cc}$)), amidinyl (—C(=NR$_{bb}$)N(R$_{bb}$)(R$_{cc}$) or —N(R$_{bb}$)C(=NR$_{bb}$)(R$_{aa}$), thiol (—SR$_{bb}$), sulfinyl (—S(O)R$_{bb}$), sulfonyl (—S(O)$_2$R$_{bb}$) and sulfonamidyl (—S(O)$_2$N(R$_{bb}$)(R$_{cc}$) or —N(R$_{bb}$)S—(O)$_2$R$_{bb}$). Wherein each R$_{aa}$, R$_{bb}$ and R$_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications one or more nucleoside (including modifications to the sugar moiety and/or the nucleobase) and/or modifications to one or more internucleoside linkage.

Certain Sugar Moieties

In certain embodiments, oligomeric compounds of the invention comprise one or more modified nucleosides comprising a modified sugar moiety. Such oligomeric compounds comprising one or more sugar-modified nucleosides may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substitued sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, T-OCH$_3$ ("OMe" or "O-methyl"), and 2'-O (CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O—(CH$_2$)$_2$—O—N(CH$_3$)$_2$, —O(CH$_2$)$_2$O(CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-(CH$_2$)$_2$-2',4'-(CH$_2$)—O-2' (LNA); 4'-(CH$_2$)—S-2; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$-β-N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., *J. Org. Chem.*, 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

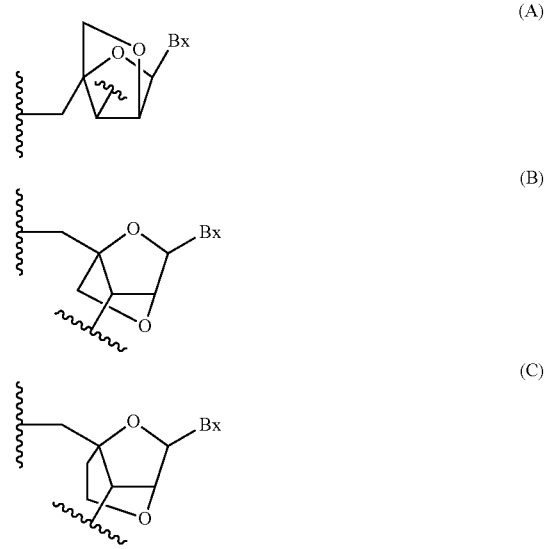

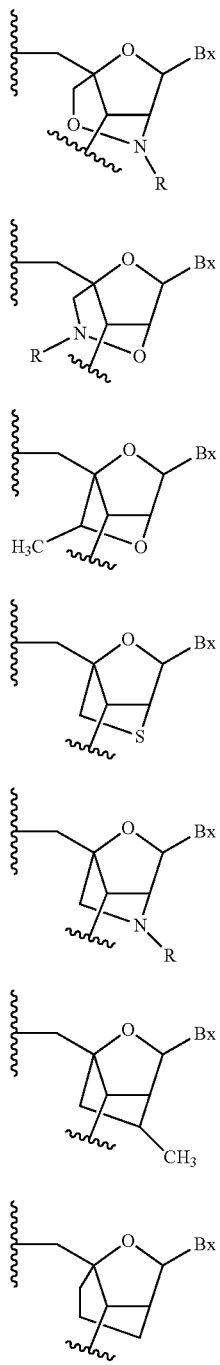

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129 (26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

VII

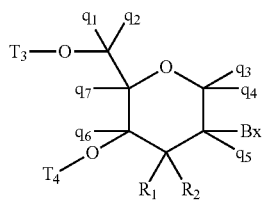

wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

Certain Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine(1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134, 066; 5,175,273; 5,367,066; 5,432,272; 5,457,187; 5,459, 255; 5,484,908; 5,502,177; 5,525,711; 5,552,540; 5,587, 469; 5,594,121; 5,596,091; 5,614,617; 5,645,985; 5,681, 941; 5,750,692; 5,763,588; 5,830,653 and 6,005,096, certain of which are commonly owned with the instant application, and each of which is herein incorporated by reference in its entirety.

Certain Internucleoside Linkages

In certain embodiments, the present invention provides oligomeric compounds comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—$CH_2$—N($CH_3$)—O—$CH_2$—), thiodiester (—O—C(O)—S—), thionocarbamate (—O—C(O)(NH)—S—); siloxane (—O—Si(H)$_2$—O—); and N,N'-dimethylhydrazine (—$CH_2$—N($CH_3$)—N($CH_3$)—). Modified linkages, compared to natural phosphodiester linkages, can be used to alter, typically increase, nuclease resistance of the oligomeric compound. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

Certain Motifs

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified sugars. In certain embodiments, chemically modified oligonucleotides comprise one or more modified nucleobases. In certain embodiments, chemically modified oligonucleotides comprise one or more modified internucleoside linkages. In certain embodiments, the chemically modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar modification motifs of the two wings are the same as one another (symmetric gapmer). In certain embodiments, the sugar modification motifs of the 5'-wing differs from the sugar modification motif of the 3'-wing (asymmetric gapmer).

Certain 5'-Wings

In certain embodiments, the 5'-wing of a gapmer consists of 1 to 5 linked nucleosides. In certain embodiments, the 5'-wing of a gapmer consists of 2 to 5 linked nucleosides. In certain embodiments, the 5'-wing of a gapmer consists of 3 to 5 linked nucleosides. In certain embodiments, the 5'-wing of a gapmer consists of 4 or 5 linked nucleosides. In certain embodiments, the 5'-wing of a gapmer consists of 1 to 4 linked nucleosides. In certain embodiments, the 5'-wing of a gapmer consists of 1 to 3 linked nucleosides. In certain embodiments, the 5'-wing of a gapmer consists of 1 or 2 linked nucleosides. In certain embodiments, the 5'-wing of a gapmer consists of 2 to 4 linked nucleosides. In certain embodiments, the 5'-wing of a gapmer consists of 2 or 3 linked nucleosides. In certain embodiments, the 5'-wing of a gapmer consists of 3 or 4 linked nucleosides. In certain embodiments, the 5'-wing of a gapmer consists of 1 nucleoside. In certain embodiments, the 5'-wing of a gapmer consists of 2 linked nucleosides. In certain embodiments, the 5'-wing of a gapmer consists of 3 linked nucleosides. In certain embodiments, the 5'-wing of a gapmer consists of 4 linked nucleosides. In certain embodiments, the 5'-wing of a gapmer consists of 5 linked nucleosides.

In certain embodiments, the 5'-wing of a gapmer comprises at least one bicyclic nucleoside. In certain embodiments, the 5'-wing of a gapmer comprises at least two bicyclic nucleosides. In certain embodiments, the 5'-wing of a gapmer comprises at least three bicyclic nucleosides. In certain embodiments, the 5'-wing of a gapmer comprises at least four bicyclic nucleosides. In certain embodiments, the 5'-wing of a gapmer comprises at least one constrained ethyl nucleoside. In certain embodiments, the 5'-wing of a gapmer comprises at least one LNA nucleoside. In certain embodiments, each nucleoside of the 5'-wing of a gapmer is a bicyclic nucleoside. In certain embodiments, each nucleoside of the 5'-wing of a gapmer is a constrained ethyl nucleoside. In certain embodiments, each nucleoside of the 5'-wing of a gapmer is a LNA nucleoside.

In certain embodiments, the 5'-wing of a gapmer comprises at least one non-bicyclic modified nucleoside. In certain embodiments, the 5'-wing of a gapmer comprises at least one 2'-substituted nucleoside. In certain embodiments, the 5'-wing of a gapmer comprises at least one 2'-MOE nucleoside. In certain embodiments, the 5'-wing of a gapmer comprises at least one 2'-OMe nucleoside. In certain embodiments, each nucleoside of the 5'-wing of a gapmer is a non-bicyclic modified nucleoside. In certain embodiments, each nucleoside of the 5'-wing of a gapmer is a 2'-substituted nucleoside. In certain embodiments, each nucleoside of the 5'-wing of a gapmer is a 2'-MOE nucleoside. In certain embodiments, each nucleoside of the 5'-wing of a gapmer is a 2'-OMe nucleoside.

In certain embodiments, the 5'-wing of a gapmer comprises at least one 2'-deoxynucleoside. In certain embodiments, each nucleoside of the 5'-wing of a gapmer is a 2'-deoxynucleoside. In a certain embodiments, the 5'-wing of a gapmer comprises at least one ribonucleoside. In certain embodiments, each nucleoside of the 5'-wing of a gapmer is a ribonucleoside.

In certain embodiments, the 5'-wing of a gapmer comprises at least one bicyclic nucleoside and at least one non-bicyclic modified nucleoside. In certain embodiments, the 5'-wing of a gapmer comprises at least one bicyclic nucleoside and at least one 2'-substituted nucleoside. In certain embodiments, the 5'-wing of a gapmer comprises at least one bicyclic nucleoside and at least one 2'-MOE nucleoside. In certain embodiments, the 5'-wing of a gapmer comprises at least one bicyclic nucleoside and at least one 2'-OMe nucleoside. In certain embodiments, the 5'-wing of a gapmer comprises at least one bicyclic nucleoside and at least one 2'-deoxynucleoside.

In certain embodiments, the 5'-wing of a gapmer comprises at least one constrained ethyl nucleoside and at least one non-bicyclic modified nucleoside. In certain embodiments, the 5'-wing of a gapmer comprises at least one constrained ethyl nucleoside and at least one 2'-substituted nucleoside. In certain embodiments, the 5'-wing of a gapmer comprises at least one constrained ethyl nucleoside and at least one 2'-MOE nucleoside. In certain embodiments, the 5'-wing of a gapmer comprises at least one constrained ethyl nucleoside and at least one 2'-OMe nucleoside. In certain embodiments, the 5'-wing of a gapmer comprises at least one constrained ethyl nucleoside and at least one 2'-deoxynucleoside.

In certain embodiments, the 5'-wing of a gapmer comprises at least one LNA nucleoside and at least one non-bicyclic modified nucleoside. In certain embodiments, the 5'-wing of a gapmer comprises at least one LNA nucleoside and at least one 2'-substituted nucleoside. In certain embodiments, the 5'-wing of a gapmer comprises at least one LNA nucleoside and at least one 2'-MOE nucleoside. In certain embodiments, the 5'-wing of a gapmer comprises at least one LNA nucleoside and at least one 2'-OMe nucleoside. In certain embodiments, the 5'-wing of a gapmer comprises at least one LNA nucleoside and at least one 2'-deoxynucleoside.

In certain embodiments, the 5'-wing of a gapmer comprises at least one bicyclic nucleoside, at least one non-bicyclic modified nucleoside, and at least one 2'-deoxynucleoside. In certain embodiments, the 5'-wing of a gapmer comprises at least one constrained ethyl nucleoside, at least one non-bicyclic modified nucleoside, and at least one 2'-deoxynucleoside. In certain embodiments, the 5'-wing of a gapmer comprises at least one LNA nucleoside, at least one non-bicyclic modified nucleoside, and at least one 2'-deoxynucleoside.

In certain embodiments, the 5'-wing of a gapmer comprises at least one bicyclic nucleoside, at least one 2'-substituted nucleoside, and at least one 2'-deoxynucleoside. In certain embodiments, the 5'-wing of a gapmer comprises at least one constrained ethyl nucleoside, at least one 2'-substituted nucleoside, and at least one 2'-deoxynucleoside. In certain embodiments, the 5'-wing of a gapmer comprises at least one LNA nucleoside, at least one 2'-substituted nucleoside, and at least one 2'-deoxynucleoside.

In certain embodiments, the 5'-wing of a gapmer comprises at least one bicyclic nucleoside, at least one 2'-MOE nucleoside, and at least one 2'-deoxynucleoside. In certain embodiments, the 5'-wing of a gapmer comprises at least one constrained ethyl nucleoside, at least one 2'-MOE nucleoside, and at least one 2'-deoxynucleoside. In certain embodiments, the 5'-wing of a gapmer comprises at least one LNA nucleoside, at least one 2'-MOE nucleoside, and at least one 2'-deoxynucleoside.

In certain embodiments, the 5'-wing of a gapmer comprises at least one bicyclic nucleoside, at least one 2'-OMe nucleoside, and at least one 2'-deoxynucleoside. In certain embodiments, the 5'-wing of a gapmer comprises at least one constrained ethyl nucleoside, at least one 2'-OMe nucleoside, and at least one 2'-deoxynucleoside. In certain embodiments, the 5'-wing of a gapmer comprises at least one LNA nucleoside, at least one 2'-OMe nucleoside, and at least one 2'-deoxynucleoside.

In certain embodiments, the 5'-wing of a gapmer has a sugar motif selected from among those listed in the following non-limiting table:

TABLE 1

Certain 5'-Wing Sugar Motifs

| 5'-wing sugar motif # | motif | 5'-wing sugar motif # | motif | 5'-wing sugar motif # | motif |
| --- | --- | --- | --- | --- | --- |
| 1a | A-B-B | 1d | A-L-L | 1g | A-K-K |
| 2a | A-A-B | 2d | A-A-L | 2g | A-A-K |
| 3a | A-D-B | 3d | A-D-L | 3g | A-D-K |
| 4a | B-D-A | 4d | L-D-A | 4g | K-D-A |
| 5a | B-A-A | 5d | L-A-A | 5g | K-A-A |
| 6a | B-B-B | 6d | L-L-L | 6g | K-K-K |
| 7a | A-A-A | 7d | A-A-A | 7g | A-A-A |
| 8a | A-D-D-B | 8d | A-D-D-L | 8g | A-D-D-K |
| 9a | B-D-D-A | 9d | L-D-D-A | 9g | K-D-D-A |
| 10a | A-A-A-B | 10d | A-A-A-L | 10g | A-A-A-K |
| 11a | B-A-A-A | 11d | L-A-A-A | 11g | K-A-A-A |
| 12a | A-A-A-A | 12d | A-A-A-A | 12g | A-A-A-A |
| 13a | B-D-D-B | 13d | L-D-D-L | 13g | K-D-D-K |
| 14a | A-A-A-A | 14d | A-A-A-A | 14g | A-A-A-A |
| 15a | B-B-B-B | 15d | L-L-L-L | 15g | K-K-K-K |
| 16a | A-A-A-A-A | 16d | A-A-A-A-A | 16g | A-A-A-A-A |
| 17a | A-D-A-D-B | 17d | A-D-A-D-L | 17g | A-D-A-D-K |
| 18a | A-D-B-D-A | 18d | A-D-L-D-A | 18g | A-D-K-D-A |
| 19a | B-D-A-D-A | 19d | L-D-A-D-A | 19g | K-D-A-D-A |
| 20a | A-A-A-A-B | 20d | A-A-A-A-L | 20g | A-A-A-A-K |
| 21a | A-A-B-A-A | 21d | A-A-L-A-A | 21g | A-A-K-A-A |
| 22a | B-A-A-A-A | 22d | L-A-A-A-A | 22g | K-A-A-A-A |
| 1b | E-B-B | 1e | E-L-L | 1h | E-K-K |
| 2b | E-E-B | 2e | E-E-L | 2h | E-E-K |
| 3b | E-D-B | 3e | E-D-L | 3h | E-D-K |
| 4b | B-D-E | 4e | L-D-E | 4h | K-D-E |
| 5b | B-E-E | 5e | L-E-E | 5h | K-E-E |
| 6b | B-B-B | 6e | L-L-L | 6h | K-K-K |
| 7b | E-E-E | 7e | E-E-E | 7h | E-E-E |
| 8b | E-D-D-B | 8e | E-D-D-L | 8h | E-D-D-K |
| 9b | B-D-D-E | 9e | L-D-D-E | 9h | K-D-D-E |
| 10b | E-E-E-B | 10e | E-E-E-L | 10h | E-E-E-K |

TABLE 1-continued

Certain 5'-Wing Sugar Motifs

| 5'-wing sugar motif # | motif | 5'-wing sugar motif # | motif | 5'-wing sugar motif # | motif |
|---|---|---|---|---|---|
| 11b | B-E-E-E | 11e | L-E-E-E | 11h | K-E-E-E |
| 12b | E-E-E-E | 12e | E-E-E-E | 12h | E-E-E-E |
| 13b | B-D-D-B | 13e | L-D-D-L | 13h | K-D-D-K |
| 14b | E-E-E-E | 14e | E-E-E-E | 14h | E-E-E-E |
| 15b | B-B-B-B | 15e | L-L-L-L | 15h | K-K-K-K |
| 16b | E-E-E-E-E | 16e | E-E-E-E-E | 16h | E-E-E-E-E |
| 17b | E-D-E-D-B | 17e | E-D-E-D-L | 17h | E-D-E-D-K |
| 18b | E-D-B-D-E | 18e | E-D-L-D-E | 18h | E-D-K-D-E |
| 19b | B-D-E-D-E | 19e | L-D-E-D-E | 19h | K-D-E-D-E |
| 20b | E-E-E-E-B | 20e | E-E-E-E-L | 20h | E-E-E-E-K |
| 21b | E-E-B-E-E | 21e | E-E-L-E-E | 21h | E-E-K-E-E |
| 22b | B-E-E-E-E | 22e | L-E-E-E-E | 22h | K-E-E-E-E |
| 1c | M-B-B | 1f | M-L-L | 1i | M-K-K |
| 2c | M-M-B | 2f | M-M-L | 2i | M-M-K |
| 3c | M-D-B | 3f | M-D-L | 3i | M-D-K |
| 4c | B-D-M | 4f | L-D-M | 4i | K-D-M |
| 5c | B-M-M | 5f | L-M-M | 5i | K-M-M |
| 6c | B-B-B | 6f | L-L-L | 6i | K-K-K |
| 7c | M-M-M | 7f | M-M-M | 7i | M-M-M |
| 8c | M-D-D-B | 8f | M-D-D-L | 8i | M-D-D-K |
| 9c | B-D-D-M | 9f | L-D-D-M | 9i | K-D-D-M |
| 10c | M-M-M-B | 10f | M-M-M-L | 10i | M-M-M-K |
| 11c | B-M-M-M | 11f | L-M-M-M | 11i | K-M-M-M |
| 12c | M-M-M-M | 12f | M-M-M-M | 12i | M-M-M-M |
| 13c | B-D-D-B | 13f | L-D-D-L | 13i | K-D-D-K |
| 14c | M-M-M-M | 14f | M-M-M-M | 14i | M-M-M-M |
| 15c | B-B-B-B | 15f | L-L-L-L | 15i | K-K-K-K |
| 16c | M-M-M-M-M | 16f | M-M-M-M-M | 16i | M-M-M-M-M |
| 17c | M-D-M-D-B | 17f | M-D-M-D-L | 17i | M-D-M-D-K |
| 18c | M-D-B-D-M | 18f | M-D-L-D-M | 18i | M-D-K-D-M |
| 19c | B-D-M-D-M | 19f | L-D-M-D-M | 19i | K-D-M-D-M |
| 20c | M-M-M-M-B | 20f | M-M-M-M-L | 20i | M-M-M-M-K |
| 21c | M-M-B-M-M | 21f | M-M-L-M-M | 21i | M-M-K-M-M |
| 22c | B-M-M-M-M | 22f | L-M-M-M-M | 22i | K-M-M-M-M |
| 1j | A-L-K | 1k | A-K-L | 1l | E-L-K |
| 2j | M-E-K | 2k | M-E-L | 2l | E-M-K |
| 3j | L-D-K | 3k | K-D-L | 3l | B-D-K |
| 4j | K-D-A | 4k | L-D-K | 4l | K-B-L |
| 5j | B-M-E | 5k | L-M-E | 5l | K-M-E |
| 6j | K-L-L | 6k | L-K-L | 6l | L-K-K |
| 7j | E-M-E | 7k | M-E-M | 7l | M-E-E |
| 8j | E-D-D-M | 8k | K-D-D-L | 8l | L-D-D-K |
| 9j | M-D-D-E | 9k | L-D-K-E | 9l | K-D-L-E |
| 10j | E-M-E-B | 10k | E-M-E-L | 10l | E-M-E-K |
| 11j | B-E-E-M | 11k | L-E-E-M | 11l | K-E-E-M |
| 12j | E-E-E-M | 12k | M-E-E-E | 12l | E-M-E-E |
| 13j | K-L-D-K | 13k | L-K-D-L | 13l | K-D-L-K |
| 14j | E-M-E-M | 14k | M-EM-E | 14l | E-E-M-E |
| 15j | K-L-L-K | 15k | L-K-L-K | 15l | K-L-K-K |
| 16j | E-E-M-E-E | 16k | M-E-E-E-M | 16l | E-E-M-M-E |
| 17j | E-D-M-D-K | 17k | E-D-M-D-L | 17l | M-D-E-D-K |
| 18j | E-D-K-D-M | 18k | E-D-L-D-M | 18l | M-D-K-D-E |
| 19j | B-D-A-D-A | 19k | L-D-A-D-A | 19l | K-D-A-D-A |
| 20j | E-M-E-E-L | 20k | E-M-M-E-L | 20l | M-E-E-E-K |
| 21j | E-E-K-M-M | 21k | E-E-L-M-M | 21l | E-M-K-E-E |
| 22j | B-E-M-E-A | 22k | L-E-A-M-A | 22l | K-E-A-A-A |
| 1k | K-D-K-D-K | | | | |

In the above table, "A" represents a nucleoside comprising a 2'-substituted sugar moiety; "B" represents a bicyclic nucleoside; "D" represents a 2'-deoxynucleoside; "K" represents a constrained ethyl nucleoside; "L" represents an LNA nucleoside; "E" represents a 2'-MOE nucleoside; and "M" represents a 2'-OMe nucleoside.

In certain embodiments, an oligonucleotide comprises any 5'-wing motif provided herein. In certain such embodiments, the oligonucleotide is a 5'-hemimer (does not comprise a 3'-wing). In certain embodiments, such an oligonucleotide is a gapmer. In certain such embodiments, the 3'-wing of the gapmer may comprise any sugar modification motif.

In certain embodiments, the 5'-wing of a gapmer has a sugar motif selected from among those listed in the following non-limiting tables:

TABLE 2

Certain 5'-Wing Sugar Motifs
Certain 5'-Wing Sugar Motifs

| AAAAA | ABCBB | BABCC | BCBBA | CBACC |
| AAAAB | ABCBC | BACAA | BCBBB | CBBAA |
| AAAAC | ABCCA | BACAB | BCBBC | CBBAB |
| AAABA | ABCCB | BACAC | BCBCA | CBBAC |
| AAABB | ABCCC | BACBA | BCBCB | CBBBA |

TABLE 2-continued

Certain 5'-Wing Sugar Motifs
Certain 5'-Wing Sugar Motifs

| | | | | |
|---|---|---|---|---|
| AAABC | ACAAA | BACBB | BCBCC | CBBBB |
| AAACA | ACAAB | BACBC | BCCAA | CBBBC |
| AAACB | ACAAC | BACCA | BCCAB | CBBCA |
| AAACC | ACABA | BACCB | BCCAC | CBBCB |
| AABAA | ACABB | BACCC | BCCBA | CBBCC |
| AABAB | ACABC | BBAAA | BCCBB | CBCAA |
| AABAC | ACACA | BBAAB | BCCBC | CBCAB |
| AABBA | ACACB | BBAAC | BCCCA | CBCAC |
| AABBB | ACACC | BBABA | BCCCB | CBCBA |
| AABBC | ACBAA | BBABB | BCCCC | CBCBB |
| AABCA | ACBAB | BBABC | CAAAA | CBCBC |
| AABCB | ACBAC | BBACA | CAAAB | CBCCA |
| AABCC | ACBBA | BBACB | CAAAC | CBCCB |
| AACAA | ACBBB | BBACC | CAABA | CBCCC |
| AACAB | ACBBC | BBBAA | CAABB | CCAAA |
| AACAC | ACBCA | BBBAB | CAABC | CCAAB |
| AACBA | ACBCB | BBBAC | CAACA | CCAAC |
| AACBB | ACBCC | BBBBA | CAACB | CCABA |
| AACBC | ACCAA | BBBBB | CAACC | CCABB |
| AACCA | ACCAB | BBBBC | CABAA | CCABC |
| AACCB | ACCAC | BBBCA | CABAB | CCACA |
| AACCC | ACCBA | BBBCB | CABAC | CCACB |
| ABAAA | ACCBB | BBBCC | CABBA | CCACC |
| ABAAB | ACCBC | BBCAA | CABBB | CCBAA |
| ABAAC | ACCCA | BBCAB | CABBC | CCBAB |
| ABABA | ACCCB | BBCAC | CABCA | CCBAC |
| ABABB | ACCCC | BBCBA | CABCB | CCBBA |
| ABABC | BAAAA | BBCBB | CABCC | CCBBB |
| ABACA | BAAAB | BBCBC | CACAA | CCBBC |
| ABACB | BAAAC | BBCCA | CACAB | CCBCA |
| ABACC | BAABA | BBCCB | CACAC | CCBCB |
| ABBAA | BAABB | BBCCC | CACBA | CCBCC |
| ABBAB | BAABC | BCAAA | CACBB | CCCAA |
| ABBAC | BAACA | BCAAB | CACBC | CCCAB |
| ABBBA | BAACB | BCAAC | CACCA | CCCAC |
| ABBBB | BAACC | BCABA | CACCB | CCCBA |
| ABBBC | BABAA | BCABB | CACCC | CCCBB |
| ABBCA | BABAB | BCABC | CBAAA | CCCBC |
| ABBCB | BABAC | BCACA | CBAAB | CCCCA |
| ABBCC | BABBA | BCACB | CBAAC | CCCCB |
| ABCAA | BABBB | BCACC | CBABA | CCCCC |
| ABCAB | BABBC | BCBAA | CBABB | |
| ABCAC | BABCA | BCBAB | CBABC | |
| ABCBA | BABCB | BCBAC | CBACA | |

TABLE 3

Certain 5'-Wing Sugar Motifs
Certain 5'-Wing Sugar Motifs

| | | | | |
|---|---|---|---|---|
| AAAAA | BABC | CBAB | ABBB | BAA |
| AAAAB | BACA | CBAC | BAAA | BAB |
| AAABA | BACB | CBBA | BAAB | BBA |
| AAABB | BACC | CBBB | BABA | BBB |
| AABAA | BBAA | CBBC | BABB | AA |
| AABAB | BBAB | CBCA | BBAA | AB |
| AABBA | BBAC | CBCB | BBAB | AC |
| AABBB | BBBA | CBCC | BBBA | BA |
| ABAAA | BBBB | CCAA | BBBB | BB |
| ABAAB | BBBC | CCAB | AAA | BC |
| ABABA | BBCA | CCAC | AAB | CA |
| ABABB | BBCB | CCBA | AAC | CB |
| ABBAA | BBCC | CCBB | ABA | CC |
| ABBAB | BCAA | CCBC | ABB | AA |
| ABBBA | BCAB | CCCA | ABC | AB |
| ABBBB | BCAC | CCCB | ACA | BA |
| BAAAA | ABCB | BCBA | ACB | |
| BAAAB | ABCC | BCBB | ACC | |
| BAABA | ACAA | BCBC | BAA | |
| BAABB | ACAB | BCCA | BAB | |
| BABAA | ACAC | BCCB | BAC | |
| BABAB | ACBA | BCCC | BBA | |
| BABBA | ACBB | CAAA | BBB | |
| BABBB | ACBC | CAAB | BBC | |

TABLE 3-continued

Certain 5'-Wing Sugar Motifs
Certain 5'-Wing Sugar Motifs

| | | | |
|---|---|---|---|
| BBAAA | ACCA | CAAC | BCA |
| BBAAB | ACCB | CABA | BCB |
| BBABA | ACCC | CABB | BCC |
| BBABB | BAAA | CABC | CAA |
| BBBAA | BAAB | CACA | CAB |
| BBBAB | BAAC | CACB | CAC |
| BBBBA | BABA | CACC | CBA |
| BBBBB | BABB | CBAA | CBB |
| AAAA | AACC | CCCC | CBC |
| AAAB | ABAA | AAAA | CCA |
| AAAC | ABAB | AAAB | CCB |
| AABA | ABAC | AABA | CCC |
| AABB | ABBA | AABB | AAA |
| AABC | ABBB | ABAA | AAB |
| AACA | ABBC | ABAB | ABA |
| AACB | ABCA | ABBA | ABB |

In certain embodiments, each A, each B, and each C located at the 3'-most 5'-wing nucleoside is a modified nucleoside. For example, in certain embodiments the 5'-wing motif is selected from among AB<u>B</u>, BB<u>B</u>, and CB<u>B</u>, wherein the underlined nucleoside represents the 3'-most 5'-wing nucleoside and wherein the underlined nucleoside is a modified nucleoside.

In certain embodiments, each A comprises an unmodified 2'-deoxyfuranose sugar moiety. In certain embodiments, each A comprises a modified sugar moiety. In certain embodiments, each A comprises a 2'-substituted sugar moiety. In certain embodiments, each A comprises a 2'-substituted sugar moiety selected from among F, ara-F, $OCH_3$ and $O(CH_2)_2$—$OCH_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside. In certain embodiments, each A comprises an HNA. In certain embodiments, each A comprises an F-HNA.

In certain embodiments, each B comprises an unmodified 2'-deoxyfuranose sugar moiety. In certain embodiments, each B comprises a modified sugar moiety. In certain embodiments, each B comprises a 2'-substituted sugar moiety. In certain embodiments, each B comprises a 2'-substituted sugar moiety selected from among F, (ara)-F, $OCH_3$ and $O(CH_2)_2$—$OCH_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne urindine nucleoside. In certain embodiments, each B comprises an HNA. In certain embodiments, each B comprises an F-HNA.

In certain embodiments, each C comprises an unmodified 2'-deoxyfuranose sugar moiety. In certain embodiments, each C comprises a modified sugar moiety. In certain embodiments, each C comprises a 2'-substituted sugar moiety. In certain embodiments, each C comprises a 2'-substituted sugar moiety selected from among F, (ara)-F, $OCH_3$ and $O(CH_2)_2$—$OCH_3$. In certain embodiments, each C comprises a 5'-substituted sugar moiety. In certain embodiments, each C comprises a 5'-substituted sugar moiety selected from among 5'-Me, and 5'-(R)-Me. In certain embodiments, each C comprises a bicyclic sugar moiety. In certain embodiments, each C comprises a bicyclic sugar moiety selected from among cEt, cMOE, LNA, α-L-LNA, ENA and 2'-thio LNA. In certain embodiments, each C comprises a modified nucleobase. In certain embodiments, each C comprises a modified nucleobase selected from among 2-thio-thymidine and 5-propyne uridine. In certain embodiments, each C comprises a 2-thio-thymidine nucleoside. In certain embodiments, each C comprises an HNA. In certain embodiments, each C comprises an F-HNA.

In certain embodiments, at least one of A or B comprises an unmodified 2'-deoxyfuranose sugar moiety, and the other comprises a 2'-substituted sugar moiety. In certain embodiments, at least one of A or B comprises an unmodified 2'-deoxyfuranose sugar moiety, and the other comprises a bicyclic sugar moiety.

In certain embodiments, at least one of A or B comprises a bicyclic sugar moiety, and the other comprises a 2'-substituted sugar moiety. In certain embodiments, one of A or B is an LNA nucleoside and the other of A or B comprises a 2'-substituted sugar moiety. In certain embodiments, one of A or B is a cEt nucleoside and the other of A or B comprises a 2'-substituted sugar moiety. In certain embodiments, one of A or B is an α-L-LNA nucleoside and the other of A or B comprises a 2'-substituted sugar moiety. In certain embodiments, one of A or B is an LNA nucleoside and the other of A or B comprises a 2'-MOE sugar moiety. In certain embodiments, one of A or B is a cEt nucleoside and the other of A or B comprises a 2'-MOE sugar moiety. In certain embodiments, one of A or B is an α-L-LNA nucleoside and the other of A or B comprises a 2'-MOE sugar moiety. In certain embodiments, one of A or B is an LNA nucleoside and the other of A or B comprises a 2'-F sugar moiety. In certain embodiments, one of A or B is a cEt nucleoside and the other of A or B comprises a 2'-F sugar moiety. In certain embodiments, one of A or B is an α-L-LNA nucleoside and the other of A or B comprises a 2'-F sugar moiety. In certain embodiments, one of A or B is an LNA nucleoside and the other of A or B comprises a 2'-(ara)-F sugar moiety. In certain embodiments, one of A or B is a cEt nucleoside and the other of A or B comprises a 2'-(ara)-F sugar moiety. In certain embodiments, one of A or B is an α-L-LNA nucleoside and the other of A or B comprises a 2'-(ara)-F sugar moiety.

In certain embodiments, at least one of A or B comprises an unmodified 2'-deoxyfuranose sugar moiety, and the other comprises a 2'-substituted sugar moiety. In certain embodiments, one of A or B is an unmodified 2'-deoxyfuranose sugar moiety and the other of A or B comprises a 2'-substituted sugar moiety. In certain embodiments, one of A or B is an unmodified 2'-deoxyfuranose sugar moiety and the other of A or B comprises a 2'-MOE sugar moiety. In certain embodiments, one of A or B is an unmodified 2'-deoxyfuranose sugar moiety and the other of A or B comprises a 2'-F sugar moiety. In certain embodiments, one of A or B is an unmodified 2'-deoxyfuranose sugar moiety and the other of A or B comprises a 2'-(ara)-F sugar moiety. In certain embodiments, at least one of A or B comprises a bicyclic sugar moiety, and the other comprises an unmodified 2'-deoxyfuranose sugar moiety. In certain embodiments, one of A or B is an LNA nucleoside and the other of A or B comprises an unmodified 2'-deoxyfuranose sugar moiety. In certain embodiments, one of A or B is a cEt nucleoside and the other of A or B comprises an unmodified 2'-deoxyfuranose sugar moiety. In certain embodiments, one of A or B is an α-L-LNA nucleoside and the other of A or B comprises an unmodified 2'-deoxyfuranose sugar moiety. In certain embodiments, one of A or B is an LNA nucleoside and the other of A or B comprises an unmodified 2'-deoxyfuranose sugar moiety. In certain embodiments, one of A or B is a cEt nucleoside and the other of A or B comprises an unmodified 2'-deoxyfuranose sugar moiety. In certain embodiments, one of A or B is an α-L-LNA nucleoside and the other of A or B comprises an unmodified 2'-deoxyfuranose sugar moiety.

In certain embodiments, A comprises a bicyclic sugar moiety, and B comprises a 2'-substituted sugar moiety. In certain embodiments, A is an LNA nucleoside and B comprises a 2'-substituted sugar moiety. In certain embodiments, A is a cEt nucleoside and B comprises a 2'-substituted sugar moiety. In certain embodiments, A is an α-L-LNA nucleoside and B comprises a 2'-substituted sugar moiety.

In certain embodiments, A comprises a bicyclic sugar moiety, and B comprises a 2'-MOE sugar moiety. In certain embodiments, A is an LNA nucleoside and B comprises a 2'-MOE sugar moiety. In certain embodiments, A is a cEt nucleoside and B comprises a 2'-MOE sugar moiety. In certain embodiments, A is an α-L-LNA nucleoside and B comprises a 2'-MOE sugar moiety.

In certain embodiments, A comprises a bicyclic sugar moiety, and B comprises a 2'-F sugar moiety. In certain embodiments, A is an LNA nucleoside and B comprises a 2'-F sugar moiety. In certain embodiments, A is a cEt nucleoside and B comprises a 2'-F sugar moiety. In certain embodiments, A is an α-L-LNA nucleoside and B comprises a 2'-F sugar moiety.

In certain embodiments, A comprises a bicyclic sugar moiety, and B comprises a 2'-(ara)-F sugar moiety. In certain embodiments, A is an LNA nucleoside and B comprises a 2'-(ara)-F sugar moiety. In certain embodiments, A is a cEt nucleoside and B comprises a 2'-(ara)-F sugar moiety. In certain embodiments, A is an α-L-LNA nucleoside and B comprises a 2'-(ara)-F sugar moiety.

In certain embodiments, B comprises a bicyclic sugar moiety, and A comprises a 2'-MOE sugar moiety. In certain embodiments, B is an LNA nucleoside and A comprises a 2'-MOE sugar moiety. In certain embodiments, B is a cEt nucleoside and A comprises a 2'-MOE sugar moiety. In certain embodiments, B is an α-L-LNA nucleoside and A comprises a 2'-MOE sugar moiety.

In certain embodiments, B comprises a bicyclic sugar moiety, A comprises a 2'-MOE sugar moiety, and C comprises an unmodified 2'-deoxyfuranose sugar moiety. In certain embodiments, B is an LNA nucleoside, A comprises a 2'-MOE sugar moiety, and C comprises an unmodified 2'-deoxyfuranose sugar moiety. In certain embodiments, B is a cEt nucleoside, A comprises a 2'-MOE sugar moiety, and C comprises an unmodified 2'-deoxyfuranose sugar moiety. In certain embodiments, B is an α-L-LNA nucleoside and A comprises a 2'-MOE sugar moiety.

In certain embodiments, B comprises a bicyclic sugar moiety, and A comprises a 2'-F sugar moiety. In certain embodiments, B is an LNA nucleoside and A comprises a 2'-F sugar moiety. In certain embodiments, B is a cEt nucleoside and A comprises a 2'-F sugar moiety. In certain embodiments, B is an α-L-LNA nucleoside and A comprises a 2'-F sugar moiety.

In certain embodiments, B comprises a bicyclic sugar moiety, and A comprises a 2'-(ara)-F sugar moiety. In certain embodiments, B is an LNA nucleoside and A comprises a 2'-(ara)-F sugar moiety. In certain embodiments, B is a cEt nucleoside and A comprises a 2'-(ara)-F sugar moiety. In certain embodiments, B is an α-L-LNA nucleoside and A comprises a 2'-(ara)-F sugar moiety.

In certain embodiments, at least one of A or B comprises a bicyclic sugar moiety, another of A or B comprises a 2'-substituted sugar moiety and C comprises a modified nucleobase. In certain embodiments, one of A or B is an LNA nucleoside, another of A or B comprises a 2'-substituted sugar moiety, and C comprises a modified nucleobase. In certain embodiments, one of A or B is a cEt nucleoside, another of A or B comprises a 2'-substituted sugar moiety, and C comprises a modified nucleobase. In certain embodiments, one of A or B is an α-L-LNA nucleoside, another of A or B comprises a 2'-substituted sugar moiety, and C comprises a modified nucleobase.

In certain embodiments, one of A or B comprises a bicyclic sugar moiety, another of A or B comprises a 2'-MOE sugar moiety, and C comprises a modified nucleobase. In certain embodiments, one of A or B is an LNA nucleoside, another of A or B comprises a 2'-MOE sugar moiety, and C comprises a modified nucleobase. In certain embodiments, one of A or B is a cEt nucleoside, another of A or B comprises a 2'-MOE sugar moiety, and C comprises a modified nucleobase. In certain embodiments, one of A or B is an α-L-LNA nucleoside, another of A or B comprises a 2'-MOE sugar moiety, and C comprises a modified nucleobase.

In certain embodiments, one of A or B comprises a bicyclic sugar moiety, another of A or B comprises a 2'-F sugar moiety, and C comprises a modified nucleobase. In certain embodiments, one of A or B is an LNA nucleoside, another of A or B comprises a 2'-F sugar moiety, and C comprises a modified nucleobase. In certain embodiments, one of A or B is a cEt nucleoside, another of A or B comprises a 2'-F sugar moiety, and C comprises a modified nucleobase. In certain embodiments, one of A or B is an α-L-LNA nucleoside, another of A or B comprises a 2'-F sugar moiety, and C comprises a modified nucleobase.

In certain embodiments, one of A or B comprises a bicyclic sugar moiety, another of A or B comprises a 2'-(ara)-F sugar moiety, and C comprises a modified nucleobase. In certain embodiments, one of A or B is an LNA nucleoside, another of A or B comprises a 2'-(ara)-F sugar moiety, and C comprises a modified nucleobase. In certain embodiments, one of A or B is a cEt nucleoside, another of A or B comprises a 2'-(ara)-F sugar moiety, and C comprises a modified nucleobase. In certain embodiments, one of A or B is an α-L-LNA nucleoside, another of A or B comprises a 2'-(ara)-F sugar moiety, and C comprises a modified nucleobase.

In certain embodiments, one of A or B comprises a bicyclic sugar moiety, another of A or B comprises a 2'-substituted sugar moiety, and C comprises a 2-thio-thymidine nucleobase. In certain embodiments, one of A or B is an LNA nucleoside, another of A or B comprises a 2'-substituted sugar moiety, and C comprises a 2-thio-thymidine nucleobase. In certain embodiments, one of A or B is a cEt nucleoside, another of A or B comprises a 2'-substituted sugar moiety, and C comprises a 2-thio-thymidine nucleobase. In certain embodiments, one of A or B is an α-L-LNA nucleoside, another of A or B comprises a 2'-substituted sugar moiety, and C comprises a 2-thio-thymidine nucleobase.

In certain embodiments, one of A or B comprises a bicyclic sugar moiety, another of A or B comprises a 2'-MOE sugar moiety, and C comprises a 2-thio-thymidine nucleobase. In certain embodiments, one of A or B is an LNA nucleoside, another of A or B comprises a 2'-MOE sugar moiety, and C comprises a 2-thio-thymidine nucleobase. In certain embodiments, one of A or B is a cEt nucleoside, another of A or B comprises a 2'-MOE sugar moiety, and C comprises a 2-thio-thymidine nucleobase. In certain embodiments, one of A or B is an α-L-LNA nucleoside, another of A or B comprises a 2'-MOE sugar moiety, and C comprises a 2-thio-thymidine nucleobase.

In certain embodiments, one of A or B comprises a bicyclic sugar moiety, another of A or B comprises a 2'-F sugar moiety, and C comprises a 2-thio-thymidine nucleobase. In certain embodiments, one of A or B is an LNA nucleoside, another of A or B comprises a 2'-F sugar moiety, and C comprises a 2-thio-thymidine nucleobase. In certain embodiments, one of A or B is a cEt nucleoside, another of A or B comprises a 2'-F sugar moiety, and C comprises a 2-thio-thymidine nucleobase. In certain embodiments, one of A or B is an α-L-LNA nucleoside, another of A or B comprises a 2'-F sugar moiety, and C comprises a 2-thio-thymidine nucleobase.

In certain embodiments, one of A or B comprises a bicyclic sugar moiety, another of A or B comprises a 2'-(ara)-F sugar moiety, and C comprises a 2-thio-thymidine nucleobase. In certain embodiments, one of A or B is an LNA nucleoside, another of A or B comprises a 2'-(ara)-F sugar moiety, and C comprises a 2-thio-thymidine nucleobase. In certain embodiments, one of A or B is a cEt nucleoside, another of A or B comprises a 2'-(ara)-F sugar moiety, and C comprises a 2-thio-thymidine nucleobase. In certain embodiments, one of A or B is an α-L-LNA nucleoside, another of A or B comprises a 2'-(ara)-F sugar moiety, and C comprises 2-thio-thymidine nucleobase.

In certain embodiments, one of A or B comprises a bicyclic sugar moiety, another of A or B comprises a 2'-MOE sugar moiety, and C comprises a 5-propyne uridine nucleobase. In certain embodiments, one of A or B is an LNA nucleoside, another of A or B comprises a 2'-MOE sugar moiety, and C comprises a 5-propyne uridine nucleobase. In certain embodiments, one of A or B is a cEt nucleoside, another of A or B comprises a 2'-MOE sugar moiety, and C comprises a 5-propyne uridine nucleobase. In certain embodiments, one of A or B is an α-L-LNA nucleoside, another of A or B comprises a 2'-MOE sugar moiety, and C comprises a 5-propyne uridine nucleobase.

In certain embodiments, one of A or B comprises a bicyclic sugar moiety, another of A or B comprises a 2'-MOE sugar moiety, and C comprises an unmodified 2'-deoxyfuranose sugar moiety. In certain embodiments, one of A or B is an LNA nucleoside, another of A or B comprises a 2'-MOE sugar moiety, and C comprises a 5-propyne uridine nucleobase. In certain embodiments, one of A or B is a cEt nucleoside, another of A or B comprises a 2'-MOE sugar moiety, and C comprises a 5-propyne uridine nucleobase. In certain embodiments, one of A or B is an α-L-LNA nucleoside, another of A or B comprises a 2'-MOE sugar moiety, and C comprises a 5-propyne uridine nucleobase.

In certain embodiments, one of A or B comprises a bicyclic sugar moiety, another of A or B comprises a 2'-F sugar moiety, and C comprises a 5-propyne uridine nucleobase. In certain embodiments, one of A or B is an LNA nucleoside, another of A or B comprises a 2'-F sugar moiety, and C comprises a 5-propyne uridine nucleobase. In certain embodiments, one of A or B is a cEt nucleoside, another of A or B comprises a 2'-F sugar moiety, and C comprises a 5-propyne uridine nucleobase. In certain embodiments, one of A or B is an α-L-LNA nucleoside, another of A or B comprises a 2'-F sugar moiety, and C comprises a 5-propyne uridine nucleobase.

In certain embodiments, one of A or B comprises a bicyclic sugar moiety, another of A or B comprises a 2'-(ara)-F sugar moiety, and C comprises a 5-propyne uridine nucleobase. In certain embodiments, one of A or B is an LNA nucleoside, another of A or B comprises a 2'-(ara)-F sugar moiety, and C comprises a 5-propyne uridine nucleobase. In certain embodiments, one of A or B is a cEt nucleoside, another of A or B comprises a 2'-(ara)-F sugar moiety, and C comprises a 5-propyne uridine nucleobase. In certain embodiments, one of A or B is an α-L-LNA nucleoside, another of A or B comprises a 2'-(ara)-F sugar moiety, and C comprises a 5-propyne uridine nucleobase.

In certain embodiments, one of A or B comprises a bicyclic sugar moiety, another of A or B comprises a 2'-MOE sugar moiety, and C comprises a sugar surrogate. In certain embodiments, one of A or B is an LNA nucleoside, another of A or B comprises a 2'-MOE sugar moiety, and C comprises a sugar surrogate. In certain embodiments, one of A or B is a cEt nucleoside, another of A or B comprises a 2'-MOE sugar moiety, and C comprises a sugar surrogate. In certain embodiments, one of A or B is an α-L-LNA nucleoside, another of A or B comprises a 2'-MOE sugar moiety, and C comprises a sugar surrogate.

In certain embodiments, one of A or B comprises a bicyclic sugar moiety, another of A or B comprises a 2'-F sugar moiety, and C comprises a sugar surrogate. In certain embodiments, one of A or B is an LNA nucleoside, another of A or B comprises a 2'-F sugar moiety, and C comprises a sugar surrogate. In certain embodiments, one of A or B is a cEt nucleoside, another of A or B comprises a 2'-F sugar moiety, and C comprises a sugar surrogate. In certain embodiments, one of A or B is an α-L-LNA nucleoside, another of A or B comprises a 2'-F sugar moiety, and C comprises a sugar surrogate.

In certain embodiments, one of A or B comprises a bicyclic sugar moiety, another of A or B comprises a 2'-(ara)-F sugar moiety, and C comprises a sugar surrogate. In certain embodiments, one of A or B is an LNA nucleoside, another of A or B comprises a 2'-(ara)-F sugar moiety, and C comprises a sugar surrogate. In certain embodiments, one of A or B is a cEt nucleoside, another of A or B comprises a 2'-(ara)-F sugar moiety, and C comprises a sugar surrogate. In certain embodiments, one of A or B is an α-L-LNA nucleoside, another of A or B comprises a 2'-(ara)-F sugar moiety, and C comprises sugar surrogate.

In certain embodiments, one of A or B comprises a bicyclic sugar moiety, another of A or B comprises a 2'-MOE sugar moiety, and C comprises a HNA sugar surrogate. In certain embodiments, one of A or B is an LNA nucleoside, another of A or B comprises a 2'-MOE sugar moiety, and C comprises a HNA sugar surrogate. In certain embodiments, one of A or B is a cEt nucleoside, another of A or B comprises a 2'-MOE sugar moiety, and C comprises a HNA sugar surrogate. In certain embodiments, one of A or B is an α-L-LNA nucleoside, another of A or B comprises a 2'-MOE sugar moiety, and C comprises a HNA sugar surrogate.

In certain embodiments, one of A or B comprises a bicyclic sugar moiety, another of A or B comprises a 2'-F sugar moiety, and C comprises a HNA sugar surrogate. In certain embodiments, one of A or B is an LNA nucleoside, another of A or B comprises a 2'-F sugar moiety, and C comprises a HNA sugar surrogate. In certain embodiments, one of A or B is a cEt nucleoside, another of A or B comprises a 2'-F sugar moiety, and C comprises a HNA sugar surrogate. In certain embodiments, one of A or B is an α-L-LNA nucleoside, another of A or B comprises a 2'-F sugar moiety, and C comprises a sugar HNA surrogate.

In certain embodiments, one of A or B comprises a bicyclic sugar moiety, another of A or B comprises a 2'-(ara)-F sugar moiety, and C comprises a HNA sugar surrogate. In certain embodiments, one of A or B is an LNA nucleoside, another of A or B comprises a 2'-(ara)-F sugar moiety, and C comprises a HNA sugar surrogate. In certain embodiments, one of A or B is a cEt nucleoside, another of A or B comprises a 2'-(ara)-F sugar moiety, and C comprises a HNA sugar surrogate. In certain embodiments, one of A or B is an α-L-LNA nucleoside, another of A or B comprises a 2'-(ara)-F sugar moiety, and C comprises a HNA sugar surrogate.

In certain embodiments, one of A or B comprises a bicyclic sugar moiety, another of A or B comprises a 2'-MOE sugar moiety, and C comprises a F-HNA sugar surrogate. In certain embodiments, one of A or B is an LNA nucleoside, another of A or B comprises a 2'-MOE sugar moiety, and C comprises a F-HNA sugar surrogate. In certain embodiments, one of A or B is a cEt nucleoside, another of A or B comprises a 2'-MOE sugar moiety, and C comprises a F-HNA sugar surrogate. In certain embodiments, one of A or B is an α-L-LNA nucleoside, another of A or B comprises a 2'-MOE sugar moiety, and C comprises a F-HNA sugar surrogate.

In certain embodiments, one of A or B comprises a bicyclic sugar moiety, another of A or B comprises a 2'-F sugar moiety, and C comprises a F-HNA sugar surrogate. In certain embodiments, one of A or B is an LNA nucleoside, another of A or B comprises a 2'-F sugar moiety, and C comprises a F-HNA sugar surrogate. In certain embodiments, one of A or B is a cEt nucleoside, another of A or B comprises a 2'-F sugar moiety, and C comprises a F-HNA sugar surrogate. In certain embodiments, one of A or B is an α-L-LNA nucleoside, another of A or B comprises a 2'-F sugar moiety, and C comprises a F-HNA sugar surrogate.

In certain embodiments, one of A or B comprises a bicyclic sugar moiety, another of A or B comprises a 2'-(ara)-F sugar moiety, and C comprises a F-HNA sugar surrogate. In certain embodiments, one of A or B is an LNA nucleoside, another of A or B comprises a 2'-(ara)-F sugar moiety, and C comprises a F-HNA sugar surrogate. In certain embodiments, one of A or B is a cEt nucleoside, another of A or B comprises a 2'-(ara)-F sugar moiety, and C comprises a F-HNA sugar surrogate. In certain embodiments, one of A or B is an α-L-LNA nucleoside, another of A or B comprises a 2'-(ara)-F sugar moiety, and C comprises a F-HNA sugar surrogate.

In certain embodiments, one of A or B comprises a bicyclic sugar moiety, another of A or B comprises a 2'-MOE sugar moiety, and C comprises a 5'-Me DNA sugar moiety. In certain embodiments, one of A or B is an LNA nucleoside, another of A or B comprises a 2'-MOE sugar moiety, and C comprises a 5'-Me DNA sugar moiety. In certain embodiments, one of A or B is a cEt nucleoside, another of A or B comprises a 2'-MOE sugar moiety, and C comprises a 5'-Me DNA sugar moiety. In certain embodiments, one of A or B is an α-L-LNA nucleoside, another of A or B comprises a 2'-MOE sugar moiety, and C comprises a 5'-Me DNA sugar moiety.

In certain embodiments, one of A or B comprises a bicyclic sugar moiety, another of A or B comprises a 2'-F sugar moiety, and C comprises a 5'-Me DNA sugar moiety. In certain embodiments, one of A or B is an LNA nucleoside, another of A or B comprises a 2'-F sugar moiety, and C comprises a 5'-Me DNA sugar moiety. In certain embodiments, one of A or B is a cEt nucleoside, another of A or B comprises a 2'-F sugar moiety, and C comprises a 5'-Me DNA sugar moiety. In certain embodiments, one of A or B is an α-L-LNA nucleoside, another of A or B comprises a 2'-F sugar moiety, and C comprises a 5'-Me DNA sugar moiety.

In certain embodiments, one of A or B comprises a bicyclic sugar moiety, another of A or B comprises a 2'-(ara)-F sugar moiety, and C comprises a 5'-Me DNA sugar moiety. In certain embodiments, one of A or B is an LNA nucleoside, another of A or B comprises a 2'-(ara)-F sugar moiety, and C comprises a 5'-Me DNA sugar moiety. In certain embodiments, one of A or B is a cEt nucleoside, another of A or B comprises a 2'-(ara)-F sugar moiety, and C comprises a 5'-Me DNA sugar moiety. In certain embodiments, one of A or B is an α-L-LNA nucleoside, another of A or B comprises a 2'-(ara)-F sugar moiety, and C comprises a 5'-Me DNA sugar moiety.

In certain embodiments, one of A or B comprises a bicyclic sugar moiety, another of A or B comprises a 2'-MOE sugar moiety, and C comprises a 5'-(R)-Me DNA sugar moiety. In certain embodiments, one of A or B is an LNA nucleoside, another of A or B comprises a 2'-MOE sugar moiety, and C comprises a 5'-(R)-Me DNA sugar moiety. In certain embodiments, one of A or B is a cEt nucleoside, another of A or B comprises a 2'-MOE sugar moiety, and C comprises a 5'-(R)-Me DNA sugar moiety. In certain embodiments, one of A or B is an α-L-LNA nucleoside, another of A or B comprises a 2'-MOE sugar moiety, and C comprises a 5'-(R)-Me DNA sugar moiety.

In certain embodiments, one of A or B comprises a bicyclic sugar moiety, another of A or B comprises a 2'-F sugar moiety, and C comprises a 5'-(R)-Me DNA sugar moiety. In certain embodiments, one of A or B is an LNA nucleoside, another of A or B comprises a 2'-F sugar moiety, and C comprises a 5'-(R)-Me DNA sugar moiety. In certain embodiments, one of A or B is a cEt nucleoside, another of A or B comprises a 2'-F sugar moiety, and C comprises a 5'-(R)-Me DNA sugar moiety. In certain embodiments, one of A or B is an α-L-LNA nucleoside, another of A or B comprises a 2'-F sugar moiety, and C comprises a 5'-(R)-Me DNA sugar moiety.

In certain embodiments, one of A or B comprises a bicyclic sugar moiety, another of A or B comprises a 2'-(ara)-F sugar moiety, and C comprises a 5'-(R)-Me DNA sugar moiety. In certain embodiments, one of A or B is an LNA nucleoside, another of A or B comprises a 2'-(ara)-F sugar moiety, and C comprises a 5'-(R)-Me DNA sugar moiety. In certain embodiments, one of A or B is a cEt nucleoside, another of A or B comprises a 2'-(ara)-F sugar moiety, and C comprises a 5'-(R)-Me DNA sugar moiety. In certain embodiments, one of A or B is an α-L-LNA nucleoside, another of A or B comprises a 2'-(ara)-F sugar moiety, and C comprises a 5'-(R)-Me DNA sugar moiety.

In certain embodiments, at least two of A, B or C comprises a 2'-substituted sugar moiety, and the other comprises a bicyclic sugar moiety. In certain embodiments, at least two of A, B or C comprises a bicyclic sugar moiety, and the other comprises a 2'-substituted sugar moiety.

In certain embodiments, at least two of A, B or C comprises a 2'-substituted sugar moiety, and the other comprises an unmodified 2'-deoxyfuranose sugar moiety. In certain embodiments, at least two of A, B or C comprises a bicyclic sugar moiety, and the other comprises an unmodified 2'-deoxyfuranose sugar moiety.

Certain 3'-Wings

In certain embodiments, the 3'-wing of a gapmer consists of 1 to 5 linked nucleosides. In certain embodiments, the 3'-wing of a gapmer consists of 2 to 5 linked nucleosides. In certain embodiments, the 3'-wing of a gapmer consists of 3 to 5 linked nucleosides. In certain embodiments, the 3'-wing of a gapmer consists of 4 or 5 linked nucleosides. In certain embodiments, the 3'-wing of a gapmer consists of 1 to 4 linked nucleosides. In certain embodiments, the 3'-wing of a gapmer consists of 1 to 3 linked nucleosides. In certain embodiments, the 3'-wing of a gapmer consists of 1 or 2 linked nucleosides. In certain embodiments, the 3'-wing of a gapmer consists of 2 to 4 linked nucleosides. In certain embodiments, the 3'-wing of a gapmer consists of 2 or 3 linked nucleosides. In certain embodiments, the 3'-wing of a gapmer consists of 3 or 4 linked nucleosides. In certain embodiments, the 3'-wing of a gapmer consists of 1 nucleoside. In certain embodiments, the 3'-wing of a gapmer consists of 2 linked nucleosides. In certain embodiments, the 3'-wing of a gapmer consists of 3 linked nucleosides. In certain embodiments, the 3'-wing of a gapmer consists of 4 linked nucleosides. In certain embodiments, the 3'-wing of a gapmer consists of 5 linked nucleosides.

In certain embodiments, the 3'-wing of a gapmer comprises at least one bicyclic nucleoside. In certain embodiments, the 3'-wing of a gapmer comprises at least one constrained ethyl nucleoside. In certain embodiments, the 3'-wing of a gapmer comprises at least one LNA nucleoside. In certain embodiments, each nucleoside of the 3'-wing of a gapmer is a bicyclic nucleoside. In certain embodiments, each nucleoside of the 3'-wing of a gapmer is a constrained ethyl nucleoside. In certain embodiments, each nucleoside of the 3'-wing of a gapmer is a LNA nucleoside.

In certain embodiments, the 3'-wing of a gapmer comprises at least one non-bicyclic modified nucleoside. In certain embodiments, the 3'-wing of a gapmer comprises at least two non-bicyclic modified nucleosides. In certain embodiments, the 3'-wing of a gapmer comprises at least three non-bicyclic modified nucleosides. In certain embodiments, the 3'-wing of a gapmer comprises at least four non-bicyclic modified nucleosides. In certain embodiments, the 3'-wing of a gapmer comprises at least one 2'-substituted nucleoside. In certain embodiments, the 3'-wing of a gapmer comprises at least one 2'-MOE nucleoside. In certain embodiments, the 3'-wing of a gapmer comprises at least one 2'-OMe nucleoside. In certain embodiments, each nucleoside of the 3'-wing of a gapmer is a non-bicyclic modified nucleoside. In certain embodiments, each nucleoside of the 3'-wing of a gapmer is a 2'-substituted nucleoside. In certain embodiments, each nucleoside of the 3'-wing of a gapmer is a 2'-MOE nucleoside. In certain embodiments, each nucleoside of the 3'-wing of a gapmer is a 2'-OMe nucleoside.

In certain embodiments, the 3'-wing of a gapmer comprises at least one 2'-deoxynucleoside. In certain embodiments, each nucleoside of the 3'-wing of a gapmer is a 2'-deoxynucleoside. In a certain embodiments, the 3'-wing of a gapmer comprises at least one ribonucleoside. In certain embodiments, each nucleoside of the 3'-wing of a gapmer is a ribonucleoside.

In certain embodiments, the 3'-wing of a gapmer comprises at least one bicyclic nucleoside and at least one non-bicyclic modified nucleoside. In certain embodiments, the 3'-wing of a gapmer comprises at least one bicyclic nucleoside and at least one 2'-substituted nucleoside. In certain embodiments, the 3'-wing of a gapmer comprises at least one bicyclic nucleoside and at least one 2'-MOE nucleoside. In certain embodiments, the 3'-wing of a gapmer comprises at least one bicyclic nucleoside and at least one 2'-OMe nucleoside. In certain embodiments, the 3'-wing of a gapmer comprises at least one bicyclic nucleoside and at least one 2'-deoxynucleoside.

In certain embodiments, the 3'-wing of a gapmer comprises at least one constrained ethyl nucleoside and at least one non-bicyclic modified nucleoside. In certain embodiments, the 3'-wing of a gapmer comprises at least one constrained ethyl nucleoside and at least one 2'-substituted nucleoside. In certain embodiments, the 3'-wing of a gapmer comprises at least one constrained ethyl nucleoside and at least one 2'-MOE nucleoside. In certain embodiments, the 3'-wing of a gapmer comprises at least one constrained ethyl nucleoside and at least one 2'-OMe nucleoside. In certain embodiments, the 3'-wing of a gapmer comprises at least one constrained ethyl nucleoside and at least one 2'-deoxynucleoside.

In certain embodiments, the 3'-wing of a gapmer comprises at least one LNA nucleoside and at least one non-bicyclic modified nucleoside. In certain embodiments, the 3'-wing of a gapmer comprises at least one LNA nucleoside and at least one 2'-substituted nucleoside. In certain embodiments, the 3'-wing of a gapmer comprises at least one LNA nucleoside and at least one 2'-MOE nucleoside. In certain embodiments, the 3'-wing of a gapmer comprises at least one LNA nucleoside and at least one 2'-OMe nucleoside. In certain embodiments, the 3'-wing of a gapmer comprises at least one LNA nucleoside and at least one 2'-deoxynucleoside.

In certain embodiments, the 3'-wing of a gapmer comprises at least one bicyclic nucleoside, at least one non-bicyclic modified nucleoside, and at least one 2'-deoxynucleoside. In certain embodiments, the 3'-wing of a gapmer comprises at least one constrained ethyl nucleoside, at least one non-bicyclic modified nucleoside, and at least one 2'-deoxynucleoside. In certain embodiments, the 3'-wing of a gapmer comprises at least one LNA nucleoside, at least one non-bicyclic modified nucleoside, and at least one 2'-deoxynucleoside.

In certain embodiments, the 3'-wing of a gapmer comprises at least one bicyclic nucleoside, at least one 2'-substituted nucleoside, and at least one 2'-deoxynucleoside. In certain embodiments, the 3'-wing of a gapmer comprises at least one constrained ethyl nucleoside, at least one 2'-substituted nucleoside, and at least one 2'-deoxynucleoside. In certain embodiments, the 3'-wing of a gapmer comprises at least one LNA nucleoside, at least one 2'-substituted nucleoside, and at least one 2'-deoxynucleoside.

In certain embodiments, the 3'-wing of a gapmer comprises at least one bicyclic nucleoside, at least one 2'-MOE nucleoside, and at least one 2'-deoxynucleoside. In certain embodiments, the 3'-wing of a gapmer comprises at least one constrained ethyl nucleoside, at least one 2'-MOE nucleoside, and at least one 2'-deoxynucleoside. In certain embodiments, the 3'-wing of a gapmer comprises at least one LNA nucleoside, at least one 2'-MOE nucleoside, and at least one 2'-deoxynucleoside.

In certain embodiments, the 3'-wing of a gapmer comprises at least one bicyclic nucleoside, at least one 2'-OMe nucleoside, and at least one 2'-deoxynucleoside. In certain embodiments, the 3'-wing of a gapmer comprises at least one constrained ethyl nucleoside, at least one 2'-OMe nucleoside, and at least one 2'-deoxynucleoside. In certain embodiments, the 3'-wing of a gapmer comprises at least one LNA nucleoside, at least one 2'-OMe nucleoside, and at least one 2'-deoxynucleoside.

In certain embodiments, the 3'-wing of a gapmer has a sugar motif selected from among those listed in the following non-limiting table:

TABLE 4

Certain 3'-Wing Sugar Motifs

| 3'-wing sugar motif # | motif | 3'-wing sugar motif # | motif | 3'-wing sugar motif # | motif |
|---|---|---|---|---|---|
| 1a | B-B-A | 1d | L-L-A | 1g | K-K-A |
| 2a | B-B-B | 2d | L-L-L | 2g | K-K-K |
| 3a | A-A-B | 3d | A-A-L | 3g | A-A-K |
| 4a | B-A-B | 4d | L-A-L | 4g | K-A-K |
| 5a | B-A-B-A | 5d | L-A-L-A | 5g | K-A-K-A |
| 6a | B-B-B-A | 6d | L-L-L-A | 6g | K-K-K-A |
| 7a | B-D-B-A | 7d | L-D-L-A | 7g | K-D-K-A |
| 8a | B-B-B-B | 8d | L-L-L-L | 8g | K-K-K-K |
| 9a | B-D-D-B | 9d | L-D-D-L | 9g | K-D-D-K |
| 10a | A-B-B-A | 10d | A-L-L-A | 10g | A-K-K-A |
| 1b | B-B-E | 1e | L-L-E | 1h | K-K-E |
| 2b | B-B-B | 2e | L-L-L | 2h | K-K-K |
| 3b | E-E-B | 3e | E-E-L | 3h | E-E-K |
| 4b | B-E-B | 4e | L-E-L | 4h | K-E-K |
| 5b | B-E-B-E | 5e | L-E-L-E | 5h | K-E-K-E |
| 6b | B-B-B-E | 6e | L-L-L-E | 6h | K-K-K-E |
| 7b | B-D-B-E | 7e | L-D-L-E | 7h | K-D-K-E |
| 8b | B-B-B-B | 8e | L-L-L-L | 8h | K-K-K-K |
| 9b | B-D-D-B | 9e | L-D-D-L | 9h | K-D-D-K |
| 10b | E-B-B-E | 10e | E-L-L-E | 10h | E-K-K-E |
| 1c | B-B-M | 1f | L-L-M | 1i | K-K-M |
| 2c | B-B-B | 2f | L-L-L | 2i | K-K-K |
| 3c | M-M-B | 3f | M-M-L | 3i | M-M-K |
| 4c | B-M-B | 4f | L-M-L | 4i | K-M-K |
| 5c | B-M-B-M | 5f | L-M-L-M | 5i | K-M-K-M |
| 6c | B-B-B-M | 6f | L-L-L-M | 6i | K-K-K-M |
| 7c | B-D-B-M | 7f | L-D-L-M | 7i | K-D-K-M |
| 8c | B-B-B-B | 8f | L-L-L-L | 8i | K-K-K-K |
| 9c | B-D-D-B | 9f | L-D-D-L | 9i | K-D-D-K |
| 10c | M-B-B-M | 10f | M-L-L-M | 10i | M-K-K-M |
| 1j | K-K-A | 1k | L-K-A | 1l | K-L-E |
| 2j | K-L-L | 2k | K-K-L | 2l | K-L-K |
| 3j | E-M-B | 3k | E-M-L | 3l | E-K-K |
| 4j | K-A-L | 4k | L-A-K | 4l | L-E-K |
| 5j | K-A-L-A | 5k | L-A-K-A | 5l | K-E-L-E |
| 6j | K-L-K-A | 6k | K-K-L-A | 6l | K-L-K-A |
| 7j | L-D-K-A | 7k | K-D-L-A | 7l | K-D-L-E |
| 8j | B-K-L-B | 8k | K-L-L-L | 8l | K-K-L-K |
| 9j | K-D-D-B | 9k | K-D-D-L | 9l | L-D-D-K |
| 10j | A-K-B-A | 10k | A-K-L-A | 10l | A-B-K-A |
| 1m | E-E | | | | |

In the above table, "A" represents a nucleoside comprising a 2'-substituted sugar moiety; "B" represents a bicyclic nucleoside; "D" represents a 2'-deoxynucleoside; "K" represents a constrained ethyl nucleoside; "L" represents an LNA nucleoside; "E" represents a 2'-MOE nucleoside; and "M" represents a 2'-OMe nucleoside.

In certain embodiments, an oligonucleotide comprises any 3'-wing motif provided herein. In certain such embodiments, the oligonucleotide is a 3'-hemimer (does not comprise a 5'-wing). In certain embodiments, such an oligonucleotide is a gapmer. In certain such embodiments, the 5'-wing of the gapmer may comprise any sugar modification motif.

In certain embodiments, the 5'-wing of a gapmer has a sugar motif selected from among those listed in the following non-limiting tables:

TABLE 5

Certain 3'-Wing Sugar Motifs
Certain 3'-Wing Sugar Motifs

| AAAAA | ABCBB | BABCC | BCBBA | CBACC |
| AAAAB | ABCBC | BACAA | BCBBB | CBBAA |
| AAAAC | ABCCA | BACAB | BCBBC | CBBAB |
| AAABA | ABCCB | BACAC | BCBCA | CBBAC |

TABLE 5-continued

Certain 3'-Wing Sugar Motifs
Certain 3'-Wing Sugar Motifs

| | | | | |
|---|---|---|---|---|
| AAABB | ABCCC | BACBA | BCBCB | CBBBA |
| AAABC | ACAAA | BACBB | BCBCC | CBBBB |
| AAACA | ACAAB | BACBC | BCCAA | CBBBC |
| AAACB | ACAAC | BACCA | BCCAB | CBBCA |
| AAACC | ACABA | BACCB | BCCAC | CBBCB |
| AABAA | ACABB | BACCC | BCCBA | CBBCC |
| AABAB | ACABC | BBAAA | BCCBB | CBCAA |
| AABAC | ACACA | BBAAB | BCCBC | CBCAB |
| AABBA | ACACB | BBAAC | BCCCA | CBCAC |
| AABBB | ACACC | BBABA | BCCCB | CBCBA |
| AABBC | ACBAA | BBABB | BCCCC | CBCBB |
| AABCA | ACBAB | BBABC | CAAAA | CBCBC |
| AABCB | ACBAC | BBACA | CAAAB | CBCCA |
| AABCC | ACBBA | BBACB | CAAAC | CBCCB |
| AACAA | ACBBB | BBACC | CAABA | CBCCC |
| AACAB | ACBBC | BBBAA | CAABB | CCAAA |
| AACAC | ACBCA | BBBAB | CAABC | CCAAB |
| AACBA | ACBCB | BBBAC | CAACA | CCAAC |
| AACBB | ACBCC | BBBBA | CAACB | CCABA |
| AACBC | ACCAA | BBBBB | CAACC | CCABB |
| AACCA | ACCAB | BBBBC | CABAA | CCABC |
| AACCB | ACCAC | BBBCA | CABAB | CCACA |
| AACCC | ACCBA | BBBCB | CABAC | CCACB |
| ABAAA | ACCBB | BBBCC | CABBA | CCACC |
| ABAAB | ACCBC | BBCAA | CABBB | CCBAA |
| ABAAC | ACCCA | BBCAB | CABBC | CCBAB |
| ABABA | ACCCB | BBCAC | CABCA | CCBAC |
| ABABB | ACCCC | BBCBA | CABCB | CCBBA |
| ABABC | BAAAA | BBCBB | CABCC | CCBBB |
| ABACA | BAAAB | BBCBC | CACAA | CCBBC |
| ABACB | BAAAC | BBCCA | CACAB | CCBCA |
| ABACC | BAABA | BBCCB | CACAC | CCBCB |
| ABBAA | BAABB | BBCCC | CACBA | CCBCC |
| ABBAB | BAABC | BCAAA | CACBB | CCCAA |
| ABBAC | BAACA | BCAAB | CACBC | CCCAB |
| ABBBA | BAACB | BCAAC | CACCA | CCCAC |
| ABBBB | BAACC | BCABA | CACCB | CCCBA |
| ABBBC | BABAA | BCABB | CACCC | CCCBB |
| ABBCA | BABAB | BCABC | CBAAA | CCCBC |
| ABBCB | BABAC | BCACA | CBAAB | CCCCA |
| ABBCC | BABBA | BCACB | CBAAC | CCCCB |
| ABCAA | BABBB | BCACC | CBABA | CCCCC |
| ABCAB | BABBC | BCBAA | CBABB | |
| ABCAC | BABCA | BCBAB | CBABC | |
| ABCBA | BABCB | BCBAC | CBACA | |

TABLE 6

Certain 3'-Wing Sugar Motifs
Certain 3'-Wing Sugar Motifs

| | | | | |
|---|---|---|---|---|
| AAAAA | BABC | CBAB | ABBB | BAA |
| AAAAB | BACA | CBAC | BAAA | BAB |
| AAABA | BACB | CBBA | BAAB | BBA |
| AAABB | BACC | CBBB | BABA | BBB |
| AABAA | BBAA | CBBC | BABB | AA |
| AABAB | BBAB | CBCA | BBAA | AB |
| AABBA | BBAC | CBCB | BBAB | AC |
| AABBB | BBBA | CBCC | BBBA | BA |
| ABAAA | BBBB | CCAA | BBBB | BB |
| ABAAB | BBBC | CCAB | AAA | BC |
| ABABA | BBCA | CCAC | AAB | CA |
| ABABB | BBCB | CCBA | AAC | CB |
| ABBAA | BBCC | CCBB | ABA | CC |
| ABBAB | BCAA | CCBC | ABB | AA |
| ABBBA | BCAB | CCCA | ABC | AB |
| ABBBB | BCAC | CCCB | ACA | BA |
| BAAAA | ABCB | BCBA | ACB | |
| BAAAB | ABCC | BCBB | ACC | |
| BAABA | ACAA | BCBC | BAA | |
| BAABB | ACAB | BCCA | BAB | |
| BABAA | ACAC | BCCB | BAC | |
| BABAB | ACBA | BCCC | BBA | |
| BABBA | ACBB | CAAA | BBB | |

TABLE 6-continued

Certain 3'-Wing Sugar Motifs
Certain 3'-Wing Sugar Motifs

| | | | |
|---|---|---|---|
| BABBB | ACBC | CAAB | BBC |
| BBAAA | ACCA | CAAC | BCA |
| BBAAB | ACCB | CABA | BCB |
| BBABA | ACCC | CABB | BCC |
| BBABB | BAAA | CABC | CAA |
| BBBAA | BAAB | CACA | CAB |
| BBBAB | BAAC | CACB | CAC |
| BBBBA | BABA | CACC | CBA |
| BBBBB | BABB | CBAA | CBB |
| AAAA | AACC | CCCC | CBC |
| AAAB | ABAA | AAAA | CCA |
| AAAC | ABAB | AAAB | CCB |
| AABA | ABAC | AABA | CCC |
| AABB | ABBA | AABB | AAA |
| AABC | ABBB | ABAA | AAB |
| AACA | ABBC | ABAB | ABA |
| AACB | ABCA | ABBA | ABB |

In certain embodiments, each A, each B, and each C located at the 5'-most 3'-wing region nucleoside is a modified nucleoside. For example, in certain embodiments the 3'-wing motif is selected from among <u>A</u>BB, <u>B</u>BB, and <u>C</u>BB, wherein the underlined nucleoside represents the 5'-most 3'-wing region nucleoside and wherein the underlined nucleoside is a modified nucleoside.

In certain embodiments, each A comprises an unmodified 2'-deoxyfuranose sugar moiety. In certain embodiments, each A comprises a modified sugar moiety. In certain embodiments, each A comprises a 2'-substituted sugar moiety. In certain embodiments, each A comprises a 2'-substituted sugar moiety selected from among F, ara-F, OCH$_3$ and O(CH$_2$)$_2$—OCH$_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside.

In certain embodiments, each B comprises an unmodified 2'-deoxyfuranose sugar moiety. In certain embodiments, each B comprises a modified sugar moiety. In certain embodiments, each B comprises a 2'-substituted sugar moiety. In certain embodiments, each B comprises a 2'-substituted sugar moiety selected from among F, (ara)-F, OCH$_3$ and O(CH$_2$)$_2$—OCH$_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne urindine nucleoside.

In certain embodiments, each C comprises an unmodified 2'-deoxyfuranose sugar moiety. In certain embodiments, each C comprises a modified sugar moiety. In certain embodiments, each C comprises a 2'-substituted sugar moiety. In certain embodiments, each C comprises a 2'-substituted sugar moiety selected from among F, (ara)-F, OCH$_3$ and O(CH$_2$)$_2$—OCH$_3$. In certain embodiments, each C comprises a 5'-substituted sugar moiety. In certain embodiments, each C comprises a 5'-substituted sugar moiety selected from among 5'-Me, and 5'-(R)-Me. In certain embodiments, each C comprises a bicyclic sugar moiety. In certain embodiments, each C comprises a bicyclic sugar moiety selected from among cEt, cMOE, LNA, α-L-LNA, ENA and 2'-thio LNA. In certain embodiments, each C comprises a modified nucleobase. In certain embodiments, each C comprises a modified nucleobase selected from among 2-thio-thymidine and 5-propyne uridine. In certain embodiments, each C comprises a 2-thio-thymidine nucleoside.

In certain embodiments, at least one of A or B comprises an unmodified 2'-deoxyfuranose sugar moiety, and the other comprises a 2'-substituted sugar moiety. In certain embodiments, at least one of A or B comprises an unmodified 2'-deoxyfuranose sugar moiety, and the other comprises a bicyclic sugar moiety.

In certain embodiments, at least one of A or B comprises a bicyclic sugar moiety, and the other comprises a 2'-substituted sugar moiety. In certain embodiments, one of A or B is an LNA nucleoside and the other of A or B comprises a 2'-substituted sugar moiety. In certain embodiments, one of A or B is a cEt nucleoside and the other of A or B comprises a 2'-substituted sugar moiety. In certain embodiments, one of A or B is an α-L-LNA nucleoside and the other of A or B comprises a 2'-substituted sugar moiety. In certain embodiments, one of A or B is an LNA nucleoside and the other of A or B comprises a 2'-MOE sugar moiety. In certain embodiments, one of A or B is a cEt nucleoside and the other of A or B comprises a 2'-MOE sugar moiety. In certain embodiments, one of A or B is an α-L-LNA nucleoside and the other of A or B comprises a 2'-MOE sugar moiety. In certain embodiments, one of A or B is an LNA nucleoside and the other of A or B comprises a 2'-F sugar moiety. In certain embodiments, one of A or B is a cEt nucleoside and the other of A or B comprises a 2'-F sugar moiety. In certain embodiments, one of A or B is an α-L-LNA nucleoside and the other of A or B comprises a 2'-F sugar moiety. In certain embodiments, one of A or B is an LNA nucleoside and the other of A or B comprises a 2'-(ara)-F sugar moiety. In certain embodiments, one of A or B is a cEt nucleoside and the other of A or B comprises a 2'-(ara)-F sugar moiety. In certain embodiments, one of A or B is an α-L-LNA nucleoside and the other of A or B comprises a 2'-(ara)-F sugar moiety.

In certain embodiments, at least one of A or B comprises an unmodified 2'-deoxyfuranose sugar moiety, and the other comprises a 2'-substituted sugar moiety. In certain embodiments, one of A or B is an unmodified 2'-deoxyfuranose sugar moiety and the other of A or B comprises a 2'-substituted sugar moiety. In certain embodiments, one of A or B is an unmodified 2'-deoxyfuranose sugar moiety and the other of A or B comprises a 2'-MOE sugar moiety. In certain embodiments, one of A or B is an unmodified 2'-deoxyfuranose sugar moiety and the other of A or B comprises a 2'-F sugar moiety. In certain embodiments, one of A or B is an unmodified 2'-deoxyfuranose sugar moiety and the other of A or B comprises a 2'-(ara)-F sugar moiety. In certain embodiments, at least one of A or B comprises a bicyclic sugar moiety, and the other comprises an unmodified 2'-deoxyfuranose sugar moiety. In certain embodiments, one of A or B is an LNA nucleoside and the other of A or B comprises an unmodified 2'-deoxyfuranose sugar moiety. In certain embodiments, one of A or B is a cEt nucleoside and the other of A or B comprises an unmodified 2'-deoxyfuranose sugar moiety. In certain embodiments, one of A or B is an α-L-LNA nucleoside and the other of A or B comprises an unmodified 2'-deoxyfuranose sugar moiety. In certain embodiments, one of A or B is an LNA nucleoside and the other of A or B comprises an unmodified 2'-deoxyfuranose sugar moiety. In certain embodiments, one of A or B is a cEt nucleoside and the other of A or B comprises an unmodified 2'-deoxyfuranose sugar moiety. In certain embodiments, one of A or B is an α-L-LNA nucleoside and the other of A or B comprises an unmodified 2'-deoxyfuranose sugar moiety.

In certain embodiments, A comprises a bicyclic sugar moiety, and B comprises a 2'-substituted sugar moiety. In certain embodiments, A is an LNA nucleoside and B comprises a 2'-substituted sugar moiety. In certain embodiments, A is a cEt nucleoside and B comprises a 2'-substituted sugar moiety. In certain embodiments, A is an α-L-LNA nucleoside and B comprises a 2'-substituted sugar moiety.

In certain embodiments, A comprises a bicyclic sugar moiety, and B comprises a 2'-MOE sugar moiety. In certain embodiments, A is an LNA nucleoside and B comprises a 2'-MOE sugar moiety. In certain embodiments, A is a cEt nucleoside and B comprises a 2'-MOE sugar moiety. In certain embodiments, A is an α-L-LNA nucleoside and B comprises a 2'-MOE sugar moiety.

In certain embodiments, A comprises a bicyclic sugar moiety, and B comprises a 2'-F sugar moiety. In certain embodiments, A is an LNA nucleoside and B comprises a 2'-F sugar moiety. In certain embodiments, A is a cEt nucleoside and B comprises a 2'-F sugar moiety. In certain embodiments, A is an α-L-LNA nucleoside and B comprises a 2'-F sugar moiety.

In certain embodiments, A comprises a bicyclic sugar moiety, and B comprises a 2'-(ara)-F sugar moiety. In certain embodiments, A is an LNA nucleoside and B comprises a 2'-(ara)-F sugar moiety. In certain embodiments, A is a cEt nucleoside and B comprises a 2'-(ara)-F sugar moiety. In certain embodiments, A is an α-L-LNA nucleoside and B comprises a 2'-(ara)-F sugar moiety.

In certain embodiments, B comprises a bicyclic sugar moiety, and A comprises a 2'-MOE sugar moiety. In certain embodiments, B is an LNA nucleoside and A comprises a 2'-MOE sugar moiety. In certain embodiments, B is a cEt nucleoside and A comprises a 2'-MOE sugar moiety. In certain embodiments, B is an α-L-LNA nucleoside and A comprises a 2'-MOE sugar moiety.

In certain embodiments, B comprises a bicyclic sugar moiety, A comprises a 2'-MOE sugar moiety, and C comprises an unmodified 2'-deoxyfuranose sugar moiety. In certain embodiments, B is an LNA nucleoside, A comprises a 2'-MOE sugar moiety, and C comprises an unmodified 2'-deoxyfuranose sugar moiety. In certain embodiments, B is a cEt nucleoside, A comprises a 2'-MOE sugar moiety, and C comprises an unmodified 2'-deoxyfuranose sugar moiety. In certain embodiments, B is an α-L-LNA nucleoside and A comprises a 2'-MOE sugar moiety.

In certain embodiments, B comprises a bicyclic sugar moiety, and A comprises a 2'-F sugar moiety. In certain embodiments, B is an LNA nucleoside and A comprises a 2'-F sugar moiety. In certain embodiments, B is a cEt nucleoside and A comprises a 2'-F sugar moiety. In certain embodiments, B is an α-L-LNA nucleoside and A comprises a 2'-F sugar moiety.

In certain embodiments, B comprises a bicyclic sugar moiety, and A comprises a 2'-(ara)-F sugar moiety. In certain embodiments, B is an LNA nucleoside and A comprises a 2'-(ara)-F sugar moiety. In certain embodiments, B is a cEt nucleoside and A comprises a 2'-(ara)-F sugar moiety. In certain embodiments, B is an α-L-LNA nucleoside and A comprises a 2'-(ara)-F sugar moiety.

In certain embodiments, at least one of A or B comprises a bicyclic sugar moiety, another of A or B comprises a 2'-substituted sugar moiety and C comprises a modified nucleobase. In certain embodiments, one of A or B is an LNA nucleoside, another of A or B comprises a 2'-substituted sugar moiety, and C comprises a modified nucleobase. In certain embodiments, one of A or B is a cEt nucleoside, another of A or B comprises a 2'-substituted sugar moiety, and C comprises a modified nucleobase. In certain embodiments, one of A or B is an α-L-LNA nucleoside, another of A or B comprises a 2'-substituted sugar moiety, and Ccomprises a modified nucleobase.

In certain embodiments, one of A or B comprises a bicyclic sugar moiety, another of A or B comprises a 2'-MOE sugar moiety, and C comprises a modified nucleobase. In certain embodiments, one of A or B is an LNA nucleoside, another of A or B comprises a 2'-MOE sugar moiety, and C comprises a modified nucleobase. In certain embodiments, one of A or B is a cEt nucleoside, another of A or B comprises a 2'-MOE sugar moiety, and C comprises a modified nucleobase. In certain embodiments, one of A or B is an α-L-LNA nucleoside, another of A or B comprises a 2'-MOE sugar moiety, and Ccomprises a modified nucleobase.

In certain embodiments, one of A or B comprises a bicyclic sugar moiety, another of A or B comprises a 2'-F sugar moiety, and C comprises a modified nucleobase. In certain embodiments, one of A or B is an LNA nucleoside, another of A or B comprises a 2'-F sugar moiety, and Ccomprises a modified nucleobase. In certain embodiments, one of A or B is a cEt nucleoside, another of A or B comprises a 2'-F sugar moiety, and C comprises a modified nucleobase. In certain embodiments, one of A or B is an α-L-LNA nucleoside, another of A or B comprises a 2'-F sugar moiety, and C comprises a modified nucleobase.

In certain embodiments, one of A or B comprises a bicyclic sugar moiety, another of A or B comprises a 2'-(ara)-F sugar moiety, and C comprises a modified nucleobase. In certain embodiments, one of A or B is an LNA nucleoside, another of A or B comprises a 2'-(ara)-F sugar moiety, and C comprises a modified nucleobase. In certain embodiments, one of A or B is a cEt nucleoside, another of A or B comprises a 2'-(ara)-F sugar moiety, and C comprises a modified nucleobase. In certain embodiments, one of A or B is an α-L-LNA nucleoside, another of A or B comprises a 2'-(ara)-F sugar moiety, and C comprises a modified nucleobase.

In certain embodiments, one of A or B comprises a bicyclic sugar moiety, another of A or B comprises a 2'-substituted sugar moiety, and C comprises a 2-thio-thymidine nucleobase. In certain embodiments, one of A or B is an LNA nucleoside, another of A or B comprises a 2'-substituted sugar moiety, and C comprises a 2-thio-thymidine nucleobase. In certain embodiments, one of A or B is a cEt nucleoside, another of A or B comprises a 2'-substituted sugar moiety, and C comprises a 2-thio-thymidine nucleobase. In certain embodiments, one of A or B is an α-L-LNA nucleoside, another of A or B comprises a 2'-substituted sugar moiety, and C comprises a 2-thio-thymidine nucleobase.

In certain embodiments, one of A or B comprises a bicyclic sugar moiety, another of A or B comprises a 2'-MOE sugar moiety, and C comprises a 2-thio-thymidine nucleobase. In certain embodiments, one of A or B is an LNA nucleoside, another of A or B comprises a 2'-MOE sugar moiety, and C comprises a 2-thio-thymidine nucleobase. In certain embodiments, one of A or B is a cEt nucleoside, another of A or B comprises a 2'-MOE sugar moiety, and C comprises a 2-thio-thymidine nucleobase. In certain embodiments, one of A or B is an α-L-LNA nucleoside, another of A or B comprises a 2'-MOE sugar moiety, and C comprises a 2-thio-thymidine nucleobase.

In certain embodiments, one of A or B comprises a bicyclic sugar moiety, another of A or B comprises a 2'-F sugar moiety, and C comprises a 2-thio-thymidine nucleobase. In certain embodiments, one of A or B is an LNA nucleoside, another of A or B comprises a 2'-F sugar moiety, and C comprises a 2-thio-thymidine nucleobase. In certain embodiments, one of A or B is a cEt nucleoside, another of A or B comprises a 2'-F sugar moiety, and C comprises a 2-thio-thymidine nucleobase. In certain embodiments, one of A or B is an α-L-LNA nucleoside, another of A or B comprises a 2'-F sugar moiety, and C comprises a 2-thio-thymidine nucleobase.

In certain embodiments, one of A or B comprises a bicyclic sugar moiety, another of A or B comprises a 2'-(ara)-F sugar moiety, and C comprises a 2-thio-thymidine nucleobase. In certain embodiments, one of A or B is an LNA nucleoside, another of A or B comprises a 2'-(ara)-F sugar moiety, and C comprises a 2-thio-thymidine nucleobase. In certain embodiments, one of A or B is a cEt nucleoside, another of A or B comprises a 2'-(ara)-F sugar moiety, and C comprises a 2-thio-thymidine nucleobase. In certain embodiments, one of A or B is an α-L-LNA nucleoside, another of A or B comprises a 2'-(ara)-F sugar moiety, and C comprises 2-thio-thymidine nucleobase.

In certain embodiments, one of A or B comprises a bicyclic sugar moiety, another of A or B comprises a 2'-MOE sugar moiety, and C comprises a 5-propyne uridine nucleobase. In certain embodiments, one of A or B is an LNA nucleoside, another of A or B comprises a 2'-MOE sugar moiety, and C comprises a 5-propyne uridine nucleobase. In certain embodiments, one of A or B is a cEt nucleoside, another of A or B comprises a 2'-MOE sugar moiety, and C comprises a 5-propyne uridine nucleobase. In certain embodiments, one of A or B is an α-L-LNA nucleoside, another of A or B comprises a 2'-MOE sugar moiety, and C comprises a 5-propyne uridine nucleobase.

In certain embodiments, one of A or B comprises a bicyclic sugar moiety, another of A or B comprises a 2'-MOE sugar moiety, and C comprises an unmodified 2'-deoxyfuranose sugar moiety. In certain embodiments, one of A or B is an LNA nucleoside, another of A or B comprises a 2'-MOE sugar moiety, and C comprises a 5-propyne uridine nucleobase. In certain embodiments, one of A or B is a cEt nucleoside, another of A or B comprises a 2'-MOE sugar moiety, and C comprises a 5-propyne uridine nucleobase. In certain embodiments, one of A or B is an α-L-LNA nucleoside, another of A or B comprises a 2'-MOE sugar moiety, and C comprises a 5-propyne uridine nucleobase.

In certain embodiments, one of A or B comprises a bicyclic sugar moiety, another of A or B comprises a 2'-F sugar moiety, and C comprises a 5-propyne uridine nucleobase. In certain embodiments, one of A or B is an LNA nucleoside, another of A or B comprises a 2'-F sugar moiety, and C comprises a 5-propyne uridine nucleobase. In certain embodiments, one of A or B is a cEt nucleoside, another of A or B comprises a 2'-F sugar moiety, and C comprises a 5-propyne uridine nucleobase. In certain embodiments, one of A or B is an α-L-LNA nucleoside, another of A or B comprises a 2'-F sugar moiety, and C comprises a 5-propyne uridine nucleobase.

In certain embodiments, one of A or B comprises a bicyclic sugar moiety, another of A or B comprises a 2'-(ara)-F sugar moiety, and C comprises a 5-propyne uridine nucleobase. In certain embodiments, one of A or B is an LNA nucleoside, another of A or B comprises a 2'-(ara)-F sugar moiety, and C comprises a 5-propyne uridine nucleobase. In certain embodiments, one of A or B is a cEt nucleoside, another of A or B comprises a 2'-(ara)-F sugar moiety, and C comprises a 5-propyne uridine nucleobase. In certain embodiments, one of A or B is an α-L-LNA nucleoside, another of A or B comprises a 2'-(ara)-F sugar moiety, and C comprises a 5-propyne uridine nucleobase.

In certain embodiments, one of A or B comprises a bicyclic sugar moiety, another of A or B comprises a 2'-MOE sugar moiety, and C comprises a sugar surrogate. In certain embodiments, one of A or B is an LNA nucleoside, another of A or B comprises a 2'-MOE sugar moiety, and C comprises a sugar surrogate. In certain embodiments, one of A or B is a cEt nucleoside, another of A or B comprises a 2'-MOE sugar moiety, and C comprises a sugar surrogate. In certain embodiments, one of A or B is an α-L-LNA nucleoside, another of A or B comprises a 2'-MOE sugar moiety, and C comprises a sugar surrogate.

In certain embodiments, one of A or B comprises a bicyclic sugar moiety, another of A or B comprises a 2'-F sugar moiety, and C comprises a sugar surrogate. In certain embodiments, one of A or B is an LNA nucleoside, another of A or B comprises a 2'-F sugar moiety, and C comprises a sugar surrogate. In certain embodiments, one of A or B is a cEt nucleoside, another of A or B comprises a 2'-F sugar moiety, and C comprises a sugar surrogate. In certain embodiments, one of A or B is an α-L-LNA nucleoside, another of A or B comprises a 2'-F sugar moiety, and C comprises a sugar surrogate.

In certain embodiments, one of A or B comprises a bicyclic sugar moiety, another of A or B comprises a 2'-(ara)-F sugar moiety, and C comprises a sugar surrogate. In certain embodiments, one of A or B is an LNA nucleoside, another of A or B comprises a 2'-(ara)-F sugar moiety, and C comprises a sugar surrogate. In certain embodiments, one of A or B is a cEt nucleoside, another of A or B comprises a 2'-(ara)-F sugar moiety, and C comprises a sugar surrogate. In certain embodiments, one of A or B is an α-L-LNA nucleoside, another of A or B comprises a 2'-(ara)-F sugar moiety, and C comprises sugar surrogate.

In certain embodiments, one of A or B comprises a bicyclic sugar moiety, another of A or B comprises a 2'-MOE sugar moiety, and C comprises a HNA sugar surrogate. In certain embodiments, one of A or B is an LNA nucleoside, another of A or B comprises a 2'-MOE sugar moiety, and C comprises a HNA sugar surrogate. In certain embodiments, one of A or B is a cEt nucleoside, another of A or B comprises a 2'-MOE sugar moiety, and C comprises a HNA sugar surrogate. In certain embodiments, one of A or B is an α-L-LNA nucleoside, another of A or B comprises a 2'-MOE sugar moiety, and C comprises a HNA sugar surrogate.

In certain embodiments, one of A or B comprises a bicyclic sugar moiety, another of A or B comprises a 2'-F sugar moiety, and C comprises a HNA sugar surrogate. In certain embodiments, one of A or B is an LNA nucleoside, another of A or B comprises a 2'-F sugar moiety, and C comprises a HNA sugar surrogate. In certain embodiments, one of A or B is a cEt nucleoside, another of A or B comprises a 2'-F sugar moiety, and C comprises a HNA sugar surrogate. In certain embodiments, one of A or B is an α-L-LNA nucleoside, another of A or B comprises a 2'-F sugar moiety, and C comprises a sugar HNA surrogate.

In certain embodiments, one of A or B comprises a bicyclic sugar moiety, another of A or B comprises a 2'-(ara)-F sugar moiety, and C comprises a HNA sugar surrogate. In certain embodiments, one of A or B is an LNA nucleoside, another of A or B comprises a 2'-(ara)-F sugar moiety, and C comprises a HNA sugar surrogate. In certain embodiments, one of A or B is a cEt nucleoside, another of A or B comprises a 2'-(ara)-F sugar moiety, and C comprises a HNA sugar surrogate. In certain embodiments, one of A or B is an α-L-LNA nucleoside, another of A or B comprises a 2'-(ara)-F sugar moiety, and C comprises a HNA sugar surrogate.

In certain embodiments, one of A or B comprises a bicyclic sugar moiety, another of A or B comprises a 2'-MOE sugar moiety, and C comprises a F-HNA sugar surrogate. In certain embodiments, one of A or B is an LNA nucleoside, another of A or B comprises a 2'-MOE sugar moiety, and C comprises a F-HNA sugar surrogate. In certain embodiments, one of A or B is a cEt nucleoside, another of A or B comprises a 2'-MOE sugar moiety, and C comprises a F-HNA sugar surrogate. In certain embodiments, one of A or B is an α-L-LNA nucleoside, another of A or B comprises a 2'-MOE sugar moiety, and C comprises a F-HNA sugar surrogate.

In certain embodiments, one of A or B comprises a bicyclic sugar moiety, another of A or B comprises a 2'-F sugar moiety, and C comprises a F-HNA sugar surrogate. In certain embodiments, one of A or B is an LNA nucleoside, another of A or B comprises a 2'-F sugar moiety, and C comprises a F-HNA sugar surrogate. In certain embodiments, one of A or B is a cEt nucleoside, another of A or B comprises a 2'-F sugar moiety, and C comprises a F-HNA sugar surrogate. In certain embodiments, one of A or B is an α-L-LNA nucleoside, another of A or B comprises a 2'-F sugar moiety, and C comprises a F-HNA sugar surrogate.

In certain embodiments, one of A or B comprises a bicyclic sugar moiety, another of A or B comprises a 2'-(ara)-F sugar moiety, and C comprises a F-HNA sugar surrogate. In certain embodiments, one of A or B is an LNA nucleoside, another of A or B comprises a 2'-(ara)-F sugar moiety, and C comprises a F-HNA sugar surrogate. In certain embodiments, one of A or B is a cEt nucleoside, another of A or B comprises a 2'-(ara)-F sugar moiety, and C comprises a F-HNA sugar surrogate. In certain embodiments, one of A or B is an α-L-LNA nucleoside, another of A or B comprises a 2'-(ara)-F sugar moiety, and C comprises a F-HNA sugar surrogate.

In certain embodiments, one of A or B comprises a bicyclic sugar moiety, another of A or B comprises a 2'-MOE sugar moiety, and C comprises a 5'-Me DNA sugar moiety. In certain embodiments, one of A or B is an LNA nucleoside, another of A or B comprises a 2'-MOE sugar moiety, and C comprises a 5'-Me DNA sugar moiety. In certain embodiments, one of A or B is a cEt nucleoside, another of A or B comprises a 2'-MOE sugar moiety, and C comprises a 5'-Me DNA sugar moiety. In certain embodiments, one of A or B is an α-L-LNA nucleoside, another of A or B comprises a 2'-MOE sugar moiety, and C comprises a 5'-Me DNA sugar moiety.

In certain embodiments, one of A or B comprises a bicyclic sugar moiety, another of A or B comprises a 2'-F sugar moiety, and C comprises a 5'-Me DNA sugar moiety. In certain embodiments, one of A or B is an LNA nucleoside, another of A or B comprises a 2'-F sugar moiety, and C comprises a 5'-Me DNA sugar moiety. In certain embodiments, one of A or B is a cEt nucleoside, another of A or B comprises a 2'-F sugar moiety, and C comprises a 5'-Me DNA sugar moiety. In certain embodiments, one of A or B is an α-L-LNA nucleoside, another of A or B comprises a 2'-F sugar moiety, and C comprises a 5'-Me DNA sugar moiety.

In certain embodiments, one of A or B comprises a bicyclic sugar moiety, another of A or B comprises a 2'-(ara)-F sugar moiety, and C comprises a 5'-Me DNA sugar moiety. In certain embodiments, one of A or B is an LNA nucleoside, another of A or B comprises a 2'-(ara)-F sugar moiety, and C comprises a 5'-Me DNA sugar moiety. In certain embodiments, one of A or B is a cEt nucleoside, another of A or B comprises a 2'-(ara)-F sugar moiety, and C comprises a 5'-Me DNA sugar moiety. In certain embodiments, one of A or B is an α-L-LNA nucleoside, another of A or B comprises a 2'-(ara)-F sugar moiety, and C comprises a 5'-Me DNA sugar moiety.

In certain embodiments, one of A or B comprises a bicyclic sugar moiety, another of A or B comprises a 2'-MOE sugar moiety, and C comprises a 5'-(R)-Me DNA sugar moiety. In certain embodiments, one of A or B is an LNA nucleoside, another of A or B comprises a 2'-MOE sugar moiety, and C comprises a 5'-(R)-Me DNA sugar moiety. In certain embodiments, one of A or B is a cEt nucleoside, another of A or B comprises a 2'-MOE sugar moiety, and C comprises a 5'-(R)-Me DNA sugar moiety. In certain embodiments, one of A or B is an α-L-LNA nucleoside, another of A or B comprises a 2'-MOE sugar moiety, and C comprises a 5'-(R)-Me DNA sugar moiety.

In certain embodiments, one of A or B comprises a bicyclic sugar moiety, another of A or B comprises a 2'-F sugar moiety, and C comprises a 5'-(R)-Me DNA sugar moiety. In certain embodiments, one of A or B is an LNA nucleoside, another of A or B comprises a 2'-F sugar moiety, and C comprises a 5'-(R)-Me DNA sugar moiety. In certain embodiments, one of A or B is a cEt nucleoside, another of A or B comprises a 2'-F sugar moiety, and C comprises a 5'-(R)-Me DNA sugar moiety. In certain embodiments, one of A or B is an α-L-LNA nucleoside, another of A or B comprises a 2'-F sugar moiety, and C comprises a 5'-(R)-Me DNA sugar moiety.

In certain embodiments, one of A or B comprises a bicyclic sugar moiety, another of A or B comprises a 2'-(ara)-F sugar moiety, and C comprises a 5'-(R)-Me DNA sugar moiety. In certain embodiments, one of A or B is an LNA nucleoside, another of A or B comprises a 2'-(ara)-F sugar moiety, and C comprises a 5'-(R)-Me DNA sugar moiety. In certain embodiments, one of A or B is a cEt nucleoside, another of A or B comprises a 2'-(ara)-F sugar moiety, and C comprises a 5'-(R)-Me DNA sugar moiety. In certain embodiments, one of A or B is an α-L-LNA nucleoside, another of A or B comprises a 2'-(ara)-F sugar moiety, and C comprises a 5'-(R)-Me DNA sugar moiety.

In certain embodiments, at least two of A, B or C comprises a 2'-substituted sugar moiety, and the other comprises a bicyclic sugar moiety. In certain embodiments, at least two of A, B or C comprises a bicyclic sugar moiety, and the other comprises a 2'-substituted sugar moiety.

In certain embodiments, at least two of A, B or C comprises a 2'-substituted sugar moiety, and the other comprises an unmodified 2'-deoxyfuranose sugar moiety. In certain embodiments, at least two of A, B or C comprises a bicyclic sugar moiety, and the other comprises an unmodified 2'-deoxyfuranose sugar moiety.

Certain Gaps

In certain embodiments, the gap of a gapmer consists of 6 to 20 linked nucleosides. In certain embodiments, the gap of a gapmer consists of 6 to 15 linked nucleosides. In certain embodiments, the gap of a gapmer consists of 6 to 12 linked nucleosides. In certain embodiments, the gap of a gapmer consists of 6 to 10 linked nucleosides. In certain embodiments, the gap of a gapmer consists of 6 to 9 linked nucleosides. In certain embodiments, the gap of a gapmer consists of 6 to 8 linked nucleosides. In certain embodiments, the gap of a gapmer consists of 6 or 7 linked nucleosides. In certain embodiments, the gap of a gapmer consists of 7 to 10 linked nucleosides. In certain embodiments, the gap of a gapmer consists of 7 to 9 linked nucleosides. In certain embodiments, the gap of a gapmer consists of 7 or 8 linked nucleosides. In certain embodiments, the gap of a gapmer consists of 8 to 10 linked nucleosides. In certain embodiments, the gap of a gapmer consists of 8 or 9 linked nucleosides. In certain embodiments, the gap of a gapmer consists of 6 linked nucleosides. In certain embodiments, the gap of a gapmer consists of 7 linked nucleosides. In certain embodiments, the gap of a gapmer consists of 8 linked nucleosides. In certain embodiments, the gap of a gapmer consists of 9 linked nucleosides. In certain embodiments, the gap of a gapmer consists of 10 linked nucleosides. In certain embodiments, the gap of a gapmer consists of 11 linked nucleosides. In certain embodiments, the gap of a gapmer consists of 12 linked nucleosides.

In certain embodiments, each nucleotide of the gap of a gapmer is a 2'-deoxynucleoside. In certain embodiments, the gap comprises one or more modified nucleosides. In certain embodiments, each nucleotide of the gap of a gapmer is a 2'-deoxynucleoside or is a modified nucleoside that is "DNA-like." In such embodiments, "DNA-like" means that the nucleoside has similar characteristics to DNA, such that a duplex comprising the gapmer and an RNA molecule is capable of activating RNase H. For example, under certain conditions, 2'-fluoro (arabino) nucleosides (also referred to as FANA) have been shown to support RNase H activation, and thus is DNA-like. In certain embodiments, one or more nucleosides of the gap of a gapmer is not a 2'-deoxynucleoside and is not DNA-like. In certain such embodiments, the gapmer nonetheless supports RNase H activation (e.g., by virtue of the number or placement of the non-DNA nucleosides).

Certain Gapmer Motifs

In certain embodiments, a gapmer comprises a 5'-wing, a gap, and a 3' wing, wherein the 5'-wing, gap, and 3' wing are independently selected from among those discussed above. For example, in certain embodiments, a gapmer has a 5'-wing selected from any of the 5'-wing motifs in Tables 1, 2, and 3 above and a 3'-wing selected from any of the 3'-wing motifs in Tables, 4, 5, and 6. For example, in certain embodiments, a gapmer has a 5'-wing, a gap, and a 3'-wing having features selected from among those listed in the following non-limiting table:

TABLE 7

Certain Gapmer Sugar Motifs

| Gapmer motif # | 5-wing | Gap | 3'-wing |
|---|---|---|---|
| 1 | At least one non-bicyclic modified nucleoside | All 2'-deoxynucleosides | At least one bicyclic nucleoside |
| 2 | At least one non-bicyclic modified nucleoside | All 2'-deoxynucleosides | At least one LNA nucleoside |

TABLE 7-continued

Certain Gapmer Sugar Motifs

| Gapmer motif # | 5'-wing | Gap | 3'-wing |
|---|---|---|---|
| 3 | At least one non-bicyclic modified nucleoside | All 2'-deoxynucleosides | At least one cEt nucleoside |
| 4 | At least one 2'-substituted nucleoside | All 2'-deoxynucleosides | At least one bicyclic nucleoside |
| 5 | At least one 2'-substituted nucleoside | All 2'-deoxynucleosides | At least one LNA nucleoside |
| 6 | At least one 2'-substituted nucleoside | All 2'-deoxynucleosides | At least one cEt nucleoside |
| 7 | At least one 2'-MOE nucleoside | All 2'-deoxynucleosides | At least one bicyclic nucleoside |
| 8 | At least one 2'-MOE nucleoside | All 2'-deoxynucleosides | At least one LNA nucleoside |
| 9 | At least one 2'-MOE nucleoside | All 2'-deoxynucleosides | At least one cEt nucleoside |
| 10 | At least one 2'-OMe nucleoside | All 2'-deoxynucleosides | At least one bicyclic nucleoside |
| 11 | At least one 2'-OMe nucleoside | All 2'-deoxynucleosides | At least one LNA nucleoside |
| 12 | At least one 2'-OMe nucleoside | All 2'-deoxynucleosides | At least one cEt nucleoside |
| 13 | At least one 2'-deoxynucleoside | All 2'-deoxynucleosides | At least one bicyclic nucleoside |
| 14 | At least one 2'-deoxynucleoside | All 2'-deoxynucleosides | At least one LNA nucleoside |
| 15 | At least one 2'-deoxynucleoside | All 2'-deoxynucleosides | At least one cEt nucleoside |
| 16 | At least one bicyclic nucleoside | All 2'-deoxynucleosides | At least one non-bicyclic modified nucleoside |
| 17 | At least one LNA nucleoside | All 2'-deoxynucleosides | At least one non-bicyclic modified nucleoside |
| 18 | At least one cEt nucleoside | All 2'-deoxynucleosides | At least one non-bicyclic modified nucleoside |
| 19 | At least one bicyclic nucleoside | All 2'-deoxynucleosides | At least one 2'-substituted nucleoside |
| 20 | At least one LNA nucleoside | All 2'-deoxynucleosides | At least one 2'-substituted nucleoside |
| 21 | At least one cEt nucleoside | All 2'-deoxynucleosides | At least one 2'-substituted nucleoside |
| 22 | At least one bicyclic nucleoside | All 2'-deoxynucleosides | At least one 2'-MOE nucleoside |
| 23 | At least one LNA nucleoside | All 2'-deoxynucleosides | At least one 2'-MOE nucleoside |
| 24 | At least one cEt nucleoside | All 2'-deoxynucleosides | At least one 2'-MOE nucleoside |
| 25 | At least one bicyclic nucleoside | All 2'-deoxynucleosides | At least one 2'-OMe nucleoside |
| 26 | At least one LNA nucleoside | All 2'-deoxynucleosides | At least one 2'-OMe nucleoside |
| 27 | At least one cEt nucleoside | All 2'-deoxynucleosides | At least one 2'-OMe nucleoside |
| 28 | At least one bicyclic nucleoside | All 2'-deoxynucleosides | At least one 2'-deoxynucleoside |
| 29 | At least one LNA nucleoside | All 2'-deoxynucleosides | At least one 2'-deoxynucleoside |
| 30 | At least one cEt nucleoside | All 2'-deoxynucleosides | At least one 2'-deoxynucleoside |
| 31 | At least one bicyclic nucleoside and at least one 2'-substituted nucleoside | All 2'-deoxynucleosides | At least one bicyclic nucleoside and at least one 2'-substituted nucleoside |
| 32 | At least one bicyclic nucleoside and at least one 2'-substituted nucleoside | All 2'-deoxynucleosides | At least two bicyclic nucleosides |
| 33 | At least one cEt nucleoside and at least one 2'-substituted nucleoside | All 2'-deoxynucleosides | At least one bicyclic nucleoside and at least one 2'-substituted nucleoside |
| 34 | At least one cEt nucleoside and at least one 2'-substituted nucleoside | All 2'-deoxynucleosides | At least two bicyclic nucleosides |
| 35 | At least one LNA nucleoside and at least one 2'-substituted nucleoside | All 2'-deoxynucleosides | At least one bicyclic nucleoside and at least one 2'-substituted nucleoside |
| 36 | At least one LNA nucleoside and at least one 2'-substituted nucleoside | All 2'-deoxynucleosides | At least two bicyclic nucleosides |
| 37 | At least one bicyclic nucleoside and at least one 2'-substituted nucleoside | All 2'-deoxynucleosides | At least one LNA nucleoside and at least one 2'-substituted nucleoside |
| 38 | At least one bicyclic nucleoside and at least one 2'-substituted nucleoside | All 2'-deoxynucleosides | At least two LNA nucleosides |

TABLE 7-continued

Certain Gapmer Sugar Motifs

| Gapmer motif # | 5'-wing | Gap | 3'-wing |
|---|---|---|---|
| 39 | At least one cEt nucleoside and at least one 2'-substituted nucleoside | All 2'-deoxynucleosides | At least one LNA nucleoside and at least one 2'-substituted nucleoside |
| 40 | At least one cEt nucleoside and at least one 2'-substituted nucleoside | All 2'-deoxynucleosides | At least two LNA nucleosides |
| 41 | At least one LNA nucleoside and at least one 2'-substituted nucleoside | All 2'-deoxynucleosides | At least one LNA nucleoside and at least one 2'-substituted nucleoside |
| 42 | At least one LNA nucleoside and at least one 2'-substituted nucleoside | All 2'-deoxynucleosides | At least two LNA nucleosides |
| 43 | At least one bicyclic nucleoside and at least one 2'-deoxynucleoside | All 2'-deoxynucleosides | At least one bicyclic nucleoside and at least one 2'-substituted nucleoside |
| 44 | At least one bicyclic nucleoside and at least one 2'-deoxynucleoside | All 2'-deoxynucleosides | At least two bicyclic nucleosides |
| 45 | At least one cEt nucleoside and at least one 2'-deoxynucleoside | All 2'-deoxynucleosides | At least one bicyclic nucleoside and at least one 2'-substituted nucleoside |
| 46 | At least one cEt nucleoside and at least one 2'-deoxynucleoside | All 2'-deoxynucleosides | At least two bicyclic nucleosides |
| 47 | At least one LNA nucleoside and at least one 2'-deoxynucleoside | All 2'-deoxynucleosides | At least one bicyclic nucleoside and at least one 2'-substituted nucleoside |
| 48 | At least one LNA nucleoside and at least one 2'-deoxynucleoside | All 2'-deoxynucleosides | At least two bicyclic nucleosides |
| 49 | At least one bicyclic nucleoside and at least one 2'-deoxynucleoside | All 2'-deoxynucleosides | At least one LNA nucleoside and at least one 2'-substituted nucleoside |
| 50 | At least one bicyclic nucleoside and at least one 2'-deoxynucleoside | All 2'-deoxynucleosides | At least two LNA nucleosides |
| 51 | At least one cEt nucleoside and at least one 2'-deoxynucleoside | All 2'-deoxynucleosides | At least one LNA nucleoside and at least one 2'-substituted nucleoside |
| 52 | At least one cEt nucleoside and at least one 2'-deoxynucleoside | All 2'-deoxynucleosides | At least two LNA nucleosides |
| 53 | At least one LNA nucleoside and at least one 2'-deoxynucleoside | All 2'-deoxynucleosides | At least one LNA nucleoside and at least one 2'-substituted nucleoside |
| 54 | At least one LNA nucleoside and at least one 2'-deoxynucleoside | All 2'-deoxynucleosides | At least two LNA nucleosides |
| 55 | At least two 2'-substituted nucleosides | All 2'-deoxynucleosides | At least one bicyclic nucleoside and at least one 2'-substituted nucleoside |
| 56 | At least two 2'-substituted nucleosides | All 2'-deoxynucleosides | At least two bicyclic nucleosides |
| 57 | At least two 2'-substituted nucleosides | All 2'-deoxynucleosides | At least one LNA nucleoside and at least one 2'-substituted nucleoside |
| 58 | At least two 2'-substituted nucleosides | All 2'-deoxynucleosides | At least two LNA nucleosides |

In certain embodiments, a gapmer comprises a 5'-wing, a gap, and a 3' wing, wherein the 5'-wing, gap, and 3' wing are independently selected from among those discussed above. For example, in certain embodiments, a gapmer has a 5'-wing, a gap, and a 3'-wing wherein the 5'-wing and the 3'-wing have features selected from among those listed in the tables above. In certain embodiments, any 5'-wing may be paired with any 3'-wing. In certain embodiments the 5'-wing may comprise ABBBB and the 3'-wing may comprise BBA. In certain embodiments the 5'-wing may comprise ACACA and the 3'-wing may comprise BB. For example, in certain embodiments, a gapmer has a 5'-wing, a gap, and a 3'-wing having features selected from among those listed in the following non-limiting table, wherein each motif is represented as (5'-wing)-(gap)-(3'-wing), wherein each number represents the number of linked nucleosides in each portion of the motif, for example, a 5-10-5 motif would have a 5'-wing comprising 5 nucleosides, a gap comprising 10 nucleosides, and a 3'-wing comprising 5 nucleosides:

TABLE 8

Certain Gapmer Sugar Motifs
Certain Gapmer Sugar Motifs

| | | | |
|---|---|---|---|
| 2-10-2 | 3-10-2 | 4-10-2 | 5-10-2 |
| 2-10-3 | 3-10-3 | 4-10-3 | 5-10-3 |
| 2-10-4 | 3-10-4 | 4-10-4 | 5-10-4 |
| 2-10-5 | 3-10-5 | 4-10-5 | 5-10-5 |
| 2-9-2 | 3-9-2 | 4-9-2 | 5-9-2 |

TABLE 8-continued

Certain Gapmer Sugar Motifs

| | | | |
|---|---|---|---|
| 2-9-3 | 3-9-3 | 4-9-3 | 5-9-3 |
| 2-9-4 | 3-9-4 | 4-9-4 | 5-9-4 |
| 2-9-5 | 3-9-5 | 4-9-5 | 5-9-5 |
| 2-11-2 | 3-11-2 | 4-11-2 | 5-11-2 |
| 2-11-3 | 3-11-3 | 4-11-3 | 5-11-3 |
| 2-11-4 | 3-11-4 | 4-11-4 | 5-11-4 |
| 2-11-5 | 3-11-5 | 4-11-5 | 5-11-5 |
| 2-8-2 | 3-8-2 | 4-8-2 | 5-8-2 |
| 2-8-3 | 3-8-3 | 4-8-3 | 5-8-3 |
| 2-8-4 | 3-8-4 | 4-8-4 | 5-8-4 |
| 2-8-5 | 3-8-5 | 4-8-5 | 5-8-5 |

In certain embodiments, gapmers have a motif described by Formula I as follows:

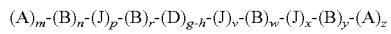

wherein:
each A is independently a 2'-substituted nucleoside;
each B is independently a bicyclic nucleoside;
each J is independently either a 2'-substituted nucleoside or a 2'-deoxynucleoside;
each D is a 2'-deoxynucleoside;
m is 0-4; n is 0-2; p is 0-2; r is 0-2; t is 0-2; v is 0-2; w is 0-4; x is 0-2; y is 0-2; z is 0-4; g is 6; and h is 14;
provided that:
  at least one of m, n, and r is other than 0;
  at least one of w and y is other than 0;
  the sum of m, n, p, r, and t is from 2 to 5; and
  the sum of v, w, x, y, and z is from 2 to 5.

In certain embodiments, one or more 2'-substituted nucleoside is a 2'-MOE nucleoside. In certain embodiments, one or more 2'-substituted nucleoside is a 2'-OMe nucleoside. In certain In certain embodiments, one or more bicyclic nucleoside is a cEt nucleoside. In certain embodiments, one or more bicyclic nucleoside is an LNA nucleoside.

In certain embodiments, a gapmer of Formula I has a motif selected from among gapmer motifs 1-58.

In certain embodiments, gapmers have a motif described by Formula II as follows:

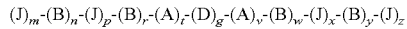

wherein:
each A is independently a 2'-substituted nucleoside;
each B is independently a bicyclic nucleoside;
each J is independently either a 2'-substituted nucleoside or a 2'-deoxynucleoside;
each D is a 2'-deoxynucleoside;
m is 0-4; n is 0-2; p is 0-2; r is 0-2; t is 0-2; v is 0-2; w is 0-4; x is 0-2; y is 0-2; z is 0-4; g is 6-14;
provided that:
  at least one of m, n, and r is other than 0;
  at least one of w and y is other than 0;
  the sum of m, n, p, r, and t is from 1 to 5; and
  the sum of v, w, x, y, and z is from 1 to 5.

In certain embodiments, one or more 2'-substituted nucleoside is a 2'-MOE nucleoside. In certain embodiments, one or more 2'-substituted nucleoside is a 2'-OMe nucleoside. In certain embodiments, one or more bicyclic nucleoside is a cEt nucleoside. In certain embodiments, one or more bicyclic nucleoside is an LNA nucleoside.

In certain embodiments, each 2'-substituted nucleoside is a 2'-MOE nucleoside. In certain embodiments, each 2'-substituted nucleoside is a 2'-OMe nucleoside. In certain embodiments, each bicyclic nucleoside is a cEt nucleoside. In certain embodiments, each bicyclic nucleoside is an LNA nucleoside.

In certain embodiments, each A is the same 2'-substituted nucleoside. In certain embodiments, each B is the same bicyclic nucleoside. In certain embodiments each A is the same 2'-modified nucleoside and each B is the same bicyclic nucleoside. In certain embodiments, each J is a 2'-modified nucleoside. In certain embodiments each J is the same 2'-modified nucleoside. In certain embodiments, each J and each A is the same 2'-modified nucleoside.

In certain embodiments, a gapmer of Formula II has a motif selected from among gapmer motifs 1-58.

In certain embodiments, a gapmer comprises a 5'-wing, a gap, and a 3' wing, independently selected from among those proved in the above tables, for example as provided in the following table:

TABLE 9

Certain Gapmer Sugar Motifs

| Gapmer motif # | 5-wing sugar motif (from table 1) | Gap | 3'-wing sugar motif (from table 2) |
|---|---|---|---|
| 59 | 1(a-i) | All 2'-deoxynucleosides | 1(a-i) |
| 60 | 2(a-i) | All 2'-deoxynucleosides | 1(a-i) |
| 61 | 3(a-i) | All 2'-deoxynucleosides | 1(a-i) |
| 62 | 4(a-i) | All 2'-deoxynucleosides | 1(a-i) |
| 63 | 5(a-i) | All 2'-deoxynucleosides | 1(a-i) |
| 64 | 6(a-i) | All 2'-deoxynucleosides | 1(a-i) |
| 65 | 7(a-i) | All 2'-deoxynucleosides | 1(a-i) |
| 66 | 8(a-i) | All 2'-deoxynucleosides | 1(a-i) |
| 67 | 9(a-i) | All 2'-deoxynucleosides | 1(a-i) |
| 68 | 10(a-i) | All 2'-deoxynucleosides | 1(a-i) |
| 69 | 11(a-i) | All 2'-deoxynucleosides | 1(a-i) |
| 70 | 12(a-i) | All 2'-deoxynucleosides | 1(a-i) |
| 71 | 13(a-i) | All 2'-deoxynucleosides | 1(a-i) |
| 72 | 14(a-i) | All 2'-deoxynucleosides | 1(a-i) |
| 73 | 15(a-i) | All 2'-deoxynucleosides | 1(a-i) |
| 74 | 16(a-i) | All 2'-deoxynucleosides | 1(a-i) |
| 75 | 17(a-i) | All 2'-deoxynucleosides | 1(a-i) |
| 76 | 18(a-i) | All 2'-deoxynucleosides | 1(a-i) |
| 77 | 19(a-i) | All 2'-deoxynucleosides | 1(a-i) |
| 78 | 20(a-i) | All 2'-deoxynucleosides | 1(a-i) |
| 79 | 21(a-i) | All 2'-deoxynucleosides | 1(a-i) |
| 80 | 22(a-i) | All 2'-deoxynucleosides | 1(a-i) |
| 81 | 1(a-i) | All 2'-deoxynucleosides | 2(a-i) |
| 82 | 2(a-i) | All 2'-deoxynucleosides | 2(a-i) |
| 83 | 3(a-i) | All 2'-deoxynucleosides | 2(a-i) |
| 84 | 4(a-i) | All 2'-deoxynucleosides | 2(a-i) |
| 85 | 5(a-i) | All 2'-deoxynucleosides | 2(a-i) |
| 86 | 6(a-i) | All 2'-deoxynucleosides | 2(a-i) |
| 87 | 7(a-i) | All 2'-deoxynucleosides | 2(a-i) |
| 88 | 8(a-i) | All 2'-deoxynucleosides | 2(a-i) |
| 89 | 9(a-i) | All 2'-deoxynucleosides | 2(a-i) |
| 90 | 10(a-i) | All 2'-deoxynucleosides | 2(a-i) |
| 91 | 11(a-i) | All 2'-deoxynucleosides | 2(a-i) |
| 92 | 12(a-i) | All 2'-deoxynucleosides | 2(a-i) |
| 93 | 13(a-i) | All 2'-deoxynucleosides | 2(a-i) |
| 94 | 14(a-i) | All 2'-deoxynucleosides | 2(a-i) |
| 94 | 15(a-i) | All 2'-deoxynucleosides | 2(a-i) |
| 96 | 16(a-i) | All 2'-deoxynucleosides | 2(a-i) |
| 97 | 17(a-i) | All 2'-deoxynucleosides | 2(a-i) |
| 98 | 18(a-i) | All 2'-deoxynucleosides | 2(a-i) |
| 99 | 19(a-i) | All 2'-deoxynucleosides | 2(a-i) |
| 100 | 20(a-i) | All 2'-deoxynucleosides | 2(a-i) |
| 101 | 21(a-i) | All 2'-deoxynucleosides | 2(a-i) |
| 102 | 22(a-i) | All 2'-deoxynucleosides | 2(a-i) |
| 103 | 1(a-i) | All 2'-deoxynucleosides | 3(a-i) |
| 104 | 2(a-i) | All 2'-deoxynucleosides | 3(a-i) |
| 105 | 3(a-i) | All 2'-deoxynucleosides | 3(a-i) |
| 106 | 4(a-i) | All 2'-deoxynucleosides | 3(a-i) |
| 107 | 5(a-i) | All 2'-deoxynucleosides | 3(a-i) |
| 108 | 6(a-i) | All 2'-deoxynucleosides | 3(a-i) |
| 109 | 7(a-i) | All 2'-deoxynucleosides | 3(a-i) |

TABLE 9-continued

Certain Gapmer Sugar Motifs

| Gapmer motif # | 5-wing sugar motif (from table 1) | Gap | 3'-wing sugar motif (from table 2) |
|---|---|---|---|
| 110 | 8(a-i) | All 2'-deoxynucleosides | 3(a-i) |
| 111 | 9(a-i) | All 2'-deoxynucleosides | 3(a-i) |
| 112 | 10(a-i) | All 2'-deoxynucleosides | 3(a-i) |
| 113 | 11(a-i) | All 2'-deoxynucleosides | 3(a-i) |
| 114 | 12(a-i) | All 2'-deoxynucleosides | 3(a-i) |
| 115 | 13(a-i) | All 2'-deoxynucleosides | 3(a-i) |
| 116 | 14(a-i) | All 2'-deoxynucleosides | 3(a-i) |
| 117 | 15(a-i) | All 2'-deoxynucleosides | 3(a-i) |
| 118 | 16(a-i) | All 2'-deoxynucleosides | 3(a-i) |
| 119 | 17(a-i) | All 2'-deoxynucleosides | 3(a-i) |
| 120 | 18(a-i) | All 2'-deoxynucleosides | 3(a-i) |
| 121 | 19(a-i) | All 2'-deoxynucleosides | 3(a-i) |
| 122 | 20(a-i) | All 2'-deoxynucleosides | 3(a-i) |
| 123 | 21(a-i) | All 2'-deoxynucleosides | 3(a-i) |
| 124 | 22(a-i) | All 2'-deoxynucleosides | 3(a-i) |
| 125 | 1(a-i) | All 2'-deoxynucleosides | 4(a-i) |
| 126 | 2(a-i) | All 2'-deoxynucleosides | 4(a-i) |
| 127 | 3(a-i) | All 2'-deoxynucleosides | 4(a-i) |
| 128 | 4(a-i) | All 2'-deoxynucleosides | 4(a-i) |
| 129 | 5(a-i) | All 2'-deoxynucleosides | 4(a-i) |
| 130 | 6(a-i) | All 2'-deoxynucleosides | 4(a-i) |
| 131 | 7(a-i) | All 2'-deoxynucleosides | 4(a-i) |
| 132 | 8(a-i) | All 2'-deoxynucleosides | 4(a-i) |
| 133 | 9(a-i) | All 2'-deoxynucleosides | 4(a-i) |
| 134 | 10(a-i) | All 2'-deoxynucleosides | 4(a-i) |
| 135 | 11(a-i) | All 2'-deoxynucleosides | 4(a-i) |
| 136 | 12(a-i) | All 2'-deoxynucleosides | 4(a-i) |
| 137 | 13(a-i) | All 2'-deoxynucleosides | 4(a-i) |
| 138 | 14(a-i) | All 2'-deoxynucleosides | 4(a-i) |
| 139 | 15(a-i) | All 2'-deoxynucleosides | 4(a-i) |
| 140 | 16(a-i) | All 2'-deoxynucleosides | 4(a-i) |
| 141 | 17(a-i) | All 2'-deoxynucleosides | 4(a-i) |
| 142 | 18(a-i) | All 2'-deoxynucleosides | 4(a-i) |
| 143 | 19(a-i) | All 2'-deoxynucleosides | 4(a-i) |
| 144 | 20(a-i) | All 2'-deoxynucleosides | 4(a-i) |
| 145 | 21(a-i) | All 2'-deoxynucleosides | 4(a-i) |
| 146 | 22(a-i) | All 2'-deoxynucleosides | 4(a-i) |
| 147 | 1(a-i) | All 2'-deoxynucleosides | 5(a-i) |
| 148 | 2(a-i) | All 2'-deoxynucleosides | 5(a-i) |
| 149 | 3(a-i) | All 2'-deoxynucleosides | 5(a-i) |
| 150 | 4(a-i) | All 2'-deoxynucleosides | 5(a-i) |
| 151 | 5(a-i) | All 2'-deoxynucleosides | 5(a-i) |
| 152 | 6(a-i) | All 2'-deoxynucleosides | 5(a-i) |
| 153 | 7(a-i) | All 2'-deoxynucleosides | 5(a-i) |
| 154 | 8(a-i) | All 2'-deoxynucleosides | 5(a-i) |
| 155 | 9(a-i) | All 2'-deoxynucleosides | 5(a-i) |
| 156 | 10(a-i) | All 2'-deoxynucleosides | 5(a-i) |
| 157 | 11(a-i) | All 2'-deoxynucleosides | 5(a-i) |
| 158 | 12(a-i) | All 2'-deoxynucleosides | 5(a-i) |
| 159 | 13(a-i) | All 2'-deoxynucleosides | 5(a-i) |
| 160 | 14(a-i) | All 2'-deoxynucleosides | 5(a-i) |
| 161 | 15(a-i) | All 2'-deoxynucleosides | 5(a-i) |
| 162 | 16(a-i) | All 2'-deoxynucleosides | 5(a-i) |
| 163 | 17(a-i) | All 2'-deoxynucleosides | 5(a-i) |
| 164 | 18(a-i) | All 2'-deoxynucleosides | 5(a-i) |
| 165 | 19(a-i) | All 2'-deoxynucleosides | 5(a-i) |
| 166 | 20(a-i) | All 2'-deoxynucleosides | 5(a-i) |
| 167 | 21(a-i) | All 2'-deoxynucleosides | 5(a-i) |
| 168 | 22(a-i) | All 2'-deoxynucleosides | 5(a-i) |
| 169 | 1(a-i) | All 2'-deoxynucleosides | 6(a-i) |
| 170 | 2(a-i) | All 2'-deoxynucleosides | 6(a-i) |
| 171 | 3(a-i) | All 2'-deoxynucleosides | 6(a-i) |
| 172 | 4(a-i) | All 2'-deoxynucleosides | 6(a-i) |
| 173 | 5(a-i) | All 2'-deoxynucleosides | 6(a-i) |
| 174 | 6(a-i) | All 2'-deoxynucleosides | 6(a-i) |
| 175 | 7(a-i) | All 2'-deoxynucleosides | 6(a-i) |
| 176 | 8(a-i) | All 2'-deoxynucleosides | 6(a-i) |
| 177 | 9(a-i) | All 2'-deoxynucleosides | 6(a-i) |
| 178 | 10(a-i) | All 2'-deoxynucleosides | 6(a-i) |
| 179 | 11(a-i) | All 2'-deoxynucleosides | 6(a-i) |
| 180 | 12(a-i) | All 2'-deoxynucleosides | 6(a-i) |
| 181 | 13(a-i) | All 2'-deoxynucleosides | 6(a-i) |
| 182 | 14(a-i) | All 2'-deoxynucleosides | 6(a-i) |
| 183 | 15(a-i) | All 2'-deoxynucleosides | 6(a-i) |
| 184 | 16(a-i) | All 2'-deoxynucleosides | 6(a-i) |
| 184 | 17(a-i) | All 2'-deoxynucleosides | 6(a-i) |
| 186 | 18(a-i) | All 2'-deoxynucleosides | 6(a-i) |
| 187 | 19(a-i) | All 2'-deoxynucleosides | 6(a-i) |
| 188 | 20(a-i) | All 2'-deoxynucleosides | 6(a-i) |
| 189 | 21(a-i) | All 2'-deoxynucleosides | 6(a-i) |
| 190 | 22(a-i) | All 2'-deoxynucleosides | 6(a-i) |
| 191 | 1(a-i) | All 2'-deoxynucleosides | 7(a-i) |
| 192 | 2(a-i) | All 2'-deoxynucleosides | 7(a-i) |
| 193 | 3(a-i) | All 2'-deoxynucleosides | 7(a-i) |
| 194 | 4(a-i) | All 2'-deoxynucleosides | 7(a-i) |
| 195 | 5(a-i) | All 2'-deoxynucleosides | 7(a-i) |
| 196 | 6(a-i) | All 2'-deoxynucleosides | 7(a-i) |
| 197 | 7(a-i) | All 2'-deoxynucleosides | 7(a-i) |
| 198 | 8(a-i) | All 2'-deoxynucleosides | 7(a-i) |
| 199 | 9(a-i) | All 2'-deoxynucleosides | 7(a-i) |
| 200 | 10(a-i) | All 2'-deoxynucleosides | 7(a-i) |
| 201 | 11(a-i) | All 2'-deoxynucleosides | 7(a-i) |
| 202 | 12(a-i) | All 2'-deoxynucleosides | 7(a-i) |
| 203 | 13(a-i) | All 2'-deoxynucleosides | 7(a-i) |
| 204 | 14(a-i) | All 2'-deoxynucleosides | 7(a-i) |
| 205 | 15(a-i) | All 2'-deoxynucleosides | 7(a-i) |
| 206 | 16(a-i) | All 2'-deoxynucleosides | 7(a-i) |
| 207 | 17(a-i) | All 2'-deoxynucleosides | 7(a-i) |
| 208 | 18(a-i) | All 2'-deoxynucleosides | 7(a-i) |
| 209 | 19(a-i) | All 2'-deoxynucleosides | 7(a-i) |
| 210 | 20(a-i) | All 2'-deoxynucleosides | 7(a-i) |
| 211 | 21(a-i) | All 2'-deoxynucleosides | 7(a-i) |
| 212 | 22(a-i) | All 2'-deoxynucleosides | 7(a-i) |
| 213 | 1(a-i) | All 2'-deoxynucleosides | 8(a-i) |
| 214 | 2(a-i) | All 2'-deoxynucleosides | 8(a-i) |
| 215 | 3(a-i) | All 2'-deoxynucleosides | 8(a-i) |
| 216 | 4(a-i) | All 2'-deoxynucleosides | 8(a-i) |
| 217 | 5(a-i) | All 2'-deoxynucleosides | 8(a-i) |
| 218 | 6(a-i) | All 2'-deoxynucleosides | 8(a-i) |
| 219 | 7(a-i) | All 2'-deoxynucleosides | 8(a-i) |
| 220 | 8(a-i) | All 2'-deoxynucleosides | 8(a-i) |
| 221 | 9(a-i) | All 2'-deoxynucleosides | 8(a-i) |
| 222 | 10(a-i) | All 2'-deoxynucleosides | 8(a-i) |
| 223 | 11(a-i) | All 2'-deoxynucleosides | 8(a-i) |
| 224 | 12(a-i) | All 2'-deoxynucleosides | 8(a-i) |
| 225 | 13(a-i) | All 2'-deoxynucleosides | 8(a-i) |
| 226 | 14(a-i) | All 2'-deoxynucleosides | 8(a-i) |
| 227 | 15(a-i) | All 2'-deoxynucleosides | 8(a-i) |
| 228 | 16(a-i) | All 2'-deoxynucleosides | 8(a-i) |
| 229 | 17(a-i) | All 2'-deoxynucleosides | 8(a-i) |
| 230 | 18(a-i) | All 2'-deoxynucleosides | 8(a-i) |
| 231 | 19(a-i) | All 2'-deoxynucleosides | 8(a-i) |
| 232 | 20(a-i) | All 2'-deoxynucleosides | 8(a-i) |
| 233 | 21(a-i) | All 2'-deoxynucleosides | 8(a-i) |
| 234 | 22(a-i) | All 2'-deoxynucleosides | 8(a-i) |
| 235 | 1(a-i) | All 2'-deoxynucleosides | 9(a-i) |
| 236 | 2(a-i) | All 2'-deoxynucleosides | 9(a-i) |
| 237 | 3(a-i) | All 2'-deoxynucleosides | 9(a-i) |
| 238 | 4(a-i) | All 2'-deoxynucleosides | 9(a-i) |
| 239 | 5(a-i) | All 2'-deoxynucleosides | 9(a-i) |
| 240 | 6(a-i) | All 2'-deoxynucleosides | 9(a-i) |
| 241 | 7(a-i) | All 2'-deoxynucleosides | 9(a-i) |
| 242 | 8(a-i) | All 2'-deoxynucleosides | 9(a-i) |
| 243 | 9(a-i) | All 2'-deoxynucleosides | 9(a-i) |
| 244 | 10(a-i) | All 2'-deoxynucleosides | 9(a-i) |
| 245 | 11(a-i) | All 2'-deoxynucleosides | 9(a-i) |
| 246 | 12(a-i) | All 2'-deoxynucleosides | 9(a-i) |
| 247 | 13(a-i) | All 2'-deoxynucleosides | 9(a-i) |
| 248 | 14(a-i) | All 2'-deoxynucleosides | 9(a-i) |
| 249 | 15(a-i) | All 2'-deoxynucleosides | 9(a-i) |
| 250 | 16(a-i) | All 2'-deoxynucleosides | 9(a-i) |
| 251 | 17(a-i) | All 2'-deoxynucleosides | 9(a-i) |
| 252 | 18(a-i) | All 2'-deoxynucleosides | 9(a-i) |
| 253 | 19(a-i) | All 2'-deoxynucleosides | 9(a-i) |
| 254 | 20(a-i) | All 2'-deoxynucleosides | 9(a-i) |
| 255 | 21(a-i) | All 2'-deoxynucleosides | 9(a-i) |
| 256 | 22(a-i) | All 2'-deoxynucleosides | 9(a-i) |
| 257 | 1(a-i) | All 2'-deoxynucleosides | 10(a-i) |

TABLE 9-continued

Certain Gapmer Sugar Motifs

| Gapmer motif # | 5-wing sugar motif (from table 1) | Gap | 3'-wing sugar motif (from table 2) |
|---|---|---|---|
| 258 | 2(a-i) | All 2'-deoxynucleosides | 10(a-i) |
| 259 | 3(a-i) | All 2'-deoxynucleosides | 10(a-i) |
| 260 | 4(a-i) | All 2'-deoxynucleosides | 10(a-i) |
| 261 | 5(a-i) | All 2'-deoxynucleosides | 10(a-i) |
| 262 | 6(a-i) | All 2'-deoxynucleosides | 10(a-i) |
| 263 | 7(a-i) | All 2'-deoxynucleosides | 10(a-i) |
| 264 | 8(a-i) | All 2'-deoxynucleosides | 10(a-i) |
| 265 | 9(a-i) | All 2'-deoxynucleosides | 10(a-i) |
| 266 | 10(a-i) | All 2'-deoxynucleosides | 10(a-i) |
| 267 | 11(a-i) | All 2'-deoxynucleosides | 10(a-i) |
| 268 | 12(a-i) | All 2'-deoxynucleosides | 10(a-i) |
| 269 | 13(a-i) | All 2'-deoxynucleosides | 10(a-i) |
| 270 | 14(a-i) | All 2'-deoxynucleosides | 10(a-i) |
| 271 | 15(a-i) | All 2'-deoxynucleosides | 10(a-i) |
| 272 | 16(a-i) | All 2'-deoxynucleosides | 10(a-i) |
| 273 | 17(a-i) | All 2'-deoxynucleosides | 10(a-i) |
| 274 | 18(a-i) | All 2'-deoxynucleosides | 10(a-i) |
| 275 | 19(a-i) | All 2'-deoxynucleosides | 10(a-i) |
| 276 | 20(a-i) | All 2'-deoxynucleosides | 10(a-i) |
| 277 | 21(a-i) | All 2'-deoxynucleosides | 10(a-i) |
| 278 | 22(a-i) | All 2'-deoxynucleosides | 10(a-i) |
| 279 | 1(a)-22(a) | All 2'-deoxynucleosides | 1(a)-10(a) |
| 280 | 1(b)-22(b) | All 2'-deoxynucleosides | 1(a)-10(a) |
| 281 | 1(c)-22(c) | All 2'-deoxynucleosides | 1(a)-10(a) |
| 282 | 1(d)-22(d) | All 2'-deoxynucleosides | 1(a)-10(a) |
| 283 | 1(e)-22(e) | All 2'-deoxynucleosides | 1(a)-10(a) |
| 284 | 1(f)-22(f) | All 2'-deoxynucleosides | 1(a)-10(a) |
| 285 | 1(g)-22(g) | All 2'-deoxynucleosides | 1(a)-10(a) |
| 286 | 1(h)-22(h) | All 2'-deoxynucleosides | 1(a)-10(a) |
| 287 | 1(i)-22(i) | All 2'-deoxynucleosides | 1(a)-10(a) |
| 288 | 1(a)-22(a) | All 2'-deoxynucleosides | 1(b)-10(b) |
| 289 | 1(b)-22(b) | All 2'-deoxynucleosides | 1(b)-10(b) |
| 290 | 1(c)-22(c) | All 2'-deoxynucleosides | 1(b)-10(b) |
| 291 | 1(d)-22(d) | All 2'-deoxynucleosides | 1(b)-10(b) |
| 292 | 1(e)-22(e) | All 2'-deoxynucleosides | 1(b)-10(b) |
| 293 | 1(f)-22(f) | All 2'-deoxynucleosides | 1(b)-10(b) |
| 294 | 1(g)-22(g) | All 2'-deoxynucleosides | 1(b)-10(b) |
| 295 | 1(h)-22(h) | All 2'-deoxynucleosides | 1(b)-10(b) |
| 296 | 1(i)-22(i) | All 2'-deoxynucleosides | 1(b)-10(b) |
| 297 | 1(a)-22(a) | All 2'-deoxynucleosides | 1(c)-10(c) |
| 298 | 1(b)-22(b) | All 2'-deoxynucleosides | 1(c)-10(c) |
| 299 | 1(c)-22(c) | All 2'-deoxynucleosides | 1(c)-10(c) |
| 300 | 1(d)-22(d) | All 2'-deoxynucleosides | 1(c)-10(c) |
| 301 | 1(e)-22(e) | All 2'-deoxynucleosides | 1(c)-10(c) |
| 302 | 1(f)-22(f) | All 2'-deoxynucleosides | 1(c)-10(c) |
| 303 | 1(g)-22(g) | All 2'-deoxynucleosides | 1(c)-10(c) |
| 304 | 1(h)-22(h) | All 2'-deoxynucleosides | 1(c)-10(c) |
| 305 | 1(i)-22(i) | All 2'-deoxynucleosides | 1(c)-10(c) |
| 306 | 1(a)-22(a) | All 2'-deoxynucleosides | 1(d)-10(d) |
| 307 | 1(b)-22(b) | All 2'-deoxynucleosides | 1(d)-10(d) |
| 308 | 1(c)-22(c) | All 2'-deoxynucleosides | 1(d)-10(d) |
| 309 | 1(d)-22(d) | All 2'-deoxynucleosides | 1(d)-10(d) |
| 310 | 1(e)-22(e) | All 2'-deoxynucleosides | 1(d)-10(d) |
| 311 | 1(f)-22(f) | All 2'-deoxynucleosides | 1(d)-10(d) |
| 312 | 1(g)-22(g) | All 2'-deoxynucleosides | 1(d)-10(d) |
| 313 | 1(h)-22(h) | All 2'-deoxynucleosides | 1(d)-10(d) |
| 314 | 1(i)-22(i) | All 2'-deoxynucleosides | 1(d)-10(d) |
| 315 | 1(a)-22(a) | All 2'-deoxynucleosides | 1(e)-10(e) |
| 316 | 1(b)-22(b) | All 2'-deoxynucleosides | 1(e)-10(e) |
| 317 | 1(c)-22(c) | All 2'-deoxynucleosides | 1(e)-10(e) |
| 318 | 1(d)-22(d) | All 2'-deoxynucleosides | 1(e)-10(e) |
| 319 | 1(e)-22(e) | All 2'-deoxynucleosides | 1(e)-10(e) |
| 320 | 1(f)-22(f) | All 2'-deoxynucleosides | 1(e)-10(e) |
| 321 | 1(g)-22(g) | All 2'-deoxynucleosides | 1(e)-10(e) |
| 322 | 1(h)-22(h) | All 2'-deoxynucleosides | 1(e)-10(e) |
| 323 | 1(i)-22(i) | All 2'-deoxynucleosides | 1(e)-10(e) |
| 324 | 1(a)-22(a) | All 2'-deoxynucleosides | 1(f)-10(f) |
| 325 | 1(b)-22(b) | All 2'-deoxynucleosides | 1(f)-10(f) |
| 326 | 1(c)-22(c) | All 2'-deoxynucleosides | 1(f)-10(f) |
| 327 | 1(d)-22(d) | All 2'-deoxynucleosides | 1(f)-10(f) |
| 328 | 1(e)-22(e) | All 2'-deoxynucleosides | 1(f)-10(f) |
| 329 | 1(f)-22(f) | All 2'-deoxynucleosides | 1(f)-10(f) |
| 330 | 1(g)-22(g) | All 2'-deoxynucleosides | 1(f)-10(f) |
| 331 | 1(h)-22(h) | All 2'-deoxynucleosides | 1(f)-10(f) |
| 332 | 1(i)-22(i) | All 2'-deoxynucleosides | 1(f)-10(f) |
| 333 | 1(a)-22(a) | All 2'-deoxynucleosides | 1(g)-10(g) |
| 334 | 1(b)-22(b) | All 2'-deoxynucleosides | 1(g)-10(g) |
| 335 | 1(c)-22(c) | All 2'-deoxynucleosides | 1(g)-10(g) |
| 336 | 1(d)-22(d) | All 2'-deoxynucleosides | 1(g)-10(g) |
| 337 | 1(e)-22(e) | All 2'-deoxynucleosides | 1(g)-10(g) |
| 338 | 1(f)-22(f) | All 2'-deoxynucleosides | 1(g)-10(g) |
| 339 | 1(g)-22(g) | All 2'-deoxynucleosides | 1(g)-10(g) |
| 340 | 1(h)-22(h) | All 2'-deoxynucleosides | 1(g)-10(g) |
| 341 | 1(i)-22(i) | All 2'-deoxynucleosides | 1(g)-10(g) |
| 342 | 1(a)-22(a) | All 2'-deoxynucleosides | 1(h)-10(h) |
| 343 | 1(b)-22(b) | All 2'-deoxynucleosides | 1(h)-10(h) |
| 344 | 1(c)-22(c) | All 2'-deoxynucleosides | 1(h)-10(h) |
| 345 | 1(d)-22(d) | All 2'-deoxynucleosides | 1(h)-10(h) |
| 346 | 1(e)-22(e) | All 2'-deoxynucleosides | 1(h)-10(h) |
| 347 | 1(f)-22(f) | All 2'-deoxynucleosides | 1(h)-10(h) |
| 348 | 1(g)-22(g) | All 2'-deoxynucleosides | 1(h)-10(h) |
| 349 | 1(h)-22(h) | All 2'-deoxynucleosides | 1(h)-10(h) |
| 350 | 1(i)-22(i) | All 2'-deoxynucleosides | 1(h)-10(h) |
| 351 | 1(a)-22(a) | All 2'-deoxynucleosides | 1(i)-10(i) |
| 352 | 1(b)-22(b) | All 2'-deoxynucleosides | 1(i)-10(i) |
| 353 | 1(c)-22(c) | All 2'-deoxynucleosides | 1(i)-10(i) |
| 354 | 1(d)-22(d) | All 2'-deoxynucleosides | 1(i)-10(i) |
| 355 | 1(e)-22(e) | All 2'-deoxynucleosides | 1(i)-10(i) |
| 356 | 1(f)-22(f) | All 2'-deoxynucleosides | 1(i)-10(i) |
| 357 | 1(g)-22(g) | All 2'-deoxynucleosides | 1(i)-10(i) |
| 358 | 1(h)-22(h) | All 2'-deoxynucleosides | 1(i)-10(i) |
| 359 | 1(i)-22(i) | All 2'-deoxynucleosides | 1(i)-10(i) |
| 360 | 1(a-l) | All 2'-deoxynucleosides | 1(a-l) |
| 361 | 2(a-l) | All 2'-deoxynucleosides | 1(a-l) |
| 362 | 3(a-l) | All 2'-deoxynucleosides | 1(a-l) |
| 363 | 4(a-l) | All 2'-deoxynucleosides | 1(a-l) |
| 364 | 5(a-l) | All 2'-deoxynucleosides | 1(a-l) |
| 365 | 6(a-l) | All 2'-deoxynucleosides | 1(a-l) |
| 366 | 7(a-l) | All 2'-deoxynucleosides | 1(a-l) |
| 367 | 8(a-l) | All 2'-deoxynucleosides | 1(a-l) |
| 368 | 9(a-l) | All 2'-deoxynucleosides | 1(a-l) |
| 369 | 10(a-l) | All 2'-deoxynucleosides | 1(a-l) |
| 370 | 11(a-l) | All 2'-deoxynucleosides | 1(a-l) |
| 371 | 12(a-l) | All 2'-deoxynucleosides | 1(a-l) |
| 372 | 13(a-l) | All 2'-deoxynucleosides | 1(a-l) |
| 373 | 14(a-l) | All 2'-deoxynucleosides | 1(a-l) |
| 374 | 15(a-l) | All 2'-deoxynucleosides | 1(a-l) |
| 375 | 16(a-l) | All 2'-deoxynucleosides | 1(a-l) |
| 376 | 17(a-l) | All 2'-deoxynucleosides | 1(a-l) |
| 377 | 18(a-l) | All 2'-deoxynucleosides | 1(a-l) |
| 378 | 19(a-l) | All 2'-deoxynucleosides | 1(a-l) |
| 379 | 20(a-l) | All 2'-deoxynucleosides | 1(a-l) |
| 380 | 21(a-l) | All 2'-deoxynucleosides | 1(a-l) |
| 381 | 22(a-l) | All 2'-deoxynucleosides | 1(a-l) |
| 382 | 1(a-l) | All 2'-deoxynucleosides | 2(a-l) |
| 383 | 2(a-l) | All 2'-deoxynucleosides | 2(a-l) |
| 384 | 3(a-l) | All 2'-deoxynucleosides | 2(a-l) |
| 385 | 4(a-l) | All 2'-deoxynucleosides | 2(a-l) |
| 386 | 5(a-l) | All 2'-deoxynucleosides | 2(a-l) |
| 387 | 6(a-l) | All 2'-deoxynucleosides | 2(a-l) |
| 388 | 7(a-l) | All 2'-deoxynucleosides | 2(a-l) |
| 389 | 8(a-l) | All 2'-deoxynucleosides | 2(a-l) |
| 390 | 9(a-l) | All 2'-deoxynucleosides | 2(a-l) |
| 391 | 10(a-l) | All 2'-deoxynucleosides | 2(a-l) |
| 392 | 11(a-l) | All 2'-deoxynucleosides | 2(a-l) |
| 393 | 12(a-l) | All 2'-deoxynucleosides | 2(a-l) |
| 394 | 13(a-l) | All 2'-deoxynucleosides | 2(a-l) |
| 395 | 14(a-l) | All 2'-deoxynucleosides | 2(a-l) |
| 396 | 15(a-l) | All 2'-deoxynucleosides | 2(a-l) |
| 397 | 16(a-l) | All 2'-deoxynucleosides | 2(a-l) |
| 398 | 17(a-l) | All 2'-deoxynucleosides | 2(a-l) |
| 399 | 18(a-l) | All 2'-deoxynucleosides | 2(a-l) |
| 400 | 19(a-l) | All 2'-deoxynucleosides | 2(a-l) |
| 401 | 20(a-l) | All 2'-deoxynucleosides | 2(a-l) |
| 402 | 21(a-l) | All 2'-deoxynucleosides | 2(a-l) |
| 403 | 22(a-l) | All 2'-deoxynucleosides | 2(a-l) |
| 404 | 1(a-l) | All 2'-deoxynucleosides | 3(a-l) |
| 405 | 2(a-l) | All 2'-deoxynucleosides | 3(a-l) |

TABLE 9-continued

Certain Gapmer Sugar Motifs

| Gapmer motif # | 5-wing sugar motif (from table 1) | Gap | 3'-wing sugar motif (from table 2) |
|---|---|---|---|
| 406 | 3(a-l) | All 2'-deoxynucleosides | 3(a-l) |
| 407 | 4(a-l) | All 2'-deoxynucleosides | 3(a-l) |
| 408 | 5(a-l) | All 2'-deoxynucleosides | 3(a-l) |
| 409 | 6(a-l) | All 2'-deoxynucleosides | 3(a-l) |
| 410 | 7(a-l) | All 2'-deoxynucleosides | 3(a-l) |
| 411 | 8(a-l) | All 2'-deoxynucleosides | 3(a-l) |
| 412 | 9(a-l) | All 2'-deoxynucleosides | 3(a-l) |
| 413 | 10(a-l) | All 2'-deoxynucleosides | 3(a-l) |
| 414 | 11(a-l) | All 2'-deoxynucleosides | 3(a-l) |
| 415 | 12(a-l) | All 2'-deoxynucleosides | 3(a-l) |
| 416 | 13(a-l) | All 2'-deoxynucleosides | 3(a-l) |
| 417 | 14(a-l) | All 2'-deoxynucleosides | 3(a-l) |
| 418 | 15(a-l) | All 2'-deoxynucleosides | 3(a-l) |
| 419 | 16(a-l) | All 2'-deoxynucleosides | 3(a-l) |
| 420 | 17(a-l) | All 2'-deoxynucleosides | 3(a-l) |
| 421 | 18(a-l) | All 2'-deoxynucleosides | 3(a-l) |
| 422 | 19(a-l) | All 2'-deoxynucleosides | 3(a-l) |
| 423 | 20(a-l) | All 2'-deoxynucleosides | 3(a-l) |
| 424 | 21(a-l) | All 2'-deoxynucleosides | 3(a-l) |
| 425 | 22(a-l) | All 2'-deoxynucleosides | 3(a-l) |
| 426 | 1(a-l) | All 2'-deoxynucleosides | 4(a-l) |
| 427 | 2(a-l) | All 2'-deoxynucleosides | 4(a-l) |
| 428 | 3(a-l) | All 2'-deoxynucleosides | 4(a-l) |
| 429 | 4(a-l) | All 2'-deoxynucleosides | 4(a-l) |
| 430 | 5(a-l) | All 2'-deoxynucleosides | 4(a-l) |
| 431 | 6(a-l) | All 2'-deoxynucleosides | 4(a-l) |
| 432 | 7(a-l) | All 2'-deoxynucleosides | 4(a-l) |
| 433 | 8(a-l) | All 2'-deoxynucleosides | 4(a-l) |
| 434 | 9(a-l) | All 2'-deoxynucleosides | 4(a-l) |
| 435 | 10(a-l) | All 2'-deoxynucleosides | 4(a-l) |
| 436 | 11(a-l) | All 2'-deoxynucleosides | 4(a-l) |
| 437 | 12(a-l) | All 2'-deoxynucleosides | 4(a-l) |
| 438 | 13(a-l) | All 2'-deoxynucleosides | 4(a-l) |
| 439 | 14(a-l) | All 2'-deoxynucleosides | 4(a-l) |
| 440 | 15(a-l) | All 2'-deoxynucleosides | 4(a-l) |
| 441 | 16(a-l) | All 2'-deoxynucleosides | 4(a-l) |
| 442 | 17(a-l) | All 2'-deoxynucleosides | 4(a-l) |
| 443 | 18(a-l) | All 2'-deoxynucleosides | 4(a-l) |
| 444 | 19(a-l) | All 2'-deoxynucleosides | 4(a-l) |
| 445 | 20(a-l) | All 2'-deoxynucleosides | 4(a-l) |
| 446 | 21(a-l) | All 2'-deoxynucleosides | 4(a-l) |
| 447 | 22(a-l) | All 2'-deoxynucleosides | 4(a-l) |
| 448 | 1(a-l) | All 2'-deoxynucleosides | 5(a-l) |
| 449 | 2(a-l) | All 2'-deoxynucleosides | 5(a-l) |
| 450 | 3(a-l) | All 2'-deoxynucleosides | 5(a-l) |
| 451 | 4(a-l) | All 2'-deoxynucleosides | 5(a-l) |
| 452 | 5(a-l) | All 2'-deoxynucleosides | 5(a-l) |
| 453 | 6(a-l) | All 2'-deoxynucleosides | 5(a-l) |
| 454 | 7(a-l) | All 2'-deoxynucleosides | 5(a-l) |
| 455 | 8(a-l) | All 2'-deoxynucleosides | 5(a-l) |
| 456 | 9(a-l) | All 2'-deoxynucleosides | 5(a-l) |
| 457 | 10(a-l) | All 2'-deoxynucleosides | 5(a-l) |
| 458 | 11(a-l) | All 2'-deoxynucleosides | 5(a-l) |
| 459 | 12(a-l) | All 2'-deoxynucleosides | 5(a-l) |
| 460 | 13(a-l) | All 2'-deoxynucleosides | 5(a-l) |
| 461 | 14(a-l) | All 2'-deoxynucleosides | 5(a-l) |
| 462 | 15(a-l) | All 2'-deoxynucleosides | 5(a-l) |
| 463 | 16(a-l) | All 2'-deoxynucleosides | 5(a-l) |
| 464 | 17(a-l) | All 2'-deoxynucleosides | 5(a-l) |
| 465 | 18(a-l) | All 2'-deoxynucleosides | 5(a-l) |
| 466 | 19(a-l) | All 2'-deoxynucleosides | 5(a-l) |
| 467 | 20(a-l) | All 2'-deoxynucleosides | 5(a-l) |
| 468 | 21(a-l) | All 2'-deoxynucleosides | 5(a-l) |
| 469 | 22(a-l) | All 2'-deoxynucleosides | 5(a-l) |
| 470 | 1(a-l) | All 2'-deoxynucleosides | 6(a-l) |
| 471 | 2(a-l) | All 2'-deoxynucleosides | 6(a-l) |
| 472 | 3(a-l) | All 2'-deoxynucleosides | 6(a-l) |
| 473 | 4(a-l) | All 2'-deoxynucleosides | 6(a-l) |
| 474 | 5(a-l) | All 2'-deoxynucleosides | 6(a-l) |
| 475 | 6(a-l) | All 2'-deoxynucleosides | 6(a-l) |
| 476 | 7(a-l) | All 2'-deoxynucleosides | 6(a-l) |
| 477 | 8(a-l) | All 2'-deoxynucleosides | 6(a-l) |
| 478 | 9(a-l) | All 2'-deoxynucleosides | 6(a-l) |
| 479 | 10(a-l) | All 2'-deoxynucleosides | 6(a-l) |
| 480 | 11(a-l) | All 2'-deoxynucleosides | 6(a-l) |
| 481 | 12(a-l) | All 2'-deoxynucleosides | 6(a-l) |
| 482 | 13(a-l) | All 2'-deoxynucleosides | 6(a-l) |
| 483 | 14(a-l) | All 2'-deoxynucleosides | 6(a-l) |
| 484 | 15(a-l) | All 2'-deoxynucleosides | 6(a-l) |
| 485 | 16(a-l) | All 2'-deoxynucleosides | 6(a-l) |
| 486 | 17(a-l) | All 2'-deoxynucleosides | 6(a-l) |
| 487 | 18(a-l) | All 2'-deoxynucleosides | 6(a-l) |
| 488 | 19(a-l) | All 2'-deoxynucleosides | 6(a-l) |
| 489 | 20(a-l) | All 2'-deoxynucleosides | 6(a-l) |
| 490 | 21(a-l) | All 2'-deoxynucleosides | 6(a-l) |
| 491 | 22(a-l) | All 2'-deoxynucleosides | 6(a-l) |
| 492 | 1(a-l) | All 2'-deoxynucleosides | 7(a-l) |
| 493 | 2(a-l) | All 2'-deoxynucleosides | 7(a-l) |
| 494 | 3(a-l) | All 2'-deoxynucleosides | 7(a-l) |
| 495 | 4(a-l) | All 2'-deoxynucleosides | 7(a-l) |
| 496 | 5(a-l) | All 2'-deoxynucleosides | 7(a-l) |
| 497 | 6(a-l) | All 2'-deoxynucleosides | 7(a-l) |
| 498 | 7(a-l) | All 2'-deoxynucleosides | 7(a-l) |
| 499 | 8(a-l) | All 2'-deoxynucleosides | 7(a-l) |
| 500 | 9(a-l) | All 2'-deoxynucleosides | 7(a-l) |
| 501 | 10(a-l) | All 2'-deoxynucleosides | 7(a-l) |
| 502 | 11(a-l) | All 2'-deoxynucleosides | 7(a-l) |
| 503 | 12(a-l) | All 2'-deoxynucleosides | 7(a-l) |
| 504 | 13(a-l) | All 2'-deoxynucleosides | 7(a-l) |
| 505 | 14(a-l) | All 2'-deoxynucleosides | 7(a-l) |
| 506 | 15(a-l) | All 2'-deoxynucleosides | 7(a-l) |
| 507 | 16(a-l) | All 2'-deoxynucleosides | 7(a-l) |
| 508 | 17(a-l) | All 2'-deoxynucleosides | 7(a-l) |
| 509 | 18(a-l) | All 2'-deoxynucleosides | 7(a-l) |
| 510 | 19(a-l) | All 2'-deoxynucleosides | 7(a-l) |
| 511 | 20(a-l) | All 2'-deoxynucleosides | 7(a-l) |
| 512 | 21(a-l) | All 2'-deoxynucleosides | 7(a-l) |
| 513 | 22(a-l) | All 2'-deoxynucleosides | 7(a-l) |
| 514 | 1(a-l) | All 2'-deoxynucleosides | 8(a-l) |
| 515 | 2(a-l) | All 2'-deoxynucleosides | 8(a-l) |
| 516 | 3(a-l) | All 2'-deoxynucleosides | 8(a-l) |
| 517 | 4(a-l) | All 2'-deoxynucleosides | 8(a-l) |
| 518 | 5(a-l) | All 2'-deoxynucleosides | 8(a-l) |
| 519 | 6(a-l) | All 2'-deoxynucleosides | 8(a-l) |
| 520 | 7(a-l) | All 2'-deoxynucleosides | 8(a-l) |
| 521 | 8(a-l) | All 2'-deoxynucleosides | 8(a-l) |
| 522 | 9(a-l) | All 2'-deoxynucleosides | 8(a-l) |
| 523 | 10(a-l) | All 2'-deoxynucleosides | 8(a-l) |
| 524 | 11(a-l) | All 2'-deoxynucleosides | 8(a-l) |
| 525 | 12(a-l) | All 2'-deoxynucleosides | 8(a-l) |
| 526 | 13(a-l) | All 2'-deoxynucleosides | 8(a-l) |
| 527 | 14(a-l) | All 2'-deoxynucleosides | 8(a-l) |
| 528 | 15(a-l) | All 2'-deoxynucleosides | 8(a-l) |
| 529 | 16(a-l) | All 2'-deoxynucleosides | 8(a-l) |
| 530 | 17(a-l) | All 2'-deoxynucleosides | 8(a-l) |
| 531 | 18(a-l) | All 2'-deoxynucleosides | 8(a-l) |
| 532 | 19(a-l) | All 2'-deoxynucleosides | 8(a-l) |
| 533 | 20(a-l) | All 2'-deoxynucleosides | 8(a-l) |
| 534 | 21(a-l) | All 2'-deoxynucleosides | 8(a-l) |
| 535 | 22(a-l) | All 2'-deoxynucleosides | 8(a-l) |
| 536 | 1(a-l) | All 2'-deoxynucleosides | 9(a-l) |
| 537 | 2(a-l) | All 2'-deoxynucleosides | 9(a-l) |
| 538 | 3(a-l) | All 2'-deoxynucleosides | 9(a-l) |
| 539 | 4(a-l) | All 2'-deoxynucleosides | 9(a-l) |
| 540 | 5(a-l) | All 2'-deoxynucleosides | 9(a-l) |
| 541 | 6(a-l) | All 2'-deoxynucleosides | 9(a-l) |
| 542 | 7(a-l) | All 2'-deoxynucleosides | 9(a-l) |
| 543 | 8(a-l) | All 2'-deoxynucleosides | 9(a-l) |
| 544 | 9(a-l) | All 2'-deoxynucleosides | 9(a-l) |
| 545 | 10(a-l) | All 2'-deoxynucleosides | 9(a-l) |
| 546 | 11(a-l) | All 2'-deoxynucleosides | 9(a-l) |
| 547 | 12(a-l) | All 2'-deoxynucleosides | 9(a-l) |
| 548 | 13(a-l) | All 2'-deoxynucleosides | 9(a-l) |
| 549 | 14(a-l) | All 2'-deoxynucleosides | 9(a-l) |
| 550 | 15(a-l) | All 2'-deoxynucleosides | 9(a-l) |
| 551 | 16(a-l) | All 2'-deoxynucleosides | 9(a-l) |
| 552 | 17(a-l) | All 2'-deoxynucleosides | 9(a-l) |
| 553 | 18(a-l) | All 2'-deoxynucleosides | 9(a-l) |

TABLE 9-continued

Certain Gapmer Sugar Motifs

| Gapmer motif # | 5-wing sugar motif (from table 1) | Gap | 3'-wing sugar motif (from table 2) |
|---|---|---|---|
| 554 | 19(a-l) | All 2'-deoxynucleosides | 9(a-l) |
| 555 | 20(a-l) | All 2'-deoxynucleosides | 9(a-l) |
| 556 | 21(a-l) | All 2'-deoxynucleosides | 9(a-l) |
| 557 | 22(a-l) | All 2'-deoxynucleosides | 9(a-l) |
| 558 | 1(a-l) | All 2'-deoxynucleosides | 10(a-l) |
| 559 | 2(a-l) | All 2'-deoxynucleosides | 10(a-l) |
| 560 | 3(a-l) | All 2'-deoxynucleosides | 10(a-l) |
| 561 | 4(a-l) | All 2'-deoxynucleosides | 10(a-l) |
| 562 | 5(a-l) | All 2'-deoxynucleosides | 10(a-l) |
| 563 | 6(a-l) | All 2'-deoxynucleosides | 10(a-l) |
| 564 | 7(a-l) | All 2'-deoxynucleosides | 10(a-l) |
| 565 | 8(a-l) | All 2'-deoxynucleosides | 10(a-l) |
| 566 | 9(a-l) | All 2'-deoxynucleosides | 10(a-l) |
| 567 | 10(a-l) | All 2'-deoxynucleosides | 10(a-l) |
| 568 | 11(a-l) | All 2'-deoxynucleosides | 10(a-l) |
| 569 | 12(a-l) | All 2'-deoxynucleosides | 10(a-l) |
| 570 | 13(a-l) | All 2'-deoxynucleosides | 10(a-l) |
| 571 | 14(a-l) | All 2'-deoxynucleosides | 10(a-l) |
| 572 | 15(a-l) | All 2'-deoxynucleosides | 10(a-l) |
| 573 | 16(a-l) | All 2'-deoxynucleosides | 10(a-l) |
| 574 | 17(a-l) | All 2'-deoxynucleosides | 10(a-l) |
| 575 | 18(a-l) | All 2'-deoxynucleosides | 10(a-l) |
| 576 | 19(a-l) | All 2'-deoxynucleosides | 10(a-l) |
| 577 | 20(a-l) | All 2'-deoxynucleosides | 10(a-l) |
| 578 | 21(a-l) | All 2'-deoxynucleosides | 10(a-l) |
| 579 | 22(a-l) | All 2'-deoxynucleosides | 10(a-l) |
| 580 | 1(j)-22(j) | All 2'-deoxynucleosides | 1(a)-10(a) |
| 581 | 1(k)-22(k) | All 2'-deoxynucleosides | 1(a)-10(a) |
| 582 | 1(l)-22(l) | All 2'-deoxynucleosides | 1(a)-10(a) |
| 583 | 1(j)-22(j) | All 2'-deoxynucleosides | 1(b)-10(b) |
| 584 | 1(k)-22(k) | All 2'-deoxynucleosides | 1(b)-10(b) |
| 585 | 1(l)-22(l) | All 2'-deoxynucleosides | 1(b)-10(b) |
| 586 | 1(j)-22(j) | All 2'-deoxynucleosides | 1(c)-10(c) |
| 587 | 1(k)-22(k) | All 2'-deoxynucleosides | 1(c)-10(c) |
| 588 | 1(l)-22(l) | All 2'-deoxynucleosides | 1(c)-10(c) |
| 589 | 1(j)-22(j) | All 2'-deoxynucleosides | 1(d)-10(d) |
| 590 | 1(k)-22(k) | All 2'-deoxynucleosides | 1(d)-10(d) |
| 591 | 1(l)-22(l) | All 2'-deoxynucleosides | 1(d)-10(d) |
| 592 | 1(j)-22(j) | All 2'-deoxynucleosides | 1(e)-10(e) |
| 593 | 1(k)-22(k) | All 2'-deoxynucleosides | 1(e)-10(e) |
| 594 | 1(l)-22(l) | All 2'-deoxynucleosides | 1(e)-10(e) |
| 595 | 1(j)-22(j) | All 2'-deoxynucleosides | 1(f)-10(f) |
| 596 | 1(k)-22(k) | All 2'-deoxynucleosides | 1(f)-10(f) |
| 597 | 1(l)-22(l) | All 2'-deoxynucleosides | 1(f)-10(f) |
| 598 | 1(j)-22(j) | All 2'-deoxynucleosides | 1(g)-10(g) |
| 599 | 1(k)-22(k) | All 2'-deoxynucleosides | 1(g)-10(g) |
| 600 | 1(l)-22(l) | All 2'-deoxynucleosides | 1(g)-10(g) |
| 601 | 1(j)-22(j) | All 2'-deoxynucleosides | 1(h)-10(h) |
| 602 | 1(k)-22(k) | All 2'-deoxynucleosides | 1(h)-10(h) |
| 603 | 1(l)-22(l) | All 2'-deoxynucleosides | 1(h)-10(h) |
| 604 | 1(j)-22(j) | All 2'-deoxynucleosides | 1(i)-10(i) |
| 605 | 1(k)-22(k) | All 2'-deoxynucleosides | 1(i)-10(i) |
| 606 | 1(l)-22(l) | All 2'-deoxynucleosides | 1(i)-10(i) |
| 607 | 1(j)-22(j) | All 2'-deoxynucleosides | 1(j)-10(j) |
| 608 | 1(k)-22(k) | All 2'-deoxynucleosides | 1(j)-10(j) |
| 609 | 1(l)-22(l) | All 2'-deoxynucleosides | 1(j)-10(j) |
| 610 | 1(j)-22(j) | All 2'-deoxynucleosides | 1(k)-10(k) |
| 611 | 1(k)-22(k) | All 2'-deoxynucleosides | 1(k)-10(k) |
| 612 | 1(l)-22(l) | All 2'-deoxynucleosides | 1(k)-10(k) |
| 612 | 1(j)-22(j) | All 2'-deoxynucleosides | 1(l)-10(l) |
| 614 | 1(k)-22(k) | All 2'-deoxynucleosides | 1(l)-10(l) |
| 615 | 1(l)-22(l) | All 2'-deoxynucleosides | 1(l)-10(l) |
| 616 | 1k | All 2'-deoxynucleosides | 1m |

In certain embodiments, a gapmer comprises a 5'-wing selected from among the 5'-wings provided herein and any 3'-wing. In certain embodiments, a gapmer comprises a 5'-wing selected from among 1(a-i) to 22(a-i). In certain embodiments, a gapmer comprises a 5'-wing selected from among 1(a-l) to 22(a-l). In certain embodiments, a gapmer comprises a 3'-wing selected from among the 3'-wings provided herein and any 5'-wing. In certain embodiments, a gapmer comprises a 3'-wing selected from among 1(a-i) to 10(a-i). In certain embodiments, a gapmer comprises a 3'-wing selected from among 1(a-l) to 10(a-l).

In certain embodiments, a gapmer has a sugar motif other than: E-K-K-(D)$_9$-K-K-E; E-E-E-E-K-(D)$_9$-E-E-E-E-E; E-K-K-K-(D)$_9$-K-K-K-E; K-E-E-K-(D)$_9$-K-E-E-K; K-D-D-K-(D)$_9$-K-D-D-K; K-E-K-E-K-(D)$_9$-K-E-K-E-K; K-D-K-D-K-(D)$_9$-K-D-K-D-K; E-K-E-K-(D)$_9$-K-E-K-E; E-E-E-E-K-(D)$_8$-E-E-E-E; or E-K-E-K-E-(D)$_9$-E-K-E-K-E. In certain embodiments, a gapmer not having one of the above motifs has a sugar motif of Formula I. In certain embodiments, a gapmer not having one of the above motifs has a sugar motif selected from motifs 1-58. In certain embodiments, a gapmer not having one of the above motifs has a sugar motif of Formula I and selected from sugar motifs 1-58. In certain embodiments, a gapmer not having one of the above motifs has a sugar motif of Formula II. In certain embodiments, a gapmer not having one of the above motifs has a sugar motif selected from motifs 1-615. In certain embodiments, a gapmer not having one of the above motifs has a sugar motif of Formula II and selected from sugar motifs 1-615.

In certain embodiments a gapmer comprises a A-(D)$_4$-A-(D)$_4$-A-(D)$_4$-AA motif. In certain embodiments a gapmer comprises a B-(D)$_4$-A-(D)$_4$-A-(D)$_4$-AA motif. In certain embodiments a gapmer comprises a A-(D)$_4$-B-(D)$_4$-A-(D)$_4$-AA motif. In certain embodiments a gapmer comprises a A-(D)$_4$-A-(D)$_4$-B-(D)$_4$-AA motif. In certain embodiments a gapmer comprises a A-(D)$_4$-A-(D)$_4$-A-(D)$_4$-BA motif. In certain embodiments a gapmer comprises a A-(D)$_4$-A-(D)$_4$-A-(D)$_4$-BB motif. In certain embodiments a gapmer comprises a K-(D)$_4$-K-(D)$_4$-K-(D)$_4$-K-E motif.

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The sugar modification motif is independently selected, so such oligonucleotides having a gapped internucleoside linkage motif may or may not have a gapped sugar modification motif and if it does have a gapped sugar motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

In certain embodiments, any of the gapmer motifs provided above, including but not limited to gapmer motifs 1-278 provided in Tables 3 and 4, may have any of the above lengths. One of skill in the art will appreciate that certain lengths may not be possible for certain motifs. For example: a gapmer having a 5'-wing region consisting of four nucleotides, a gap consisting of at least six nucleotides, and a 3'-wing region consisting of three nucleotides cannot have an overall length less than 13 nucleotides. Thus, one would understand that the lower length limit is 13 and that the limit of 10 in "10-20" has no effect in that embodiment.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range. For example, an oligonucleotide consisting of 20-25 linked nucleosides comprising a 5'-wing consisting of 5 linked nucleosides; a 3'-wing consisting of 5 linked nucleosides and a central gap consisting of 10 linked nucleosides (5+5+10=20) may have up to 5 nucleosides that are not part of the 5'-wing, the 3'-wing, or the gap (before reaching the overall length limitation of 25). Such additional nucleosides may be 5' of the 5'-wing and/or 3' of the 3' wing.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides, such as those provided in the non-limiting Table 5 below.

TABLE 10

Certain Oligonucleotides

| Overall Length | Sugar motif | Internucleoside Linkage Motif | Nucleobase Mod. Motif |
|---|---|---|---|
| 12 | Gapmer motif selected from 1-278 | uniform PS | uniform unmodified |
| 14 | Gapmer motif selected from 1-278 | 2-14-2 gapmer: PO in wings and PS in gap | uniform unmodified |
| 14 | Gapmer motif selected from 1-278 | uniform PS | uniform unmodified; all C's are 5-meC |
| 16 | Gapmer of Formula I | uniform PS | uniform unmodified; no Cs are 5-meC) |
| 16 | Gapmer of Formula I | uniform PS | uniform unmodified; at least one nucleobase is a 5-meC |
| 16 | Gapmer of Formula I and having motif selected from 1-58 | uniform PS | uniform unmodified |
| 17 | Gapmer of Formula I and having motif selected from 1-58 | uniform PO | uniform unmodified |
| 17 | Gapmer motif selected from 1-278 | uniform PS | uniform unmodified |
| 17 | Gapmer of Formula I | uniform PS | uniform unmodified |
| 18 | Gapmer of Formula I and having motif selected from 1-58 | uniform PS | uniform unmodified |
| 18 | Gapmer motif selected from 1-278 | uniform PS | uniform unmodified |
| 20 | Gapmer of Formula I | uniform PS | uniform unmodified |
| 12 | Gapmer motif selected from 1-359 | uniform PS | uniform unmodified |
| 14 | Gapmer motif selected from 1-359 | 2-14-2 gapmer: PO in wings and PS in gap | uniform unmodified |
| 14 | Gapmer motif selected from 1-359 | uniform PS | uniform unmodified; all C's are 5-meC |
| 16 | Gapmer of Formula II | uniform PS | uniform unmodified; no Cs are 5-meC) |
| 16 | Gapmer of Formula II | uniform PS | uniform unmodified; at least one nucleobase is a 5-meC |
| 16 | Gapmer of Formula II and having motif selected from 1-359 | uniform PS | uniform unmodified |
| 17 | Gapmer of Formula II and having motif selected from 1-359 | uniform PO | uniform unmodified |
| 17 | Gapmer motif selected from 1-359 | uniform PS | uniform unmodified |
| 17 | Gapmer of Formula II | uniform PS | uniform unmodified |
| 18 | Gapmer of Formula I and having motif selected from 1-359 | uniform PS | uniform unmodified |
| 18 | Gapmer motif selected from 1-359 | uniform PS | uniform unmodified |
| 20 | Gapmer of Formula II | uniform PS | uniform unmodified |
| 12 | Gapmer motif selected from 1-615 | uniform PS | uniform unmodified |
| 14 | Gapmer motif selected from 1-615 | 2-14-2 gapmer: PO in wings and PS in gap | uniform unmodified |
| 14 | Gapmer motif selected from 1-615 | uniform PS | uniform unmodified; all C's are 5-meC |
| 16 | Gapmer of Formula I and having motif selected from 1-615 | uniform PS | uniform unmodified |

TABLE 10-continued

Certain Oligonucleotides

| Overall Length | Sugar motif | Internucleoside Linkage Motif | Nucleobase Mod. Motif |
|---|---|---|---|
| 17 | Gapmer of Formula I and having motif selected from 1-615 | uniform PO | uniform unmodified |
| 17 | Gapmer motif selected from 1-615 | uniform PS | uniform unmodified |
| 18 | Gapmer of Formula I and having motif selected from 1-615 | uniform PS | uniform unmodified |
| 18 | Gapmer motif selected from 1-615 | uniform PS | uniform unmodified |

The above table is intended only to illustrate and not to limit the various combinations of the parameters of oligonucleotides of the present invention. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3' end of an oligomeric compound, but before one or more terminal group nucleosides. In certain embodiments, conjugate groups are placed within a terminal group. In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Compounds

In certain embodiments, oligomeric compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

Certain Antisense Activities and Mechanisms

In certain antisense activities, hybridization of an antisense compound results in recruitment of a protein that cleaves of the target nucleic acid. For example, certain antisense compounds result in RNase H mediated cleavage of target nucleic acid. RNase H is a cellular endonuclease that cleaves the RNA strand of an RNA:DNA duplex. The "DNA" in such an RNA:DNA duplex, need not be unmodified DNA. In certain embodiments, the invention provides antisense compounds that are sufficiently "DNA-like" to elicit RNase H activity. Such DNA-like antisense compounds include, but are not limited to gapmers having unmodified deoxyfuronose sugar moieties in the nucleosides of the gap and modified sugar moieties in the nucleosides of the wings.

Antisense activities may be observed directly or indirectly. In certain embodiments, observation or detection of an antisense activity involves observation or detection of a change in an amount of a target nucleic acid or protein encoded by such target nucleic acid; a change in the ratio of splice variants of a nucleic acid or protein; and/or a phenotypic change in a cell or animal.

In certain embodiments, compounds comprising oligonucleotides having a gapmer motif described herein have desirable properties compared to non-gapmer oligonucleotides or to gapmers having other motifs. In certain circumstances, it is desirable to identify motifs resulting in a favorable combination of potent antisense activity and relatively low toxicity. In certain embodiments, compounds of the present invention have a favorable therapeutic index (measure of potency divided by measure of toxicity).

Certain Target Nucleic Acids

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid encodes a protein. In certain such embodiments, the target nucleic acid is selected from: an mRNA and a pre-mRNA, including intronic, exonic and untranslated regions. In certain embodiments, oligomeric compounds are at least partially complementary to more than one target nucleic acid. For example, antisense compounds of the present invention may mimic microRNAs, which typically bind to multiple targets.

In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is selected from among non-coding RNA, including exonic regions of pre-mRNA. In certain embodiments, the target nucleic acid is a ribosomal RNA (rRNA). In certain embodiments, the target nucleic acid is a non-coding RNA associated with splicing of other pre-mRNAs. In certain embodiments, the target nucleic acid is a nuclear-retained non-coding RNA.

In certain embodiments, antisense compounds described herein are complementary to a target nucleic acid comprising a single-nucleotide polymorphism. In certain such embodiments, the antisense compound is capable of modulating expression of one allele of the single-nucleotide polymorphism-containing-target nucleic acid to a greater or lesser extent than it modulates another allele. In certain embodiments an antisense compound hybridizes to a single-nucleotide polymorphism-containing-target nucleic acid at the single-nucleotide polymorphism site. In certain embodiments an antisense compound hybridizes to a single-nucleotide polymorphism-containing-target nucleic acid near the single-nucleotide polymorphism site. In certain embodiments, the target nucleic acid is a Huntingtin gene transcript. In certain embodiments, the target nucleic acid is a single-nucleotide polymorphism-containing-target nucleic acid other than a Huntingtin gene transcript. In certain embodiments, the target nucleic acid is any nucleic acid other than a Huntingtin gene transcript.

Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics.

Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising an oligomeric compound of the present invention to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures.

NONLIMITING DISCLOSURE AND INCORPORATION BY REFERENCE

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Where nucleobase sequences are not provided, to allow assessment of the relative effects of nucleobase sequence and chemical modification, throughout the examples, oligomeric compounds are assigned a "Sequence Code." Oligomeric compounds having the same Sequence Code have the same nucleobase sequence. Oligomeric compounds having different Sequence Codes have different nucleobase sequences.

Example 1: Modified Antisense Oligonucleotides Targeting Human Target-X

Antisense oligonucleotides were designed targeting a Target-X nucleic acid and were tested for their effects on Target-X mRNA in vitro. ISIS 407939, which was described in an earlier publication (WO 2009/061851) was also tested.

The newly designed chimeric antisense oligonucleotides and their motifs are described in Table 11. The internucleoside linkages throughout each gapmer are phosphorothioate linkages (P=S). Nucleosides followed by "d" indicate 2'-deoxyribonucleosides. Nucleosides followed by "k" indicate constrained ethyl (cEt) nucleosides. Nucleosides followed by "e" indicate 2'-O-methythoxyethyl (2'-MOE) nucleosides. "N" indicates modified or naturally occurring nucleobases (A, T, C, G, U, or 5-methyl C).

Each gapmer listed in Table 11 is targeted to the human Target-X genomic sequence.

Activity of the newly designed gapmers was compared to a 5-10-5 2'-MOE gapmer, ISIS 407939 targeting human Target-X and is further described in USPN XXX, incorporated herein by reference. Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 was used to measure mRNA levels. Target-X mRNA levels were adjusted according to total RNA content, as measured by RIBOGREEN®. Results are presented as percent inhibition of Target-X, relative to untreated control cells, and indicate that several of the newly designed antisense oligonucleotides are more potent than ISIS 407939. A total of 771 oligonucleotides were tested. Only those oligonucleotides which were selected for further studies are shown in Table 11. Each of the newly designed antisense oligonucleotides provided in Table 10 achieved greater than 80% inhibition and, therefore, are more active than ISIS 407939.

TABLE 11

Inhibition of human Target-X mRNA levels by chimeric antisense oligonucleotides targeted to Target-X

| Sequence (5' to 3') | ISIS NO | % inhibition | Gap Motif | Chemistry | Wing Chemistry 5' | Wing Chemistry 3' | SEQ CODE | SEQ ID NO |
|---|---|---|---|---|---|---|---|---|
| NkNkNkNdNdNdNdNkNd NdNdNdNdNeNeNe | 473359 | 92 | 3-10-3 | Deoxy/cEt | kkk | eee | 21 | 19 |
| NkNkNkNdNdNdNdNkNd NdNdNdNdNeNeNe | 473360 | 96 | 3-10-3 | Deoxy/cEt | kkk | eee | 22 | 19 |
| NkNkNkNdNdNdNdNdNd NdNdNdNdNkNkNk | 473168 | 94 | 3-10-3 | Full deoxy | kkk | kkk | 23 | 19 |
| NkNkNkNdNdNdNdNdNd NdNdNdNdNeNeNe | 473317 | 95 | 3-10-3 | Full deoxy | kkk | eee | 23 | 19 |
| NkNkNkNdNdNdNdNkNd NdNdNdNdNeNeNe | 473471 | 90 | 3-10-3 | Deoxy/cEt | kkk | eee | 23 | 19 |
| NkNdNkNdNkNdNdNdNd NdNdNdNdNdNeNe | 473620 | 94 | 5-9-2 | Full deoxy | kdkdk | ee | 23 | 19 |
| NkNkNdNdNdNdNdNdNd NdNdNdNkNk | 473019 | 88 | 2-10-2 | Full deoxy | kk | kk | 24 | 20 |
| NkNkNdNdNdNdNdNdNd NdNdNdNkNk | 473020 | 93 | 2-10-2 | Full deoxy | kk | kk | 25 | 20 |
| NkNkNkNdNdNdNdNdNd NdNdNdNdNeNeNe | 473321 | 93 | 3-10-3 | Full deoxy | kkk | eee | 26 | 19 |
| NkNkNkNdNdNdNdNdNd NdNdNdNdNeNeNe | 473322 | 94 | 3-10-3 | Full deoxy | kkk | eee | 27 | 19 |
| NkNkNkNdNdNdNdNdNd NdNdNdNdNeNeNe | 473323 | 96 | 3-10-3 | Full deoxy | kkk | eee | 28 | 19 |
| NkNkNkNdNdNdNdNdNd NdNdNdNdNeNeNe | 473326 | 94 | 3-10-3 | Full deoxy | kkk | eee | 29 | 19 |
| NkNkNkNdNdNdNdNkNd NdNdNdNdNeNeNe | 473480 | 92 | 3-10-3 | Deoxy/cEt | kkk | eee | 29 | 19 |
| NkNkNkNdNdNdNdNdNd NdNdNdNdNkNkNk | 473178 | 96 | 3-10-3 | Full deoxy | kkk | kkk | 30 | 19 |
| NkNkNkNdNdNdNdNdNd NdNdNdNdNeNeNe | 473327 | 96 | 3-10-3 | Full deoxy | kkk | eee | 30 | 19 |
| NkNkNkNdNdNdNdNkNd NdNdNdNdNeNeNe | 473481 | 93 | 3-10-3 | Deoxy/cEt | kkk | eee | 30 | 19 |
| NkNkNdNkNdNkNdNdNd NdNdNdNdNdNeNe | 473630 | 89 | 5-9-2 | Full deoxy | kdkdk | ee | 30 | 19 |

TABLE 11-continued

Inhibition of human Target-X mRNA levels by chimeric antisense oligonucleotides targeted to Target-X

| Sequence (5' to 3') | ISIS NO | % inhibition | Gap Motif | Chemistry | Wing Chemistry 5' | Wing Chemistry 3' | SEQ CODE | SEQ ID NO |
|---|---|---|---|---|---|---|---|---|
| NkNkNdNdNdNdNdNdNd NdNdNdNkNk | 473029 | 96 | 2-10-2 | Full deoxy | kk | kk | 31 | 20 |
| NkNkNdNdNdNdNdNdNd NdNdNdNkNk | 472925 | 93 | 2-10-2 | Full deoxy | kk | kk | 32 | 20 |
| NkNkNdNdNdNdNdNdNd NdNdNdNkNk | 472926 | 85 | 2-10-2 | Full deoxy | kk | kk | 33 | 20 |
| NkNkNkNdNdNdNdNdNd NdNdNdNkNkNk | 473195 | 97 | 3-10-3 | Full deoxy | kkk | kkk | 34 | 19 |
| NkNkNdNdNdNdNdNdNd NdNdNdNkNk | 473046 | 90 | 2-10-2 | Full deoxy | kk | kk | 35 | 20 |
| NkNkNdNdNdNdNdNdNd NdNdNdNkNk | 472935 | 92 | 2-10-2 | Full deoxy | kk | kk | 36 | 20 |
| NkNkNkNdNdNdNdNdNd NdNdNdNkNkNk | 473089 | 95 | 3-10-3 | Full deoxy | kkk | kkk | 37 | 19 |
| NkNkNkNdNdNdNdNdNd NdNdNdNeNeNe | 473350 | 93 | 3-10-3 | Full deoxy | kkk | eee | 38 | 19 |
| NkNkNkNdNdNdNdNdNd NdNdNdNeNeNe | 473353 | 93 | 3-10-3 | Full deoxy | kkk | eee | 39 | 19 |
| NkNkNdNdNdNdNdNdNd NdNdNdNkNk | 473055 | 91 | 2-10-2 | Full deoxy | kk | kk | 40 | 20 |
| NkNkNkNdNdNdNdNkNd NdNdNdNdNeNeNe | 473392 | 95 | 3-10-3 | Deoxy/cEt | kkk | eee | 41 | 19 |
| NkNkNkNdNdNdNdNdNd NdNdNdNkNkNk | 473095 | 100 | 3-10-3 | Full deoxy | kkk | kkk | 42 | 19 |
| NkNkNkNdNdNdNdNdNd NdNdNdNeNeNe | 473244 | 99 | 3-10-3 | Full deoxy | kkk | eee | 42 | 19 |
| NkNkNkNdNdNdNdNkNd NdNdNdNeNeNe | 473393 | 99 | 3-10-3 | Deoxy/cEt | kkk | eee | 42 | 19 |
| NkNdNkNdNkNdNdNdNd NdNdNdNdNeNe | 473547 | 98 | 5-9-2 | Full deoxy | kdkdk | ee | 42 | 19 |
| NlNkNdNdNdNdNdNdNd NdNdNdNkNk | 472942 | 87 | 2-10-2 | Full deoxy | kk | kk | 43 | 20 |
| NkNkNkNdNdNdNdNdNd NdNdNdNkNkNk | 473098 | 97 | 3-10-3 | Full deoxy | kkk | kkk | 44 | 19 |
| NkNkNkNdNdNdNdNkNd NdNdNdNeNeNe | 473408 | 92 | 3-10-3 | Deoxy/cEt | kkk | eee | 45 | 19 |
| NkNkNdNdNdNdNdNdNd NdNdNdNkNk | 472958 | 89 | 2-10-2 | Full deoxy | kk | kk | 46 | 20 |
| NkNkNdNdNdNdNdNdNd NdNdNdNkNk | 472959 | 90 | 2-10-2 | Full deoxy | kk | kk | 47 | 20 |
| NkNdNkNdNkNdNdNdNd NdNdNdNdNeNe | 473566 | 94 | 5-9-2 | Full deoxy | kdkdk | ee | 48 | 19 |
| NkNdNkNdNkNdNdNdNd NdNdNdNdNeNe | 473567 | 95 | 5-9-2 | Full deoxy | kdkdk | ee | 49 | 19 |
| NkNdNkNdNkNdNdNdNd NdNdNdNdNeNe | 473569 | 92 | 5-9-2 | Full deoxy | kdkdk | ee | 50 | 19 |
| NkNkNdNdNdNdNdNdNd NdNdNdNkNk | 457851 | 90 | 2-10-2 | Full deoxy | kk | kk | 51 | 20 |

TABLE 11-continued

Inhibition of human Target-X mRNA levels by chimeric antisense oligonucleotides targeted to Target-X

| Sequence (5' to 3') | ISIS NO | % inhibition | Gap Motif | Chemistry | Wing Chemistry 5' | Wing Chemistry 3' | SEQ CODE | SEQ ID NO |
|---|---|---|---|---|---|---|---|---|
| NkNkNdNdNdNdNdNdNdNdNdNdNkNk | 472970 | 91 | 2-10-2 | Full deoxy | kk | kk | 32 | 20 |
| NkNkNkNdNdNdNdNdNdNdNdNdNkNkNk | 473125 | 90 | 3-10-3 | Full deoxy | kkk | kkk | 53 | 19 |
| NkNkNkNdNdNdNdNdNdNdNdNdNeNeNe | 473274 | 98 | 3-10-3 | Full deoxy | kkk | eee | 53 | 19 |
| NkNkNkNdNdNdNdNkNdNdNdNdNeNeNe | 473428 | 90 | 3-10-3 | Deoxy/cEt | kkk | eee | 53 | 19 |
| NkNkNdNdNkNdNdNdNdNdNdNdNdNeNe | 473577 | 93 | 5-9-2 | Full deoxy | kdkdk | ee | 53 | 19 |
| NkNkNdNdNdNdNdNdNdNdNdNdNkNk | 472976 | 97 | 2-10-2 | Full deoxy | kk | kk | 54 | 20 |
| NkNkNdNdNdNdNdNdNdNdNdNdNkNk | 472983 | 94 | 2-10-2 | Full deoxy | kk | kk | 55 | 20 |
| NkNkNdNdNdNdNdNdNdNdNdNdNkNk | 472984 | 90 | 2-10-2 | Full deoxy | kk | kk | 56 | 20 |
| NkNkNkNdNdNdNdNdNdNdNdNkNkNk | 473135 | 97 | 3-10-3 | Full deoxy | kkk | kkk | 57 | 19 |
| NkNkNdNdNdNdNdNdNdNdNdNdNkNk | 472986 | 95 | 2-10-2 | Full deoxy | kk | kk | 58 | 20 |
| NkNkNkNdNdNdNdNdNdNdNdNkNkNk | 473137 | 95 | 3-10-3 | Full deoxy | kkk | kkk | 59 | 19 |
| NkNkNkNdNdNdNdNdNdNdNdNeNeNe | 473286 | 95 | 3-10-3 | Full deoxy | kkk | eee | 59 | 19 |
| NkNkNkNdNdNdNdNkNdNdNdNdNeNeNe | 473440 | 88 | 3-10-3 | Deoxy/cEt | kkk | eee | 59 | 19 |
| NkNdNkNdNkNdNdNdNdNdNdNdNdNeNe | 473589 | 97 | 5-9-2 | Full deoxy | kdkdk | ee | 59 | 19 |
| NkNkNdNdNdNdNdNdNdNdNdNdNkNk | 472988 | 85 | 2-10-2 | Full deoxy | kk | kk | 60 | 20 |
| NkNkNkNdNdNdNdNdNdNdNdNdNkNkNk | 473140 | 96 | 3-10-3 | Full deoxy | kkk | kkk | 61 | 19 |
| NkNkNdNdNdNdNdNdNdNdNdNdNkNk | 472991 | 90 | 2-10-2 | Full deoxy | kk | kk | 62 | 20 |
| NkNkNkNdNdNdNdNkNdNdNdNdNeNeNe | 473444 | 94 | 3-10-3 | Deoxy/cEt | kkk | eee | 63 | 19 |
| NkNkNkNdNdNdNdNdNdNdNdNkNkNk | 473142 | 96 | 3-10-3 | Full deoxy | kkk | kkk | 64 | 19 |
| NkNkNkNdNdNdNdNdNdNdNdNdNeNeNe | 473291 | 95 | 3-10-3 | Full deoxy | kkk | eee | 64 | 19 |
| NkNdNkNdNkNdNdNdNdNdNdNdNdNeNe | 473594 | 95 | 5-9-2 | Full deoxy | kdkdk | ee | 64 | 19 |
| NkNkNkNdNdNdNdNdNdNdNdNkNkNk | 473143 | 97 | 3-10-3 | Full deoxy | kkk | kkk | 65 | 19 |
| NkNkNkNdNdNdNdNdNdNdNdNeNeNe | 473292 | 96 | 3-10-3 | Full deoxy | kkk | eee | 65 | 19 |
| NkNkNkNdNdNdNdNkNdNdNdNdNeNeNe | 473446 | 96 | 3-10-3 | Deoxy/cEt | kkk | eee | 65 | 19 |

TABLE 11-continued

Inhibition of human Target-X mRNA levels by chimeric antisense oligonucleotides targeted to Target-X

| Sequence (5' to 3') | ISIS NO | % inhibition | Gap Motif | Chemistry | Wing Chemistry 5' | Wing Chemistry 3' | SEQ CODE | SEQ ID NO |
|---|---|---|---|---|---|---|---|---|
| NkNdNkNdNkNdNdNdNd NdNdNdNdNdNeNe | 473595 | 84 | 5-9-2 | Full deoxy | kdkdk | ee | 65 | 19 |
| NkNkNdNdNdNdNdNdNd NdNdNdNdNkNk | 472994 | 96 | 2-10-2 | Full deoxy | kk | kk | 66 | 20 |
| NkNkNkNdNdNdNdNdNd NdNdNdNdNkNkNk | 473144 | 98 | 3-10-3 | Full deoxy | kkk | kkk | 67 | 19 |
| NkNkNkNdNdNdNdNdNd NdNdNdNdNeNeNe | 473293 | 96 | 3-10-3 | Full deoxy | kkk | eee | 67 | 19 |
| NkNkNdNdNdNdNdNdNd NdNdNdNkNk | 472995 | 96 | 2-10-2 | Full deoxy | kk | kk | 68 | 20 |
| NkNkNkNdNdNdNdNdNd NdNdNdNdNeNeNe | 473294 | 91 | 3-10-3 | Full deoxy | kkk | eee | 69 | 19 |
| NkNdNkNdNkNdNdNdNd NdNdNdNdNeNe | 473597 | 94 | 5-9-2 | Full deoxy | kdkdk | ee | 69 | 19 |
| NkNkNdNdNdNdNdNdNd NdNdNdNkNk | 472996 | 94 | 2-10-2 | Full deoxy | kk | kk | 70 | 20 |
| NkNkNkNdNdNdNdNd NdNdNdNdNeNeNe | 473295 | 92 | 3-10-3 | Full deoxy | kkk | eee | 71 | 19 |
| NeNeNeNeNeNdNdNdNd NdNdNdNdNdNeNeNeNeNe | 407939 | 80 | 5-10-5 | Full deoxy | eeeee | eeeee | 72 | 21 |
| NkNkNkNdNdNdNdNdNd NdNdNdNdNeNeNe | 473296 | 98 | 3-10-3 | Full deoxy | kkk | eee | 73 | 19 |
| NkNkNkNdNdNdNdNkNd NdNdNdNdNeNeNe | 473450 | 95 | 3-10-3 | Deoxy/ cEt | kkk | eee | 73 | 19 |
| NkNkNdNdNdNdNdNdNd NdNdNdNkNk | 472998 | 97 | 2-10-2 | Full deoxy | kk | kk | 74 | 20 | e = 2'-MOE,
k = cEt,
d = 2'-deoxyribonucleoside

Example 2: Modified Antisense Oligonucleotides Comprising Constrained Ethyl (cEt) and F-HNAmodifications Targeting Human Target-X Additional antisense oligonucleotides were designed targeting a Target-X nucleic acid and were tested for their effects on Target-X mRNA in vitro. ISIS 407939 was also tested.

The newly designed chimeric antisense oligonucleotides and their motifs are described in Table 12. The internucleoside linkages throughout each gapmer are phosphorothioate linkages (P=S). Nucleosides followed by "d" indicate 2'-deoxyribonucleosides. Nucleosides followed by "k" indicate constrained ethyl (cEt) nucleosides. Nucleosides followed by "e" indicate 2'-O-methythoxyethyl (2'-MOE) modified nucleosides. Nucleosides followed by 'g' indicate F-HNA modified nucleosides. "N" indicates modified or naturally occurring nucleobases (A, T, C, G, U, or 5-methyl C).

Each gapmer listed in Table 12 is targeted to the human Target-X genomic sequence.

Activity of the newly designed gapmers was compared to a 5-10-5 2'-MOE gapmer, ISIS 407939 targeting human Target-X. Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 was used to measure mRNA levels. Target-X mRNA levels were adjusted according to total RNA content, as measured by RIBOGREEN®. Results are presented as percent inhibition of Target-X, relative to untreated control cells, and demonstrate that several of the newly designed gapmers are more potent than ISIS 407939. A total of 765 oligonucleotides were tested. Only those oligonucleotides which were selected for further studies are shown in Table 12. All but one of the newly designed antisense oligonucleotides provided in Table 12 achieved greater than 30% inhibition and, therefore, are more active than ISIS 407939.

TABLE 12

Inhibition of human Target-X mRNA levels by chimeric antisense oligonucleotides targeted to Target-X

| Sequence (5' to 3') | ISIS No | % inhibition | Motif | Gap Chemistry | Wing Chemistry 5' | Wing Chemistry 3' | SEQ CODE | SEQ ID NO |
|---|---|---|---|---|---|---|---|---|
| NgNgNdNdNdNdNdNd NdNdNdNgNg | 482838 | 81 | 2-10-2 | Full deoxy | gg | gg | 25 | 20 |
| NgNgNgNdNdNdNdNd NdNdNdNgNgNg | 482992 | 93 | 3-10-3 | Full deoxy | ggg | ggg | 28 | 19 |
| NgNgNgNdNdNdNdNd NdNdNdNgNgNg | 482996 | 97 | 3-10-3 | Full deoxy | ggg | ggg | 30 | 19 |
| NgNdNgNdNgNdNdNd NdNdNdNdNeNe | 483284 | 82 | 5-9-2 | Full deoxy | gdgdg | ee | 23 | 19 |
| NgNdNgNdNgNdNdNd NdNdNdNdNeNe | 483289 | 70 | 5-9-2 | Full deoxy | gdgdg | ee | 27 | 19 |
| NgNdNgNdNgNdNdNd NdNdNdNdNeNe | 483290 | 80 | 5-9-2 | Full deoxy | gdgdg | ee | 28 | 19 |
| NgNdNgNdNgNdNdNd NdNdNdNdNeNe | 483294 | 69 | 5-9-2 | Full deoxy | gdgdg | ee | 30 | 19 |
| NgNgNdNdNdNdNdNd NdNdNeNeNeNe | 483438 | 81 | 2-10-4 | Full deoxy | gg | eeee | 23 | 19 |
| NgNgNdNdNdNdNdNd NdNdNeNeNeNe | 483444 | 84 | 2-10-4 | Full deoxy | gg | eeee | 28 | 19 |
| NgNgNdNdNdNdNdNd NdNdNeNeNeNe | 483448 | 77 | 2-10-4 | Full deoxy | gg | eeee | 30 | 19 |
| NgNgNdNdNdNdNdNd NdNdNdNgNg | 482847 | 79 | 2-10-2 | Full deoxy | gg | gg | 31 | 20 |
| NgNgNdNdNdNdNdNd NdNdNdNgNg | 482747 | 85 | 2-10-2 | Full deoxy | gg | gg | 32 | 20 |
| NgNgNdNdNdNdNdNd NdNdNdNgNg | 482873 | 81 | 2-10-2 | Full deoxy | gg | gg | 40 | 20 |
| NgNgNdNdNdNdNdNd NdNdNgNg | 482874 | 82 | 2-10-2 | Full deoxy | gg | gg | 75 | 20 |
| NgNgNdNdNdNdNd NdNdNdNdNgNg | 482875 | 82 | 2-10-2 | Full deoxy | gg | gg | 76 | 20 |
| NgNgNgNdNdNdNd NdNdNdNdNgNgNg | 482896 | 95 | 3-10-3 | Full deoxy | ggg | ggg | 77 | 19 |
| NgNgNgNdNdNdNdNd NdNdNdNgNgNg | 483019 | 89 | 3-10-3 | Full deoxy | ggg | ggg | 38 | 19 |
| NgNdNgNdNdNdNdNd NdNdNdNgNdNg | 483045 | 92 | 3-10-3 | Full deoxy | gdg | gdg | 77 | 19 |
| NgNdNgNdNgNdNdNd NdNdNdNdNeNe | 483194 | 64 | 3-10-3 | Full deoxy | gdg | gdg | 77 | 19 |
| NgNdNgNdNgNdNdNd NdNdNdNdNeNe | 483317 | 79 | 5-9-2 | Full deoxy | gdgdg | ee | 38 | 19 |
| NgNgNdNdNdNdNdNd NdNdNeNeNeNe | 483343 | 75 | 2-10-4 | Full deoxy | gg | eeee | 57 | 19 |
| NgNgNdNdNdNdNdNdNd NdNdNeNeNeNe | 483471 | 76 | 2-10-4 | Full deoxy | gg | eeee | 38 | 19 |
| NgNgNdNdNdNdNdNd NdNdNeNeNeNe | 483478 | 20 | 2-10-4 | Full deoxy | gg | eeee | 78 | 19 |
| NeNeNeNeNeNdNdNdNd NdNdNdNdNdNeNeNeNeNe | 407939 | 30 | 5-10-5 | Full deoxy | eeeee | eeeee | 72 | 21 |

TABLE 12-continued

Inhibition of human Target-X mRNA levels by chimeric antisense oligonucleotides targeted to Target-X

| Sequence (5' to 3') | ISIS No | % inhibition | Motif | Gap Chemistry | Wing Chemistry 5' | Wing Chemistry 3' | SEQ CODE | SEQ ID NO |
|---|---|---|---|---|---|---|---|---|
| NgNgNdNdNdNdNdNd NdNdNdNdNgNg | 482784 | 83 | 2-10-2 | Full deoxy | gg | gg | 79 | 20 |
| NgNgNdNdNdNdNdNd NdNdNdNdNgNg | 482794 | 91 | 2-10-2 | Full deoxy | gg | gg | 54 | 20 |
| NgNgNdNdNdNdNdNd NdNdNdNdNgNg | 482804 | 80 | 2-10-2 | Full deoxy | gg | gg | 58 | 20 |
| NgNgNdNdNdNdNdNd NdNdNdNdNgNg | 482812 | 81 | 2-10-2 | Full deoxy | gg | gg | 66 | 20 |
| NgNgNdNdNdNdNdNd NdNdNdNdNgNg | 482813 | 92 | 2-10-2 | Full deoxy | gg | gg | 68 | 20 |
| NgNgNdNdNdNdNdNd NdNdNdNdNgNg | 482814 | 94 | 2-10-2 | Full deoxy | gg | gg | 70 | 20 |
| NgNgNdNdNdNdNdNd NdNdNdNdNgNg | 482815 | 81 | 2-10-2 | Full deoxy | gg | gg | 80 | 20 |
| NgNgNdNdNdNdNdNd NdNdNdNdNgNg | 482816 | 71 | 2-10-2 | Full deoxy | gg | gg | 74 | 20 |
| NgNgNgNdNdNdNdNd NdNdNdNdNgNgNg | 482916 | 90 | 3-10-3 | Full deoxy | ggg | ggg | 44 | 19 |
| NgNgNgNdNdNdNdNd NdNdNdNdNgNgNg | 482932 | 89 | 3-10-3 | Full deoxy | ggg | ggg | 48 | 19 |
| NgNgNgNdNdNdNdNd NdNdNdNdNgNgNg | 482953 | 93 | 3-10-3 | Full deoxy | ggg | ggg | 57 | 19 |
| NgNgNgNdNdNdNdNd NdNdNdNdNgNgNg | 482962 | 97 | 3-10-3 | Full deoxy | ggg | ggg | 67 | 19 |
| NgNgNgNdNdNdNdNd NdNdNdNdNgNgNg | 482963 | 96 | 3-10-3 | Full deoxy | ggg | ggg | 69 | 19 |
| NgNgNgNdNdNdNdNd NdNdNdNdNgNgNg | 482965 | 89 | 3-10-3 | Full deoxy | ggg | ggg | 73 | 19 |
| NgNgNgNdNdNdNdNd NdNdNdNdNgNdNg | 483065 | 69 | 3-10-3 | Full deoxy | ggg | ggg | 44 | 19 |
| NgNdNgNdNdNdNdNd NdNdNdNdNgNdNg | 483092 | 89 | 3-10-3 | Full deoxy | gdg | gdg | 53 | 19 |
| NgNdNgNdNgNdNdNd NdNdNdNdNdNeNe | 483241 | 79 | 5-9-2 | Full deoxy | gdgdg | ee | 53 | 19 |
| NgNdNgNdNgNdNdNd NdNdNdNdNdNeNe | 483253 | 76 | 5-9-2 | Full deoxy | gdgdg | ee | 59 | 19 |
| NgNdNgNdNgNdNdNd NdNdNdNdNdNeNe | 483258 | 70 | 5-9-2 | Full deoxy | gdgdg | ee | 64 | 19 |
| NgNdNgNdNgNdNdNd NdNdNdNdNdNeNe | 483260 | 62 | 5-9-2 | Full deoxy | gdgdg | ee | 67 | 19 |
| NgNdNgNdNgNdNdNd NdNdNdNdNdNeNe | 483261 | 76 | 5-9-2 | Full deoxy | gdgdg | ee | 69 | 19 |
| NgNdNgNdNgNdNdNd NdNdNdNdNdNeNe | 483262 | 75 | 5-9-2 | Full deoxy | gdgdg | ee | 71 | 19 |
| NgNdNgNdNgNdNdNd NdNdNdNdNdNeNe | 483263 | 73 | 5-9-2 | Full deoxy | gdgdg | ee | 73 | 19 |
| NgNgNdNdNdNdNdNd NdNdNdNdNeNeNeNe | 483364 | 78 | 2-10-4 | Full deoxy | gg | eeee | 81 | 19 |

TABLE 12-continued

Inhibition of human Target-X mRNA levels by chimeric antisense oligonucleotides targeted to Target-X

| Sequence (5' to 3') | ISIS No | % inhibition | Motif | Gap Chemistry | Wing Chemistry 5' | Wing Chemistry 3' | SEQ CODE | SEQ ID NO |
|---|---|---|---|---|---|---|---|---|
| NgNgNdNdNdNdNdNd NdNdNdNdNeNeNeNe | 483395 | 86 | 2-10-4 | Full deoxy | gg | eeee | 53 | 19 |
| NgNgNdNdNdNdNdNd NdNdNdNdNeNeNeNe | 483413 | 83 | 2-10-4 | Full deoxy | gg | eeee | 65 | 19 |
| NgNgNdNdNdNdNdNd NdNdNdNdNeNeNeNe | 483414 | 76 | 2-10-4 | Full deoxy | gg | eeee | 67 | 19 |
| NgNgNdNdNdNdNdNd NdNdNdNdNeNeNeNe | 483415 | 85 | 2-10-4 | Full deoxy | gg | eeee | 69 | 19 |
| NgNgNdNdNdNdNdNd NdNdNdNdNeNeNeNe | 483416 | 77 | 2-10-4 | Full deoxy | gg | eeee | 71 | 19 |
| NgNgNdNdNdNdNdNd NdNdNdNdNeNeNeNe | 483417 | 83 | 2-10-4 | Full deoxy | gg | eeee | 73 | 19 | e = 2'-MOE, d = 2'-deoxyribonucleoside, g = F-HNA

Example 3: Modified Antisense Oligonucleotides Comprising 2'-MOE and Constrained Ethyl (cEt) Modifications Targeting Human Target-X Additional antisense oligonucleotides were designed targeting a Target-X nucleic acid and were tested for their effects on Target-X mRNA in vitro. ISIS 403052, ISIS 407594, ISIS 407606, ISIS 407939, and ISIS 416438, which were described in an earlier publication (WO 2009/061851) were also tested.

The newly designed chimeric antisense oligonucleotides are 16 nucleotides in length and their motifs are described in Table 13. The chemistry column of Table 12 presents the sugar motif of each oligonucleotide, wherein "e" indicates a 2'-O-methythoxylethyl (2'-MOE) nucleoside, "k" indicates a constrained ethyl (cEt) and "d" indicates a 2'-deoxyribonucleoside. The internucleoside linkages throughout each gapmer are hosphorothioate (P=S) linkages. All cytosine residues throughout each oligonucleotide are 5-methylcytosines.

Each gapmer listed in Table 13 is targeted to the human Target-X genomic sequence.

Activity of the newly designed gapmers was compared to ISIS 403052, ISIS 407594, ISIS 407606, ISIS 407939, and ISIS 416438. Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 (described hereinabove in Example 1) was used to measure mRNA levels. Target-X mRNA levels were adjusted according to total RNA content, as measured by RIBOGREEN. Results are presented as percent inhibition of Target-X, relative to untreated control cells. A total of 380 oligonucleotides were tested. Only those oligonucleotides which were selected for further studies are shown in Table 13. Each of the newly designed antisense oligonucleotides provided in Table 13 achieved greater than 64% inhibition and, therefore, are more potent than each of ISIS 403052, ISIS 407594, ISIS 407606, ISIS 407939, and ISIS 416438.

TABLE 13

Inhibition of human Target-X mRNA levels by chimeric antisense oligonucleotides targeted to Target-X

| ISIS No | Chemistry | Motif | % inhibition | SEQ CODE |
|---|---|---|---|---|
| 403052 | eeeee-(d10)-eeeee | 5-10-5 | 64 | 82 |
| 407594 | eeeee-(d10)-eeeee | 5-10-5 | 40 | 83 |
| 407606 | eeeee-(d10)-eeeee | 5-10-5 | 39 | 84 |
| 407939 | eeeee-(d10)-eeeee | 5-10-5 | 57 | 72 |
| 416438 | eeeee-(d10)-eeeee | 5-10-5 | 62 | 85 |
| 484487 | kdk-(d10)-dkdk | 3-10-3 | 91 | 77 |
| 484539 | kdk-d(10)-kdk | 3-10-3 | 92 | 53 |
| 484546 | kdk-d(10)-kdk | 3-10-3 | 92 | 86 |
| 484547 | kdk-d(10)-kdk | 3-10-3 | 89 | 87 |
| 484549 | kdk-d(10)-kdk | 3-10-3 | 91 | 57 |
| 484557 | kdk-d(10)-kdk | 3-10-3 | 92 | 65 |
| 484558 | kdk-d(10)-kdk | 3-10-3 | 94 | 67 |
| 484559 | kdk-d(10)-kdk | 3-10-3 | 90 | 69 |
| 484582 | kdk-d(10)-kdk | 3-10-3 | 88 | 23 |
| 484632 | kk-d(10)-eeee | 2-10-4 | 90 | 88 |
| 484641 | kk-d(10)-eeee | 2-10-4 | 91 | 77 |
| 484679 | kk-d(10)-eeee | 2-10-4 | 90 | 49 |
| 484693 | kk-d(10)-eeee | 2-10-4 | 93 | 53 |
| 484711 | kk-d(10)-eeee | 2-10-4 | 92 | 65 |
| 484712 | kk-d(10)-eeee | 2-10-4 | 92 | 67 |
| 484713 | kk-d(10)-eeee | 2-10-4 | 85 | 69 |
| 484714 | kk-d(10)-eeee | 2-10-4 | 83 | 71 |
| 484715 | kk-d(10)-eeee | 2-10-4 | 93 | 73 |
| 484736 | kk-d(10)-eeee | 2-10-4 | 89 | 23 |
| 484742 | kk-d(10)-eeee | 2-10-4 | 93 | 28 |
| 484746 | kk-d(10)-eeee | 2-10-4 | 88 | 30 |
| 484771 | kk-d(10)-eeee | 2-10-4 | 89 | 89 | e = 2'-MOE,
k = cEt,
d = 2'-deoxyribonucleoside

Example 4: Antisense Inhibition of Human Target-X with 5-10-5 2'-MOE Gapmers Additional antisense oligonucleotides were designed targeting a Target-X nucleic acid and were tested for their effects on Target-X mRNA in vitro. Also tested were ISIS 403094, ISIS 407641, ISIS 407643, ISIS 407662, ISIS 407900, ISIS 407910, ISIS 407935, ISIS 407936, ISIS 407939, ISIS 416446, ISIS 416449, ISIS 416455, ISIS 416472, ISIS 416477, ISIS 416507, ISIS 416508, ISIS 422086, ISIS 422087, ISIS 422140, and ISIS 422142, 5-10-5 2'-MOE gapmers targeting human Target-X, which were described in an earlier publication (WO 2009/061851), incorporated herein by reference.

The newly designed modified antisense oligonucleotides are 20 nucleotides in length and their motifs are described in Tables 14 and 15. The chemistry column of Tables 14 and 15 present the sugar motif of each oligonucleotide, wherein "e" indicates a 2'-O-methythoxylethyl (2'-MOE) nucleoside and "d" indicates a 2'-deoxyribonucleoside. The internucleoside linkages throughout each gapmer are hosphorothioate (P=S) linkages. All cytosine residues throughout each oligonucleotide are 5-methylcytosines.

Each gapmer listed in Table 14 is targeted to the human Target-X genomic sequence.

Activity of the newly designed gapmers was compared to ISIS 403094, ISIS 407641, ISIS 407643, ISIS 407662, ISIS 407900, ISIS 407910, ISIS 407935, ISIS 407936, ISIS 407939, ISIS 416446, ISIS 416449, ISIS 416455, ISIS 416472, ISIS 416477, ISIS 416507, ISIS 416508, ISIS 422086, ISIS 422087, ISIS 422140, and ISIS 422142. Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 (described hereinabove in Example 1) was used to measure mRNA levels. Target-X mRNA levels were adjusted according to total RNA content, as measured by RIBOGREEN. Results are presented as percent inhibition of Target-X, relative to untreated control cells. A total of 916 oligonucleotides were tested. Only those oligonucleotides which were selected for further studies are shown in Tables 14 and 15.

TABLE 14

Inhibition of human Target-X mRNA levels by chimeric antisense oligonucleotides targeted to Target-X

| ISIS No | Chemistry | % inhibition | SEQ CODE |
|---|---|---|---|
| 490275 | e5-d(10)-e5 | 35 | 90 |
| 490277 | e5-d(10)-e5 | 73 | 91 |
| 490278 | e5-d(10)-e5 | 78 | 92 |
| 490279 | e5-d(10)-e5 | 66 | 93 |
| 490323 | e5-d(10)-e5 | 65 | 94 |
| 490368 | e5-d(10)-e5 | 78 | 95 |
| 490396 | e5-d(10)-e5 | 76 | 96 |
| 416507 | e5-d(10)-e5 | 73 | 97 |
| 422140 | e5-d(10)-e5 | 59 | 98 |
| 422142 | e5-d(10)-e5 | 73 | 99 |
| 416508 | e5-d(10)-e5 | 75 | 100 |
| 490424 | e5-d(10)-e5 | 57 | 101 |
| 490803 | e5-d(10)-e5 | 70 | 102 |
| 416446 | e5-d(10)-e5 | 73 | 103 |
| 416449 | e5-d(10)-e5 | 33 | 104 |
| 407900 | e5-d(10)-e5 | 66 | 105 |
| 490103 | e5-d(10)-e5 | 87 | 106 |
| 416455 | e5-d(10)-e5 | 42 | 107 |
| 407910 | e5-d(10)-e5 | 25 | 108 |
| 490149 | e5-d(10)-e5 | 82 | 109 |
| 403094 | e5-d(10)-e5 | 60 | 110 |
| 416472 | e5-d(10)-e5 | 78 | 111 |
| 407641 | e5-d(10)-e5 | 64 | 112 |
| 416477 | e5-d(10)-e5 | 25 | 113 |
| 407643 | e5-d(10)-e5 | 78 | 114 |
| 490196 | e5-d(10)-e5 | 81 | 115 |
| 490197 | e5-d(10)-e5 | 85 | 116 |
| 490208 | e5-d(10)-e5 | 89 | 117 |
| 490209 | e5-d(10)-e5 | 81 | 118 |
| 422086 | e5-d(10)-e5 | 90 | 119 |
| 407935 | e5-d(10)-e5 | 91 | 120 |

TABLE 14-continued

Inhibition of human Target-X mRNA levels by chimeric antisense oligonucleotides targeted to Target-X

| ISIS No | Chemistry | % inhibition | SEQ CODE |
|---|---|---|---|
| 422087 | e5-d(10)-e5 | 89 | 121 |
| 407936 | e5-d(10)-e5 | 80 | 122 |
| 407939 | e5-d(10)-e5 | 67 | 72 | e = 2'-MOE,
d = 2'-deoxynucleoside

TABLE 15

Inhibition of human Target-X mRNA levels by chimeric antisense oligonucleotides targeted to Target-X

| ISIS No | Motif | % inhibition | SEQ CODE |
|---|---|---|---|
| 407662 | e5-d(10)-e5 | 76 | 123 |
| 416446 | e5-d(10)-e5 | 73 | 103 | e = 2'-MOE,
d = 2'-deoxynucleoside

Example 5: Modified Chimeric Antisense Oligonucleotides Comprising Constrained Ethyl (cEt) Modifications at 5' and 3' Wing Regions Targeting Human Target-X Additional antisense oligonucleotides were designed targeting a Target-X nucleic acid and were tested for their effects on Target-X mRNA in vitro. ISIS 407939, which was described in an earlier publication (WO 2009/061851) were also tested. ISIS 457851, ISIS 472925, ISIS 472926, ISIS 472935, ISIS 472942, ISIS 472958, ISIS 472959, ISIS 472970, ISIS 472976, ISIS 472983, ISIS 472984, ISIS 472988, ISIS 472991, ISIS 472994, ISIS 472995, ISIS 472996, ISIS 472998, and ISIS 473020, described in the Examples above were also included in the screen.

The newly designed chimeric antisense oligonucleotides in Table 16 were designed as 2-10-2 cEt gapmers. The newly designed gapmers are 14 nucleosides in length, wherein the central gap segment comprises of ten 2'-deoxyribonucleosides and is flanked by wing segments on the 5' direction and the 3' direction comprising five nucleosides each. Each nucleoside in the 5' wing segment and each nucleoside in the 3' wing segment comprises constrained ethyl (cEt) modification. The internucleoside linkages throughout each gapmer are phosphorothioate (P=S) linkages. All cytosine residues throughout each gapmer are 5-methylcytosines.

Each gapmer listed in Table 16 is targeted to the human Target-X genomic sequence.

Activity of the newly designed oligonucleotides was compared to ISIS 407939. Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 (described hereinabove in Example 1) was used to measure mRNA levels. Target-X mRNA levels were adjusted according to total RNA content, as measured by RIBOGREEN. Results are presented as percent inhibition of Target-X, relative to untreated control cells. A total of 614 oligonucleotides were tested. Only those oligonucleotides which were selected for further studies are shown in Table 16. Many of the newly designed antisense oligonucleotides provided in Table 16 achieved greater than 72% inhibition and, therefore, are more potent than ISIS 407939.

TABLE 16

Inhibition of human Target-X mRNA levels by chimeric antisense oligonucleotides targeted to Target-X

| ISIS No | % inhibition | Motif | Wing Chemistry | SEQ CODE |
|---|---|---|---|---|
| 407939 | 72 | 5-10-5 | cEt | 72 |
| 473020 | 90 | 2-10-2 | cEt | 25 |
| 492465 | 83 | 2-10-2 | cEt | 124 |
| 492467 | 74 | 2-10-2 | cEt | 125 |
| 492492 | 84 | 2-10-2 | cEt | 126 |
| 492494 | 91 | 2-10-2 | cEt | 127 |
| 492503 | 89 | 2-10-2 | cEt | 128 |
| 492530 | 91 | 2-10-2 | cEt | 129 |
| 492534 | 91 | 2-10-2 | cEt | 130 |
| 492536 | 90 | 2-10-2 | cEt | 131 |
| 492541 | 84 | 2-10-2 | cEt | 132 |
| 492545 | 89 | 2-10-2 | cEt | 133 |
| 492566 | 90 | 2-10-2 | cEt | 134 |
| 492571 | 82 | 2-10-2 | cEt | 135 |
| 492572 | 89 | 2-10-2 | cEt | 136 |
| 492573 | 90 | 2-10-2 | cEt | 137 |
| 492574 | 92 | 2-10-2 | cEt | 138 |
| 492575 | 88 | 2-10-2 | cEt | 139 |
| 492593 | 83 | 2-10-2 | cEt | 140 |
| 492617 | 91 | 2-10-2 | cEt | 141 |
| 492618 | 92 | 2-10-2 | cEt | 142 |
| 492619 | 90 | 2-10-2 | cEt | 143 |
| 492621 | 75 | 2-10-2 | cEt | 144 |
| 492104 | 89 | 2-10-2 | cEt | 145 |
| 492105 | 86 | 2-10-2 | cEt | 146 |
| 492189 | 88 | 2-10-2 | cEt | 147 |
| 492194 | 92 | 2-10-2 | cEt | 148 |
| 492195 | 90 | 2-10-2 | cEt | 149 |
| 472925 | 87 | 2-10-2 | cEt | 32 |
| 492196 | 91 | 2-10-2 | cEt | 150 |
| 472926 | 88 | 2-10-2 | cEt | 33 |
| 492205 | 92 | 2-10-2 | cEt | 151 |
| 492215 | 77 | 2-10-2 | cEt | 152 |
| 492221 | 79 | 2-10-2 | cEt | 153 |
| 472935 | 82 | 2-10-2 | cEt | 36 |
| 492234 | 86 | 2-10-2 | cEt | 154 |
| 472942 | 85 | 2-10-2 | cEt | 43 |
| 492276 | 75 | 2-10-2 | cEt | 155 |
| 492277 | 75 | 2-10-2 | cEt | 156 |
| 492306 | 85 | 2-10-2 | cEt | 157 |
| 492317 | 93 | 2-10-2 | cEt | 158 |
| 472958 | 92 | 2-10-2 | cEt | 46 |
| 472959 | 88 | 2-10-2 | cEt | 47 |
| 492329 | 88 | 2-10-2 | cEt | 159 |
| 492331 | 95 | 2-10-2 | cEt | 160 |
| 492333 | 85 | 2-10-2 | cEt | 161 |
| 492334 | 88 | 2-10-2 | cEt | 162 |
| 457851 | 89 | 2-10-2 | cEt | 51 |
| 472970 | 92 | 2-10-2 | cEt | 52 |
| 492365 | 69 | 2-10-2 | cEt | 163 |
| 472976 | 94 | 2-10-2 | cEt | 54 |
| 472983 | 76 | 2-10-2 | cEt | 55 |
| 472984 | 72 | 2-10-2 | cEt | 56 |
| 492377 | 70 | 2-10-2 | cEt | 164 |
| 492380 | 80 | 2-10-2 | cEt | 165 |
| 492384 | 61 | 2-10-2 | cEt | 166 |
| 472988 | 59 | 2-10-2 | cEt | 60 |
| 492388 | 70 | 2-10-2 | cEt | 167 |
| 492389 | 70 | 2-10-2 | cEt | 168 |
| 492390 | 89 | 2-10-2 | cEt | 169 |
| 492391 | 80 | 2-10-2 | cEt | 170 |
| 472991 | 84 | 2-10-2 | cEt | 62 |
| 492398 | 88 | 2-10-2 | cEt | 171 |
| 492399 | 94 | 2-10-2 | cEt | 172 |
| 492401 | 91 | 2-10-2 | cEt | 173 |
| 492403 | 78 | 2-10-2 | cEt | 174 |
| 472994 | 95 | 2-10-2 | cEt | 66 |
| 472995 | 91 | 2-10-2 | cEt | 68 |
| 492404 | 84 | 2-10-2 | cEt | 175 |
| 492405 | 87 | 2-10-2 | cEt | 176 |
| 472996 | 85 | 2-10-2 | cEt | 70 |

TABLE 16-continued

Inhibition of human Target-X mRNA levels by chimeric antisense oligonucleotides targeted to Target-X

| ISIS No | % inhibition | Motif | Wing Chemistry | SEQ CODE |
|---|---|---|---|---|
| 492406 | 43 | 2-10-2 | cEt | 177 |
| 472998 | 92 | 2-10-2 | cEt | 74 |
| 492440 | 89 | 2-10-2 | cEt | 178 |

Example 6: Modified Chimeric Antisense Oligonucleotides Comprising Constrained Ethyl (cEt) Modifications at 5' and 3' Wing Regions Targeting Human Target-X Additional antisense oligonucleotides were designed targeting a Target-X nucleic acid and were tested for their effects on Target-X mRNA in vitro. Also tested was ISIS 407939, a 5-10-5 MOE gapmer targeting human Target-X, which was described in an earlier publication (WO 2009/061851). ISIS 472998 and ISIS 473046, described in the Examples above were also included in the screen.

The newly designed chimeric antisense oligonucleotides in Table 17 were designed as 2-10-2 cEt gapmers. The newly designed gapmers are 14 nucleosides in length, wherein the central gap segment comprises of ten 2'-deoxyribonucleosides and is flanked by wing segments on the 5' direction and the 3' direction comprising five nucleosides each. Each nucleoside in the 5' wing segment and each nucleoside in the 3' wing segment comprise constrained ethyl (cEt) modification. The internucleoside linkages throughout each gapmer are phosphorothioate (P=S) linkages. All cytosine residues throughout each gapmer are 5-methylcytosines.

Each gapmer listed in Table 17 is targeted to the human Target-X genomic sequence.

Activity of the newly designed gapmers was compared to ISIS 407939. Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 (described hereinabove in Example 1) was used to measure mRNA levels. Target-X mRNA levels were adjusted according to total RNA content, as measured by RIBOGREEN. Results are presented as percent inhibition of Target-X, relative to untreated control cells. A total of 757 oligonucleotides were tested. Only those oligonucleotides which were selected for further studies are shown in Table 17. Each of the newly designed antisense oligonucleotides provided in Table 17 achieved greater than 67% inhibition and, therefore, are more potent than 407939.

TABLE 17

Inhibition of human Target-X mRNA levels by chimeric antisense oligonucleotides targeted to Target-X

| ISIS No | % inhibition | Motif | Wing chemistry | SEQ CODE |
|---|---|---|---|---|
| 407939 | 67 | 5-10-5 | cEt | 72 |
| 492651 | 77 | 2-10-2 | cEt | 179 |
| 492652 | 84 | 2-10-2 | cEt | 180 |
| 492658 | 87 | 2-10-2 | cEt | 181 |
| 492725 | 74 | 2-10-2 | cEt | 182 |
| 492730 | 78 | 2-10-2 | cEt | 183 |
| 492731 | 72 | 2-10-2 | cEt | 184 |

TABLE 17-continued

Inhibition of human Target-X mRNA levels by chimeric antisense oligonucleotides targeted to Target-X

| ISIS No | % inhibition | Motif | Wing chemistry | SEQ CODE |
|---|---|---|---|---|
| 492784 | 72 | 2-10-2 | cEt | 185 |
| 492816 | 70 | 2-10-2 | cEt | 186 |
| 492818 | 73 | 2-10-2 | cEt | 187 |
| 492877 | 83 | 2-10-2 | cEt | 188 |
| 492878 | 79 | 2-10-2 | cEt | 189 |
| 492913 | 73 | 2-10-2 | cEt | 190 |
| 492914 | 82 | 2-10-2 | cEt | 191 |
| 492928 | 76 | 5-10-5 | cEt | 192 |
| 492938 | 80 | 2-10-2 | cEt | 193 |
| 492991 | 91 | 2-10-2 | cEt | 194 |
| 492992 | 73 | 2-10-2 | cEt | 195 |
| 493087 | 81 | 2-10-2 | cEt | 196 |
| 493114 | 80 | 2-10-2 | cEt | 197 |
| 493178 | 86 | 2-10-2 | cEt | 198 |
| 493179 | 69 | 2-10-2 | cEt | 199 |
| 493182 | 79 | 2-10-2 | cEt | 200 |
| 493195 | 71 | 2-10-2 | cEt | 201 |
| 473046 | 79 | 2-10-2 | cEt | 35 |
| 493201 | 86 | 2-10-2 | cEt | 202 |
| 493202 | 76 | 2-10-2 | cEt | 203 |
| 493255 | 80 | 2-10-2 | cEt | 204 |
| 493291 | 84 | 2-10-2 | cEt | 205 |
| 493292 | 90 | 2-10-2 | cEt | 206 |
| 493296 | 82 | 2-10-2 | cEt | 207 |
| 493298 | 77 | 2-10-2 | cEt | 208 |
| 493299 | 76 | 5-10-5 | cEt | 209 |
| 493304 | 77 | 2-10-2 | cEt | 210 |
| 493312 | 75 | 2-10-2 | cEt | 211 |
| 493333 | 76 | 2-10-2 | cEt | 212 |
| 472998 | 85 | 2-10-2 | cEt | 74 |

Example 7: Dose-Dependent Antisense Inhibition of Human Target-X in Hep3B Cells Antisense oligonucleotides from the studies above, exhibiting in vitro inhibition of Target-X mRNA, were selected and tested at various doses in Hep3B cells. Cells were plated at a density of 20,000 cells per well and transfected using electroporation with 0.67 µM, 2.00 µM, 1.11 µM, and 6.00 µM concentrations of antisense oligonucleotide, as specified in Table 18. After a treatment period of approximately 16 hours, RNA was isolated from the cells and Target-X mRNA levels were measured by quantitative real-time PCR. Human Target-X primer probe set RTS2927 was used to measure mRNA levels. Target-X mRNA levels were adjusted according to total RNA content, as measured by RIBOGREEN®. Results are presented as percent inhibition of Target-X, relative to untreated control cells.

The half maximal inhibitory concentration ($IC_{50}$) of each oligonucleotide is also presented in Table 18. As illustrated in Table 18, Target-X mRNA levels were reduced in a dose-dependent manner in antisense oligonucleotide treated cells. The data also confirms that several of the newly designed gapmers are more potent than ISIS 407939 of the previous publication.

TABLE 18

Dose-dependent antisense inhibition of human Target-X in Hep3B cells using electroporation

| ISIS No | 666.6667 nM | 2000.0 nM | 6000.0 nM | $IC_{50}$ (µM) |
|---|---|---|---|---|
| 407939 | 47 | 68 | 85 | 0.7 |
| 457851 | 60 | 80 | 93 | <0.6 |
| 472916 | 53 | 80 | 87 | <0.6 |
| 472925 | 62 | 86 | 95 | <0.6 |
| 472926 | 66 | 77 | 85 | <0.6 |
| 472935 | 54 | 84 | 94 | <0.6 |
| 472958 | 66 | 82 | 88 | <0.6 |
| 472959 | 64 | 81 | 93 | <0.6 |
| 472970 | 72 | 87 | 86 | <0.6 |
| 472976 | 78 | 92 | 97 | <0.6 |
| 472994 | 79 | 92 | 96 | <0.6 |
| 472995 | 61 | 82 | 93 | <0.6 |
| 472996 | 73 | 91 | 95 | <0.6 |
| 472998 | 63 | 90 | 95 | <0.6 |
| 473019 | 55 | 80 | 86 | <0.6 |
| 473020 | 61 | 76 | 85 | <0.6 |
| 473046 | 61 | 80 | 94 | <0.6 |
| 473055 | 55 | 84 | 94 | <0.6 |
| 492104 | 53 | 76 | 88 | <0.6 |
| 492105 | 62 | 80 | 90 | <0.6 |
| 492189 | 57 | 80 | 92 | <0.6 |
| 492194 | 57 | 83 | 91 | <0.6 |
| 492195 | 58 | 81 | 95 | <0.6 |
| 492196 | 62 | 86 | 95 | <0.6 |
| 492205 | 62 | 87 | 95 | <0.6 |
| 492215 | 60 | 78 | 89 | <0.6 |
| 492221 | 63 | 76 | 92 | <0.6 |
| 492234 | 51 | 74 | 91 | 0.5 |
| 492276 | 50 | 56 | 95 | 0.8 |
| 492277 | 58 | 73 | 81 | <0.6 |
| 492306 | 61 | 75 | 84 | <0.6 |
| 492317 | 59 | 80 | 93 | <0.6 |
| 492329 | 59 | 70 | 89 | <0.6 |
| 492331 | 69 | 87 | 95 | <0.6 |
| 492333 | 47 | 70 | 85 | 0.7 |
| 492334 | 57 | 77 | 90 | <0.6 |
| 492390 | 72 | 88 | 95 | <0.6 |
| 492399 | 68 | 91 | 96 | <0.6 |
| 492401 | 68 | 89 | 95 | <0.6 |
| 492404 | 65 | 87 | 94 | <0.6 |
| 492405 | 44 | 81 | 90 | 0.7 |
| 492406 | 65 | 82 | 92 | <0.6 |
| 492440 | 50 | 70 | 89 | 0.6 |
| 492465 | 16 | 80 | 79 | 1.4 |
| 492467 | 58 | 77 | 92 | <0.6 |
| 492492 | 45 | 80 | 94 | 0.7 |
| 492494 | 63 | 82 | 93 | <0.6 |
| 492503 | 55 | 81 | 93 | <0.6 |
| 492530 | 70 | 86 | 90 | <0.6 |
| 492534 | 67 | 85 | 91 | <0.6 |
| 492536 | 54 | 81 | 89 | <0.6 |
| 492541 | 54 | 71 | 85 | <0.6 |
| 492545 | 59 | 78 | 89 | <0.6 |
| 492566 | 59 | 84 | 85 | <0.6 |
| 492571 | 52 | 81 | 89 | <0.6 |
| 492572 | 67 | 83 | 90 | <0.6 |
| 492573 | 69 | 83 | 92 | <0.6 |
| 492574 | 65 | 82 | 91 | <0.6 |
| 492575 | 72 | 83 | 91 | <0.6 |
| 492593 | 61 | 78 | 90 | <0.6 |
| 492617 | 62 | 80 | 93 | <0.6 |
| 492618 | 47 | 79 | 94 | 0.6 |
| 492619 | 54 | 82 | 95 | <0.6 |
| 492621 | 44 | 85 | 92 | 0.6 |
| 492651 | 53 | 66 | 91 | 0.6 |
| 492652 | 61 | 78 | 88 | <0.6 |
| 492658 | 59 | 79 | 88 | <0.6 |
| 492725 | 43 | 84 | 89 | 0.6 |
| 492730 | 51 | 87 | 93 | 0.4 |
| 492731 | 46 | 82 | 90 | 0.6 |
| 492784 | 56 | 88 | 96 | <0.6 |
| 492816 | 68 | 89 | 97 | <0.6 |
| 492818 | 64 | 84 | 96 | <0.6 |
| 492877 | 67 | 91 | 93 | <0.6 |
| 492878 | 80 | 89 | 93 | <0.6 |

TABLE 18-continued

Dose-dependent antisense inhibition of human
Target-X in Hep3B cells using electroporation

| ISIS No | 666.6667 nM | 2000.0 nM | 6000.0 nM | IC$_{50}$ (μM) |
|---|---|---|---|---|
| 492913 | 53 | 87 | 92 | <0.6 |
| 492914 | 75 | 89 | 96 | <0.6 |
| 492928 | 60 | 83 | 94 | <0.6 |
| 492938 | 70 | 90 | 92 | <0.6 |
| 492991 | 67 | 93 | 99 | <0.6 |
| 492992 | 0 | 82 | 95 | 2.1 |
| 493087 | 54 | 81 | 90 | <0.6 |
| 493114 | 50 | 73 | 90 | 0.6 |
| 493178 | 71 | 88 | 96 | <0.6 |
| 493179 | 47 | 82 | 95 | 0.6 |
| 493182 | 79 | 87 | 91 | <0.6 |
| 493195 | 55 | 78 | 90 | <0.6 |
| 493201 | 87 | 93 | 96 | <0.6 |
| 493202 | 68 | 89 | 94 | <0.6 |
| 493255 | 57 | 79 | 93 | <0.6 |
| 493291 | 57 | 87 | 93 | <0.6 |
| 493292 | 70 | 89 | 93 | <0.6 |
| 493296 | 35 | 84 | 91 | 0.9 |
| 493298 | 57 | 84 | 92 | <0.6 |
| 493299 | 65 | 84 | 93 | <0.6 |
| 493304 | 68 | 86 | 94 | <0.6 |
| 493312 | 53 | 82 | 91 | <0.6 |
| 493333 | 66 | 84 | 87 | <0.6 |

Example 8: Dose-Dependent Antisense Inhibition of Human Target-X in Hep3B Cells Additional antisense oligonucleotides from the studies described above, exhibiting in vitro inhibition of Target-X mRNA, were selected and tested at various doses in Hep3B cells. Cells were plated at a density of 20,000 cells per well and transfected using electroporation with 0.67 μM, 2.00 μM, 1.11 μM, and 6.00 μM concentrations of antisense oligonucleotide, as specified in Table 19. After a treatment period of approximately 16 hours, RNA was isolated from the cells and Target-X mRNA levels were measured by quantitative real-time PCR. Human Target-X primer probe set RTS2927 was used to measure mRNA levels. Target-X mRNA levels were adjusted according to total RNA content, as measured by RIBOGREEN®. Results are presented as percent inhibition of Target-X, relative to untreated control cells. As illustrated in Table 19, Target-X mRNA levels were reduced in a dose-dependent manner in antisense oligonucleotide treated cells. The data also confirms that several of the newly designed gapmers are more potent than ISIS 407939.

TABLE 19

Dose-dependent antisense inhibition of human
Target-X in Hep3B cells using electroporation

| ISIS No | 0.67 μM | 2.00 μM | 6.00 μM | IC$_{50}$ (μM) |
|---|---|---|---|---|
| 407939 | 52 | 71 | 86 | 0.6 |
| 472983 | 49 | 83 | 97 | 0.5 |
| 472984 | 51 | 82 | 95 | 0.5 |
| 472991 | 49 | 82 | 95 | 0.5 |
| 472998 | 59 | 88 | 96 | <0.6 |
| 492365 | 74 | 91 | 96 | <0.6 |
| 492377 | 56 | 76 | 91 | <0.6 |
| 492380 | 63 | 79 | 95 | <0.6 |
| 492384 | 67 | 84 | 94 | <0.6 |
| 492388 | 69 | 87 | 97 | <0.6 |
| 492389 | 62 | 90 | 96 | <0.6 |
| 492391 | 56 | 84 | 94 | <0.6 |
| 492398 | 63 | 80 | 95 | <0.6 |
| 492403 | 58 | 81 | 91 | <0.6 |

Example 9: Modified Chimeric Antisense Oligonucleotides Comprising 2'-Methoxyethyl (2'-MOE) Modifications at 5' and 3' Wing Regions Targeting Human Target-X Additional antisense oligonucleotides were designed targeting a Target-X nucleic acid and were tested for their effects on Target-X mRNA in vitro. Also tested were ISIS 403052, ISIS 407939, ISIS 416446, ISIS 416472, ISIS 416507, ISIS 416508, ISIS 422087, ISIS 422096, ISIS 422130, and ISIS 422142 which were described in an earlier publication (WO 2009/061851), incorporated herein by reference. ISIS 490149, ISIS 490197, ISIS 490209, ISIS 490275, ISIS 490277, and ISIS 490424, described in the Examples above, were also included in the screen.

The newly designed chimeric antisense oligonucleotides in Table 20 were designed as 3-10-4 2'-MOE gapmers. These gapmers are 17 nucleosides in length, wherein the central gap segment comprises of ten 2'-deoxyribonucleosides and is flanked by wing segments on the 5' direction with three nucleosides and the 3' direction with four nucleosides. Each nucleoside in the 5' wing segment and each nucleoside in the 3' wing segment has 2'-MOE modifications. The internucleoside linkages throughout each gapmer are phosphorothioate (P=S) linkages. All cytosine residues throughout each gapmer are 5-methylcytosines.

Each gapmer listed in Table 20 is targeted to the human Target-X genomic sequence.

Activity of the newly designed oligonucleotides was compared to ISIS 403052, ISIS 407939, ISIS 416446, ISIS 416472, ISIS 416507, ISIS 416508, ISIS 422087, ISIS 422096, ISIS 422130, and ISIS 422142. Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 (described hereinabove in Example 1) was used to measure mRNA levels. Target-X mRNA levels were adjusted according to total RNA content, as measured by RIBOGREEN®. Results are presented as percent inhibition of Target-X, relative to untreated control cells. A total of 272 oligonucleotides were tested. Only those oligonucleotides which were selected for further studies are shown in Table 20. Several of the newly designed antisense oligonucleotides provided in Table 19 are more potent than antisense oligonucleotides from the previous publication.

TABLE 20

Inhibition of human Target-X mRNA levels by chimeric
antisense oligonucleotides targeted to Target-X

| ISIS No | % inhibition | Motif | Wing Chemistry | SEQ CODE |
|---|---|---|---|---|
| 403052 | 51 | 5-10-5 | 2'-MOE | 82 |
| 407939 | 78 | 5-10-5 | 2'-MOE | 72 |

TABLE 20-continued

Inhibition of human Target-X mRNA levels by chimeric antisense oligonucleotides targeted to Target-X

| ISIS No | % inhibition | Motif | Wing Chemistry | SEQ CODE |
|---|---|---|---|---|
| 416446 | 70 | 5-10-5 | 2'-MOE | 103 |
| 416472 | 79 | 5-10-5 | 2'-MOE | 111 |
| 416507 | 84 | 5-10-5 | 2'-MOE | 97 |
| 416508 | 80 | 5-10-5 | 2'-MOE | 100 |
| 422087 | 89 | 5-10-5 | 2'-MOE | 121 |
| 422096 | 78 | 5-10-5 | 2'-MOE | 219 |
| 422130 | 81 | 5-10-5 | 2'-MOE | 225 |
| 422142 | 84 | 5-10-5 | 2'-MOE | 99 |
| 490275 | 77 | 5-10-5 | 2'-MOE | 90 |
| 513462 | 79 | 3-10-4 | 2'-MOE | 213 |
| 513463 | 81 | 3-10-4 | 2'-MOE | 214 |
| 490277 | 74 | 5-10-5 | 2'-MOE | 91 |
| 513487 | 83 | 3-10-4 | 2'-MOE | 215 |
| 513504 | 81 | 3-10-4 | 2'-MOE | 216 |
| 513507 | 86 | 3-10-4 | 2'-MOE | 217 |
| 513508 | 85 | 3-10-4 | 2'-MOE | 218 |
| 490424 | 69 | 5-10-5 | 2'-MOE | 101 |
| 491122 | 87 | 5-10-5 | 2'-MOE | 220 |
| 513642 | 79 | 3-10-4 | 2'-MOE | 221 |
| 490149 | 71 | 5-10-5 | 2'-MOE | 109 |
| 513419 | 90 | 3-10-4 | 2'-MOE | 222 |
| 513420 | 89 | 3-10-4 | 2'-MOE | 223 |
| 513421 | 88 | 3-10-4 | 2'-MOE | 224 |
| 490197 | 77 | 5-10-5 | 2'-MOE | 116 |
| 513446 | 89 | 3-10-4 | 2'-MOE | 226 |
| 513447 | 83 | 3-10-4 | 2'-MOE | 227 |
| 490209 | 79 | 5-10-5 | 2'-MOE | 118 |
| 513454 | 84 | 3-10-4 | 2'-MOE | 228 |
| 513455 | 92 | 3-10-4 | 2'-MOE | 229 |
| 513456 | 89 | 3-10-4 | 2'-MOE | 230 |
| 513457 | 83 | 3-10-4 | 2'-MOE | 231 |

Example 10: Dose-Dependent Antisense Inhibition of Human Target-X in Hep3B Cells Antisense oligonucleotides from the studies above, exhibiting in vitro inhibition of Target-X mRNA, were selected and tested at various doses in Hep3B cells. ISIS 403052, ISIS 407643, ISIS 407935, ISIS 407936, ISIS 407939, ISIS 416446, ISIS 416459, ISIS 416472, ISIS 416507, ISIS 416508, ISIS 416549, ISIS 422086, ISIS 422087, ISIS 422130, ISIS and 422142, 5-10-5 MOE gapmers targeting human Target-X, which were described in an earlier publication (WO 2009/061851).

Cells were plated at a density of 20,000 cells per well and transfected using electroporation with 0.625 µM, 1.25 µM, 2.50 µM, 5.00 µM and 10.00 µM concentrations of antisense oligonucleotide, as specified in Table 21. After a treatment period of approximately 16 hours, RNA was isolated from the cells and Target-X mRNA levels were measured by quantitative real-time PCR. Human Target-X primer probe set RTS2927 was used to measure mRNA levels. Target-X mRNA levels were adjusted according to total RNA content, as measured by RIBOGREEN®. Results are presented as percent inhibition of Target-X, relative to untreated control cells.

The half maximal inhibitory concentration ($IC_{50}$) of each oligonucleotide is also presented in Table 21. As illustrated in Table 21, Target-X mRNA levels were reduced in a dose-dependent manner in antisense oligonucleotide treated cells. The data also confirms that the newly designed gapmers are potent than gapmers from the previous publication.

TABLE 21

Dose-dependent antisense inhibition of human Target-X in Hep3B cells using electroporation

| ISIS No | 0.625 µM | 1.25 µM | 2.50 µM | 5.00 µM | 10.00 µM | $IC_{50}$ (µM) |
|---|---|---|---|---|---|---|
| 403052 | 21 | 35 | 63 | 82 | 89 | 1.9 |
| 407643 | 29 | 46 | 67 | 83 | 90 | 1.4 |
| 407935 | 52 | 68 | 80 | 89 | 91 | <0.6 |
| 407936 | 31 | 51 | 62 | 78 | 84 | 1.4 |
| 407939 | 30 | 61 | 74 | 83 | 88 | 1.0 |
| 416446 | 37 | 53 | 64 | 76 | 83 | 1.2 |
| 416459 | 51 | 76 | 83 | 90 | 92 | <0.6 |
| 416472 | 37 | 52 | 66 | 78 | 85 | 1.2 |
| 416507 | 45 | 68 | 82 | 87 | 90 | 0.7 |
| 416508 | 33 | 56 | 74 | 84 | 89 | 1.1 |
| 416549 | 57 | 71 | 78 | 82 | 85 | <0.6 |
| 422086 | 46 | 67 | 77 | 89 | 92 | 0.7 |
| 422087 | 50 | 69 | 74 | 86 | 91 | 0.6 |
| 422130 | 32 | 65 | 78 | 92 | 93 | 0.9 |
| 422142 | 59 | 73 | 84 | 86 | 88 | <0.6 |
| 490103 | 52 | 57 | 66 | 83 | 88 | 0.9 |
| 490149 | 34 | 58 | 71 | 85 | 91 | 1.0 |
| 490196 | 26 | 59 | 66 | 79 | 84 | 1.3 |
| 490197 | 39 | 63 | 74 | 81 | 90 | 0.8 |
| 490208 | 44 | 70 | 76 | 83 | 88 | 0.6 |
| 490275 | 36 | 58 | 76 | 85 | 89 | 1.0 |
| 490277 | 37 | 63 | 73 | 87 | 87 | 0.8 |
| 490279 | 40 | 54 | 72 | 83 | 89 | 1.0 |
| 490323 | 49 | 68 | 79 | 86 | 90 | <0.6 |
| 490368 | 39 | 62 | 76 | 86 | 91 | 0.8 |
| 490396 | 36 | 53 | 69 | 80 | 87 | 1.1 |
| 490424 | 45 | 65 | 69 | 76 | 82 | 0.6 |
| 490803 | 57 | 74 | 85 | 89 | 92 | <0.6 |
| 513419 | 60 | 71 | 85 | 95 | 96 | <0.6 |
| 513420 | 37 | 69 | 79 | 94 | 96 | 0.7 |
| 513421 | 46 | 64 | 84 | 95 | 97 | 0.6 |
| 513446 | 47 | 81 | 88 | 95 | 96 | <0.6 |
| 513447 | 56 | 74 | 81 | 92 | 96 | <0.6 |
| 513454 | 50 | 77 | 82 | 93 | 95 | <0.6 |
| 513455 | 74 | 82 | 91 | 96 | 96 | <0.6 |
| 513456 | 66 | 80 | 88 | 94 | 95 | <0.6 |
| 513457 | 54 | 67 | 80 | 87 | 89 | <0.6 |
| 513462 | 49 | 72 | 84 | 87 | 89 | <0.6 |
| 513463 | 36 | 62 | 76 | 85 | 89 | 0.9 |
| 513487 | 42 | 56 | 73 | 87 | 93 | 0.9 |
| 513504 | 47 | 65 | 81 | 90 | 91 | 0.6 |
| 513505 | 39 | 50 | 78 | 85 | 92 | 1.0 |
| 513507 | 52 | 73 | 83 | 89 | 93 | <0.6 |
| 513508 | 56 | 78 | 85 | 91 | 94 | <0.6 |

Example 11: Dose-Dependent Antisense Inhibition of Human Target-X in Hep3B Cells Additional antisense oligonucleotides from the studies above, exhibiting in vitro inhibition of Target-X mRNA, were tested at various doses in Hep3B cells. ISIS 407935, ISIS 407939, ISIS 416446, ISIS 416472, ISIS 416507, ISIS 416549, ISIS 422086, ISIS 422087, ISIS 422096, and ISIS 422142 5-10-5 MOE gapmers targeting human Target-X, which were described in an earlier publication (WO 2009/061851).

Cells were plated at a density of 20,000 cells per well and transfected using electroporation with 0.3125 µM, 0.625 µM, 1.25 µM, 2.50 µM, 5.00 µM and 10.00 µM concentrations of antisense oligonucleotide, as specified in Table 22. After a treatment period of approximately 16 hours, RNA was isolated from the cells and Target-X mRNA levels were measured by quantitative real-time PCR. Human Target-X primer probe set RTS2927 was used to measure mRNA levels. Target-X mRNA levels were adjusted according to total RNA content, as measured by RIBOGREEN®. Results are presented as percent inhibition of Target-X, relative to untreated control cells. As illustrated in Table 22, Target-X mRNA levels were reduced in a dose-dependent manner in antisense oligonucleotide treated cells. The data also confirms that the newly designed gapmers are more potent than gapmers from the previous publication.

TABLE 22

Dose-dependent antisense inhibition of human Target-X in Hep3B cells using electroporation

| ISIS No | 0.3125 µM | 0.625 µM | 1.250 µM | 2.500 µM | 5.000 µM | 10.000 µM | $IC_{50}$ (µM) |
|---|---|---|---|---|---|---|---|
| 407935 | 30 | 49 | 75 | 86 | 91 | 94 | 0.6 |
| 407939 | 30 | 48 | 61 | 78 | 85 | 90 | 0.8 |
| 416446 | 27 | 52 | 63 | 75 | 85 | 90 | 0.7 |
| 416472 | 38 | 51 | 72 | 83 | 88 | 94 | 0.5 |
| 416507 | 58 | 81 | 76 | 84 | 89 | 92 | <0.3 |
| 416549 | 52 | 67 | 75 | 81 | 88 | 89 | 0.3 |
| 422086 | 48 | 49 | 68 | 78 | 86 | 91 | 0.5 |
| 422087 | 30 | 56 | 66 | 83 | 72 | 92 | 0.6 |
| 422096 | 47 | 63 | 70 | 77 | 83 | 85 | <0.3 |
| 422142 | 69 | 85 | 87 | 85 | 89 | 91 | <0.3 |
| 490103 | 52 | 57 | 68 | 78 | 87 | 93 | 0.4 |
| 490149 | 33 | 64 | 62 | 77 | 86 | 93 | 0.5 |
| 490197 | 38 | 46 | 60 | 75 | 87 | 93 | 0.7 |
| 490208 | 46 | 62 | 73 | 83 | 88 | 91 | 0.4 |
| 490209 | 40 | 54 | 72 | 79 | 85 | 94 | 0.5 |
| 490275 | 52 | 61 | 67 | 78 | 85 | 91 | 0.3 |
| 490277 | 33 | 59 | 77 | 79 | 91 | 94 | 0.5 |
| 490323 | 43 | 61 | 72 | 69 | 84 | 87 | 0.4 |
| 490368 | 50 | 64 | 78 | 83 | 90 | 92 | <0.3 |
| 490396 | 46 | 64 | 68 | 84 | 84 | 90 | 0.3 |
| 490424 | 24 | 47 | 58 | 72 | 76 | 82 | 1.0 |
| 490803 | 45 | 60 | 70 | 84 | 88 | 89 | 0.3 |
| 513419 | 32 | 53 | 76 | 88 | 93 | 95 | 0.5 |
| 513420 | 35 | 59 | 72 | 82 | 94 | 97 | 0.5 |
| 513421 | 46 | 67 | 78 | 86 | 94 | 96 | <0.3 |
| 513446 | 26 | 61 | 77 | 89 | 91 | 97 | 0.5 |
| 513447 | 22 | 48 | 60 | 82 | 91 | 95 | 0.8 |
| 513454 | 25 | 59 | 76 | 86 | 94 | 96 | 0.5 |
| 513455 | 60 | 73 | 85 | 89 | 95 | 96 | <0.3 |
| 513456 | 49 | 60 | 81 | 88 | 94 | 95 | <0.3 |
| 513457 | 43 | 50 | 72 | 77 | 87 | 92 | 0.5 |
| 513462 | 25 | 48 | 58 | 76 | 83 | 88 | 0.8 |
| 513463 | 22 | 45 | 66 | 73 | 85 | 88 | 0.9 |
| 513487 | 41 | 56 | 65 | 79 | 86 | 90 | 0.4 |
| 513504 | 19 | 48 | 63 | 76 | 87 | 92 | 0.9 |
| 513505 | 11 | 21 | 54 | 73 | 85 | 90 | 1.4 |
| 513507 | 47 | 55 | 72 | 82 | 90 | 91 | 0.3 |
| 513508 | 31 | 59 | 74 | 85 | 92 | 93 | 0.5 |
| 513642 | 43 | 55 | 67 | 80 | 88 | 92 | 0.4 |

Example 12: Tolerability of 2'-MOE Gapmers Targeting Human Target-X in BALB/c Mice BALB/c mice are a multipurpose mice model, frequently utilized for safety and efficacy testing. The mice were treated with ISIS antisense oligonucleotides selected from studies described above and evaluated for changes in the levels of various plasma chemistry markers.

Treatment

Groups of male BALB/c mice were injected subcutaneously twice a week for 3 weeks with 50 mg/kg of ISIS 407935, ISIS 416472, ISIS 416549, ISIS 422086, ISIS 422087, ISIS 422096, ISIS 422142, ISIS 490103, ISIS 490149, ISIS 490196, ISIS 490208, ISIS 490209, ISIS 513419, ISIS 513420, ISIS 513421, ISIS 513454, ISIS 513455, ISIS 513456, ISIS 513457, ISIS 513462, ISIS 513463, ISIS 513487, ISIS 513504, ISIS 513508, and ISIS 513642. One group of male BALB/c mice was injected subcutaneously twice a week for 3 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, and BUN were measured using an automated clinical chemistry analyzer (Hitachi Olympus AU400e, Melville, N.Y.).

ISIS oligonucleotides that did not cause any increase in the levels of transaminases, or which caused an increase within three times the upper limit of normal (ULN) were deemed very tolerable. ISIS oligonucleotides that caused an increase in the levels of transaminases between three times and seven times the ULN were deemed tolerable. Based on these criteria, ISIS 407935, ISIS 416472, ISIS 416549, ISIS 422087, ISIS 422096, ISIS 490103, ISIS 490196, ISIS 490208, ISIS 513454, ISIS 513455, ISIS 513456, ISIS 513457, ISIS 513487, ISIS 513504, and ISIS 513508 were considered very tolerable in terms of liver function. Based on these criteria, ISIS 422086, ISIS 490209, ISIS 513419, ISIS 513420, and ISIS 513463 were considered tolerable in terms of liver function.

Example 13: Dose-Dependent Antisense Inhibition of Human Target-X in Hep3B Cells Additional antisense oligonucleotides from the studies above, exhibiting in vitro inhibition of Target-X mRNA were selected and tested at various doses in Hep3B cells. Also tested was ISIS 407939, a 5-10-5 MOE gapmer, which was described in an earlier publication (WO 2009/061851).

Cells were plated at a density of 20,000 cells per well and transfected using electroporation with 0.074 µM, 0.222 µM, 0.667 µM, 2.000 µM, and 6.000 µM concentrations of antisense oligonucleotide, as specified in Table 23. After a treatment period of approximately 16 hours, RNA was isolated from the cells and Target-X mRNA levels were measured by quantitative real-time PCR. Human Target-X primer probe set RTS2927 (described hereinabove in Example 1) was used to measure mRNA levels. Target-X mRNA levels were adjusted according to total RNA content, as measured by RIBOGREEN®. Results are presented as percent inhibition of Target-X, relative to untreated control cells.

The half maximal inhibitory concentration (IC$_{50}$) of each oligonucleotide is also presented in Table 23. As illustrated in Table 23, Target-X mRNA levels were reduced in a dose-dependent manner in antisense oligonucleotide treated cells. Many of the newly designed antisense oligonucleotides provided in Table 23 achieved an IC$_{50}$ of less than 0.9 µM and, therefore, are more potent than ISIS 407939.

TABLE 23

Dose-dependent antisense inhibition of human Target-X in Hep3B cells using electroporation

| ISIS No | 0.074 µM | 0.222 µM | 0.667 µM | 2.000 µM | 6.000 µM | IC$_{50}$ (µM) |
|---|---|---|---|---|---|---|
| 407939 | 2 | 17 | 53 | 70 | 87 | 0.9 |
| 472970 | 17 | 47 | 75 | 92 | 95 | 0.3 |
| 472988 | 0 | 8 | 21 | 54 | 92 | 1.4 |
| 472996 | 18 | 59 | 74 | 93 | 95 | 0.2 |
| 473244 | 91 | 95 | 97 | 99 | 99 | <0.07 |
| 473286 | 6 | 53 | 85 | 92 | 98 | 0.3 |
| 473359 | 2 | 3 | 20 | 47 | 67 | 2.6 |
| 473392 | 71 | 85 | 88 | 92 | 96 | <0.07 |
| 473393 | 91 | 96 | 97 | 98 | 99 | <0.07 |
| 473547 | 85 | 88 | 93 | 97 | 98 | <0.07 |
| 473567 | 0 | 25 | 66 | 88 | 95 | 0.7 |
| 473589 | 8 | 47 | 79 | 94 | 99 | 0.3 |
| 482814 | 23 | 68 | 86 | 93 | 96 | 0.1 |
| 482815 | 6 | 48 | 65 | 90 | 96 | 0.4 |
| 482963 | 3 | 68 | 85 | 94 | 96 | 0.2 |
| 483241 | 14 | 33 | 44 | 76 | 93 | 0.6 |
| 483261 | 14 | 21 | 41 | 72 | 88 | 0.7 |
| 483290 | 0 | 1 | 41 | 69 | 92 | 1.0 |
| 483414 | 8 | 1 | 36 | 76 | 91 | 0.9 |
| 483415 | 0 | 40 | 52 | 84 | 94 | 0.6 |
| 484559 | 26 | 51 | 78 | 87 | 97 | 0.2 |
| 484713 | 6 | 5 | 53 | 64 | 88 | 0.9 |

Example 14: Modified Antisense Oligonucleotides Comprising 2'-O-Methoxyethyl (2'-MOE) and Constrained Ethyl (cEt) Modifications Targeting Human Target-X Additional antisense oligonucleotides were designed targeting a Target-X nucleic acid and were tested for their effects on Target-X mRNA in vitro. Also tested was ISIS 407939, a 5-10-5 MOE gapmer targeting human Target-X, which was described in an earlier publication (WO 2009/061851). ISIS 472998, ISIS 492878, and ISIS 493201 and 493182, 2-10-2 cEt gapmers, described in the Examples above were also included in the screen.

The newly designed modified antisense oligonucleotides are 16 nucleotides in length and their motifs are described in Table 24. The chemistry column of Table 24 presents the sugar motif of each oligonucleotide, wherein "e" indicates a 2'-O-methythoxyethyl (2'-MOE) nucleoside, "k" indicates a constrained ethyl (cEt) nucleoside and "d" indicates a 2'-deoxyribonucleoside. The internucleoside linkages throughout each gapmer are phosphorothioate (P=S) linkages. All cytosine residues throughout each oligonucleotide are 5-methylcytosines.

Each gapmer listed in Table 24 is targeted to the human Target-X genomic sequence.

Activity of newly designed gapmers was compared to ISIS 407939. Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 was used to measure mRNA levels. Target-X mRNA levels were adjusted according to total RNA content, as measured by RIBOGREEN®. Results are presented as percent inhibition of Target-X, relative to untreated control cells and demonstrate that several of the newly designed gapmers are more potent than ISIS 407939. A total of 685 oligonucleotides were tested. Only those oligonucleotides which were selected for further studies are shown in Table 24.

TABLE 24

Inhibition of human Target-X mRNA levels by chimeric antisense oligonucleotides targeted to Target-X

| ISIS No | % inhibition | Chemistry | SEQ CODE |
|---|---|---|---|
| 407939 | 68 | eeeee-d(10)-eeeee | 72 |
| 492878 | 73 | kk-d(10)-kk | |
| 493182 | 80 | kk-d(10)-kk | |
| 493201 | 84 | kk-d(10)-kk | |
| 472998 | 91 | kk-d(10)-kk | |
| 515640 | 75 | eee-d(10)-kkk | 23 |
| 515637 | 77 | eee-d(10)-kkk | 232 |
| 515554 | 72 | eee-d(10)-kkk | 233 |
| 515406 | 80 | kkk-d(10)-eee | 234 |
| 515558 | 81 | eee-d(10)-kkk | 234 |
| 515407 | 88 | kkk-d(10)-eee | 235 |
| 515408 | 85 | kkk-d(10)-eee | 236 |
| 515422 | 86 | kkk-d(10)-eee | 237 |
| 515423 | 90 | kkk-d(10)-eee | 238 |
| 515575 | 84 | eee-d(10)-kkk | 238 |
| 515424 | 87 | kkk-d(10)-eee | 239 |
| 515432 | 78 | kkk-d(10)-eee | 240 |
| 515433 | 71 | kkk-d(10)-eee | 241 |
| 515434 | 76 | kkk-d(10)-eee | 242 |
| 515334 | 85 | kkk-d(10)-eee | 243 |
| 515649 | 61 | eee-d(10)-kkk | 88 |
| 515338 | 86 | kkk-d(10)-eee | 244 |
| 515438 | 76 | kkk-d(10)-eee | 245 |
| 515439 | 75 | kkk-d(10)-eee | 246 |
| 516003 | 87 | eee-d(10)-kkk | 247 |
| 515647 | 60 | eee-d(10)-kkk | 77 |
| 515639 | 78 | eee-d(10)-kkk | 34 |
| 493201 | 84 | eee-d(10)-kkk | 202 |
| 515648 | 36 | kkk-d(10)-eee | 248 |
| 515641 | 69 | kk-d(10)-eeee | 39 |
| 515650 | 76 | kkk-d(10)-eee | 44 |
| 515354 | 87 | eee-d(10)-kkk | 249 |
| 515926 | 87 | eee-d(10)-kkk | 250 |
| 515366 | 87 | kk-d(10)-eeee | 251 |
| 515642 | 58 | kkk-d(10)-eee | 252 |
| 515643 | 81 | eee-d(10)-kkk | 53 |
| 515944 | 84 | kk-d(10)-eeee | 253 |
| 515380 | 90 | kkk-d(10)-eee | 254 |
| 515532 | 83 | kkk-d(10)-eee | 254 |
| 515945 | 85 | kk-d(10)-eeee | 254 |
| 515381 | 82 | kk-d(10)-eeee | 255 |
| 515382 | 95 | kkk-d(10)-eee | 256 |
| 515948 | 94 | eee-d(10)-kkk | 256 |
| 515949 | 87 | eee-d(10)-kkk | 257 |

TABLE 24-continued

Inhibition of human Target-X mRNA levels by chimeric antisense oligonucleotides targeted to Target-X

| ISIS No | % inhibition | Chemistry | SEQ CODE |
|---------|--------------|-----------|----------|
| 515384 | 89 | kkk-d(10)-eee | 258 |
| 515635 | 82 | kk-d(10)-eeee | 65 |
| 515638 | 90 | kkk-d(10)-eee | 67 |
| 515386 | 92 | kk-d(10)-eeee | 259 |
| 515951 | 84 | eee-d(10)-kkk | 259 |
| 515387 | 78 | kkk-d(10)-eee | 260 |
| 515952 | 89 | kkk-d(10)-eee | 260 |
| 515636 | 90 | kkk-d(10)-eee | 69 |
| 515388 | 84 | eee-d(10)-kkk | 261 | e = 2'-MOE,
k = cEt,
d = 2'-deoxyribonucleoside

Example 15: Tolerability of Modified Oligonucleotides Comprising 2'-O-Methoxyethyl (2'-MOE) and Constrained Ethyl (cEt) Modifications Targeting Human Target-X in BALB/c Mice BALB/c mice were treated with ISIS antisense oligonucleotides selected from studies described above and evaluated for changes in the levels of various plasma chemistry markers.

Additionally, the newly designed modified antisense oligonucleotides were also added to this screen. The newly designed chimeric antisense oligonucleotides are 16 nucleotides in length and their motifs are described in Table 25. The chemistry column of Table 25 presents the sugar motif of each oligonucleotide, wherein "e" indicates a 2'-O-methythoxylethyl (2'-MOE) nucleoside, "k" indicates a constrained ethyl (cEt) nucleoside and "d" indicates a 2'-deoxynucleoside. The internucleoside linkages throughout each gapmer are hosphorothioate (P=S) linkages. All cytosine residues throughout each oligonucleotide are 5-methylcytosines.

Each gapmer listed in Table 25 is targeted to either the human Target-X genomic sequence.

TABLE 25

Modified chimeric antisense oligonucleotides targeted to Target-X

| ISIS No | Chemistry | SEQ CODE |
|---------|-----------|----------|
| 516044 | eee-d(10)-kkk | 21 |
| 516045 | eee-d(10)-kkk | 22 |
| 516058 | eee-d(10)-kkk | 26 |
| 516059 | eee-d(10)-kkk | 27 |
| 516060 | eee-d(10)-kkk | 28 |
| 516061 | eee-d(10)-kkk | 29 |
| 516062 | eee-d(10)-kkk | 30 |
| 516046 | eee-d(10)-kkk | 37 |
| 516063 | eee-d(10)-kkk | 38 |
| 516064 | eee-d(10)-kkk | 89 |
| 516065 | eee-d(10)-kkk | 262 |
| 516066 | eee-d(10)-kkk | 263 |
| 516047 | eee-d(10)-kkk | 41 |
| 516048 | eee-d(10)-kkk | 42 |
| 516049 | eee-d(10)-kkk | 81 |
| 516050 | eee-d(10)-kkk | 45 |
| 516051 | eee-d(10)-kkk | 48 |
| 516052 | eee-d(10)-kkk | 49 |
| 515652 | eee-d(10)-kkk | 50 |
| 508039 | eee-d(10)-kkk | 264 |
| 516053 | eee-d(10)-kkk | 265 |
| 515654 | eee-d(10)-kkk | 76 |
| 515656 | eee-d(10)-kkk | 77 |
| 516054 | eee-d(10)-kkk | 57 |
| 516055 | eee-d(10)-kkk | 59 |
| 515655 | eee-d(10)-kkk | 61 |
| 516056 | eee-d(10)-kkk | 63 |
| 516057 | eee-d(10)-kkk | 64 |
| 515653 | eee-d(10)-kkk | 71 |
| 515657 | eee-d(10)-kkk | 73 | e = 2'-MOE,
k = cEt,
d = 2'-deoxynucleoside

Treatment

Groups of 4-6-week old male BALB/c mice were injected subcutaneously twice a week for 3 weeks with 50 mg/kg/week of ISIS 457851, ISIS 515635, ISIS 515636, ISIS 515637, ISIS 515638, ISIS 515639, ISIS 515640, ISIS 515641, ISIS 515642, ISIS 515643, ISIS 515647, ISIS 515648, ISIS 515649, ISSI 515650, ISIS 515652, ISIS 515653, ISIS 515654, ISIS 515655, ISIS 515656, ISIS 515657, ISIS 516044, ISIS 516045, ISIS 516046, ISIS 516047, ISIS 516048, ISIS 516049, ISIS 516050, ISIS 516051, ISIS 516052, ISIS 516053, ISIS 516054, ISIS 516055, ISIS 516056, ISIS 516057, ISIS 516058, ISIS 516059, ISIS 516060, ISIS 516061, ISIS 516062, ISIS 516063, ISIS 516064, ISIS 516065, and ISIS 516066. One group of 4-6-week old male BALB/c mice was injected subcutaneously twice a week for 3 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, and BUN were measured using an automated clinical chemistry analyzer (Hitachi Olympus AU400e, Melville, N.Y.).

ISIS oligonucleotides that did not cause any increase in the levels of transaminases, or which caused an increase within three times the upper limit of normal (ULN) were deemed very tolerable. ISIS oligonucleotides that caused an increase in the levels of transaminases between three times and seven times the ULN were deemed tolerable. Based on these criteria, ISIS 515636, ISIS 515639, ISIS 515641, ISIS 515642, ISIS 515648, ISIS 515650, ISIS 515652, ISIS 515653, ISIS 515655, ISIS 515657, ISIS 516044, ISIS 516045, ISIS 516047, ISIS 516048, ISIS 516051, ISIS 516052, ISIS 516053, ISIS 516055, ISIS 516056, ISIS 516058, ISIS 516059, ISIS 516060, ISIS 516061, ISIS 516062, ISIS 516063, ISIS 516064, ISIS 516065, and ISIS 516066 were considered very tolerable in terms of liver function. Based on these criteria, ISIS 457851, ISIS 515635, ISIS 515637, ISIS 515638, ISIS 515643, ISIS 515647, ISIS 515649, ISIS 515650, ISIS 515652, ISIS 515654, ISIS 515656, ISIS 516056, and ISIS 516057 were considered tolerable in terms of liver function.

Example 16: Efficacy of Modified Oligonucleotides Comprising 2'-O-Methoxyethyl (2'-MOE) and Constrained Ethyl (cEt) Modifications Targeting Human Target-X in Transgenic Mice Transgenic mice were developed at Taconic farms harboring a Target-X genomic DNA fragment. The mice were treated with ISIS antisense oligonucleotides selected from studies described above and evaluated for efficacy.

Treatment

Groups of 3-4 male and female transgenic mice were injected subcutaneously twice a week for 3 weeks with 20 mg/kg/week of ISIS 457851, ISIS 515636, ISIS 515639, ISIS 515653, ISIS 516053, ISIS 516065, and ISIS 516066. One group of mice was injected subcutaneously twice a week for 3 weeks with control oligonucleotide, ISIS 141923 (CCTTCCCTGAAGGTTCCTCC, 5-10-5 MOE gapmer with no known murine target, SEQ ID NO: 22). One group of mice was injected subcutaneously twice a week for 3 weeks with PBS. Mice were euthanized 48 hours after the last dose, and organs and plasma were harvested for further analysis.

RNA Analysis

RNA was extracted from plasma for real-time PCR analysis of Target-X, using primer probe set RTS2927. The mRNA levels were normalized using RIBOGREEN®. Results are presented as percent inhibition of Target-X, relative to control. As shown in Table 26, each of the antisense oligonucleotides achieved reduction of human Target-X mRNA expression over the PBS control. Treatment with the control oligonucleotide did not achieve reduction in Target-X levels, as expected.

TABLE 26

Percent inhibition of Target-X mRNA in transgenic mice

| ISIS No | % inhibition |
|---------|--------------|
| 141923  | 0            |
| 457851  | 76           |
| 515636  | 66           |
| 515639  | 49           |
| 515653  | 78           |
| 516053  | 72           |
| 516065  | 59           |
| 516066  | 39           |

Protein Analysis

Plasma protein levels of Target-X were estimated using a Target-X ELISA kit (purchased from Hyphen Bio-Med). Results are presented as percent inhibition of Target-X, relative to control. As shown in Table 27, several antisense oligonucleotides achieved reduction of human Target-X protein expression over the PBS control. 'n.d.' indicates that the value for that particular oligonucleotide was not measured.

TABLE 27

Percent inhibition of Target-X protein levels in transgenic mice

| ISIS No | % inhibition |
|---------|--------------|
| 141923  | 0            |
| 457851  | 64           |
| 515636  | 68           |
| 515639  | 46           |
| 515653  | 0            |
| 516053  | 19           |
| 516065  | 0            |
| 516066  | 7            |

Example 17: Efficacy of Modified Oligonucleotides Comprising 2'-O-Methoxyethyl (2'-MOE) and Constrained Ethyl (cEt) Modifications Targeting Human Target-X in Transgenic Mice Transgenic mice were treated with ISIS antisense oligonucleotides selected from studies described above and evaluated for efficacy.

Treatment

Groups of 2-4 male and female transgenic mice were injected subcutaneously twice a week for 3 weeks with 10 mg/kg/week of ISIS 407935, ISIS 416472, ISIS 416549, ISIS 422087, ISIS 422096, ISIS 473137, ISIS 473244, ISIS 473326, ISIS 473327, ISIS 473359, ISIS 473392, ISIS 473393, ISIS 473547, ISIS 473567, ISIS 473589, ISIS 473630, ISIS 484559, ISIS 484713, ISIS 490103, ISIS 490196, ISIS 490208, ISIS 513419, ISIS 513454, ISIS 513455, ISIS 513456, ISIS 513457, ISIS 513487, ISIS 513508, ISIS 515640, ISIS 515641, ISIS 515642, ISIS 515648, ISIS 515655, ISIS 515657, ISIS 516045, ISIS 516046, ISIS 516047, ISIS 516048, ISIS 516051, ISIS 516052, ISIS 516055, ISIS 516056, ISIS 516059, ISIS 516061, ISIS 516062, and ISIS 516063. One group of mice was injected subcutaneously twice a week for 3 weeks with PBS. Mice were euthanized 48 hours after the last dose, and organs and plasma were harvested for further analysis.

Protein Analysis

Plasma protein levels of Target-X were estimated using a Target-X ELISA kit (purchased from Hyphen Bio-Med). Results are presented as percent inhibition of Target-X, relative to control. As shown in Table 28, several antisense oligonucleotides achieved reduction of human Target-X over the PBS control.

TABLE 28

Percent inhibition of Target-X plasma protein levels in transgenic mice

| ISIS No | % inhibition |
|---------|--------------|
| 407935  | 80           |
| 416472  | 49           |
| 416549  | 29           |
| 422087  | 12           |
| 422096  | 21           |
| 473137  | 57           |
| 473244  | 67           |
| 473326  | 42           |
| 473327  | 100          |
| 473359  | 0            |
| 473392  | 22           |
| 473393  | 32           |
| 473547  | 73           |
| 473567  | 77           |
| 473589  | 96           |
| 473630  | 75           |
| 484559  | 75           |
| 484713  | 56           |
| 490103  | 0            |
| 490196  | 74           |
| 490208  | 90           |
| 513419  | 90           |
| 513454  | 83           |
| 513455  | 91           |
| 513456  | 81           |
| 513457  | 12           |
| 513487  | 74           |
| 513508  | 77           |
| 515640  | 83           |
| 515641  | 87           |
| 515642  | 23           |
| 515648  | 32           |

TABLE 28-continued

Percent inhibition of Target-X plasma
protein levels in transgenic mice

| ISIS No | % inhibition |
|---------|--------------|
| 515655 | 79 |
| 515657 | 81 |
| 516045 | 52 |
| 516046 | 79 |
| 516047 | 65 |
| 516048 | 79 |
| 516051 | 84 |
| 516052 | 72 |
| 516055 | 70 |
| 516056 | 0 |
| 516059 | 39 |
| 516061 | 64 |
| 516062 | 96 |
| 516063 | 24 |

Example 18: Dose-Dependent Antisense Inhibition of Human Target-X in Hep3B Cells Antisense oligonucleotides exhibiting in vitro inhibition of Target-X mRNA were selected and tested at various doses in Hep3B cells. Also tested was ISIS 407939, a 5-10-5 MOE gapmer targeting human Target-X, which was described in an earlier publication (WO 2009/061851).

Cells were plated at a density of 20,000 cells per well and transfected using electroporation with 0.074 µM, 0.222 µM, 0.667 µM, 2.000 µM, and 6.000 µM concentrations of antisense oligonucleotide, as specified in Table 29. After a treatment period of approximately 16 hours, RNA was isolated from the cells and Target-X mRNA levels were measured by quantitative real-time PCR. Human Target-X primer probe set RTS2927 (described hereinabove in Example 1) was used to measure mRNA levels. Target-X mRNA levels were adjusted according to total RNA content, as measured by RIBOGREEN®. Results are presented as percent inhibition of Target-X, relative to untreated control cells.

The half maximal inhibitory concentration ($IC_{50}$) of each oligonucleotide is also presented in Table 29. As illustrated in Table 29, Target-X mRNA levels were reduced in a dose-dependent manner in antisense oligonucleotide treated cells. Many of the newly designed antisense oligonucleotides provided in Table 29 achieved an $IC_{50}$ of less than 2.0 µM and, therefore, are more potent than ISIS 407939.

TABLE 29

Dose-dependent antisense inhibition of human
Target-X in Hep3B cells using electroporation

| ISIS No | 0.074 µM | 0.222 µM | 0.667 µM | 2.000 µM | 6.000 µM | $IC_{50}$ (µM) |
|---------|----------|----------|----------|----------|----------|-------|
| 407939 | 0 | 9 | 21 | 58 | 76 | 2.0 |
| 515636 | 14 | 32 | 50 | 62 | 81 | 0.7 |
| 515639 | 10 | 24 | 41 | 61 | 67 | 1.3 |
| 515640 | 4 | 16 | 35 | 52 | 63 | 2.0 |
| 515641 | 0 | 21 | 27 | 55 | 66 | 1.9 |
| 515642 | 3 | 13 | 36 | 44 | 66 | 2.2 |
| 515648 | 8 | 10 | 10 | 5 | 16 | >6.0 |
| 515653 | 9 | 35 | 26 | 55 | 71 | 1.5 |
| 515655 | 0 | 0 | 6 | 13 | 42 | >6.0 |
| 515657 | 0 | 13 | 17 | 38 | 51 | 6.0 |
| 516045 | 0 | 6 | 15 | 19 | 40 | >6.0 |
| 516046 | 0 | 7 | 32 | 48 | 69 | 2.1 |
| 516047 | 12 | 27 | 41 | 50 | 63 | 1.8 |
| 516051 | 9 | 8 | 34 | 52 | 66 | 2.0 |
| 516052 | 17 | 42 | 27 | 53 | 75 | 1.2 |
| 516053 | 9 | 7 | 28 | 63 | 77 | 1.3 |
| 516055 | 0 | 3 | 27 | 54 | 75 | 2.0 |
| 516056 | 0 | 4 | 14 | 52 | 66 | 2.6 |
| 516057 | 0 | 34 | 33 | 51 | 70 | 1.6 |
| 516058 | 13 | 12 | 25 | 47 | 74 | 2.0 |
| 516059 | 4 | 15 | 36 | 47 | 68 | 1.9 |
| 516060 | 0 | 1 | 39 | 29 | 63 | 3.2 |
| 516061 | 0 | 0 | 24 | 0 | 3 | <6.0 |
| 516062 | 0 | 20 | 43 | 65 | 78 | 1.0 |
| 516063 | 0 | 8 | 10 | 37 | 61 | 3.8 |
| 516064 | 0 | 3 | 13 | 45 | 69 | 2.7 |
| 516065 | 0 | 14 | 38 | 63 | 76 | 1.3 |
| 516066 | 0 | 3 | 30 | 55 | 75 | 1.7 |

Example 19: Modified Oligonucleotides Comprising 2'-O-Methoxyethyl (2'-MOE) and Constrained Ethyl (cEt) Modifications Targeting Human Target-X Additional antisense oligonucleotides were designed targeting a Target-X nucleic acid and were tested for their effects on Target-X mRNA in vitro. ISIS 472998, ISIS 515652, ISIS 515653, ISIS 515654, ISIS 515655, ISIS 515656, and ISIS 515657, described in the Examples above were also included in the screen.

The newly designed chimeric antisense oligonucleotides are 16 or 17 nucleotides in length and their motifs are described in Table 30. The chemistry column of Table 30 presents the sugar motif of each oligonucleotide, wherein "e" indicates a 2'-O-methythoxylethyl (2'-MOE) nucleoside, "k" indicates a constrained ethyl (cEt) nucleoside and "d" indicates a 2'-deoxynucleoside. The internucleoside linkages throughout each gapmer are hosphorothioate (P=S) linkages. All cytosine residues throughout each oligonucleotide are 5-methylcytosines.

Each gapmer listed in Table 30 is targeted to the human Target-X genomic sequence.

Activity of newly designed gapmers was compared to ISIS 407939. Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 (described hereinabove in Example 1) was used to measure mRNA levels. Target-X mRNA levels were adjusted according to total RNA content, as measured by RIBOGREEN®. Results are presented as percent inhibition of Target-X, relative to untreated control cells.

TABLE 30

Inhibition of human Target-X mRNA levels by chimeric
antisense oligonucleotides targeted to Target-X

| ISIS No | % inhibition | Chemistry | SEQ CODE |
|---------|--------------|-----------|----------|
| 472998 | 85 | kk-d(10)-kk | 74 |
| 515652 | 63 | eee-d(10)-kkk | 50 |
| 515653 | 67 | eee-d(10)-kkk | 71 |

TABLE 30-continued

Inhibition of human Target-X mRNA levels by chimeric antisense oligonucleotides targeted to Target-X

| ISIS No | % inhibition | Chemistry | SEQ CODE |
|---|---|---|---|
| 515654 | 78 | eee-d(10)-kkk | 86 |
| 515655 | 41 | eee-d(10)-kkk | 61 |
| 515656 | 74 | eee-d(10)-kkk | 87 |
| 515657 | 49 | eee-d(10)-kkk | 73 |
| 529265 | 52 | eek-d(10)-keke | 267 |
| 529332 | 82 | eek-d(10)-keke | 268 |
| 529334 | 78 | eek-d(10)-keke | 269 |
| 529186 | 85 | eek-d(10)-keke | 213 |
| 529223 | 81 | eek-d(10)-kkke | 213 |
| 529129 | 75 | eee-d(10)-kkk | 270 |
| 529149 | 82 | kkk-d(10)-eee | 270 |
| 529177 | 77 | eek-d(10)-keke | 214 |
| 529214 | 78 | eek-d(10)-kkke | 214 |
| 529178 | 79 | eek-d(10)-keke | 271 |
| 529215 | 82 | eek-d(10)-kkke | 271 |
| 529179 | 71 | eek-d(10)-keke | 272 |
| 529216 | 77 | eek-d(10)-kkke | 272 |
| 529193 | 69 | eek-d(10)-keke | 273 |
| 529230 | 70 | eek-d(10)-kkke | 273 |
| 529136 | 48 | eee-d(10)-kkk | 274 |
| 529156 | 68 | kkk-d(10)-eee | 274 |
| 529194 | 44 | eek-d(10)-keke | 275 |
| 529231 | 56 | eek-d(10)-kkke | 275 |
| 529137 | 34 | eee-d(10)-kkk | 276 |
| 529157 | 79 | kkk-d(10)-eee | 276 |
| 529336 | 57 | eek-d(10)-keke | 277 |
| 529338 | 73 | eek-d(10)-kke | 278 |
| 529195 | 55 | eek-d(10)-keke | 279 |
| 529232 | 68 | eek-d(10)-kkke | 279 |
| 529340 | 65 | eek-d(10)-keke | 280 |
| 529342 | 69 | eek-d(10)-keke | 281 |
| 529812 | 69 | k-d(10)-kekee | 282 |
| 529831 | 62 | k-d(10)-kdkee | 282 |
| 529733 | 64 | ke-d(10)-keke | 283 |
| 529753 | 52 | ek-d(10)-keke | 283 |
| 529773 | 57 | ke-d(10)-kdke | 283 |
| 529793 | 36 | ek-d(10)-kdke | 283 |
| 529862 | 48 | kde-d(10)-kdke | 284 |
| 529882 | 35 | edk-d(10)-kdke | 284 |
| 529902 | 44 | k-(d4)-k-(d4)-k-(d4)-ke | 284 |
| 529559 | 71 | eek-d(10)-kke | 26 |
| 529584 | 57 | kee-d(10)-kke | 26 |
| 529609 | 58 | edk-d(10)-kke | 26 |
| 529634 | 49 | kde-d(10)-kke | 26 |
| 529659 | 52 | kddk-d(9)-kke | 26 |
| 529684 | 48 | kdde-d(9)-kke | 26 |
| 529709 | 61 | eddk-d(9)-kke | 26 |
| 529922 | 52 | eeee-d(9)-kke | 26 |
| 529344 | 50 | eek-d(10)-keke | 285 |
| 529138 | 32 | eee-d(10)-kkk | 286 |
| 529158 | 75 | kkk-d(10)-eee | 286 |
| 529184 | 75 | eek-d(10)-keke | 215 |
| 529221 | 78 | eek-d(10)-kkke | 215 |
| 529127 | 67 | eee-d(10)-kkk | 287 |
| 529147 | 79 | kkk-d(10)-eee | 287 |
| 529346 | 58 | eek-d(10)-keke | 288 |
| 529348 | 65 | eek-d(10)-keke | 289 |
| 529350 | 77 | eek-d(10)-keke | 290 |
| 529813 | 20 | k-d(10)-kekee | 291 |
| 529832 | 47 | k-d(10)-kdkee | 291 |
| 529734 | 63 | ke-d(10)-keke | 292 |
| 529754 | 58 | ek-d(10)-keke | 292 |
| 529774 | 49 | ke-d(10)-kdke | 292 |
| 529794 | 51 | ek-d(10)-kdke | 292 |
| 529863 | 64 | kde-d(10)-kdke | 293 |
| 529883 | 78 | edk-d(10)-kdke | 293 |
| 529903 | 36 | k-d(4)-k-d(4)-k-d(4)-ke | 293 |
| 529560 | 71 | eek-d(10)-kke | 27 |
| 529585 | 70 | kee-d(10)-kke | 27 |
| 529610 | 66 | edk-d(10)-kke | 27 |
| 529635 | 45 | kde-d(10)-kke | 27 |
| 529660 | 53 | kddk-d(9)-kke | 27 |
| 529685 | 42 | kdde-d(9)-kke | 27 |
| 529710 | 60 | eddk-d(9)-kke | 27 |
| 529923 | 63 | eeee-d(9)-kke | 27 |
| 529196 | 74 | eek-d(10)-keke | 294 |
| 529233 | 80 | eek-d(10)-kkke | 294 |
| 529139 | 75 | eee-d(10)-kkk | 295 |
| 529159 | 62 | kkk-d(10)-eee | 295 |
| 529352 | 74 | eek-d(10)-keke | 296 |
| 529354 | 67 | eek-d(10)-keke | 297 |
| 529197 | 43 | eek-d(10)-keke | 298 |
| 529234 | 58 | eek-d(10)-kkke | 298 |
| 529140 | 29 | eee-d(10)-kkk | 299 |
| 529160 | 59 | kkk-d(10)-eee | 299 |
| 529180 | 80 | eek-d(10)-keke | 216 |
| 529217 | 79 | eek-d(10)-kkke | 216 |
| 529814 | 51 | k-d(10)-kekee | 300 |
| 529833 | 52 | k-d(10)-kdkee | 300 |
| 529735 | 43 | ke-d(10)-keke | 301 |
| 529755 | 60 | ek-d(10)-keke | 301 |
| 529775 | 38 | ke-d(10)-kdke | 301 |
| 529795 | 58 | ek-d(10)-kdke | 301 |
| 529864 | 41 | kde-d(10)-kdke | 302 |
| 529884 | 48 | edk-d(10)-kdke | 302 |
| 529904 | 44 | k-d(4)-k-(d4)-k-d(4)-ke | 302 |
| 529934 | 61 | eek-d(10)-keke | 302 |
| 529356 | 71 | eek-d(10)-keke | 303 |
| 529561 | 75 | eek-d(10)-kke | 28 |
| 529586 | 65 | kee-d(10)-kke | 28 |
| 529611 | 54 | edk-d(10)-kke | 28 |
| 529636 | 39 | kde-d(10)-kke | 28 |
| 529661 | 67 | kddk-d(9)-kke | 28 |
| 529686 | 66 | kdde-d(9)-kke | 28 |
| 529711 | 60 | eddk-d(9)-kke | 28 |
| 529924 | 62 | eeee-d(9)-kke | 28 |
| 529358 | 82 | eek-d(10)-keke | 304 |
| 529181 | 79 | eek-d(10)-keke | 217 |
| 529218 | 73 | eek-d(10)-kkke | 217 |
| 529182 | 85 | eek-d(10)-keke | 218 |
| 529219 | 84 | eek-d(10)-kkke | 218 |
| 529360 | 84 | eek-d(10)-keke | 305 |
| 529362 | 87 | eek-d(10)-keke | 306 |
| 529364 | 81 | eek-d(10)-keke | 307 |
| 529366 | 77 | eek-d(10)-keke | 308 |
| 529198 | 28 | eek-d(10)-keke | 309 |
| 529235 | 8 | eek-d(10)-kkke | 309 |
| 529141 | 34 | eee-d(10)-kkk | 310 |
| 529161 | 66 | kkk-d(10)-eee | 310 |
| 529368 | 27 | eek-d(10)-keke | 311 |
| 529370 | 44 | eek-d(10)-keke | 312 |
| 529372 | 61 | eek-d(10)-keke | 313 |
| 529374 | 71 | eek-d(10)-keke | 314 |
| 529376 | 63 | eek-d(10)-keke | 315 |
| 529378 | 68 | eek-d(10)-keke | 316 |
| 529380 | 79 | eek-d(10)-keke | 317 |
| 529382 | 77 | eek-d(10)-keke | 318 |
| 529384 | 75 | eek-d(10)-keke | 319 |
| 529386 | 40 | eek-d(10)-keke | 320 |
| 529240 | 73 | eek-d(10)-keke | 321 |
| 529241 | 67 | eek-d(10)-keke | 322 |
| 529242 | 42 | eek-d(10)-keke | 323 |
| 529243 | 60 | eek-d(10)-keke | 324 |
| 529388 | 65 | eek-d(10)-keke | 325 |
| 529815 | 37 | k-d(10)-kekee | 326 |
| 529834 | 44 | k-d(10)-kdkee | 326 |
| 529736 | 47 | ke-d(10)-keke | 327 |
| 529756 | 78 | ek-d(10)-keke | 327 |
| 529776 | 37 | ke-d(10)-kdke | 327 |
| 529796 | 71 | ek-d(10)-kdke | 327 |
| 529865 | 70 | kde-d(10)-kdke | 328 |
| 529885 | 59 | edk-d(10)-kdke | 328 |
| 529905 | 54 | k-d(4)-k-d(4)-k-d(4)-ke | 328 |
| 529935 | 70 | eek-d(10)-keke | 328 |
| 529562 | 87 | eek-d(10)-kke | 29 |
| 529587 | 68 | kee-d(10)-kke | 29 |
| 529612 | 67 | edk-d(10)-kke | 29 |
| 529637 | 64 | kde-d(10)-kke | 29 |

TABLE 30-continued

Inhibition of human Target-X mRNA levels by chimeric antisense oligonucleotides targeted to Target-X

| ISIS No | % inhibition | Chemistry | SEQ CODE |
|---|---|---|---|
| 529662 | 62 | kddk-d(9)-kke | 29 |
| 529687 | 63 | kdde-d(9)-kke | 29 |
| 529712 | 61 | eddk-d(9)-kke | 29 |
| 529925 | 61 | eeee-d(9)-kke | 29 |
| 529816 | 77 | k-d(10)-kekee | 329 |
| 529835 | 80 | k-d(10)-kdkee | 329 |
| 529737 | 82 | ke-d(10)-keke | 330 |
| 529757 | 83 | ek-d(10)-keke | 330 |
| 529777 | 68 | ke-d(10)-kdke | 330 |
| 529797 | 77 | ek-d(10)-kdke | 330 |
| 529866 | 15 | kde-d(10)-kdke | 331 |
| 529886 | 71 | edk-d(10)-kdke | 331 |
| 529906 | 63 | k-(d4)-k-(d4)-k-(d4)-ke | 331 |
| 529936 | 78 | eek-d(10)-keke | 331 |
| 529563 | 89 | eek-d(10)-kke | 30 |
| 529588 | 84 | kee-d(10)-kke | 30 |
| 529613 | 80 | edk-d(10)-kke | 30 |
| 529638 | 48 | kde-d(10)-kke | 30 |
| 529663 | 85 | kddk-d(9)-kke | 30 |
| 529688 | 42 | kdde-d(9)-kke | 30 |
| 529713 | 81 | eddk-d(9)-kke | 30 |
| 529926 | 67 | eeee-d(9)-kke | 30 |
| 529390 | 53 | eek-d(10)-keke | 332 |
| 529392 | 63 | eek-d(10)-keke | 333 |
| 529394 | 58 | eek-d(10)-keke | 334 |
| 529396 | 56 | eek-d(10)-keke | 335 |
| 529398 | 62 | eek-d(10)-keke | 336 |
| 529400 | 44 | eek-d(10)-keke | 337 |
| 529402 | 39 | eek-d(10)-keke | 338 |
| 529404 | 46 | eek-d(10)-keke | 339 |
| 529406 | 63 | eek-d(10)-keke | 340 |
| 529244 | 58 | eek-d(10)-keke | 341 |
| 529245 | 68 | eek-d(10)-keke | 342 |
| 529246 | 60 | eek-d(10)-keke | 343 |
| 529247 | 36 | eek-d(10)-keke | 344 |
| 529248 | 43 | eek-d(10)-keke | 345 |
| 529249 | 23 | eek-d(10)-keke | 346 |
| 529250 | 69 | eek-d(10)-keke | 347 |
| 529251 | 15 | eek-d(10)-keke | 348 |
| 529252 | 44 | eek-d(10)-keke | 349 |
| 529253 | 42 | eek-d(10)-keke | 350 |
| 529408 | 67 | eek-d(10)-keke | 351 |
| 529410 | 19 | eek-d(10)-keke | 352 |
| 529412 | 57 | eek-d(10)-keke | 353 |
| 529414 | 80 | eek-d(10)-keke | 354 |
| 529416 | 85 | eek-d(10)-keke | 355 |
| 529418 | 70 | eek-d(10)-keke | 356 |
| 529420 | 78 | eek-d(10)-keke | 357 |
| 529422 | 19 | eek-d(10)-keke | 358 |
| 529424 | 48 | eek-d(10)-keke | 359 |
| 529426 | 66 | eek-d(10)-keke | 360 |
| 529428 | 59 | eek-d(10)-keke | 361 |
| 529430 | 83 | eek-d(10)-keke | 362 |
| 529432 | 84 | eek-d(10)-keke | 363 |
| 529199 | 71 | eek-d(10)-keke | 364 |
| 529236 | 76 | eek-d(10)-kkke | 364 |
| 529142 | 64 | eee-d(10)-kkk | 365 |
| 529162 | 60 | kkk-d(10)-eee | 365 |
| 529254 | 46 | eek-d(10)-keke | 366 |
| 529255 | 52 | eek-d(10)-keke | 367 |
| 529256 | 57 | eek-d(10)-keke | 368 |
| 529257 | 55 | eek-d(10)-keke | 369 |
| 529258 | 3 | eek-d(10)-keke | 370 |
| 529259 | 71 | eek-d(10)-keke | 371 |
| 529260 | 72 | eek-d(10)-keke | 372 |
| 529261 | 56 | eek-d(10)-keke | 373 |
| 529262 | 56 | eek-d(10)-keke | 374 |
| 529263 | 59 | eek-d(10)-keke | 375 |
| 529264 | 49 | eek-d(10)-keke | 376 |
| 529434 | 83 | eek-d(10)-keke | 377 |
| 529436 | 80 | eek-d(10)-keke | 378 |
| 529438 | 79 | eek-d(10)-keke | 379 |
| 529440 | 87 | eek-d(10)-keke | 380 |
| 529442 | 68 | eek-d(10)-keke | 381 |
| 529443 | 72 | eek-d(10)-keke | 382 |
| 529444 | 68 | eek-d(10)-keke | 383 |
| 529445 | 85 | eek-d(10)-keke | 384 |
| 529446 | 72 | eek-d(10)-keke | 385 |
| 529447 | 60 | eek-d(10)-keke | 386 |
| 529448 | 77 | eek-d(10)-keke | 387 |
| 529807 | 78 | k-d(10)-kekee | 388 |
| 529826 | 61 | k-d(10)-kdkee | 388 |
| 529449 | 81 | eek-d(10)-keke | 389 |
| 529728 | 75 | ke-d(10)-keke | 390 |
| 529748 | 80 | ek-d(10)-keke | 390 |
| 529768 | 68 | ke-d(10)-kdke | 390 |
| 529788 | 74 | ek-d(10)-kdke | 390 |
| 529857 | 67 | kde-d(10)-kdke | 389 |
| 529877 | 77 | edk-d(10)-kdke | 389 |
| 529897 | 26 | k-(d4)-k-(d4)-k-(d4)-ke | 389 |
| 529200 | 78 | eek-d(10)-keke | 391 |
| 529237 | 84 | eek-d(10)-kkke | 391 |
| 529564 | 90 | eek-d(10)-kke | 34 |
| 529589 | 86 | kee-d(10)-kke | 34 |
| 529614 | 82 | edk-d(10)-kke | 34 |
| 529639 | 80 | kde-d(10)-kke | 34 |
| 529664 | 69 | kddk-d(9)-kke | 34 |
| 529689 | 71 | kdde-d(9)-kke | 34 |
| 529714 | 73 | eddk-d(9)-kke | 34 |
| 529917 | 73 | eeee-d(9)-kke | 34 |
| 529143 | 68 | eee-d(10)-kkk | 392 |
| 529163 | 50 | kkk-d(10)-eee | 392 |
| 529201 | 76 | eek-d(10)-keke | 393 |
| 529238 | 72 | eek-d(10)-kkke | 393 |
| 529144 | 57 | eee-d(10)-kkk | 394 |
| 529164 | 71 | kkk-d(10)-eee | 394 |
| 529450 | 91 | eek-d(10)-keke | 395 |
| 529451 | 85 | eek-d(10)-keke | 396 |
| 529266 | 63 | eek-d(10)-keke | 397 |
| 529806 | 52 | k-d(10)-kekee | 398 |
| 529825 | 44 | k-d(10)-kdkee | 398 |
| 529267 | 56 | eek-d(10)-keke | 399 |
| 529727 | 67 | ke-d(10)-keke | 400 |
| 529747 | 63 | ek-d(10)-keke | 400 |
| 529767 | 67 | ke-d(10)-kdke | 400 |
| 529787 | 68 | ek-d(10)-kdke | 400 |
| 529856 | 42 | kde-d(10)-kdke | 399 |
| 529876 | 36 | edk-d(10)-kdke | 399 |
| 529896 | 56 | k-(d4)-k-(d4)-k-(d4)-ke | 399 |
| 529546 | 65 | eek-d(10)-kke | 248 |
| 529571 | 80 | kee-d(10)-kke | 248 |
| 529596 | 43 | edk-d(10)-kke | 248 |
| 529621 | 38 | kde-d(10)-kke | 248 |
| 529646 | 68 | kddk-d(9)-kke | 248 |
| 529671 | 50 | kdde-d(9)-kke | 248 |
| 529696 | 53 | eddk-d(9)-kke | 248 |
| 529916 | 22 | eeee-d(9)-kke | 248 |
| 529547 | 86 | eek-d(10)-kke | 37 |
| 529572 | 75 | kee-d(10)-kke | 37 |
| 529597 | 58 | edk-d(10)-kke | 37 |
| 529622 | 58 | kde-d(10)-kke | 37 |
| 529647 | 18 | kddk-d(9)-kke | 37 |
| 529672 | 23 | kdde-d(9)-kke | 37 |
| 529697 | 28 | eddk-d(9)-kke | 37 |
| 529928 | 36 | eeee-d(9)-kke | 37 |
| 529452 | 63 | eek-d(10)-keke | 401 |
| 529453 | 73 | eek-d(10)-keke | 402 |
| 529454 | 82 | eek-d(10)-keke | 403 |
| 529455 | 84 | eek-d(10)-keke | 404 |
| 529202 | 61 | eek-d(10)-keke | 405 |
| 529239 | 59 | eek-d(10)-kkke | 405 |
| 529145 | 54 | eee-d(10)-kkk | 406 |
| 529165 | 77 | kkk-d(10)-eee | 406 |
| 529456 | 69 | eek-d(10)-keke | 407 |
| 529457 | 81 | eek-d(10)-keke | 408 |
| 529458 | 72 | eek-d(10)-keke | 409 |
| 529459 | 86 | eek-d(10)-keke | 410 |
| 529460 | 88 | eek-d(10)-keke | 411 |

TABLE 30-continued

Inhibition of human Target-X mRNA levels by chimeric antisense oligonucleotides targeted to Target-X

| ISIS No | % inhibition | Chemistry | SEQ CODE |
|---|---|---|---|
| 529817 | 46 | k-d(10)-kekee | 412 |
| 529836 | 49 | k-d(10)-kdkee | 412 |
| 529738 | 51 | ke-d(10)-keke | 413 |
| 529758 | 53 | ek-d(10)-keke | 413 |
| 529778 | 39 | ke-d(10)-kdke | 413 |
| 529798 | 52 | ek-d(10)-kdke | 413 |
| 529867 | 56 | kde-d(10)-kdke | 414 |
| 529887 | 68 | edk-d(10)-kdke | 414 |
| 529907 | 28 | k-(d4)-k-(d4)-k-(d4)-ke | 414 |
| 529938 | 64 | eek-d(10)-keke | 414 |
| 529565 | 81 | eek-d(10)-kke | 38 |
| 529590 | 49 | kee-d(10)-kke | 38 |
| 529615 | 65 | edk-d(10)-kke | 38 |
| 529640 | 54 | kde-d(10)-kke | 38 |
| 529665 | 77 | kddk-d(9)-kke | 38 |
| 529690 | 77 | kdde-d(9)-kke | 38 |
| 529715 | 63 | eddk-d(9)-kke | 38 |
| 529927 | 62 | eeee-d(9)-kke | 38 |
| 529185 | 66 | eek-d(10)-keke | 221 |
| 529222 | 62 | eek-d(10)-kkke | 221 |
| 529808 | 75 | k-d(10)-kekee | 89 |
| 529827 | 67 | k-d(10)-kdkee | 89 |
| 529128 | 64 | eee-d(10)-kkk | 415 |
| 529148 | 78 | kkk-d(10)-eee | 415 |
| 529461 | 87 | eek-d(10)-keke | 416 |
| 529729 | 71 | ke-d(10)-keke | 415 |
| 529749 | 83 | ek-d(10)-keke | 415 |
| 529769 | 63 | ke-d(10)-kdke | 415 |
| 529789 | 10 | ek-d(10)-kdke | 415 |
| 529800 | 69 | k-d(10)-kekee | 415 |
| 529819 | 78 | k-d(10)-kdkee | 415 |
| 529858 | 60 | kde-d(10)-kdke | 416 |
| 529878 | 75 | edk-d(10)-kdke | 416 |
| 529898 | 34 | k-(d4)-k-(d4)-k-(d4)-ke | 416 |
| 529566 | 61 | eek-d(10)-kke | 39 |
| 529591 | 71 | kee-d(10)-kke | 39 |
| 529616 | 71 | edk-d(10)-kke | 39 |
| 529641 | 65 | kde-d(10)-kke | 39 |
| 529666 | 70 | kddk-d(9)-kke | 39 |
| 529691 | 67 | kdde-d(9)-kke | 39 |
| 529716 | 75 | eddk-d(9)-kke | 39 |
| 529721 | 71 | ke-d(10)-keke | 39 |
| 529741 | 81 | ek-d(10)-keke | 39 |
| 529761 | 66 | ke-d(10)-kdke | 39 |
| 529781 | 65 | ek-d(10)-kdke | 39 |
| 529801 | 71 | k-d(10)-kekee | 39 |
| 529820 | 74 | k-d(10)-kdkee | 39 |
| 529850 | 63 | kde-d(10)-kdke | 417 |
| 529870 | 72 | edk-d(10)-kdke | 417 |
| 529890 | 23 | k-(d4)-k-(d4)-k-(d4)-ke | 417 |
| 529918 | 54 | eeee-d(9)-kke | 39 |
| 529567 | 75 | eek-d(10)-kke | 262 |
| 529592 | 80 | kee-d(10)-kke | 262 |
| 529617 | 65 | edk-d(10)-kke | 262 |
| 529642 | 62 | kde-d(10)-kke | 262 |
| 529667 | 75 | kddk-d(9)-kke | 262 |
| 529692 | 53 | kdde-d(9)-kke | 262 |
| 529717 | 69 | eddk-d(9)-kke | 262 |
| 529722 | 74 | ke-d(10)-keke | 262 |
| 529742 | 81 | ek-d(10)-keke | 262 |
| 529762 | 66 | ke-d(10)-kdke | 262 |
| 529782 | 68 | ek-d(10)-kdke | 262 |
| 529851 | 68 | kde-d(10)-kdke | 418 |
| 529871 | 77 | edk-d(10)-kdke | 418 |
| 529891 | 36 | k-(d4)-k-(d4)-k-(d4)-ke | 418 |
| 529910 | 60 | eeee-d(9)-kke | 262 |
| 529568 | 79 | eek-d(10)-kke | 263 |
| 529593 | 70 | kee-d(10)-kke | 263 |
| 529618 | 77 | edk-d(10)-kke | 263 |
| 529643 | 72 | kde-d(10)-kke | 263 |
| 529668 | 73 | kddk-d(9)-kke | 263 |
| 529693 | 62 | kdde-d(9)-kke | 263 |
| 529718 | 69 | eddk-d(9)-kke | 263 |
| 529911 | 66 | eeee-d(9)-kke | 263 |
| 529462 | 76 | eek-d(10)-keke | 419 |
| 529268 | 18 | eek-d(10)-keke | 420 |
| 529187 | 46 | eek-d(10)-keke | 421 |
| 529224 | 48 | eek-d(10)-kkke | 421 |
| 529130 | 34 | eee-d(10)-kkk | 422 |
| 529150 | 51 | kkk-d(10)-eee | 422 |
| 529549 | 85 | eek-d(10)-kke | 42 |
| 529574 | 81 | kee-d(10)-kke | 42 |
| 529599 | 64 | edk-d(10)-kke | 42 |
| 529624 | 68 | kde-d(10)-kke | 42 |
| 529649 | 77 | kddk-d(9)-kke | 42 |
| 529674 | 65 | kdde-d(9)-kke | 42 |
| 529699 | 63 | eddk-d(9)-kke | 42 |
| 529931 | 59 | eeee-d(9)-kke | 42 |
| 529810 | 80 | k-d(10)-kekee | 423 |
| 529829 | 67 | k-d(10)-kdkee | 423 |
| 529269 | 65 | eek-d(10)-keke | 424 |
| 529731 | 66 | ke-d(10)-keke | 425 |
| 529751 | 76 | ek-d(10)-keke | 425 |
| 529771 | 73 | ke-d(10)-kdke | 425 |
| 529791 | 65 | ek-d(10)-kdke | 425 |
| 529860 | 73 | kde-d(10)-kdke | 424 |
| 529880 | 74 | edk-d(10)-kdke | 424 |
| 529900 | 62 | k-(d4)-k-(d4)-k-(d4)-ke | 424 |
| 529270 | 69 | eek-d(10)-keke | 480 |
| 529550 | 81 | eek-d(10)-kke | 44 |
| 529575 | 88 | kee-d(10)-kke | 44 |
| 529600 | 78 | edk-d(10)-kke | 44 |
| 529625 | 74 | kde-d(10)-kke | 44 |
| 529650 | 81 | kddk-d(9)-kke | 44 |
| 529675 | 76 | kdde-d(9)-kke | 44 |
| 529700 | 73 | eddk-d(9)-kke | 44 |
| 529920 | 67 | eeee-d(9)-kke | 44 |
| 529271 | 43 | eek-d(10)-keke | 427 |
| 529272 | 0 | eek-d(10)-keke | 428 |
| 529273 | 62 | eek-d(10)-keke | 429 |
| 529274 | 78 | eek-d(10)-keke | 430 |
| 529275 | 70 | eek-d(10)-keke | 431 |
| 529276 | 73 | eek-d(10)-keke | 432 |
| 529277 | 71 | eek-d(10)-keke | 433 |
| 529278 | 72 | eek-d(10)-keke | 434 |
| 529279 | 10 | eek-d(10)-keke | 435 |
| 529280 | 11 | eek-d(10)-keke | 436 |
| 529281 | 82 | eek-d(10)-keke | 437 |
| 529282 | 87 | eek-d(10)-keke | 438 |
| 529803 | 71 | k-d(10)-kekee | 250 |
| 529822 | 72 | k-d(10)-kdkee | 250 |
| 529724 | 76 | ke-d(10)-keke | 439 |
| 529744 | 81 | ek-d(10)-keke | 439 |
| 529764 | 65 | ke-d(10)-kdke | 439 |
| 529784 | 68 | ek-d(10)-kdke | 439 |
| 529853 | 64 | kde-d(10)-kdke | 440 |
| 529873 | 69 | edk-d(10)-kdke | 440 |
| 529893 | 45 | k-(d4)-k-(d4)-k-(d4)-ke | 440 |
| 529937 | 81 | eek-d(10)-keke | 440 |
| 529551 | 88 | eek-d(10)-kke | 48 |
| 529576 | 71 | kee-d(10)-kke | 48 |
| 529601 | 74 | edk-d(10)-kke | 48 |
| 529626 | 72 | kde-d(10)-kke | 48 |
| 529651 | 85 | kddk-d(9)-kke | 48 |
| 529676 | 67 | kdde-d(9)-kke | 48 |
| 529701 | 82 | eddk-d(9)-kke | 48 |
| 529913 | 76 | eeee-d(9)-kke | 48 |
| 529811 | 56 | k-d(10)-kekee | 441 |
| 529830 | 46 | k-d(10)-kdkee | 441 |
| 529732 | 63 | ke-d(10)-keke | 442 |
| 529752 | 72 | ek-d(10)-keke | 442 |
| 529772 | 61 | ke-d(10)-kdke | 442 |
| 529792 | 68 | ek-d(10)-kdke | 442 |
| 529861 | 54 | kde-d(10)-kdke | 443 |
| 529881 | 78 | edk-d(10)-kdke | 443 |
| 529901 | 29 | k-(d4)-k-(d4)-k-(d4)-ke | 443 |
| 529939 | 67 | eek-d(10)-keke | 443 |
| 529283 | 70 | eek-d(10)-keke | 444 |

TABLE 30-continued

Inhibition of human Target-X mRNA levels by chimeric antisense oligonucleotides targeted to Target-X

| ISIS No | % inhibition | Chemistry | SEQ CODE |
|---|---|---|---|
| 529552 | 72 | eek-d(10)-kke | 49 |
| 529577 | 80 | kee-d(10)-kke | 49 |
| 529602 | 64 | edk-d(10)-kke | 49 |
| 529627 | 56 | kde-d(10)-kke | 49 |
| 529652 | 57 | kddk-d(9)-kke | 49 |
| 529677 | 43 | kdde-d(9)-kke | 49 |
| 529702 | 54 | eddk-d(9)-kke | 49 |
| 529921 | 42 | eeee-d(9)-kke | 49 |
| 529284 | 76 | eek-d(10)-keke | 445 |
| 529285 | 77 | eek-d(10)-keke | 446 |
| 529286 | 68 | eek-d(10)-keke | 447 |
| 529287 | 65 | eek-d(10)-keke | 448 |
| 529719 | 73 | ke-d(10)-keke | 264 |
| 529739 | 83 | ek-d(10)-keke | 264 |
| 529759 | 63 | ke-d(10)-kdke | 264 |
| 529779 | 70 | ek-d(10)-kdke | 244 |
| 529848 | 60 | kde-d(10)-kdke | 449 |
| 529868 | 63 | edk-d(10)-kdke | 449 |
| 529888 | 53 | k-(d4)-k-(d4)-k-(d4)-ke | 449 |
| 529553 | 81 | eek-d(10)-kke | 265 |
| 529578 | 65 | kee-d(10)-kke | 265 |
| 529603 | 60 | edk-d(10)-kke | 265 |
| 529628 | 59 | kde-d(10)-kke | 265 |
| 529653 | 76 | kddk-d(9)-kke | 265 |
| 529678 | 56 | kdde-d(9)-kke | 265 |
| 529703 | 68 | eddk-d(9)-kke | 265 |
| 529908 | 69 | eeee-d(9)-kke | 265 |
| 529168 | 64 | eek-d(10)-keke | 450 |
| 529205 | 62 | eek-d(10)-kkke | 450 |
| 529290 | 53 | eek-d(10)-keke | 451 |
| 529802 | 57 | k-d(10)-kekee | 452 |
| 529821 | 61 | k-d(10)-kdkee | 452 |
| 529292 | 74 | eek-d(10)-keke | 453 |
| 529723 | 68 | ke-d(10)-keke | 454 |
| 529743 | 84 | ek-d(10)-keke | 454 |
| 529763 | 64 | ke-d(10)-kdke | 454 |
| 529783 | 72 | ek-d(10)-kdke | 454 |
| 529852 | 66 | kde-d(10)-kdke | 453 |
| 529872 | 62 | edk-d(10)-kdke | 453 |
| 529892 | 43 | k-(d4)-k-(d4)-k-(d4)-ke | 453 |
| 529554 | 80 | eek-d(10)-kke | 252 |
| 529579 | 83 | kee-d(10)-kke | 252 |
| 529604 | 73 | edk-d(10)-kke | 252 |
| 529629 | 64 | kde-d(10)-kke | 252 |
| 529654 | 69 | kddk-d(9)-kke | 252 |
| 529679 | 52 | kdde-d(9)-kke | 252 |
| 529704 | 63 | eddk-d(9)-kke | 252 |
| 529912 | 64 | eeee-d(9)-kke | 252 |
| 529294 | 74 | eek-d(10)-keke | 455 |
| 529296 | 52 | eek-d(10)-keke | 456 |
| 529298 | 60 | eek-d(10)-keke | 457 |
| 529300 | 71 | eek-d(10)-keke | 458 |
| 529188 | 79 | eek-d(10)-keke | 459 |
| 529225 | 78 | eek-d(10)-kkke | 459 |
| 529131 | 58 | eee-d(10)-kkk | 460 |
| 529151 | 71 | kkk-d(10)-eee | 460 |
| 529302 | 74 | eek-d(10)-keke | 461 |
| 529189 | 64 | eek-d(10)-keke | 222 |
| 529226 | 50 | eek-d(10)-kkke | 222 |
| 529132 | 78 | eee-d(10)-kkk | 462 |
| 529152 | 62 | kkk-d(10)-eee | 462 |
| 529190 | 76 | eek-d(10)-keke | 223 |
| 529227 | 88 | eek-d(10)-kkke | 250 |
| 529133 | 81 | eee-d(10)-kkk | 463 |
| 529153 | 68 | kkk-d(10)-eee | 463 |
| 529191 | 78 | eek-d(10)-keke | 224 |
| 529228 | 85 | eek-d(10)-kkke | 224 |
| 529134 | 75 | eee-d(10)-kkk | 464 |
| 529154 | 61 | kkk-d(10)-eee | 464 |
| 529304 | 89 | eek-d(10)-keke | 465 |
| 529306 | 84 | eek-d(10)-keke | 466 |
| 529308 | 68 | eek-d(10)-keke | 467 |
| 529310 | 59 | eek-d(10)-keke | 468 |
| 529169 | 79 | eek-d(10)-keke | 469 |
| 529206 | 82 | eek-d(10)-kkke | 469 |
| 529312 | 68 | eek-d(10)-keke | 470 |
| 529314 | 61 | eek-d(10)-keke | 471 |
| 529316 | 62 | eek-d(10)-keke | 472 |
| 529555 | 78 | eek-d(10)-kke | 59 |
| 529580 | 73 | kee-d(10)-kke | 59 |
| 529605 | 71 | edk-d(10)-kke | 59 |
| 529630 | 64 | kde-d(10)-kke | 59 |
| 529655 | 63 | kddk-d(9)-kke | 59 |
| 529680 | 43 | kdde-d(9)-kke | 59 |
| 529705 | 63 | eddk-d(9)-kke | 59 |
| 529932 | 60 | eeee-d(9)-kke | 59 |
| 529318 | 82 | eek-d(10)-keke | 473 |
| 529170 | 85 | eek-d(10)-keke | 474 |
| 529207 | 88 | eek-d(10)-kkke | 474 |
| 529171 | 81 | eek-d(10)-keke | 475 |
| 529208 | 84 | eek-d(10)-kkke | 475 |
| 529805 | 40 | k-d(10)-kekee | 476 |
| 529824 | 32 | k-d(10)-kdkee | 476 |
| 529320 | 74 | eek-d(10)-keke | 477 |
| 529726 | 80 | ke-d(10)-keke | 478 |
| 529746 | 82 | ek-d(10)-keke | 478 |
| 529766 | 63 | ke-d(10)-kdke | 478 |
| 529786 | 69 | ek-d(10)-kdke | 478 |
| 529855 | 39 | kde-d(10)-kdke | 477 |
| 529875 | 40 | edk-d(10)-kdke | 477 |
| 529895 | 27 | k-(d4)-k-(d4)-k-(d4)-ke | 477 |
| 529556 | 72 | eek-d(10)-kke | 61 |
| 529581 | 68 | kee-d(10)-kke | 61 |
| 529606 | 54 | edk-d(10)-kke | 61 |
| 529631 | 29 | kde-d(10)-kke | 61 |
| 529656 | 74 | kddk-d(9)-kke | 61 |
| 529681 | 32 | kdde-d(9)-kke | 61 |
| 529706 | 41 | eddk-d(9)-kke | 61 |
| 529915 | 51 | eeee-d(9)-kke | 61 |
| 529172 | 88 | eek-d(10)-keke | 226 |
| 529209 | 87 | eek-d(10)-kkke | 226 |
| 529173 | 92 | eek-d(10)-keke | 227 |
| 529210 | 89 | eek-d(10)-kkke | 227 |
| 529811 | 85 | eek-d(10)-kkke | 479 |
| 529220 | 92 | eek-d(10)-kkke | 479 |
| 529126 | 83 | eee-d(10)-kkk | 257 |
| 529146 | 84 | kkk-d(10)-eee | 257 |
| 529174 | 85 | eek-d(10)-keke | 480 |
| 529211 | 86 | eek-d(10)-kkke | 480 |
| 529322 | 71 | eek-d(10)-keke | 481 |
| 529324 | 79 | eek-d(10)-keke | 482 |
| 529326 | 85 | eek-d(10)-keke | 483 |
| 529175 | 92 | eek-d(10)-keke | 228 |
| 529212 | 92 | eek-d(10)-kkke | 228 |
| 529176 | 89 | eek-d(10)-keke | 229 |
| 529213 | 90 | eek-d(10)-kkke | 229 |
| 529804 | 89 | k-d(10)-kekee | 259 |
| 529823 | 89 | k-d(10)-kdkee | 259 |
| 529166 | 83 | eek-d(10)-keke | 230 |
| 529203 | 86 | eek-d(10)-kkke | 230 |
| 529725 | 92 | ke-d(10)-keke | 260 |
| 529745 | 91 | ek-d(10)-keke | 260 |
| 529765 | 88 | ke-d(10)-kdke | 260 |
| 529785 | 91 | ek-d(10)-kdke | 260 |
| 529799 | 89 | k-d(10)-kekee | 260 |
| 529818 | 88 | k-d(10)-kdkee | 260 |
| 529854 | 90 | kde-d(10)-kdke | 230 |
| 529874 | 81 | edk-d(10)-kdke | 230 |
| 529894 | 60 | k-(d4)-k-(d4)-k-(d4)-ke | 230 |
| 529167 | 71 | eek-d(10)-keke | 231 |
| 529204 | 70 | eek-d(10)-kkke | 231 |
| 529557 | 86 | eek-d(10)-kke | 69 |
| 529582 | 86 | kee-d(10)-kke | 69 |
| 529607 | 84 | edk-d(10)-kke | 69 |
| 529632 | 81 | kde-d(10)-kke | 69 |
| 529657 | 85 | kddk-d(9)-kke | 69 |
| 529682 | 78 | kdde-d(9)-kke | 69 |
| 529707 | 79 | eddk-d(9)-kke | 69 |

TABLE 30-continued

Inhibition of human Target-X mRNA levels by chimeric antisense oligonucleotides targeted to Target-X

| ISIS No | % inhibition | Chemistry | SEQ CODE |
|---|---|---|---|
| 529720 | 75 | ke-d(10)-keke | 69 |
| 529740 | 70 | ek-d(10)-keke | 69 |
| 529760 | 78 | ke-d(10)-kdke | 69 |
| 529780 | 83 | ek-d(10)-kdke | 69 |
| 529849 | 80 | kde-d(10)-kdke | 231 |
| 529869 | 72 | edk-d(10)-kdke | 231 |
| 529889 | 49 | k-(d4)-k-(d4)-k-(d4)-ke | 231 |
| 529914 | 69 | eeee-d(9)-kke | 69 |
| 529328 | 68 | eek-d(10)-keke | 484 |
| 529558 | 71 | eek-d(10)-kke | 71 |
| 529583 | 81 | kee-d(10)-kke | 71 |
| 529608 | 68 | edk-d(10)-kke | 71 |
| 529633 | 73 | kde-d(10)-kke | 71 |
| 529658 | 63 | kddk-d(9)-kke | 71 |
| 529683 | 74 | kdde-d(9)-kke | 71 |
| 529708 | 70 | eddk-d(9)-kke | 71 |
| 529909 | 59 | eeee-d(9)-kke | 71 |
| 529192 | 51 | eek-d(10)-keke | 485 |
| 529229 | 69 | eek-d(10)-kkke | 485 |
| 529135 | 54 | eee-d(10)-kkk | 486 |
| 529155 | 56 | kkk-d(10)-eee | 486 |
| 529330 | 37 | eek-d(10)-keke | 487 | e = 2'-MOE,
k = cEt,
d = 2'-deoxynucleoside

Example 20: Design of Modified Oligonucleotides Comprising 2'-O-Methoxyethyl (2'-MOE) or Constrained Ethyl (cEt) Modifications Based on the activity of the antisense oligonucleotides listed above, additional antisense oligonucleotides were designed targeting a Target-X nucleic acid targeting start positions 1147, 1154 or 12842 of Target-X The newly designed chimeric antisense oligonucleotides are 16 or 17 nucleotides in length and their motifs are described in Table 31. The chemistry column of Table 31 presents the sugar motif of each oligonucleotide, wherein "e" indicates a 2'-O-methythoxylethyl (2'-MOE) nucleoside, "k" indicates a constrained ethyl (cEt) nucleoside and "d" indicates a 2'-deoxyribonucleoside. The internucleoside linkages throughout each gapmer are hosphorothioate (P=S) linkages. All cytosine residues throughout each oligonucleotide are 5-methylcytosine.

Each gapmer listed in Table 31 is targeted to the human Target-X genomic sequence.

TABLE 31

Chimeric antisense oligonucleotides targeted to Target-X

| ISIS No | Chemistry | SEQ CODE |
|---|---|---|
| 529544 | eek-d(10)-kke | 21 |
| 529569 | kee-d(10)-kke | 21 |
| 529594 | edk-d(10)-kke | 21 |
| 529619 | kde-d(10)-kke | 21 |
| 529644 | kddk-d(9)-kke | 21 |
| 529669 | kdde-d(9)-kke | 21 |
| 529694 | eddk-d(9)-kke | 21 |
| 529929 | eeee-d(9)-kke | 21 |
| 529809 | k-d(10)-kekee | 488 |
| 529828 | k-d(10)-kdkee | 488 |
| 529730 | ke-d(10)-keke | 489 |
| 529750 | ek-d(10)-keke | 489 |
| 529770 | ke-d(10)-kdke | 489 |
| 529790 | ek-d(10)-kdke | 489 |
| 529859 | kde-d(10)-kdke | 490 |
| 529879 | edk-d(10)-kdke | 490 |
| 529899 | k-d(4)-k-d(4)-k-d(4)-ke | 490 |
| 529545 | eek-d(10)-kke | 22 |
| 529570 | kee-d(10)-kke | 22 |
| 529595 | edk-d(10)-kke | 22 |
| 529620 | kde-d(10)-kke | 22 |
| 529645 | kddk-d(9)-kke | 22 |
| 529670 | kdde-d(9)-kke | 22 |
| 529695 | eddk-d(9)-kke | 22 |
| 529919 | eeee-d(9)-kke | 22 |
| 529548 | eek-d(10)-kke | 41 |
| 529573 | kee-d(10)-kke | 41 |
| 529598 | edk-d(10)-kke | 41 |
| 529623 | kde-d(10)-kke | 41 |
| 529648 | kddk-d(9)-kke | 41 |
| 529673 | kdde-d(9)-kke | 41 |
| 529698 | eddk-d(9)-kke | 41 |
| 529930 | eeee-d(9)-kke | 41 | e = 2'-MOE,
k = cEt,
d = 2'-deoxynucleoside

Example 21: Modified Oligonucleotides Comprising 2'-O-Methoxyethyl (2'-MOE) and Constrained Ethyl (cEt) Modifications Targeting Human Target-X Additional antisense oligonucleotides were designed targeting a Target-X nucleic acid and were tested for their effects on Target-X mRNA in vitro. ISIS 472998 and ISIS 515554, described in the Examples above were also included in the screen.

The newly designed chimeric antisense oligonucleotides are 16 nucleotides in length and their motifs are described in Table 32. The chemistry column of Table 32 presents the sugar motif of each oligonucleotide, wherein "e" indicates a 2'-O-methythoxylethyl (2'-MOE) nucleoside, "k" indicates a constrained ethyl (cEt) nucleoside and "d" indicates a 2'-deoxyribonucleoside. The internucleoside linkages throughout each gapmer are hosphorothioate (P=S) linkages. All cytosine residues throughout each oligonucleotide are 5-methylcytosines.

Each gapmer listed in Table 32 is targeted to the human Target-X genomic sequence.

Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set RTS2927 was used to measure mRNA levels. Target-X mRNA levels were adjusted according to total RNA content, as measured by RIBOGREEN®. Results are presented as percent inhibition of Target-X, relative to untreated control cells.

TABLE 32

Inhibition of human Target-X mRNA levels by chimeric antisense oligonucleotides targeted to Target-X

| ISIS No | % inhibition | Chemistry | SEQ CODE |
|---|---|---|---|
| 472998 | 88 | kk-d(10)-kk | 74 |
| 515554 | 75 | eee-d(10)-kkk | 493 |
| 534530 | 92 | keke-d(9)-kek | 491 |
| 534563 | 92 | kek-d(9)-ekek | 491 |
| 534596 | 88 | ekee-d(9)-kke | 491 |
| 534629 | 89 | eke-d(9)-ekke | 491 |
| 534662 | 87 | eekk-d(9)-eke | 491 |
| 534695 | 92 | eek-d(9)-keke | 491 |
| 534732 | 90 | ekek-d(8)-keke | 491 |
| 534767 | 92 | keek-d(8)-keek | 491 |
| 534802 | 93 | ekk-d(10)-kke | 491 |
| 534832 | 83 | edk-d(10)-kke | 491 |
| 534862 | 72 | kde-d(10)-kke | 491 |
| 534892 | 82 | eek-d(10)-kke | 491 |
| 534922 | 80 | kddk-d(9)-kke | 491 |
| 534952 | 72 | kdde-d(9)-kke | 491 |
| 534982 | 77 | eddk-d(9)-kke | 491 |
| 535012 | 70 | eeee-d(9)-kke | 491 |
| 535045 | 84 | eeee-d(9)-kkk | 491 |
| 535078 | 87 | eeek-d(9)-kke | 491 |
| 535111 | 63 | eeeee-d(8)-kke | 491 |
| 535144 | 69 | ededk-d(8)-kke | 491 |
| 535177 | 68 | edkde-d(8)-kke | 491 |
| 534531 | 61 | keke-d(9)-kek | 492 |
| 534564 | 30 | kek-d(9)-ekek | 492 |
| 534597 | 67 | ekee-d(9)-kke | 492 |
| 534630 | 54 | eke-d(9)-ekke | 492 |
| 534663 | 94 | eekk-d(9)-eke | 492 |
| 534696 | 68 | eek-d(9)-keke | 492 |
| 534733 | 44 | ekek-d(8)-keke | 492 |
| 534768 | 55 | keek-d(8)-keek | 492 |
| 534803 | 73 | ekk-d(10)-kke | 492 |
| 534833 | 65 | edk-d(10)-kke | 492 |
| 534863 | 53 | kde-d(10)-kke | 492 |
| 534893 | 61 | eek-d(10)-kke | 492 |
| 534923 | 70 | kddk-d(9)-kke | 492 |
| 534953 | 54 | kdde-d(9)-kke | 492 |
| 534983 | 58 | eddk-d(9)-kke | 492 |
| 535013 | 52 | eeee-d(9)-kke | 492 |
| 535046 | 67 | eeee-d(9)-kkk | 492 |
| 535079 | 57 | eeek-d(9)-kke | 492 |
| 535112 | 42 | eeeee-d(8)-kke | 492 |
| 535145 | 41 | ededk-d(8)-kke | 492 |
| 535178 | 35 | edkde-d(8)-kke | 492 |
| 534565 | 87 | kek-d(9)-ekek | 493 |
| 534598 | 72 | ekee-d(9)-kke | 493 |
| 534631 | 70 | eke-d(9)-ekke | 493 |
| 534664 | 94 | eekk-d(9)-eke | 493 |
| 534697 | 90 | eek-d(9)-keke | 493 |
| 534734 | 74 | ekek-d(8)-keke | 493 |
| 534769 | 80 | keek-d(8)-keek | 493 |
| 534804 | 87 | ekk-d(10)-kke | 493 |
| 534834 | 76 | edk-d(10)-kke | 493 |
| 534864 | 56 | kde-d(10)-kke | 493 |
| 534894 | 67 | eek-d(10)-kke | 493 |
| 534924 | 71 | kddk-d(9)-kke | 493 |
| 534954 | 54 | kdde-d(9)-kke | 493 |
| 534984 | 48 | eddk-d(9)-kke | 493 |
| 535014 | 43 | eeee-d(9)-kke | 493 |
| 535047 | 60 | eeee-d(9)-kkk | 493 |
| 535080 | 64 | eeek-d(9)-kke | 493 |
| 535113 | 32 | eeeee-d(8)-kke | 493 |
| 535146 | 31 | ededk-d(8)-kke | 493 |
| 535179 | 28 | edkde-d(8)-kke | 493 |
| 534533 | 82 | keke-d(9)-kek | 494 |
| 534566 | 88 | kek-d(9)-ekek | 494 |
| 534599 | 65 | ekee-d(9)-kke | 494 |
| 534632 | 69 | eke-d(9)-ekke | 494 |
| 534665 | 87 | eekk-d(9)-eke | 494 |
| 534698 | 64 | eek-d(9)-keke | 494 |
| 534735 | 63 | ekek-d(8)-keke | 494 |
| 534770 | 66 | keek-d(8)-keek | 494 |
| 534805 | 87 | ekk-d(10)-kke | 494 |
| 534835 | 68 | edk-d(10)-kke | 494 |
| 534865 | 66 | kde-d(10)-kke | 494 |
| 534895 | 57 | eek-d(10)-kke | 494 |
| 534925 | 82 | kddk-d(9)-kke | 494 |
| 534955 | 76 | kdde-d(9)-kke | 494 |
| 534985 | 71 | eddk-d(9)-kke | 494 |
| 535015 | 59 | eeee-d(9)-kke | 494 |
| 535048 | 69 | eeee-d(9)-kkk | 494 |
| 535081 | 67 | eeek-d(9)-kke | 494 |
| 535114 | 37 | eeeee-d(8)-kke | 494 |
| 535147 | 32 | ededk-d(8)-kke | 494 |
| 535180 | 31 | edkde-d(8)-kke | 494 |
| 534534 | 94 | keke-d(9)-kek | 234 |
| 534567 | 92 | kek-d(9)-ekek | 234 |
| 534600 | 92 | ekee-d(9)-kke | 234 |
| 534633 | 91 | eke-d(9)-ekke | 234 |
| 534666 | 89 | eekk-d(9)-eke | 234 |
| 534699 | 91 | eek-d(9)-keke | 234 |
| 534736 | 83 | ekek-d(8)-keke | 234 |
| 534771 | 80 | keek-d(8)-keek | 234 |
| 534806 | 96 | ekk-d(10)-kke | 234 |
| 534836 | 86 | edk-d(10)-kke | 234 |
| 534866 | 82 | kde-d(10)-kke | 234 |
| 534896 | 82 | eek-d(10)-kke | 234 |
| 534926 | 89 | kddk-d(9)-kke | 234 |
| 534956 | 91 | kdde-d(9)-kke | 234 |
| 534986 | 87 | eddk-d(9)-kke | 234 |
| 535016 | 83 | eeee-d(9)-kke | 234 |
| 535049 | 87 | eeee-d(9)-kkk | 234 |
| 535082 | 87 | eeek-d(9)-kke | 234 |
| 535115 | 77 | eeeee-d(8)-kke | 234 |
| 535148 | 73 | ededk-d(8)-kke | 234 |
| 535181 | 68 | edkde-d(8)-kke | 234 |
| 534535 | 66 | keke-d(9)-kek | 236 |
| 534568 | 85 | kek-d(9)-ekek | 236 |
| 534601 | 51 | ekee-d(9)-kke | 236 |
| 534634 | 80 | eke-d(9)-ekke | 236 |
| 534667 | 90 | eekk-d(9)-eke | 236 |
| 534700 | 88 | eek-d(9)-keke | 236 |
| 534737 | 65 | ekek-d(8)-keke | 236 |
| 534772 | 77 | keek-d(8)-keek | 236 |
| 534807 | 84 | ekk-d(10)-kke | 236 |
| 534837 | 78 | edk-d(10)-kke | 236 |
| 534867 | 44 | kde-d(10)-kke | 236 |
| 534897 | 82 | eek-d(10)-kke | 236 |
| 534927 | 61 | kddk-d(9)-kke | 236 |
| 534957 | 58 | kdde-d(9)-kke | 236 |
| 534987 | 49 | eddk-d(9)-kke | 236 |
| 535017 | 38 | eeee-d(9)-kke | 236 |
| 535050 | 32 | eeee-d(9)-kkk | 236 |
| 535083 | 43 | eeek-d(9)-kke | 236 |
| 535116 | 9 | eeeee-d(8)-kke | 236 |
| 535149 | 23 | ededk-d(8)-kke | 236 |
| 535182 | 18 | edkde-d(8)-kke | 236 |
| 534536 | 89 | keke-d(9)-kek | 238 |
| 534569 | 90 | kek-d(9)-ekek | 238 |
| 534602 | 85 | ekee-d(9)-kke | 238 |
| 534635 | 87 | eke-d(9)-ekke | 238 |
| 534668 | 90 | eekk-d(9)-eke | 238 |
| 534701 | 92 | eek-d(9)-keke | 238 |
| 534738 | 81 | ekek-d(8)-keke | 238 |
| 534773 | 79 | keek-d(8)-keek | 238 |
| 534808 | 90 | ekk-d(10)-kke | 238 |
| 534838 | 88 | edk-d(10)-kke | 238 |
| 534868 | 67 | kde-d(10)-kke | 238 |
| 534898 | 89 | eek-d(10)-kke | 238 |
| 534928 | 81 | kddk-d(9)-kke | 238 |
| 534958 | 78 | kdde-d(9)-kke | 238 |
| 534988 | 66 | eddk-d(9)-kke | 238 |
| 535018 | 78 | eeee-d(9)-kke | 238 |
| 535051 | 76 | eeee-d(9)-kkk | 238 |
| 535084 | 80 | eeek-d(9)-kke | 238 |
| 535117 | 58 | eeeee-d(8)-kke | 238 |
| 535150 | 51 | ededk-d(8)-kke | 238 |
| 535183 | 53 | edkde-d(8)-kke | 238 |
| 534537 | 91 | keke-d(9)-kek | 239 |
| 534570 | 85 | kek-d(9)-ekek | 239 |

TABLE 32-continued

Inhibition of human Target-X mRNA levels by chimeric antisense oligonucleotides targeted to Target-X

| ISIS No | % inhibition | Chemistry | SEQ CODE |
|---|---|---|---|
| 534603 | 79 | ekee-d(9)-kke | 239 |
| 534636 | 72 | eke-d(9)-ekke | 239 |
| 534669 | 85 | eekk-d(9)-eke | 239 |
| 534702 | 85 | eek-d(9)-keke | 239 |
| 534739 | 73 | ekek-d(8)-keke | 239 |
| 534774 | 77 | keek-d(8)-keek | 239 |
| 534809 | 91 | ekk-d(10)-kke | 239 |
| 534839 | 86 | edk-d(10)-kke | 239 |
| 534869 | 71 | kde-d(10)-kke | 239 |
| 534899 | 82 | eek-d(10)-kke | 239 |
| 534929 | 83 | kddk-d(9)-kke | 239 |
| 534959 | 80 | kdde-d(9)-kke | 239 |
| 534989 | 79 | eddk-d(9)-kke | 239 |
| 535019 | 76 | eeee-d(9)-kke | 239 |
| 535052 | 79 | eeee-d(9)-kkk | 239 |
| 535085 | 81 | eeek-d(9)-kke | 239 |
| 535118 | 58 | eeeee-d(8)-kke | 239 |
| 535151 | 65 | ededk-d(8)-kke | 239 |
| 535184 | 60 | edkde-d(8)-kke | 239 |
| 534516 | 77 | keke-d(9)-kek | 495 |
| 534549 | 80 | kek-d(9)-ekek | 495 |
| 534582 | 73 | ekee-d(9)-kke | 495 |
| 534615 | 79 | eke-d(9)-ekke | 495 |
| 534648 | 67 | eekk-d(9)-eke | 495 |
| 534681 | 87 | eek-d(9)-keke | 495 |
| 534718 | 46 | ekek-d(8)-keke | 495 |
| 534753 | 68 | keek-d(8)-keek | 495 |
| 534788 | 84 | ekk-d(10)-kke | 495 |
| 534818 | 82 | edk-d(10)-kke | 495 |
| 534848 | 75 | kde-d(10)-kke | 495 |
| 534878 | 72 | eek-d(10)-kke | 495 |
| 534908 | 81 | kddk-d(9)-kke | 495 |
| 534938 | 69 | kdde-d(9)-kke | 495 |
| 534968 | 77 | eddk-d(9)-kke | 495 |
| 534998 | 76 | eeee-d(9)-kke | 495 |
| 535031 | 76 | eeee-d(9)-kkk | 495 |
| 535064 | 70 | eeek-d(9)-kke | 495 |
| 535097 | 57 | eeeee-d(8)-kke | 495 |
| 535130 | 69 | ededk-d(8)-kke | 495 |
| 535163 | 58 | edkde-d(8)-kke | 495 |
| 534538 | 71 | keke-d(9)-kek | 241 |
| 534571 | 64 | kek-d(9)-ekek | 241 |
| 534604 | 66 | ekee-d(9)-kke | 241 |
| 534637 | 74 | eke-d(9)-ekke | 241 |
| 534670 | 87 | eekk-d(9)-eke | 241 |
| 534703 | 72 | eek-d(9)-keke | 241 |
| 534740 | 56 | ekek-d(8)-keke | 241 |
| 534775 | 53 | keek-d(8)-keek | 241 |
| 534810 | 78 | ekk-d(10)-kke | 241 |
| 534840 | 73 | edk-d(10)-kke | 241 |
| 534870 | 65 | kde-d(10)-kke | 241 |
| 534900 | 69 | eek-d(10)-kke | 241 |
| 534930 | 67 | kddk-d(9)-kke | 241 |
| 534960 | 62 | kdde-d(9)-kke | 241 |
| 534990 | 66 | eddk-d(9)-kke | 241 |
| 535020 | 61 | eeee-d(9)-kke | 241 |
| 535053 | 47 | eeee-d(9)-kkk | 241 |
| 535086 | 61 | eeek-d(9)-kke | 241 |
| 535119 | 49 | eeeee-d(8)-kke | 241 |
| 535152 | 48 | ededk-d(8)-kke | 241 |
| 535185 | 57 | edkde-d(8)-kke | 241 |
| 534539 | 70 | keke-d(9)-kek | 496 |
| 534572 | 82 | kek-d(9)-ekek | 496 |
| 534605 | 59 | ekee-d(9)-kke | 496 |
| 534638 | 69 | eke-d(9)-ekke | 496 |
| 534671 | 89 | eekk-d(9)-eke | 496 |
| 534704 | 83 | eek-d(9)-keke | 496 |
| 534741 | 47 | ekek-d(8)-keke | 496 |
| 534776 | 46 | keek-d(8)-keek | 496 |
| 534811 | 71 | ekk-d(10)-kke | 496 |
| 534841 | 61 | edk-d(10)-kke | 496 |
| 534871 | 53 | kde-d(10)-kke | 496 |
| 534901 | 55 | eek-d(10)-kke | 496 |
| 534931 | 73 | kddk-d(9)-kke | 496 |
| 534961 | 53 | kdde-d(9)-kke | 496 |
| 534991 | 56 | eddk-d(9)-kke | 496 |
| 535021 | 58 | eeee-d(9)-kke | 496 |
| 535054 | 59 | eeee-d(9)-kkk | 496 |
| 535087 | 0 | eeek-d(9)-kke | 496 |
| 535120 | 41 | eeeee-d(8)-kke | 496 |
| 535153 | 44 | ededk-d(8)-kke | 496 |
| 535186 | 35 | edkde-d(8)-kke | 496 |
| 534573 | 76 | kek-d(9)-ekek | 497 |
| 534606 | 55 | ekee-d(9)-kke | 497 |
| 534639 | 72 | eke-d(9)-ekke | 497 |
| 534672 | 89 | eekk-d(9)-eke | 497 |
| 534705 | 87 | eek-d(9)-keke | 497 |
| 534742 | 84 | ekek-d(8)-keke | 497 |
| 534777 | 79 | keek-d(8)-keek | 497 |
| 534812 | 76 | ekk-d(10)-kke | 497 |
| 534842 | 74 | edk-d(10)-kke | 497 |
| 534872 | 53 | kde-d(10)-kke | 497 |
| 534902 | 70 | eek-d(10)-kke | 497 |
| 534932 | 73 | kddk-d(9)-kke | 497 |
| 534962 | 60 | kdde-d(9)-kke | 497 |
| 534992 | 61 | eddk-d(9)-kke | 497 |
| 535022 | 38 | eeee-d(9)-kke | 497 |
| 535055 | 42 | eeee-d(9)-kkk | 497 |
| 535088 | 56 | eeek-d(9)-kke | 497 |
| 535121 | 5 | eeeee-d(8)-kke | 497 |
| 535154 | 22 | ededk-d(8)-kke | 497 |
| 535187 | 16 | edkde-d(8)-kke | 497 |
| 534541 | 86 | keke-d(9)-kek | 498 |
| 534574 | 89 | kek-d(9)-ekek | 498 |
| 534607 | 59 | ekee-d(9)-kke | 498 |
| 534640 | 76 | eke-d(9)-ekke | 498 |
| 534673 | 89 | eekk-d(9)-eke | 498 |
| 534706 | 86 | eek-d(9)-keke | 498 |
| 534743 | 79 | ekek-d(8)-keke | 498 |
| 534778 | 80 | keek-d(8)-keek | 498 |
| 534813 | 83 | ekk-d(10)-kke | 498 |
| 534843 | 82 | edk-d(10)-kke | 498 |
| 534873 | 83 | kde-d(10)-kke | 498 |
| 534903 | 78 | eek-d(10)-kke | 498 |
| 534933 | 83 | kddk-d(9)-kke | 498 |
| 534963 | 70 | kdde-d(9)-kke | 498 |
| 534993 | 78 | eddk-d(9)-kke | 498 |
| 535023 | 56 | eeee-d(9)-kke | 498 |
| 535056 | 59 | eeee-d(9)-kkk | 498 |
| 535089 | 73 | eeek-d(9)-kke | 498 |
| 535122 | 39 | eeeee-d(8)-kke | 498 |
| 535155 | 60 | ededk-d(8)-kke | 498 |
| 535188 | 41 | edkde-d(8)-kke | 498 |
| 534542 | 75 | keke-d(9)-kek | 499 |
| 534575 | 82 | kek-d(9)-ekek | 499 |
| 534608 | 72 | ekee-d(9)-kke | 499 |
| 534641 | 69 | eke-d(9)-ekke | 499 |
| 534674 | 84 | eekk-d(9)-eke | 499 |
| 534707 | 78 | eek-d(9)-keke | 499 |
| 534744 | 72 | ekek-d(8)-keke | 499 |
| 534779 | 75 | keek-d(8)-keek | 499 |
| 534814 | 81 | ekk-d(10)-kke | 499 |
| 534844 | 75 | edk-d(10)-kke | 499 |
| 534874 | 70 | kde-d(10)-kke | 499 |
| 534904 | 71 | eek-d(10)-kke | 499 |
| 534934 | 73 | kddk-d(9)-kke | 499 |
| 534964 | 72 | kdde-d(9)-kke | 499 |
| 534994 | 69 | eddk-d(9)-kke | 499 |
| 535024 | 56 | eeee-d(9)-kke | 499 |
| 535057 | 63 | eeee-d(9)-kkk | 499 |
| 535090 | 64 | eeek-d(9)-kke | 499 |
| 535123 | 40 | eeeee-d(8)-kke | 499 |
| 535156 | 47 | ededk-d(8)-kke | 499 |
| 535189 | 48 | edkde-d(8)-kke | 499 |
| 534515 | 52 | keke-d(9)-kek | 34 |
| 534548 | 85 | kek-d(9)-ekek | 34 |
| 534581 | 75 | ekee-d(9)-kke | 34 |
| 534614 | 83 | eke-d(9)-ekke | 34 |
| 534647 | 65 | eekk-d(9)-eke | 34 |
| 534680 | 88 | eek-d(9)-keke | 34 |

TABLE 32-continued

Inhibition of human Target-X mRNA levels by chimeric antisense oligonucleotides targeted to Target-X

| ISIS No | % inhibition | Chemistry | SEQ CODE |
|---|---|---|---|
| 534717 | 76 | ekek-d(8)-keke | 34 |
| 534752 | 79 | keek-d(8)-keek | 34 |
| 534787 | 90 | ekk-d(10)-kke | 34 |
| 535030 | 77 | eeee-d(9)-kkk | 34 |
| 535063 | 75 | eeek-d(9)-kke | 34 |
| 535096 | 54 | eeeee-d(8)-kke | 34 |
| 535129 | 66 | ededk-d(8)-kke | 34 |
| 535162 | 49 | edkde-d(8)-kke | 34 |
| 534543 | 66 | keke-d(9)-kek | 500 |
| 534576 | 69 | kek-d(9)-ekek | 500 |
| 534609 | 77 | ekee-d(9)-kke | 500 |
| 534642 | 62 | eke-d(9)-ekke | 500 |
| 534675 | 80 | eekk-d(9)-eke | 500 |
| 534708 | 81 | eek-d(9)-keke | 500 |
| 534745 | 68 | ekek-d(8)-keke | 500 |
| 534780 | 69 | keek-d(8)-keek | 500 |
| 534815 | 85 | ekk-d(10)-kke | 500 |
| 534845 | 72 | edk-d(10)-kke | 500 |
| 534875 | 56 | kde-d(10)-kke | 500 |
| 534905 | 65 | eek-d(10)-kke | 500 |
| 534935 | 78 | kddk-d(9)-kke | 500 |
| 534965 | 48 | kdde-d(9)-kke | 500 |
| 534995 | 62 | eddk-d(9)-kke | 500 |
| 535025 | 58 | eeee-d(9)-kke | 500 |
| 535058 | 60 | eeee-d(9)-kkk | 500 |
| 535091 | 61 | eeek-d(9)-kke | 500 |
| 535124 | 51 | eeeee-d(8)-kke | 500 |
| 535157 | 55 | ededk-d(8)-kke | 500 |
| 535190 | 47 | edkde-d(8)-kke | 500 |
| 534517 | 71 | keke-d(9)-kek | 501 |
| 534550 | 80 | kek-d(9)-ekek | 501 |
| 534583 | 70 | ekee-d(9)-kke | 501 |
| 534616 | 84 | eke-d(9)-ekke | 501 |
| 534649 | 68 | eekk-d(9)-eke | 501 |
| 534682 | 87 | eek-d(9)-keke | 501 |
| 534719 | 90 | ekek-d(8)-keke | 501 |
| 534754 | 83 | keek-d(8)-keek | 501 |
| 534789 | 86 | ekk-d(10)-kke | 501 |
| 534819 | 69 | edk-d(10)-kke | 501 |
| 534849 | 62 | kde-d(10)-kke | 501 |
| 534879 | 69 | eek-d(10)-kke | 501 |
| 534909 | 73 | kddk-d(9)-kke | 501 |
| 534939 | 49 | kdde-d(9)-kke | 501 |
| 534969 | 47 | eddk-d(9)-kke | 501 |
| 534999 | 51 | eeee-d(9)-kke | 501 |
| 535032 | 51 | eeee-d(9)-kkk | 501 |
| 535065 | 64 | eeek-d(9)-kke | 501 |
| 535098 | 31 | eeeee-d(8)-kke | 501 |
| 535131 | 31 | ededk-d(8)-kke | 501 |
| 535164 | 40 | edkde-d(8)-kke | 501 |
| 534518 | 81 | keke-d(9)-kek | 502 |
| 534551 | 88 | kek-d(9)-ekek | 502 |
| 534584 | 78 | ekee-d(9)-kke | 502 |
| 534617 | 80 | eke-d(9)-ekke | 502 |
| 534650 | 83 | eekk-d(9)-eke | 502 |
| 534683 | 93 | eek-d(9)-keke | 502 |
| 534720 | 87 | ekek-d(8)-keke | 502 |
| 534755 | 82 | keek-d(8)-keek | 502 |
| 534790 | 89 | ekk-d(10)-kke | 502 |
| 534820 | 64 | edk-d(10)-kke | 502 |
| 534850 | 38 | kde-d(10)-kke | 502 |
| 534880 | 68 | eek-d(10)-kke | 502 |
| 534910 | 60 | kddk-d(9)-kke | 502 |
| 534940 | 37 | kdde-d(9)-kke | 502 |
| 534970 | 59 | eddk-d(9)-kke | 502 |
| 535000 | 30 | eeee-d(9)-kke | 502 |
| 535033 | 44 | eeee-d(9)-kkk | 502 |
| 535066 | 64 | eeek-d(9)-kke | 502 |
| 535099 | 22 | eeeee-d(8)-kke | 502 |
| 535132 | 54 | ededk-d(8)-kke | 502 |
| 535165 | 45 | edkde-d(8)-kke | 502 |
| 534544 | 80 | keke-d(9)-kek | 503 |
| 534577 | 83 | kek-d(9)-ekek | 503 |
| 534610 | 62 | ekee-d(9)-kke | 503 |
| 534643 | 66 | eke-d(9)-ekke | 503 |
| 534676 | 95 | eekk-d(9)-eke | 503 |
| 534709 | 86 | eek-d(9)-keke | 503 |
| 534746 | 73 | ekek-d(8)-keke | 503 |
| 534781 | 71 | keek-d(8)-keek | 503 |
| 534816 | 83 | ekk-d(10)-kke | 503 |
| 534846 | 73 | edk-d(10)-kke | 503 |
| 534876 | 39 | kde-d(10)-kke | 503 |
| 534906 | 67 | eek-d(10)-kke | 503 |
| 534936 | 66 | kddk-d(9)-kke | 503 |
| 534966 | 48 | kdde-d(9)-kke | 503 |
| 534996 | 56 | eddk-d(9)-kke | 503 |
| 535026 | 39 | eeee-d(9)-kke | 503 |
| 535059 | 45 | eeee-d(9)-kkk | 503 |
| 535092 | 48 | eeek-d(9)-kke | 503 |
| 535125 | 26 | eeeee-d(8)-kke | 503 |
| 535158 | 44 | ededk-d(8)-kke | 503 |
| 535191 | 34 | edkde-d(8)-kke | 503 |
| 534545 | 83 | keke-d(9)-kek | 504 |
| 534578 | 81 | kek-d(9)-ekek | 504 |
| 534611 | 78 | ekee-d(9)-kke | 504 |
| 534644 | 72 | eke-d(9)-ekke | 504 |
| 534677 | 92 | eekk-d(9)-eke | 504 |
| 534710 | 78 | eek-d(9)-keke | 504 |
| 534747 | 85 | ekek-d(8)-keke | 504 |
| 534782 | 85 | keek-d(8)-keek | 504 |
| 534817 | 88 | ekk-d(10)-kke | 504 |
| 534847 | 73 | edk-d(10)-kke | 504 |
| 534877 | 66 | kde-d(10)-kke | 504 |
| 534907 | 73 | eek-d(10)-kke | 504 |
| 534937 | 85 | kddk-d(9)-kke | 504 |
| 534967 | 80 | kdde-d(9)-kke | 504 |
| 534997 | 74 | eddk-d(9)-kke | 504 |
| 535027 | 64 | eeee-d(9)-kke | 504 |
| 535060 | 68 | eeee-d(9)-kkk | 504 |
| 535093 | 73 | eeek-d(9)-kke | 504 |
| 535126 | 42 | eeeee-d(8)-kke | 504 |
| 535159 | 49 | ededk-d(8)-kke | 504 |
| 535192 | 51 | edkde-d(8)-kke | 504 |
| 534519 | 87 | keke-d(9)-kek | 505 |
| 534552 | 85 | kek-d(9)-ekek | 505 |
| 534585 | 76 | ekee-d(9)-kke | 505 |
| 534618 | 78 | eke-d(9)-ekke | 505 |
| 534651 | 79 | eekk-d(9)-eke | 505 |
| 534684 | 87 | eek-d(9)-keke | 505 |
| 534721 | 89 | ekek-d(8)-keke | 505 |
| 534756 | 90 | keek-d(8)-keek | 505 |
| 534791 | 84 | ekk-d(10)-kke | 505 |
| 534821 | 79 | edk-d(10)-kke | 505 |
| 534851 | 64 | kde-d(10)-kke | 505 |
| 534881 | 65 | eek-d(10)-kke | 505 |
| 534911 | 85 | kddk-d(9)-kke | 505 |
| 534941 | 66 | kdde-d(9)-kke | 505 |
| 534971 | 75 | eddk-d(9)-kke | 505 |
| 535001 | 62 | eeee-d(9)-kke | 505 |
| 535034 | 65 | eeee-d(9)-kkk | 505 |
| 535067 | 76 | eeek-d(9)-kke | 505 |
| 535100 | 5 | eeeee-d(8)-kke | 505 |
| 535133 | 30 | ededk-d(8)-kke | 505 |
| 535166 | 23 | edkde-d(8)-kke | 505 |
| 534520 | 87 | keke-d(9)-kek | 251 |
| 534553 | 79 | kek-d(9)-ekek | 251 |
| 534586 | 60 | ekee-d(9)-kke | 251 |
| 534619 | 62 | eke-d(9)-ekke | 251 |
| 534652 | 84 | eekk-d(9)-eke | 251 |
| 534685 | 84 | eek-d(9)-keke | 251 |
| 534722 | 75 | ekek-d(8)-keke | 251 |
| 534757 | 81 | keek-d(8)-keek | 251 |
| 534792 | 87 | ekk-d(10)-kke | 251 |
| 534822 | 80 | edk-d(10)-kke | 251 |
| 534852 | 38 | kde-d(10)-kke | 251 |
| 534882 | 75 | eek-d(10)-kke | 251 |
| 534912 | 74 | kddk-d(9)-kke | 251 |
| 534942 | 58 | kdde-d(9)-kke | 251 |
| 534972 | 59 | eddk-d(9)-kke | 251 |
| 535002 | 50 | eeee-d(9)-kke | 251 |

TABLE 32-continued

Inhibition of human Target-X mRNA levels by chimeric antisense oligonucleotides targeted to Target-X

| ISIS No | % inhibition | Chemistry | SEQ CODE |
|---|---|---|---|
| 535035 | 57 | eeee-d(9)-kkk | 251 |
| 535068 | 67 | eeek-d(9)-kke | 251 |
| 535101 | 24 | eeeee-d(8)-kke | 251 |
| 535134 | 23 | ededk-d(8)-kke | 251 |
| 535167 | 26 | edkde-d(8)-kke | 251 |
| 534513 | 90 | keke-d(9)-kek | 252 |
| 534546 | 92 | kek-d(9)-ekek | 252 |
| 534579 | 78 | ekee-d(9)-kke | 252 |
| 534612 | 82 | eke-d(9)-ekke | 252 |
| 534645 | 73 | eekk-d(9)-eke | 252 |
| 534678 | 91 | eek-d(9)-keke | 252 |
| 534715 | 87 | ekek-d(8)-keke | 252 |
| 534750 | 88 | keek-d(8)-keek | 252 |
| 534785 | 89 | ekk-d(10)-kke | 252 |
| 535028 | 52 | eeee-d(9)-kkk | 252 |
| 535061 | 73 | eeek-d(9)-kke | 252 |
| 535094 | 61 | eeeee-d(8)-kke | 252 |
| 535127 | 59 | ededk-d(8)-kke | 252 |
| 535160 | 62 | edkde-d(8)-kke | 252 |
| 534521 | 86 | keke-d(9)-kek | 506 |
| 534554 | 87 | kek-d(9)-ekek | 506 |
| 534587 | 62 | ekee-d(9)-kke | 506 |
| 534620 | 68 | eke-d(9)-ekke | 506 |
| 534653 | 77 | eekk-d(9)-eke | 506 |
| 534686 | 90 | eek-d(9)-keke | 506 |
| 534723 | 88 | ekek-d(8)-keke | 506 |
| 534758 | 79 | keek-d(8)-keek | 506 |
| 534793 | 85 | ekk-d(10)-kke | 506 |
| 534823 | 81 | edk-d(10)-kke | 506 |
| 534853 | 59 | kde-d(10)-kke | 506 |
| 534883 | 69 | eek-d(10)-kke | 506 |
| 534913 | 76 | kddk-d(9)-kke | 506 |
| 534943 | 53 | kdde-d(9)-kke | 506 |
| 534973 | 61 | eddk-d(9)-kke | 506 |
| 535003 | 53 | eeee-d(9)-kke | 506 |
| 535036 | 35 | eeee-d(9)-kkk | 506 |
| 535069 | 62 | eeek-d(9)-kke | 506 |
| 535102 | 31 | eeeee-d(8)-kke | 506 |
| 535135 | 44 | ededk-d(8)-kke | 506 |
| 535168 | 34 | edkde-d(8)-kke | 506 |
| 534522 | 83 | keke-d(9)-kek | 507 |
| 534555 | 81 | kek-d(9)-ekek | 507 |
| 534588 | 72 | ekee-d(9)-kke | 507 |
| 534621 | 74 | eke-d(9)-ekke | 507 |
| 534654 | 78 | eekk-d(9)-eke | 507 |
| 534687 | 91 | eek-d(9)-keke | 507 |
| 534724 | 84 | ekek-d(8)-keke | 507 |
| 534759 | 86 | keek-d(8)-keek | 507 |
| 534794 | 78 | ekk-d(10)-kke | 507 |
| 534824 | 75 | edk-d(10)-kke | 507 |
| 534854 | 63 | kde-d(10)-kke | 507 |
| 534884 | 60 | eek-d(10)-kke | 507 |
| 534914 | 75 | kddk-d(9)-kke | 507 |
| 534944 | 69 | kdde-d(9)-kke | 507 |
| 534974 | 66 | eddk-d(9)-kke | 507 |
| 535004 | 56 | eeee-d(9)-kke | 507 |
| 535037 | 50 | eeee-d(9)-kkk | 507 |
| 535070 | 68 | eeek-d(9)-kke | 507 |
| 535103 | 55 | eeeee-d(8)-kke | 507 |
| 535136 | 51 | ededk-d(8)-kke | 507 |
| 535169 | 54 | edkde-d(8)-kke | 507 |
| 534523 | 89 | keke-d(9)-kek | 253 |
| 534556 | 91 | kek-d(9)-ekek | 253 |
| 534589 | 88 | ekee-d(9)-kke | 253 |
| 534622 | 93 | eke-d(9)-ekke | 253 |
| 534655 | 72 | eekk-d(9)-eke | 253 |
| 534688 | 92 | eek-d(9)-keke | 253 |
| 534725 | 87 | ekek-d(8)-keke | 253 |
| 534760 | 92 | keek-d(8)-keek | 253 |
| 534795 | 93 | ekk-d(10)-kke | 253 |
| 534825 | 82 | edk-d(10)-kke | 253 |
| 534855 | 73 | kde-d(10)-kke | 253 |
| 534885 | 82 | eek-d(10)-kke | 253 |
| 534915 | 88 | kddk-d(9)-kke | 253 |
| 534945 | 82 | kdde-d(9)-kke | 253 |
| 534975 | 68 | eddk-d(9)-kke | 253 |
| 535005 | 69 | eeee-d(9)-kke | 253 |
| 535038 | 72 | eeee-d(9)-kkk | 253 |
| 535071 | 74 | eeek-d(9)-kke | 253 |
| 535104 | 61 | eeeee-d(8)-kke | 253 |
| 535137 | 67 | ededk-d(8)-kke | 253 |
| 535170 | 51 | edkde-d(8)-kke | 253 |
| 534524 | 95 | keke-d(9)-kek | 254 |
| 534557 | 98 | kek-d(9)-ekek | 254 |
| 534590 | 91 | ekee-d(9)-kke | 254 |
| 534623 | 91 | eke-d(9)-ekke | 254 |
| 534656 | 90 | eekk-d(9)-eke | 254 |
| 534689 | 92 | eek-d(9)-keke | 254 |
| 534726 | 57 | ekek-d(8)-keke | 254 |
| 534761 | 89 | keek-d(8)-keek | 254 |
| 534796 | 93 | ekk-d(10)-kke | 254 |
| 534826 | 89 | edk-d(10)-kke | 254 |
| 534856 | 87 | kde-d(10)-kke | 254 |
| 534886 | 85 | eek-d(10)-kke | 254 |
| 534916 | 87 | kddk-d(9)-kke | 254 |
| 534946 | 86 | kdde-d(9)-kke | 254 |
| 534976 | 77 | eddk-d(9)-kke | 254 |
| 535006 | 83 | eeee-d(9)-kke | 254 |
| 535039 | 86 | eeee-d(9)-kkk | 254 |
| 535072 | 87 | eeek-d(9)-kke | 254 |
| 535105 | 68 | eeeee-d(8)-kke | 254 |
| 535138 | 70 | ededk-d(8)-kke | 254 |
| 535171 | 65 | edkde-d(8)-kke | 254 |
| 534558 | 92 | kek-d(9)-ekek | 255 |
| 534591 | 91 | ekee-d(9)-kke | 255 |
| 534624 | 86 | eke-d(9)-ekke | 255 |
| 534657 | 90 | eekk-d(9)-eke | 255 |
| 534690 | 76 | eek-d(9)-keke | 255 |
| 534727 | 92 | ekek-d(8)-keke | 255 |
| 534762 | 91 | keek-d(8)-keek | 255 |
| 534797 | 94 | ekk-d(10)-kke | 255 |
| 534827 | 90 | edk-d(10)-kke | 255 |
| 534857 | 80 | kde-d(10)-kke | 255 |
| 534887 | 76 | eek-d(10)-kke | 255 |
| 534917 | 91 | kddk-d(9)-kke | 255 |
| 534947 | 91 | kdde-d(9)-kke | 255 |
| 534977 | 86 | eddk-d(9)-kke | 255 |
| 535007 | 80 | eeee-d(9)-kke | 255 |
| 535040 | 86 | eeee-d(9)-kkk | 255 |
| 535073 | 87 | eeek-d(9)-kke | 255 |
| 535106 | 70 | eeeee-d(8)-kke | 255 |
| 535139 | 73 | ededk-d(8)-kke | 255 |
| 535172 | 69 | edkde-d(8)-kke | 255 |
| 534514 | 90 | keke-d(9)-kek | 61 |
| 534547 | 92 | kek-d(9)-ekek | 61 |
| 534580 | 78 | ekee-d(9)-kke | 61 |
| 534613 | 80 | eke-d(9)-ekke | 61 |
| 534646 | 79 | eekk-d(9)-eke | 61 |
| 534679 | 93 | eek-d(9)-keke | 61 |
| 534716 | 94 | ekek-d(8)-keke | 61 |
| 534751 | 86 | keek-d(8)-keek | 61 |
| 534786 | 83 | ekk-d(10)-kke | 61 |
| 535029 | 45 | eeee-d(9)-kkk | 61 |
| 535062 | 81 | eeek-d(9)-kke | 61 |
| 535095 | 57 | eeeee-d(8)-kke | 61 |
| 535128 | 58 | ededk-d(8)-kke | 61 |
| 535161 | 49 | edkde-d(8)-kke | 61 |
| 534526 | 94 | keke-d(9)-kek | 256 |
| 534559 | 95 | kek-d(9)-ekek | 256 |
| 534592 | 93 | ekee-d(9)-kke | 256 |
| 534625 | 93 | eke-d(9)-ekke | 256 |
| 534658 | 93 | eekk-d(9)-eke | 256 |
| 534691 | 96 | eek-d(9)-keke | 256 |
| 534728 | 93 | ekek-d(8)-keke | 256 |
| 534763 | 93 | keek-d(8)-keek | 256 |
| 534798 | 97 | ekk-d(10)-kke | 256 |
| 534828 | 94 | edk-d(10)-kke | 256 |
| 534858 | 92 | kde-d(10)-kke | 256 |
| 534888 | 93 | eek-d(10)-kke | 256 |
| 534918 | 95 | kddk-d(9)-kke | 256 |

TABLE 32-continued

Inhibition of human Target-X mRNA levels by chimeric antisense oligonucleotides targeted to Target-X

| ISIS No | % inhibition | Chemistry | SEQ CODE |
|---|---|---|---|
| 534948 | 93 | kdde-d(9)-kke | 256 |
| 534978 | 91 | eddk-d(9)-kke | 256 |
| 535008 | 88 | eeee-d(9)-kke | 256 |
| 535041 | 87 | eeee-d(9)-kkk | 256 |
| 535074 | 90 | eeek-d(9)-kke | 256 |
| 535107 | 78 | eeeee-d(8)-kke | 256 |
| 535140 | 81 | ededk-d(8)-kke | 256 |
| 535173 | 81 | edkde-d(8)-kke | 256 |
| 534527 | 95 | keke-d(9)-kek | 258 |
| 534560 | 96 | kek-d(9)-ekek | 258 |
| 534593 | 87 | ekee-d(9)-kke | 258 |
| 534626 | 85 | eke-d(9)-ekke | 258 |
| 534659 | 90 | eekk-d(9)-eke | 258 |
| 534692 | 91 | eek-d(9)-keke | 258 |
| 534729 | 91 | ekek-d(8)-keke | 258 |
| 534764 | 91 | keek-d(8)-keek | 258 |
| 534799 | 96 | ekk-d(10)-kke | 258 |
| 534829 | 91 | edk-d(10)-kke | 258 |
| 534859 | 87 | kde-d(10)-kke | 258 |
| 534889 | 81 | eek-d(10)-kke | 258 |
| 534919 | 92 | kddk-d(9)-kke | 258 |
| 534949 | 91 | kdde-d(9)-kke | 258 |
| 534979 | 84 | eddk-d(9)-kke | 258 |
| 535009 | 78 | eeee-d(9)-kke | 258 |
| 535042 | 76 | eeee-d(9)-kkk | 258 |
| 535075 | 83 | eeek-d(9)-kke | 258 |
| 535108 | 64 | eeeee-d(8)-kke | 258 |
| 535141 | 69 | ededk-d(8)-kke | 258 |
| 535174 | 65 | edkde-d(8)-kke | 258 |
| 534528 | 94 | keke-d(9)-kek | 260 |
| 534561 | 0 | kek-d(9)-ekek | 260 |
| 534594 | 92 | ekee-d(9)-kke | 260 |
| 534627 | 90 | eke-d(9)-ekke | 260 |
| 534660 | 92 | eekk-d(9)-eke | 260 |
| 534693 | 95 | eek-d(9)-keke | 260 |
| 534730 | 93 | ekek-d(8)-keke | 260 |
| 534765 | 92 | keek-d(8)-keek | 260 |
| 534800 | 93 | ekk-d(10)-kke | 260 |
| 534830 | 93 | edk-d(10)-kke | 260 |
| 534860 | 85 | kde-d(10)-kke | 260 |
| 534890 | 91 | eek-d(10)-kke | 260 |
| 534920 | 93 | kddk-d(9)-kke | 260 |
| 534950 | 90 | kdde-d(9)-kke | 260 |
| 534980 | 88 | eddk-d(9)-kke | 260 |
| 535010 | 88 | eeee-d(9)-kke | 260 |
| 535043 | 89 | eeee-d(9)-kkk | 260 |
| 535076 | 88 | eeek-d(9)-kke | 260 |
| 535109 | 76 | eeeee-d(8)-kke | 260 |
| 535142 | 86 | ededk-d(8)-kke | 260 |
| 535175 | 71 | edkde-d(8)-kke | 260 |
| 534529 | 70 | keke-d(9)-kek | 261 |
| 534562 | 86 | kek-d(9)-ekek | 261 |
| 534595 | 56 | ekee-d(9)-kke | 261 |
| 534628 | 73 | eke-d(9)-ekke | 261 |
| 534661 | 64 | eekk-d(9)-eke | 261 |
| 534694 | 75 | eek-d(9)-keke | 261 |
| 534731 | 47 | ekek-d(8)-keke | 261 |
| 534766 | 30 | keek-d(8)-keek | 261 |
| 534801 | 83 | ekk-d(10)-kke | 261 |
| 534831 | 84 | edk-d(10)-kke | 261 |
| 534861 | 71 | kde-d(10)-kke | 261 |
| 534891 | 73 | eek-d(10)-kke | 261 |
| 534921 | 55 | kddk-d(9)-kke | 261 |
| 534951 | 61 | kdde-d(9)-kke | 261 |
| 534981 | 48 | eddk-d(9)-kke | 261 |
| 535011 | 54 | eeee-d(9)-kke | 261 |
| 535044 | 46 | eeee-d(9)-kkk | 261 |
| 535077 | 29 | eeek-d(9)-kke | 261 |
| 535110 | 19 | eeeee-d(8)-kke | 261 |
| 535143 | 15 | ededk-d(8)-kke | 261 |
| 535176 | 37 | edkde-d(8)-kke | 261 | e = 2'-MOE,
k = cEt,
d = 2'-deoxynucleoside

Example 22: Modified Antisense Oligonucleotides Comprising 2'-O-Methoxyethyl (2'-MOE) and Constrained Ethyl (cEt) Modifications Targeting Human Target-X Targeting Intronic Repeats Additional antisense oligonucleotides were designed targeting the intronic repeat regions of Target-X The newly designed chimeric antisense oligonucleotides and their motifs are described in Table 33. The internucleoside linkages throughout each gapmer are phosphorothioate linkages (P=S) and are designated as "s". Nucleosides followed by "d" indicate 2'-deoxyribonucleosides. Nucleosides followed by "k" indicate constrained ethyl (cEt) nucleosides. Nucleosides followed by "e" indicate 2'-O-methythoxyethyl (2'-MOE) nucleosides. "N" indicates modified or naturally occurring nucleobases (A, T, C, G, U, or 5-methyl C).

Each gapmer listed in Table 33 is targeted to the intronic region of human Target-X genomic sequence, designated herein as Target-X.

Cultured Hep3B cells at a density of 20,000 cells per well were transfected using electroporation with 2,000 nM antisense oligonucleotide. After a treatment period of approximately 24 hours, RNA was isolated from the cells and Target-X mRNA levels were measured by quantitative real-time PCR. Human primer probe set was used to measure mRNA levels. Target-X mRNA levels were adjusted according to total RNA content, as measured by RIBOGREEN®. Results are presented as percent inhibition of Target-X, relative to untreated control cells.

TABLE 33

Inhibition of human Target-X mRNA levels by chimeric antisense oligonucleotides targeted to Target-X

| Sequence (5' to 3') | ISIS No | % inhibition | SEQ CODE | SEQ ID NO |
|---|---|---|---|---|
| Nks Nks Nds Nds Nds Nds Nds Nds Nds Nds Nds Nds Nks Nk | 472998 | 90 | 508 | 20 |
| Nks Nks Nks Nds Nds Nds Nds Nds Nds Nds Nds Nds Nes Nes Ne | 473327 | 88 | 30 | 19 |
| Nes Nes Nes Nds Nds Nds Nds Nds Nds Nds Nds Nds Nks Nks Nk | 537024 | 74 | 509 | 19 |

TABLE 33-continued

Inhibition of human Target-X mRNA levels by chimeric antisense oligonucleotides targeted to Target-X

| Sequence (5' to 3') | ISIS No | % inhibition | SEQ CODE | SEQ ID NO |
|---|---|---|---|---|
| Nes Nes Nes Nds Nds Nds Nds Nds Nds Nds Nds Nds Nks Nks Nk | 537025 | 79 | 510 | 19 |
| Nes Nes Nes Nds Nds Nds Nds Nds Nds Nds Nds Nds Nks Nks Nk | 537026 | 76 | 511 | 19 |
| Nes Nes Nes Nds Nds Nds Nds Nds Nds Nds Nds Nds Nks Nks Nk | 537028 | 37 | 512 | 19 |
| Nes Nes Nes Nds Nds Nds Nds Nds Nds Nds Nds Nds Nks Nks Nk | 537029 | 45 | 513 | 19 |
| Nes Nes Nes Nds Nds Nds Nds Nds Nds Nds Nds Nds Nks Nks Nk | 537030 | 67 | 514 | 19 |
| Nes Nes Nes Nds Nds Nds Nds Nds Nds Nds Nds Nds Nks Nks Nk | 537031 | 59 | 515 | 19 |
| Nes Nes Nes Nds Nds Nds Nds Nds Nds Nds Nds Nds Nks Nks Nk | 537032 | 9 | 516 | 19 |
| Nes Nes Nes Nds Nds Nds Nds Nds Nds Nds Nds Nds Nks Nks Nk | 537033 | 65 | 517 | 19 |
| Nes Nes Nes Nds Nds Nds Nds Nds Nds Nds Nds Nds Nks Nks Nk | 537034 | 71 | 518 | 19 |
| Nes Nes Nes Nds Nds Nds Nds Nds Nds Nds Nds Nds Nks Nks Nk | 537035 | 68 | 519 | 19 |
| Nes Nes Nes Nds Nds Nds Nds Nds Nds Nds Nds Nds Nks Nks Nk | 537036 | 74 | 520 | 19 |
| Nes Nes Nes Nds Nds Nds Nds Nds Nds Nds Nds Nds Nks Nks Nk | 537038 | 69 | 521 | 19 |
| Nes Nes Nes Nds Nds Nds Nds Nds Nds Nds Nds Nds Nks Nks Nk | 537039 | 67 | 522 | 19 |
| Nes Nes Nes Nds Nds Nds Nds Nds Nds Nds Nds Nds Nks Nks Nk | 537040 | 68 | 523 | 19 |
| Nes Nes Nes Nds Nds Nds Nds Nds Nds Nds Nds Nds Nks Nks Nk | 537041 | 76 | 524 | 19 |
| Nes Nes Nes Nds Nds Nds Nds Nds Nds Nds Nds Nds Nks Nks Nk | 537042 | 77 | 525 | 19 |
| Nes Nes Nes Nds Nds Nds Nds Nds Nds Nds Nds Nds Nks Nks Nk | 537043 | 70 | 526 | 19 |
| Nes Nes Nes Nds Nds Nds Nds Nds Nds Nds Nds Nds Nks Nks Nk | 537044 | 82 | 527 | 19 |
| Nes Nes Nes Nds Nds Nds Nds Nds Nds Nds Nds Nds Nks Nks Nk | 537045 | 69 | 528 | 19 |
| Nes Nes Nes Nds Nds Nds Nds Nds Nds Nds Nds Nds Nks Nks Nk | 537047 | 35 | 529 | 19 |
| Nes Nes Nes Nds Nds Nds Nds Nds Nds Nds Nds Nds Nks Nks Nk | 537049 | 62 | 530 | 19 |
| Nes Nes Nes Nds Nds Nds Nds Nds Nds Nds Nds Nds Nks Nks Nk | 537051 | 62 | 531 | 19 |
| Nes Nes Nes Nds Nds Nds Nds Nds Nds Nds Nds Nds Nks Nks Nk | 537055 | 16 | 532 | 19 |
| Nes Nes Nes Nds Nds Nds Nds Nds Nds Nds Nds Nds Nks Nks Nk | 537056 | 25 | 533 | 19 |

TABLE 33-continued

Inhibition of human Target-X mRNA levels by chimeric antisense oligonucleotides targeted to Target-X

| Sequence (5' to 3') | ISIS No | % inhibition | SEQ CODE | SEQ ID NO |
|---|---|---|---|---|
| Nes Nes Nes Nds Nds Nds Nds Nds Nds Nds Nds Nds Nks Nks Nk | 537057 | 49 | 534 | 19 |
| Nes Nes Nes Nds Nds Nds Nds Nds Nds Nds Nds Nds Nks Nks Nk | 537058 | 49 | 535 | 19 |
| Nes Nes Nes Nds Nds Nds Nds Nds Nds Nds Nds Nds Nks Nks Nk | 537059 | 53 | 536 | 19 |
| Nes Nes Nes Nds Nds Nds Nds Nds Nds Nds Nds Nds Nks Nks Nk | 537060 | 73 | 537 | 19 |
| Nes Nes Nes Nds Nds Nds Nds Nds Nds Nds Nds Nds Nks Nks Nk | 537061 | 70 | 538 | 19 |
| Nes Nes Nes Nds Nds Nds Nds Nds Nds Nds Nds Nds Nks Nks Nk | 537062 | 69 | 539 | 19 |
| Nes Nes Nes Nds Nds Nds Nds Nds Nds Nds Nds Nds Nks Nks Nk | 537063 | 68 | 540 | 19 |
| Nes Nes Nes Nds Nds Nds Nds Nds Nds Nds Nds Nds Nks Nks Nk | 537064 | 71 | 541 | 19 |
| Nes Nes Nes Nds Nds Nds Nds Nds Nds Nds Nds Nds Nks Nks Nk | 537065 | 67 | 542 | 19 |
| Nes Nes Nes Nds Nds Nds Nds Nds Nds Nds Nds Nds Nks Nks Nk | 537066 | 68 | 543 | 19 |
| Nes Nes Nes Nds Nds Nds Nds Nds Nds Nds Nds Nds Nks Nks Nk | 537067 | 71 | 544 | 19 |
| Nes Nes Nes Nds Nds Nds Nds Nds Nds Nds Nds Nds Nks Nks Nk | 537068 | 86 | 545 | 19 |
| Nes Nes Nes Nds Nds Nds Nds Nds Nds Nds Nds Nds Nks Nks Nk | 537069 | 82 | 546 | 19 |
| Nes Nes Nes Nds Nds Nds Nds Nds Nds Nds Nds Nds Nks Nks Nk | 537070 | 87 | 547 | 19 |
| Nes Nes Nes Nds Nds Nds Nds Nds Nds Nds Nds Nds Nks Nks Nk | 537792 | 36 | 548 | 19 |
| Nes Nes Nes Nds Nds Nds Nds Nds Nds Nds Nds Nds Nks Nks Nk | 537793 | 35 | 549 | 19 |
| Nes Nes Nes Nds Nds Nds Nds Nds Nds Nds Nds Nds Nks Nks Nk | 537794 | 35 | 550 | 19 |
| Nes Nes Nes Nds Nds Nds Nds Nds Nds Nds Nds Nds Nks Nks Nk | 537795 | 33 | 551 | 19 |
| Nes Nes Nes Nds Nds Nds Nds Nds Nds Nds Nds Nds Nks Nks Nk | 537796 | 49 | 552 | 19 |
| Nes Nes Nes Nds Nds Nds Nds Nds Nds Nds Nds Nds Nks Nks Nk | 537797 | 54 | 553 | 19 |
| Nes Nes Nes Nds Nds Nds Nds Nds Nds Nds Nds Nds Nks Nks Nk | 537798 | 68 | 554 | 19 |
| Nes Nes Nes Nds Nds Nds Nds Nds Nds Nds Nds Nds Nks Nks Nk | 537799 | 72 | 555 | 19 |
| Nes Nes Nes Nds Nds Nds Nds Nds Nds Nds Nds Nds Nks Nks Nk | 537800 | 69 | 556 | 19 |
| Nes Nes Nes Nds Nds Nds Nds Nds Nds Nds Nds Nds Nks Nks Nk | 537801 | 82 | 557 | 19 |
| Nes Nes Nes Nds Nds Nds Nds Nds Nds Nds Nds Nds Nks Nks Nk | 537802 | 72 | 558 | 19 |

TABLE 33-continued

Inhibition of human Target-X mRNA levels by chimeric antisense oligonucleotides targeted to Target-X

| Sequence (5' to 3') | ISIS No | % inhibition | SEQ CODE | SEQ ID NO |
|---|---|---|---|---|
| Nes Nes Nes Nds Nds Nds Nds Nds Nds Nds Nds Nds Nks Nks Nk | 537803 | 72 | 559 | 19 |
| Nes Nes Nes Nds Nds Nds Nds Nds Nds Nds Nds Nds Nks Nks Nk | 537804 | 67 | 560 | 19 |
| Nes Nes Nes Nds Nds Nds Nds Nds Nds Nds Nds Nds Nks Nks Nk | 537805 | 74 | 561 | 19 |
| Nes Nes Nes Nds Nds Nds Nds Nds Nds Nds Nds Nds Nks Nks Nk | 537806 | 70 | 562 | 19 |
| Nes Nes Nes Nds Nds Nds Nds Nds Nds Nds Nds Nds Nks Nks Nk | 537809 | 60 | 563 | 19 |
| Nes Nes Nes Nds Nds Nds Nds Nds Nds Nds Nds Nds Nks Nks Nk | 537810 | 71 | 564 | 19 |
| Nes Nes Nes Nds Nds Nds Nds Nds Nds Nds Nds Nds Nks Nks Nk | 537811 | 69 | 565 | 19 |
| Nes Nes Nes Nds Nds Nds Nds Nds Nds Nds Nds Nds Nks Nks Nk | 537812 | 80 | 566 | 19 |
| Nes Nes Nes Nds Nds Nds Nds Nds Nds Nds Nds Nds Nks Nks Nk | 537813 | 74 | 567 | 19 |
| Nes Nes Nes Nds Nds Nds Nds Nds Nds Nds Nds Nds Nks Nks Nk | 537814 | 54 | 568 | 19 |
| Nes Nes Nes Nds Nds Nds Nds Nds Nds Nds Nds Nds Nks Nks Nk | 537837 | 70 | 569 | 19 |
| Nes Nes Nes Nds Nds Nds Nds Nds Nds Nds Nds Nds Nks Nks Nk | 537838 | 76 | 570 | 19 |
| Nes Nes Nes Nds Nds Nds Nds Nds Nds Nds Nds Nds Nks Nks Nk | 537839 | 76 | 571 | 19 |
| Nes Nes Nes Nds Nds Nds Nds Nds Nds Nds Nds Nds Nks Nks Nk | 537840 | 80 | 572 | 19 |
| Nes Nes Nes Nds Nds Nds Nds Nds Nds Nds Nds Nds Nks Nks Nk | 537841 | 81 | 573 | 19 |
| Nes Nes Nes Nds Nds Nds Nds Nds Nds Nds Nds Nds Nks Nks Nk | 537842 | 75 | 574 | 19 |
| Nes Nes Nes Nds Nds Nds Nds Nds Nds Nds Nds Nds Nks Nks Nk | 537843 | 70 | 575 | 19 |
| Nes Nes Nes Nds Nds Nds Nds Nds Nds Nds Nds Nds Nks Nks Nk | 537844 | 73 | 576 | 19 |
| Nes Nes Nes Nds Nds Nds Nds Nds Nds Nds Nds Nds Nks Nks Nk | 537845 | 59 | 577 | 19 |
| Nes Nes Nes Nds Nds Nds Nds Nds Nds Nds Nds Nds Nks Nks Nk | 537846 | 51 | 578 | 19 |
| Nes Nes Nes Nds Nds Nds Nds Nds Nds Nds Nds Nds Nks Nks Nk | 537847 | 52 | 579 | 19 |
| Nes Nes Nes Nds Nds Nds Nds Nds Nds Nds Nds Nds Nks Nks Nk | 537848 | 41 | 580 | 19 |
| Nes Nes Nes Nds Nds Nds Nds Nds Nds Nds Nds Nds Nks Nks Nk | 537849 | 44 | 581 | 19 |
| Nes Nes Nes Nds Nds Nds Nds Nds Nds Nds Nds Nds Nks Nks Nk | 538160 | 69 | 582 | 19 |

TABLE 33-continued

Inhibition of human Target-X mRNA levels by chimeric antisense oligonucleotides targeted to Target-X

| Sequence (5' to 3') | ISIS No | % inhibition | SEQ CODE | SEQ ID NO |
|---|---|---|---|---|
| Nes Nes Nes Nds Nds Nds Nds Nds Nds Nds Nds Nds Nks Nks Nk | 538172 | 24 | 583 | 19 |
| Nes Nes Nes Nds Nds Nds Nds Nds Nds Nds Nds Nds Nks Nks Nk | 538173 | 23 | 584 | 19 |
| Nes Nes Nes Nds Nds Nds Nds Nds Nds Nds Nds Nds Nks Nks Nk | 538185 | 68 | 585 | 19 |
| Nes Nes Nes Nds Nds Nds Nds Nds Nds Nds Nds Nds Nks Nks Nk | 538187 | 69 | 585 | 19 |
| Nes Nes Nes Nds Nds Nds Nds Nds Nds Nds Nds Nds Nks Nks Nk | 538189 | 81 | 587 | 19 |
| Nes Nes Nes Nds Nds Nds Nds Nds Nds Nds Nds Nds Nks Nks Nk | 538191 | 66 | 588 | 19 |
| Nes Nes Nes Nds Nds Nds Nds Nds Nds Nds Nds Nds Nks Nks Nk | 538192 | 59 | 589 | 19 |
| Nes Nes Nes Nds Nds Nds Nds Nds Nds Nds Nds Nds Nks Nks Nk | 538193 | 16 | 590 | 19 |
| Nes Nes Nes Nds Nds Nds Nds Nds Nds Nds Nds Nds Nks Nks Nk | 538194 | 10 | 591 | 19 |
| Nes Nes Nes Nds Nds Nds Nds Nds Nds Nds Nds Nds Nks Nks Nk | 538195 | 15 | 592 | 19 |
| Nes Nes Nes Nds Nds Nds Nds Nds Nds Nds Nds Nds Nks Nks Nk | 538196 | 3 | 593 | 19 |
| Nes Nes Nes Nds Nds Nds Nds Nds Nds Nds Nds Nds Nks Nks Nk | 538197 | 36 | 594 | 19 |
| Nes Nes Nes Nds Nds Nds Nds Nds Nds Nds Nds Nds Nks Nks Nk | 538198 | 49 | 595 | 19 |
| Nes Nes Nes Nds Nds Nds Nds Nds Nds Nds Nds Nds Nks Nks Nk | 538199 | 47 | 596 | 19 |
| Nes Nes Nes Nds Nds Nds Nds Nds Nds Nds Nds Nds Nks Nks Nk | 538200 | 57 | 597 | 19 |
| Nes Nes Nes Nds Nds Nds Nds Nds Nds Nds Nds Nds Nks Nks Nk | 538201 | 71 | 598 | 19 |
| Nes Nes Nes Nds Nds Nds Nds Nds Nds Nds Nds Nds Nks Nks Nk | 538202 | 60 | 599 | 19 |
| Nes Nes Nes Nds Nds Nds Nds Nds Nds Nds Nds Nds Nks Nks Nk | 538203 | 55 | 600 | 19 |
| Nes Nes Nes Nds Nds Nds Nds Nds Nds Nds Nds Nds Nks Nks Nk | 538204 | 62 | 601 | 19 |
| Nes Nes Nes Nds Nds Nds Nds Nds Nds Nds Nds Nds Nks Nks Nk | 538205 | 68 | 602 | 19 |
| Nes Nes Nes Nds Nds Nds Nds Nds Nds Nds Nds Nds Nks Nks Nk | 538228 | 63 | 603 | 19 |
| Nes Nes Nes Nds Nds Nds Nds Nds Nds Nds Nds Nds Nks Nks Nk | 538229 | 26 | 604 | 19 |
| Nes Nes Nes Nds Nds Nds Nds Nds Nds Nds Nds Nds Nks Nks Nk | 538230 | 75 | 605 | 19 |
| Nes Nes Nes Nds Nds Nds Nds Nds Nds Nds Nds Nds Nks Nks Nk | 538231 | 75 | 606 | 19 |
| Nes Nes Nes Nds Nds Nds Nds Nds Nds Nds Nds Nds Nks Nks Nk | 538233 | 52 | 607 | 19 |

TABLE 33-continued

Inhibition of human Target-X mRNA levels by chimeric antisense oligonucleotides targeted to Target-X

| Sequence (5' to 3') | ISIS No | % inhibition | SEQ CODE | SEQ ID NO |
|---|---|---|---|---|
| Nes Nes Nes Nds Nds Nds Nds Nds Nds Nds Nds Nds Nks Nks Nk | 538235 | 26 | 608 | 19 |
| Nes Nes Nes Nds Nds Nds Nds Nds Nds Nds Nds Nds Nks Nks Nk | 538237 | 28 | 609 | 19 |
| Nes Nes Nes Nds Nds Nds Nds Nds Nds Nds Nds Nds Nks Nks Nk | 538239 | 54 | 610 | 19 |
| Nes Nes Nes Nds Nds Nds Nds Nds Nds Nds Nds Nds Nks Nks Nk | 538241 | 73 | 611 | 19 |
| Nes Nes Nes Nds Nds Nds Nds Nds Nds Nds Nds Nds Nks Nks Nk | 538242 | 68 | 612 | 19 |
| Nes Nes Nes Nds Nds Nds Nds Nds Nds Nds Nds Nds Nks Nks Nk | 538243 | 61 | 613 | 19 |
| Nes Nes Nes Nds Nds Nds Nds Nds Nds Nds Nds Nds Nks Nks Nk | 538245 | 75 | 614 | 19 |
| Nes Nes Nes Nds Nds Nds Nds Nds Nds Nds Nds Nds Nks Nks Nk | 538253 | 37 | 615 | 19 |
| Nes Nes Nes Nds Nds Nds Nds Nds Nds Nds Nds Nds Nks Nks Nk | 538254 | 45 | 616 | 19 |
| Nes Nes Nes Nds Nds Nds Nds Nds Nds Nds Nds Nds Nks Nks Nk | 538361 | 56 | 617 | 19 |
| Nes Nes Nes Nds Nds Nds Nds Nds Nds Nds Nds Nds Nks Nks Nk | 538378 | 70 | 618 | 19 |
| Nes Nes Nes Nds Nds Nds Nds Nds Nds Nds Nds Nds Nks Nks Nk | 538380 | 68 | 619 | 19 |
| Nes Nes Nes Nds Nds Nds Nds Nds Nds Nds Nds Nds Nks Nks Nk | 538381 | 57 | 620 | 19 |
| Nes Nes Nes Nds Nds Nds Nds Nds Nds Nds Nds Nds Nks Nks Nk | 540361 | 71 | 621 | 19 |
| Nes Nes Nes Nds Nds Nds Nds Nds Nds Nds Nds Nds Nks Nks Nk | 540362 | 73 | 622 | 19 |
| Nes Nes Nes Nds Nds Nds Nds Nds Nds Nds Nds Nds Nks Nks Nk | 540363 | 78 | 623 | 19 |
| Nes Nes Nes Nds Nds Nds Nds Nds Nds Nds Nds Nds Nks Nks Nk | 540364 | 89 | 624 | 19 |
| Nes Nes Nes Nds Nds Nds Nds Nds Nds Nds Nds Nds Nks Nks Nk | 540365 | 83 | 625 | 19 |
| Nes Nes Nes Nds Nds Nds Nds Nds Nds Nds Nds Nds Nks Nks Nk | 540366 | 84 | 626 | 19 |
| Nes Nes Nes Nds Nds Nds Nds Nds Nds Nds Nds Nds Nks Nks Nk | 540367 | 65 | 627 | 19 |
| Nes Nes Nes Nds Nds Nds Nds Nds Nds Nds Nds Nds Nks Nks Nk | 540368 | 55 | 628 | 19 |
| Nes Nes Nes Nds Nds Nds Nds Nds Nds Nds Nds Nds Nks Nks Nk | 540369 | 82 | 629 | 19 |
| Nes Nes Nes Nds Nds Nds Nds Nds Nds Nds Nds Nds Nks Nks Nk | 540370 | 86 | 630 | 19 |
| Nes Nes Nes Nds Nds Nds Nds Nds Nds Nds Nds Nds Nks Nks Nk | 540371 | 74 | 631 | 19 |

TABLE 33-continued

Inhibition of human Target-X mRNA levels by chimeric antisense oligonucleotides targeted to Target-X

| Sequence (5' to 3') | ISIS No | % inhibition | SEQ CODE | SEQ ID NO |
|---|---|---|---|---|
| Nes Nes Nes Nds Nds Nds Nds Nds Nds Nds Nds Nds Nks Nks Nk | 540372 | 82 | 632 | 19 |
| Nes Nes Nes Nds Nds Nds Nds Nds Nds Nds Nds Nds Nks Nks Nk | 540373 | 81 | 633 | 19 |
| Nes Nes Nes Nds Nds Nds Nds Nds Nds Nds Nds Nds Nks Nks Nk | 540374 | 87 | 634 | 19 |
| Nes Nes Nes Nds Nds Nds Nds Nds Nds Nds Nds Nds Nks Nks Nk | 540375 | 78 | 635 | 19 |
| Nes Nes Nes Nds Nds Nds Nds Nds Nds Nds Nds Nds Nks Nks Nk | 540376 | 69 | 636 | 19 |
| Nes Nes Nes Nds Nds Nds Nds Nds Nds Nds Nds Nds Nks Nks Nk | 540377 | 88 | 637 | 19 |
| Nes Nes Nes Nds Nds Nds Nds Nds Nds Nds Nds Nds Nks Nks Nk | 540378 | 85 | 638 | 19 |
| Nes Nes Nes Nds Nds Nds Nds Nds Nds Nds Nds Nds Nks Nks Nk | 540379 | 77 | 639 | 19 |
| Nes Nes Nes Nds Nds Nds Nds Nds Nds Nds Nds Nds Nks Nks Nk | 540380 | 84 | 640 | 19 |
| Nes Nes Nes Nds Nds Nds Nds Nds Nds Nds Nds Nds Nks Nks Nk | 540381 | 85 | 641 | 19 |
| Nes Nes Nes Nds Nds Nds Nds Nds Nds Nds Nds Nds Nks Nks Nk | 540382 | 69 | 642 | 19 |
| Nes Nes Nes Nds Nds Nds Nds Nds Nds Nds Nds Nds Nks Nks Nk | 540383 | 85 | 643 | 19 |
| Nes Nes Nes Nds Nds Nds Nds Nds Nds Nds Nds Nds Nks Nks Nk | 540384 | 88 | 644 | 19 |
| Nes Nes Nes Nds Nds Nds Nds Nds Nds Nds Nds Nds Nks Nks Nk | 540385 | 87 | 645 | 19 |
| Nes Nes Nes Nds Nds Nds Nds Nds Nds Nds Nds Nds Nks Nks Nk | 540386 | 86 | 646 | 19 |
| Nes Nes Nes Nds Nds Nds Nds Nds Nds Nds Nds Nds Nks Nks Nk | 540387 | 77 | 647 | 19 |
| Nes Nes Nes Nds Nds Nds Nds Nds Nds Nds Nds Nds Nks Nks Nk | 540388 | 86 | 648 | 19 |
| Nes Nes Nes Nds Nds Nds Nds Nds Nds Nds Nds Nds Nks Nks Nk | 540389 | 86 | 649 | 19 |
| Nes Nes Nes Nds Nds Nds Nds Nds Nds Nds Nds Nds Nks Nks Nk | 540390 | 85 | 650 | 19 |
| Nes Nes Nes Nds Nds Nds Nds Nds Nds Nds Nds Nds Nks Nks Nk | 540391 | 83 | 651 | 19 |
| Nes Nes Nes Nds Nds Nds Nds Nds Nds Nds Nds Nds Nks Nks Nk | 540392 | 43 | 652 | 19 |
| Nes Nes Nes Nds Nds Nds Nds Nds Nds Nds Nds Nds Nks Nks Nk | 540393 | 88 | 653 | 19 |
| Nes Nes Nes Nds Nds Nds Nds Nds Nds Nds Nds Nds Nks Nks Nk | 540394 | 68 | 654 | 19 |
| Nes Nes Nes Nds Nds Nds Nds Nds Nds Nds Nds Nds Nks Nks Nk | 540395 | 87 | 655 | 19 |
| Nes Nes Nes Nds Nds Nds Nds Nds Nds Nds Nds Nds Nks Nks Nk | 540396 | 87 | 656 | 19 |

TABLE 33-continued

Inhibition of human Target-X mRNA levels by chimeric antisense oligonucleotides targeted to Target-X

| Sequence (5' to 3') | ISIS No | % inhibition | SEQ CODE | SEQ ID NO |
|---|---|---|---|---|
| Nes Nes Nes Nds Nds Nds Nds Nds Nds Nds Nds Nds Nks Nks Nk | 540397 | 59 | 657 | 19 |
| Nes Nes Nes Nds Nds Nds Nds Nds Nds Nds Nds Nds Nks Nks Nk | 540398 | 36 | 658 | 19 |
| Nes Nes Nes Nds Nds Nds Nds Nds Nds Nds Nds Nds Nks Nks Nk | 540399 | 81 | 659 | 19 |

Example 23: High Dose Tolerability of Modified Oligonucleotides Comprising 2'-O-Methoxyethyl (2'-MOE) and 6'-(S)—CH3 Bicyclic Nucleoside (e.g cEt) Modifications Targeting Human Target-X in BALB/c Mice BALB/c mice were treated at a high dose with ISIS antisense oligonucleotides selected from studies described above and evaluated for changes in the levels of various plasma chemistry markers.

Additionally, the newly designed antisense oligonucleotides were created with the same sequences as the antisense oligonucleotides from the study described above and were also added to this screen targeting intronic repeat regions of Target-X.

The newly designed modified antisense oligonucleotides and their motifs are described in Table 34. The internucleoside linkages throughout each gapmer are phosphorothioate linkages (P=S). Nucleosides followed by "d" indicate 2'-deoxyribonucleosides. Nucleosides followed by "k" indicate 6'-(S)—CH3 bicyclic nucleoside (e.g cEt) nucleosides. Nucleosides followed by "e" indicate 2'-O-methythoxylethyl (2'-MOE) nucleosides. "N" indicates modified or naturally occurring nucleobases (A, T, C, G, U, or 5-methyl C).

Each gapmer listed in Table 34 is targeted to the intronic region of human Target-X genomic sequence, designated herein as Target-X.

TABLE 34

Modified antisense oligonucleotides targeted to Target-X

| Sequence (5' to 3') | ISIS No | SEQ CODE | SEQ ID NO |
|---|---|---|---|
| Nks Nks Nks Nds Nds Nds Nds Nds Nds Nds Nds Nds Nds Nes Nes Ne | 537721 | 509 | 19 |
| Nks Nks Nks Nds Nds Nds Nds Nds Nds Nds Nds Nds Nds Nes Nes Ne | 537738 | 524 | 19 |
| Nks Nks Nks Nds Nds Nds Nds Nds Nds Nds Nds Nds Nds Nes Nes Ne | 537759 | 539 | 19 |
| Nks Nks Nks Nds Nds Nds Nds Nds Nds Nds Nds Nds Nds Nes Nes Ne | 537761 | 541 | 19 |
| Nks Nks Nks Nds Nds Nds Nds Nds Nds Nds Nds Nds Nds Nes Nes Ne | 537763 | 543 | 19 |
| Nks Nks Nks Nds Nds Nds Nds Nds Nds Nds Nds Nds Nds Nes Nes Ne | 537850 | 548 | 19 |
| Nks Nks Nks Nds Nds Nds Nds Nds Nds Nds Nds Nds Nds Nes Nes Ne | 537858 | 556 | 19 |
| Nks Nks Nks Nds Nds Nds Nds Nds Nds Nds Nds Nds Nds Nes Nes Ne | 537864 | 562 | 19 |
| Nks Nks Nks Nds Nds Nds Nds Nds Nds Nds Nds Nds Nds Nes Nes Ne | 537869 | 565 | 19 |
| Nks Nks Nks Nds Nds Nds Nds Nds Nds Nds Nds Nds Nds Nes Nes Ne | 537872 | 568 | 19 |
| Nks Nks Nks Nds Nds Nds Nds Nds Nds Nds Nds Nds Nds Nes Nes Ne | 537897 | 571 | 19 |
| Nks Nks Nks Nds Nds Nds Nds Nds Nds Nds Nds Nds Nds Nes Nes Ne | 540118 | 582 | 19 |
| Nks Nks Nks Nds Nds Nds Nds Nds Nds Nds Nds Nds Nds Nes Nes Ne | 540138 | 602 | 19 |
| Nks Nks Nks Nds Nds Nds Nds Nds Nds Nds Nds Nds Nds Nes Nes Ne | 540139 | 603 | 19 |
| Nks Nks Nks Nds Nds Nds Nds Nds Nds Nds Nds Nds Nds Nes Nes Ne | 540148 | 612 | 19 |
| Nks Nks Nks Nds Nds Nds Nds Nds Nds Nds Nds Nds Nds Nes Nes Ne | 540153 | 617 | 19 |
| Nks Nks Nks Nds Nds Nds Nds Nds Nds Nds Nds Nds Nds Nes Nes Ne | 540155 | 619 | 19 |
| Nes Nes Nks Nds Nds Nds Nds Nds Nds Nds Nds Nds Nds Nks Nks Ne | 540162 | 624 | 19 |

TABLE 34-continued

Modified antisense oligonucleotides targeted to Target-X

| Sequence (5' to 3') | ISIS No | SEQ CODE | SEQ ID NO |
|---|---|---|---|
| Nes Nes Nks Nds Nds Nds Nds Nds Nds Nds Nds Nds Nds Nks Nks Ne | 540164 | 626 | 19 |
| Nes Nes Nks Nds Nds Nds Nds Nds Nds Nds Nds Nds Nds Nks Nks Ne | 540168 | 630 | 19 |
| Nes Nes Nks Nds Nds Nds Nds Nds Nds Nds Nds Nds Nds Nks Nks Ne | 540172 | 634 | 19 |
| Nes Nes Nks Nds Nds Nds Nds Nds Nds Nds Nds Nds Nds Nks Nks Ne | 540175 | 637 | 19 |
| Nes Nes Nks Nds Nds Nds Nds Nds Nds Nds Nds Nds Nds Nks Nks Ne | 540176 | 638 | 19 |
| Nes Nes Nks Nds Nds Nds Nds Nds Nds Nds Nds Nds Nds Nks Nks Ne | 540178 | 640 | 19 |
| Nes Nes Nks Nds Nds Nds Nds Nds Nds Nds Nds Nds Nds Nks Nks Ne | 540179 | 641 | 19 |
| Nes Nes Nks Nds Nds Nds Nds Nds Nds Nds Nds Nds Nds Nks Nks Ne | 540181 | 643 | 19 |
| Nes Nes Nks Nds Nds Nds Nds Nds Nds Nds Nds Nds Nds Nks Nks Ne | 540182 | 644 | 19 |
| Nes Nes Nks Nds Nds Nds Nds Nds Nds Nds Nds Nds Nds Nks Nks Ne | 540183 | 645 | 19 |
| Nes Nes Nks Nds Nds Nds Nds Nds Nds Nds Nds Nds Nds Nks Nks Ne | 540184 | 646 | 19 |
| Nes Nes Nks Nds Nds Nds Nds Nds Nds Nds Nds Nds Nds Nks Nks Ne | 540186 | 648 | 19 |
| Nes Nes Nks Nds Nds Nds Nds Nds Nds Nds Nds Nds Nds Nks Nks Ne | 540187 | 649 | 19 |
| Nes Nes Nks Nds Nds Nds Nds Nds Nds Nds Nds Nds Nds Nks Nks Ne | 540188 | 650 | 19 |
| Nes Nes Nks Nds Nds Nds Nds Nds Nds Nds Nds Nds Nds Nks Nks Ne | 540191 | 653 | 19 |
| Nes Nes Nks Nds Nds Nds Nds Nds Nds Nds Nds Nds Nds Nks Nks Ne | 540193 | 655 | 19 |
| Nes Nes Nks Nds Nds Nds Nds Nds Nds Nds Nds Nds Nds Nks Nks Ne | 540194 | 656 | 19 |
| Nes Nes Nks Nds Nds Nds Nds Nds Nds Nds Nds Nds Nds Nks Nks Ne | 544811 | 547 | 19 |
| Nes Nes Nks Nds Nds Nds Nds Nds Nds Nds Nds Nds Nds Nks Nks Ne | 544812 | 545 | 19 |
| Nes Nes Nks Nds Nds Nds Nds Nds Nds Nds Nds Nds Nds Nks Nks Ne | 544813 | 527 | 19 |
| Nes Nes Nks Nds Nds Nds Nds Nds Nds Nds Nds Nds Nds Nks Nks Ne | 544814 | 557 | 19 |
| Nes Nes Nks Nds Nds Nds Nds Nds Nds Nds Nds Nds Nds Nks Nks Ne | 544815 | 546 | 19 |
| Nes Nes Nks Nds Nds Nds Nds Nds Nds Nds Nds Nds Nds Nks Nks Ne | 544816 | 573 | 19 |
| Nes Nes Nks Nds Nds Nds Nds Nds Nds Nds Nds Nds Nds Nks Nks Ne | 544817 | 572 | 19 |
| Nes Nes Nks Nds Nds Nds Nds Nds Nds Nds Nds Nds Nds Nks Nks Ne | 544818 | 566 | 19 |
| Nes Nes Nks Nds Nds Nds Nds Nds Nds Nds Nds Nds Nds Nks Nks Ne | 544819 | 510 | 19 |
| Nes Nes Nks Nds Nds Nds Nds Nds Nds Nds Nds Nds Nds Nks Nks Ne | 544820 | 525 | 19 |
| Nes Nes Nks Nds Nds Nds Nds Nds Nds Nds Nds Nds Nds Nks Nks Ne | 544821 | 567 | 19 |
| Nes Nes Nks Nds Nds Nds Nds Nds Nds Nds Nds Nds Nds Nks Nks Ne | 544826 | 537 | 19 |
| Nes Nes Nks Nds Nds Nds Nds Nds Nds Nds Nds Nds Nds Nks Nks Ne | 544827 | 538 | 19 |
| Nes Nes Nks Nds Nds Nds Nds Nds Nds Nds Nds Nds Nds Nks Nks Ne | 544828 | 539 | 19 |
| Nes Nes Nks Nds Nds Nds Nds Nds Nds Nds Nds Nds Nds Nks Nks Ne | 544829 | 540 | 19 |
| Nes Nes Nks Nds Nds Nds Nds Nds Nds Nds Nds Nds Nds Nks Nks Ne | 544830 | 541 | 19 |
| Nes Nes Nks Nds Nds Nds Nds Nds Nds Nds Nds Nds Nds Nks Nks Ne | 545471 | 542 | 19 |
| Nes Nes Nks Nds Nds Nds Nds Nds Nds Nds Nds Nds Nds Nks Nks Ne | 545472 | 543 | 19 |
| Nes Nes Nks Nds Nds Nds Nds Nds Nds Nds Nds Nds Nds Nks Nks Ne | 545473 | 544 | 19 |
| Nes Nes Nks Nds Nds Nds Nds Nds Nds Nds Nds Nds Nds Nks Nks Ne | 545474 | 558 | 19 |
| Nes Nes Nks Nds Nds Nds Nds Nds Nds Nds Nds Nds Nds Nks Nks Ne | 545475 | 559 | 19 |

TABLE 34-continued

Modified antisense oligonucleotides targeted to Target-X

| Sequence (5' to 3') | ISIS No | SEQ CODE | SEQ ID NO |
|---|---|---|---|
| Nes Nes Nks Nds Nds Nds Nds Nds Nds Nds Nds Nds Nds Nks Nks Ne | 545476 | 560 | 19 |
| Nes Nes Nks Nds Nds Nds Nds Nds Nds Nds Nds Nds Nds Nks Nks Ne | 545477 | 561 | 19 |
| Nes Nes Nks Nds Nds Nds Nds Nds Nds Nds Nds Nds Nds Nks Nks Ne | 545478 | 562 | 19 |
| Nes Nes Nks Nds Nds Nds Nds Nds Nds Nds Nds Nds Nds Nks Nks Ne | 545479 | 556 | 19 |
| Nks Nks Nks Nds Nds Nds Nds Nds Nds Nds Nds Nds Nds Nes Nes Ne | 537727 | 514 | 19 |

Treatment

Male BALB/c mice were injected subcutaneously with a single dose of 200 mg/kg of ISIS 422142, ISIS 457851, ISIS 473294, ISIS 473295, ISIS 473327, ISIS 484714, ISIS 515334, ISIS 515338, ISIS 515354, ISIS 515366, ISIS 515380, ISIS 515381, ISIS 515382, ISIS 515384, ISIS 515386, ISIS 515387, ISIS 515388, ISIS 515406, ISIS 515407, ISIS 515408, ISIS 515422, ISIS 515423, ISIS 515424, ISIS 515532, ISIS 515533, ISIS 515534, ISIS 515538, ISIS 515539, ISIS 515558, ISIS 515656, ISIS 515575, ISIS 515926, ISIS 515944, ISIS 515945, ISIS 515948, ISIS 515949, ISIS 515951, ISIS 515952, ISSI 516003, ISIS 516055, ISIS 516057, ISIS 516060, ISIS 516062, ISIS 529126, ISIS 529146, ISIS 529166, ISIS 529170, ISIS 529172, ISIS 529173, ISIS 529174, ISIS 529175, ISSI 529176, ISIS 529182, ISIS 529183, ISIS 529186, ISIS 529282, ISIS 529304, ISIS 529306, ISIS 529360, ISIS 529450, ISIS 529459, ISIS 529460, ISIS 529461, ISIS 529547, ISIS 529550, ISIS 529551, ISIS 529553, ISIS 529557, ISIS 529562, ISIS 529563, ISIS 529564, ISIS 529565, ISIS 529575, ISIS 529582, ISIS 529589, ISIS 529607, ISIS 529614, ISIS 529632, ISIS 529650, ISIS 529651, ISIS 529657, ISIS 529663, ISIS 529725, ISIS 529745, ISIS 529765, ISIS 529785, ISIS 529804, ISIS 529818, ISIS 529823, ISIS 529854, ISIS 534528, ISIS 534534, ISIS 534594, ISIS 534660, ISIS 534663, ISIS 534664, ISIS 534676, ISIS 534677, ISIS 537679, ISIS 537683, ISIS 534693, ISIS 534701, ISIS 534716, ISIS 534730, ISIS 534765, ISIS 534795, ISIS 534796, ISIS 534797, ISIS 534798, ISIS 534799, ISIS 534800, ISIS 534802, ISIS 534806, ISSI 534830, ISIS 534838, ISIS 534888, ISIS 534890, ISIS 534898, ISIS 534911, ISIS 534920, ISIS 534926, ISIS 534937, ISIS 534950, ISSI 534956, ISIS 534980, ISIS 534986, ISIS 535010, ISIS 535043, ISIS 535049, ISIS 535076, ISIS 535082, ISSI 535142, ISIS 537024, ISIS 537030, ISIS 537041, ISIS 537062, ISIS 537064, ISIS 537066, ISIS 537721, ISIS 537727, ISIS 537738, ISIS 537759, ISIS 537761, ISIS 537763, ISIS 537792, ISIS 537800, ISIS 537806, ISIS 537811, ISIS 537814, ISIS 537839, ISIS 537850, ISSI 537858, ISIS 537864, ISIS 537869, ISIS 537872, ISIS 537897, ISIS 538160, ISIS 538196, ISIS 538205, ISIS 538228, ISIS 538242, ISIS 538361, ISIS 538380, ISIS 540118, ISIS 540138, ISIS 540139, ISIS 540148, ISIS 540153, ISIS 540155, ISIS 540162, ISIS 540164, ISIS 540168, ISIS 540172, ISIS 540175, ISIS 540176, ISIS 540178, ISIS 540179, ISIS 540181, ISIS 540182, ISIS 540183, ISIS 540184, ISIS 540186, ISIS 540187, ISIS 540188, ISIS 540191, ISIS 540193, ISIS 540194, ISIS 544811, ISIS 544812, ISIS 544813, ISIS 544814, ISIS 544815, ISIS 544816, ISIS 544817, ISIS 544818, ISIS 544819, ISIS 544820, ISIS 544821, ISIS 544826, ISIS 544827, ISIS 544828, ISIS 544829, ISIS 544830, ISIS 545471, ISIS 545472, ISIS 545473, ISIS 545474, ISIS 545475, ISIS 545476, ISIS 545477, ISIS 545478, and ISIS 545479. One set of male BALB/c mice was injected with a single dose of PBS. Mice were euthanized 96 hours later, and organs and plasma were harvested for further analysis.

Plasma Chemistry Markers

To evaluate the effect of ISIS oligonucleotides on liver and kidney function, plasma levels of transaminases, bilirubin, albumin, and BUN were measured using an automated clinical chemistry analyzer (Hitachi Olympus AU400e, Melville, N.Y.).

ISIS oligonucleotides that did not cause any increase in the levels of transaminases, or which caused an increase within three times the upper limit of normal (ULN) were deemed very tolerable. ISIS oligonucleotides that caused an increase in the levels of transaminases between three times and seven times the ULN were deemed tolerable. Based on these criteria, ISIS 529166, ISIS 529170, ISIS 529175, ISIS 529176, ISIS 529186, ISIS 529282, ISIS 529360, ISIS 529450, ISIS 529459, ISIS 529460, ISIS 529547, ISIS 529549, ISIS 529551, ISIS 529553, ISIS 529557, ISIS 529562, ISIS 529575, ISIS 529582, ISIS 529607, ISIS 529589, ISIS 529632, ISIS 529657, ISIS 529725, ISIS 529745, ISIS 529785, ISIS 529799, ISIS 529804, ISIS 529818, ISIS 529823, ISIS 534950, ISIS 534980, ISIS 535010, ISIS 537030, ISIS 537041, ISIS 537062, ISIS 537064, ISIS 537066, ISIS 537759, ISIS 537792, ISIS 537800, ISIS 537839, ISIS 538228, ISIS 473294, ISIS 473295, ISIS 484714, ISIS 515338, ISIS 515366, ISIS 515380, ISIS 515381, ISIS 515387, ISIS 515408, ISIS 515423, ISIS 515424, ISIS 515532, ISIS 515534, ISIS 515538, ISIS 515539, ISIS 515558, ISIS 515575, ISIS 515926, ISIS 515944, ISIS 515945, ISIS 515951, ISIS 515952, ISIS 529126, ISIS 529765, ISIS 534528, ISIS 534534, ISIS 534594, ISIS 534663, ISIS 534676, ISIS 534677, ISIS 534679, ISIS 534683, ISIS 534693, ISIS 534701, ISIS 534716, ISIS 534730, ISIS 534806, ISIS 534830, ISIS 534838, ISIS 534890, ISIS 534898, ISIS 534911, ISIS 534937, ISIS 534956, ISIS 534986, ISIS 535043, ISIS 535049, ISIS 535076, ISIS 535082, ISIS 535142, ISIS 538160, ISIS 538242, ISIS 538361, ISIS 538380, ISIS 534795, ISIS 534796, ISIS 534797, ISIS 540162, ISIS 540164, ISIS 540168, ISIS 540172, ISIS 540175, ISIS 540176, ISIS 540178, ISIS 540179, ISIS 540181, ISIS 540182, ISIS 540183, ISIS 540184, ISIS 540186, ISIS 540187, ISIS 540188, ISIS 540191, ISIS 540193, ISIS 540194, ISIS 544813, ISIS 544814, ISIS 544816, ISIS 544826, ISIS 544827, ISIS 544828, ISIS 544829, ISIS 545473, and ISIS 545474 were considered very tolerable in terms of liver function. Based on these criteria, ISIS 529173, ISIS 529854, ISIS 529614, ISIS 515386, ISIS 515388, ISIS 515949, ISIS 544817, and ISIS 545479 were considered tolerable in terms of liver function.

Example 24: Tolerability of Antisense Oligonucleotides Targeting Human Target-X in Sprague-Dawley Rats Sprague-Dawley rats are a multipurpose model used for safety and efficacy evaluations. The rats were treated with ISIS antisense oligonucleotides from the studies described in the Examples above and evaluated for changes in the levels of various plasma chemistry markers.

Treatment

Six-eight week old male Sprague-Dawley rats were maintained on a 12-hour light/dark cycle and fed ad libitum with Teklad normal rat chow. Groups of four Sprague-Dawley rats each were injected subcutaneously twice a week for 6 weeks with 25 mg/kg of ISIS 473286, ISIS 473547, ISIS 473567, ISIS 473589, ISIS 473630, ISIS 484559, ISIS 515636, ISIS 515640, ISIS 515641, ISIS 515655, ISIS 515657, ISIS 516046, ISIS 516048, ISIS 516051, ISIS 516052, and ISIS 516062. A group of four Sprague-Dawley rats was injected subcutaneously twice a week for 6 weeks with PBS. Forty eight hours after the last dose, rats were euthanized and organs and plasma were harvested for further analysis.

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured. Plasma levels of Bilirubin and BUN were also measured using the same clinical chemistry analyzer.

ISIS oligonucleotides that did not cause any increase in the levels of transaminases, or which caused an increase within three times the upper limit of normal (ULN) were deemed very tolerable. ISIS oligonucleotides that caused an increase in the levels of transaminases between three times and seven times the ULN were deemed tolerable. Based on these criteria, ISIS 473286, ISIS 473547, ISSI 473589, ISIS 473630, ISIS 484559, ISIS 515636, ISIS 515640, ISIS 515655, ISIS 516046, and ISIS 516051 were considered very tolerable in terms of liver function. Based on these criteria, ISIS 473567, ISIS 515641, ISIS 515657, ISIS 516048, and ISIS 516051 were considered tolerable in terms of liver function.

Example 25: Tolerability of Chimeric Antisense Oligonucleotides Comprising 2'-O-Methoxyethyl (2'-MOE) Modifications Targeting Human Target-X in Sprague-Dawley Rats Sprague-Dawley rats were treated with ISIS antisense oligonucleotides from the studies described in the Examples above and evaluated for changes in the levels of various plasma chemistry markers.

Treatment

Six-eight week old male Sprague-Dawley rats were maintained on a 12-hour light/dark cycle and fed ad libitum with Purina normal rat chow. Groups of four Sprague-Dawley rats each were injected subcutaneously twice a week for 6 weeks with 50 mg/kg of ISIS 407936, ISIS 416507, ISIS 416508, ISIS 490208, ISIS 490279, ISIS 490323, ISIS 490368, ISIS 490396, ISIS 490803, ISIS 491122, ISIS 513419, ISIS 513446, ISIS 513454, ISIS 513455, ISIS 513456, ISIS 513504, ISIS 513507, and ISIS 513508. A group of four Sprague-Dawley rats was injected subcutaneously twice a week for 6 weeks with PBS. Forty eight hours after the last dose, rats were euthanized and organs and plasma were harvested for further analysis.

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of Bilirubin and BUN were also measured using the same clinical chemistry analyzer.

ISIS oligonucleotides that did not cause any increase in the levels of transaminases, or which caused an increase within three times the upper limit of normal (ULN) were deemed very tolerable. ISIS oligonucleotides that caused an increase in the levels of transaminases between three times and seven times the ULN were deemed tolerable. Based on these criteria, ISIS 416507, ISIS 490208, ISIS 490368, ISIS 490396, ISIS 490803, ISIS 491122, ISIS 513446, ISIS 513454, ISIS 513455, ISIS 513456, ISIS 513504, and ISIS 513508 were considered very tolerable in terms of liver function. Based on these criteria, ISIS 407936, ISIS 416508, ISIS 490279, and ISIS 513507 were considered tolerable in terms of liver function.

Example 26: Tolerability of Chimeric Antisense Oligonucleotides Comprising 2'-O-Methoxyethyl (2'-MOE) Modifications Targeting Human Target-X in CD-1 Mice CD-1 mice are a multipurpose mice model, frequently utilized for safety and efficacy testing. The mice were treated with ISIS antisense oligonucleotides selected from studies described above and evaluated for changes in the levels of various plasma chemistry markers.

Treatment

Groups of 3 male CD-1 mice each were injected subcutaneously twice a week for 6 weeks with 50 mg/kg of ISIS 473244, ISIS 473295, ISIS 484714, ISIS 515386, ISIS 515424, ISIS 515534, ISIS 515558, ISIS 515926, ISIS 515949, ISIS 515951, ISIS 515952, ISIS 529126, ISIS 529166, ISIS 529173, ISIS 529186, ISIS 529360, ISIS 529461, ISIS 529553, ISIS 529564, ISIS 529582, ISIS 529614, ISIS 529725, ISIS 529745, ISIS 529765, ISIS 529785, ISIS 529799, ISIS 529818, ISIS 529823, ISIS 534528, ISIS 534594, and ISIS 534664. One group of male CD-1 mice was injected subcutaneously twice a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, and BUN were measured using an automated clinical chemistry analyzer (Hitachi Olympus AU400e, Melville, N.Y.).

ISIS oligonucleotides that did not cause any increase in the levels of transaminases, or which caused an increase within three times the upper limit of normal (ULN) were deemed very tolerable. ISIS oligonucleotides that caused an increase in the levels of transaminases between three times and seven times the ULN were deemed tolerable. Based on these criteria, ISIS 473295, ISIS 473714, ISIS 515558, ISIS 515926, 515951, ISIS 515952, ISIS 529126, ISIS 529166, 529564, ISIS 529582, ISIS 529614, ISIS 529725, ISIS 529765, ISIS 529799, ISIS 529823, and ISIS 534594 were considered very tolerable in terms of liver function. Based on these criteria, ISIS 515424, ISIS 515534, ISIS 515926, ISIS 529785, and ISIS 534664 were considered tolerable in terms of liver function.

Example 27: Tolerability of Chimeric Antisense Oligonucleotides Comprising 2'-O-Methoxyethyl (2'-MOE) Modifications Targeting Human Target-X in CD-1 Mice CD-1 mice were treated with ISIS antisense oligonucleotides selected from studies described above and evaluated for changes in the levels of various plasma chemistry markers.
Treatment
Groups of 3 male CD-1 mice each were injected subcutaneously twice a week for 6 weeks with 100 mg/kg of ISIS 490208, ISIS 490279, ISIS 490323, ISIS 490368, ISIS 490396, ISIS 490803, ISIS 491122, ISIS 513419, ISIS 513446, ISIS 513454, ISIS 513455, ISIS 513456, ISIS 513504, ISIS 513507, and ISIS 513508. Groups of 3 male CD-1 mice each were injected subcutaneously twice a week for 6 weeks with 100 mg/kg of ISIS 407936, ISIS 416507, and ISIS 416508, which are gapmers described in a previous publication. One group of male CD-1 mice was injected subcutaneously twice a week for 6 weeks with PBS. Mice were euthanized 48 hours after the last dose, and organs and plasma were harvested for further analysis.
Plasma Chemistry Markers
To evaluate the effect of ISIS oligonucleotides on liver and kidney function, plasma levels of transaminases, bilirubin, and BUN were measured using an automated clinical chemistry analyzer (Hitachi Olympus AU400e, Melville, N.Y.).

ISIS oligonucleotides that did not cause any increase in the levels of transaminases, or which caused an increase within three times the upper limit of normal (ULN) were deemed very tolerable. ISIS oligonucleotides that caused an increase in the levels of transaminases between three times and seven times the ULN were deemed tolerable. Based on these criteria, ISIS 407936, ISIS 416507, ISIS 490279, ISIS 490368, ISIS 490396, ISIS 490803, ISIS 491122, ISIS 513446, ISIS 513454, ISIS 513456, and ISIS 513504 were considered very tolerable in terms of liver function. Based on these criteria, ISIS 490208, ISIS 513455, ISIS 513507, and ISIS 513508 were considered tolerable in terms of liver function.

Example 28: Efficacy of Modified Oligonucleotides Comprising 2'-O-Methoxyethyl (2'-MOE) and Constrained Ethyl (cEt) Modifications Targeting Human Target-X in Transgenic Mice Transgenic mice were treated with ISIS antisense oligonucleotides selected from studies described above and evaluated for efficacy.
Treatment
Groups of 2-3 male and female transgenic mice were injected subcutaneously twice a week for 3 weeks with 5 mg/kg/week of ISIS 473244, ISIS 473295, ISIS 484714, ISIS 515926, ISIS 515951, ISIS 515952, ISIS 516062, ISIS 529126, ISIS 529553, ISIS 529745, ISIS 529799, ISIS 534664, ISIS 534826, ISIS 540168, ISIS 540175, ISIS 544826, ISIS 544827, ISIS 544828, and ISIS 544829. One group of mice was injected subcutaneously twice a week for 3 weeks with PBS. Mice were euthanized 48 hours after the last dose, and organs and plasma were harvested for further analysis.
Protein Analysis
Plasma protein levels of Target-X were estimated using a Target-X ELISA kit (purchased from Hyphen Bio-Med). Results are presented as percent inhibition of Target-X, relative to control. As shown in Table 35, several antisense oligonucleotides achieved reduction of human Target-X over the PBS control. 'n.d.' indicates that the value for that particular oligonucleotide was not measured.

TABLE 35

Percent inhibition of Target-X plasma protein levels in transgenic mice

| ISIS No | % inhibition |
| --- | --- |
| 473244 | 2 |
| 473295 | 13 |
| 484714 | 19 |
| 515926 | 11 |
| 515951 | 13 |
| 515952 | 0 |
| 516062 | 62 |
| 529126 | 0 |
| 529553 | 0 |
| 529745 | 22 |
| 529799 | 26 |
| 534664 | 32 |
| 534826 | n.d. |
| 540168 | 94 |
| 540175 | 98 |
| 544813 | 0 |
| 544826 | 23 |
| 544827 | 60 |
| 544828 | 33 |
| 544829 | 53 |

Example 29: Efficacy of Modified Oligonucleotides Comprising 2'-Methoxyethyl (2'-MOE) and Constrained Ethyl (cEt) Modifications Targeting Human Target-X in Transgenic Mice Transgenic mice were treated with ISIS antisense oligonucleotides selected from studies described above and evaluated for efficacy.
Treatment
Groups of 2-3 male and female transgenic mice were injected subcutaneously twice a week for 3 weeks with 1 mg/kg/week of ISIS 407936, ISIS 490197, ISIS 490275, ISIS 490278, ISIS 490279, ISIS 490323, ISIS 490368, ISIS 490396, ISIS 490803, ISIS 491122, ISIS 513446, ISIS 513447, ISIS 513504, ISIS 516062, ISIS 529166, ISIS 529173, ISIS 529360, ISIS 529725, ISIS 534557, ISIS 534594, ISIS 534664, ISIS 534688, ISIS 534689, ISIS 534915, ISIS 534916, ISIS 534917, and ISIS 534980. One group of mice was injected subcutaneously twice a week for 3 weeks with PBS. Mice were euthanized 48 hours after the last dose, and organs and plasma were harvested for further analysis.
Protein Analysis
Plasma protein levels of Target-X were estimated using a Target-X ELISA kit (purchased from Hyphen Bio-Med). Results are presented as percent inhibition of Target-X, relative to control. As shown in Table 36, several antisense oligonucleotides achieved reduction of human Target-X over the PBS control.

TABLE 36

Percent inhibition of Target-X plasm protein levels in transgenic mice

| ISIS No | % inhibition |
|---|---|
| 407936 | 28 |
| 490197 | 50 |
| 490275 | 21 |
| 490278 | 20 |
| 490279 | 59 |
| 490323 | 54 |
| 490368 | 22 |
| 490396 | 31 |
| 490803 | 30 |
| 491122 | 51 |
| 513446 | 29 |
| 513447 | 44 |
| 513504 | 45 |
| 516062 | 75 |
| 529166 | 37 |
| 529173 | 64 |
| 529360 | 43 |
| 529725 | 53 |
| 534557 | 76 |
| 534594 | 40 |
| 534664 | 14 |
| 534687 | 12 |
| 534688 | 48 |
| 534689 | 25 |
| 534915 | 40 |
| 534916 | 45 |
| 534917 | 66 |
| 534980 | 62 |

Example 30: Tolerability of Antisense Oligonucleotides Targeting Human Target-X in Sprague-Dawley Rats Sprague-Dawley rats were treated with ISIS antisense oligonucleotides from the studies described in the Examples above and evaluated for changes in the levels of various plasma chemistry markers.

Treatment

Six-eight week old male Sprague-Dawley rats were maintained on a 12-hour light/dark cycle and fed ad libitum with Teklad normal rat chow. Groups of four Sprague-Dawley rats each were injected subcutaneously twice a week for 4 weeks with ISIS 515380, ISIS 515381, ISIS 515387, ISIS 529175, ISIS 529176, ISIS 529575, ISIS 529804, and ISIS 537064. Doses 1, 5, 6, 7, and 8 were 25 mg/kg; dose 2 was 75 mg/kg; doses 3 and 4 were 50 mg/kg. One group of four Sprague-Dawley rats was injected subcutaneously twice a week for 4 weeks with PBS. Forty eight hours after the last dose, rats were euthanized and organs and plasma were harvested for further analysis.

Liver Function

To evaluate the effect of ISIS oligonucleotides on hepatic function, plasma levels of transaminases ALT (alanine transaminase) and AST (aspartate transaminase) were measured using an automated clinical chemistry analyzer (Hitachi Olympus AU400e, Melville, N.Y.). Plasma levels of Bilirubin and BUN were also measured using the same clinical chemistry analyzer.

ISIS oligonucleotides that did not cause any increase in the levels of transaminases, or which caused increase in the levels within three times the upper limit of normal levels of transaminases were deemed very tolerable. ISIS oligonucleotides that caused increase in the levels of transaminases between three times and seven times the upper limit of normal levels were deemed tolerable. Based on these criteria, ISIS 515380, ISIS 515387, ISIS 529175, ISIS 529176, ISIS 529804, and ISIS 537064 were considered very tolerable in terms of liver function. Based on these criteria, ISIS 515381 was considered tolerable in terms of liver function.

Example 31: Efficacy of Antisense Oligonucleotides Targeting Human Target-X in Transgenic Mice Transgenic mice were treated with ISIS antisense oligonucleotides selected from studies described above and evaluated for efficacy.

Treatment

Two groups of 3 male and female transgenic mice were injected subcutaneously twice a week for 2 weeks with 0.5 mg/kg/week or 1.5 mg/kg/week of ISIS 407935 and ISIS 513455. Another group of mice was subcutaneously twice a week for 2 weeks with 0.6 mg/kg/week or 2.0 mg/kg/week of ISIS 473286. Another 16 groups of mice were subcutaneously twice a week for 2 weeks with 0.1 mg/kg/week or 0.3 mg/kg/week of ISIS 473589, ISIS 515380, ISIS 515423, ISIS 529804, ISIS 534676, ISIS 534796, ISIS 540162, ISIS 540164, ISIS 540175, ISIS 540179, ISIS 540181, ISIS 540182, ISIS 540186, ISIS 540191, ISIS 540193, ISIS 544827, or ISIS 545474. Another 3 groups of mice were injected subcutaneously twice a week for 2 weeks with 0.3 mg/kg/week of ISIS 516062, ISIS 534528 or ISIS 534693. One group of mice was injected subcutaneously twice a week for 2 weeks with PBS. Mice were euthanized 48 hours after the last dose, and organs and plasma were harvested for further analysis.

Protein Analysis

Plasma protein levels of Target-X were estimated using a Target-X ELISA kit (purchased from Hyphen Bio-Med). Results are presented as percent inhibition of Target-X, relative to control. As shown in Table 37, several antisense oligonucleotides achieved reduction of human Target-X over the PBS control.

TABLE 37

Percent inhibition of Target-X plasma protein levels in transgenic mice

| ISIS No | Dose (mg/kg/wk) | % inhibition |
|---|---|---|
| 407935 | 1.5 | 65 |
| | 0.5 | 31 |
| 513455 | 1.5 | 64 |
| | 0.5 | 52 |
| 473286 | 2 | 67 |
| | 0.6 | 11 |
| 473589 | 0.3 | 42 |
| | 0.1 | 12 |
| 515380 | 0.3 | 64 |
| | 0.1 | 32 |
| 515423 | 0.3 | 72 |
| | 0.1 | 37 |
| 529804 | 0.3 | 36 |
| | 0.1 | 24 |
| 534676 | 0.3 | 31 |
| | 0.1 | 18 |
| 534796 | 0.3 | 54 |
| | 0.1 | 43 |
| 540162 | 0.3 | 84 |
| | 0.1 | 42 |
| 540164 | 0.3 | 25 |
| | 0.1 | 17 |
| 540175 | 0.3 | 90 |
| | 0.1 | 55 |
| 540179 | 0.3 | 29 |
| | 0.1 | 24 |

TABLE 37-continued

Percent inhibition of Target-X plasma protein levels in transgenic mice

| ISIS No | Dose (mg/kg/wk) | % inhibition |
|---|---|---|
| 540181 | 0.3 | 53 |
|  | 0.1 | 0 |
| 540182 | 0.3 | 78 |
|  | 0.1 | 21 |
| 540186 | 0.3 | 72 |
|  | 0.1 | 46 |
| 540191 | 0.3 | 62 |
|  | 0.1 | 35 |
| 540193 | 0.3 | 74 |
|  | 0.1 | 46 |
| 544827 | 0.3 | 28 |
|  | 0.1 | 19 |
| 545474 | 0.3 | 59 |
|  | 0.1 | 0 |
| 516062 | 0.3 | 33 |
| 534528 | 0.3 | 41 |
| 534693 | 0.3 | 34 |

Example 32: Tolerability of Antisense Oligonucleotides Targeting Human Target-X in Sprague-Dawley Rats Sprague-Dawley rats were treated with ISIS antisense oligonucleotides from the studies described in the Examples above and evaluated for changes in the levels of various plasma chemistry markers.

Treatment

Five-six week old male Sprague-Dawley rats were maintained on a 12-hour light/dark cycle and fed ad libitum with Teklad normal rat chow. Groups of four Sprague-Dawley rats each were injected subcutaneously twice a week for 4 weeks with 50 mg/kg of ISIS 515423, ISIS 515424, ISIS 515640, ISIS 534676, ISIS 534796, ISIS 534797, ISIS 540162, ISIS 540164, ISIS 540172, ISIS 540175, ISIS 540179, ISIS 540181, ISIS 540182, ISIS 540183, ISIS 540186, ISIS 540191, and ISIS 545474. A group of four Sprague-Dawley rats was injected subcutaneously twice a week for 4 weeks with PBS. Forty eight hours after the last dose, rats were euthanized and organs and plasma were harvested for further analysis.

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured. Plasma levels of Bilirubin and BUN were also measured using the same clinical chemistry analyzer.

ISIS oligonucleotides that did not cause any increase in the levels of transaminases, or which caused an increase within three times the upper limit of normal (ULN) were deemed very tolerable. ISIS oligonucleotides that caused an increase in the levels of transaminases between three times and seven times the ULN were deemed tolerable. Based on these criteria, ISIS 540164, ISIS 540172, and ISIS 540175 were considered very tolerable in terms of liver function. Based on these criteria, ISIS 534676, ISIS 534796, ISIS 534797, ISIS 540162, and ISIS 540179 were considered tolerable in terms of liver function.

Example 33: Dose-Dependent Antisense Inhibition of Human Target-X in Hep3B Cells Antisense oligonucleotides selected from the studies described above were tested at various doses in Hep3B cells. Cells were plated at a density of 20,000 cells per well and transfected using electroporation with 0.05 µM, 0.15 µM, 0.44 µM, 1.33 µM, and 4.00 µM concentrations of antisense oligonucleotide, as specified in Table 38. After a treatment period of approximately 16 hours, RNA was isolated from the cells and Target-X mRNA levels were measured by quantitative real-time PCR. Human Target-X primer probe set RTS2927 was used to measure mRNA levels. Target-X mRNA levels were adjusted according to total RNA content, as measured by RIBOGREEN®. Results are presented as percent inhibition of Target-X, relative to untreated control cells.

The half maximal inhibitory concentration ($IC_{50}$) of each oligonucleotide is also presented in Table 38. As illustrated in Table 38, Target-X mRNA levels were reduced in a dose-dependent manner in several of the antisense oligonucleotide treated cells.

TABLE 38

Dose-dependent antisense inhibition of human Target-X in Hep3B cells using electroporation

| ISIS No | 0.05 µM | 0.15 µM | 0.44 µM | 1.33 µM | 4.00 µM | $IC_{50}$ (µM) |
|---|---|---|---|---|---|---|
| 473286 | 0 | 1 | 13 | 12 | 15 | >4.0 |
| 457851 | 23 | 32 | 57 | 80 | 93 | 0.3 |
| 473286 | 3 | 20 | 43 | 71 | 88 | 0.5 |
| 473286 | 15 | 26 | 24 | 28 | 36 | >4.0 |
| 473286 | 6 | 3 | 10 | 26 | 29 | >4.0 |
| 473327 | 14 | 28 | 35 | 67 | 90 | 0.5 |
| 473589 | 29 | 53 | 76 | 89 | 95 | 0.1 |
| 515380 | 44 | 72 | 85 | 93 | 95 | <0.05 |
| 515423 | 43 | 64 | 87 | 95 | 98 | <0.05 |
| 515424 | 38 | 55 | 85 | 92 | 97 | 0.1 |
| 515636 | 21 | 33 | 74 | 82 | 93 | 0.2 |
| 516046 | 29 | 23 | 29 | 48 | 78 | 0.9 |
| 516048 | 35 | 24 | 41 | 67 | 87 | 0.4 |
| 516052 | 18 | 6 | 48 | 63 | 80 | 0.6 |
| 516062 | 24 | 14 | 21 | 47 | 68 | 1.6 |
| 529166 | 16 | 47 | 75 | 87 | 94 | 0.2 |
| 529173 | 14 | 49 | 77 | 91 | 96 | 0.2 |
| 529175 | 30 | 69 | 88 | 93 | 96 | 0.1 |
| 529176 | 34 | 63 | 85 | 93 | 96 | 0.1 |
| 529360 | 35 | 53 | 74 | 91 | 93 | 0.1 |
| 529725 | 53 | 69 | 85 | 92 | 95 | <0.05 |
| 529804 | 37 | 41 | 71 | 90 | 94 | 0.1 |
| 534528 | 50 | 68 | 78 | 93 | 97 | <0.05 |
| 534557 | 48 | 78 | 90 | 94 | 95 | <0.05 |
| 534594 | 39 | 47 | 76 | 87 | 94 | 0.1 |
| 534676 | 29 | 20 | 40 | 64 | 87 | 0.5 |
| 534687 | 41 | 37 | 56 | 80 | 93 | 0.2 |
| 534688 | 16 | 56 | 88 | 94 | 96 | 0.1 |
| 534689 | 21 | 59 | 82 | 94 | 95 | 0.1 |
| 534693 | 18 | 58 | 81 | 93 | 95 | 0.1 |
| 534795 | 19 | 43 | 68 | 90 | 94 | 0.2 |
| 534796 | 25 | 59 | 80 | 93 | 96 | 0.1 |
| 534890 | 31 | 55 | 77 | 90 | 96 | 0.1 |
| 534898 | 22 | 61 | 80 | 94 | 97 | 0.1 |
| 534915 | 19 | 26 | 51 | 77 | 94 | 0.3 |
| 534916 | 20 | 36 | 66 | 86 | 93 | 0.2 |
| 534917 | 34 | 53 | 82 | 89 | 94 | 0.1 |
| 540162 | 40 | 64 | 84 | 90 | 92 | <0.05 |
| 540164 | 34 | 60 | 83 | 91 | 92 | 0.1 |
| 540168 | 51 | 79 | 90 | 92 | 94 | <0.05 |
| 540172 | 40 | 66 | 80 | 88 | 92 | <0.05 |
| 540175 | 30 | 61 | 80 | 88 | 91 | 0.1 |
| 540176 | 7 | 17 | 50 | 75 | 85 | 0.5 |
| 540179 | 11 | 22 | 25 | 16 | 19 | >4.0 |
| 540181 | 19 | 46 | 72 | 86 | 91 | 0.2 |
| 540182 | 16 | 66 | 83 | 86 | 92 | 0.1 |
| 540183 | 39 | 74 | 87 | 92 | 93 | <0.05 |
| 540186 | 31 | 69 | 85 | 91 | 94 | 0.1 |
| 540191 | 38 | 54 | 80 | 88 | 91 | 0.1 |
| 540193 | 57 | 67 | 84 | 94 | 97 | <0.05 |
| 540194 | 30 | 45 | 62 | 77 | 91 | 0.2 |

TABLE 38-continued

Dose-dependent antisense inhibition of human
Target-X in Hep3B cells using electroporation

| ISIS No | 0.05 µM | 0.15 µM | 0.44 µM | 1.33 µM | 4.00 µM | IC$_{50}$ (µM) |
|---|---|---|---|---|---|---|
| 544827 | 37 | 42 | 67 | 82 | 96 | 0.1 |
| 544829 | 26 | 41 | 42 | 71 | 93 | 0.3 |
| 545473 | 28 | 27 | 49 | 80 | 97 | 0.3 |
| 545474 | 23 | 27 | 55 | 84 | 96 | 0.3 |

Example 34: Tolerability of Antisense Oligonucleotides Targeting Human Target-X in CD-1 Mice CD-1 mice were treated with ISIS antisense oligonucleotides selected from studies described above and evaluated for changes in the levels of various plasma chemistry markers.

Treatment

Two groups of 4 male 6-8 week old CD-1 mice each were injected subcutaneously twice a week for 6 weeks with 50 mg/kg of ISIS 407935 and ISIS 490279. Another seven groups of 4 male 6-8 week old CD-1 mice each were injected subcutaneously twice a week for 6 weeks with 25 mg/kg of ISIS 473589, ISIS 529804, ISIS 534796, ISIS 540162, ISIS 540175, ISIS 540182, and ISIS 540191. One group of male CD-1 mice was injected subcutaneously twice a week for 6 weeks with PBS. Mice were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, and BUN were measured using an automated clinical chemistry analyzer (Hitachi Olympus AU400e, Melville, N.Y.). The results are presented in Table 39. Treatment with the newly designed antisense oligonucleotides were more tolerable compared to treatment with ISIS 407935 (disclosed in an earlier publication), which caused elevation of ALT levels greater than seven times the upper limit of normal (ULN).

TABLE 39

Effect of antisense oligonucleotide treatment
on liver function in CD-1 mice

| Motif | Dose (mg/kg/wk) | ALT (IU/L) | AST (IU/L) | BUN (mg/dL) | Bilirubin (mg/dL) |
|---|---|---|---|---|---|
| PBS | — | — | 37 | 47 | 28 | 0.2 |
| 407935 e5-d(10)-e5 | 100 | 373 | 217 | 24 | 0.2 |
| 490279 kdkdk-d(9)-ee | 100 | 96 | 82 | 24 | 0.2 |
| 473589 e5-d(10)-e5 | 50 | 93 | 116 | 22 | 0.2 |
| 529804 k-d(10)-kekee | 50 | 54 | 74 | 27 | 0.2 |
| 534796 ekk-d(10)-kke | 50 | 60 | 63 | 27 | 0.2 |
| 540162 eek-d(10)-kke | 50 | 43 | 55 | 29 | 0.2 |
| 540175 eek-d(10)-kke | 50 | 113 | 78 | 24 | 0.3 |
| 540182 eek-d(10)-kke | 50 | 147 | 95 | 26 | 0.1 |
| 540191 eek-d(10)-kke | 50 | 79 | 88 | 28 | 0.2 | e = 2'-MOE,
k = cEt,
d = 2'-deoxynucleoside Body and organ weights

Body weights, as well as liver, heart, lungs, spleen and kidney weights were measured at the end of the study, and are presented in Table 40. Several of the ISIS oligonucleotides did not cause any changes in organ weights outside the expected range and were therefore deemed tolerable in terms of organ weight

TABLE 40

Body and organ weights (grams) of CD-1 mice

| Motif | Dose (mg/kg/wk) | Body weight | Liver | Spleen | Kidney |
|---|---|---|---|---|---|
| PBS | — | 42 | 2.2 | 0.12 | 0.64 |
| 407935 e5-d(10)-e5 | 100 | 40 | 2.6 | 0.20 | 0.62 |
| 490279 kdkdk-d(9)-ee | 100 | 42 | 2.8 | 0.17 | 0.61 |
| 473589 e5-d(10)-e5 | 50 | 41 | 2.5 | 0.16 | 0.67 |
| 529804 k-d(10)-kekee | 50 | 40 | 2.3 | 0.14 | 0.62 |
| 534796 ekk-d(10)-kke | 50 | 37 | 2.6 | 0.15 | 0.51 |
| 540162 eek-d(10)-kke | 50 | 42 | 2.4 | 0.15 | 0.60 |
| 540175 eek-d(10)-kke | 50 | 39 | 2.2 | 0.11 | 0.62 |
| 540182 eek-d(10)-kke | 50 | 41 | 2.6 | 0.16 | 0.61 |
| 540191 eek-d(10)-kke | 50 | 40 | 2.4 | 0.13 | 0.60 | e = 2'-MOE,
k = cEt,
d = 2'-deoxynucleoside

Example 35: Tolerability of Antisense Oligonucleotides Targeting Human Target-X in Sprague-Dawley Rats Sprague-Dawley rats were treated with ISIS antisense oligonucleotides selected from studies described above and evaluated for changes in the levels of various plasma chemistry markers.

Treatment

Two groups of 4 male 7-8 week old Sprague-Dawley rats each were injected subcutaneously twice a week for 6 weeks with 50 mg/kg of ISIS 407935 and ISIS 490279. Another seven groups of 4 male 6-8 week old Sprague-Dawley rats each were injected subcutaneously twice a week for 6 weeks with 25 mg/kg of ISIS 473589, ISIS 529804, ISIS 534796, ISIS 540162, ISIS 540175, ISIS 540182, and ISIS 540191. One group of male Sprague-Dawley rats was injected subcutaneously twice a week for 6 weeks with PBS. The rats were euthanized 48 hours after the last dose, and organs and plasma were harvested for further analysis.

Plasma Chemistry Markers

To evaluate the effect of ISIS oligonucleotides on liver and kidney function, plasma levels of transaminases, bilirubin, albumin, and BUN were measured using an automated clinical chemistry analyzer (Hitachi Olympus AU400e, Melville, N.Y.). The results are presented in Table 41. Treatment with the all antisense oligonucleotides was tolerable in terms of plasma chemistry markers in this model.

TABLE 41

Effect of antisense oligonucleotide treatment on
liver function in Sprague-Dawley rats

| Motif | Dose (mg/kg/wk) | ALT (IU/L) | AST (IU/L) | BUN (mg/dL) | Bilirubin (mg/dL) |
|---|---|---|---|---|---|
| PBS | — | 71 | 83 | 19 | 0.2 |
| 407935 e5-d(10)-e5 | 100 | 74 | 96 | 22 | 0.2 |
| 490279 kdkdk-d(9)-ee | 100 | 96 | 181 | 22 | 0.4 |
| 473589 e5-d(10)-e5 | 50 | 57 | 73 | 21 | 0.2 |
| 529804 k-d(10)-kekee | 50 | 54 | 78 | 21 | 0.2 |
| 534796 ekk-d(10)-kke | 50 | 68 | 98 | 22 | 0.2 |

TABLE 41-continued

Effect of antisense oligonucleotide treatment on liver function in Sprague-Dawley rats

| Motif | Dose (mg/kg/wk) | ALT (IU/L) | AST (IU/L) | BUN (mg/dL) | Bilirubin (mg/dL) |
|---|---|---|---|---|---|
| 540162 eek-d(10)-kke | 50 | 96 | 82 | 21 | 0.1 |
| 540175 eek-d(10)-kke | 50 | 55 | 73 | 18 | 0.2 |
| 540182 eek-d(10)-kke | 50 | 45 | 87 | 21 | 0.2 |
| 540191 eek-d(10)-kke | 50 | 77 | 104 | 21 | 0.2 | e = 2'-MOE,
k = cEt,
d = 2'-deoxynucleoside

Body and Organ Weights

Body weights, as well as liver, heart, lungs, spleen and kidney weights were measured at the end of the study, and are presented in Table 42. Treatment with all the antisense oligonucleotides was tolerable in terms of body and organ weights in this model.

TABLE 42

Body and organ weights (grams) of Sprague-Dawley rats

| Motif | Dose (mg/kg/wk) | Body weight | Liver | Spleen | Kidney |
|---|---|---|---|---|---|
| PBS | — | — | 443 | 16 | 0.8 | 3.5 |
| ISIS 407935 e5-d(10)-e5 | 100 | 337 | 14 | 1.8 | 3.2 |
| ISIS 490279 kdkdk-d(9)-ee | 100 | 365 | 18 | 2.2 | 2.9 |
| ISIS 473589 e5-d(10)-e5 | 50 | 432 | 18 | 1.3 | 3.3 |
| ISIS 529804 k-d(10)-kekee | 50 | 429 | 18 | 2.2 | 3.4 |
| ISIS 534796 ekk-d(10)-kke | 50 | 434 | 15 | 1.4 | 3.3 |
| ISIS 540162 eek-d(10)-kke | 50 | 446 | 18 | 1.1 | 3.3 |
| ISIS 540175 eek-d(10)-kke | 50 | 467 | 16 | 1.0 | 3.5 |
| ISIS 540182 eek-d(10)-kke | 50 | 447 | 22 | 2.5 | 4.5 |
| ISIS 540191 eek-d(10)-kke | 50 | 471 | 21 | 1.4 | 3.9 | e = 2'-MOE,
k = cEt,
d = 2'-deoxynucleoside

Example 36: Dose-Dependent Antisense Inhibition of Human Target-X in Cynomolgos Monkey Primary Hepatocytes Antisense oligonucleotides selected from the studies described above were tested at various doses in cynomolgous monkey primary hepatocytes. Cells were plated at a density of 35,000 cells per well and transfected using electroporation with 0.009 µM, 0.03 µM, 0.08 µM, 0.25 µM, 0.74 µM, 2.22 µM, 6.67 µM, and 20.00 µM concentrations of antisense oligonucleotide, as specified in Table 43. After a treatment period of approximately 16 hours, RNA was isolated from the cells and Target-X mRNA levels were measured by quantitative real-time PCR. Target-X primer probe set RTS2927 was used to measure mRNA levels. Target-X mRNA levels were adjusted according to total RNA content, as measured by RIBOGREEN®. Results are presented as percent inhibition of Target-X, relative to untreated control cells. As illustrated in Table 43, Target-X mRNA levels were reduced in a dose-dependent manner with some of the antisense oligonucleotides that are cross-reactive with the rhesus monkey genomic sequence designated herein as Target-X.

TABLE 43

Dose-dependent antisense inhibition of Target-X in cynomolgous monkey primary hepatocytes using electroporation

| ISIS No | 0.009 µM | 0.03 µM | 0.08 µM | 0.25 µM | 0.74 µM | 2.22 µM | 6.67 µM | 20.00 µM |
|---|---|---|---|---|---|---|---|---|
| 407935 | 10 | 18 | 15 | 29 | 56 | 73 | 82 | 88 |
| 490279 | 19 | 12 | 13 | 0 | 6 | 18 | 27 | 22 |
| 473589 | 5 | 10 | 19 | 42 | 64 | 76 | 88 | 92 |
| 529804 | 10 | 3 | 23 | 25 | 57 | 80 | 86 | 91 |
| 534796 | 0 | 28 | 23 | 49 | 71 | 81 | 87 | 90 |
| 540162 | 9 | 14 | 9 | 6 | 13 | 13 | 11 | 31 |
| 540175 | 0 | 4 | 12 | 9 | 10 | 16 | 12 | 22 |
| 540182 | 0 | 7 | 0 | 6 | 36 | 12 | 10 | 0 |
| 540191 | 6 | 7 | 0 | 0 | 0 | 0 | 21 | 42 |

Example 37: Dose-Dependent Antisense Inhibition of Human Target-X in Hep3B Cells Antisense oligonucleotides from the study described above were also tested at various doses in Hep3B cells. Cells were plated at a density of 20,000 cells per well and transfected using electroporation with 0.009 µM, 0.03 µM, 0.08 µM, 0.25 µM, 0.74 µM, 2.22 µM, 6.67 µM, and 20.00 µM concentrations of antisense oligonucleotide, as specified in Table 44. After a treatment period of approximately 16 hours, RNA was isolated from the cells and Target-X mRNA levels were measured by quantitative real-time PCR. Target-X primer probe set RTS2927 was used to measure mRNA levels. Target-X mRNA levels were adjusted according to total RNA content, as measured by RIBOGREEN®. Results are presented as percent inhibition of Target-X, relative to untreated control cells. As illustrated in Table 44, Target-X mRNA levels were reduced in a dose-dependent manner with several of the antisense oligonucleotides.

TABLE 44

Dose-dependent antisense inhibition of Target-X in Hep3B cells using electroporation

| ISIS No | 0.009 μM | 0.03 μM | 0.08 μM | 0.25 μM | 0.74 μM | 2.22 μM | 6.67 μM | 20.00 μM | IC$_{50}$ (μM) |
|---|---|---|---|---|---|---|---|---|---|
| 407935 | 3 | 9 | 11 | 35 | 64 | 83 | 87 | 93 | 4.5 |
| 473244 | 20 | 33 | 50 | 69 | 77 | 89 | 7 | 14 | 0.9 |
| 473589 | 0 | 14 | 23 | 44 | 74 | 88 | 90 | 94 | 2.7 |
| 490279 | 0 | 5 | 7 | 15 | 25 | 61 | 76 | 78 | 11.6 |
| 515533 | 0 | 12 | 21 | 36 | 63 | 78 | 88 | 94 | 3.6 |
| 515952 | 0 | 12 | 27 | 57 | 76 | 89 | 93 | 94 | 2.2 |
| 516066 | 6 | 0 | 12 | 26 | 52 | 70 | 81 | 86 | 6.0 |
| 529459 | 0 | 4 | 24 | 40 | 61 | 78 | 88 | 94 | 3.5 |
| 529553 | 9 | 7 | 17 | 40 | 58 | 74 | 87 | 93 | 4.6 |
| 529804 | 0 | 3 | 34 | 64 | 83 | 89 | 93 | 95 | 2.0 |
| 534796 | 8 | 18 | 43 | 67 | 82 | 89 | 95 | 96 | 1.4 |
| 537806 | 6 | 11 | 5 | 20 | 37 | 69 | 79 | 86 | 7.1 |
| 540162 | 18 | 33 | 63 | 75 | 87 | 91 | 91 | 92 | 0.7 |
| 540175 | 10 | 25 | 55 | 76 | 86 | 89 | 89 | 93 | 1.0 |
| 540182 | 13 | 36 | 61 | 75 | 84 | 88 | 90 | 93 | 0.7 |
| 540191 | 3 | 12 | 28 | 61 | 79 | 80 | 88 | 94 | 2.2 |

Example 38: Efficacy of Antisense Oligonucleotides Targeting Human Target-X in Transgenic Mice Transgenic mice were treated with ISIS antisense oligonucleotides selected from studies described above and evaluated for efficacy.

Treatment

Eight groups of 3 transgenic mice each were injected subcutaneously twice a week for 3 weeks with 20 mg/kg/week, 10 mg/kg/week, 5 mg/kg/week, or 2.5 mg/kg/week of ISIS 407935 or ISIS 490279. Another 24 groups of 3 transgenic mice each were subcutaneously twice a week for 3 weeks with 5 mg/kg/week, 2.5 mg/kg/week, 1.25 mg/kg/week, or 0.625 mg/kg/week of ISIS 473589, ISIS 529804, ISIS 534796, ISIS 540162, ISIS 540175, or ISIS 540191. One group of mice was injected subcutaneously twice a week for 3 weeks with PBS. Mice were euthanized 48 hours after the last dose, and organs and plasma were harvested for further analysis.

RNA Analysis

RNA was extracted from plasma for real-time PCR analysis of Target-X, using primer probe set RTS2927. The mRNA levels were normalized using RIBOGREEN®. As shown in Table 45, several antisense oligonucleotides achieved reduction of human Target-X over the PBS control. Results are presented as percent inhibition of Target-X, relative to control. Treatment with newly designed 2'-MOE gapmer, ISIS 490279, caused greater reduction in human Target-X mRNA levels than treatment with ISIS 407935, the 2'-MOE gapmer from the earlier publication. Treatment with several of the newly designed oligonucleotides also caused greater reduction in human Target-X mRNA levels than treatment with ISIS 407935.

TABLE 45

Percent inhibition of Target-X mRNA in transgenic mice

| ISIS No | Motif | Dose (mg/kg/wk) | % inhibition |
|---|---|---|---|
| 407935 | e5-d(10)-e5 | 20.0 | 85 |
|  |  | 10.0 | 57 |
|  |  | 5.0 | 45 |
|  |  | 2.5 | 28 |
| 490279 | kdkdk-d(9)-ee | 20.0 | 88 |
|  |  | 10.0 | 70 |
|  |  | 5.0 | 51 |
|  |  | 2.5 | 33 |
| 473589 | e5-d(10)-e5 | 5.00 | 80 |
|  |  | 2.50 | 62 |
|  |  | 1.25 | 44 |
|  |  | 0.625 | 25 |
| 529804 | k-d(10)-kekee | 5.00 | 55 |
|  |  | 2.50 | 41 |
|  |  | 1.25 | 0 |
|  |  | 0.625 | 1 |
| 534796 | ekk-d(10)-kke | 5.00 | 56 |
|  |  | 2.50 | 41 |
|  |  | 1.25 | 5 |
|  |  | 0.625 | 0 |
| 540162 | eek-d(10)-kke | 5.00 | 97 |
|  |  | 2.50 | 92 |
|  |  | 1.25 | 69 |
|  |  | 0.625 | 78 |
| 540175 | eek-d(10)-kke | 5.00 | 95 |
|  |  | 2.50 | 85 |
|  |  | 1.25 | 65 |
|  |  | 0.625 | 55 |
| 540182 | eek-d(10)-kke | 5.00 | 97 |
|  |  | 2.50 | 83 |
|  |  | 1.25 | 54 |
|  |  | 0.625 | 10 |
| 540191 | eek-d(10)-kke | 5.00 | 91 |
|  |  | 2.50 | 74 |
|  |  | 1.25 | 58 |
|  |  | 0.625 | 34 | e = 2'-MOE,
k = cEt,
d = 2'-deoxynucleoside

Protein Analysis

Plasma protein levels of Target-X were estimated using a Target-X ELISA kit (purchased from Hyphen Bio-Med). As shown in Table 46, several antisense oligonucleotides achieved reduction of human Target-X over the PBS control. Results are presented as percent inhibition of Target-X, relative to control.

TABLE 46

Percent inhibition of Target-X plasm protein levels in transgenic mice

| ISIS No | Motif | Dose (mg/kg/wk) | % inhibition |
|---|---|---|---|
| 407935 | e5-d(10)-e5 | 20 | 65 |
|  |  | 10 | 47 |
|  |  | 5 | 0 |
|  |  | 2.5 | 3 |
| 490279 | kdkdk-d(9)-ee | 20 | 91 |
|  |  | 10 | 75 |
|  |  | 5 | 31 |
|  |  | 2.5 | 23 |
| 473589 | e5-d(10)-e5 | 5 | 78 |
|  |  | 2.5 | 40 |
|  |  | 1.25 | 6 |
|  |  | 0.625 | 0 |
| 529804 | k-d(10)-kekee | 5 | 50 |
|  |  | 2.5 | 36 |
|  |  | 1.25 | 0 |
|  |  | 0.625 | 8 |
| 534796 | ekk-d(10)-kke | 5 | 45 |
|  |  | 2.5 | 26 |
|  |  | 1.25 | 0 |
|  |  | 0.625 | 8 |
| 540162 | eek-d(10)-kke | 5 | 98 |
|  |  | 2.5 | 96 |
|  |  | 1.25 | 78 |
|  |  | 0.625 | 74 |
| 540175 | eek-d(10)-kke | 5 | 93 |
|  |  | 2.5 | 83 |
|  |  | 1.25 | 49 |
|  |  | 0.625 | 24 |
| 540182 | eek-d(10)-kke | 5 | 97 |
|  |  | 2.5 | 71 |
|  |  | 1.25 | 50 |
|  |  | 0.625 | 0 |
| 540191 | eek-d(10)-kke | 5 | 97 |
|  |  | 2.5 | 74 |
|  |  | 1.25 | 46 |
|  |  | 0.625 | 25 | e = 2'-MOE,
k = cEt,
d = 2'-deoxynucleoside

Example 39: Effect of ISIS Antisense Oligonucleotides Targeting Human Target-X in Cynomolgus Monkeys Cynomolgus monkeys were treated with ISIS antisense oligonucleotides selected from studies described above, including ISIS 407935, ISIS 490279, ISIS 473589, ISIS 529804, ISIS 534796, ISIS 540162, ISIS 540175, ISIS 540182, and ISIS 540191. Antisense oligonucleotide efficacy was evaluated. ISIS 407935, from the earlier publication, was included in the study for comparison.

Treatment

Prior to the study, the monkeys were kept in quarantine for at least a 30-day period, during which the animals were observed daily for general health. Standard panels of serum chemistry and hematology, examination of fecal samples for ova and parasites, and a tuberculosis test were conducted immediately after the animals' arrival to the quarantine area. The monkeys were 2-4 years old at the start of treatment and weighed between 2 and 4 kg. Ten groups of four randomly assigned male cynomolgus monkeys each were injected subcutaneously with ISIS oligonucleotide or PBS using a stainless steel dosing needle and syringe of appropriate size into one of 4 sites on the back of the monkeys; each site used in clock-wise rotation per dose administered. Nine groups of monkeys were dosed four times a week for the first week (days 1, 3, 5, and 7) as loading doses, and subsequently once a week for weeks 2-12, with 35 mg/kg of ISIS 407935, ISIS 490279, ISIS 473589, ISIS 529804, ISIS 534796, ISIS 540162, ISIS 540175, ISIS 540182, or ISIS 540191. A control group of cynomolgus monkeys was injected with PBS subcutaneously thrice four times a week for the first week (days 1, 3, 5, and 7), and subsequently once a week for weeks 2-12. The protocols described in the Example were approved by the Institutional Animal Care and Use Committee (IACUC).

Hepatic Target Reduction

RNA Analysis

On day 86, RNA was extracted from liver tissue for real-time PCR analysis of Target-X using primer probe set RTS2927. Results are presented as percent inhibition of Target-X mRNA, relative to PBS control, normalized to RIBOGREEN® or to the house keeping gene, GAPDH. As shown in Table 52, treatment with ISIS antisense oligonucleotides resulted in reduction of Target-X mRNA in comparison to the PBS control.

TABLE 52

Percent Inhibition of cynomolgus monkey Target-X mRNA in the cynomolgus monkey liver relative to the PBS control

| ISIS No | Motif | RTS2927/Ribogreen | RTS2927/GAPDH |
|---|---|---|---|
| 407935 | e5-d(10)-e5 | 90 | 90 |
| 490279 | kdkdk-d(9)-ee | 72 | 66 |
| 473589 | e5-d(10)-e5 | 96 | 96 |
| 529804 | k-d(10)-kekee | 90 | 87 |
| 534796 | ekk-d(10)-kke | 80 | 78 |
| 540162 | eek-d(10)-kke | 66 | 58 |
| 540175 | eek-d(10)-kke | 68 | 66 |
| 540182 | eek-d(10)-kke | 0 | 0 |
| 540191 | eek-d(10)-kke | 34 | 14 | e = 2'-MOE,
k = cEt,
d = 2'-deoxynucleoside

Protein Levels and Activity Analysis

Plasma Target-X levels were measured prior to dosing, and on day 3, day 5, day 7, day 16, day 30, day 44, day 65, and day 86 of treatment. Target-X activity was measured using Target-X deficiuent plasma. Approximately 1.5 mL of blood was collected from all available study animals into tubes containing 3.2% sodium citrate. The samples were placed on ice immediately after collection. Collected blood samples were processed to platelet poor plasma and the tubes were centrifuged at 3,000 rpm for 10 min at 4° C. to obtain plasma.

Protein levels of Target-X were measured by a Target-X elisa kit (purchased from Hyphen BioMed). The results are presented in Table 53.

TABLE 53

Plasma Target-X protein levels (% reduction compared to the baseline) in the cynomolgus monkey plasma

| ISIS No | Day 3 | Day 5 | Day 7 | Day 16 | Day 30 | Day 44 | Day 65 | Day 86 |
|---|---|---|---|---|---|---|---|---|
| 407935 | 21 | 62 | 69 | 82 | 84 | 85 | 84 | 90 |
| 490279 | 0 | 29 | 35 | 30 | 38 | 45 | 51 | 58 |
| 473589 | 12 | 67 | 85 | 97 | 98 | 98 | 98 | 98 |
| 529804 | 19 | 65 | 76 | 87 | 88 | 89 | 90 | 90 |
| 534796 | 1 | 46 | 54 | 64 | 64 | 67 | 66 | 70 |
| 540162 | 0 | 24 | 26 | 37 | 45 | 49 | 49 | 50 |
| 540175 | 0 | 28 | 36 | 38 | 47 | 52 | 55 | 55 |
| 540182 | 0 | 17 | 8 | 0 | 0 | 0 | 5 | 0 |
| 540191 | 0 | 12 | 4 | 0 | 0 | 4 | 9 | 10 |

Example 40: Inhibition of Chimeric Antisense Oligonucleotides Targeting Target-Y A series of modified oligonucleotides were designed based on the parent gapmer, ISIS XXXX01, wherein the central gap region contains ten 2'-deoxyribonucleosides. These modified oligonucleotides were designed by having the central gap region shortened to nine, eight or seven 2'-deoxynucleosides and by introducing 2'-O-methoxyethyl (MOE) modifications at one or both wing regions. The newly designed oligonucleotides (except for ISIS XXXX09) were evaluated for their effects in reducing Target-Y mRNA levels in vitro.

The gapmers and their motifs are described in Table 52. The internucleoside linkages throughout each gapmer are phosphorothioate linkages (P=S). Nucleosides followed by a subscript "d" indicate 2'-deoxynucleosides. Nucleosides followed by a subscript "e" indicate 2'-O-methoxyethyl (MOE) nucleosides. Nucleosides followed by a subscript "k" indicate constrained ethyl (cEt) nucleosides. "N" indicates modified or naturally occurring nucleobases (A, T, C, G, U, or 5-methyl C).

The newly designed gapmers were tested in vitro. Mouse primary hepatocytes were plated at a density of 20,000 cells per well and transfected using electroporation with 15 μM concentration of antisense oligonucleotide. After a treatment period of approximately 24 hours, RNA was isolated from the cells and Target-Y mRNA levels were measured by quantitative real-time PCR. Mouse Target-Y primer probe set RTS2898 was used to measure mRNA levels. Target-Y mRNA levels were adjusted according to total RNA content, as measured by RIBOGREEN®. The results in Table 53 are presented as Target-Y mRNA expression relative to untreated control cells (% UTC).

The parent gapmer, ISIS XXXX01 was included in the study as a bench mark oligonucleotide against which the activity of the newly designed gapmers targeting Target-Y could be compared.

As illustrated, most of the newly designed gapmers showed similar activity as compared to ISIS 464917.

TABLE 52

Chimeric antisense oligonucleotides targeting Target-Y

| ISIS NO. | Sequence (5' to 3') | Motif | Gap chemistry | Wing chemistry 5' | Wing chemistry 3' | SEQ ID NO |
|---|---|---|---|---|---|---|
| XXXX01 | $N_kN_kN_kN_dN_dN_dN_dN_dN_dN_dN_dN_dN_dN_kN_kN_k$ | 3-10-3 | Full deoxy | kkk | kkk | 19 |
| XXXX02 | $N_kN_kN_kN_dN_dN_dN_dN_dN_dN_dN_dN_dN_dN_eN_eN_e$ | 3-10-3 | Full deoxy | kkk | eee | 19 |
| XXXX03 | $N_eN_kN_kN_dN_dN_dN_dN_dN_dN_dN_dN_dN_dN_kN_kN_e$ | 3-10-3 | Full deoxy | ekk | kke | 19 |
| XXXX04 | $N_eN_eN_kN_kN_dN_dN_dN_dN_dN_dN_dN_dN_dN_kN_kN_e$ | 4-9-3 | Full deoxy | eekk | kke | 19 |
| XXXX05 | $N_eN_eN_eN_kN_kN_dN_dN_dN_dN_dN_dN_dN_dN_kN_kN_e$ | 5-8-3 | Full deoxy | eeekk | kke | 19 |
| XXXX06 | $N_eN_kN_kN_dN_dN_dN_dN_dN_dN_dN_dN_dN_kN_kN_eN_e$ | 3-9-4 | Full deoxy | ekk | kkee | 19 |
| XXXX07 | $N_eN_kN_kN_dN_dN_dN_dN_dN_dN_dN_dN_kN_kN_eN_eN_e$ | 3-8-5 | Full deoxy | ekk | kkeee | 19 |
| XXXX08 | $N_eN_eN_kN_kN_dN_dN_dN_dN_dN_dN_dN_dN_kN_kN_eN_e$ | 4-8-4 | Full deoxy | eekk | kkee | 19 |
| XXXX09 | $N_eN_eN_eN_kN_kN_dN_dN_dN_dN_dN_dN_dN_kN_kN_eN_e$ | 5-7-4 | Full deoxy | eeekk | kkee | 19 |
| XXXX10 | $N_eN_eN_kN_kN_dN_dN_dN_dN_dN_dN_dN_kN_kN_eN_eN_e$ | 4-7-5 | Full deoxy | eekk | kkeee | 19 | e = 2'-MOE, k = cEt, d = 2'-deoxynucleoside

TABLE 53

Inhibition of modified oligonucleotides targeting Target-Y

| ISIS NO. | % UTC 15 μM | Motif | Gap chemistry | Wing chemistry 5' | Wing chemistry 3' |
|---|---|---|---|---|---|
| XXXX01 | 8.5 | 3-10-3 | Full deoxy | kkk | kkk |
| XXXX02 | 9.1 | 3-10-3 | Full deoxy | kkk | eee |
| XXXX03 | 8.3 | 3-10-3 | Full deoxy | ekk | kke |
| XXXX04 | 7.1 | 4-9-3 | Full deoxy | eekk | kke |
| XXXX05 | 8.6 | 5-8-3 | Full deoxy | eeekk | kke |
| XXXX06 | 7.4 | 3-9-4 | Full deoxy | ekk | kkee |
| XXXX07 | 8.5 | 3-8-5 | Full deoxy | ekk | kkeee |
| XXXX08 | 12.5 | 4-8-4 | Full deoxy | eekk | kkee |
| XXXX10 | 11.2 | 4-7-5 | Full deoxy | eekk | kkeee | e = 2'-MOE,
k = cEt,
d = 2'-deoxynucleoside

Example 41: Dose-Dependent Inhibition of Chimeric Antisense Oligonucleotides Targeting Target-Y Additional chimeric antisense oligonucleotides were designed based on the parent gapmer, ISIS XXXX11, wherein the central gap region contains ten 2'-deoxynucleosides. These modified oligonucleotides were designed in a similar manner as the chimeric antisense oligonucleotides described in Example 40 and were evaluated for their effect in reducing Target-Y mRNA levels in vitro.

The gapmers and their motifs are described in Table 54. The internucleoside linkages throughout each gapmer are phosphorothioate linkages (P=S). Nucleosides followed by a subscript "d" indicate 2'-deoxynucleosides. Nucleosides followed by a subscript "e" indicate 2'-O-methoxyethyl (MOE) nucleosides. Nucleosides followed by a subscript "k" indicate constrained ethyl (cEt) nucleosides. "N" indicates modified or naturally occurring nucleobases (A, T, C, G, U, or 5-methyl C).

The newly designed gapmers were tested in vitro. Mouse primary hepatocytes were plated at a density of 20,000 cells per well and transfected using electroporation with 0.6 µM, 3.0 µM and 15 µM concentrations of antisense oligonucleotides. After a treatment period of approximately 24 hours, RNA was isolated from the cells and Target-Y mRNA levels were measured by quantitative real-time PCR. Mouse Target-Y primer probe set RTS2898 was used to measure mRNA levels. Target-Y mRNA levels were adjusted according to total RNA content, as measured by RIBOGREEN®. The results in Table 55 are presented as Target-Y mRNA expression relative to untreated control cells (% UTC).

The parent gapmer, ISIS XXXX11 was included in the study as a bench mark oligonucleotide against which the activity of the newly designed gapmers targeting Target-Y could be compared.

As illustrated in Table 55, several of the newly designed gapmers exhibited similar activity as compared to ISIS XXXX11. The data also confirms that Target-Y mRNA levels were reduced in a dose-dependent manner in antisense oligonucleotide treated cells.

TABLE 54

Chimeric antisense oligonucleotides targeting Target-Y

| ISIS NO. | Sequence (5' to 3') | Motif | Gap chemistry | Wing chemistry 5' | Wing chemistry 3' | SEQ ID NO. |
|---|---|---|---|---|---|---|
| XXXX11 | $N_kN_kN_kN_dN_dN_dN_dN_dN_dN_dN_dN_dN_kN_kN_k$ | 3-10-3 | Full deoxy | kkk | kkk | 19 |
| XXXX12 | $N_kN_kN_kN_dN_dN_dN_dN_dN_dN_dN_dN_dN_eN_eN_e$ | 3-10-3 | Full deoxy | kkk | eee | 19 |
| XXXX13 | $N_eN_kN_kN_dN_dN_dN_dN_dN_dN_dN_dN_dN_kN_kN_e$ | 3-10-3 | Full deoxy | ekk | kke | 19 |
| XXXX14 | $N_eN_eN_kN_kN_dN_dN_dN_dN_dN_dN_dN_dN_dN_kN_kN_e$ | 4-9-3 | Full deoxy | eekk | kke | 19 |
| XXXX15 | $N_eN_eN_eN_kN_kN_dN_dN_dN_dN_dN_dN_dN_dN_dN_kN_kN_e$ | 5-8-3 | Full deoxy | eeekk | kke | 19 |
| XXXX16 | $N_eN_kN_kN_dN_dN_dN_dN_dN_dN_dN_dN_kN_kN_eN_e$ | 3-9-4 | Full deoxy | ekk | kkee | 19 |
| XXXX17 | $N_eN_kN_kN_dN_dN_dN_dN_dN_dN_dN_dN_kN_kN_eN_eN_e$ | 3-8-5 | Full deoxy | ekk | kkeee | 19 |
| XXXX18 | $N_eN_eN_kN_kN_dN_dN_dN_dN_dN_dN_dN_dN_kN_kN_eN_e$ | 4-8-4 | Full deoxy | eekk | kkee | 19 |
| XXXX19 | $N_eN_eN_eN_kN_kN_dN_dN_dN_dN_dN_dN_dN_dN_kN_kN_eN_e$ | 5-7-4 | Full deoxy | eeekk | kkee | 19 |
| XXXX20 | $N_eN_eN_kN_kN_dN_dN_dN_dN_dN_dN_dN_kN_kN_eN_eN_e$ | 4-7-5 | Full deoxy | eekk | kkeee | 19 | e = 2'-MOE, k = cEt, d = 2'-deoxynucleoside

TABLE 55

Dose-dependent inhibition of chimeric antisense oligonucleotides targeting Target-Y

| | % UTC | | | | Gap chemistry | Wing chemistry | |
|---|---|---|---|---|---|---|---|
| ISIS NO. | 0.6 µM | 3.0 µM | 15 µM | Motif | | 5' | 3' |
| XXXX11 | 19.4 | 14.1 | 12.5 | 3-10-3 | Full deoxy | kkk | kkk |
| XXXX12 | 23.4 | 12.5 | 9.9 | 3-10-3 | Full deoxy | kkk | eee |
| XXXX13 | 29.8 | 13.7 | 11.2 | 3-10-3 | Full deoxy | ekk | kke |
| XXXX14 | 28.3 | 15.5 | 11.6 | 4-9-3 | Full deoxy | eekk | kke |
| XXXX15 | 41.3 | 16.7 | 11.6 | 5-8-3 | Full deoxy | eeekk | kke |
| XXXX16 | 31.6 | 16.7 | 11.7 | 3-9-4 | Full deoxy | ekk | kkee |
| XXXX17 | 39.2 | 16.8 | 11.1 | 3-8-5 | Full deoxy | ekk | kkeee |
| XXXX18 | 40.5 | 18.2 | 13.6 | 4-8-4 | Full deoxy | eekk | kkee |
| XXXX19 | 118.4 | 123.8 | 13.3 | 5-7-4 | Full deoxy | eeekk | kkee |
| XXXX20 | 52.3 | 27.6 | 12.4 | 4-7-5 | Full deoxy | eekk | kkeee |

Saline = 100
e = 2'-MOE, k = cEt, d = 2'-deoxynucleoside

Example 42: Dose-Dependent Inhibition of Chimeric Antisense Oligonucleotides Targeting Target-Y Additional chimeric oligonucleotides were designed based on the parent gapmer, ISIS XXXX01, wherein the central gap region contains ten 2'-deoxynucleosides. These modified oligonucleotides were designed by having the central gap region shortened to eight 2'-deoxynucleosides and by introducing one or more 2'-O-methoxyethyl (MOE)

modification(s) at the 3' wing region. The modified oligonucleotides designed by microwalk were evaluated for their effects in reducing Target-Y mRNA levels in vitro.

XXXX01. The data also confirms that Target-Y mRNA levels were reduced in a dose-dependent manner in antisense oligonucleotide treated cells.

TABLE 56

Chimeric antisense oligonucleotides designed by microwalk targeting Target-Y

| ISIS NO. | Sequence (5' to 3') | Motif | Gap chemistry | Wing chemistry 5' | 3' | SEQ ID NO. |
|---|---|---|---|---|---|---|
| XXXX01 | $N_kN_kN_kN_dN_dN_dN_dN_dN_dN_dN_dN_dN_kN_kN_k$ | 3-10-3 | Full deoxy | kkk | kkk | 19 |
| XXXX21 | $N_kN_kN_kN_dN_dN_dN_dN_dN_dN_dN_dN_dN_eN_eN_e$ | 3-10-3 | Full deoxy | kkk | eee | 19 |
| XXXX22 | $N_kN_kN_kN_dN_dN_dN_dN_dN_dN_dN_dN_kN_eN_eN_eN_e$ | 3-8-5 | Full deoxy | kkk | keeee | 19 |
| XXXX23 | $N_kN_kN_kN_dN_dN_dN_dN_dN_dN_dN_dN_kN_eN_eN_eN_e$ | 3-8-5 | Full deoxy | kkk | keeee | 19 |
| XXXX24 | $N_kN_kN_kN_dN_dN_dN_dN_dN_dN_dN_dN_kN_eN_eN_eN_e$ | 3-8-5 | Full deoxy | kkk | keeee | 19 |
| XXXX25 | $N_kN_kN_kN_dN_dN_dN_dN_dN_dN_dN_dN_kN_eN_eN_eN_e$ | 3-8-5 | Full deoxy | kkk | keeee | 19 |
| XXXX26 | $N_kN_kN_kN_dN_dN_dN_dN_dN_dN_dN_dN_kN_eN_eN_eN_e$ | 3-8-5 | Full deoxy | kkk | keeee | 19 |
| XXXX27 | $N_kN_kN_kN_dN_dN_dN_dN_dN_dN_dN_dN_kN_eN_eN_eN_e$ | 3-8-5 | Full deoxy | kkk | keeee | 19 |
| XXXX28 | $N_kN_kN_kN_dN_dN_dN_dN_dN_dN_dN_dN_kN_eN_eN_eN_e$ | 3-8-5 | Full deoxy | kkk | keeee | 19 |
| XXXX29 | $N_kN_kN_kN_dN_dN_dN_dN_dN_dN_dN_dN_kN_eN_eN_eN_e$ | 3-8-5 | Full deoxy | kkk | keeee | 19 |
| XXXX30 | $N_kN_kN_kN_dN_dN_dN_dN_dN_dN_dN_dN_kN_eN_eN_eN_e$ | 3-8-5 | Full deoxy | kkk | keeee | 19 | e = 2'-MOE, k = cEt, d = 2'-deoxynucleoside

The gapmers and their motifs are described in Table 56. The internucleoside linkages throughout each gapmer are phosphorothioate linkages (P=S). Nucleosides followed by a subscript "d" indicate 2'-deoxynucleoside. Nucleosides followed by a subscript "e" indicate 2'-O-methoxyethyl (MOE) nucleosides. Nucleosides followed by a subscript "k" indicate constrained ethyl (cEt) nucleosides. "N" indicates modified or naturally occurring nucleobases (A, T, C, G, U, or 5-methyl C).

The newly designed gapmers were tested in vitro. Mouse primary hepatocytes were plated at a density of 20,000 cells per well and transfected using electroporation with 0.6 μM, 3.0 μM and 15 μM concentrations of antisense oligonucleotides. After a treatment period of approximately 24 hours, RNA was isolated from the cells and Target-Y mRNA levels were measured by quantitative real-time PCR. Mouse Target-Y primer probe set RTS2898 was used to measure mRNA levels. Target-Y mRNA levels were adjusted according to total RNA content, as measured by RIBOGREEN®. The results in Table 57 are presented as Target-Y mRNA expression relative to untreated control cells (% UTC).

The parent gapmer, ISIS XXXX01 was included in the study as a bench mark oligonucleotide against which the activity of the newly designed gapmers targeting Target-Y could be compared.

As illustrated in Table 57, most of the newly designed gapmers demonstrated improvement in activity at low concentrations (0.6 μM and 3.0 μM) as compared to ISIS

TABLE 57

Dose-dependent inhibition of chimeric antisense oligonucleotides designed by microwalk targeting Target-Y

| | % UTC | | | | | Wing chemistry | |
|---|---|---|---|---|---|---|---|
| ISIS NO. | 0.6 μM | 3.0 μM | 15 μM | Motif | Gap chemistry | 5' | 3' |
| XXXX01 | 83.9 | 94.3 | 8.5 | 3-10-3 | Full deoxy | kkk | kkk |
| XXXX21 | 39.8 | 21.2 | 9.1 | 3-10-3 | Full deoxy | kkk | eee |
| XXXX22 | 52.5 | 35.1 | 13.0 | 3-8-5 | Full deoxy | kkk | keeee |
| XXXX23 | 60.7 | 40.9 | 13.6 | 3-8-5 | Full deoxy | kkk | keeee |
| XXXX24 | 52.3 | 23.8 | 7.3 | 3-8-5 | Full deoxy | kkk | keeee |
| XXXX25 | 58.9 | 32.1 | 9.3 | 3-8-5 | Full deoxy | kkk | keeee |
| XXXX26 | 41.7 | 21.1 | 8.8 | 3-8-5 | Full deoxy | kkk | keeee |
| XXXX27 | 45.6 | 25.2 | 8.5 | 3-8-5 | Full deoxy | kkk | keeee |
| XXXX28 | 39.1 | 20.1 | 9.2 | 3-8-5 | Full deoxy | kkk | keeee |
| XXXX29 | 61.4 | 28.4 | 9.9 | 3-8-5 | Full deoxy | kkk | keeee |
| XXXX30 | 81.3 | 52.2 | 16.2 | 3-8-5 | Full deoxy | kkk | keeee |

Saline = 100
e = 2'-MOE, k = cEt, d = 2'-deoxynucleoside

Example 43: Dose-Dependent Inhibition of Chimeric Antisense Oligonucleotides Targeting Target-Y Additional chimeric oligonucleotides were designed based on the parent gapmer, ISIS XXXX11, wherein the central gap region contains ten 2'-deoxynucleosides. These modified oligonucleotides were designed by in the same manner as the oligonucleotides described in Example 42. The modified oligonucleotides designed by microwalk were evaluated for their effects in reducing Target-Y mRNA levels in vitro.

The gapmers and their motifs are described in Table 58. The internucleoside linkages throughout each gapmer are phosphorothioate linkages (P=S). Nucleosides followed by a subscript "d" indicate 2'-deoxynucleoside. Nucleosides followed by a subscript "e" indicate 2'-O-methoxyethyl (MOE) nucleosides. Nucleosides followed by a subscript "k" indicate constrained ethyl (cEt) nucleosides. "N" indicates modified or naturally occurring nucleobases (A, T, C, G, U, or 5-methyl C).

The newly designed gapmers were tested in vitro. Mouse primary hepatocytes were plated at a density of 20,000 cells per well and transfected using electroporation with 0.6 µM, 3.0 µM and 15 µM concentrations of antisense oligonucleotides. After a treatment period of approximately 24 hours, RNA was isolated from the cells and Target-Y mRNA levels were measured by quantitative real-time PCR. Mouse Target-Y primer probe set RTS2898 was used to measure mRNA levels. Target-Y mRNA levels were adjusted according to total RNA content, as measured by RIBOGREEN®. The results in Table 59 are presented as Target-Y mRNA expression relative to untreated control cells (% UTC).

The parent gapmer, ISIS XXXX11 was included in the study as a bench mark oligonucleotide against which the activity of the newly designed gapmers targeting Target-Y could be compared.

TABLE 59

Dose-dependent inhibition of chimeric antisense oligonucleotides designed by microwalk targeting Target-Y

| ISIS NO. | % UTC 0.6 µM | % UTC 3.0 µM | % UTC 15 µM | Motif | Gap chemistry | Wing chemistry 5' | Wing chemistry 3' |
|---|---|---|---|---|---|---|---|
| XXXX11 | 19.4 | 14.1 | 12.5 | 3-10-3 | Full deoxy | kkk | kkk |
| XXXX31 | 50.5 | 23.0 | 14.2 | 3-8-5 | Full deoxy | kkk | keeee |
| XXXX32 | 50.2 | 19.4 | 8.7 | 3-8-5 | Full deoxy | kkk | keeee |
| XXXX33 | 55.2 | 19.3 | 11.9 | 3-8-5 | Full deoxy | kkk | keeee |
| XXXX34 | 53.3 | 15.3 | 11.9 | 3-8-5 | Full deoxy | kkk | keeee |
| XXXX35 | 35.5 | 18.7 | 11.1 | 3-8-5 | Full deoxy | kkk | keeee |
| XXXX36 | 39.7 | 22.3 | 16.8 | 3-8-5 | Full deoxy | kkk | keeee |
| XXXX37 | 24.1 | 16.7 | 9.5 | 3-8-5 | Full deoxy | kkk | keeee |
| XXXX38 | 26.3 | 13.8 | 10.9 | 3-8-5 | Full deoxy | kkk | keeee |
| XXXX39 | 36.9 | 16.4 | 10.4 | 3-8-5 | Full deoxy | kkk | keeee |

Saline = 100
e = 2'-MOE, k = cEt, d = 2'-deoxynucleoside

Example 44: Dose-Dependent Inhibition of Chimeric Antisense Oligonucleotides Targeting PTEN A series of modified oligonucleotides were designed based on the parent gapmer, ISIS 482050, wherein the central gap region contains ten 2'-deoxynucleosides. These modified oligonucleotides were designed by having the central gap region shortened to nine, eight or seven 2'-deoxynucleosides and by introducing 2'-O-methoxyethyl (MOE) modifications at one or both wing regions. The

TABLE 58

Chimeric antisense oligonucleotides designed by microwalk targeting Target-Y

| ISIS NO. | Sequence (5' to 3') | Motif | Gap chemistry | Wing chemistry 5' | Wing chemistry 3' | SEQ ID NO |
|---|---|---|---|---|---|---|
| XXXX11 | $N_kN_kN_kN_dN_dN_dN_dN_dN_dN_dN_dN_dN_kN_kN_k$ | 3-10-3 | Full deoxy | kkk | kkk | 19 |
| XXXX31 | $N_kN_kN_kN_dN_dN_dN_dN_dN_dN_dN_dN_kN_eN_eN_eN_e$ | 3-8-5 | Full deoxy | kkk | keeee | 19 |
| XXXX32 | $N_kN_kN_kN_dN_dN_dN_dN_dN_dN_dN_dN_kN_eN_eN_eN_e$ | 3-8-5 | Full deoxy | kkk | keeee | 19 |
| XXXX33 | $N_kN_kN_kN_dN_dN_dN_dN_dN_dN_dN_dN_kN_eN_eN_eN_e$ | 3-8-5 | Full deoxy | kkk | keeee | 19 |
| XXXX34 | $N_kN_kN_kN_dN_dN_dN_dN_dN_dN_dN_dN_kN_eN_eN_eN_e$ | 3-8-5 | Full deoxy | kkk | keeee | 19 |
| XXXX35 | $N_kN_kN_kN_dN_dN_dN_dN_dN_dN_dN_dN_kN_eN_eN_eN_e$ | 3-8-5 | Full deoxy | kkk | keeee | 19 |
| XXXX36 | $N_kN_kN_kN_dN_dN_dN_dN_dN_dN_dN_dN_kN_eN_eN_eN_e$ | 3-8-5 | Full deoxy | kkk | keeee | 19 |
| XXXX37 | $N_kN_kN_kN_dN_dN_dN_dN_dN_dN_dN_dN_kN_eN_eN_eN_e$ | 3-8-5 | Full deoxy | kkk | keeee | 19 |
| XXXX38 | $N_kN_kN_kN_dN_dN_dN_dN_dN_dN_dN_dN_kN_eN_eN_eN_e$ | 3-8-5 | Full deoxy | kkk | keeee | 19 |
| XXXX39 | $N_kN_kN_kN_dN_dN_dN_dN_dN_dN_dN_dN_kN_eN_eN_eN_e$ | 3-8-5 | Full deoxy | kkk | keeee | 19 | e = 2'-MOE, k = cEt, d = 2'-deoxynucleoside newly designed oligonucleotides were evaluated for their effects in reducing PTEN mRNA levels in vitro.

The gapmers and their motifs are described in Table 60. The internucleoside linkages throughout each gapmer are phosphorothioate linkages (P=S). Nucleosides followed by a subscript "d" indicate 2'-deoxynucleosides. Nucleosides followed by a subscript "e" indicate 2'-O-methoxyethyl (MOE) nucleosides. Nucleosides followed by a subscript "k" indicate constrained ethyl (cEt) nucleosides. "N" indicates modified or naturally occurring nucleobases (A, T, C, G, U, or 5-methyl C).

The newly designed gapmers were tested in vitro. Mouse primary hepatocytes were plated at a density of 20,000 cells per well and transfected using electroporation with 0.6 µM, 3.0 µM and 15 µM concentrations of antisense oligonucleotides. After a treatment period of approximately 24 hours, RNA was isolated from the cells and PTEN mRNA levels were measured by quantitative real-time PCR. Mouse PTEN primer probe set RTS186 was used to measure mRNA levels. PTEN mRNA levels were adjusted according to total RNA content, as measured by RIBOGREEN®. The results in Table 61 are presented as PTEN mRNA expression relative to untreated control cells (% UTC).

The parent gapmer, ISIS 482050 was included in the study as a bench mark oligonucleotide against which the activity of the newly designed gapmers targeting PTEN could be compared.

TABLE 61

Dose-response effect of chimeric antisense oligonucleotides targeting PTEN

| | % UTC | | | | Wing chemistry | |
| --- | --- | --- | --- | --- | --- | --- |
| | 0.6 | 3.0 | 15 | | | |
| ISIS NO. | µM | µM | µM | Motif | Gap chemistry | 5' | 3' |
| 482050 | 45.4 | 23.8 | 8.4 | 3-10-3 | Full deoxy | kkk | kkk |
| 508033 | 52.2 | 28.8 | 7.6 | 3-10-3 | Full deoxy | kkk | eee |
| 573351 | 66.0 | 24.0 | 12.4 | 3-10-3 | Full deoxy | ekk | kke |
| 573352 | 69.0 | 38.1 | 12.5 | 4-9-3 | Full deoxy | eekk | kke |
| 573353 | 59.8 | 36.5 | 13.8 | 5-8-3 | Full deoxy | eeekk | kke |
| 573355 | 52.1 | 37.4 | 11.4 | 3-9-4 | Full deoxy | ekk | kkee |
| 573356 | 52.9 | 46.4 | 15.4 | 3-8-5 | Full deoxy | ekk | kkeee |
| 573357 | 82.4 | 81.8 | 52.5 | 3-7-6 | Full deoxy | ekk | kkeeee |
| 573358 | 67.4 | 46.7 | 14.5 | 4-8-4 | Full deoxy | eekk | kkee |
| 573359 | 70.5 | 49.8 | 31.6 | 5-7-4 | Full deoxy | eeekk | kkee |
| 573360 | 62.2 | 50.8 | 17.6 | 4-7-5 | Full deoxy | eekk | kkeee |

Saline = 100 e = 2'-MOE, k = cEt, d = 2'-deoxynucleoside

TABLE 60

Chimeric antisense oligonucleotides targeting PTEN

| ISIS NO. | Sequence (5' to 3') | Motif | Gap chemistry | Wing chemistry 5' | 3' | SEQ ID NO |
| --- | --- | --- | --- | --- | --- | --- |
| 482050 | $A_kT_k{}^mC_kA_dT_dG_dG_d{}^mC_dT_dG_d{}^mC_dA_dG_d{}^mC_kT_kT_k$ | 3-10-3 | Full deoxy | kkk | kkk | 23 |
| 508033 | $A_kT_k{}^mC_kA_dT_dG_dG_d{}^mC_dT_dG_d{}^mC_dA_dG_d{}^mC_eT_eT_e$ | 3-10-3 | Full deoxy | kkk | eee | 23 |
| 573351 | $A_eT_k{}^mC_kA_dT_dG_dG_d{}^mC_dT_dG_d{}^mC_dA_dG_d{}^mC_kT_kT_e$ | 3-10-3 | Full deoxy | ekk | kke | 23 |
| 573352 | $A_eT_e{}^mC_kA_kT_dG_dG_d{}^mC_dT_dG_d{}^mC_dA_dG_d{}^mC_kT_kT_e$ | 4-9-3 | Full deoxy | eekk | kke | 23 |
| 573353 | $A_eT_e{}^mC_eA_kT_kG_dG_d{}^mC_dT_dG_d{}^mC_dA_dG_d{}^mC_kT_kT_e$ | 5-8-3 | Full deoxy | eeekk | kke | 23 |
| 573355 | $A_eT_k{}^mC_kA_dT_dG_dG_d{}^mC_dT_dG_d{}^mC_dA_dG_d{}^mC_kT_eT_e$ | 3-9-4 | Full deoxy | ekk | kkee | 23 |
| 573356 | $A_eT_k{}^mC_kA_dT_dG_dG_d{}^mC_dT_dG_d{}^mC_dA_kG_k{}^mC_eT_eT_e$ | 3-8-5 | Full deoxy | ekk | kkeee | 23 |
| 573357 | $A_kT_k{}^mC_kA_dT_dG_dG_d{}^mC_dT_dG_d{}^mC_kA_kG_e{}^mC_eT_eT_e$ | 3-7-6 | Full deoxy | ekk | kkeeee | 23 |
| 573358 | $A_eT_e{}^mC_kA_kT_dG_dG_d{}^mC_dT_dG_d{}^mC_dA_dG_k{}^mC_eT_eT_e$ | 4-8-4 | Full deoxy | eekk | kkee | 23 |
| 573359 | $A_eT_e{}^mC_eA_kT_kG_dG_d{}^mC_dT_dG_d{}^mC_dA_dG_k{}^mC_eT_eT_e$ | 5-7-4 | Full deoxy | eeekk | kkee | 23 |
| 573360 | $A_eT_e{}^mC_kA_kT_dG_dG_d{}^mC_dT_dG_d{}^mC_dA_kG_k{}^mC_eT_eT_e$ | 4-7-5 | Full deoxy | eekk | kkeee | 23 | e = 2'-MOE, k = cEt, d = 2'-deoxynucleoside

Example 45: Dose-Dependent Inhibition of Chimeric Antisense Oligonucleotides Targeting PTEN Additional chimeric oligonucleotides were designed based on the parent gapmer, ISIS 482050, wherein the central gap region contains ten 2'-deoxynucleosides. These modified oligonucleotides were designed by having the central gap region shortened to eight 2'-deoxynucleosides and by introducing one or more 2'-O-methoxyethyl (MOE) modification(s) at the 3' wing region. The modified oligonucleotides designed by microwalk were evaluated for their effects in reducing PTEN mRNA levels in vitro.

The gapmers and their motifs are described in Table 62. The internucleoside linkages throughout each gapmer are phosphorothioate linkages (P=S). Nucleosides followed by a subscript "d" indicate 2'-deoxynucleoside. Nucleosides followed by a subscript "e" indicate 2'-O-methoxyethyl (MOE) nucleosides. Nucleosides followed by a subscript "k" indicate constrained ethyl (cEt) nucleosides. $^m$C indicates a 5-methyl nucleoside.

The newly designed gapmers were tested in vitro. Mouse primary hepatocytes were plated at a density of 20,000 cells per well and transfected using electroporation with 0.6 µM, 3.0 µM and 15 µM concentrations of antisense oligonucleotides. After a treatment period of approximately 24 hours, RNA was isolated from the cells and PTEN mRNA levels were measured by quantitative real-time PCR. Mouse PTEN primer probe set RTS186 was used to measure mRNA levels. PTEN mRNA levels were adjusted according to total RNA content, as measured by RIBOGREEN®. The results in Table 63 are presented as PTEN mRNA expression relative to untreated control cells (% UTC).

The parent gapmer, ISIS 482050 was included in the study as a bench mark oligonucleotide against which the activity of the newly designed gapmers targeting PTEN could be compared.

TABLE 62

Chimeric antisense oligonucleotides designed by microwalk targeting PTEN

| ISIS NO. | Sequence (5' to 3') | Gap Motif | Gap chemistry | Wing chemistry 5' | Wing chemistry 3' | SEQ ID NO. |
|---|---|---|---|---|---|---|
| 482050 | $A_k T_k {}^m C_k A_d T_d G_d G_d {}^m C_d T_d G_d {}^m C_d A_d G_d {}^m C_k T_k T_k$ | 3-10-3 | Full deoxy | kkk | kkk | 24 |
| 573797 | $T_k G_k G_k {}^m C_d T_d G_d {}^m C_d A_d G_d {}^m C_d T_d T_e {}^m C_e {}^m C_e G_e A_e$ | 3-8-5 | Full deoxy | kkk | keeee | 25 |
| 573798 | $A_k T_k G_k G_d {}^m C_d T_d G_d {}^m C_d A_d G_d {}^m C_d T_k T_e {}^m C_e {}^m C_e G_e$ | 3-8-5 | Full deoxy | kkk | keeee | 26 |
| 573799 | $^m C_k A_k T_k G_d G_d {}^m C_d T_d G_d {}^m C_d A_d G_d {}^m C_k T_e T_e {}^m C_e {}^m C_e$ | 3-8-5 | Full deoxy | kkk | keeee | 27 |
| 573800 | $T_k {}^m C_k A_k T_d G_d G_d {}^m C_d T_d G_d {}^m C_d A_d G_k {}^m C_e T_e T_e {}^m C_e$ | 3-8-5 | Full deoxy | kkk | keeee | 28 |
| 573801 | $A_k T_k {}^m C_k A_d T_d G_d G_d {}^m C_d T_d G_d {}^m C_d A_k G_k {}^m C_e T_e T_e$ | 3-8-5 | Full deoxy | kkk | keeee | 24 |
| 573802 | $^m C_k A_k T_k {}^m C_d A_d T_d G_d G_d {}^m C_d T_d G_d {}^m C_k A_e G_e {}^m C_e T_e$ | 3-8-5 | Full deoxy | kkk | keeee | 29 |
| 573803 | $^m C_k {}^m C_k A_k T_d {}^m C_d A_d T_d G_d G_d {}^m C_d T_d G_k {}^m C_e A_e G_e {}^m C_e$ | 3-8-5 | Full deoxy | kkk | keeee | 30 |
| 573804 | $T_k {}^m C_k {}^m C_k A_d T_d {}^m C_d A_d T_d G_d G_d {}^m C_d T_k G_e {}^m C_e A_e G_e$ | 3-8-5 | Full deoxy | kkk | keeee | 31 |
| 573805 | $T_k T_k {}^m C_k {}^m C_d A_d T_d {}^m C_d A_d T_d G_d G_d {}^m C_k T_e G_e {}^m C_e A_e$ | 3-8-5 | Full deoxy | kkk | keeee | 32 | e = 2'-MOE, k = cEt, d = 2'-deoxynucleoside

TABLE 63

Dose-dependent inhibition of chimeric antisense oligonucleotides designed by microwalk targeting PTEN

| | % UTC | | | | | Wing chemistry | |
|---|---|---|---|---|---|---|---|
| ISIS NO. | 0.6 µM | 3.0 µM | 15 µM | Motif | Gap chemistry | 5' | 3' |
| 482050 | 45.4 | 23.8 | 8.4 | 3-10-3 | Full deuxy | kkk | kkk |
| 573797 | 56.8 | 55.4 | 13.1 | 3-8-5 | Full deoxy | kkk | keeee |
| 573798 | 50.9 | 33.5 | 9.6 | 3-8-5 | Full deoxy | kkk | keeee |
| 573799 | 62.6 | 27.7 | 10.3 | 3-8-5 | Full deoxy | kkk | keeee |
| 573800 | 68.6 | 38.9 | 12.0 | 3-8-5 | Full deoxy | kkk | keeee |
| 573801 | 54.6 | 46.3 | 11.8 | 3-8-5 | Full deoxy | kkk | keeee |
| 573802 | 60.7 | 40.4 | 13.0 | 3-8-5 | Full deoxy | kkk | keeee |
| 573803 | 47.0 | 29.8 | 8.5 | 3-8-5 | Full deoxy | kkk | keeee |
| 573804 | 62.5 | 34.1 | 11.3 | 3-8-5 | Full deoxy | kkk | keeee |
| 573805 | 70.3 | 31.6 | 15.2 | 3-8-5 | Full deoxy | kkk | keeee |

Saline = 100
e = 2'-MOE, k = cEt, d = 2'-deoxynucleoside

Example 46: Antisense Inhibition of Target-Z mRNA in HepG2 Cells

Antisense oligonucleotides were designed targeting a Target-Z nucleic acid and were tested for their effects on Target-Z mRNA in vitro. The antisense oligonucleotides were tested in a series of experiments that had similar culture conditions. The results for each experiment are presented in separate tables shown below. ISIS 146786, 509934, ISIS 509959, and ISIS 510100, were also included in these studies for comparison. Cultured HepG2 cells at a density of 28,000 cells per well were transfected using LipofectAMINE2000® with 70 nM antisense oligonucleotide. After a treatment period of approximately 24 hours, RNA was isolated from the cells and Target-Z mRNA levels were measured by quantitative real-time PCR. Viral primer probe set RTS3370 (forward sequence CTTGGTCATGGGCCATCAG, designated herein as SEQ ID NO: 33; reverse sequence CGGCTAGGAGTTCCGCAGTA, designated herein as SEQ ID NO: 34; probe sequence TGCGTGGAACCTTTTCGGCTCC, designated herein as SEQ ID NO: 35) was used to measure mRNA levels. Levels were also measured using primer probe set RTS3371 (forward sequence CCAAACCTTCGGACGGAAA, designated herein as SEQ ID NO: 36; reverse sequence TGAGGCCCACTCCCATAGG, designated herein as SEQ ID NO: 37; probe sequence CCCATCATCCTGGGCTTTCGGAAAAT, designated herein as SEQ ID NO: 38). Target-Z mRNA levels were adjusted according to total RNA content, as measured by RIBOGREEN®. Results are presented as percent inhibition of Target-Z, relative to untreated control cells.

The newly designed chimeric antisense oligonucleotides and their motifs are described in Tables 64-69. The gapmers are 16 nucleotides in length, wherein the central gap region comprises ten 2'-deoxynucleosides. Nucleosides followed by 'k' indicate constrained ethyl (cEt) nucleosides. Nucleosides followed by "e" indicate 2'-O-methoxyethyl (2'-MOE) nucleosides. The internucleoside linkages throughout each gapmer are phosphorothioate (P=S) linkages. All cytosine residues throughout each oligonucleotide are 5-methylcytosines.

Each gapmer listed in Tables 64-69 is targeted to the viral genomic sequence, designated herein as Target-Z. The activity of the newly designed oligonucleotides was compared with ISIS 146786, ISIS 509934, ISIS 509959, and ISIS 510100.

TABLE 64

Inhibition of viral Target-Z mRNA levels by chimeric antisense oligonucleotides measured with RTS3370

| ISIS No | Motif | % inhibition |
|---|---|---|
| 509934 | eeeee-d(10)-eeeee | 30 |
| 552787 | ekk-d(10)-kke | 57 |
| 552788 | ekk-d(10)-kke | 60 |
| 552789 | ekk-d(10)-kke | 67 |
| 552790 | ekk-d(10)-kke | 67 |
| 552791 | ekk-d(10)-kke | 65 |
| 552792 | ekk-d(10)-kke | 44 |
| 552793 | ekkd(10)kke | 0 |
| 552794 | ekk-d(10)-kke | 54 |
| 552795 | ekk-d(10)-kke | 55 |
| 552796 | ekk-d(10)-kke | 62 |
| 552797 | ekk-d(10)-kke | 59 |
| 552798 | ekk-d(10)-kke | 59 |
| 552799 | ekk-d(10)-kke | 58 |
| 552800 | ekk-d(10)-kke | 62 |
| 552801 | ekk-d(10)-kke | 65 |
| 552802 | ekk-d(10)-kke | 53 |
| 552803 | ekk-d(10)-kke | 67 |
| 552804 | ekk-d(10)-kke | 75 |
| 552805 | ekk-d(10)-kke | 72 |
| 552806 | ekk-d(10)-kke | 64 |

TABLE 64-continued

Inhibition of viral Target-Z mRNA levels by chimeric antisense oligonucleotides measured with RTS3370

| ISIS No | Motif | % inhibition |
|---|---|---|
| 552807 | ekk-d(10)-kke | 68 |
| 552808 | ekk-d(10)-kke | 65 |
| 552809 | ekk-d(10)-kke | 60 |
| 552810 | ekk-d(10)-kke | 59 |
| 552811 | ekk-d(10)-kke | 64 |
| 552812 | ekk-d(10)-kke | 69 |
| 552813 | ekk-d(10)-kke | 64 |
| 552814 | ekk-d(10)-kke | 62 |
| 552815 | ekk-d(10)-kke | 61 |
| 552816 | ekk-d(10)-kke | 63 |
| 552817 | ekk-d(10)-kke | 42 |
| 552818 | ekk-d(10)-kke | 44 |
| 552819 | ekk-d(10)-kke | 56 |
| 552820 | ekk-d(10)-kke | 59 |
| 552821 | ekk-d(10)-kke | 76 |
| 552822 | ekk-d(10)-kke | 77 |
| 552823 | ekk-d(10)-kke | 73 |
| 552824 | ekk-d(10)-kke | 73 |
| 552825 | ekk-d(10)-kke | 51 |
| 552826 | ekk-d(10)-kke | 55 |
| 552827 | ekk-d(10)-kke | 67 |
| 552828 | ekk-d(10)-kke | 78 |
| 552829 | ekk-d(10)-kke | 72 |
| 552830 | ekk-d(10)-kke | 71 |
| 552831 | ekk-d(10)-kke | 69 |
| 552832 | ekk-d(10)-kke | 67 |
| 552833 | ekk-d(10)-kke | 65 |
| 552834 | ekk-d(10)-kke | 78 |
| 552835 | ekk-d(10)-kke | 70 |
| 552836 | ekk-d(10)-kke | 64 |
| 552837 | ekk-d(10)-kke | 65 |
| 552838 | ekk-d(10)-kke | 64 |
| 552839 | ekk-d(10)-kke | 60 |
| 552840 | ekk-d(10)-kke | 35 |
| 552841 | ekk-d(10)-kke | 62 |
| 552842 | ekk-d(10)-kke | 67 |
| 552843 | ekk-d(10)-kke | 77 |
| 552844 | ekk-d(10)-kke | 81 |
| 552845 | ekk-d(10)-kke | 63 |
| 552846 | ekk-d(10)-kke | 79 |
| 552847 | ekk-d(10)-kke | 47 |
| 552848 | ekk-d(10)-kke | 69 |
| 552849 | ekk-d(10)-kke | 59 |
| 552850 | ekk-d(10)-kke | 83 |
| 552851 | ekk-d(10)-kke | 90 |
| 552852 | ekk-d(10)-kke | 89 |
| 552853 | ekk-d(10)-kke | 83 |
| 552854 | ekk-d(10)-kke | 80 |
| 552855 | ekk-d(10)-kke | 75 |
| 552856 | ekk-d(10)-kke | 69 |
| 552857 | ekk-d(10)-kke | 68 |
| 552858 | ekk-d(10)-kke | 79 |
| 552859 | ekk-d(10)-kke | 79 |
| 552860 | ekk-d(10)-kke | 71 |
| 552861 | ekk-d(10)-kke | 68 |
| 552862 | ekk-d(10)-kke | 65 |
| 552863 | ekk-d(10)-kke | 70 |
| 552864 | ekk-d(10)-kke | 71 | e = 2'-MOE,
k = cEt,
d = 2'-deoxynucleoside

TABLE 65

Inhibition of viral Target-Z mRNA levels by chimeric antisense oligonucleotides measured with RTS3371

| ISIS No | Motif | % inhibition |
|---|---|---|
| 552787 | ekk-d(10)-kke | 53 |
| 552788 | ekk-d(10)-kke | 45 |
| 552789 | ekk-d(10)-kke | 75 |

TABLE 65-continued

Inhibition of viral Target-Z mRNA levels by chimeric antisense oligonucleotides measured with RTS3371

| ISIS No | Motif | % inhibition |
|---|---|---|
| 552790 | ekk-d(10)-kke | 68 |
| 552791 | ekk-d(10)-kke | 51 |
| 552792 | ekk-d(10)-kke | 38 |
| 552793 | ekk-d(10)-kke | 0 |
| 552794 | ekk-d(10)-kke | 44 |
| 552795 | ekk-d(10)-kke | 56 |
| 552796 | ekk-d(10)-kke | 45 |
| 552797 | ekk-d(10)-kke | 46 |
| 552798 | ekk-d(10)-kke | 53 |
| 552799 | elck-d(10)-kke | 48 |
| 552800 | ekk-d(10)-kke | 54 |
| 552801 | ekk-d(10)-kke | 63 |
| 552802 | ekk-d(10)-kke | 49 |
| 552803 | ekk-d(10)-kke | 71 |
| 552804 | ekk-d(10)-kke | 64 |
| 552805 | ekk-d(10)-kke | 70 |
| 552806 | ekk-d(10)-kke | 67 |
| 552807 | ekk-d(10)-kke | 61 |
| 552808 | ekk-d(10)-kke | 83 |
| 552809 | ekk-d(10)-kke | 59 |
| 552810 | ekk-d(10)-kke | 56 |
| 552811 | ekk-d(10)-kke | 62 |
| 552812 | ekk-d(10)-kke | 66 |
| 552813 | ekk-d(10)-kke | 63 |
| 552814 | ekk-d(10)-kke | 65 |
| 552815 | ekk-d(10)-kke | 63 |
| 552816 | ekk-d(10)-kke | 88 |
| 552817 | ekk-d(10)-kke | 94 |
| 552818 | ekk-d(10)-kke | 82 |
| 552819 | ekk-d(10)-kke | 80 |
| 552820 | ekk-d(10)-kke | 84 |
| 552821 | ekk-d(10)-kke | 71 |
| 552822 | ekk-d(10)-kke | 85 |
| 552823 | ekk-d(10)-kke | 71 |
| 552824 | ekk-d(10)-kke | 81 |
| 552825 | ekk-d(10)-kke | 51 |
| 552826 | ekk-d(10)-kke | 64 |
| 552827 | ekk-d(10)-kke | 61 |
| 552828 | eklc-d(10)-kke | 76 |
| 552829 | ekk-d(10)-kke | 61 |
| 552830 | ekk-d(10)-kke | 59 |
| 552831 | ekk-d(10)-kke | 58 |
| 552832 | ekk-d(10)-kke | 64 |
| 552833 | ekk-d(10)-kke | 75 |
| 552834 | ekk-d(10)-kke | 84 |
| 552835 | ekk-d(10)-kke | 57 |
| 552836 | ekk-d(10)-kke | 51 |
| 552837 | ekk-d(10)-kke | 53 |
| 552838 | ekk-d(10)-kke | 48 |
| 552839 | ekk-d(10)-kke | 50 |
| 552840 | ekk-d(10)-kke | 54 |
| 552841 | ekk-d(10)-kke | 61 |
| 552842 | ekk-d(10)-kke | 71 |
| 552843 | ekk-d(10)-kke | 75 |
| 552844 | ekk-d(10)-kke | 78 |
| 552845 | ekk-d(10)-kke | 52 |
| 552846 | ekk-d(10)-kke | 76 |
| 552847 | ekk-d(10)-kke | 61 |
| 552848 | ekk-d(10)-kke | 72 |
| 552849 | ekk-d(10)-kke | 87 |
| 552850 | ekk-d(10)-kke | 76 |
| 552851 | ekk-d(10)-kke | 76 |
| 552852 | ekk-d(10)-kke | 79 |
| 552853 | ekk-d(10)-kke | 82 |
| 552854 | ekk-d(10)-kke | 85 |
| 552855 | ekk-d(10)-kke | 78 |
| 552856 | ekk-d(10)-kke | 77 |
| 552857 | ekk-d(10)-kke | 75 |
| 552858 | ekk-d(10)-kke | 75 |
| 552859 | ekk-d(10)-kke | 79 |
| 552860 | ekk-d(10)-kke | 71 |
| 552861 | ekk-d(10)-kke | 74 |
| 552862 | ekk-d(10)-kke | 66 |
| 552863 | ekk-d(10)-kke | 70 |
| 552864 | ekk-d(10)-kke | 73 | e = 2'-MOE,
k = cEt,
d = 2'-deoxynucleoside

TABLE 66

Inhibition of viral Target-Z mRNA levels by chimeric antisense oligonucleotides measured with RTS3371

| ISIS No | Motif | % inhibition |
|---|---|---|
| 146786 | eeeee-d(10)-eeeee | 60 |
| 552889 | ek-d(10)-keke | 59 |
| 552890 | ek-d(10)-keke | 56 |
| 552891 | ek-d(10)-keke | 67 |
| 552892 | ek-d(10)-keke | 65 |
| 552893 | ek-d(10)-keke | 68 |
| 552894 | ek-d(10)-keke | 71 |
| 552895 | ek-d(10)-keke | 51 |
| 552896 | ek-d(10)-keke | 51 |
| 552897 | ek-d(10)-keke | 43 |
| 552898 | ek-d(10)-keke | 43 |
| 552899 | ek-d(10)-keke | 55 |
| 552900 | ek-d(10)-keke | 34 |
| 552901 | ek-d(10)-keke | 42 |
| 552902 | ek-d(10)-keke | 60 |
| 552903 | ek-d(10)-keke | 76 |
| 552904 | ek-d(10)-keke | 74 |
| 552905 | ek-d(10)-keke | 66 |
| 552907 | ek-d(10)-keke | 69 |
| 552908 | ek-d(10)-keke | 63 |
| 552909 | ek-d(10)-keke | 70 |
| 552910 | ek-d(10)-keke | 72 |
| 552911 | ek-d(10)-keke | 72 |
| 552912 | ek-d(10)-keke | 67 |
| 552913 | ek-d(10)-keke | 74 |
| 552914 | ek-d(10)-keke | 75 |
| 552915 | ek-d(10)-keke | 58 |
| 552916 | ek-d(10)-keke | 74 |
| 552917 | ek-d(10)-keke | 76 |
| 552918 | ek-d(10)-keke | 75 |
| 552919 | ek-d(10)-keke | 55 |
| 552920 | ek-d(10)-keke | 49 |
| 552921 | ek-d(10)-keke | 45 |
| 552922 | ek-d(10)-keke | 83 |
| 552923 | ek-d(10)-keke | 83 |
| 552924 | ek-d(10)-keke | 0 |
| 552925 | ek-d(10)-keke | 85 |
| 552926 | ek-d(10)-keke | 50 |
| 552927 | ek-d(10)-keke | 76 |
| 552928 | ek-d(10)-keke | 78 |
| 552929 | ek-d(10)-keke | 75 |
| 552930 | ek-d(10)-keke | 78 |
| 552931 | ek-d(10)-keke | 74 |
| 552932 | ek-d(10)-keke | 86 |
| 552933 | ek-d(10)-keke | 82 |
| 552934 | ek-d(10)-keke | 74 |
| 552935 | ek-d(10)-keke | 76 |
| 552936 | ek-d(10)-keke | 81 |
| 552937 | ek-d(10)-keke | 80 |
| 552938 | ek-d(10)-keke | 78 |
| 552939 | ek-d(10)-keke | 75 |
| 552940 | ek-d(10)-keke | 63 |
| 552941 | ekk-d(10)-kke | 78 |
| 552942 | ekk-d(10)-kke | 80 |
| 552865 | ekk-d(10)-kke | 67 |
| 552866 | ekk-d(10)-kke | 68 |
| 552868 | ekk-d(10)-kke | 55 |
| 552869 | ekk-d(10)-kke | 48 |

TABLE 66-continued

Inhibition of viral Target-Z mRNA levels by chimeric antisense oligonucleotides measured with RTS3371

| ISIS No | Motif | % inhibition |
|---|---|---|
| 552870 | ekk-d(10)-kke | 55 |
| 552871 | ekk-d(10)-kke | 57 |
| 552872 | ekk-d(10)-kke | 70 |
| 552873 | ekk-d(10)-kke | 49 |
| 552874 | ekk-d(10)-kke | 42 |
| 552875 | ekk-d(10)-kke | 41 |
| 552876 | ekk-d(10)-kke | 50 |
| 552877 | ek-d(10)-keke | 39 |
| 552878 | ekk-d(10)-kke | 31 |
| 552879 | ekk-d(10)-kke | 5 |
| 552880 | ekk-d(10)-kke | 5 |
| 552881 | ekk-d(10)-kke | 10 |
| 552882 | ekk-d(10)-kke | 11 |
| 552883 | ekk-d(10)-kke | 27 |
| 552884 | ekk-d(10)-kke | 36 |
| 552885 | ekk-d(10)-kke | 12 |
| 552886 | ekk-d(10)-kke | 32 |
| 552888 | ekk-d(10)-kke | 1 | e = 2'-MOE,
k = cEt,
d = 2'-deoxynucleoside

TABLE 67

Inhibition of viral Target-Z mRNA levels by chimeric antisense oligonucleotides measured with RTS3371

| ISIS No | Motif | % inhibition |
|---|---|---|
| 146786 | eeeee-d(10)-eeeee | 59 |
| 552955 | eee-d(10)-kkk | 60 |
| 552956 | eee-d(10)-kkk | 60 |
| 552957 | eee-d(10)-kkk | 64 |
| 552958 | eee-d(10)-kkk | 56 |
| 552959 | eee-d(10)-kkk | 59 |
| 552960 | eee-d(10)-kkk | 42 |
| 552961 | eee-d(10)-kkk | 41 |
| 552962 | eee-d(10)-kkk | 35 |
| 552963 | eee-d(10)-kkk | 19 |
| 552964 | eee-d(10)-kkk | 34 |
| 552965 | eee-d(10)-kkk | 42 |
| 552966 | eee-d(10)-kkk | 60 |
| 552967 | eee-d(10)-kkk | 38 |
| 552968 | eee-d(10)-kkk | 35 |
| 552969 | eee-d(10)-kkk | 67 |
| 552970 | eee-d(10)-kkk | 56 |
| 552971 | eee-d(10)-kkk | 69 |
| 552972 | eee-d(10)-kkk | 75 |
| 552973 | eee-d(10)-kkk | 59 |
| 552974 | eee-d(10)-kkk | 71 |
| 552975 | eee-d(10)-kkk | 56 |
| 552976 | eee-d(10)-kkk | 50 |
| 552977 | eee-d(10)-kkk | 56 |
| 552978 | eee-d(10)-kkk | 43 |
| 552979 | eee-d(10)-kkk | 71 |
| 552980 | eee-d(10)-kkk | 80 |
| 552981 | eee-d(10)-kkk | 64 |
| 552982 | ek-d(10)-keke | 61 |
| 552983 | eee-d(10)-kkk | 77 |
| 552984 | eee-d(10)-kkk | 65 |
| 552985 | eee-d(10)-kkk | 41 |
| 552986 | eee-d(10)-kkk | 30 |
| 552987 | eee-d(10)-kkk | 41 |
| 552988 | eee-d(10)-kkk | 74 |
| 552989 | eee-d(10)-kkk | 85 |
| 552990 | eee-d(10)-kkk | 72 |
| 552991 | eee-d(10)-kkk | 73 |
| 552992 | eee-d(10)-kkk | 60 |
| 552993 | eee-d(10)-kkk | 52 |
| 552994 | eee-d(10)-kkk | 58 |
| 552995 | eee-d(10)-kkk | 70 |
| 552996 | eee-d(10)-kkk | 74 |

TABLE 67-continued

Inhibition of viral Target-Z mRNA levels by chimeric antisense oligonucleotides measured with RTS3371

| ISIS No | Motif | % inhibition |
|---|---|---|
| 552997 | eee-d(10)-kkk | 59 |
| 552998 | eee-d(10)-kkk | 82 |
| 552999 | eee-d(10)-kkk | 70 |
| 553000 | eee-d(10)-kkk | 67 |
| 553001 | eee-d(10)-kkk | 67 |
| 553002 | eee-d(10)-kkk | 74 |
| 553003 | eee-d(10)-kkk | 72 |
| 553004 | eee-d(10)-kkk | 73 |
| 553005 | eee-d(10)-kkk | 67 |
| 553006 | eee-d(10)-kkk | 69 |
| 553007 | eee-d(10)-kkk | 60 |
| 553008 | eee-d(10)-kkk | 71 |
| 552943 | ek-d(10)-keke | 77 |
| 553009 | eee-d(10)-kkk | 78 |
| 552944 | ek-d(10)-keke | 74 |
| 553010 | eee-d(10)-kkk | 78 |
| 552945 | ek-d(10)-keke | 76 |
| 553011 | eee-d(10)-kkk | 72 |
| 552946 | ek-d(10)-keke | 71 |
| 553012 | eee-d(10)-kkk | 74 |
| 552947 | ek-d(10)-keke | 54 |
| 553013 | eee-d(10)-kkk | 39 |
| 552948 | ek-d(10)-keke | 50 |
| 553014 | eee-d(10)-kkk | 37 |
| 552949 | ek-d(10)-keke | 8 |
| 553015 | eee-d(10)-kkk | 45 |
| 552950 | ek-d(10)-keke | 44 |
| 553016 | eee-d(10)-kkk | 47 |
| 552951 | ek-d(10)-keke | 60 |
| 553017 | eee-d(10)-kkk | 47 |
| 552952 | ek-d(10)-keke | 35 |
| 553018 | eee-d(10)-kkk | 30 |
| 552953 | ek-d(10)-keke | 37 |
| 553019 | eee-d(10)-kkk | 37 |
| 552954 | ek-d(10)-keke | 40 |
| 553020 | eee-d(10)-kkk | 24 | e = 2'-MOE,
k = cEt,
d = 2'-deoxynucleoside

TABLE 68

Inhibition of viral Target-Z mRNA levels by chimeric antisense oligonucleotides measured with RTS3370

| ISIS No | Motif | % inhibition |
|---|---|---|
| 552889 | ek-d(10)-keke | 42 |
| 552890 | ek-d(10)-keke | 56 |
| 552891 | ek-d(10)-keke | 55 |
| 552892 | ek-d(10)-keke | 53 |
| 552893 | ek-d(10)-keke | 56 |
| 552894 | ek-d(10)-keke | 53 |
| 552895 | ek-d(10)-keke | 38 |
| 552896 | ek-d(10)-keke | 43 |
| 552897 | ek-d(10)-keke | 40 |
| 552898 | ek-d(10)-keke | 50 |
| 552899 | ek-d(10)-keke | 37 |
| 552900 | ek-d(10)-keke | 43 |
| 552901 | ek-d(10)-keke | 56 |
| 552902 | ek-d(10)-keke | 43 |
| 552903 | ek-d(10)-keke | 78 |
| 552904 | ek-d(10)-keke | 75 |
| 552905 | ek-d(10)-keke | 52 |
| 552907 | ek-d(10)-keke | 75 |
| 552908 | ek-d(10)-keke | 57 |
| 552909 | ek-d(10)-keke | 66 |
| 552910 | ek-d(10)-keke | 60 |
| 552911 | ek-d(10)-keke | 65 |
| 552912 | ek-d(10)-keke | 37 |
| 552913 | ek-d(10)-keke | 76 |
| 552914 | ek-d(10)-keke | 79 |

TABLE 68-continued

Inhibition of viral Target-Z mRNA levels by chimeric antisense oligonucleotides measured with RTS3370

| ISIS No | Motif | % inhibition |
|---|---|---|
| 552915 | ek-d(10)-keke | 71 |
| 552916 | ek-d(10)-keke | 82 |
| 552917 | ek-d(10)-keke | 78 |
| 552918 | ek-d(10)-keke | 64 |
| 552919 | ek-d(10)-keke | 38 |
| 552920 | ek-d(10)-keke | 43 |
| 552921 | ek-d(10)-keke | 49 |
| 552922 | ek-d(10)-keke | 90 |
| 552923 | ek-d(10)-keke | 92 |
| 552924 | ek-d(10)-keke | 30 |
| 552925 | ek-d(10)-keke | 81 |
| 552926 | ek-d(10)-keke | 39 |
| 552927 | ek-d(10)-keke | 53 |
| 552928 | ek-d(10)-keke | 48 |
| 552929 | ek-d(10)-keke | 68 |
| 552930 | ek-d(10)-keke | 87 |
| 552931 | ek-d(10)-keke | 87 |
| 552932 | ek-d(10)-keke | 88 |
| 552933 | ek-d(10)-keke | 75 |
| 552934 | ek-d(10)-keke | 76 |
| 552935 | ek-d(10)-keke | 71 |
| 552936 | ek-d(10)-keke | 80 |
| 552937 | ek-d(10)-keke | 81 |
| 552938 | ek-d(10)-keke | 85 |
| 552939 | ek-d(10)-keke | 82 |
| 552940 | ek-d(10)-keke | 76 |
| 552941 | ekk-d(10)-kke | 72 |
| 552942 | ek-d(10)-keke | 85 |
| 552865 | ekk-d(10)-kke | 70 |
| 552866 | ekk-d(10)-kke | 65 |
| 552868 | ekk-d(10)-kke | 36 |
| 552869 | ekk-d(10)-kke | 23 |
| 552870 | ekk-d(10)-kke | 49 |
| 552871 | ekk-d(10)-kke | 46 |
| 552872 | ekk-d(10)-kke | 73 |
| 552873 | ekk-d(10)-kke | 41 |
| 552874 | ekk-d(10)-kke | 18 |
| 552875 | ekk-d(10)-kke | 0 |
| 552876 | ekk-d(10)-kke | 49 |
| 552877 | ek-d(10)-keke | 37 |
| 552878 | ekk-d(10)-kke | 28 |
| 552879 | ekk-d(10)-kke | 0 |
| 552880 | ekk-d(10)-kke | 12 |
| 552881 | ekk-d(10)-kke | 0 |
| 552882 | ekk-d(10)-kke | 0 |
| 552883 | ekk-d(10)-kke | 12 |
| 552884 | ekk-d(10)-kke | 39 |
| 552885 | ekk-d(10)-kke | 37 |
| 552886 | ekk-d(10)-kke | 15 |
| 552888 | ekk-d(10)-kke | 0 | e = 2'-MOE,
k = cEt,
d = 2'-deoxynucleoside

TABLE 69

Inhibition of viral Target-Z mRNA levels by chimeric antisense oligonucleotides measured with RTS3370

| ISIS No | Motif | % inhibition |
|---|---|---|
| 552955 | eee-d(10)-kkk | 67 |
| 552956 | eee-d(10)-kkk | 60 |
| 552957 | eee-d(10)-kkk | 73 |
| 552958 | eee-d(10)-kkk | 63 |
| 552959 | eee-d(10)-kkk | 58 |
| 552960 | eee-d(10)-kkk | 67 |
| 552961 | eee-d(10)-kkk | 78 |
| 552962 | eee-d(10)-kkk | 29 |
| 552963 | eee-d(10)-kkk | 25 |
| 552964 | eee-d(10)-kkk | 33 |
| 552965 | eee-d(10)-kkk | 55 |

TABLE 69-continued

Inhibition of viral Target-Z mRNA levels by chimeric antisense oligonucleotides measured with RTS3370

| ISIS No | Motif | % inhibition |
|---|---|---|
| 552966 | eee-d(10)-kkk | 71 |
| 552967 | eee-d(10)-kkk | 23 |
| 552968 | eee-d(10)-kkk | 41 |
| 552969 | eee-d(10)-kkk | 76 |
| 552970 | eee-d(10)-kkk | 44 |
| 552971 | eee-d(10)-kkk | 77 |
| 552972 | eee-d(10)-kkk | 74 |
| 552973 | eee-d(10)-kkk | 61 |
| 552974 | eee-d(10)-kkk | 73 |
| 552975 | eee-d(10)-kkk | 66 |
| 552976 | eee-d(10)-kkk | 70 |
| 552977 | eee-d(10)-kkk | 65 |
| 552978 | eee-d(10)-kkk | 40 |
| 552979 | eee-d(10)-kkk | 79 |
| 552980 | eee-d(10)-kkk | 81 |
| 552981 | eee-d(10)-kkk | 74 |
| 552982 | ek-d(10)-keke | 52 |
| 552983 | eee-d(10)-kkk | 78 |
| 552984 | eee-d(10)-kkk | 71 |
| 552985 | eee-d(10)-kkk | 38 |
| 552986 | eee-d(10)-kkk | 48 |
| 552987 | eee-d(10)-kkk | 54 |
| 552988 | eee-d(10)-kkk | 85 |
| 552989 | eee-d(10)-kkk | 84 |
| 552990 | eee-d(10)-kkk | 79 |
| 552991 | eee-d(10)-kkk | 53 |
| 552992 | eee-d(10)-kkk | 68 |
| 552993 | eee-d(10)-kkk | 67 |
| 552994 | eee-d(10)-kkk | 69 |
| 552995 | eee-d(10)-kkk | 62 |
| 552996 | eee-d(10)-kkk | 82 |
| 552997 | eee-d(10)-kkk | 58 |
| 552998 | eee-d(10)-kkk | 86 |
| 552999 | eee-d(10)-kkk | 63 |
| 553000 | eee-d(10)-kkk | 67 |
| 553001 | eee-d(10)-kkk | 70 |
| 553002 | eee-d(10)-kkk | 84 |
| 553003 | eee-d(10)-kkk | 83 |
| 553004 | eee-d(10)-kkk | 68 |
| 553005 | eee-d(10)-kkk | 57 |
| 553006 | eee-d(10)-kkk | 74 |
| 553007 | eee-d(10)-kkk | 62 |
| 553008 | eee-d(10)-kkk | 50 |
| 552943 | ek-d(10)-keke | 86 |
| 553009 | eee-d(10)-kkk | 79 |
| 552944 | ek-d(10)-keke | 83 |
| 553010 | eee-d(10)-kkk | 74 |
| 552945 | ek-d(10)-keke | 79 |
| 553011 | eee-d(10)-kkk | 60 |
| 552946 | ek-d(10)-keke | 68 |
| 553012 | eee-d(10)-kkk | 78 |
| 552947 | ek-d(10)-keke | 51 |
| 553013 | eee-d(10)-kkk | 45 |
| 552948 | ek-d(10)-keke | 56 |
| 553014 | eee-d(10)-kkk | 53 |
| 552949 | ek-d(10)-keke | 1 |
| 553015 | eee-d(10)-kkk | 55 |
| 552950 | ek-d(10)-keke | 52 |
| 553016 | eee-d(10)-kkk | 65 |
| 552951 | ek-d(10)-keke | 59 |
| 553017 | eee-d(10)-kkk | 36 |
| 552952 | ek-d(10)-keke | 34 |
| 553018 | eee-d(10)-kkk | 20 |
| 552953 | ek-d(10)-keke | 55 |
| 553019 | eee-d(10)-kkk | 34 |
| 552954 | ek-d(10)-keke | 51 |
| 553020 | eee-d(10)-kkk | 28 | e = 2'-MOE,
k = cEt,
d = 2'-deoxynucleoside

Example 47: Dose-Dependent Antisense Inhibition of Target-Z mRNA in HepG2 Cells Antisense oligonucleotides from the study described in Example 46 exhibiting in vitro inhibition of Target-Z mRNA were selected and tested at various doses in HepG2 cells. Cells were plated at a density of 28,000 cells per well and transfected using LipofectAMINE2000® with 9.26 nM, 27.78 nM, 83.33 nM, and 250.00 nM concentrations of antisense oligonucleotide, as specified in Table 70. After a treatment period of approximately 16 hours, RNA was isolated from the cells and Target-Z mRNA levels were measured by quantitative real-time PCR. Target-Z primer probe set RTS3371 was used to measure mRNA levels. Target-Z mRNA levels were adjusted according to total RNA content, as measured by RIBOGREEN®. Results are presented as percent inhibition of Target-Z, relative to untreated control cells.

As illustrated in Table 70, Target-Z mRNA levels were reduced in a dose-dependent manner in antisense oligonucleotide treated cells.

Example 48: Efficacy of Antisense Oligonucleotides Targeting Target-Z in Transgenic Mice Mice harboring a Target-Z gene fragment (Guidotti, L. G. et al., J. Virol. 1995, 69, 6158-6169) were used. The mice were treated with ISIS antisense oligonucleotides selected from studies described above as illustrated in Table 71 and evaluated for their efficacy in this model.

Treatment

Groups of 10 mice each were injected subcutaneously twice a week for the first with 50 mg/kg and, subsequently, twice a week for the next 3 weeks with 25 mg/kg of ISIS 146786 or ISIS 510100. Control groups of 10 mice each were treated in a similar manner with ISIS 141923 (5-10-5 MOE gapmer with no known murine target) or ISIS 459024 (3-10-4 MOE gapmer with no known murine target). Mice were euthanized 48 hours after the last dose, and organs and serum were harvested for further analysis.

TABLE 70

Dose-dependent antisense inhibition of human Target-Z in HepG2 cells

| ISIS No | Motif | 9.2593 nM | 27.7778 nM | 83.3333 nM | 250.0 nM |
|---|---|---|---|---|---|
| 146786 | eeeee-d(10)-eeeee | 10 | 43 | 74 | 89 |
| 552808 | ekk-d(10)-kke | 13 | 14 | 55 | 70 |
| 552816 | ekk-d(10)-kke | 38 | 73 | 87 | 92 |
| 552818 | ekk-d(10)-kke | 29 | 63 | 87 | 85 |
| 552820 | ekk-d(10)-kke | 58 | 83 | 90 | 90 |
| 552821 | ekk-d(10)-kke | 33 | 49 | 71 | 88 |
| 552822 | ekk-d(10)-kke | 24 | 55 | 74 | 88 |
| 552824 | ekk-d(10)-kke | 8 | 24 | 65 | 87 |
| 552834 | ekk-d(10)-kke | 11 | 28 | 68 | 89 |
| 552849 | ekk-d(10)-kke | 12 | 25 | 73 | 84 |
| 552851 | ekk-d(10)-kke | 13 | 42 | 74 | 89 |
| 552852 | ekk-d(10)-kke | 4 | 35 | 70 | 87 |
| 552853 | ekk-d(10)-kke | 19 | 52 | 86 | 93 |
| 552854 | ekk-d(10)-kke | 28 | 57 | 80 | 89 |
| 552916 | ek-d(10)-keke | 5 | 26 | 64 | 82 |
| 552922 | ek-d(10)-keke | 25 | 44 | 77 | 89 |
| 552923 | ek-d(10)-keke | 22 | 49 | 82 | 91 |
| 552925 | ek-d(10)-keke | 33 | 56 | 80 | 92 |
| 552930 | ek-d(10)-keke | 12 | 49 | 79 | 89 |
| 552931 | ek-d(10)-keke | 12 | 40 | 62 | 82 |
| 552932 | ek-d(10)-keke | 24 | 62 | 84 | 91 |
| 552933 | ek-d(10)-keke | 20 | 40 | 75 | 89 |
| 552936 | ek-d(10)-keke | 18 | 36 | 75 | 88 |
| 552937 | ek-d(10)-keke | 22 | 51 | 82 | 88 |
| 552938 | ek-d(10)-keke | 12 | 36 | 67 | 80 |
| 552939 | ek-d(10)-keke | 17 | 40 | 65 | 79 |
| 552942 | ek-d(10)-keke | 21 | 48 | 74 | 88 |
| 552943 | ek-d(10)-keke | 5 | 39 | 70 | 85 |
| 552944 | ek-d(10)-keke | 14 | 33 | 70 | 77 |
| 552980 | eee-d(10)-kkk | 15 | 40 | 69 | 86 |
| 552988 | eee-d(10)-kkk | 4 | 36 | 58 | 84 |
| 552989 | eee-d(10)-kkk | 0 | 50 | 74 | 81 |
| 552996 | eee-d(10)-kkk | 0 | 25 | 53 | 72 |
| 552998 | eee-d(10)-kkk | 17 | 49 | 79 | 90 |
| 553002 | eee-d(10)-kkk | 0 | 32 | 68 | 86 |
| 553003 | eee-d(10)-kkk | 15 | 42 | 67 | 88 | e = 2'-MOE,
k = cEt,
d = 2'-deoxynucleoside

TABLE 71

Antisense oligonucleotides targeting Target-Z in transgenic mice

| ISIS NO. | Sequence (5' to 3') | Motif | SEQ ID NO. |
|---|---|---|---|
| 146786 | $G_{es}T_{es}G_{es}A_{es}A_{es}G_{ds}C_{ds}G_{ds}A_{ds}A_{ds}G_{ds}T_{ds}G_{ds}C_{ds}A_{ds}C_{es}A_{es}C_{es}G_{es}G_{es}$ | e5-d(10)-e5 | 39 |
| 510100 | $G_{es}G_{es}{}^mC_{es}A_{ds}T_{ds}A_{ds}G_{ds}{}^mC_{ds}A_{ds}G_{ds}{}^mC_{ds}A_{ds}G_{ds}G_{es}A_{es}T_{es}G_e$ | eee-d(10)-eeee | 40 |
| 141923 | ${}^mC_{es}{}^mC_{es}T_{es}T_{es}{}^mC_{es}{}^mC_{ds}{}^mC_{es}{}^mC_{ds}T_{ds}G_{ds}A_{ds}A_{ds}G_{ds}G_{ds}T_{ds}T_{ds}{}^mC_{es}{}^mC_{es}T_{es}{}^mC_{es}{}^mC_e$ | e5-d(10)-e5 | 41 |
| 459024 | ${}^mC_{es}G_{es}G_{es}T_{ds}{}^mC_{ds}{}^mC_{ds}T_{ds}T_{ds}G_{ds}G_{ds}A_{ds}G_{ds}G_{ds}A_{es}T_{es}G_{es}{}^mC_e$ | eee-d(10)-eeee | 42 | e = 2'-MOE (e.g. e5 = eeeee), d = 2'-deoxynucleoside

DNA and RNA Analysis

RNA was extracted from liver tissue for real-time PCR analysis of Target-Z DNA, using primer probe sets RTS3370, RTS3371, or RTS3372 (forward sequence ATCCTATCAACACTTCCGGAAACT, designated SEQ ID NO: 43; reverse sequence CGACGCGGCGATTGAG, designated SEQ ID NO: 44; probe sequence AAGAACTCCCTCGCCTCGCAGACG, designated SEQ ID NO: 45). The DNA levels were normalized to picogreen. Target-Z RNA samples were also assayed with primer probe sets RTS3370 and RTS3371 after RT-PCR analysis. The mRNA levels were normalized to RIBOGREEN®. The data is presented in Table 72. Serum DNA samples were analyzed after the study period. The data is presented in Table 73, expressed relative to the levels measured in the control group. As shown in Tables 72 and 73, the antisense oligonucleotides achieved reduction of Target-Z DNA and RNA over the PBS control. Treatment with either control oligonucleotide did not cause any changes in RNA or DNA levels, as expected.

Example 49: Efficacy of Antisense Oligonucleotides Targeting Target-Z in Transgenic Mice Transgenic mice were treated with ISIS antisense oligonucleotides selected from studies described above and evaluated for their efficacy in this model.

Treatment

A group of 6 mice was injected subcutaneously twice a week for 4 weeks with 25 mg/kg of ISIS 146786. Groups of 6 mice each were injected subcutaneously twice a week for 4 weeks with 10 mg/kg of ISIS 552803, ISIS 552903, ISIS 552817, ISIS 552822, and ISIS 552907. One group of 10 mice was injected subcutaneously twice a week for 4 weeks with PBS. Mice were euthanized 48 hours after the last dose, and organs and plasma were harvested for further analysis.

DNA and RNA Analysis

RNA was extracted from liver tissue for real-time PCR analysis of Target-Z DNA, using primer probe set RTS3371. The DNA levels were normalized to picogreen. Target-Z RNA samples were also assayed with primer probe set RTS3371 after RT-PCR analysis. The mRNA levels were normalized to RIBOGREEN®. The data is presented in Table 74. Serum DNA samples were analyzed after the study period. The data is presented in Table 75, expressed relative to the levels measured in the control group. As shown in Tables 74 and 75, the antisense oligonucleotides achieved reduction of Target-Z DNA and RNA over the PBS control.

TABLE 72

Percent inhibition of Target-Z RNA and DNA in the liver of transgenic mice

| ISIS No | Motif | % inhibition DNA (RTS3370) | % inhibition DNA (RTS3371) | % inhibition DNA (RTS3372) | % inhibition RNA (RTS3370) | % inhibition RNA (RTS3371) | % inhibition RNA (RTS3372) |
|---|---|---|---|---|---|---|---|
| 146786 | e5-d(10)-e5 | 97 | 97 | 95 | 86 | 85 | 89 |
| 510100 | eee-d(10)-eeee | 95 | 94 | 94 | 56 | 64 | 77 |
| 141923 | e5-d(10)-e5 | 2 | 0 | 13 | 0 | 7 | 31 |
| 459024 | eee-d(10)-eeee | 19 | 0 | 8 | 0 | 0 | 0 | e = 2'-MOE (e.g. e5 = eeeee), d = 2'-deoxynucleoside

TABLE 73

Percent inhibition of Target-Z DNA in the serum of transgenic mice

| ISIS No | Motif | % inhibition (RTS3370) | % inhibition (RTS3371) |
|---|---|---|---|
| 146786 | e5-d(10)-e5 | 98 | 98 |
| 510100 | eee-d(10)-eeee | 99 | 98 |
| 141923 | e5-d(10)-e5 | 0 | 0 |
| 459024 | eee-d(10)-eeee | 0 | 0 | e = 2'-MOE (e.g. e5 = eeeee),
d = 2'-deoxynucleoside

TABLE 74

Percent inhibition of Target-Z RNA and DNA in transgenic mice

| ISIS No | Motif | Dose (mg/kg/wk) | % inhibition of RNA | % inhibition of DNA |
|---|---|---|---|---|
| 146786 | e5-d(10)-e5 | 50 | 81 | 91 |
| 552803 | ekk-d(10)-kke | 20 | 71 | 95 |

TABLE 74-continued

Percent inhibition of Target-Z RNA and DNA in transgenic mice

| ISIS No | Motif | Dose (mg/kg/wk) | % inhibition of RNA | % inhibition of DNA |
|---|---|---|---|---|
| 552817 | ekk-d(10)-kke | 20 | 86 | 51 |
| 552822 | ekk-d(10)-kke | 20 | 90 | 89 |
| 552903 | ek-d(10)-keke | 20 | 56 | 82 |
| 552907 | ek-d(10)-keke | 20 | 41 | 45 | e = 2'-MOE (e.g. e5 = eeeee),
d = 2'-deoxynucleoside

TABLE 75

Serum levels of Target-Z DNA in transgenic mice, relative to control levels

| ISIS No | Motif | Dose (mg/kg/wk) | Post-dose DNA levels |
|---|---|---|---|
| 146786 | e5-d(10)-e5 | 50 | 0.1 |
| 552803 | ekk-d(10)-kke | 20 | 0.2 |
| 552817 | ekk-d(10)-kke | 20 | 1.3 |
| 552822 | ekk-d(10)-kke | 20 | 0.0 |
| 552903 | ek-d(10)-keke | 20 | 2.9 |
| 552907 | ek-d(10)-keke | 20 | 1.0 | e = 2'-MOE (e.g. e5 = eeeee),
d = 2'-deoxynucleoside

Liver Function

To evaluate the effect of ISIS oligonucleotides on hepatic function, plasma concentrations of ALT were measured using an automated clinical chemistry analyzer (Hitachi Olympus AU400e, Melville, N.Y.) (Nyblom, H. et al., Alcohol & Alcoholism 39: 336-339, 2004; Tietz N W (Ed): Clinical Guide to Laboratory Tests, 3rd ed. W. B. Saunders, Philadelphia, Pa., 1995). The results are presented in Table 76 expressed in IU/L. All the ISIS oligonucleotides were considered tolerable in the mice, as demonstrated by their liver transaminase profile.

TABLE 76

ALT levels (IU/L) of transgenic mice

| | Motif | Dose (mg/kg/wk) | ALT |
|---|---|---|---|
| PBS | — | — | 77 |
| ISIS 146786 | e5-d(10)-e5 | 50 | 21 |
| ISIS 552803 | ekk-d(10)-kke | 20 | 74 |
| ISIS 552817 | ekk-d(10)-kke | 20 | 38 |
| ISIS 552822 | ekk-d(10)-kke | 20 | 47 |
| ISIS 552903 | ek-d(10)-keke | 20 | 57 |
| ISIS 552907 | ek-d(10)-keke | 20 | 28 | e = 2'-MOE (e.g. e5 = eeeee),
d = 2'-deoxynucleoside

Example 50: Efficacy of Antisense Oligonucleotides Targeting Target-Z in Transgenic Mice Transgenic mice were treated with ISIS antisense oligonucleotides selected from studies described above and evaluated for their efficacy in this model.

Treatment

A group of 6 mice was injected subcutaneously twice a week for 4 weeks with 25 mg/kg of ISIS 146786. Groups of 6 mice each were injected subcutaneously twice a week for 4 weeks with 10 mg/kg of ISIS 552853, ISIS 552854, ISIS 552932, and ISIS 552938. One group of 10 mice was injected subcutaneously twice a week for 4 weeks with PBS. Mice were euthanized 48 hours after the last dose, and organs and plasma were harvested for further analysis.

DNA and RNA Analysis

RNA was extracted from liver tissue for real-time PCR analysis of Target-Z DNA, using primer probe set RTS3371. The DNA levels were normalized to picogreen. Target-Z RNA samples were also assayed with primer probe set RTS3371 after RT-PCR analysis. The mRNA levels were normalized to RIBOGREEN®. As shown in Table 77, the antisense oligonucleotides achieved reduction of Target-Z DNA and RNA over the PBS control. Results are presented as percent inhibition of Target-Z mRNA or DNA, relative to control.

TABLE 77

Percent inhibition of Target-Z DNA and RNA in transgenic mice

| | Motif | Dose (mg/kg/wk) | % inhibition (DNA) | % inhibition (RNA) |
|---|---|---|---|---|
| PBS | — | — | | |
| ISIS 146786 | e5-d(10)-e5 | 50 | 90 | 60 |
| ISIS 552853 | ekk-d(10)-kke | 20 | 94 | 60 |
| ISIS 552854 | ekk-d(10)-kke | 20 | 61 | 23 |
| ISIS 552932 | ekk-d(10)-kke | 20 | 75 | 70 |
| ISIS 552938 | ek-d(10)-keke | 20 | 67 | 56 |

= 2'-MOE(e.g. e5 = eeeee),
d = 2'-deoxynucleoside

Example 51: Efficacy of Antisense Oligonucleotides Targeting Target-Z in Transgenic Mice Transgenic mice were treated with ISIS antisense oligonucleotides selected from studies described above and evaluated for their efficacy in this model.

Treatment

A group of 6 mice was injected subcutaneously twice a week for 4 weeks with 25 mg/kg of ISIS 146786. Groups of 6 mice each were injected subcutaneously twice a week for 4 weeks with 10 mg/kg of ISIS 552922, ISIS 552923, ISIS 552942, ISIS 552872, ISIS 552925, ISIS 552937, and ISIS 552939. One group of 10 mice was injected subcutaneously twice a week for 4 weeks with PBS. Mice were euthanized 48 hours after the last dose, and organs and plasma were harvested for further analysis.

DNA and RNA Analysis

RNA was extracted from liver tissue for real-time PCR analysis of Target-Z DNA, using primer probe set RTS3371. The DNA levels were normalized to picogreen. Target-Z RNA samples were also assayed with primer probe set RTS3371 after RT-PCR analysis. The mRNA levels were normalized to RIBOGREEN®. As shown in Table 78, the antisense oligonucleotides achieved reduction of Target-Z DNA and RNA over the PBS control. Results are presented as percent inhibition of Target-Z mRNA or DNA, relative to control.

TABLE 78

Percent inhibition of Target-Z DNA and RNA in transgenic mice

| ISIS No | Motif | Dose (mg/kg/wk) | % inhibition (DNA) | % inhibition (RNA) |
|---|---|---|---|---|
| 146786 | e5-d(10)-e5 | 50 | 52 | 57 |
| 552922 | ek-d(10)-keke | 20 | 61 | 50 |

TABLE 78-continued

Percent inhibition of Target-Z DNA and RNA in transgenic mice

| ISIS No | Motif | Dose (mg/kg/wk) | % inhibition (DNA) | % inhibition (RNA) |
|---|---|---|---|---|
| 552923 | ek-d(10)-keke | 20 | 89 | 76 |
| 552942 | ek-d(10)-keke | 20 | 58 | 52 |
| 552872 | ekk-d(10)-kke | 20 | 77 | 46 |
| 552925 | ek-d(10)-keke | 20 | 89 | 65 |
| 552937 | ek-d(10)-keke | 20 | 59 | 35 |
| 552939 | ek-d(10)-keke | 20 | 57 | 19 |

= 2'-MOE (e.g. e5 = eeeee),
d = 2'-deoxynucleoside

Example 52: Antisense Inhibition of Target-Z mRNA in HepG2 Cells

Antisense oligonucleotides were designed targeting a Target-Z nucleic acid and were tested for their effects on Target-Z mRNA in vitro. The antisense oligonucleotides were tested in a series of experiments that had similar culture conditions. The results for each experiment are presented in separate tables. ISIS 146786, 509934, ISIS 509959, and ISIS 510100, from the studies described above, were also included. Cultured HepG2 cells at a density of 28,000 cells per well were transfected using LipofectAMINE2000® with 70 nM antisense oligonucleotide. After a treatment period of approximately 24 hours, RNA was isolated from the cells and Target-Z mRNA levels were measured by quantitative real-time PCR. Primer probe set RTS3370 (forward sequence CTTGGTCATGGGCCATCAG, designated herein as SEQ ID NO: 33; reverse sequence CGGCTAGGAGT-TCCGCAGTA, designated herein as SEQ ID NO: 34; probe sequence TGCGTGGAACCTTTTCGGCTCC, designated herein as SEQ ID NO: 35) was used to measure mRNA levels. Levels were also measured using primer probe set RTS3371 (forward sequence CCAAACCTTCGGACG-GAAA, designated herein as SEQ ID NO: 36; reverse sequence TGAGGCCCACTCCCATAGG, designated herein as SEQ ID NO: 37; probe sequence CCCATCATC-CTGGGCTTTCGGAAAAT, designated herein as SEQ ID NO: 38). Target-Z mRNA levels were adjusted according to total RNA content, as measured by RIBOGREEN®. Results are presented as percent inhibition of Target-Z, relative to untreated control cells.

The newly designed chimeric antisense oligonucleotides and their motifs are described in Tables 79-96. The modified oligonucleotides are 16, 17 or 20 nucleotides in length, wherein the central gap segment comprises of nine or ten 2'-deoxynucleosides and is flanked by wing segments on the 5' direction and the 3' direction comprising 2'-O-methoxyethyl (2'-MOE) modifications. The internucleoside linkages throughout each gapmer are phosphorothioate (P=S) linkages. All cytosine residues throughout each oligonucleotide are 5-methylcytosines.

Each gapmer listed in the Tables is targeted to the viral genomic sequence, designated herein as Target-Z. The activity of the newly designed oligonucleotides was compared with ISIS 146786, 509934, ISIS 509959, and ISIS 510100, the information of which have been placed at the top of each table.

TABLE 79

Inhibition of viral Target-Z mRNA levels by chimeric antisense oligonucleotides measured with RTS3370

| ISIS No | Motif | Wing chemistry | % inhibition |
|---|---|---|---|
| 146786 | 5-10-5 | 2'-MOE | 50 |
| 510100 | 3-10-4 | 2'-MOE | 62 |
| 552276 | 5-9-3 | 2'-MOE | 42 |
| 552277 | 5-9-3 | 2'-MOE | 46 |
| 552278 | 5-9-3 | 2'-MOE | 31 |
| 552279 | 5-9-3 | 2'-MOE | 41 |
| 552280 | 5-9-3 | 2'-MOE | 5 |
| 552281 | 5-9-3 | 2'-MOE | 11 |
| 552282 | 5-9-3 | 2'-MOE | 20 |
| 552283 | 5-9-3 | 2'-MOE | 28 |
| 552230 | 4-9-4 | 2'-MOE | 57 |
| 552284 | 5-9-3 | 2'-MOE | 0 |
| 552231 | 4-9-4 | 2'-MOE | 29 |
| 552285 | 5-9-3 | 2'-MOE | 61 |
| 552232 | 4-9-4 | 2'-MOE | 35 |
| 552286 | 5-9-3 | 2'-MOE | 47 |
| 552233 | 4-9-4 | 2'-MOE | 38 |
| 552287 | 5-9-3 | 2'-MOE | 45 |
| 552234 | 4-9-4 | 2'-MOE | 0 |
| 552288 | 5-9-3 | 2'-MOE | 50 |
| 552235 | 4-9-4 | 2'-MOE | 0 |
| 552289 | 5-9-3 | 2'-MOE | 46 |
| 552236 | 4-9-4 | 2'-MOE | 45 |
| 552290 | 5-9-3 | 2'-MOE | 41 |
| 552237 | 4-9-4 | 2'-MOE | 44 |
| 552291 | 5-9-3 | 2'-MOE | 26 |
| 552239 | 4-9-4 | 2'-MOE | 62 |
| 552293 | 5-9-3 | 2'-MOE | 67 |
| 552240 | 4-9-4 | 2'-MOE | 61 |
| 552294 | 5-9-3 | 2'-MOE | 71 |
| 552241 | 4-9-4 | 2'-MOE | 55 |
| 552295 | 5-9-3 | 2'-MOE | 58 |
| 552242 | 4-9-4 | 2'-MOE | 60 |
| 552296 | 5-9-3 | 2'-MOE | 59 |
| 552243 | 4-9-4 | 2'-MOE | 57 |
| 552297 | 5-9-3 | 2'-MOE | 55 |
| 552244 | 4-9-4 | 2'-MOE | 33 |
| 552298 | 5-9-3 | 2'-MOE | 48 |
| 552245 | 4-9-4 | 2'-MOE | 48 |
| 552299 | 5-9-3 | 2'-MOE | 34 |
| 552246 | 4-9-4 | 2'-MOE | 81 |
| 552300 | 5-9-3 | 2'-MOE | 56 |
| 552247 | 4-9-4 | 2'-MOE | 87 |
| 552301 | 5-9-3 | 2'-MOE | 86 |
| 552248 | 4-9-4 | 2'-MOE | 72 |
| 552302 | 5-9-3 | 2'-MOE | 77 |
| 552249 | 4-9-4 | 2'-MOE | 56 |
| 552303 | 5-9-3 | 2'-MOE | 65 |
| 552250 | 4-9-4 | 2'-MOE | 52 |
| 552304 | 5-9-3 | 2'-MOE | 57 |
| 552251 | 4-9-4 | 2'-MOE | 43 |
| 552305 | 5-9-3 | 2'-MOE | 56 |
| 552252 | 4-9-4 | 2'-MOE | 62 |
| 552306 | 5-9-3 | 2'-MOE | 75 |
| 552253 | 4-9-4 | 2'-MOE | 82 |
| 552307 | 5-9-3 | 2'-MOE | 90 |
| 552254 | 4-9-4 | 2'-MOE | 74 |
| 552255 | 4-9-4 | 2'-MOE | 78 |
| 552256 | 4-9-4 | 2'-MOE | 65 |
| 552257 | 4-9-4 | 2'-MOE | 62 |
| 552258 | 4-9-4 | 2'-MOE | 72 |
| 552259 | 4-9-4 | 2'-MOE | 63 |
| 552260 | 4-9-4 | 2'-MOE | 58 |
| 552261 | 4-9-4 | 2'-MOE | 63 |
| 552262 | 4-9-4 | 2'-MOE | 50 |
| 552263 | 4-9-4 | 2'-MOE | 60 |
| 552264 | 4-9-4 | 2'-MOE | 52 |
| 552265 | 4-9-4 | 2'-MOE | 68 |
| 552266 | 4-9-4 | 2'-MOE | 62 |
| 552267 | 4-9-4 | 2'-MOE | 58 |
| 552268 | 4-9-4 | 2'-MOE | 62 |
| 552269 | 4-9-4 | 2'-MOE | 52 |
| 552270 | 4-9-4 | 2'-MOE | 54 |
| 552271 | 4-9-4 | 2'-MOE | 58 |

TABLE 79-continued

Inhibition of viral Target-Z mRNA levels by chimeric antisense oligonucleotides measured with RTS3370

| ISIS No | Motif | Wing chemistry | % inhibition |
|---|---|---|---|
| 552272 | 4-9-4 | 2'-MOE | 40 |
| 552273 | 4-9-4 | 2'-MOE | 34 |
| 552274 | 4-9-4 | 2'-MOE | 34 |
| 552275 | 4-9-4 | 2'-MOE | 39 |

TABLE 80

Inhibition of viral Target-Z mRNA levels by chimeric antisense oligonucleotides measured with RTS3370

| ISIS No | Motif | Wing chemistry | % inhibition |
|---|---|---|---|
| 146786 | 5-10-5 | 2'-MOE | 49 |
| 509959 | 3-10-3 | 2'-MOE | 43 |
| 510100 | 3-10-4 | 2'-MOE | 54 |
| 552384 | 2-9-5 | 2'-MOE | 29 |
| 552440 | 3-9-4 | 2'-MOE | 58 |
| 552385 | 2-9-5 | 2'-MOE | 57 |
| 552441 | 3-9-4 | 2'-MOE | 42 |
| 552386 | 2-9-5 | 2'-MOE | 53 |
| 552442 | 3-9-4 | 2'-MOE | 53 |
| 552387 | 2-9-5 | 2'-MOE | 48 |
| 552443 | 3-9-4 | 2'-MOE | 59 |
| 552388 | 2-9-5 | 2'-MOE | 40 |
| 552444 | 3-9-4 | 2'-MOE | 51 |
| 552389 | 2-9-5 | 2'-MOE | 39 |
| 552445 | 3-9-4 | 2'-MOE | 60 |
| 552390 | 2-9-5 | 2'-MOE | 52 |
| 552446 | 3-9-4 | 2'-MOE | 54 |
| 552391 | 2-9-5 | 2'-MOE | 57 |
| 552447 | 3-9-4 | 2'-MOE | 54 |
| 552392 | 2-9-5 | 2'-MOE | 0 |
| 552448 | 3-9-4 | 2'-MOE | 58 |
| 552393 | 2-9-5 | 2'-MOE | 59 |
| 552449 | 3-9-4 | 2'-MOE | 60 |
| 552394 | 2-9-5 | 2'-MOE | 53 |
| 552450 | 3-9-4 | 2'-MOE | 53 |
| 552395 | 2-9-5 | 2'-MOE | 57 |
| 552451 | 3-9-4 | 2'-MOE | 39 |
| 552396 | 2-9-5 | 2'-MOE | 62 |
| 552452 | 3-9-4 | 2'-MOE | 57 |
| 552238 | 4-9-4 | 2'-MOE | 38 |
| 552292 | 5-9-3 | 2'-MOE | 48 |
| 552346 | 6-9-2 | 2'-MOE | 0 |
| 552397 | 2-9-5 | 2'-MOE | 63 |
| 552453 | 3-9-4 | 2'-MOE | 56 |
| 552398 | 2-9-5 | 2'-MOE | 61 |
| 552454 | 3-9-4 | 2'-MOE | 48 |
| 552399 | 2-9-5 | 2'-MOE | 52 |
| 552400 | 2-9-5 | 2'-MOE | 57 |
| 552401 | 2-9-5 | 2'-MOE | 52 |
| 552402 | 2-9-5 | 2'-MOE | 54 |
| 552403 | 2-9-5 | 2'-MOE | 74 |
| 552404 | 2-9-5 | 2'-MOE | 43 |
| 552405 | 2-9-5 | 2'-MOE | 15 |
| 552406 | 2-9-5 | 2'-MOE | 37 |
| 552407 | 2-9-5 | 2'-MOE | 37 |
| 552408 | 2-9-5 | 2'-MOE | 76 |
| 552409 | 2-9-5 | 2'-MOE | 76 |
| 552410 | 2-9-5 | 2'-MOE | 63 |
| 552411 | 2-9-5 | 2'-MOE | 70 |
| 552412 | 2-9-5 | 2'-MOE | 62 |
| 552413 | 2-9-5 | 2'-MOE | 56 |
| 552414 | 2-9-5 | 2'-MOE | 63 |
| 552415 | 2-9-5 | 2'-MOE | 52 |
| 552416 | 2-9-5 | 2'-MOE | 67 |
| 552417 | 2-9-5 | 2'-MOE | 50 |
| 552418 | 2-9-5 | 2'-MOE | 79 |
| 552419 | 2-9-5 | 2'-MOE | 70 |
| 552420 | 2-9-5 | 2'-MOE | 71 |

TABLE 80-continued

Inhibition of viral Target-Z mRNA levels by chimeric antisense oligonucleotides measured with RTS3370

| ISIS No | Motif | Wing chemistry | % inhibition |
|---|---|---|---|
| 552421 | 2-9-5 | 2'-MOE | 69 |
| 552422 | 2-9-5 | 2'-MOE | 68 |
| 552423 | 2-9-5 | 2'-MOE | 65 |
| 552424 | 2-9-5 | 2'-MOE | 70 |
| 552425 | 2-9-5 | 2'-MOE | 51 |
| 552426 | 2-9-5 | 2'-MOE | 40 |
| 552427 | 2-9-5 | 2'-MOE | 35 |
| 552428 | 2-9-5 | 2'-MOE | 58 |
| 552429 | 2-9-5 | 2'-MOE | 46 |
| 552430 | 2-9-5 | 2'-MOE | 53 |
| 552431 | 2-9-5 | 2'-MOE | 51 |
| 552432 | 2-9-5 | 2'-MOE | 57 |
| 552433 | 2-9-5 | 2'-MOE | 54 |
| 552434 | 2-9-5 | 2'-MOE | 44 |
| 552435 | 2-9-5 | 2'-MOE | 46 |
| 552436 | 2-9-5 | 2'-MOE | 36 |
| 552437 | 2-9-5 | 2'-MOE | 27 |
| 552438 | 2-9-5 | 2'-MOE | 27 |
| 552439 | 2-9-5 | 2'-MOE | 13 |

TABLE 81

Inhibition of viral Target-Z mRNA levels by chimeric antisense oligonucleotides measured with RTS3370

| ISIS No | Motif | Wing chemistry | % inhibition |
|---|---|---|---|
| 146786 | 5-10-5 | 2'-MOE | 35 |
| 509959 | 3-10-3 | 2'-MOE | 52 |
| 552496 | 4-9-3 | 2'-MOE | 47 |
| 552497 | 4-9-3 | 2'-MOE | 57 |
| 552498 | 4-9-3 | 2'-MOE | 45 |
| 552499 | 4-9-3 | 2'-MOE | 52 |
| 552500 | 4-9-3 | 2'-MOE | 46 |
| 552501 | 4-9-3 | 2'-MOE | 44 |
| 552502 | 4-9-3 | 2'-MOE | 57 |
| 552503 | 4-9-3 | 2'-MOE | 52 |
| 552504 | 4-9-3 | 2'-MOE | 45 |
| 552505 | 4-9-3 | 2'-MOE | 56 |
| 552506 | 4-9-3 | 2'-MOE | 54 |
| 552507 | 4-9-3 | 2'-MOE | 34 |
| 552508 | 4-9-3 | 2'-MOE | 34 |
| 552509 | 4-9-3 | 2'-MOE | 48 |
| 552510 | 4-9-3 | 2'-MOE | 50 |
| 552455 | 3-9-4 | 2'-MOE | 66 |
| 552511 | 4-9-3 | 2'-MOE | 66 |
| 552456 | 3-9-4 | 2'-MOE | 64 |
| 552512 | 4-9-3 | 2'-MOE | 62 |
| 552457 | 3-9-4 | 2'-MOE | 14 |
| 552513 | 4-9-3 | 2'-MOE | 56 |
| 552458 | 3-9-4 | 2'-MOE | 59 |
| 552514 | 4-9-3 | 2'-MOE | 52 |
| 552459 | 3-9-4 | 2'-MOE | 69 |
| 552515 | 4-9-3 | 2'-MOE | 57 |
| 552460 | 3-9-4 | 2'-MOE | 0 |
| 552516 | 4-9-3 | 2'-MOE | 54 |
| 552461 | 3-9-4 | 2'-MOE | 20 |
| 552517 | 4-9-3 | 2'-MOE | 52 |
| 552462 | 3-9-4 | 2'-MOE | 46 |
| 552518 | 4-9-3 | 2'-MOE | 34 |
| 552463 | 3-9-4 | 2'-MOE | 48 |
| 552519 | 4-9-3 | 2'-MOE | 44 |
| 552464 | 3-9-4 | 2'-MOE | 81 |
| 552520 | 4-9-3 | 2'-MOE | 69 |
| 552465 | 3-9-4 | 2'-MOE | 84 |
| 552521 | 4-9-3 | 2'-MOE | 80 |
| 552466 | 3-9-4 | 2'-MOE | 75 |
| 552522 | 4-9-3 | 2'-MOE | 76 |
| 552467 | 3-9-4 | 2'-MOE | 65 |
| 552523 | 4-9-3 | 2'-MOE | 71 |

TABLE 81-continued

Inhibition of viral Target-Z mRNA levels by chimeric antisense oligonucleotides measured with RTS3370

| ISIS No | Motif | Wing chemistry | % inhibition |
|---|---|---|---|
| 552468 | 3-9-4 | 2'-MOE | 53 |
| 552524 | 4-9-3 | 2'-MOE | 43 |
| 552469 | 3-9-4 | 2'-MOE | 51 |
| 552525 | 4-9-3 | 2'-MOE | 57 |
| 552470 | 3-9-4 | 2'-MOE | 46 |
| 552526 | 4-9-3 | 2'-MOE | 60 |
| 552471 | 3-9-4 | 2'-MOE | 54 |
| 552527 | 4-9-3 | 2'-MOE | 72 |
| 552472 | 3-9-4 | 2'-MOE | 78 |
| 552528 | 4-9-3 | 2'-MOE | 78 |
| 552473 | 3-9-4 | 2'-MOE | 67 |
| 552529 | 4-9-3 | 2'-MOE | 77 |
| 552474 | 3-9-4 | 2'-MOE | 79 |
| 552530 | 4-9-3 | 2'-MOE | 78 |
| 552475 | 3-9-4 | 2'-MOE | 74 |
| 552531 | 4-9-3 | 2'-MOE | 68 |
| 552476 | 3-9-4 | 2'-MOE | 52 |
| 552477 | 3-9-4 | 2'-MOE | 76 |
| 552478 | 3-9-4 | 2'-MOE | 70 |
| 552479 | 3-9-4 | 2'-MOE | 67 |
| 552480 | 3-9-4 | 2'-MOE | 68 |
| 552481 | 3-9-4 | 2'-MOE | 57 |
| 552482 | 3-9-4 | 2'-MOE | 51 |
| 552483 | 3-9-4 | 2'-MOE | 48 |
| 552484 | 3-9-4 | 2'-MOE | 58 |
| 552485 | 3-9-4 | 2'-MOE | 51 |
| 552486 | 3-9-4 | 2'-MOE | 55 |
| 552487 | 3-9-4 | 2'-MOE | 62 |
| 552488 | 3-9-4 | 2'-MOE | 51 |
| 552489 | 3-9-4 | 2'-MOE | 49 |
| 552490 | 3-9-4 | 2'-MOE | 51 |
| 552491 | 3-9-4 | 2'-MOE | 51 |
| 552492 | 3-9-4 | 2'-MOE | 38 |
| 552493 | 3-9-4 | 2'-MOE | 52 |
| 552494 | 3-9-4 | 2'-MOE | 17 |
| 552495 | 3-9-4 | 2'-MOE | 49 |

TABLE 82

Inhibition of viral Target-Z mRNA levels by chimeric antisense oligonucleotides measured with RTS3370

| ISIS No | Motif | Wing chemistry | % inhibition |
|---|---|---|---|
| 146786 | 5-10-5 | 2'-MOE | 47 |
| 509959 | 3-10-3 | 2'-MOE | 38 |
| 552552 | 5-9-2 | 2'-MOE | 33 |
| 552553 | 5-9-2 | 2'-MOE | 46 |
| 552554 | 5-9-2 | 2'-MOE | 54 |
| 552555 | 5-9-2 | 2'-MOE | 50 |
| 552556 | 5-9-2 | 2'-MOE | 46 |
| 552557 | 5-9-2 | 2'-MOE | 57 |
| 552558 | 5-9-2 | 2'-MOE | 55 |
| 552559 | 5-9-2 | 2'-MOE | 66 |
| 552560 | 5-9-2 | 2'-MOE | 44 |
| 552561 | 5-9-2 | 2'-MOE | 48 |
| 552562 | 5-9-2 | 2'-MOE | 52 |
| 552563 | 5-9-2 | 2'-MOE | 45 |
| 552564 | 5-9-2 | 2'-MOE | 41 |
| 552565 | 5-9-2 | 2'-MOE | 54 |
| 552566 | 5-9-2 | 2'-MOE | 56 |
| 552567 | 5-9-2 | 2'-MOE | 71 |
| 552568 | 5-9-2 | 2'-MOE | 64 |
| 552569 | 5-9-2 | 2'-MOE | 59 |
| 552570 | 5-9-2 | 2'-MOE | 60 |
| 552571 | 5-9-2 | 2'-MOE | 55 |
| 552572 | 5-9-2 | 2'-MOE | 60 |
| 552573 | 5-9-2 | 2'-MOE | 24 |
| 552574 | 5-9-2 | 2'-MOE | 34 |
| 552575 | 5-9-2 | 2'-MOE | 36 |

TABLE 82-continued

Inhibition of viral Target-Z mRNA levels by chimeric antisense oligonucleotides measured with RTS3370

| ISIS No | Motif | Wing chemistry | % inhibition |
|---|---|---|---|
| 552576 | 5-9-2 | 2'-MOE | 67 |
| 552577 | 5-9-2 | 2'-MOE | 64 |
| 552578 | 5-9-2 | 2'-MOE | 75 |
| 552579 | 5-9-2 | 2'-MOE | 75 |
| 552580 | 5-9-2 | 2'-MOE | 59 |
| 552581 | 5-9-2 | 2'-MOE | 54 |
| 552582 | 5-9-2 | 2'-MOE | 61 |
| 552583 | 5-9-2 | 2'-MOE | 69 |
| 552584 | 5-9-2 | 2'-MOE | 74 |
| 552585 | 5-9-2 | 2'-MOE | 62 |
| 552586 | 5-9-2 | 2'-MOE | 79 |
| 552587 | 5-9-2 | 2'-MOE | 71 |
| 552532 | 4-9-3 | 2'-MOE | 48 |
| 552588 | 5-9-2 | 2'-MOE | 70 |
| 552533 | 4-9-3 | 2'-MOE | 43 |
| 552589 | 5-9-2 | 2'-MOE | 59 |
| 552534 | 4-9-3 | 2'-MOE | 62 |
| 552590 | 5-9-2 | 2'-MOE | 70 |
| 552535 | 4-9-3 | 2'-MOE | 55 |
| 552591 | 5-9-2 | 2'-MOE | 51 |
| 552536 | 4-9-3 | 2'-MOE | 3 |
| 552592 | 5-9-2 | 2'-MOE | 50 |
| 552537 | 4-9-3 | 2'-MOE | 14 |
| 552593 | 5-9-2 | 2'-MOE | 46 |
| 552538 | 4-9-3 | 2'-MOE | 52 |
| 552594 | 5-9-2 | 2'-MOE | 55 |
| 552539 | 4-9-3 | 2'-MOE | 47 |
| 552595 | 5-9-2 | 2'-MOE | 60 |
| 552540 | 4-9-3 | 2'-MOE | 60 |
| 552596 | 5-9-2 | 2'-MOE | 63 |
| 552541 | 4-9-3 | 2'-MOE | 60 |
| 552597 | 5-9-2 | 2'-MOE | 61 |
| 552542 | 4-9-3 | 2'-MOE | 64 |
| 552598 | 5-9-2 | 2'-MOE | 57 |
| 552543 | 4-9-3 | 2'-MOE | 46 |
| 552600 | 5-9-2 | 2'-MOE | 59 |
| 552544 | 4-9-3 | 2'-MOE | 53 |
| 552602 | 5-9-2 | 2'-MOE | 6 |
| 552545 | 4-9-3 | 2'-MOE | 33 |
| 552604 | 5-9-2 | 2'-MOE | 47 |
| 552546 | 4-9-3 | 2'-MOE | 42 |
| 552606 | 5-9-2 | 2'-MOE | 53 |
| 552547 | 4-9-3 | 2'-MOE | 51 |
| 552608 | 5-9-2 | 2'-MOE | 53 |
| 552548 | 4-9-3 | 2'-MOE | 52 |
| 552610 | 5-9-2 | 2'-MOE | 47 |
| 552549 | 4-9-3 | 2'-MOE | 38 |
| 552612 | 5-9-2 | 2'-MOE | 39 |
| 552550 | 4-9-3 | 2'-MOE | 19 |
| 552614 | 5-9-2 | 2'-MOE | 24 |
| 552551 | 4-9-3 | 2'-MOE | 24 |
| 552616 | 5-9-2 | 2'-MOE | 15 |

TABLE 83

Inhibition of viral Target-Z mRNA levels by chimeric antisense oligonucleotides measured with RTS3370

| ISIS No | Motif | Wing chemistry | % inhibition |
|---|---|---|---|
| 146786 | 5-10-5 | 2'-MOE | 51 |
| 509934 | 5-10-5 | 2'-MOE | 76 |
| 552007 | 6-10-4 | 2'-MOE | 61 |
| 552039 | 7-10-3 | 2'-MOE | 84 |
| 552008 | 6-10-4 | 2'-MOE | 48 |
| 552040 | 7-10-3 | 2'-MOE | 48 |
| 552009 | 6-10-4 | 2'-MOE | 77 |
| 552041 | 7-10-3 | 2'-MOE | 73 |
| 552010 | 6-10-4 | 2'-MOE | 63 |
| 552042 | 7-10-3 | 2'-MOE | 66 |

TABLE 83-continued

Inhibition of viral Target-Z mRNA levels by chimeric antisense oligonucleotides measured with RTS3370

| ISIS No | Motif | Wing chemistry | % inhibition |
|---|---|---|---|
| 552011 | 6-10-4 | 2'-MOE | 52 |
| 552043 | 7-10-3 | 2'-MOE | 54 |
| 552012 | 6-10-4 | 2'-MOE | 73 |
| 552044 | 7-10-3 | 2'-MOE | 86 |
| 552013 | 6-10-4 | 2'-MOE | 73 |
| 552045 | 7-10-3 | 2'-MOE | 65 |
| 552014 | 6-10-4 | 2'-MOE | 76 |
| 552046 | 7-10-3 | 2'-MOE | 93 |
| 552015 | 6-10-4 | 2'-MOE | 70 |
| 552047 | 7-10-3 | 2'-MOE | 77 |
| 552016 | 6-10-4 | 2'-MOE | 61 |
| 552048 | 7-10-3 | 2'-MOE | 66 |
| 552017 | 6-10-4 | 2'-MOE | 73 |
| 552049 | 7-10-3 | 2'-MOE | 73 |
| 552018 | 6-10-4 | 2'-MOE | 98 |
| 552050 | 7-10-3 | 2'-MOE | 98 |
| 552019 | 6-10-4 | 2'-MOE | 98 |
| 552051 | 7-10-3 | 2'-MOE | 99 |
| 551986 | 4-10-6 | 2'-MOE | 92 |
| 552020 | 6-10-4 | 2'-MOE | 97 |
| 552052 | 7-10-3 | 2'-MOE | 98 |
| 551987 | 4-10-6 | 2'-MOE | 95 |
| 552021 | 6-10-4 | 2'-MOE | 97 |
| 552053 | 7-10-3 | 2'-MOE | 98 |
| 551988 | 4-10-6 | 2'-MOE | 50 |
| 552005 | 5-10-5 | 2'-MOE | 99 |
| 552022 | 6-10-4 | 2'-MOE | 99 |
| 552054 | 7-10-3 | 2'-MOE | 99 |
| 551989 | 4-10-6 | 2'-MOE | 96 |
| 552023 | 6-10-4 | 2'-MOE | 99 |
| 552055 | 7-10-3 | 2'-MOE | 98 |
| 551990 | 4-10-6 | 2'-MOE | 86 |
| 552024 | 6-10-4 | 2'-MOE | 89 |
| 552056 | 7-10-3 | 2'-MOE | 88 |
| 551991 | 4-10-6 | 2'-MOE | 0 |
| 552025 | 6-10-4 | 2'-MOE | 90 |
| 552057 | 7-10-3 | 2'-MOE | 92 |
| 551992 | 4-10-6 | 2'-MOE | 72 |
| 552026 | 6-10-4 | 2'-MOE | 88 |
| 552058 | 7-10-3 | 2'-MOE | 86 |
| 551993 | 4-10-6 | 2'-MOE | 82 |
| 552027 | 6-10-4 | 2'-MOE | 87 |
| 552059 | 7-10-3 | 2'-MOE | 88 |
| 551994 | 4-10-6 | 2'-MOE | 85 |
| 552028 | 6-10-4 | 2'-MOE | 83 |
| 552060 | 7-10-3 | 2'-MOE | 82 |
| 551995 | 4-10-6 | 2'-MOE | 84 |
| 552029 | 6-10-4 | 2'-MOE | 88 |
| 552061 | 7-10-3 | 2'-MOE | 85 |
| 551996 | 4-10-6 | 2'-MOE | 87 |
| 552030 | 6-10-4 | 2'-MOE | 88 |
| 552062 | 7-10-3 | 2'-MOE | 85 |
| 551997 | 4-10-6 | 2'-MOE | 83 |
| 552031 | 6-10-4 | 2'-MOE | 82 |
| 551998 | 4-10-6 | 2'-MOE | 85 |
| 552032 | 6-10-4 | 2'-MOE | 87 |
| 551999 | 4-10-6 | 2'-MOE | 82 |
| 552033 | 6-10-4 | 2'-MOE | 87 |
| 552000 | 4-10-6 | 2'-MOE | 83 |
| 552006 | 5-10-5 | 2'-MOE | 88 |
| 552034 | 6-10-4 | 2'-MOE | 89 |
| 552001 | 4-10-6 | 2'-MOE | 65 |
| 552035 | 6-10-4 | 2'-MOE | 60 |
| 552002 | 4-10-6 | 2'-MOE | 63 |
| 552036 | 6-10-4 | 2'-MOE | 65 |
| 552003 | 4-10-6 | 2'-MOE | 65 |
| 552037 | 6-10-4 | 2'-MOE | 58 |
| 552004 | 4-10-6 | 2'-MOE | 58 |
| 552038 | 6-10-4 | 2'-MOE | 70 |

TABLE 84

Inhibition of viral Target-Z mRNA levels by chimeric antisense oligonucleotides measured with RTS3370

| ISIS No | Motif | Wing chemistry | % inhibition |
|---|---|---|---|
| 146786 | 5-10-5 | 2'-MOE | 64 |
| 510100 | 3-10-4 | 2'-MOE | 62 |
| 552168 | 3-9-5 | 2'-MOE | 79 |
| 552222 | 4-9-4 | 2'-MOE | 79 |
| 552169 | 3-9-5 | 2'-MOE | 67 |
| 552223 | 4-9-4 | 2'-MOE | 40 |
| 552170 | 3-9-5 | 2'-MOE | 69 |
| 552224 | 4-9-4 | 2'-MOE | 64 |
| 552171 | 3-9-5 | 2'-MOE | 65 |
| 552225 | 4-9-4 | 2'-MOE | 69 |
| 552172 | 3-9-5 | 2'-MOE | 33 |
| 552226 | 4-9-4 | 2'-MOE | 48 |
| 552173 | 3-9-5 | 2'-MOE | 41 |
| 552227 | 4-9-4 | 2'-MOE | 32 |
| 552174 | 3-9-5 | 2'-MOE | 31 |
| 552228 | 4-9-4 | 2'-MOE | 42 |
| 552175 | 3-9-5 | 2'-MOE | 59 |
| 552176 | 3-9-5 | 2'-MOE | 68 |
| 552177 | 3-9-5 | 2'-MOE | 55 |
| 552178 | 3-9-5 | 2'-MOE | 66 |
| 552179 | 3-9-5 | 2'-MOE | 70 |
| 552180 | 3-9-5 | 2'-MOE | 66 |
| 552181 | 3-9-5 | 2'-MOE | 51 |
| 552182 | 3-9-5 | 2'-MOE | 69 |
| 552183 | 3-9-5 | 2'-MOE | 69 |
| 552184 | 3-9-5 | 2'-MOE | 43 |
| 552185 | 3-9-5 | 2'-MOE | 66 |
| 552186 | 3-9-5 | 2'-MOE | 54 |
| 552187 | 3-9-5 | 2'-MOE | 74 |
| 552188 | 3-9-5 | 2'-MOE | 78 |
| 552189 | 3-9-5 | 2'-MOE | 57 |
| 552190 | 3-9-5 | 2'-MOE | 39 |
| 552191 | 3-9-5 | 2'-MOE | 60 |
| 552192 | 3-9-5 | 2'-MOE | 85 |
| 552193 | 3-9-5 | 2'-MOE | 86 |
| 552194 | 3-9-5 | 2'-MOE | 68 |
| 552195 | 3-9-5 | 2'-MOE | 73 |
| 552196 | 3-9-5 | 2'-MOE | 60 |
| 552197 | 3-9-5 | 2'-MOE | 60 |
| 552198 | 3-9-5 | 2'-MOE | 61 |
| 552199 | 3-9-5 | 2'-MOE | 89 |
| 552200 | 3-9-5 | 2'-MOE | 85 |
| 552201 | 3-9-5 | 2'-MOE | 81 |
| 552202 | 3-9-5 | 2'-MOE | 76 |
| 552203 | 3-9-5 | 2'-MOE | 74 |
| 552204 | 3-9-5 | 2'-MOE | 71 |
| 552151 | 2-9-6 | 2'-MOE | 77 |
| 552205 | 3-9-5 | 2'-MOE | 78 |
| 552152 | 2-9-6 | 2'-MOE | 72 |
| 552206 | 3-9-5 | 2'-MOE | 77 |
| 552153 | 2-9-6 | 2'-MOE | 67 |
| 552207 | 3-9-5 | 2'-MOE | 81 |
| 552154 | 2-9-6 | 2'-MOE | 56 |
| 552208 | 3-9-5 | 2'-MOE | 70 |
| 552155 | 2-9-6 | 2'-MOE | 61 |
| 552209 | 3-9-5 | 2'-MOE | 63 |
| 552156 | 2-9-6 | 2'-MOE | 20 |
| 552210 | 3-9-5 | 2'-MOE | 75 |
| 552157 | 2-9-6 | 2'-MOE | 39 |
| 552211 | 3-9-5 | 2'-MOE | 75 |
| 552158 | 2-9-6 | 2'-MOE | 70 |
| 552212 | 3-9-5 | 2'-MOE | 67 |
| 552159 | 2-9-6 | 2'-MOE | 74 |
| 552213 | 3-9-5 | 2'-MOE | 70 |
| 552160 | 2-9-6 | 2'-MOE | 78 |
| 552214 | 3-9-5 | 2'-MOE | 79 |
| 552161 | 2-9-6 | 2'-MOE | 56 |
| 552215 | 3-9-5 | 2'-MOE | 61 |
| 552162 | 2-9-6 | 2'-MOE | 64 |
| 552216 | 3-9-5 | 2'-MOE | 62 |
| 552163 | 2-9-6 | 2'-MOE | 71 |
| 552217 | 3-9-5 | 2'-MOE | 58 |
| 552164 | 2-9-6 | 2'-MOE | 52 |
| 552218 | 3-9-5 | 2'-MOE | 56 |

TABLE 84-continued

Inhibition of viral Target-Z mRNA levels by chimeric antisense oligonucleotides measured with RTS3370

| ISIS No | Motif | Wing chemistry | % inhibition |
|---|---|---|---|
| 552165 | 2-9-6 | 2'-MOE | 53 |
| 552219 | 3-9-5 | 2'-MOE | 33 |
| 552166 | 2-9-6 | 2'-MOE | 41 |
| 552220 | 3-9-5 | 2'-MOE | 53 |
| 552167 | 2-9-6 | 2'-MOE | 54 |
| 552221 | 3-9-5 | 2'-MOE | 31 |

TABLE 85

Inhibition of viral Target-Z mRNA levels by chimeric antisense oligonucleotides measured with RTS3370

| ISIS No | Motif | Wing chemistry | % inhibition |
|---|---|---|---|
| 146786 | 5-10-5 | 2'-MOE | 73 |
| 509934 | 5-10-5 | 2'-MOE | 76 |
| 510100 | 3-10-4 | 2'-MOE | 73 |
| 552071 | 8-10-2 | 2'-MOE | 79 |
| 552114 | 2-9-6 | 2'-MOE | 66 |
| 552115 | 2-9-6 | 2'-MOE | 70 |
| 552116 | 2-9-6 | 2'-MOE | 68 |
| 552117 | 2-9-6 | 2'-MOE | 70 |
| 552072 | 8-10-2 | 2'-MOE | 50 |
| 552118 | 2-9-6 | 2'-MOE | 66 |
| 552119 | 2-9-6 | 2'-MOE | 62 |
| 552120 | 2-9-6 | 2'-MOE | 35 |
| 552121 | 2-9-6 | 2'-MOE | 39 |
| 552073 | 8-10-2 | 2'-MOE | 80 |
| 552122 | 2-9-6 | 2'-MOE | 55 |
| 552074 | 8-10-2 | 2'-MOE | 73 |
| 552123 | 2-9-6 | 2'-MOE | 75 |
| 552075 | 8-10-2 | 2'-MOE | 78 |
| 552124 | 2-9-6 | 2'-MOE | 64 |
| 552076 | 8-10-2 | 2'-MOE | 70 |
| 552125 | 2-9-6 | 2'-MOE | 73 |
| 552077 | 8-10-2 | 2'-MOE | 83 |
| 552126 | 2-9-6 | 2'-MOE | 64 |
| 552078 | 8-10-2 | 2'-MOE | 80 |
| 552127 | 2-9-6 | 2'-MOE | 72 |
| 552079 | 8-10-2 | 2'-MOE | 86 |
| 552128 | 2-9-6 | 2'-MOE | 76 |
| 552080 | 8-10-2 | 2'-MOE | 83 |
| 552129 | 2-9-6 | 2'-MOE | 72 |
| 552131 | 2-9-6 | 2'-MOE | 61 |
| 552132 | 2-9-6 | 2'-MOE | 73 |
| 552133 | 2-9-6 | 2'-MOE | 75 |
| 552081 | 8-10-2 | 2'-MOE | 76 |
| 552134 | 2-9-6 | 2'-MOE | 58 |
| 552135 | 2-9-6 | 2'-MOE | 67 |
| 552136 | 2-9-6 | 2'-MOE | 65 |
| 552137 | 2-9-6 | 2'-MOE | 55 |
| 552082 | 8-10-2 | 2'-MOE | 98 |
| 552138 | 2-9-6 | 2'-MOE | 82 |
| 552083 | 8-10-2 | 2'-MOE | 99 |
| 552139 | 2-9-6 | 2'-MOE | 86 |
| 552084 | 8-10-2 | 2'-MOE | 99 |
| 552140 | 2-9-6 | 2'-MOE | 74 |
| 552085 | 8-10-2 | 2'-MOE | 100 |
| 552141 | 2-9-6 | 2'-MOE | 67 |
| 552086 | 8-10-2 | 2'-MOE | 100 |
| 552142 | 2-9-6 | 2'-MOE | 45 |
| 552087 | 8-10-2 | 2'-MOE | 100 |
| 552143 | 2-9-6 | 2'-MOE | 68 |
| 552144 | 2-9-6 | 2'-MOE | 78 |
| 552145 | 2-9-6 | 2'-MOE | 88 |
| 552146 | 2-9-6 | 2'-MOE | 81 |
| 552088 | 8-10-2 | 2'-MOE | 95 |
| 552147 | 2-9-6 | 2'-MOE | 88 |
| 552089 | 8-10-2 | 2'-MOE | 93 |
| 552148 | 2-9-6 | 2'-MOE | 79 |

TABLE 85-continued

Inhibition of viral Target-Z mRNA levels by chimeric antisense oligonucleotides measured with RTS3370

| ISIS No | Motif | Wing chemistry | % inhibition |
|---|---|---|---|
| 552090 | 8-10-2 | 2'-MOE | 87 |
| 552149 | 2-9-6 | 2'-MOE | 81 |
| 552091 | 8-10-2 | 2'-MOE | 88 |
| 552092 | 8-10-2 | 2'-MOE | 90 |
| 552093 | 8-10-2 | 2'-MOE | 91 |
| 552094 | 8-10-2 | 2'-MOE | 88 |
| 552063 | 7-10-3 | 2'-MOE | 81 |
| 552095 | 8-10-2 | 2'-MOE | 89 |
| 552064 | 7-10-3 | 2'-MOE | 85 |
| 552096 | 8-10-2 | 2'-MOE | 92 |
| 552065 | 7-10-3 | 2'-MOE | 86 |
| 552097 | 8-10-2 | 2'-MOE | 93 |
| 552066 | 7-10-3 | 2'-MOE | 33 |
| 552098 | 8-10-2 | 2'-MOE | 88 |
| 552067 | 7-10-3 | 2'-MOE | 50 |
| 552099 | 8-10-2 | 2'-MOE | 70 |
| 552068 | 7-10-3 | 2'-MOE | 73 |
| 552100 | 8-10-2 | 2'-MOE | 70 |
| 552069 | 7-10-3 | 2'-MOE | 73 |
| 552101 | 8-10-2 | 2'-MOE | 76 |
| 552070 | 7-10-3 | 2'-MOE | 71 |
| 552102 | 8-10-2 | 2'-MOE | 64 |

TABLE 86

Inhibition of viral Target-Z mRNA levels by chimeric antisense oligonucleotides measured with RTS3370

| ISIS No | Motif | Wing chemistry | % inhibition |
|---|---|---|---|
| 146786 | 5-10-5 | 2'-MOE | 84 |
| 510100 | 3-10-4 | 2'-MOE | 76 |
| 552330 | 6-9-2 | 2'-MOE | 54 |
| 552331 | 6-9-2 | 2'-MOE | 66 |
| 552332 | 6-9-2 | 2'-MOE | 70 |
| 552333 | 6-9-2 | 2'-MOE | 55 |
| 552334 | 6-9-2 | 2'-MOE | 42 |
| 552335 | 6-9-2 | 2'-MOE | 39 |
| 552336 | 6-9-2 | 2'-MOE | 27 |
| 552337 | 6-9-2 | 2'-MOE | 74 |
| 552338 | 6-9-2 | 2'-MOE | 68 |
| 552339 | 6-9-2 | 2'-MOE | 71 |
| 552340 | 6-9-2 | 2'-MOE | 61 |
| 552341 | 6-9-2 | 2'-MOE | 58 |
| 552342 | 6-9-2 | 2'-MOE | 55 |
| 552343 | 6-9-2 | 2'-MOE | 63 |
| 552344 | 6-9-2 | 2'-MOE | 51 |
| 552345 | 6-9-2 | 2'-MOE | 65 |
| 552346 | 6-9-2 | 2'-MOE | 0 |
| 552347 | 6-9-2 | 2'-MOE | 84 |
| 552348 | 6-9-2 | 2'-MOE | 87 |
| 552349 | 6-9-2 | 2'-MOE | 74 |
| 552350 | 6-9-2 | 2'-MOE | 59 |
| 552351 | 6-9-2 | 2'-MOE | 60 |
| 552352 | 6-9-2 | 2'-MOE | 53 |
| 552353 | 6-9-2 | 2'-MOE | 0 |
| 552354 | 6-9-2 | 2'-MOE | 83 |
| 552355 | 6-9-2 | 2'-MOE | 90 |
| 552356 | 6-9-2 | 2'-MOE | 0 |
| 552357 | 6-9-2 | 2'-MOE | 45 |
| 552358 | 6-9-2 | 2'-MOE | 74 |
| 552359 | 6-9-2 | 2'-MOE | 72 |
| 552360 | 6-9-2 | 2'-MOE | 87 |
| 552361 | 6-9-2 | 2'-MOE | 96 |
| 552308 | 5-9-3 | 2'-MOE | 81 |
| 552362 | 6-9-2 | 2'-MOE | 92 |
| 552309 | 5-9-3 | 2'-MOE | 77 |
| 552363 | 6-9-2 | 2'-MOE | 92 |
| 552310 | 5-9-3 | 2'-MOE | 80 |
| 552364 | 6-9-2 | 2'-MOE | 87 |

TABLE 86-continued

Inhibition of viral Target-Z mRNA levels by chimeric antisense oligonucleotides measured with RTS3370

| ISIS No | Motif | Wing chemistry | % inhibition |
|---|---|---|---|
| 552311 | 5-9-3 | 2'-MOE | 13 |
| 552365 | 6-9-2 | 2'-MOE | 84 |
| 552150 | 2-9-6 | 2'-MOE | 73 |
| 552312 | 5-9-3 | 2'-MOE | 77 |
| 552366 | 6-9-2 | 2'-MOE | 87 |
| 552313 | 5-9-3 | 2'-MOE | 64 |
| 552367 | 6-9-2 | 2'-MOE | 85 |
| 552314 | 5-9-3 | 2'-MOE | 73 |
| 552368 | 6-9-2 | 2'-MOE | 77 |
| 552315 | 5-9-3 | 2'-MOE | 75 |
| 552369 | 6-9-2 | 2'-MOE | 75 |
| 552316 | 5-9-3 | 2'-MOE | 64 |
| 552370 | 6-9-2 | 2'-MOE | 63 |
| 552317 | 5-9-3 | 2'-MOE | 99 |
| 552371 | 6-9-2 | 2'-MOE | 81 |
| 552318 | 5-9-3 | 2'-MOE | 76 |
| 552372 | 6-9-2 | 2'-MOE | 65 |
| 552319 | 5-9-3 | 2'-MOE | 55 |
| 552373 | 6-9-2 | 2'-MOE | 74 |
| 552320 | 5-9-3 | 2'-MOE | 68 |
| 552374 | 6-9-2 | 2'-MOE | 78 |
| 552321 | 5-9-3 | 2'-MOE | 74 |
| 552375 | 6-9-2 | 2'-MOE | 81 |
| 552322 | 5-9-3 | 2'-MOE | 73 |
| 552376 | 6-9-2 | 2'-MOE | 78 |
| 552323 | 5-9-3 | 2'-MOE | 75 |
| 552377 | 6-9-2 | 2'-MOE | 70 |
| 552324 | 5-9-3 | 2'-MOE | 0 |
| 552378 | 6-9-2 | 2'-MOE | 72 |
| 552325 | 5-9-3 | 2'-MOE | 70 |
| 552379 | 6-9-2 | 2'-MOE | 74 |
| 552326 | 5-9-3 | 2'-MOE | 63 |
| 552380 | 6-9-2 | 2'-MOE | 53 |
| 552327 | 5-9-3 | 2'-MOE | 30 |
| 552381 | 6-9-2 | 2'-MOE | 26 |
| 552328 | 5-9-3 | 2'-MOE | 25 |
| 552382 | 6-9-2 | 2'-MOE | 13 |
| 552329 | 5-9-3 | 2'-MOE | 33 |
| 552383 | 6-9-2 | 2'-MOE | 5 |

TABLE 87

Inhibition of viral Target-Z mRNA levels by chimeric antisense oligonucleotides measured with RTS3370

| ISIS No | Motif | Wing chemistry | % inhibition |
|---|---|---|---|
| 509934 | 5-10-5 | 2'-MOE | 30 |
| 551909 | 2-10-8 | 2'-MOE | 62 |
| 551941 | 3-10-7 | 2'-MOE | 74 |
| 551973 | 4-10-6 | 2'-MOE | 64 |
| 551910 | 2-10-8 | 2'-MOE | 52 |
| 551942 | 3-10-7 | 2'-MOE | 54 |
| 551974 | 4-10-6 | 2'-MOE | 51 |
| 551911 | 2-10-8 | 2'-MOE | 58 |
| 551943 | 3-10-7 | 2'-MOE | 64 |
| 551975 | 4-10-6 | 2'-MOE | 57 |
| 551912 | 2-10-8 | 2'-MOE | 59 |
| 551944 | 3-10-7 | 2'-MOE | 66 |
| 551976 | 4-10-6 | 2'-MOE | 57 |
| 551913 | 2-10-8 | 2'-MOE | 58 |
| 551945 | 3-10-7 | 2'-MOE | 56 |
| 551977 | 4-10-6 | 2'-MOE | 56 |
| 551914 | 2-10-8 | 2'-MOE | 0 |
| 551946 | 3-10-7 | 2'-MOE | 48 |
| 551978 | 4-10-6 | 2'-MOE | 53 |
| 551915 | 2-10-8 | 2'-MOE | 44 |
| 551947 | 3-10-7 | 2'-MOE | 53 |
| 551979 | 4-10-6 | 2'-MOE | 64 |
| 551916 | 2-10-8 | 2'-MOE | 57 |
| 551948 | 3-10-7 | 2'-MOE | 68 |
| 551980 | 4-10-6 | 2'-MOE | 56 |
| 551917 | 2-10-8 | 2'-MOE | 58 |
| 551949 | 3-10-7 | 2'-MOE | 64 |
| 551981 | 4-10-6 | 2'-MOE | 63 |
| 551918 | 2-10-8 | 2'-MOE | 59 |
| 551950 | 3-10-7 | 2'-MOE | 71 |
| 551982 | 4-10-6 | 2'-MOE | 63 |
| 551919 | 2-10-8 | 2'-MOE | 76 |
| 551951 | 3-10-7 | 2'-MOE | 71 |
| 551983 | 4-10-6 | 2'-MOE | 73 |
| 551920 | 2-10-8 | 2'-MOE | 68 |
| 551952 | 3-10-7 | 2'-MOE | 76 |
| 551984 | 4-10-6 | 2'-MOE | 81 |
| 551921 | 2-10-8 | 2'-MOE | 83 |
| 551953 | 3-10-7 | 2'-MOE | 82 |
| 551985 | 4-10-6 | 2'-MOE | 76 |
| 551922 | 2-10-8 | 2'-MOE | 73 |
| 551954 | 3-10-7 | 2'-MOE | 68 |
| 551923 | 2-10-8 | 2'-MOE | 59 |
| 551955 | 3-10-7 | 2'-MOE | 71 |
| 551924 | 2-10-8 | 2'-MOE | 80 |
| 551956 | 3-10-7 | 2'-MOE | 80 |
| 551925 | 2-10-8 | 2'-MOE | 82 |
| 551957 | 3-10-7 | 2'-MOE | 88 |
| 551926 | 2-10-8 | 2'-MOE | 71 |
| 551958 | 3-10-7 | 2'-MOE | 74 |
| 551927 | 2-10-8 | 2'-MOE | 68 |
| 551959 | 3-10-7 | 2'-MOE | 69 |
| 551928 | 2-10-8 | 2'-MOE | 69 |
| 551960 | 3-10-7 | 2'-MOE | 62 |
| 551929 | 2-10-8 | 2'-MOE | 54 |
| 551961 | 3-10-7 | 2'-MOE | 20 |
| 551930 | 2-10-8 | 2'-MOE | 53 |
| 551962 | 3-10-7 | 2'-MOE | 60 |
| 551931 | 2-10-8 | 2'-MOE | 47 |
| 551963 | 3-10-7 | 2'-MOE | 63 |
| 551932 | 2-10-8 | 2'-MOE | 68 |
| 551964 | 3-10-7 | 2'-MOE | 56 |
| 551933 | 2-10-8 | 2'-MOE | 72 |
| 551965 | 3-10-7 | 2'-MOE | 67 |
| 551934 | 2-10-8 | 2'-MOE | 64 |
| 551966 | 3-10-7 | 2'-MOE | 73 |
| 551935 | 2-10-8 | 2'-MOE | 68 |
| 551967 | 3-10-7 | 2'-MOE | 60 |
| 551936 | 2-10-8 | 2'-MOE | 67 |
| 551968 | 3-10-7 | 2'-MOE | 63 |
| 551937 | 2-10-8 | 2'-MOE | 47 |
| 551969 | 3-10-7 | 2'-MOE | 36 |
| 551938 | 2-10-8 | 2'-MOE | 41 |
| 551970 | 3-10-7 | 2'-MOE | 43 |
| 551939 | 2-10-8 | 2'-MOE | 53 |
| 551971 | 3-10-7 | 2'-MOE | 55 |
| 551940 | 2-10-8 | 2'-MOE | 50 |
| 551972 | 3-10-7 | 2'-MOE | 58 |

TABLE 88

Inhibition of viral Target-Z mRNA levels by chimeric antisense oligonucleotides measured with RTS3371

| ISIS No | Motif | Wing chemistry | % inhibition |
|---|---|---|---|
| 509934 | 5-10-5 | 2'-MOE | 21 |
| 551909 | 2-10-8 | 2'-MOE | 52 |
| 551941 | 3-10-7 | 2'-MOE | 62 |
| 551973 | 4-10-6 | 2'-MOE | 58 |
| 551910 | 2-10-8 | 2'-MOE | 48 |
| 551942 | 3-10-7 | 2'-MOE | 36 |
| 551974 | 4-10-6 | 2'-MOE | 45 |

TABLE 88-continued

Inhibition of viral Target-Z mRNA levels by chimeric antisense oligonucleotides measured with RTS3371

| ISIS No | Motif | Wing chemistry | % inhibition |
|---------|-------|----------------|--------------|
| 551911 | 2-10-8 | 2'-MOE | 61 |
| 551943 | 3-10-7 | 2'-MOE | 56 |
| 551975 | 4-10-6 | 2'-MOE | 60 |
| 551912 | 2-10-8 | 2'-MOE | 53 |
| 551944 | 3-10-7 | 2'-MOE | 48 |
| 551976 | 4-10-6 | 2'-MOE | 48 |
| 551913 | 2-10-8 | 2'-MOE | 53 |
| 551945 | 3-10-7 | 2'-MOE | 54 |
| 551977 | 4-10-6 | 2'-MOE | 48 |
| 551914 | 2-10-8 | 2'-MOE | 0 |
| 551946 | 3-10-7 | 2'-MOE | 56 |
| 551978 | 4-10-6 | 2'-MOE | 36 |
| 551915 | 2-10-8 | 2'-MOE | 47 |
| 551947 | 3-10-7 | 2'-MOE | 45 |
| 551979 | 4-10-6 | 2'-MOE | 54 |
| 551916 | 2-10-8 | 2'-MOE | 44 |
| 551948 | 3-10-7 | 2'-MOE | 59 |
| 551980 | 4-10-6 | 2'-MOE | 49 |
| 551917 | 2-10-8 | 2'-MOE | 48 |
| 551949 | 3-10-7 | 2'-MOE | 60 |
| 551981 | 4-10-6 | 2'-MOE | 57 |
| 551918 | 2-10-8 | 2'-MOE | 53 |
| 551950 | 3-10-7 | 2'-MOE | 57 |
| 551982 | 4-10-6 | 2'-MOE | 57 |
| 551919 | 2-10-8 | 2'-MOE | 65 |
| 551951 | 3-10-7 | 2'-MOE | 57 |
| 551983 | 4-10-6 | 2'-MOE | 53 |
| 551920 | 2-10-8 | 2'-MOE | 57 |
| 551952 | 3-10-7 | 2'-MOE | 67 |
| 551984 | 4-10-6 | 2'-MOE | 62 |
| 551921 | 2-10-8 | 2'-MOE | 60 |
| 551953 | 3-10-7 | 2'-MOE | 57 |
| 551985 | 4-10-6 | 2'-MOE | 58 |
| 551922 | 2-10-8 | 2'-MOE | 63 |
| 551954 | 3-10-7 | 2'-MOE | 61 |
| 551923 | 2-10-8 | 2'-MOE | 50 |
| 551955 | 3-10-7 | 2'-MOE | 44 |
| 551924 | 2-10-8 | 2'-MOE | 52 |
| 551956 | 3-10-7 | 2'-MOE | 46 |
| 551925 | 2-10-8 | 2'-MOE | 54 |
| 551957 | 3-10-7 | 2'-MOE | 51 |
| 551926 | 2-10-8 | 2'-MOE | 70 |
| 551958 | 3-10-7 | 2'-MOE | 72 |
| 551927 | 2-10-8 | 2'-MOE | 60 |
| 551959 | 3-10-7 | 2'-MOE | 61 |
| 551928 | 2-10-8 | 2'-MOE | 57 |
| 551960 | 3-10-7 | 2'-MOE | 58 |
| 551929 | 2-10-8 | 2'-MOE | 49 |
| 551961 | 3-10-7 | 2'-MOE | 26 |
| 551930 | 2-10-8 | 2'-MOE | 54 |
| 551962 | 3-10-7 | 2'-MOE | 57 |
| 551931 | 2-10-8 | 2'-MOE | 46 |
| 551963 | 3-10-7 | 2'-MOE | 56 |
| 551932 | 2-10-8 | 2'-MOE | 57 |
| 551964 | 3-10-7 | 2'-MOE | 53 |
| 551933 | 2-10-8 | 2'-MOE | 65 |
| 551965 | 3-10-7 | 2'-MOE | 54 |
| 551934 | 2-10-8 | 2'-MOE | 58 |
| 551966 | 3-10-7 | 2'-MOE | 69 |
| 551935 | 2-10-8 | 2'-MOE | 63 |
| 551967 | 3-10-7 | 2'-MOE | 53 |
| 551936 | 2-10-8 | 2'-MOE | 67 |
| 551968 | 3-10-7 | 2'-MOE | 60 |
| 551937 | 2-10-8 | 2'-MOE | 51 |
| 551969 | 3-10-7 | 2'-MOE | 42 |
| 551938 | 2-10-8 | 2'-MOE | 40 |
| 551970 | 3-10-7 | 2'-MOE | 38 |
| 551939 | 2-10-8 | 2'-MOE | 32 |
| 551971 | 3-10-7 | 2'-MOE | 46 |
| 551940 | 2-10-8 | 2'-MOE | 39 |
| 551972 | 3-10-7 | 2'-MOE | 51 |

TABLE 89

Inhibition of viral Target-Z mRNA levels by chimeric antisense oligonucleotides measured with RTS3371

| ISIS No | Motif | Wing chemistry | % inhibition |
|---------|-------|----------------|--------------|
| 146786 | 5-10-5 | 2'-MOE | 40 |
| 510100 | 3-10-4 | 2'-MOE | 60 |
| 552276 | 5-9-3 | 2'-MOE | 44 |
| 552277 | 5-9-3 | 2'-MOE | 39 |
| 552278 | 5-9-3 | 2'-MOE | 37 |
| 552279 | 5-9-3 | 2'-MOE | 50 |
| 552280 | 5-9-3 | 2'-MOE | 2 |
| 552281 | 5-9-3 | 2'-MOE | 0 |
| 552282 | 5-9-3 | 2'-MOE | 13 |
| 552229 | 4-9-4 | 2'-MOE | 17 |
| 552283 | 5-9-3 | 2'-MOE | 27 |
| 552230 | 4-9-4 | 2'-MOE | 53 |
| 552284 | 5-9-3 | 2'-MOE | 0 |
| 552231 | 4-9-4 | 2'-MOE | 31 |
| 552285 | 5-9-3 | 2'-MOE | 56 |
| 552232 | 4-9-4 | 2'-MOE | 35 |
| 552286 | 5-9-3 | 2'-MOE | 43 |
| 552233 | 4-9-4 | 2'-MOE | 40 |
| 552287 | 5-9-3 | 2'-MOE | 44 |
| 552234 | 4-9-4 | 2'-MOE | 0 |
| 552288 | 5-9-3 | 2'-MOE | 44 |
| 552235 | 4-9-4 | 2'-MOE | 13 |
| 552289 | 5-9-3 | 2'-MOE | 21 |
| 552236 | 4-9-4 | 2'-MOE | 40 |
| 552290 | 5-9-3 | 2'-MOE | 34 |
| 552237 | 4-9-4 | 2'-MOE | 37 |
| 552291 | 5-9-3 | 2'-MOE | 34 |
| 552239 | 4-9-4 | 2'-MOE | 58 |
| 552293 | 5-9-3 | 2'-MOE | 61 |
| 552240 | 4-9-4 | 2'-MOE | 54 |
| 552294 | 5-9-3 | 2'-MOE | 62 |
| 552241 | 4-9-4 | 2'-MOE | 47 |
| 552295 | 5-9-3 | 2'-MOE | 63 |
| 552242 | 4-9-4 | 2'-MOE | 61 |
| 552296 | 5-9-3 | 2'-MOE | 61 |
| 552243 | 4-9-4 | 2'-MOE | 55 |
| 552297 | 5-9-3 | 2'-MOE | 52 |
| 552244 | 4-9-4 | 2'-MOE | 45 |
| 552298 | 5-9-3 | 2'-MOE | 27 |
| 552245 | 4-9-4 | 2'-MOE | 41 |
| 552299 | 5-9-3 | 2'-MOE | 32 |
| 552246 | 4-9-4 | 2'-MOE | 67 |
| 552300 | 5-9-3 | 2'-MOE | 57 |
| 552247 | 4-9-4 | 2'-MOE | 74 |
| 552301 | 5-9-3 | 2'-MOE | 76 |
| 552248 | 4-9-4 | 2'-MOE | 65 |
| 552302 | 5-9-3 | 2'-MOE | 68 |
| 552249 | 4-9-4 | 2'-MOE | 38 |
| 552303 | 5-9-3 | 2'-MOE | 59 |
| 552250 | 4-9-4 | 2'-MOE | 43 |
| 552304 | 5-9-3 | 2'-MOE | 30 |
| 552251 | 4-9-4 | 2'-MOE | 52 |
| 552305 | 5-9-3 | 2'-MOE | 49 |
| 552252 | 4-9-4 | 2'-MOE | 51 |
| 552306 | 5-9-3 | 2'-MOE | 56 |
| 552253 | 4-9-4 | 2'-MOE | 47 |
| 552307 | 5-9-3 | 2'-MOE | 49 |
| 552254 | 4-9-4 | 2'-MOE | 50 |
| 552255 | 4-9-4 | 2'-MOE | 64 |
| 552256 | 4-9-4 | 2'-MOE | 57 |
| 552257 | 4-9-4 | 2'-MOE | 51 |
| 552258 | 4-9-4 | 2'-MOE | 62 |
| 552259 | 4-9-4 | 2'-MOE | 59 |
| 552260 | 4-9-4 | 2'-MOE | 56 |
| 552261 | 4-9-4 | 2'-MOE | 54 |
| 552262 | 4-9-4 | 2'-MOE | 47 |
| 552263 | 4-9-4 | 2'-MOE | 45 |
| 552264 | 4-9-4 | 2'-MOE | 52 |
| 552265 | 4-9-4 | 2'-MOE | 58 |
| 552266 | 4-9-4 | 2'-MOE | 54 |
| 552267 | 4-9-4 | 2'-MOE | 43 |
| 552268 | 4-9-4 | 2'-MOE | 57 |
| 552269 | 4-9-4 | 2'-MOE | 34 |
| 552270 | 4-9-4 | 2'-MOE | 37 |

TABLE 89-continued

Inhibition of viral Target-Z mRNA levels by chimeric antisense oligonucleotides measured with RTS3371

| ISIS No | Motif | Wing chemistry | % inhibition |
|---|---|---|---|
| 552271 | 4-9-4 | 2'-MOE | 42 |
| 552272 | 4-9-4 | 2'-MOE | 36 |
| 552273 | 4-9-4 | 2'-MOE | 25 |
| 552274 | 4-9-4 | 2'-MOE | 11 |
| 552275 | 4-9-4 | 2'-MOE | 38 |

TABLE 90

Inhibition of viral Target-Z mRNA levels by chimeric antisense oligonucleotides measured with RTS3371

| ISIS No | Motif | Wing chemistry | % inhibition |
|---|---|---|---|
| 146786 | 5-10-5 | 2'-MOE | 38 |
| 509959 | 3-10-3 | 2'-MOE | 49 |
| 510100 | 3-10-4 | 2'-MOE | 55 |
| 552384 | 2-9-5 | 2'-MOE | 41 |
| 552440 | 3-9-4 | 2'-MOE | 57 |
| 552385 | 2-9-5 | 2'-MOE | 53 |
| 552441 | 3-9-4 | 2'-MOE | 38 |
| 552386 | 2-9-5 | 2'-MOE | 42 |
| 552442 | 3-9-4 | 2'-MOE | 72 |
| 552387 | 2-9-5 | 2'-MOE | 43 |
| 552443 | 3-9-4 | 2'-MOE | 56 |
| 552388 | 2-9-5 | 2'-MOE | 18 |
| 552444 | 3-9-4 | 2'-MOE | 39 |
| 552389 | 2-9-5 | 2'-MOE | 24 |
| 552445 | 3-9-4 | 2'-MOE | 53 |
| 552390 | 2-9-5 | 2'-MOE | 40 |
| 552446 | 3-9-4 | 2'-MOE | 57 |
| 552391 | 2-9-5 | 2'-MOE | 51 |
| 552447 | 3-9-4 | 2'-MOE | 53 |
| 552392 | 2-9-5 | 2'-MOE | 0 |
| 552448 | 3-9-4 | 2'-MOE | 57 |
| 552393 | 2-9-5 | 2'-MOE | 52 |
| 552449 | 3-9-4 | 2'-MOE | 49 |
| 552394 | 2-9-5 | 2'-MOE | 32 |
| 552450 | 3-9-4 | 2'-MOE | 44 |
| 552395 | 2-9-5 | 2'-MOE | 33 |
| 552451 | 3-9-4 | 2'-MOE | 38 |
| 552396 | 2-9-5 | 2'-MOE | 46 |
| 552452 | 3-9-4 | 2'-MOE | 30 |
| 552130 | 2-9-6 | 2'-MOE | 46 |
| 552184 | 3-9-5 | 2'-MOE | 34 |
| 552238 | 4-9-4 | 2'-MOE | 41 |
| 552292 | 5-9-3 | 2'-MOE | 45 |
| 552346 | 6-9-2 | 2'-MOE | 0 |
| 552397 | 2-9-5 | 2'-MOE | 37 |
| 552453 | 3-9-4 | 2'-MOE | 45 |
| 552398 | 2-9-5 | 2'-MOE | 42 |
| 552454 | 3-9-4 | 2'-MOE | 39 |
| 552399 | 2-9-5 | 2'-MOE | 34 |
| 552400 | 2-9-5 | 2'-MOE | 47 |
| 552401 | 2-9-5 | 2'-MOE | 53 |
| 552402 | 2-9-5 | 2'-MOE | 47 |
| 552403 | 2-9-5 | 2'-MOE | 70 |
| 552404 | 2-9-5 | 2'-MOE | 44 |
| 552405 | 2-9-5 | 2'-MOE | 0 |
| 552406 | 2-9-5 | 2'-MOE | 25 |
| 552407 | 2-9-5 | 2'-MOE | 23 |
| 552408 | 2-9-5 | 2'-MOE | 73 |
| 552409 | 2-9-5 | 2'-MOE | 71 |
| 552410 | 2-9-5 | 2'-MOE | 52 |
| 552411 | 2-9-5 | 2'-MOE | 62 |
| 552412 | 2-9-5 | 2'-MOE | 50 |
| 552413 | 2-9-5 | 2'-MOE | 55 |
| 552414 | 2-9-5 | 2'-MOE | 64 |
| 552415 | 2-9-5 | 2'-MOE | 45 |
| 552416 | 2-9-5 | 2'-MOE | 45 |
| 552417 | 2-9-5 | 2'-MOE | 37 |
| 552418 | 2-9-5 | 2'-MOE | 73 |
| 552419 | 2-9-5 | 2'-MOE | 68 |
| 552420 | 2-9-5 | 2'-MOE | 64 |
| 552421 | 2-9-5 | 2'-MOE | 54 |
| 552422 | 2-9-5 | 2'-MOE | 60 |
| 552423 | 2-9-5 | 2'-MOE | 62 |
| 552424 | 2-9-5 | 2'-MOE | 60 |
| 552425 | 2-9-5 | 2'-MOE | 46 |
| 552426 | 2-9-5 | 2'-MOE | 48 |
| 552427 | 2-9-5 | 2'-MOE | 36 |
| 552428 | 2-9-5 | 2'-MOE | 57 |
| 552429 | 2-9-5 | 2'-MOE | 36 |
| 552430 | 2-9-5 | 2'-MOE | 42 |
| 552431 | 2-9-5 | 2'-MOE | 60 |
| 552432 | 2-9-5 | 2'-MOE | 44 |
| 552433 | 2-9-5 | 2'-MOE | 55 |
| 552434 | 2-9-5 | 2'-MOE | 46 |
| 552435 | 2-9-5 | 2'-MOE | 47 |
| 552436 | 2-9-5 | 2'-MOE | 25 |
| 552437 | 2-9-5 | 2'-MOE | 19 |
| 552438 | 2-9-5 | 2'-MOE | 25 |
| 552439 | 2-9-5 | 2'-MOE | 22 |

TABLE 91

Inhibition of viral Target-Z mRNA levels by chimeric antisense oligonucleotides measured with RTS3371

| ISIS No | Motif | Wing chemistry | % inhibition |
|---|---|---|---|
| 509959 | 3-10-3 | 2'-MOE | 49 |
| 552496 | 4-9-3 | 2'-MOE | 35 |
| 552497 | 4-9-3 | 2'-MOE | 60 |
| 552498 | 4-9-3 | 2'-MOE | 20 |
| 552499 | 4-9-3 | 2'-MOE | 45 |
| 552500 | 4-9-3 | 2'-MOE | 53 |
| 552501 | 4-9-3 | 2'-MOE | 56 |
| 552502 | 4-9-3 | 2'-MOE | 50 |
| 552503 | 4-9-3 | 2'-MOE | 36 |
| 552504 | 4-9-3 | 2'-MOE | 50 |
| 552505 | 4-9-3 | 2'-MOE | 53 |
| 552506 | 4-9-3 | 2'-MOE | 49 |
| 552507 | 4-9-3 | 2'-MOE | 35 |
| 552508 | 4-9-3 | 2'-MOE | 62 |
| 552509 | 4-9-3 | 2'-MOE | 65 |
| 552510 | 4-9-3 | 2'-MOE | 54 |
| 552455 | 3-9-4 | 2'-MOE | 60 |
| 552511 | 4-9-3 | 2'-MOE | 65 |
| 552456 | 3-9-4 | 2'-MOE | 69 |
| 552512 | 4-9-3 | 2'-MOE | 63 |
| 552457 | 3-9-4 | 2'-MOE | 4 |
| 552513 | 4-9-3 | 2'-MOE | 50 |
| 552458 | 3-9-4 | 2'-MOE | 59 |
| 552514 | 4-9-3 | 2'-MOE | 53 |
| 552459 | 3-9-4 | 2'-MOE | 69 |
| 552515 | 4-9-3 | 2'-MOE | 68 |
| 552460 | 3-9-4 | 2'-MOE | 3 |
| 552516 | 4-9-3 | 2'-MOE | 65 |
| 552461 | 3-9-4 | 2'-MOE | 37 |
| 552517 | 4-9-3 | 2'-MOE | 54 |
| 552462 | 3-9-4 | 2'-MOE | 42 |
| 552518 | 4-9-3 | 2'-MOE | 23 |
| 552463 | 3-9-4 | 2'-MOE | 28 |
| 552519 | 4-9-3 | 2'-MOE | 32 |
| 552464 | 3-9-4 | 2'-MOE | 72 |
| 552520 | 4-9-3 | 2'-MOE | 61 |
| 552465 | 3-9-4 | 2'-MOE | 68 |
| 552521 | 4-9-3 | 2'-MOE | 68 |
| 552466 | 3-9-4 | 2'-MOE | 76 |
| 552522 | 4-9-3 | 2'-MOE | 71 |

TABLE 91-continued

Inhibition of viral Target-Z mRNA levels by chimeric antisense oligonucleotides measured with RTS3371

| ISIS No | Motif | Wing chemistry | % inhibition |
|---|---|---|---|
| 552467 | 3-9-4 | 2'-MOE | 72 |
| 552523 | 4-9-3 | 2'-MOE | 73 |
| 552468 | 3-9-4 | 2'-MOE | 50 |
| 552524 | 4-9-3 | 2'-MOE | 49 |
| 552469 | 3-9-4 | 2'-MOE | 65 |
| 552525 | 4-9-3 | 2'-MOE | 45 |
| 552470 | 3-9-4 | 2'-MOE | 58 |
| 552526 | 4-9-3 | 2'-MOE | 39 |
| 552471 | 3-9-4 | 2'-MOE | 30 |
| 552527 | 4-9-3 | 2'-MOE | 39 |
| 552472 | 3-9-4 | 2'-MOE | 43 |
| 552528 | 4-9-3 | 2'-MOE | 43 |
| 552473 | 3-9-4 | 2'-MOE | 25 |
| 552529 | 4-9-3 | 2'-MOE | 50 |
| 552474 | 3-9-4 | 2'-MOE | 70 |
| 552530 | 4-9-3 | 2'-MOE | 73 |
| 552475 | 3-9-4 | 2'-MOE | 64 |
| 552531 | 4-9-3 | 2'-MOE | 62 |
| 552476 | 3-9-4 | 2'-MOE | 50 |
| 552477 | 3-9-4 | 2'-MOE | 66 |
| 552478 | 3-9-4 | 2'-MOE | 68 |
| 552479 | 3-9-4 | 2'-MOE | 60 |
| 552480 | 3-9-4 | 2'-MOE | 58 |
| 552481 | 3-9-4 | 2'-MOE | 54 |
| 552482 | 3-9-4 | 2'-MOE | 44 |
| 552483 | 3-9-4 | 2'-MOE | 17 |
| 552484 | 3-9-4 | 2'-MOE | 64 |
| 552485 | 3-9-4 | 2'-MOE | 56 |
| 552486 | 3-9-4 | 2'-MOE | 26 |
| 552487 | 3-9-4 | 2'-MOE | 42 |
| 552488 | 3-9-4 | 2'-MOE | 35 |
| 552489 | 3-9-4 | 2'-MOE | 46 |
| 552490 | 3-9-4 | 2'-MOE | 41 |
| 552491 | 3-9-4 | 2'-MOE | 38 |
| 552492 | 3-9-4 | 2'-MOE | 47 |
| 552493 | 3-9-4 | 2'-MOE | 49 |
| 552494 | 3-9-4 | 2'-MOE | 22 |
| 552495 | 3-9-4 | 2'-MOE | 0 |

TABLE 92

Inhibition of viral Target-Z mRNA levels by chimeric antisense oligonucleotides measured with RTS3371

| ISIS No | Motif | Wing chemistry | % inhibition |
|---|---|---|---|
| 146786 | 5-10-5 | 2'-MOE | 56 |
| 509959 | 3-10-3 | 2'-MOE | 54 |
| 552552 | 5-9-2 | 2'-MOE | 32 |
| 552553 | 5-9-2 | 2'-MOE | 53 |
| 552554 | 5-9-2 | 2'-MOE | 48 |
| 552555 | 5-9-2 | 2'-MOE | 39 |
| 552556 | 5-9-2 | 2'-MOE | 39 |
| 552557 | 5-9-2 | 2'-MOE | 54 |
| 552558 | 5-9-2 | 2'-MOE | 41 |
| 552559 | 5-9-2 | 2'-MOE | 56 |
| 552560 | 5-9-2 | 2'-MOE | 39 |
| 552561 | 5-9-2 | 2'-MOE | 51 |
| 552562 | 5-9-2 | 2'-MOE | 56 |
| 552563 | 5-9-2 | 2'-MOE | 31 |
| 552564 | 5-9-2 | 2'-MOE | 31 |
| 552565 | 5-9-2 | 2'-MOE | 53 |
| 552566 | 5-9-2 | 2'-MOE | 46 |
| 552567 | 5-9-2 | 2'-MOE | 63 |
| 552568 | 5-9-2 | 2'-MOE | 66 |
| 552569 | 5-9-2 | 2'-MOE | 60 |
| 552570 | 5-9-2 | 2'-MOE | 60 |
| 552571 | 5-9-2 | 2'-MOE | 44 |
| 552572 | 5-9-2 | 2'-MOE | 52 |
| 552573 | 5-9-2 | 2'-MOE | 20 |

TABLE 92-continued

Inhibition of viral Target-Z mRNA levels by chimeric antisense oligonucleotides measured with RTS3371

| ISIS No | Motif | Wing chemistry | % inhibition |
|---|---|---|---|
| 552574 | 5-9-2 | 2'-MOE | 36 |
| 552575 | 5-9-2 | 2'-MOE | 19 |
| 552576 | 5-9-2 | 2'-MOE | 61 |
| 552577 | 5-9-2 | 2'-MOE | 57 |
| 552578 | 5-9-2 | 2'-MOE | 71 |
| 552579 | 5-9-2 | 2'-MOE | 59 |
| 552580 | 5-9-2 | 2'-MOE | 58 |
| 552581 | 5-9-2 | 2'-MOE | 51 |
| 552582 | 5-9-2 | 2'-MOE | 40 |
| 552583 | 5-9-2 | 2'-MOE | 35 |
| 552584 | 5-9-2 | 2'-MOE | 50 |
| 552585 | 5-9-2 | 2'-MOE | 48 |
| 552586 | 5-9-2 | 2'-MOE | 74 |
| 552587 | 5-9-2 | 2'-MOE | 68 |
| 552532 | 4-9-3 | 2'-MOE | 59 |
| 552588 | 5-9-2 | 2'-MOE | 67 |
| 552533 | 4-9-3 | 2'-MOE | 52 |
| 552589 | 5-9-2 | 2'-MOE | 47 |
| 552534 | 4-9-3 | 2'-MOE | 71 |
| 552590 | 5-9-2 | 2'-MOE | 58 |
| 552535 | 4-9-3 | 2'-MOE | 59 |
| 552591 | 5-9-2 | 2'-MOE | 46 |
| 552536 | 4-9-3 | 2'-MOE | 19 |
| 552592 | 5-9-2 | 2'-MOE | 44 |
| 552537 | 4-9-3 | 2'-MOE | 26 |
| 552593 | 5-9-2 | 2'-MOE | 39 |
| 552538 | 4-9-3 | 2'-MOE | 54 |
| 552594 | 5-9-2 | 2'-MOE | 52 |
| 552539 | 4-9-3 | 2'-MOE | 50 |
| 552595 | 5-9-2 | 2'-MOE | 57 |
| 552540 | 4-9-3 | 2'-MOE | 60 |
| 552596 | 5-9-2 | 2'-MOE | 58 |
| 552541 | 4-9-3 | 2'-MOE | 68 |
| 552597 | 5-9-2 | 2'-MOE | 52 |
| 552542 | 4-9-3 | 2'-MOE | 63 |
| 552598 | 5-9-2 | 2'-MOE | 51 |
| 552543 | 4-9-3 | 2'-MOE | 44 |
| 552600 | 5-9-2 | 2'-MOE | 51 |
| 552544 | 4-9-3 | 2'-MOE | 45 |
| 552602 | 5-9-2 | 2'-MOE | 13 |
| 552545 | 4-9-3 | 2'-MOE | 42 |
| 552604 | 5-9-2 | 2'-MOE | 42 |
| 552546 | 4-9-3 | 2'-MOE | 46 |
| 552606 | 5-9-2 | 2'-MOE | 42 |
| 552547 | 4-9-3 | 2'-MOE | 38 |
| 552608 | 5-9-2 | 2'-MOE | 37 |
| 552548 | 4-9-3 | 2'-MOE | 49 |
| 552610 | 5-9-2 | 2'-MOE | 41 |
| 552549 | 4-9-3 | 2'-MOE | 34 |
| 552612 | 5-9-2 | 2'-MOE | 23 |
| 552550 | 4-9-3 | 2'-MOE | 13 |
| 552614 | 5-9-2 | 2'-MOE | 11 |
| 552551 | 4-9-3 | 2'-MOE | 8 |
| 552616 | 5-9-2 | 2'-MOE | 6 |

TABLE 93

Inhibition of viral Target-Z mRNA levels by chimeric antisense oligonucleotides measured with RTS3371

| ISIS No | Motif | Wing chemistry | % inhibition |
|---|---|---|---|
| 146786 | 5-10-5 | 2'-MOE | 47 |
| 509934 | 5-10-5 | 2'-MOE | 67 |
| 552007 | 6-10-4 | 2'-MOE | 53 |
| 552039 | 7-10-3 | 2'-MOE | 74 |
| 552008 | 6-10-4 | 2'-MOE | 47 |
| 552040 | 7-10-3 | 2'-MOE | 57 |
| 552009 | 6-10-4 | 2'-MOE | 70 |
| 552041 | 7-10-3 | 2'-MOE | 65 |

TABLE 93-continued

Inhibition of viral Target-Z mRNA levels by chimeric antisense oligonucleotides measured with RTS3371

| ISIS No | Motif | Wing chemistry | % inhibition |
|---|---|---|---|
| 552010 | 6-10-4 | 2'-MOE | 51 |
| 552042 | 7-10-3 | 2'-MOE | 59 |
| 552011 | 6-10-4 | 2'-MOE | 47 |
| 552043 | 7-10-3 | 2'-MOE | 36 |
| 552012 | 6-10-4 | 2'-MOE | 62 |
| 552044 | 7-10-3 | 2'-MOE | 82 |
| 552013 | 6-10-4 | 2'-MOE | 72 |
| 552045 | 7-10-3 | 2'-MOE | 62 |
| 552014 | 6-10-4 | 2'-MOE | 73 |
| 552046 | 7-10-3 | 2'-MOE | 74 |
| 552015 | 6-10-4 | 2'-MOE | 66 |
| 552047 | 7-10-3 | 2'-MOE | 60 |
| 552016 | 6-10-4 | 2'-MOE | 67 |
| 552048 | 7-10-3 | 2'-MOE | 60 |
| 552017 | 6-10-4 | 2'-MOE | 72 |
| 552049 | 7-10-3 | 2'-MOE | 68 |
| 552018 | 6-10-4 | 2'-MOE | 89 |
| 552050 | 7-10-3 | 2'-MOE | 86 |
| 552019 | 6-10-4 | 2'-MOE | 87 |
| 552051 | 7-10-3 | 2'-MOE | 86 |
| 551986 | 4-10-6 | 2'-MOE | 64 |
| 552020 | 6-10-4 | 2'-MOE | 86 |
| 552052 | 7-10-3 | 2'-MOE | 87 |
| 551987 | 4-10-6 | 2'-MOE | 76 |
| 552021 | 6-10-4 | 2'-MOE | 84 |
| 552053 | 7-10-3 | 2'-MOE | 75 |
| 551988 | 4-10-6 | 2'-MOE | 5 |
| 552005 | 5-10-5 | 2'-MOE | 72 |
| 552022 | 6-10-4 | 2'-MOE | 80 |
| 552054 | 7-10-3 | 2'-MOE | 83 |
| 551989 | 4-10-6 | 2'-MOE | 64 |
| 552023 | 6-10-4 | 2'-MOE | 78 |
| 552055 | 7-10-3 | 2'-MOE | 57 |
| 551990 | 4-10-6 | 2'-MOE | 83 |
| 552024 | 6-10-4 | 2'-MOE | 89 |
| 552056 | 7-10-3 | 2'-MOE | 82 |
| 551991 | 4-10-6 | 2'-MOE | 0 |
| 552025 | 6-10-4 | 2'-MOE | 89 |
| 552057 | 7-10-3 | 2'-MOE | 89 |
| 551992 | 4-10-6 | 2'-MOE | 67 |
| 552026 | 6-10-4 | 2'-MOE | 84 |
| 552058 | 7-10-3 | 2'-MOE | 82 |
| 551993 | 4-10-6 | 2'-MOE | 78 |
| 552027 | 6-10-4 | 2'-MOE | 85 |
| 552059 | 7-10-3 | 2'-MOE | 85 |
| 551994 | 4-10-6 | 2'-MOE | 82 |
| 552028 | 6-10-4 | 2'-MOE | 82 |
| 552060 | 7-10-3 | 2'-MOE | 74 |
| 551995 | 4-10-6 | 2'-MOE | 81 |
| 552029 | 6-10-4 | 2'-MOE | 81 |
| 552061 | 7-10-3 | 2'-MOE | 81 |
| 551996 | 4-10-6 | 2'-MOE | 79 |
| 552030 | 6-10-4 | 2'-MOE | 86 |
| 552062 | 7-10-3 | 2'-MOE | 85 |
| 551997 | 4-10-6 | 2'-MOE | 80 |
| 552031 | 6-10-4 | 2'-MOE | 86 |
| 551998 | 4-10-6 | 2'-MOE | 74 |
| 552032 | 6-10-4 | 2'-MOE | 78 |
| 551999 | 4-10-6 | 2'-MOE | 79 |
| 552033 | 6-10-4 | 2'-MOE | 80 |
| 552000 | 4-10-6 | 2'-MOE | 84 |
| 552006 | 5-10-5 | 2'-MOE | 86 |
| 552034 | 6-10-4 | 2'-MOE | 81 |
| 552001 | 4-10-6 | 2'-MOE | 66 |
| 552035 | 6-10-4 | 2'-MOE | 55 |
| 552002 | 4-10-6 | 2'-MOE | 54 |
| 552036 | 6-10-4 | 2'-MOE | 58 |
| 552003 | 4-10-6 | 2'-MOE | 50 |
| 552037 | 6-10-4 | 2'-MOE | 43 |
| 552004 | 4-10-6 | 2'-MOE | 56 |
| 552038 | 6-10-4 | 2'-MOE | 66 |

TABLE 94

Inhibition of viral Target-Z mRNA levels by chimeric antisense oligonucleotides measured with RTS3371

| ISIS No | Motif | Wing chemistry | % inhibition |
|---|---|---|---|
| 146786 | 5-10-5 | 2'-MOE | 61 |
| 510100 | 3-10-4 | 2'-MOE | 66 |
| 552168 | 3-9-5 | 2'-MOE | 64 |
| 552222 | 4-9-4 | 2'-MOE | 76 |
| 552169 | 3-9-5 | 2'-MOE | 65 |
| 552223 | 4-9-4 | 2'-MOE | 41 |
| 552170 | 3-9-5 | 2'-MOE | 58 |
| 552224 | 4-9-4 | 2'-MOE | 58 |
| 552171 | 3-9-5 | 2'-MOE | 51 |
| 552225 | 4-9-4 | 2'-MOE | 49 |
| 552172 | 3-9-5 | 2'-MOE | 23 |
| 552226 | 4-9-4 | 2'-MOE | 36 |
| 552173 | 3-9-5 | 2'-MOE | 44 |
| 552227 | 4-9-4 | 2'-MOE | 20 |
| 552174 | 3-9-5 | 2'-MOE | 28 |
| 552228 | 4-9-4 | 2'-MOE | 29 |
| 552175 | 3-9-5 | 2'-MOE | 56 |
| 552176 | 3-9-5 | 2'-MOE | 66 |
| 552177 | 3-9-5 | 2'-MOE | 53 |
| 552178 | 3-9-5 | 2'-MOE | 57 |
| 552179 | 3-9-5 | 2'-MOE | 56 |
| 552180 | 3-9-5 | 2'-MOE | 51 |
| 552181 | 3-9-5 | 2'-MOE | 51 |
| 552182 | 3-9-5 | 2'-MOE | 63 |
| 552183 | 3-9-5 | 2'-MOE | 60 |
| 552185 | 3-9-5 | 2'-MOE | 67 |
| 552186 | 3-9-5 | 2'-MOE | 37 |
| 552187 | 3-9-5 | 2'-MOE | 68 |
| 552188 | 3-9-5 | 2'-MOE | 71 |
| 552189 | 3-9-5 | 2'-MOE | 51 |
| 552190 | 3-9-5 | 2'-MOE | 47 |
| 552191 | 3-9-5 | 2'-MOE | 50 |
| 552192 | 3-9-5 | 2'-MOE | 80 |
| 552193 | 3-9-5 | 2'-MOE | 73 |
| 552194 | 3-9-5 | 2'-MOE | 58 |
| 552195 | 3-9-5 | 2'-MOE | 60 |
| 552196 | 3-9-5 | 2'-MOE | 54 |
| 552197 | 3-9-5 | 2'-MOE | 64 |
| 552198 | 3-9-5 | 2'-MOE | 62 |
| 552199 | 3-9-5 | 2'-MOE | 57 |
| 552200 | 3-9-5 | 2'-MOE | 52 |
| 552201 | 3-9-5 | 2'-MOE | 73 |
| 552202 | 3-9-5 | 2'-MOE | 60 |
| 552203 | 3-9-5 | 2'-MOE | 60 |
| 552204 | 3-9-5 | 2'-MOE | 63 |
| 552151 | 2-9-6 | 2'-MOE | 71 |
| 552205 | 3-9-5 | 2'-MOE | 64 |
| 552152 | 2-9-6 | 2'-MOE | 69 |
| 552206 | 3-9-5 | 2'-MOE | 71 |
| 552153 | 2-9-6 | 2'-MOE | 63 |
| 552207 | 3-9-5 | 2'-MOE | 71 |
| 552154 | 2-9-6 | 2'-MOE | 56 |
| 552208 | 3-9-5 | 2'-MOE | 52 |
| 552155 | 2-9-6 | 2'-MOE | 61 |
| 552209 | 3-9-5 | 2'-MOE | 50 |
| 552156 | 2-9-6 | 2'-MOE | 40 |
| 552210 | 3-9-5 | 2'-MOE | 66 |
| 552157 | 2-9-6 | 2'-MOE | 45 |
| 552211 | 3-9-5 | 2'-MOE | 63 |
| 552158 | 2-9-6 | 2'-MOE | 66 |
| 552212 | 3-9-5 | 2'-MOE | 62 |
| 552159 | 2-9-6 | 2'-MOE | 68 |
| 552213 | 3-9-5 | 2'-MOE | 64 |
| 552160 | 2-9-6 | 2'-MOE | 78 |
| 552214 | 3-9-5 | 2'-MOE | 72 |
| 552161 | 2-9-6 | 2'-MOE | 57 |
| 552215 | 3-9-5 | 2'-MOE | 54 |
| 552162 | 2-9-6 | 2'-MOE | 54 |
| 552216 | 3-9-5 | 2'-MOE | 49 |
| 552163 | 2-9-6 | 2'-MOE | 65 |
| 552217 | 3-9-5 | 2'-MOE | 50 |
| 552164 | 2-9-6 | 2'-MOE | 48 |
| 552218 | 3-9-5 | 2'-MOE | 39 |
| 552165 | 2-9-6 | 2'-MOE | 46 |

TABLE 94-continued

Inhibition of viral Target-Z mRNA levels by chimeric antisense oligonucleotides measured with RTS3371

| ISIS No | Motif | Wing chemistry | % inhibition |
|---|---|---|---|
| 552219 | 3-9-5 | 2'-MOE | 41 |
| 552166 | 2-9-6 | 2'-MOE | 42 |
| 552220 | 3-9-5 | 2'-MOE | 32 |
| 552167 | 2-9-6 | 2'-MOE | 47 |
| 552221 | 3-9-5 | 2'-MOE | 33 |

TABLE 95

Inhibition of viral Target-Z mRNA levels by chimeric antisense oligonucleotides measured with RTS3371

| ISIS No | Motif | Wing chemistry | % inhibition |
|---|---|---|---|
| 146786 | 5-10-5 | 2'-MOE | |
| 509934 | 5-10-5 | 2'-MOE | 56 |
| 510100 | 3-10-4 | 2'-MOE | 69 |
| 552071 | 8-10-2 | 2'-MOE | 73 |
| 552114 | 2-9-6 | 2'-MOE | 64 |
| 552115 | 2-9-6 | 2'-MOE | 61 |
| 552116 | 2-9-6 | 2'-MOE | 53 |
| 552117 | 2-9-6 | 2'-MOE | 69 |
| 552072 | 8-10-2 | 2'-MOE | 39 |
| 552118 | 2-9-6 | 2'-MOE | 49 |
| 552119 | 2-9-6 | 2'-MOE | 49 |
| 552120 | 2-9-6 | 2'-MOE | 21 |
| 552121 | 2-9-6 | 2'-MOE | 27 |
| 552073 | 8-10-2 | 2'-MOE | 73 |
| 552122 | 2-9-6 | 2'-MOE | 48 |
| 552074 | 8-10-2 | 2'-MOE | 69 |
| 552123 | 2-9-6 | 2'-MOE | 68 |
| 552075 | 8-10-2 | 2'-MOE | 78 |
| 552124 | 2-9-6 | 2'-MOE | 47 |
| 552076 | 8-10-2 | 2'-MOE | 63 |
| 552125 | 2-9-6 | 2'-MOE | 72 |
| 552077 | 8-10-2 | 2'-MOE | 62 |
| 552126 | 2-9-6 | 2'-MOE | 64 |
| 552078 | 8-10-2 | 2'-MOE | 59 |
| 552127 | 2-9-6 | 2'-MOE | 65 |
| 552079 | 8-10-2 | 2'-MOE | 80 |
| 552128 | 2-9-6 | 2'-MOE | 78 |
| 552080 | 8-10-2 | 2'-MOE | 74 |
| 552129 | 2-9-6 | 2'-MOE | 68 |
| 552130 | 2-9-6 | 2'-MOE | 46 |
| 552131 | 2-9-6 | 2'-MOE | 61 |
| 552132 | 2-9-6 | 2'-MOE | 66 |
| 552133 | 2-9-6 | 2'-MOE | 78 |
| 552081 | 8-10-2 | 2'-MOE | 69 |
| 552134 | 2-9-6 | 2'-MOE | 68 |
| 552135 | 2-9-6 | 2'-MOE | 59 |
| 552136 | 2-9-6 | 2'-MOE | 39 |
| 552137 | 2-9-6 | 2'-MOE | 36 |
| 552082 | 8-10-2 | 2'-MOE | 86 |
| 552138 | 2-9-6 | 2'-MOE | 80 |
| 552083 | 8-10-2 | 2'-MOE | 85 |
| 552139 | 2-9-6 | 2'-MOE | 80 |
| 552084 | 8-10-2 | 2'-MOE | 86 |
| 552140 | 2-9-6 | 2'-MOE | 70 |
| 552085 | 8-10-2 | 2'-MOE | 83 |
| 552141 | 2-9-6 | 2'-MOE | 72 |
| 552086 | 8-10-2 | 2'-MOE | 83 |
| 552142 | 2-9-6 | 2'-MOE | 58 |
| 552087 | 8-10-2 | 2'-MOE | 77 |
| 552143 | 2-9-6 | 2'-MOE | 70 |
| 552144 | 2-9-6 | 2'-MOE | 66 |
| 552145 | 2-9-6 | 2'-MOE | 78 |
| 552146 | 2-9-6 | 2'-MOE | 63 |
| 552088 | 8-10-2 | 2'-MOE | 90 |
| 552147 | 2-9-6 | 2'-MOE | 80 |
| 552089 | 8-10-2 | 2'-MOE | 87 |
| 552148 | 2-9-6 | 2'-MOE | 74 |

TABLE 95-continued

Inhibition of viral Target-Z mRNA levels by chimeric antisense oligonucleotides measured with RTS3371

| ISIS No | Motif | Wing chemistry | % inhibition |
|---|---|---|---|
| 552090 | 8-10-2 | 2'-MOE | 85 |
| 552149 | 2-9-6 | 2'-MOE | 79 |
| 552091 | 8-10-2 | 2'-MOE | 84 |
| 552092 | 8-10-2 | 2'-MOE | 86 |
| 552093 | 8-10-2 | 2'-MOE | 82 |
| 552094 | 8-10-2 | 2'-MOE | 84 |
| 552063 | 7-10-3 | 2'-MOE | 79 |
| 552095 | 8-10-2 | 2'-MOE | 85 |
| 552064 | 7-10-3 | 2'-MOE | 83 |
| 552096 | 8-10-2 | 2'-MOE | 88 |
| 552065 | 7-10-3 | 2'-MOE | 86 |
| 552097 | 8-10-2 | 2'-MOE | 90 |
| 552066 | 7-10-3 | 2'-MOE | 35 |
| 552098 | 8-10-2 | 2'-MOE | 86 |
| 552067 | 7-10-3 | 2'-MOE | 53 |
| 552099 | 8-10-2 | 2'-MOE | 66 |
| 552068 | 7-10-3 | 2'-MOE | 70 |
| 552100 | 8-10-2 | 2'-MOE | 67 |
| 552069 | 7-10-3 | 2'-MOE | 68 |
| 552101 | 8-10-2 | 2'-MOE | 65 |
| 552070 | 7-10-3 | 2'-MOE | 64 |
| 552102 | 8-10-2 | 2'-MOE | 54 |

TABLE 96

Inhibition of viral Target-Z mRNA levels by chimeric antisense oligonucleotides measured with RTS3371

| ISIS No | Motif | Wing chemistry | % inhibition |
|---|---|---|---|
| 146786 | 5-10-5 | 2'-MOE | 63 |
| 510100 | 3-10-4 | 2'-MOE | 59 |
| 552330 | 6-9-2 | 2'-MOE | 50 |
| 552331 | 6-9-2 | 2'-MOE | 46 |
| 552332 | 6-9-2 | 2'-MOE | 50 |
| 552333 | 6-9-2 | 2'-MOE | 48 |
| 552334 | 6-9-2 | 2'-MOE | 42 |
| 552335 | 6-9-2 | 2'-MOE | 30 |
| 552336 | 6-9-2 | 2'-MOE | 23 |
| 552337 | 6-9-2 | 2'-MOE | 42 |
| 552338 | 6-9-2 | 2'-MOE | 40 |
| 552339 | 6-9-2 | 2'-MOE | 50 |
| 552340 | 6-9-2 | 2'-MOE | 45 |
| 552341 | 6-9-2 | 2'-MOE | 44 |
| 552342 | 6-9-2 | 2'-MOE | 51 |
| 552343 | 6-9-2 | 2'-MOE | 44 |
| 552344 | 6-9-2 | 2'-MOE | 24 |
| 552345 | 6-9-2 | 2'-MOE | 41 |
| 552346 | 6-9-2 | 2'-MOE | 0 |
| 552347 | 6-9-2 | 2'-MOE | 75 |
| 552348 | 6-9-2 | 2'-MOE | 72 |
| 552349 | 6-9-2 | 2'-MOE | 65 |
| 552350 | 6-9-2 | 2'-MOE | 42 |
| 552351 | 6-9-2 | 2'-MOE | 45 |
| 552352 | 6-9-2 | 2'-MOE | 43 |
| 552353 | 6-9-2 | 2'-MOE | 20 |
| 552354 | 6-9-2 | 2'-MOE | 70 |
| 552355 | 6-9-2 | 2'-MOE | 66 |
| 552356 | 6-9-2 | 2'-MOE | 62 |
| 552357 | 6-9-2 | 2'-MOE | 53 |
| 552358 | 6-9-2 | 2'-MOE | 57 |
| 552359 | 6-9-2 | 2'-MOE | 46 |
| 552360 | 6-9-2 | 2'-MOE | 45 |
| 552361 | 6-9-2 | 2'-MOE | 44 |
| 552308 | 5-9-3 | 2'-MOE | 38 |
| 552362 | 6-9-2 | 2'-MOE | 51 |
| 552309 | 5-9-3 | 2'-MOE | 76 |
| 552363 | 6-9-2 | 2'-MOE | 73 |
| 552310 | 5-9-3 | 2'-MOE | 58 |
| 552364 | 6-9-2 | 2'-MOE | 66 |

TABLE 96-continued

Inhibition of viral Target-Z mRNA levels by chimeric antisense oligonucleotides measured with RTS3371

| ISIS No | Motif | Wing chemistry | % inhibition |
|---|---|---|---|
| 552311 | 5-9-3 | 2'-MOE | 38 |
| 552365 | 6-9-2 | 2'-MOE | 64 |
| 552150 | 2-9-6 | 2'-MOE | 68 |
| 552312 | 5-9-3 | 2'-MOE | 75 |
| 552366 | 6-9-2 | 2'-MOE | 55 |
| 552313 | 5-9-3 | 2'-MOE | 66 |
| 552367 | 6-9-2 | 2'-MOE | 67 |
| 552314 | 5-9-3 | 2'-MOE | 56 |
| 552368 | 6-9-2 | 2'-MOE | 41 |
| 552315 | 5-9-3 | 2'-MOE | 46 |
| 552369 | 6-9-2 | 2'-MOE | 52 |
| 552316 | 5-9-3 | 2'-MOE | 55 |
| 552370 | 6-9-2 | 2'-MOE | 35 |
| 552317 | 5-9-3 | 2'-MOE | 53 |
| 552371 | 6-9-2 | 2'-MOE | 58 |
| 552318 | 5-9-3 | 2'-MOE | 59 |
| 552372 | 6-9-2 | 2'-MOE | 68 |
| 552319 | 5-9-3 | 2'-MOE | 56 |
| 552373 | 6-9-2 | 2'-MOE | 63 |
| 552320 | 5-9-3 | 2'-MOE | 62 |
| 552374 | 6-9-2 | 2'-MOE | 70 |
| 552321 | 5-9-3 | 2'-MOE | 63 |
| 552375 | 6-9-2 | 2'-MOE | 64 |
| 552322 | 5-9-3 | 2'-MOE | 52 |
| 552376 | 6-9-2 | 2'-MOE | 58 |
| 552323 | 5-9-3 | 2'-MOE | 45 |
| 552377 | 6-9-2 | 2'-MOE | 42 |
| 552324 | 5-9-3 | 2'-MOE | 49 |
| 552378 | 6-9-2 | 2'-MOE | 37 |
| 552325 | 5-9-3 | 2'-MOE | 48 |
| 552379 | 6-9-2 | 2'-MOE | 57 |
| 552326 | 5-9-3 | 2'-MOE | 50 |
| 552380 | 6-9-2 | 2'-MOE | 48 |
| 552327 | 5-9-3 | 2'-MOE | 13 |
| 552381 | 6-9-2 | 2'-MOE | 22 |
| 552328 | 5-9-3 | 2'-MOE | 9 |
| 552382 | 6-9-2 | 2'-MOE | 20 |
| 552329 | 5-9-3 | 2'-MOE | 18 |
| 552383 | 6-9-2 | 2'-MOE | 18 |

Example 53: Dose-Dependent Antisense Inhibition of Target-Z mRNA in HepG2 Cells Antisense oligonucleotides from the study described in Example 52 exhibiting in vitro inhibition of Target-Z mRNA were selected and tested at various doses in HepG2 cells. Cells were plated at a density of 28,000 cells per well and transfected using LipofectAMINE2000® with 9.26 nM, 27.78 nM, 83.33 nM, and 250.00 nM concentrations of antisense oligonucleotide, as specified in Table 97. After a treatment period of approximately 16 hours, RNA was isolated from the cells and Target-Z mRNA levels were measured by quantitative real-time PCR. Target-Z primer probe set RTS3371 was used to measure mRNA levels. Target-Z mRNA levels were adjusted according to total RNA content, as measured by RIBOGREEN®. Results are presented as percent inhibition of Target-Z, relative to untreated control cells.

As illustrated in Table 97, Target-Z mRNA levels were reduced in a dose-dependent manner in antisense oligonucleotide treated cells. 'n/a' indicates that the data for that dosage is not available.

TABLE 97

Dose-dependent antisense inhibition of human Target-Z in HepG2 cells

| ISIS No | 9.2593 nM | 27.7778 nM | 83.3333 nM | 250.0 nM |
|---|---|---|---|---|
| 146786 | 10 | 43 | 74 | 89 |
| 509934 | 12 | 31 | 52 | 79 |
| 509959 | 4 | 24 | 49 | 67 |
| 510100 | 11 | 28 | 60 | 77 |
| 510124 | 3 | 11 | 13 | 41 |
| 551926 | 1 | 26 | 51 | 76 |
| 551958 | 15 | 17 | 56 | 82 |
| 551987 | 4 | 40 | 65 | 81 |
| 551990 | 7 | 55 | 78 | 91 |
| 551993 | 15 | 30 | 70 | 80 |
| 551994 | 0 | 30 | 39 | 58 |
| 551995 | 6 | 41 | 73 | 85 |
| 551996 | 13 | 47 | 71 | 85 |
| 551997 | 16 | 38 | 68 | 89 |
| 551998 | 4 | 36 | 69 | 85 |
| 551999 | 10 | 31 | 67 | 86 |
| 552000 | 0 | 17 | 61 | 78 |
| 552006 | 6 | 37 | 74 | 89 |
| 552009 | 1 | 5 | 39 | 60 |
| 552013 | 0 | 28 | 3 | 72 |
| 552014 | 0 | 26 | 32 | 77 |
| 552018 | 6 | 27 | 63 | 81 |
| 552019 | 15 | 34 | 65 | 90 |
| 552020 | 2 | 35 | 65 | 91 |
| 552021 | 4 | 11 | 53 | 82 |
| 552022 | 6 | 35 | 57 | 79 |
| 552023 | 11 | 33 | 59 | 81 |
| 552024 | 15 | 43 | 69 | 91 |
| 552025 | 17 | 35 | 69 | 87 |
| 552026 | 14 | 26 | 66 | 86 |
| 552027 | 3 | 46 | 62 | 88 |
| 552028 | 9 | 43 | 58 | 78 |
| 552029 | 8 | 40 | 72 | 89 |
| 552030 | 18 | 48 | 77 | 92 |
| 552031 | 0 | 38 | 66 | 89 |
| 552032 | 42 | 48 | 80 | 88 |
| 552033 | 2 | 40 | 64 | 84 |
| 552034 | 6 | 40 | 70 | 81 |
| 552039 | 2 | 33 | 56 | 83 |
| 552044 | 19 | 30 | 63 | 84 |
| 552046 | 4 | 21 | 47 | 77 |
| 552050 | 15 | 44 | 70 | 92 |
| 552051 | 8 | 33 | 69 | 90 |
| 552052 | 17 | 38 | 71 | 91 |
| 552053 | 0 | 40 | 59 | 86 |
| 552054 | 7 | 15 | 58 | 75 |
| 552056 | 19 | 62 | 86 | 92 |
| 552057 | 11 | 33 | 69 | 86 |
| 552058 | 30 | 55 | 79 | 90 |
| 552059 | 11 | 25 | 69 | 90 |
| 552060 | 9 | 32 | 61 | 86 |
| 552061 | 6 | 40 | 69 | 88 |
| 552062 | 22 | 48 | 75 | 89 |
| 552064 | 23 | 49 | 69 | 90 |
| 552065 | 10 | 8 | 69 | 86 |
| 552069 | 11 | 4 | 28 | 60 |
| 552073 | 9 | 31 | 62 | 78 |
| 552075 | 21 | 18 | 33 | 65 |
| 552077 | 0 | 17 | 40 | 72 |
| 552079 | 1 | 12 | 44 | 70 |
| 552080 | 3 | 12 | 34 | 69 |
| 552082 | 13 | 29 | 66 | 87 |
| 552083 | 24 | 54 | 69 | 88 |
| 552084 | 10 | 25 | 48 | 82 |
| 552085 | 28 | 35 | 64 | 85 |
| 552086 | 0 | 24 | 65 | 84 |
| 552088 | 33 | 53 | 77 | 93 |
| 552089 | 0 | 41 | 69 | 92 |
| 552090 | 17 | 35 | 70 | 87 |
| 552091 | 13 | 31 | 69 | 89 |
| 552092 | 6 | 23 | 66 | 89 |
| 552093 | 0 | 17 | 61 | 89 |
| 552094 | 12 | 38 | 65 | 88 |
| 552095 | 20 | 42 | 73 | 88 |
| 552096 | n/a | 39 | 66 | 91 |
| 552097 | 24 | 43 | 67 | 88 |

TABLE 97-continued

Dose-dependent antisense inhibition of human Target-Z in HepG2 cells

| ISIS No | 9.2593 nM | 27.7778 nM | 83.3333 nM | 250.0 nM |
|---|---|---|---|---|
| 552098 | 0 | 24 | 56 | 85 |
| 552101 | 3 | 13 | 28 | 61 |
| 552147 | 11 | 27 | 58 | 80 |
| 552160 | 20 | 25 | 69 | 89 |
| 552163 | 0 | 21 | 22 | 53 |

TABLE 97-continued

Dose-dependent antisense inhibition of human Target-Z in HepG2 cells

| ISIS No | 9.2593 nM | 27.7778 nM | 83.3333 nM | 250.0 nM |
|---|---|---|---|---|
| 552176 | 16 | 11 | 40 | 66 |
| 552192 | 7 | 38 | 78 | 89 |
| 552222 | 0 | 24 | 65 | 79 |
| 552247 | 0 | 38 | 69 | 86 |
| 552255 | 5 | 27 | 69 | 81 |
| 552301 | 5 | 38 | 65 | 86 |
| 552309 | 8 | 26 | 62 | 85 |
| 552312 | 0 | 4 | 32 | 62 |
| 552347 | 2 | 15 | 38 | 75 |
| 552348 | 12 | 40 | 42 | 65 |
| 552354 | 10 | 35 | 44 | 76 |
| 552361 | 2 | 25 | 55 | 74 |
| 552363 | 20 | 36 | 54 | 76 |
| 552374 | 7 | 4 | 38 | 76 |
| 552379 | 0 | 12 | 24 | 46 |
| 552403 | 8 | 27 | 54 | 76 |
| 552408 | 2 | 25 | 44 | 77 |
| 552409 | 6 | 31 | 56 | 80 |
| 552418 | 0 | 30 | 72 | 84 |
| 552420 | 9 | 34 | 53 | 81 |
| 552442 | 4 | 23 | 46 | 56 |
| 552466 | 0 | 23 | 56 | 79 |
| 552474 | 11 | 34 | 66 | 87 |
| 552477 | 11 | 22 | 44 | 64 |
| 552530 | 25 | 37 | 73 | 87 |
| 552559 | 9 | 13 | 29 | 51 |

Example 54: Efficacy of Antisense Oligonucleotides Targeting Target-Z in Transgenic Mice Target-Z transgenic mice were treated with ISIS antisense oligonucleotides selected from studies described above and evaluated for their efficacy in this model.
Treatment
Groups of 12 mice each were injected subcutaneously twice a week for 4 weeks with 50 mg/kg of ISIS 510106, ISIS 510116, ISIS 505347, or ISIS 509934. A control group of 12 mice was injected subcutaneously twice a week for 4 weeks with PBS. Mice were euthanized 48 hours after the last dose, and livers were harvested for further analysis.
DNA and RNA Analysis
RNA was extracted from liver tissue for real-time PCR analysis of Target-Z DNA, using primer probe sets RTS3370, RTS3371, and RTS3372. The DNA levels were normalized to picogreen. Target-Z RNA samples were also assayed with primer probe sets RTS3370 and RTS3371 after RT-PCR analysis. The mRNA levels were normalized to RIBOGREEN®. The data is presented in Table 98, expressed as percent inhibition compared to the control group. As shown in Table 98, most of the antisense oligonucleotides achieved reduction of Target-Z DNA and RNA over the PBS control. Results are presented as percent inhibition of Target-Z mRNA or DNA, relative to control.

TABLE 98

Percent inhibition of Target-Z RNA and DNA in the liver of transgenic mice

| ISIS No | % inhibition DNA (RTS3370) | % inhibition DNA (RTS3371) | % inhibition DNA (RTS3372) | % inhibition RNA (RTS3370) | % inhibition RNA (RTS3371) | % inhibition RNA (RTS3372) |
|---|---|---|---|---|---|---|
| 510106 | 0 | 0 | 51 | 0 | 0 | 12 |
| 510116 | 68 | 79 | 68 | 49 | 54 | 66 |
| 505347 | 72 | 79 | 75 | 54 | 28 | 30 |
| 509934 | 93 | 95 | 94 | 72 | 75 | 92 |

Example 55: Efficacy of Antisense Oligonucleotides Targeting Target-Z in Transgenic Mice Target-Z transgenic mice were treated with ISIS antisense oligonucleotides selected from studies described above and evaluated for their efficacy in this model.
Treatment Groups of 6 mice each were injected subcutaneously twice a week for 4 weeks with 50 mg/kg of ISIS 146779, ISIS 505358, ISIS 146786, ISIS 509974, ISIS 509958, or ISIS 509959. A control group of 10 mice was injected subcutaneously twice a week for 4 weeks with PBS. Mice were euthanized 48 hours after the last dose, and livers were harvested for further analysis.
DNA and RNA Analysis RNA was extracted from liver tissue for real-time PCR analysis of Target-Z DNA, using primer probe sets RTS3370. The DNA levels were normalized to picogreen. Target-Z RNA samples were also assayed with primer probe sets RTS3370 after RT-PCR analysis. The mRNA levels were normalized to RIBOGREEN®. The data is presented in Table 99, expressed as percent inhibition compared to the control group. As shown in Table 99, most of the antisense oligonucleotides achieved reduction of Target-Z DNA and RNA over the PBS control. Results are presented as percent inhibition of Target-Z mRNA or DNA, relative to control.

TABLE 99

Percent inhibition of Target-Z RNA and DNA in the liver of transgenic mice

| ISIS No | % inhibition DNA | % inhibition RNA |
|---|---|---|
| 146779 | 39 | 5 |
| 505358 | 84 | 77 |
| 146786 | 83 | 73 |
| 509974 | 56 | 28 |
| 509958 | 82 | 29 |
| 509959 | 54 | 30 |

Example 56: Efficacy of Antisense Oligonucleotides Targeting Target-Z in Transgenic Mice Transgenic mice were treated with ISIS antisense oligonucleotides selected from studies described above and evaluated for their efficacy in this model.

Treatment

Groups of 6 mice each were injected subcutaneously twice a week for 4 weeks with 25 mg/kg of ISIS 146786, ISIS 552176, and ISIS 552073. One group of 10 mice was injected subcutaneously twice a week for 4 weeks with PBS. Mice were euthanized 48 hours after the last dose, and organs and plasma were harvested for further analysis.

DNA and RNA Analysis

RNA was extracted from liver tissue for real-time PCR analysis of Target-Z DNA, using primer probe set RTS3371. The DNA levels were normalized to picogreen. Target-Z RNA samples were also assayed with primer probe set RTS3371 after RT-PCR analysis. The mRNA levels were normalized to RIBOGREEN®. The data is presented in Table 100. Serum DNA samples were analyzed after the study period. The data is presented in Table 101, expressed relative to the levels measured in the control group. As shown in Tables 100 and 101, the antisense oligonucleotides achieved reduction of Target-Z DNA and RNA over the PBS control. Results are presented as percent inhibition of Target-Z mRNA or DNA, relative to control.

TABLE 100

Percent inhibition of Target-Z RNA and DNA in transgenic mice

| ISIS No | Dose (mg/kg/wk) | % inhibition of RNA | % inhibition of DNA |
| --- | --- | --- | --- |
| 146786 | 50 | 81 | 91 |
| 552073 | 50 | 39 | 22 |
| 552176 | 50 | 55 | 56 |

TABLE 101

Serum levels of Target-Z DNA in transgenic mice, relative to control levels

| ISIS No | Dose (mg/kg/wk) | Post-dose DNA levels |
| --- | --- | --- |
| 146786 | 50 | 0.1 |
| 552073 | 50 | 2.9 |
| 552176 | 50 | 2.1 |

Liver Function

To evaluate the effect of ISIS oligonucleotides on hepatic function, plasma concentrations of ALT were measured using an automated clinical chemistry analyzer (Hitachi Olympus AU400e, Melville, N.Y.) (Nyblom, H. et al., Alcohol & Alcoholism 39: 336-339, 2004; Tietz N W (Ed): Clinical Guide to Laboratory Tests, 3rd ed. W. B. Saunders, Philadelphia, Pa., 1995). The results are presented in Table 102 expressed in IU/L. Both the ISIS oligonucleotides were considered tolerable in the mice, as demonstrated by their liver transaminase profile.

TABLE 102

ALT levels (IU/L) of transgenic mice

| | Dose (mg/kg/wk) | ALT |
| --- | --- | --- |
| PBS | — | 77 |
| ISIS 146786 | 50 | 21 |
| ISIS 552073 | 50 | 19 |
| ISIS 552176 | 50 | 27 |

Example 57: Efficacy of Antisense Oligonucleotides Targeting Target-Z in Transgenic Mice Transgenic mice were treated with ISIS antisense oligonucleotides selected from studies described above and evaluated for their efficacy in this model.

Treatment

Groups of 6 mice each were injected subcutaneously twice a week for 4 weeks with 25 mg/kg of ISIS 146786, ISIS 552056, ISIS 552088, and ISIS 552309. One group of 10 mice was injected subcutaneously twice a week for 4 weeks with PBS. Mice were euthanized 48 hours after the last dose, and organs and plasma were harvested for further analysis.

DNA and RNA Analysis

RNA was extracted from liver tissue for real-time PCR analysis of Target-Z DNA, using primer probe set RTS3371. The DNA levels were normalized to picogreen. Target-Z RNA samples were also assayed with primer probe set RTS3371 after RT-PCR analysis. The mRNA levels were normalized to RIBOGREEN®. As shown in Table 103, the antisense oligonucleotides achieved reduction of Target-Z DNA and RNA over the PBS control. Results are presented as percent inhibition of Target-Z mRNA or DNA, relative to control.

TABLE 103

Percent inhibition of Target-Z DNA and RNA in transgenic mice

| | Dose (mg/kg/wk) | % inhibition (RNA) | % inhibition (DNA) |
| --- | --- | --- | --- |
| ISIS 146786 | 50 | 60 | 90 |
| ISIS 552056 | 50 | 25 | 58 |
| ISIS 552088 | 50 | 8 | 0 |
| ISIS 552309 | 50 | 35 | 84 |

Example 58: Antisense Inhibition of Human Target-1 in HuVEC Cells

Antisense oligonucleotides were designed targeting a human Target-1 nucleic acid and were tested for their effect on human Target-1 mRNA expression in vitro. The chimeric antisense oligonucleotides presented in Tables 104 and 105 were either 2-10-2 cEt gapmers or 3-10-3 cEt gapmers. The internucleoside linkages throughout each gapmer was phosphorothioate (P=S) linkages. All cytosine residues throughout each gapmer were 5'-methylcytosines.

Cultured HuVEC cells at a density of 20,000 cells per well were transfected using electroporation with 1,000 nM antisense oligonucleotide. After a treatment period of approximately 24 hours, RNA was isolated from the cells and Target-1 mRNA levels were measured by quantitative real-time PCR. Target-1 mRNA levels were adjusted according to total RNA content, as measured by RIBOGREEN®. Results are presented as percent inhibition of Target-1, relative to untreated control cells. All cEt gapmers and MOE gapmers were tested under the same conditions.

"Human Target start site" indicates the 5'-most nucleoside to which the gapmer is targeted in the human gene sequence. "Human Target stop site" indicates the 3'-most nucleoside to which the gapmer is targeted human gene sequence. Each gapmer listed in Table 104 is targeted to human Target-1 mRNA. Each gapmer listed in Table 105 is targeted to the human Target-1 genomic sequence, truncated from nucleotides 4185000 to 4264000. Throughout the Examples, oligonucleotides having the same Sequence Number have the same nucleobase sequence.

TABLE 104

Inhibition of human Target-1 mRNA levels by cEt and MOE antisense oligonucleotides targeted to Target-1 mRNA

| ISIS NO | Human Start Site | Human Stop Site | Motif | Wing Chemistry | % inhibition |
| --- | --- | --- | --- | --- | --- |
| 481353 | 240 | 255 | 3-10-3 | cEt | 78 |
| 481354 | 264 | 279 | 3-10-3 | cEt | 98 |
| 481579 | 265 | 278 | 2-10-2 | cEt | 91 |
| 481355 | 322 | 337 | 3-10-3 | cEt | 95 |
| 481580 | 323 | 336 | 2-10-2 | cEt | 76 |
| 481356 | 346 | 361 | 3-10-3 | cEt | 83 |
| 481357 | 375 | 390 | 3-10-3 | cEt | 97 |
| 481582 | 376 | 389 | 2-10-2 | cEt | 87 |
| 481358 | 403 | 418 | 3-10-3 | cEt | 85 |
| 481359 | 429 | 444 | 3-10-3 | cEt | 90 |
| 481361 | 474 | 489 | 3-10-3 | cEt | 90 |
| 481586 | 475 | 488 | 2-10-2 | cEt | 81 |
| 481363 | 511 | 526 | 3-10-3 | cEt | 84 |
| 481368 | 659 | 674 | 3-10-3 | cEt | 81 |
| 481371 | 709 | 724 | 3-10-3 | cEt | 83 |
| 481372 | 730 | 745 | 3-10-3 | cEt | 85 |
| 481597 | 731 | 744 | 2-10-2 | cEt | 80 |
| 481373 | 751 | 766 | 3-10-3 | cEt | 87 |
| 481374 | 788 | 803 | 3-10-3 | cEt | 92 |
| 481599 | 789 | 802 | 2-10-2 | cEt | 51 |
| 481376 | 868 | 883 | 3-10-3 | cEt | 82 |
| 481601 | 869 | 882 | 2-10-2 | cEt | 70 |
| 481377 | 884 | 899 | 3-10-3 | cEt | 85 |
| 481378 | 892 | 907 | 3-10-3 | cEt | 89 |
| 481379 | 955 | 970 | 3-10-3 | cEt | 91 |
| 481604 | 956 | 969 | 2-10-2 | cEt | 70 |
| 481380 | 963 | 978 | 3-10-3 | cEt | 73 |
| 481605 | 964 | 977 | 2-10-2 | cEt | 55 |
| 481382 | 1045 | 1060 | 3-10-3 | cEt | 81 |
| 481383 | 1053 | 1068 | 3-10-3 | cEt | 84 |
| 481384 | 1098 | 1113 | 3-10-3 | cEt | 76 |
| 481387 | 1225 | 1240 | 3-10-3 | cEt | 92 |
| 481612 | 1226 | 1239 | 2-10-2 | cEt | 86 |
| 481388 | 1269 | 1284 | 3-10-3 | cEt | 74 |
| 481390 | 1305 | 1320 | 3-10-3 | cEt | 92 |
| 481396 | 1480 | 1495 | 3-10-3 | cEt | 92 |
| 481621 | 1481 | 1494 | 2-10-2 | cEt | 74 |
| 481398 | 1542 | 1557 | 3-10-3 | cEt | 73 |
| 481399 | 1563 | 1578 | 3-10-3 | cEt | 73 |
| 481401 | 1589 | 1604 | 3-10-3 | cEt | 74 |
| 481405 | 1641 | 1656 | 3-10-3 | cEt | 75 |
| 481406 | 1691 | 1706 | 3-10-3 | cEt | 72 |
| 481409 | 1795 | 1810 | 3-10-3 | cEt | 86 |
| 481410 | 1825 | 1840 | 3-10-3 | cEt | 91 |
| 481412 | 1858 | 1873 | 3-10-3 | cEt | 90 |
| 481637 | 1859 | 1872 | 2-10-2 | cEt | 79 |
| 481413 | 1866 | 1881 | 3-10-3 | cEt | 80 |
| 481638 | 1867 | 1880 | 2-10-2 | cEt | 64 |
| 481414 | 1888 | 1903 | 3-10-3 | cEt | 69 |
| 481639 | 1889 | 1902 | 2-10-2 | cEt | 16 |
| 481415 | 1896 | 1911 | 3-10-3 | cEt | 88 |
| 481640 | 1897 | 1910 | 2-10-2 | cEt | 57 |
| 337332 | 1898 | 1917 | 5-10-5 | MOE | 63 |
| 481416 | 1901 | 1916 | 3-10-3 | cEt | 87 |
| 481641 | 1902 | 1915 | 2-10-2 | cEt | 68 |

TABLE 104-continued

Inhibition of human Target-1 mRNA levels by cEt and MOE antisense oligonucleotides targeted to Target-1 mRNA

| ISIS NO | Human Start Site | Human Stop Site | Motif | Wing Chemistry | % inhibition |
| --- | --- | --- | --- | --- | --- |
| 337333 | 1903 | 1922 | 5-10-5 | MOE | 49 |
| 481417 | 1903 | 1918 | 3-10-3 | cEt | 97 |
| 481418 | 1904 | 1919 | 3-10-3 | cEt | 92 |
| 481642 | 1904 | 1917 | 2-10-2 | cEt | 67 |
| 481419 | 1905 | 1920 | 3-10-3 | cEt | 83 |
| 481643 | 1905 | 1918 | 2-10-2 | cEt | 58 |
| 481644 | 1906 | 1919 | 2-10-2 | cEt | 45 |
| 481420 | 1948 | 1963 | 3-10-3 | cEt | 94 |
| 481645 | 1949 | 1962 | 2-10-2 | cEt | 50 |
| 481421 | 2021 | 2036 | 3-10-3 | cEt | 86 |
| 481422 | 2036 | 2051 | 3-10-3 | cEt | 80 |
| 481425 | 2115 | 2130 | 3-10-3 | cEt | 78 |
| 481650 | 2116 | 2129 | 2-10-2 | cEt | 79 |
| 481426 | 2131 | 2146 | 3-10-3 | cEt | 80 |
| 481651 | 2132 | 2145 | 2-10-2 | cEt | 64 |
| 481427 | 2155 | 2170 | 3-10-3 | cEt | 75 |
| 481652 | 2156 | 2169 | 2-10-2 | cEt | 82 |
| 481428 | 2164 | 2179 | 3-10-3 | cEt | 77 |
| 481653 | 2165 | 2178 | 2-10-2 | cEt | 79 |
| 481429 | 2172 | 2187 | 3-10-3 | cEt | 84 |
| 481654 | 2173 | 2186 | 2-10-2 | cEt | 70 |
| 481430 | 2190 | 2205 | 3-10-3 | cEt | 67 |
| 481431 | 2206 | 2221 | 3-10-3 | cEt | 91 |
| 481433 | 2256 | 2271 | 3-10-3 | cEt | 73 |
| 481658 | 2257 | 2270 | 2-10-2 | cEt | 62 |
| 481434 | 2266 | 2281 | 3-10-3 | cEt | 73 |
| 345785 | 2267 | 2286 | 5-10-5 | MOE | 50 |
| 481659 | 2267 | 2280 | 2-10-2 | cEt | 51 |
| 481435 | 2269 | 2284 | 3-10-3 | cEt | 49 |
| 481660 | 2270 | 2283 | 2-10-2 | cEt | 54 |
| 481436 | 2275 | 2290 | 3-10-3 | cEt | 82 |
| 481661 | 2276 | 2289 | 2-10-2 | cEt | 76 |
| 481439 | 2371 | 2386 | 3-10-3 | cEt | 82 |
| 481664 | 2372 | 2385 | 2-10-2 | cEt | 89 |
| 481440 | 2387 | 2402 | 3-10-3 | cEt | 79 |
| 481445 | 2439 | 2454 | 3-10-3 | cEt | 70 |
| 481449 | 2503 | 2518 | 3-10-3 | cEt | 77 |
| 481452 | 2631 | 2646 | 3-10-3 | cEt | 71 |
| 481453 | 2681 | 2696 | 3-10-3 | cEt | 92 |
| 481678 | 2682 | 2695 | 2-10-2 | cEt | 78 |
| 481454 | 2702 | 2717 | 3-10-3 | cEt | 85 |
| 481679 | 2703 | 2716 | 2-10-2 | cEt | 69 |
| 481455 | 2722 | 2737 | 3-10-3 | cEt | 74 |
| 481457 | 2779 | 2794 | 3-10-3 | cEt | 88 |
| 481682 | 2780 | 2793 | 2-10-2 | cEt | 77 |
| 481459 | 2908 | 2923 | 3-10-3 | cEt | 76 |
| 481684 | 2909 | 2922 | 2-10-2 | cEt | 89 |
| 481460 | 2943 | 2958 | 3-10-3 | cEt | 83 |
| 481461 | 2969 | 2984 | 3-10-3 | cEt | 75 |
| 481686 | 2970 | 2983 | 2-10-2 | cEt | 70 |
| 481462 | 2984 | 2999 | 3-10-3 | cEt | 89 |
| 481687 | 2985 | 2998 | 2-10-2 | cEt | 80 |
| 481463 | 3001 | 3016 | 3-10-3 | cEt | 88 |
| 481688 | 3002 | 3015 | 2-10-2 | cEt | 13 |
| 481464 | 3016 | 3031 | 3-10-3 | cEt | 97 |
| 481689 | 3017 | 3030 | 2-10-2 | cEt | 40 |
| 481466 | 3047 | 3062 | 3-10-3 | cEt | 74 |
| 481691 | 3048 | 3061 | 2-10-2 | cEt | 77 |
| 481467 | 3097 | 3112 | 3-10-3 | cEt | 74 |
| 481692 | 3098 | 3111 | 2-10-2 | cEt | 74 |
| 481468 | 3112 | 3127 | 3-10-3 | cEt | 71 |
| 481695 | 3462 | 3475 | 2-10-2 | cEt | 83 |
| 481472 | 3491 | 3506 | 3-10-3 | cEt | 76 |
| 481697 | 3492 | 3505 | 2-10-2 | cEt | 63 |
| 481474 | 3521 | 3536 | 3-10-3 | cEt | 80 |
| 481475 | 3536 | 3551 | 3-10-3 | cEt | 93 |
| 481700 | 3537 | 3550 | 2-10-2 | cEt | 89 |
| 481476 | 3551 | 3566 | 3-10-3 | cEt | 92 |
| 481701 | 3552 | 3565 | 2-10-2 | cEt | 60 |
| 481477 | 3567 | 3582 | 3-10-3 | cEt | 95 |
| 481702 | 3568 | 3581 | 2-10-2 | cEt | 89 |
| 481478 | 3585 | 3600 | 3-10-3 | cEt | 84 |
| 481479 | 3600 | 3615 | 3-10-3 | cEt | 80 |
| 481485 | 3717 | 3732 | 3-10-3 | cEt | 90 |

TABLE 104-continued

Inhibition of human Target-1 mRNA levels by cEt and MOE antisense oligonucleotides targeted to Target-1 mRNA

| ISIS NO | Human Start Site | Human Stop Site | Motif | Wing Chemistry | % inhibition |
|---|---|---|---|---|---|
| 481710 | 3718 | 3731 | 2-10-2 | cEt | 88 |
| 481486 | 3730 | 3745 | 3-10-3 | cEt | 75 |
| 481711 | 3731 | 3744 | 2-10-2 | cEt | 74 |
| 481490 | 3833 | 3848 | 3-10-3 | cEt | 78 |
| 481715 | 3834 | 3847 | 2-10-2 | cEt | 79 |
| 481491 | 3848 | 3863 | 3-10-3 | cEt | 70 |
| 481716 | 3849 | 3862 | 2-10-2 | cEt | 68 |
| 481495 | 3940 | 3955 | 3-10-3 | cEt | 92 |
| 481498 | 3992 | 4007 | 3-10-3 | cEt | 90 |
| 481723 | 3993 | 4006 | 2-10-2 | cEt | 49 |
| 481499 | 4007 | 4022 | 3-10-3 | cEt | 43 |
| 481724 | 4008 | 4021 | 2-10-2 | cEt | 17 |
| 481500 | 4022 | 4037 | 3-10-3 | cEt | 92 |
| 481501 | 4048 | 4063 | 3-10-3 | cEt | 91 |
| 481502 | 4063 | 4078 | 3-10-3 | cEt | 85 |
| 481727 | 4064 | 4077 | 2-10-2 | cEt | 70 |
| 481510 | 4237 | 4252 | 3-10-3 | cEt | 95 |
| 481735 | 4238 | 4251 | 2-10-2 | cEt | 22 |
| 481513 | 4290 | 4305 | 3-10-3 | cEt | 85 |
| 481738 | 4291 | 4304 | 2-10-2 | cEt | 70 |
| 481514 | 4305 | 4320 | 3-10-3 | cEt | 85 |
| 481739 | 4306 | 4319 | 2-10-2 | cEt | 60 |
| 481515 | 4325 | 4340 | 3-10-3 | cEt | 88 |
| 481740 | 4326 | 4339 | 2-10-2 | cEt | 71 |
| 481516 | 4364 | 4379 | 3-10-3 | cEt | 78 |
| 481741 | 4365 | 4378 | 2-10-2 | cEt | 80 |
| 481517 | 4394 | 4409 | 3-10-3 | cEt | 87 |
| 481742 | 4395 | 4408 | 2-10-2 | cEt | 64 |
| 481518 | 4425 | 4440 | 3-10-3 | cEt | 67 |
| 481743 | 4426 | 4439 | 2-10-2 | cEt | 75 |
| 481519 | 4437 | 4452 | 3-10-3 | cEt | 29 |
| 481744 | 4438 | 4451 | 2-10-2 | cEt | 69 |
| 481520 | 4439 | 4454 | 3-10-3 | cEt | 73 |
| 481745 | 4440 | 4453 | 2-10-2 | cEt | 74 |
| 481521 | 4459 | 4474 | 3-10-3 | cEt | 86 |
| 481746 | 4460 | 4473 | 2-10-2 | cEt | 67 |
| 481522 | 4474 | 4489 | 3-10-3 | cEt | 92 |
| 481747 | 4475 | 4488 | 2-10-2 | cEt | 95 |
| 481523 | 4489 | 4504 | 3-10-3 | cEt | 95 |
| 481524 | 4530 | 4545 | 3-10-3 | cEt | 70 |
| 481749 | 4531 | 4544 | 2-10-2 | cEt | 70 |
| 481525 | 4541 | 4556 | 3-10-3 | cEt | 93 |
| 481750 | 4542 | 4555 | 2-10-2 | cEt | 94 |
| 481526 | 4543 | 4558 | 3-10-3 | cEt | 82 |
| 481528 | 4579 | 4594 | 3-10-3 | cEt | 77 |
| 481753 | 4580 | 4593 | 2-10-2 | cEt | 71 |
| 481530 | 4630 | 4645 | 3-10-3 | cEt | 87 |
| 481755 | 4631 | 4644 | 2-10-2 | cEt | 84 |
| 481532 | 4664 | 4679 | 3-10-3 | cEt | 65 |
| 481757 | 4665 | 4678 | 2-10-2 | cEt | 81 |
| 481533 | 4666 | 4681 | 3-10-3 | cEt | 80 |
| 481758 | 4667 | 4680 | 2-10-2 | cEt | 62 |
| 481534 | 4693 | 4708 | 3-10-3 | cEt | 79 |
| 481759 | 4694 | 4707 | 2-10-2 | cEt | 74 |
| 481535 | 4767 | 4782 | 3-10-3 | cEt | 78 |
| 481760 | 4768 | 4781 | 2-10-2 | cEt | 78 |
| 481536 | 4782 | 4797 | 3-10-3 | cEt | 91 |
| 481761 | 4783 | 4796 | 2-10-2 | cEt | 78 |
| 481537 | 4830 | 4845 | 3-10-3 | cEt | 84 |
| 481538 | 4844 | 4859 | 3-10-3 | cEt | 92 |
| 481763 | 4845 | 4858 | 2-10-2 | cEt | 96 |
| 481541 | 4934 | 4949 | 3-10-3 | cEt | 71 |

TABLE 105

Inhibition of human Target-1 mRNA levels by cEt and MOE antisense oligonucleotides targeted to Target-1 Genomic Sequence

| ISIS NO | Human Start Site | Human Stop Site | Motif | Wing Chemistry | % inhibition |
|---|---|---|---|---|---|
| 481543 | 1996 | 2011 | 3-10-3 | cEt | 84 |
| 481768 | 1997 | 2010 | 2-10-2 | cEt | 95 |
| 481546 | 2113 | 2128 | 3-10-3 | cEt | 70 |
| 481771 | 2114 | 2127 | 2-10-2 | cEt | 75 |
| 481547 | 2121 | 2136 | 3-10-3 | cEt | 87 |
| 481548 | 2705 | 2720 | 3-10-3 | cEt | 78 |
| 481549 | 6476 | 6491 | 3-10-3 | cEt | 96 |
| 481774 | 6477 | 6490 | 2-10-2 | cEt | 56 |
| 481553 | 10364 | 10379 | 3-10-3 | cEt | 96 |
| 481554 | 15469 | 15484 | 3-10-3 | cEt | 86 |
| 481779 | 15470 | 15483 | 2-10-2 | cEt | 60 |
| 481555 | 24588 | 24603 | 3-10-3 | cEt | 73 |
| 481780 | 24589 | 24602 | 2-10-2 | cEt | 60 |
| 481353 | 40968 | 40983 | 3-10-3 | cEt | 78 |
| 481354 | 40992 | 41007 | 3-10-3 | cEt | 98 |
| 481579 | 40993 | 41006 | 2-10-2 | cEt | 91 |
| 481355 | 41050 | 41065 | 3-10-3 | cEt | 95 |
| 481580 | 41051 | 41064 | 2-10-2 | cEt | 76 |
| 481356 | 41074 | 41089 | 3-10-3 | cEt | 83 |
| 481581 | 41075 | 41088 | 2-10-2 | cEt | 31 |
| 481357 | 42778 | 42793 | 3-10-3 | cEt | 97 |
| 481582 | 42779 | 42792 | 2-10-2 | cEt | 87 |
| 481358 | 42806 | 42821 | 3-10-3 | cEt | 85 |
| 481359 | 42832 | 42847 | 3-10-3 | cEt | 90 |
| 481360 | 42862 | 42877 | 3-10-3 | cEt | 75 |
| 481585 | 42863 | 42876 | 2-10-2 | cEt | 77 |
| 481361 | 42877 | 42892 | 3-10-3 | cEt | 90 |
| 481586 | 42878 | 42891 | 2-10-2 | cEt | 81 |
| 481368 | 50122 | 50137 | 3-10-3 | cEt | 81 |
| 481559 | 50668 | 50683 | 3-10-3 | cEt | 72 |
| 481784 | 50669 | 50682 | 2-10-2 | cEt | 79 |
| 481371 | 50673 | 50688 | 3-10-3 | cEt | 83 |
| 481372 | 50694 | 50709 | 3-10-3 | cEt | 85 |
| 481597 | 50695 | 50708 | 2-10-2 | cEt | 80 |
| 481373 | 50715 | 50730 | 3-10-3 | cEt | 87 |
| 481376 | 51705 | 51720 | 3-10-3 | cEt | 82 |
| 481601 | 51706 | 51719 | 2-10-2 | cEt | 70 |
| 481378 | 51905 | 51920 | 3-10-3 | cEt | 89 |
| 481603 | 51906 | 51919 | 2-10-2 | cEt | 60 |
| 481379 | 51968 | 51983 | 3-10-3 | cEt | 91 |
| 481604 | 51969 | 51982 | 2-10-2 | cEt | 70 |
| 481380 | 51976 | 51991 | 3-10-3 | cEt | 73 |
| 481382 | 55443 | 55458 | 3-10-3 | cEt | 81 |
| 481383 | 55451 | 55466 | 3-10-3 | cEt | 84 |
| 481384 | 55496 | 55511 | 3-10-3 | cEt | 76 |
| 481387 | 55748 | 55763 | 3-10-3 | cEt | 92 |
| 481612 | 55749 | 55762 | 2-10-2 | cEt | 86 |
| 481388 | 55792 | 55807 | 3-10-3 | cEt | 74 |
| 481390 | 57969 | 57984 | 3-10-3 | cEt | 92 |
| 481396 | 60034 | 60049 | 3-10-3 | cEt | 92 |
| 481621 | 60035 | 60048 | 2-10-2 | cEt | 74 |
| 481398 | 63306 | 63321 | 3-10-3 | cEt | 73 |
| 481399 | 63327 | 63342 | 3-10-3 | cEt | 73 |
| 481401 | 63353 | 63368 | 3-10-3 | cEt | 74 |
| 481405 | 64459 | 64474 | 3-10-3 | cEt | 75 |
| 481409 | 64729 | 64744 | 3-10-3 | cEt | 86 |
| 481410 | 64759 | 64774 | 3-10-3 | cEt | 91 |
| 481411 | 65859 | 65874 | 3-10-3 | cEt | 72 |
| 481412 | 65877 | 65892 | 3-10-3 | cEt | 90 |
| 481637 | 65878 | 65891 | 2-10-2 | cEt | 79 |
| 481413 | 65885 | 65900 | 3-10-3 | cEt | 80 |
| 481638 | 65886 | 65899 | 2-10-2 | cEt | 64 |
| 481566 | 66127 | 66142 | 3-10-3 | cEt | 62 |
| 481791 | 66128 | 66141 | 2-10-2 | cEt | 73 |
| 481415 | 66133 | 66148 | 3-10-3 | cEt | 88 |
| 481640 | 66134 | 66147 | 2-10-2 | cEt | 57 |
| 337332 | 66135 | 66154 | 5-10-5 | MOE | 63 |
| 481416 | 66138 | 66153 | 3-10-3 | cEt | 87 |
| 481641 | 66139 | 66152 | 2-10-2 | cEt | 68 |
| 337333 | 66140 | 66159 | 5-10-5 | MOE | 49 |
| 481417 | 66140 | 66155 | 3-10-3 | cEt | 97 |
| 481418 | 66141 | 66156 | 3-10-3 | cEt | 92 |
| 481642 | 66141 | 66154 | 2-10-2 | cEt | 67 |
| 481419 | 66142 | 66157 | 3-10-3 | cEt | 83 |

TABLE 105-continued

Inhibition of human Target-1 mRNA levels by cEt and MOE antisense oligonucleotides targeted to Target-1 Genomic Sequence

| ISIS NO | Human Start Site | Human Stop Site | Motif | Wing Chemistry | % inhibition |
|---------|------------------|-----------------|-------|----------------|--------------|
| 481420 | 66185 | 66200 | 3-10-3 | cEt | 94 |
| 481645 | 66186 | 66199 | 2-10-2 | cEt | 50 |
| 481421 | 66374 | 66389 | 3-10-3 | cEt | 86 |
| 481422 | 66389 | 66404 | 3-10-3 | cEt | 80 |
| 481423 | 66430 | 66445 | 3-10-3 | cEt | 69 |
| 481424 | 66446 | 66461 | 3-10-3 | cEt | 70 |
| 481425 | 66468 | 66483 | 3-10-3 | cEt | 78 |
| 481650 | 66469 | 66482 | 2-10-2 | cEt | 79 |
| 481426 | 66993 | 67008 | 3-10-3 | cEt | 80 |
| 481651 | 66994 | 67007 | 2-10-2 | cEt | 64 |
| 481427 | 67017 | 67032 | 3-10-3 | cEt | 75 |
| 481652 | 67018 | 67031 | 2-10-2 | cEt | 82 |
| 481428 | 67026 | 67041 | 3-10-3 | cEt | 77 |
| 481653 | 67027 | 67040 | 2-10-2 | cEt | 79 |
| 481429 | 67034 | 67049 | 3-10-3 | cEt | 84 |
| 481654 | 67035 | 67048 | 2-10-2 | cEt | 70 |
| 481430 | 67052 | 67067 | 3-10-3 | cEt | 67 |
| 481431 | 67068 | 67083 | 3-10-3 | cEt | 91 |
| 481433 | 67118 | 67133 | 3-10-3 | cEt | 73 |
| 481658 | 67119 | 67132 | 2-10-2 | cEt | 62 |
| 481434 | 67128 | 67143 | 3-10-3 | cEt | 73 |
| 345785 | 67129 | 67148 | 5-10-5 | MOE | 50 |
| 481659 | 67129 | 67142 | 2-10-2 | cEt | 51 |
| 481435 | 67131 | 67146 | 3-10-3 | cEt | 49 |
| 481660 | 67132 | 67145 | 2-10-2 | cEt | 54 |
| 481436 | 67137 | 67152 | 3-10-3 | cEt | 82 |
| 481661 | 67138 | 67151 | 2-10-2 | cEt | 76 |
| 481568 | 72290 | 72305 | 3-10-3 | cEt | 85 |
| 481793 | 72291 | 72304 | 2-10-2 | cEt | 93 |
| 481569 | 72430 | 72445 | 3-10-3 | cEt | 62 |
| 481794 | 72431 | 72444 | 2-10-2 | cEt | 81 |
| 481570 | 72438 | 72453 | 3-10-3 | cEt | 79 |
| 481440 | 72586 | 72601 | 3-10-3 | cEt | 79 |
| 481443 | 72622 | 72637 | 3-10-3 | cEt | 78 |
| 481444 | 72630 | 72645 | 3-10-3 | cEt | 66 |
| 481445 | 72638 | 72653 | 3-10-3 | cEt | 70 |
| 481670 | 72639 | 72652 | 2-10-2 | cEt | 60 |
| 481449 | 73690 | 73705 | 3-10-3 | cEt | 77 |
| 481452 | 73818 | 73833 | 3-10-3 | cEt | 71 |
| 481453 | 73868 | 73883 | 3-10-3 | cEt | 92 |
| 481678 | 73869 | 73882 | 2-10-2 | cEt | 78 |
| 481454 | 73889 | 73904 | 3-10-3 | cEt | 85 |
| 481679 | 73890 | 73903 | 2-10-2 | cEt | 69 |
| 481455 | 73909 | 73924 | 3-10-3 | cEt | 74 |
| 481457 | 73966 | 73981 | 3-10-3 | cEt | 88 |
| 481682 | 73967 | 73980 | 2-10-2 | cEt | 77 |
| 481459 | 74095 | 74110 | 3-10-3 | cEt | 76 |
| 481684 | 74096 | 74109 | 2-10-2 | cEt | 89 |
| 481460 | 74130 | 74145 | 3-10-3 | cEt | 83 |
| 481685 | 74131 | 74144 | 2-10-2 | cEt | 36 |
| 481461 | 74156 | 74171 | 3-10-3 | cEt | 75 |
| 481686 | 74157 | 74170 | 2-10-2 | cEt | 70 |
| 481462 | 74171 | 74186 | 3-10-3 | cEt | 89 |
| 481687 | 74172 | 74185 | 2-10-2 | cEt | 80 |
| 481463 | 74188 | 74203 | 3-10-3 | cEt | 88 |
| 481688 | 74189 | 74202 | 2-10-2 | cEt | 13 |
| 481464 | 74203 | 74218 | 3-10-3 | cEt | 97 |
| 481689 | 74204 | 74217 | 2-10-2 | cEt | 40 |
| 481466 | 74234 | 74249 | 3-10-3 | cEt | 74 |
| 481691 | 74235 | 74248 | 2-10-2 | cEt | 77 |
| 481467 | 74284 | 74299 | 3-10-3 | cEt | 74 |
| 481692 | 74285 | 74298 | 2-10-2 | cEt | 74 |
| 481468 | 74299 | 74314 | 3-10-3 | cEt | 71 |
| 481695 | 74649 | 74662 | 2-10-2 | cEt | 83 |
| 481472 | 74678 | 74693 | 3-10-3 | cEt | 76 |
| 481697 | 74679 | 74692 | 2-10-2 | cEt | 63 |
| 481474 | 74708 | 74723 | 3-10-3 | cEt | 80 |
| 481475 | 74723 | 74738 | 3-10-3 | cEt | 93 |
| 481700 | 74724 | 74737 | 2-10-2 | cEt | 89 |
| 481476 | 74738 | 74753 | 3-10-3 | cEt | 92 |
| 481701 | 74739 | 74752 | 2-10-2 | cEt | 60 |
| 481477 | 74754 | 74769 | 3-10-3 | cEt | 95 |
| 481702 | 74755 | 74768 | 2-10-2 | cEt | 89 |
| 481478 | 74772 | 74787 | 3-10-3 | cEt | 84 |
| 481479 | 74787 | 74802 | 3-10-3 | cEt | 80 |
| 481485 | 74904 | 74919 | 3-10-3 | cEt | 90 |
| 481710 | 74905 | 74918 | 2-10-2 | cEt | 88 |
| 481486 | 74917 | 74932 | 3-10-3 | cEt | 75 |
| 481711 | 74918 | 74931 | 2-10-2 | cEt | 74 |
| 481487 | 74933 | 74948 | 3-10-3 | cEt | 66 |
| 481490 | 75020 | 75035 | 3-10-3 | cEt | 78 |
| 481715 | 75021 | 75034 | 2-10-2 | cEt | 79 |
| 481491 | 75035 | 75050 | 3-10-3 | cEt | 70 |
| 481716 | 75036 | 75049 | 2-10-2 | cEt | 68 |
| 481492 | 75050 | 75065 | 3-10-3 | cEt | 61 |
| 481495 | 75127 | 75142 | 3-10-3 | cEt | 92 |
| 481720 | 75128 | 75141 | 2-10-2 | cEt | 63 |
| 481498 | 75179 | 75194 | 3-10-3 | cEt | 90 |
| 481500 | 75209 | 75224 | 3-10-3 | cEt | 92 |
| 481725 | 75210 | 75223 | 2-10-2 | cEt | 88 |
| 481501 | 75235 | 75250 | 3-10-3 | cEt | 91 |
| 481502 | 75250 | 75265 | 3-10-3 | cEt | 85 |
| 481727 | 75251 | 75264 | 2-10-2 | cEt | 70 |
| 481510 | 75424 | 75439 | 3-10-3 | cEt | 95 |
| 481735 | 75425 | 75438 | 2-10-2 | cEt | 22 |
| 481513 | 75477 | 75492 | 3-10-3 | cEt | 85 |
| 481738 | 75478 | 75491 | 2-10-2 | cEt | 70 |
| 481514 | 75492 | 75507 | 3-10-3 | cEt | 85 |
| 481739 | 75493 | 75506 | 2-10-2 | cEt | 60 |
| 481515 | 75512 | 75527 | 3-10-3 | cEt | 88 |
| 481740 | 75513 | 75526 | 2-10-2 | cEt | 71 |
| 481516 | 75551 | 75566 | 3-10-3 | cEt | 78 |
| 481741 | 75552 | 75565 | 2-10-2 | cEt | 80 |
| 481517 | 75581 | 75596 | 3-10-3 | cEt | 87 |
| 481742 | 75582 | 75595 | 2-10-2 | cEt | 64 |
| 481518 | 75612 | 75627 | 3-10-3 | cEt | 67 |
| 481743 | 75613 | 75626 | 2-10-2 | cEt | 75 |
| 481744 | 75625 | 75638 | 2-10-2 | cEt | 69 |
| 481520 | 75626 | 75641 | 3-10-3 | cEt | 73 |
| 481745 | 75627 | 75640 | 2-10-2 | cEt | 74 |
| 481521 | 75646 | 75661 | 3-10-3 | cEt | 86 |
| 481746 | 75647 | 75660 | 2-10-2 | cEt | 67 |
| 481522 | 75661 | 75676 | 3-10-3 | cEt | 92 |
| 481747 | 75662 | 75675 | 2-10-2 | cEt | 95 |
| 481523 | 75676 | 75691 | 3-10-3 | cEt | 95 |
| 481524 | 75717 | 75732 | 3-10-3 | cEt | 70 |
| 481749 | 75718 | 75731 | 2-10-2 | cEt | 70 |
| 481525 | 75728 | 75743 | 3-10-3 | cEt | 93 |
| 481750 | 75729 | 75742 | 2-10-2 | cEt | 94 |
| 481526 | 75730 | 75745 | 3-10-3 | cEt | 82 |
| 481528 | 75766 | 75781 | 3-10-3 | cEt | 77 |
| 481753 | 75767 | 75780 | 2-10-2 | cEt | 71 |
| 481530 | 75817 | 75832 | 3-10-3 | cEt | 87 |
| 481755 | 75818 | 75831 | 2-10-2 | cEt | 84 |
| 481757 | 75852 | 75865 | 2-10-2 | cEt | 81 |
| 481533 | 75853 | 75868 | 3-10-3 | cEt | 80 |
| 481758 | 75854 | 75867 | 2-10-2 | cEt | 62 |
| 481534 | 75880 | 75895 | 3-10-3 | cEt | 79 |
| 481759 | 75881 | 75894 | 2-10-2 | cEt | 74 |
| 481535 | 75954 | 75969 | 3-10-3 | cEt | 78 |
| 481760 | 75955 | 75968 | 2-10-2 | cEt | 78 |
| 481536 | 75969 | 75984 | 3-10-3 | cEt | 91 |
| 481761 | 75970 | 75983 | 2-10-2 | cEt | 78 |
| 481537 | 76017 | 76032 | 3-10-3 | cEt | 84 |
| 481538 | 76031 | 76046 | 3-10-3 | cEt | 92 |
| 481763 | 76032 | 76045 | 2-10-2 | cEt | 96 |
| 481539 | 76047 | 76062 | 3-10-3 | cEt | 19 |
| 481541 | 76121 | 76136 | 3-10-3 | cEt | 71 |

Example 59 Antisense Inhibition of Murine Target-1 in b.END Cells

Antisense oligonucleotides tested in the study described in Example 58 were also tested for their effects on Target-1 mRNA in b.END cells. Cultured b.END cells at a density of 20,000 cells per well were transfected using electroporation with 7,000 nM antisense oligonucleotide. After a treatment period of approximately 24 hours, RNA was isolated from the cells and Target-1 mRNA levels were measured by quantitative real-time PCR. Target-1 mRNA levels were adjusted according to total RNA content, as measured by RIBOGREEN®.

Certain sequences complementary to the Target-1 mouse gene sequence showed good inhibition in b. END cells. Results are presented in Table 106 as percent inhibition of Target-1, relative to untreated control cells. The human oligonucleotides in Table 106 were compared to the mouse Target-1 genomic sequence. "Mouse Target start site" indicates the 5'-most nucleotide to which the gapmer is targeted in the murine sequence. "Mouse Target stop site" indicates the 3'-most nucleotide to which the gapmer is targeted murine sequence.

TABLE 106

Inhibition of human Target-1 mRNA levels by certain antisense oligonucleotides complementary to Murine Target-1

| ISIS NO | Mouse Start Site | Mouse Stop Site | % inhibition |
|---|---|---|---|
| 481549 | 5283 | 5298 | 96 |
| 481553 | 9913 | 9928 | 94 |
| 481768 | 3189 | 3202 | 91 |
| 481356 | 30356 | 30371 | 83 |
| 481548 | 4045 | 4060 | 82 |
| 481554 | 14662 | 14677 | 82 |
| 481426 | 48328 | 48343 | 82 |
| 481580 | 30333 | 30346 | 81 |
| 481412 | 47413 | 47428 | 81 |
| 481417 | 47636 | 47651 | 81 |
| 481418 | 47637 | 47652 | 80 |
| 481355 | 30332 | 30347 | 79 |
| 481396 | 43120 | 43135 | 79 |
| 481416 | 47634 | 47649 | 79 |
| 481420 | 47681 | 47696 | 79 |
| 481358 | 32842 | 32857 | 78 |
| 481363 | 33520 | 33535 | 78 |
| 481570 | 51870 | 51885 | 78 |
| 481382 | 37857 | 37872 | 77 |
| 481378 | 36560 | 36575 | 76 |
| 481431 | 48403 | 48418 | 76 |
| 481453 | 53034 | 53049 | 76 |
| 481621 | 43121 | 43134 | 75 |
| 481641 | 47635 | 47648 | 75 |
| 481637 | 47414 | 47427 | 74 |
| 481380 | 36631 | 36646 | 73 |
| 481574 | 53000 | 53015 | 73 |
| 481601 | 36392 | 36405 | 71 |
| 481419 | 47638 | 47653 | 71 |
| 481371 | 35938 | 35953 | 70 |
| 481642 | 47637 | 47650 | 70 |
| 481542 | 3180 | 3195 | 69 |
| 481547 | 3313 | 3328 | 69 |
| 481772 | 3314 | 3327 | 69 |
| 481362 | 32929 | 32944 | 69 |
| 481653 | 48362 | 48375 | 69 |
| 481786 | 38812 | 38825 | 68 |
| 481415 | 47629 | 47644 | 68 |
| 481543 | 3188 | 3203 | 67 |
| 481793 | 51714 | 51727 | 67 |
| 481443 | 52060 | 52075 | 67 |
| 481684 | 53229 | 53242 | 67 |
| 481398 | 45226 | 45241 | 66 |
| 481560 | 36394 | 36409 | 65 |
| 481643 | 47638 | 47651 | 65 |
| 481430 | 48387 | 48402 | 65 |
| 481440 | 52024 | 52039 | 65 |

Example 60: Tolerability of Antisense Oligonucleotides Targeting Target-1 in BALB/c Mice Forty antisense oligonucleotides exhibiting a high level of activity, selected from among the 452 compounds evaluated in Example 58, were further tested for in vivo tolerability.

Groups of 2-4 male BALB/c mice were injected subcutaneously twice a week for 3 weeks with 25 mg/kg of ISIS antisense oligonucleotides. One group of 4 male BALB/c mice was injected subcutaneously twice a week for 3 weeks with PBS. This group of mice was utilized as a control group to which the treatment groups were compared. One day after the last dose, body weights were taken, mice were euthanized, and organs and plasma were harvested for further analysis.

The body weights of the mice were measured pre-dose and at the end of the treatment period. Percent increase over the initial body weight was calculated. Liver, spleen, and kidney weights were measured at the end of the study and were compared to PBS treated mice.

To evaluate the effect of ISIS oligonucleotides on metabolic function, plasma concentrations of transaminases and BUN were measured using an automated clinical chemistry analyzer (Hitachi Olympus AU400e, Melville, N.Y.). Plasma concentrations of ALT (alanine transaminase), AST (aspartate transaminase), and BUN were measured.

Among the forty antisense oligonucleotides tested, certain antisense oligonucleotides, including ISIS 481374, ISIS 481390, ISIS 481420, ISIS 481431, ISIS 481453, ISIS 481464, ISIS 481475, ISIS 481495, ISIS 481500, ISIS 481501, ISIS 481525, ISIS 481548, ISIS 481549, ISIS 481597, ISIS 481695, ISIS 481700, ISIS 481702, ISIS 481710, ISIS 481725, ISIS 481750, and ISIS 481763 met tolerability thresholds for body weight, organ weight, ALT, AST, and BUN parameters.

Example 61: Dose-Dependent Antisense Inhibition of Human Target-1 in HuVEC Cells Gapmers from Examples 58 and 59 exhibiting in vitro inhibition of Target-1 were tested at various doses in HuVEC cells. Cells were plated at a density of 20,000 cells per well and transfected using electroporation with 31.25 nM, 62.5 nM, 125 nM, 250 nM, 500 nM, and 1,0000 nM concentrations of antisense oligonucleotide, as specified in Table 107. After a treatment period of approximately 16 hours, RNA was isolated from the cells and Target-1 mRNA levels were measured by quantitative real-time PCR. Target-1 mRNA levels were adjusted according to total RNA content, as measured by RIBOGREEN®. Results are presented as percent inhibition of Target-1, relative to untreated control cells.

The half maximal inhibitory concentration ($IC_{50}$) of each oligonucleotide is also presented in Table 107 and was calculated by plotting the concentrations of oligonucleotides used versus the percent inhibition of Target-1 mRNA expression achieved at each concentration and noting the concentration of oligonucleotide at which 50% inhibition of Target-1 mRNA expression was achieved compared to the control.

TABLE 107

Dose-dependent antisense inhibition of human Target-1 in HuVEC cells using electroporation

| ISIS No | 31.25 nM | 62.5 nM | 125.0 nM | 250.0 nM | 500.0 nM | 1000.0 nM | IC$_{50}$ (µM) |
|---|---|---|---|---|---|---|---|
| 481355 | 19 | 15 | 36 | 61 | 75 | 89 | 0.18 |
| 481374 | 25 | 42 | 52 | 72 | 82 | 88 | 0.10 |
| 481390 | 17 | 37 | 44 | 60 | 73 | 86 | 0.15 |
| 481420 | 23 | 20 | 40 | 60 | 81 | 92 | 0.16 |
| 481453 | 21 | 37 | 52 | 69 | 79 | 88 | 0.12 |
| 481464 | 57 | 73 | 81 | 90 | 94 | 94 | <0.03 |
| 481475 | 22 | 46 | 54 | 78 | 83 | 92 | 0.10 |
| 481500 | 25 | 37 | 42 | 75 | 83 | 90 | 0.12 |
| 481501 | 32 | 57 | 69 | 82 | 94 | 94 | 0.05 |
| 481523 | 35 | 60 | 74 | 85 | 90 | 93 | 0.04 |
| 481525 | 36 | 53 | 60 | 79 | 89 | 92 | 0.06 |
| 481549 | 0 | 16 | 60 | 81 | 90 | 96 | 0.15 |
| 481554 | 0 | 15 | 28 | 49 | 70 | 86 | 0.25 |
| 481597 | 8 | 18 | 39 | 48 | 64 | 83 | 0.24 |
| 481695 | 15 | 27 | 39 | 50 | 64 | 80 | 0.22 |
| 481700 | 0 | 17 | 44 | 58 | 80 | 88 | 0.20 |
| 481710 | 12 | 39 | 65 | 79 | 86 | 90 | 0.11 |
| 481715 | 11 | 26 | 32 | 44 | 53 | 69 | 0.36 |
| 481725 | 27 | 40 | 56 | 77 | 89 | 93 | 0.09 |
| 481750 | 7 | 24 | 46 | 63 | 83 | 89 | 0.16 |
| 481755 | 17 | 28 | 30 | 54 | 68 | 80 | 0.20 |
| 481768 | 7 | 21 | 27 | 44 | 67 | 85 | 0.26 |

Example 62: Dose-Dependent Antisense Inhibition of Target-1 Following Free Uptake of Antisense Oligonucleotide in SK-BR-3 Cells Gapmers from Example 61 were tested at various doses in SK-BR-3 cells. Cells were plated at a density of 4,000 cells per well. Cells were incubated with 0.02 µM, 0.1 µM, 0.5 µM, 1 µM. 2.5 µM, and 10 µM concentrations of antisense oligonucleotide, as specified in Table 108. After approximately 24 hours, RNA was isolated from the cells and Target-1 mRNA levels were measured by quantitative real-time PCR. Target-1 mRNA levels were adjusted according to total RNA content, as measured by RIBOGREEN®. Results are presented as percent inhibition of Target-1, relative to untreated control cells. The half maximal inhibitory concentration (IC$_{50}$) of each oligonucleotide is also presented in Table 108.

TABLE 108

Dose-dependent antisense inhibition of human Target 1 by free-uptake of ISIS oligonucleotide by SK-BR-3 cells

| ISIS No | 0.02 µM | 0.1 µM | 0.5 µM | 1 µM | 2.5 µM | 10 µM | IC$_{50}$ (µM) |
|---|---|---|---|---|---|---|---|
| 481374 | 10 | 18 | 18 | 16 | 8 | 25 | 15.9 |
| 481390 | 0 | 10 | 11 | 12 | 40 | 72 | 3.2 |
| 481453 | 14 | 13 | 27 | 45 | 58 | 79 | 1.3 |
| 481464 | 23 | 32 | 57 | 70 | 85 | 93 | 0.5 |
| 481475 | 0 | 0 | 35 | 49 | 72 | 88 | 1.0 |
| 481500 | 7 | 9 | 26 | 45 | 49 | 75 | 1.7 |
| 481501 | 0 | 0 | 4 | 5 | 53 | 65 | 2.7 |
| 481523 | 9 | 24 | 56 | 67 | 83 | 92 | 0.5 |
| 481525 | 0 | 17 | 13 | 15 | 32 | 68 | 4.4 |
| 481549 | 0 | 0 | 0 | 16 | 33 | 54 | 8.2 |
| 481597 | 1 | 0 | 11 | 14 | 22 | 44 | 10.6 |
| 481695 | 0 | 0 | 0 | 0 | 0 | 0 | — |
| 481710 | 5 | 0 | 10 | 13 | 27 | 66 | 6.0 |
| 481725 | 29 | 45 | 47 | 39 | 39 | 63 | 2.6 |
| 481750 | 19 | 24 | 36 | 42 | 71 | 80 | 1.1 |
| 481763 | 30 | 38 | 51 | 63 | 81 | 89 | 0.6 |
| 481768 | 12 | 5 | 34 | 25 | 32 | 35 | 12.4 |

Example 63: Dose-Dependent Antisense Inhibition of Target-1 Following Free Uptake of Antisense Oligonucleotide in U251-MG Cells Gapmers from Example 62 were further tested at various doses in U251-MG cells. Cells were plated at a density of 4,000 cells per well. Cells were incubated with 0.02 µM, 0.1 µM, 0.5 µM, 1 µM. 2.5 µM, and 10 µM concentrations of antisense oligonucleotide, as specified in Table 109. After approximately 24 hours, RNA was isolated from the cells and Target-1 mRNA levels were measured by quantitative real-time PCR. Target-1 mRNA levels were adjusted according to total RNA content, as measured by RIBOGREEN®. Results are presented as percent inhibition of Target-1, relative to untreated control cells. The half maximal inhibitory concentration (IC$_{50}$) of each oligonucleotide is also presented in Table 109.

TABLE 109

Dose-dependent antisense inhibition of Target-1 mRNA levels by free-uptake of ISIS oligonucleotide by U251-MG cells

| ISIS No | 0.02 µM | 0.1 µM | 0.5 µM | 1 µM | 2.5 µM | 10 µM | IC$_{50}$ (µM) |
|---|---|---|---|---|---|---|---|
| 481374 | 0 | 0 | 10 | 0 | 12 | 25 | 15.7 |
| 481390 | 0 | 4 | 10 | 8 | 16 | 31 | 13.9 |
| 481453 | 4 | 3 | 15 | 16 | 20 | 42 | 11.0 |
| 481464 | 13 | 11 | 41 | 42 | 54 | 79 | 1.3 |
| 481475 | 3 | 13 | 26 | 37 | 41 | 67 | 2.6 |
| 481500 | 2 | 12 | 14 | 12 | 25 | 38 | 11.7 |
| 481501 | 0 | 0 | 2 | 1 | 14 | 47 | 10.3 |
| 481523 | 22 | 27 | 39 | 45 | 63 | 83 | 1.1 |
| 481525 | 1 | 1 | 17 | 17 | 35 | 60 | 6.3 |
| 481549 | 0 | 0 | 0 | 0 | 9 | 29 | 14.5 |
| 481597 | 3 | 3 | 12 | 18 | 18 | 47 | 10.1 |
| 481695 | 0 | 14 | 12 | 22 | 25 | 33 | 12.9 |
| 481710 | 0 | 0 | 0 | 0 | 6 | 23 | 16.8 |
| 481725 | 0 | 0 | 5 | 7 | 20 | 38 | 11.8 |
| 481750 | 4 | 15 | 18 | 18 | 17 | 33 | 13.2 |
| 481763 | 15 | 16 | 25 | 36 | 36 | 64 | 3.2 |
| 481768 | 22 | 16 | 18 | 22 | 21 | 37 | 12.2 |

Example 64: Dose-Dependent Antisense Inhibition of Target-1 Following Free Uptake of Antisense Oligonucleotide in U251-MG Cells ISIS 481464 and ISIS 481549, from the studies described above, were further tested at different doses in U251-MG cells. Cells were plated at a density of 4,000 cells per well. Cells were incubated with 0.1 µM, 1 µM, 5 µM, 10 µM, and 20 µM concentrations of antisense oligonucleotide, as specified in Table 110. After approximately 24 hours, RNA was isolated from the cells and Target-1 mRNA levels were measured by quantitative real-time PCR. Target-1 mRNA levels were adjusted according to total RNA content, as measured by RIBOGREEN®. Results are presented as percent inhibition of Target-1, relative to untreated control cells.

TABLE 110

Dose-dependent antisense inhibition of Target-1 mRNA levels by free-uptake of ISIS oligonucleotide by U251-MG cells

| ISIS No | 0.1 µM | 1 µM | 5 µM | 10 µM | 20 µM | IC$_{50}$ (µM) |
|---|---|---|---|---|---|---|
| 481464 | 0 | 30 | 69 | 80 | 79 | 2.3 |
| 481549 | 0 | 0 | 26 | 35 | 38 | >20 |

Example 65: Dose-Dependent Antisense Inhibition of Target-1 Following Free Uptake of Antisense Oligonucleotide in MDA-MB-231 Cells ISIS 481464 and ISIS 481549 were further tested at different doses in MDA-MB-231 cells. Cells were plated at a density of 4,000 cells per well. Cells were incubated with 0.02 µM, 0.2 µM, 1.0 µM, 5.0 µM, and 10.0 µM concentrations of antisense oligonucleotide, as specified in Table 111. After approximately 24 hours, RNA was isolated from the cells and Target-1 mRNA levels were measured by quantitative real-time PCR. Target-1 mRNA levels were adjusted according to total RNA content, as measured by RIBOGREEN®. Results are presented as percent inhibition of Target-1, relative to untreated control cells.

TABLE 111

Dose-dependent antisense inhibition of Target-1 mRNA levels by free-uptake of ISIS oligonucleotide by MDA-MB-231 cells

| ISIS No | 0.02 µM | 0.2 µM | 1.0 µM | 5.0 µM | 10.0 µM | IC$_{50}$ (µM) |
|---|---|---|---|---|---|---|
| 481464 | 0 | 25 | 71 | 85 | 87 | 0.6 |
| 481549 | 0 | 2 | 33 | 49 | 66 | 4.4 |

Example 66: Dose-Dependent Antisense Inhibition of Target-1 Following Free Uptake of Antisense Oligonucleotide in A431 Cells ISIS 481464 and ISIS 481549 were further tested at different doses in A431 cells. Cells were plated at a density of 4,000 cells per well. Cells were incubated with 0.02 µM, 0.2 µM, 1.0 µM, 5.0 µM, and 10.0 µM concentrations of antisense oligonucleotide, as specified in Table 112. After approximately 24 hours, RNA was isolated from the cells and Target-1 mRNA levels were measured by quantitative real-time PCR. Target-1 mRNA levels were adjusted according to total. RNA content, as measured by RIBOGREEN®. Results are presented as percent inhibition of Target-1, relative to untreated control cells.

TABLE 112

Dose-dependent antisense inhibition of Target-1 mRNA levels by free-uptake of ISIS oligonucleotide by A431 cells

| ISIS No | 0.02 µM | 0.2 µM | 1.0 µM | 5.0 µM | 10.0 µM | IC$_{50}$ (µM) |
|---|---|---|---|---|---|---|
| 481464 | 79 | 93 | 98 | 98 | 98 | <0.02 |
| 481549 | 0 | 38 | 68 | 82 | 84 | 0.6 |

Example 67: Dose-Dependent Antisense Inhibition of Target-1 Following Free Uptake of Antisense Oligonucleotide in 11460 Cells ISIS 481464 and ISIS 481549 were further tested at different doses in H460 cells. Cells were plated at a density of 4,000 cells per well. Cells were incubated with 0.02 µM, 0.2 µM, 1.0 µM, 5.0 µM, and 10.0 µM concentrations of antisense oligonucleotide, as specified in Table 113. After approximately 24 hours, RNA was isolated from the cells and Target-1 mRNA levels were measured by quantitative real-time PCR. Target-1 mRNA levels were adjusted according to total RNA content, as measured by RIBOGREEN®. Results are presented as percent inhibition of Target-1, relative to untreated control cells.

TABLE 113

Dose-dependent antisense inhibition of Target-1 mRNA levels by free-uptake of ISIS oligonucleotide by H460 cells

| ISIS No | 0.02 µM | 0.2 µM | 1.0 µM | 5.0 µM | 10.0 µM | IC$_{50}$ (µM) |
|---|---|---|---|---|---|---|
| 481464 | 46 | 89 | 96 | 97 | 98 | 0.01 |
| 481549 | 8 | 53 | 78 | 96 | 98 | 0.23 |

Example 68: Antisense Inhibition of Human Target-1 in HuVEC Cells

Antisense oligonucleotides were designed targeting a human Target-1 nucleic acid and were tested for their effect on human Target-1 mRNA expression in vitro. Cultured HuVEC cells at a density of 20,000 cells per well were transfected using electroporation with 1,000 nM antisense oligonucleotide. After a treatment period of approximately 24 hours, RNA was isolated from the cells and Target-1 mRNA levels were measured by quantitative real-time PCR. Target-1 mRNA levels were adjusted according to total RNA content, as measured by RIBOGREEN®. Results are presented as percent inhibition of Target-1, relative to untreated control cells.

The chimeric antisense oligonucleotides in Table 114 were designed as 3-10-3 MOE, deoxy, and cEt gapmers as indicated in the Table. The chemistry column of Table 114 presents the sugar motif of each gapmer, wherein 'e' indicates a 2'-MOE nucleoside, 'k' indicates a constrained ethyl (cEt) nucleoside, and 'd' indicates a 2'-deoxynucleoside. The internucleoside linkages throughout each gapmer are phosphorothioate (P=S) linkages. All cytosine residues throughout each gapmer are 5'-methylcytosines.

"Human Target start site" indicates the 5'-most nucleoside to which the gapmer is targeted in the human gene sequence. "Human Target stop site" indicates the 3'-most nucleoside to which the gapmer is targeted in the human gene sequence. Each gapmer listed in Table 114 is targeted to human Target-1 mRNA.

TABLE 114

Inhibition of human Target-1 mRNA levels by chimeric antisense oligonucleotides targeted to Target-1 mRNA

| Human Start Site | Human Stop Site | ISIS No | Chemistry | % inhibition |
|---|---|---|---|---|
| 250 | 265 | 528204 | e-e-e-d(10)-k-k-k | 83 |
| 251 | 266 | 528205 | e-e-e-d(10)-k-k-k | 72 |
| 252 | 267 | 528206 | e-e-e-d(10)-k-k-k | 44 |
| 253 | 268 | 528207 | e-e-e-d(10)-k-k-k | 49 |
| 263 | 278 | 528208 | e-e-e-d(10)-k-k-k | 73 |
| 264 | 279 | 528209 | e-e-e-d(10)-k-k-k | 81 |
| 265 | 280 | 528210 | e-e-e-d(10)-k-k-k | 78 |
| 266 | 281 | 528211 | e-e-e-d(10)-k-k-k | 72 |
| 267 | 282 | 528212 | e-e-e-d(10)-k-k-k | 81 |
| 268 | 283 | 528213 | e-e-e-d(10)-k-k-k | 46 |
| 270 | 285 | 528214 | e-e-e-d(10)-k-k-k | 80 |
| 271 | 286 | 528215 | e-e-e-d(10)-k-k-k | 69 |
| 433 | 448 | 528269 | e-e-e-d(10)-k-k-k | 69 |
| 434 | 449 | 528270 | e-e-e-d(10)-k-k-k | 73 |
| 435 | 450 | 528271 | e-e-e-d(10)-k-k-k | 71 |
| 867 | 882 | 528378 | e-e-e-d(10)-k-k-k | 72 |
| 1146 | 1161 | 528501 | e-e-e-d(10)-k-k-k | 67 |
| 1147 | 1162 | 528502 | e-e-e-d(10)-k-k-k | 76 |

TABLE 114-continued

Inhibition of human Target-1 mRNA levels by chimeric antisense oligonucleotides targeted to Target-1 mRNA

| Human Start Site | Human Stop Site | ISIS No | Chemistry | % inhibition |
|---|---|---|---|---|
| 1153 | 1168 | 528503 | e-e-e-d(10)-k-k-k | 68 |
| 1154 | 1169 | 528504 | e-e-e-d(10)-k-k-k | 69 |
| 1155 | 1170 | 528505 | e-e-e-d(10)-k-k-k | 68 |
| 1206 | 1221 | 528518 | e-e-e-d(10)-k-k-k | 80 |
| 1207 | 1222 | 528519 | e-e-e-d(10)-k-k-k | 61 |
| 1208 | 1223 | 528520 | e-e-e-d(10)-k-k-k | 63 |
| 2699 | 2714 | 528833 | e-e-e-d(10)-k-k-k | 77 |
| 2980 | 2995 | 528845 | e-e-e-d(10)-k-k-k | 65 |
| 2981 | 2996 | 528846 | e-e-e-d(10)-k-k-k | 80 |
| 2982 | 2997 | 528847 | e-e-e-d(10)-k-k-k | 72 |
| 2983 | 2998 | 528848 | e-e-e-d(10)-k-k-k | 46 |
| 2984 | 2999 | 528849 | e-e-e-d(10)-k-k-k | 59 |
| 3001 | 3016 | 528850 | e-e-e-d(10)-k-k-k | 10 |
| 3008 | 3023 | 528851 | e-e-e-d(10)-k-k-k | 61 |
| 3010 | 3025 | 528852 | e-e-e-d(10)-k-k-k | 88 |
| 3012 | 3027 | 528853 | e-e-e-d(10)-k-k-k | 91 |
| 3016 | 3031 | 518349 | e-e-e-d(10)-k-k-k | 85 | e = 2'-MOE,
k = cEt,
d = 2'-deoxynucleoside

Example 69: Dose-Dependent Antisense Inhibition of Human Target-1 in HuVEC Cells Gapmers from the study described in Example 68, above, exhibiting in vitro inhibition of Target-1 were tested at various doses in HuVEC cells. Cells were plated at a density of 20,000 cells per well and transfected using electroporation with 23.4375 nM, 93.75 nM, 375.0 nM, and 1,500.0 nM concentrations of antisense oligonucleotide, as specified in Table 115. After a treatment period of approximately 16 hours, RNA was isolated from the cells and Target-1 mRNA levels were measured by quantitative real-time PCR. Target-1 mRNA levels were adjusted according to total RNA content, as measured by RIBOGREEN®. Results are presented as percent inhibition of Target-1, relative to untreated control cells.

TABLE 115

Dose-dependent antisense inhibition of human Target-1 in HuVEC cells

| ISIS No | 23.4375 nM | 93.75 nM | 375.0 nM | 1500.0 nM | IC$_{50}$ (µM) |
|---|---|---|---|---|---|
| 518340 | 0 | 8 | 28 | 63 | 1.0 |
| 518349 | 13 | 30 | 68 | 90 | 0.2 |
| 528189 | 8 | 13 | 43 | 71 | 0.5 |
| 528204 | 4 | 24 | 53 | 79 | 0.3 |
| 528205 | 0 | 9 | 59 | 80 | 0.4 |
| 528208 | 0 | 19 | 56 | 84 | 0.3 |
| 528209 | 0 | 28 | 58 | 90 | 0.3 |
| 528210 | 0 | 16 | 49 | 87 | 0.3 |
| 528211 | 0 | 10 | 47 | 86 | 0.4 |
| 528212 | 0 | 16 | 42 | 83 | 0.4 |
| 528214 | 0 | 25 | 55 | 88 | 0.3 |
| 528215 | 3 | 16 | 53 | 82 | 0.3 |
| 528237 | 13 | 19 | 33 | 73 | 0.6 |
| 528245 | 3 | 16 | 53 | 78 | 0.4 |
| 528263 | 0 | 3 | 32 | 76 | 0.6 |
| 528264 | 9 | 0 | 19 | 50 | >1.5 |
| 528268 | 0 | 7 | 25 | 63 | 1.0 |
| 528269 | 0 | 11 | 39 | 77 | 0.5 |
| 528270 | 5 | 9 | 48 | 79 | 0.4 |
| 528271 | 0 | 14 | 37 | 81 | 0.5 |
| 528327 | 0 | 0 | 26 | 72 | 0.8 |
| 528347 | 0 | 2 | 25 | 69 | 0.9 |
| 528357 | 0 | 17 | 36 | 69 | 0.6 |
| 528389 | 0 | 3 | 19 | 82 | 0.7 |
| 528501 | 0 | 17 | 40 | 69 | 0.6 |
| 528502 | 0 | 10 | 35 | 76 | 0.6 |
| 528503 | 3 | 1 | 38 | 70 | 0.7 |
| 528504 | 0 | 19 | 45 | 72 | 0.5 |
| 528505 | 0 | 7 | 41 | 73 | 0.6 |
| 528518 | 0 | 24 | 51 | 81 | 0.3 |
| 528534 | 0 | 8 | 32 | 72 | 0.7 |
| 528539 | 0 | 7 | 39 | 73 | 0.6 |
| 528557 | 0 | 9 | 26 | 53 | >1.5 |
| 528565 | 4 | 12 | 31 | 57 | 1.3 |
| 528567 | 8 | 13 | 25 | 54 | >1.5 |
| 528569 | 9 | 19 | 37 | 60 | 0.8 |
| 528574 | 5 | 17 | 32 | 62 | 0.9 |
| 528622 | 10 | 4 | 29 | 68 | 0.9 |
| 528623 | 0 | 13 | 24 | 62 | 1.1 |
| 528626 | 1 | 0 | 34 | 68 | 0.8 |
| 528627 | 22 | 19 | 30 | 64 | 1.0 |
| 528664 | 0 | 14 | 37 | 74 | 0.5 |
| 528675 | 0 | 10 | 28 | 62 | 1.0 |
| 528689 | 0 | 16 | 33 | 65 | 0.7 |
| 528691 | 0 | 3 | 34 | 61 | 0.9 |
| 528695 | 1 | 4 | 36 | 66 | 0.8 |
| 528697 | 3 | 15 | 39 | 72 | 0.5 |
| 528710 | 13 | 16 | 28 | 63 | 1.0 |
| 528711 | 8 | 13 | 14 | 62 | >1.5 |
| 528726 | 0 | 8 | 36 | 72 | 0.6 |
| 528757 | 4 | 10 | 29 | 76 | 0.6 |
| 528758 | 1 | 5 | 28 | 62 | 1.1 |
| 528772 | 0 | 2 | 21 | 63 | 1.2 |
| 528773 | 9 | 8 | 28 | 70 | 0.8 |
| 528791 | 4 | 9 | 41 | 69 | 0.6 |
| 528822 | 0 | 0 | 40 | 46 | >1.5 |
| 528833 | 0 | 23 | 47 | 82 | 0.4 |
| 528846 | 10 | 19 | 49 | 85 | 0.3 |
| 528847 | 0 | 19 | 45 | 75 | 0.4 |
| 528852 | 5 | 33 | 66 | 93 | 0.2 |
| 528853 | 19 | 46 | 77 | 95 | 0.1 |

Example 70: Antisense Inhibition of Human Target-1 in HuVEC Cells

Antisense oligonucleotides were designed targeting a human Target-1 nucleic acid and were tested for their effect on human Target-1 mRNA expression in vitro. The chimeric antisense oligonucleotides in Tables 116 and 117 are gapmers 16 or 17 nucleotides in length having various chemical modifications, as indicated in Tables 18 and 19, below. The chemistry column of Tables 116 and 117 provides the sugar motif of each gapmer, wherein 'e' indicates a 2'-MOE nucleoside, 'k' indicates a constrained ethyl (cEt) nucleoside, and 'd' indicates a 2'-deoxynucleoside. The internucleoside linkages throughout each gapmer are phosphorothioate (P=S) linkages. All cytosine residues throughout each gapmer are 5'-methylcytosines.

Cultured HuVEC cells at a density of 20,000 cells per well were transfected using electroporation with 1,000 nM antisense oligonucleotide. After a treatment period of approximately 24 hours, RNA was isolated from the cells and Target-1 mRNA levels were measured by quantitative real-time PCR. Target-1 mRNA levels were adjusted according to total RNA content, as measured by RIBOGREEN®. Results are presented as percent inhibition of Target-1, relative to untreated control cells.

"Human Target start site" indicates the 5'-most nucleoside to which the gapmer is targeted in the human gene sequence. "Human Target stop site" indicates the 3'-most nucleoside to which the gapmer is targeted in the human gene sequence.

Each gapmer listed in Table 116 is targeted to human Target-1 mRNA. Each gapmer listed in Table 117 is targeted to human Target-1 genomic sequence, truncated from nucleotides 4185000 to 4264000).

TABLE 116

Inhibition of human Target-1 mRNA levels by chimeric antisense oligonucleotides targeted to Target-1 mRNA 1

| Human Start Site | Human Stop Site | ISIS No | Chemistry | % inhibition |
|---|---|---|---|---|
| 728 | 743 | 530423 | k-d(10)-k-e-k-e-e | 70 |
| 729 | 745 | 530053 | e-e-k-d(10)-k-e-k-e | 84 |
| 729 | 744 | 530373 | e-k-d(10)-k-e-k-e | 85 |
| 730 | 745 | 530121 | e-k-k-d(10)-k-k-e | 77 |
| 730 | 745 | 530168 | e-e-k-d(10)-k-e-k-e | 75 |
| 730 | 745 | 530218 | e-d-k-d(10)-k-k-e | 61 |
| 730 | 745 | 530268 | e-d-d-k-d(9)-k-k-e | 76 |
| 730 | 745 | 530318 | e-e-e-e-d(9)-k-k-e | 27 |
| 786 | 801 | 530424 | k-d(10)-k-e-k-e-e | 42 |
| 787 | 803 | 530058 | e-e-k-d(10)-k-e-k-e | 73 |
| 787 | 802 | 530374 | e-k-d(10)-k-e-k-e | 71 |
| 788 | 803 | 530122 | e-k-k-d(10)-k-k-e | 80 |
| 788 | 803 | 530169 | e-e-k-d(10)-k-k-e | 72 |
| 788 | 803 | 530219 | e-d-k-d(10)-k-k-e | 55 |
| 788 | 803 | 530269 | e-d-d-k-d(9)-k-k-e | 76 |
| 788 | 803 | 530319 | e-e-e-e-d(9)-k-k-e | 30 |
| 897 | 912 | 528403 | e-e-e-d(10)-k-k-k | 72 |
| 962 | 977 | 528424 | e-e-e-d(10)-k-k-k | 42 |
| 1023 | 1038 | 528458 | e-e-e-d(10)-k-k-k | 70 |
| 1899 | 1914 | 530425 | k-d(10)-k-e-k-e-e | 73 |
| 1900 | 1916 | 530054 | e-e-k-d(10)-k-e-k-e | 75 |
| 1900 | 1915 | 530375 | e-k-d(10)-k-e-k-e | 77 |
| 1901 | 1916 | 530123 | e-k-k-d(10)-k-k-e | 86 |
| 1901 | 1916 | 530170 | e-e-k-d(10)-k-k-e | 87 |
| 1901 | 1916 | 530220 | e-d-k-d(10)-k-k-e | 74 |
| 1901 | 1916 | 530270 | e-d-d-k-d(9)-k-k-e | 87 |
| 1901 | 1916 | 530320 | e-e-e-e-d(9)-k-k-e | 17 |
| 1946 | 1961 | 530426 | k-d(10)-k-e-k-e-e | 55 |
| 1947 | 1963 | 530059 | e-e-k-d(10)-k-e-k-e | 73 |
| 1947 | 1962 | 530376 | e-k-d(10)-k-e-k-e | 77 |
| 1948 | 1963 | 530124 | e-k-k-d(10)-k-k-e | 79 |
| 1948 | 1963 | 530171 | e-e-k-d(10)-k-k-e | 69 |
| 1948 | 1963 | 530221 | e-d-k-d(10)-k-k-e | 64 |
| 1948 | 1963 | 530271 | e-d-d-k-d(9)-k-k-e | 73 |
| 1948 | 1963 | 530321 | e-e-e-e-d(9)-k-k-e | 44 |
| 2204 | 2219 | 530427 | k-d(10)-k-e-k-e-e | 43 |
| 2205 | 2221 | 530060 | e-e-k-d(10)-k-e-k-e | 77 |
| 2205 | 2220 | 530377 | e-k-d(10)-k-e-k-e | 66 |
| 2206 | 2221 | 530125 | e-k-k-d(10)-k-k-e | 65 |
| 2206 | 2221 | 530172 | e-e-k-d(10)-k-k-e | 59 |
| 2206 | 2221 | 530222 | e-d-k-d(10)-k-k-e | 48 |
| 2206 | 2221 | 530272 | e-d-d-k-d(9)-k-k-e | 63 |
| 2206 | 2221 | 530322 | e-e-e-e-d(9)-k-k-e | 55 |
| 2681 | 2696 | 530126 | e-k-k-d(10)-k-k-e | 70 |
| 2681 | 2696 | 530173 | e-e-k-d(10)-k-k-e | 62 |
| 2681 | 2696 | 530223 | e-d-k-d(10)-k-k-e | 44 |
| 2681 | 2696 | 530273 | e-d-d-k-d(9)-k-k-e | 63 |
| 2681 | 2696 | 530323 | e-e-e-e-d(9)-k-k-e | 63 |
| 3012 | 3027 | 530513 | k-d(10)-k-e-k-e-e | 88 |
| 3013 | 3028 | 530507 | e-k-d(10)-k-e-k-e | 86 |
| 3013 | 3028 | 530514 | k-d(10)-k-e-k-e-e | 80 |
| 3014 | 3029 | 530430 | k-d(10)-k-e-k-e-e | 87 |
| 3014 | 3029 | 530468 | e-k-k-d(10)-k-k-e | 81 |
| 3014 | 3029 | 530476 | e-e-k-d(10)-k-k-e | 82 |
| 3014 | 3029 | 530484 | e-d-k-d(10)-k-k-e | 74 |
| 3014 | 3029 | 530492 | e-d-d-k-d(9)-k-k-e | 83 |
| 3014 | 3029 | 530500 | e-e-e-e-d(9)-k-k-e | 56 |
| 3014 | 3029 | 530508 | e-k-d(10)-k-e-k-e | 83 |
| 3015 | 3031 | 530062 | e-e-k-d(10)-k-e-k-e | 94 |
| 3015 | 3030 | 530380 | e-k-d(10)-k-e-k-e | 94 |
| 3015 | 3030 | 530469 | e-k-k-d(10)-k-k-e | 91 |
| 3015 | 3030 | 530477 | e-e-k-d(10)-k-k-e | 87 |
| 3015 | 3030 | 530485 | e-d-k-d(10)-k-k-e | 87 |
| 3015 | 3030 | 530493 | e-d-d-k-d(9)-k-k-e | 81 |
| 3015 | 3030 | 530501 | e-e-e-e-d(9)-k-k-e | 74 |
| 3015 | 3030 | 530515 | k-d(10)-k-e-k-e-e | 87 |
| 3016 | 3031 | 481464 | k-k-k-d(10)-k-k-k | 93 |
| 3016 | 3031 | 518349 | e-e-e-d(10)-k-k-k | 58 |

TABLE 116-continued

Inhibition of human Target-1 mRNA levels by chimeric antisense oligonucleotides targeted to Target-1 mRNA 1

| Human Start Site | Human Stop Site | ISIS No | Chemistry | % inhibition |
|---|---|---|---|---|
| 3016 | 3031 | 519637 | e-k-k-d(10)-k-k-e | 96 |
| 3016 | 3031 | 530175 | e-e-k-d(10)-k-k-e | 93 |
| 3016 | 3031 | 530225 | e-d-k-d(10)-k-k-e | 85 |
| 3016 | 3031 | 530275 | e-d-d-k-d(9)-k-k-e | 91 |
| 3016 | 3031 | 530325 | e-e-e-e-d(9)-k-k-e | 91 |
| 3017 | 3032 | 530470 | e-k-k-d(10)-k-k-e | 91 |
| 3017 | 3032 | 530478 | e-e-k-d(10)-k-k-e | 87 |
| 3017 | 3032 | 530486 | e-d-k-d(10)-k-k-e | 84 |
| 3017 | 3032 | 530494 | e-d-d-k-d(9)-k-k-e | 60 |
| 3017 | 3032 | 530502 | e-e-e-e-d(9)-k-k-e | 64 |
| 3017 | 3032 | 530509 | e-k-d(10)-k-e-k-e | 80 |
| 3018 | 3033 | 530471 | e-k-k-d(10)-k-k-e | 83 |
| 3018 | 3033 | 530479 | e-e-k-d(10)-k-k-e | 74 |
| 3018 | 3033 | 530487 | e-d-k-d(10)-k-k-e | 71 |
| 3018 | 3033 | 530495 | e-d-d-k-d(9)-k-k-e | 68 |
| 3018 | 3033 | 530503 | e-e-e-e-d(9)-k-k-e | 53 |
| 3460 | 3476 | 530055 | e-e-k-d(10)-k-e-k-e | 45 |
| 3460 | 3475 | 530381 | e-k-d(10)-k-e-k-e | 74 |
| 3461 | 3476 | 530128 | e-k-k-d(10)-k-k-e | 52 |
| 3461 | 3476 | 530176 | e-e-k-d(10)-k-k-e | 66 |
| 3461 | 3476 | 530226 | e-d-k-d(10)-k-k-e | 51 |
| 3461 | 3476 | 530276 | e-d-d-k-d(9)-k-k-e | 70 |
| 3461 | 3476 | 530326 | e-e-e-e-d(9)-k-k-e | 52 |
| 3595 | 3610 | 530390 | k-d(10)-k-e-k-e-e | 83 |
| 3596 | 3611 | 530340 | e-k-d(10)-k-e-k-e | 89 |
| 3597 | 3612 | 528869 | e-e-e-d(10)-k-k-k | 83 |
| 3597 | 3612 | 530088 | e-k-k-d(10)-k-k-e | 90 |
| 3597 | 3612 | 530135 | e-e-k-d(10)-k-k-e | 91 |
| 3597 | 3612 | 530185 | e-d-k-d(10)-k-k-e | 85 |
| 3597 | 3612 | 530235 | e-d-d-k-d(9)-k-k-e | 28 |
| 3597 | 3612 | 530285 | e-e-e-e-d(9)-k-k-e | 86 |
| 3597 | 3612 | 530391 | k-d(10)-k-e-k-e-e | 79 |
| 3598 | 3614 | 530021 | e-e-k-d(10)-k-e-k-e | 87 |
| 3598 | 3613 | 530341 | e-k-d(10)-k-e-k-e | 88 |
| 3599 | 3614 | 530089 | e-k-k-d(10)-k-k-e | 71 |
| 3599 | 3614 | 530136 | e-e-k-d(10)-k-k-e | 66 |
| 3599 | 3614 | 530186 | e-d-k-d(10)-k-k-e | 51 |
| 3599 | 3614 | 530236 | e-d-d-k-d(9)-k-k-e | 74 |
| 3599 | 3614 | 530286 | e-e-e-e-d(9)-k-k-e | 56 |
| 3715 | 3731 | 530022 | e-e-k-d(10)-k-e-k-e | 80 |
| 3715 | 3730 | 530342 | e-k-d(10)-k-e-k-e | 70 |
| 3715 | 3730 | 530393 | k-d(10)-k-e-k-e-e | 46 |
| 3716 | 3732 | 530023 | e-e-k-d(10)-k-e-k-e | 74 |
| 3716 | 3731 | 530090 | e-k-k-d(10)-k-k-e | 78 |
| 3716 | 3731 | 530137 | e-e-k-d(10)-k-k-e | 76 |
| 3716 | 3731 | 530187 | e-d-k-d(10)-k-k-e | 68 |
| 3716 | 3731 | 530237 | e-d-d-k-d(9)-k-k-e | 36 |
| 3716 | 3731 | 530287 | e-e-e-e-d(9)-k-k-e | 56 |
| 3716 | 3731 | 530343 | e-k-d(10)-k-e-k-e | 68 |
| 3716 | 3731 | 530394 | k-d(10)-k-e-k-e-e | 49 |
| 3717 | 3732 | 518343 | e-e-e-d(10)-k-k-k | 5 |
| 3717 | 3733 | 530024 | e-e-k-d(10)-k-e-k-e | 79 |
| 3717 | 3732 | 530091 | e-k-k-d(10)-k-k-e | 81 |
| 3717 | 3732 | 530138 | e-e-k-d(10)-k-k-e | 81 |
| 3717 | 3732 | 530188 | e-d-k-d(10)-k-k-e | 78 |
| 3717 | 3732 | 530238 | e-d-d-k-d(9)-k-k-e | 29 |
| 3717 | 3732 | 530288 | e-e-e-e-d(9)-k-k-e | 69 |
| 3717 | 3732 | 530344 | e-k-d(10)-k-e-k-e | 85 |
| 3718 | 3733 | 530092 | e-k-k-d(10)-k-k-e | 85 |
| 3718 | 3733 | 530139 | e-e-k-d(10)-k-k-e | 79 |
| 3718 | 3733 | 530189 | e-d-k-d(10)-k-k-e | 77 |
| 3718 | 3733 | 530239 | e-d-d-k-d(9)-k-k-e | 61 |
| 3718 | 3733 | 530289 | e-e-e-e-d(9)-k-k-e | 75 |
| 3720 | 3735 | 528880 | e-e-e-d(10)-k-k-k | 65 |
| 4022 | 4037 | 518344 | e-e-e-d(10)-k-k-k | 89 |
| 4234 | 4249 | 530395 | k-d(10)-k-e-k-e-e | 71 |
| 4235 | 4250 | 528936 | e-e-e-d(10)-k-k-k | 71 |
| 4235 | 4251 | 530025 | e-e-k-d(10)-k-e-k-e | 90 |
| 4235 | 4250 | 530345 | e-k-d(10)-k-e-k-e | 93 |
| 4235 | 4250 | 530396 | k-d(10)-k-e-k-e-e | 71 |
| 4236 | 4251 | 528937 | e-e-e-d(10)-k-k-k | 73 |
| 4236 | 4252 | 530026 | e-e-k-d(10)-k-e-k-e | 87 |
| 4236 | 4251 | 530093 | e-k-k-d(10)-k-k-e | 95 |
| 4236 | 4251 | 530140 | e-e-k-d(10)-k-k-e | 89 |

TABLE 116-continued

Inhibition of human Target-1 mRNA levels by chimeric antisense oligonucleotides targeted to Target-1 mRNA 1

| Human Start Site | Human Stop Site | ISIS No | Chemistry | % inhibition |
|---|---|---|---|---|
| 4236 | 4251 | 530190 | e-d-k-d(10)-k-k-e | 82 |
| 4236 | 4251 | 530240 | e-d-d-k-d(9)-k-k-e | 50 |
| 4236 | 4251 | 530290 | e-e-e-e-d(9)-k-k-e | 69 |
| 4236 | 4251 | 530346 | e-k-d(10)-k-e-k-e | 89 |
| 4237 | 4252 | 528938 | e-e-e-d(10)-k-k-k | 72 |
| 4237 | 4252 | 530094 | e-k-k-d(10)-k-k-e | 88 |
| 4237 | 4252 | 530141 | e-e-k-d(10)-k-k-e | 80 |
| 4237 | 4252 | 530191 | e-d-k-d(10)-k-k-e | 74 |
| 4237 | 4252 | 530241 | e-d-d-k-d(9)-k-k-e | 53 |
| 4237 | 4252 | 530291 | e-e-e-e-d(9)-k-k-e | 68 |
| 4242 | 4257 | 528942 | e-e-e-d(10)-k-k-k | 77 |
| 4320 | 4335 | 528945 | e-e-e-d(10)-k-k-k | 74 |
| 4439 | 4454 | 530096 | e-k-k-d(10)-k-k-e | 72 |
| 4439 | 4454 | 530143 | e-e-k-d(10)-k-k-e | 74 |
| 4439 | 4454 | 530193 | e-d-k-d(10)-k-k-e | 62 |
| 4439 | 4454 | 530243 | e-d-d-k-d(9)-k-k-e | 34 |
| 4439 | 4454 | 530293 | e-e-e-e-d(9)-k-k-e | 59 |
| 4488 | 4504 | 530063 | e-e-e-k-d(10)-k-e-k-e | 74 |
| 4488 | 4503 | 530382 | e-k-d(10)-k-e-k-e | 17 |
| 4488 | 4503 | 530465 | e-k-k-d(10)-k-k-e | 63 |
| 4488 | 4503 | 530473 | e-e-k-d(10)-k-k-e | 45 |
| 4488 | 4503 | 530481 | e-d-k-d(10)-k-k-e | 14 |
| 4488 | 4503 | 530489 | e-d-d-k-d(9)-k-k-e | 13 |
| 4488 | 4503 | 530497 | e-e-e-e-d(9)-k-k-e | 7 |
| 4488 | 4503 | 530512 | k-d(10)-k-e-k-e-e | 21 |
| 4489 | 4504 | 519638 | e-k-k-d(10)-k-k-e | 86 |
| 4489 | 4504 | 530177 | e-e-e-d(10)-k-k-e | 71 |
| 4489 | 4504 | 530227 | e-d-k-d(10)-k-k-e | 51 |
| 4489 | 4504 | 530277 | e-d-d-k-d(9)-k-k-e | 70 |
| 4489 | 4504 | 530327 | e-e-e-e-d(9)-k-k-e | 61 |
| 4490 | 4505 | 530466 | e-k-k-d(10)-k-k-e | 82 |
| 4490 | 4505 | 530474 | e-e-k-d(10)-k-k-e | 62 |
| 4490 | 4505 | 530482 | e-d-k-d(10)-k-k-e | 53 |
| 4490 | 4505 | 530490 | e-d-d-k-d(9)-k-k-e | 42 |
| 4490 | 4505 | 530498 | e-e-e-e-d(9)-k-k-e | 45 |
| 4490 | 4505 | 530506 | e-k-d(10)-k-e-k-e | 70 |
| 4539 | 4554 | 530433 | k-d(10)-k-e-k-e-e | 62 |
| 4540 | 4555 | 528958 | e-e-e-d(10)-k-k-k | 66 |
| 4540 | 4556 | 530056 | e-e-e-k-d(10)-k-e-k-e | 73 |
| 4540 | 4555 | 530383 | e-k-d(10)-k-e-k-e | 64 |
| 4541 | 4556 | 518345 | e-e-e-d(10)-k-k-k | 80 |
| 4541 | 4556 | 519636 | e-k-k-d(10)-k-k-e | 90 |
| 4541 | 4556 | 530178 | e-e-e-d(10)-k-k-e | 86 |
| 4541 | 4556 | 530228 | e-d-k-d(10)-k-k-e | 77 |
| 4541 | 4556 | 530278 | e-d-d-k-d(9)-k-k-e | 86 |
| 4541 | 4556 | 530328 | e-e-e-e-d(9)-k-k-e | 80 |
| 4542 | 4557 | 528959 | e-e-e-d(10)-k-k-k | 73 |
| 4621 | 4636 | 528973 | e-e-e-d(10)-k-k-k | 71 |
| 4782 | 4797 | 530329 | e-e-e-e-d(9)-k-k-e | 61 |
| 4813 | 4829 | 530032 | e-e-e-k-d(10)-k-e-k-e | 74 |
| 4813 | 4828 | 530099 | e-k-k-d(10)-k-k-e | 73 |
| 4813 | 4828 | 530146 | e-e-k-d(10)-k-k-e | 70 |
| 4813 | 4828 | 530196 | e-d-k-d(10)-k-k-e | 67 |
| 4813 | 4828 | 530246 | e-d-d-k-d(9)-k-k-e | 39 |
| 4813 | 4828 | 530296 | e-e-e-e-d(9)-k-k-e | 67 |
| 4813 | 4828 | 530352 | e-k-d(10)-k-e-k-e | 67 |
| 4814 | 4829 | 530100 | e-k-k-d(10)-k-k-e | 77 |
| 4814 | 4829 | 530147 | e-e-k-d(10)-k-k-e | 84 |
| 4814 | 4829 | 530197 | e-d-k-d(10)-k-k-e | 71 |
| 4814 | 4829 | 530247 | e-d-d-k-d(9)-k-k-e | 53 |
| 4814 | 4829 | 530297 | e-e-e-e-d(9)-k-k-e | 75 |
| 4814 | 4829 | 530403 | k-d(10)-k-e-k-e-e | 77 |
| 4815 | 4831 | 530033 | e-e-e-k-d(10)-k-e-k-e | 65 |
| 4815 | 4830 | 530353 | e-k-d(10)-k-e-k-e | 83 |
| 4816 | 4831 | 530101 | e-k-k-d(10)-k-k-e | 59 |
| 4816 | 4831 | 530148 | e-e-k-d(10)-k-k-e | 79 |
| 4816 | 4831 | 530198 | e-d-k-d(10)-k-k-e | 54 |
| 4816 | 4831 | 530248 | e-d-d-k-d(9)-k-k-e | 32 |
| 4816 | 4831 | 530298 | e-e-e-e-d(9)-k-k-e | 73 |
| 4827 | 4842 | 530404 | k-d(10)-k-e-k-e-e | 67 |
| 4828 | 4844 | 530034 | e-e-e-k-d(10)-k-e-k-e | 69 |
| 4828 | 4843 | 530354 | e-k-d(10)-k-e-k-e | 85 |
| 4828 | 4843 | 530405 | k-d(10)-k-e-k-e-e | 55 |
| 4829 | 4845 | 530035 | e-e-e-k-d(10)-k-e-k-e | 69 |
| 4829 | 4844 | 530102 | e-k-k-d(10)-k-k-e | 71 |
| 4829 | 4844 | 530149 | e-e-k-d(10)-k-k-e | 70 |
| 4829 | 4844 | 530199 | e-d-k-d(10)-k-k-e | 58 |
| 4829 | 4844 | 530249 | e-d-d-k-d(9)-k-k-e | 47 |
| 4829 | 4844 | 530299 | e-e-e-e-d(9)-k-k-e | 47 |
| 4829 | 4844 | 530355 | e-k-d(10)-k-e-k-e | 72 |
| 4830 | 4845 | 530103 | e-k-k-d(10)-k-k-e | 77 |
| 4830 | 4845 | 530150 | e-e-k-d(10)-k-k-e | 73 |
| 4830 | 4845 | 530200 | e-d-k-d(10)-k-k-e | 63 |
| 4830 | 4845 | 530250 | e-d-d-k-d(9)-k-k-e | 59 |
| 4830 | 4845 | 530300 | e-e-e-e-d(9)-k-k-e | 65 |
| 4842 | 4857 | 530435 | k-d(10)-k-e-k-e-e | 62 |
| 4843 | 4859 | 530057 | e-e-k-d(10)-k-e-k-e | 69 |
| 4843 | 4858 | 530385 | e-k-d(10)-k-e-k-e | 70 |
| 4844 | 4859 | 529005 | e-e-e-d(10)-k-k-k | 64 |
| 4844 | 4859 | 530130 | e-k-k-d(10)-k-k-e | 85 |
| 4844 | 4859 | 530180 | e-e-k-d(10)-k-k-e | 82 |
| 4844 | 4859 | 530230 | e-d-k-d(10)-k-k-e | 65 |
| 4844 | 4859 | 530280 | e-d-d-k-d(9)-k-k-e | 75 |
| 4844 | 4859 | 530330 | e-e-e-e-d(9)-k-k-e | 52 | e = 2'-MOE,
k = cEt,
d = 2'-deoxynucleoside

TABLE 117

Inhibition of human Target-1 mRNA levels by chimeric antisense oligonucleotides targeted to Target-1 Genomic Sequence

| Human Start Site | Human Stop Site | ISIS No | Chemistry | % inhibition |
|---|---|---|---|---|
| 1794 | 1809 | 529022 | e-e-e-d(10)-k-k-k | 69 |
| 1796 | 1811 | 529023 | e-e-e-d(10)-k-k-k | 72 |
| 1906 | 1921 | 529024 | e-e-e-d(10)-k-k-k | 64 |
| 1907 | 1922 | 529025 | e-e-e-d(10)-k-k-k | 73 |
| 1966 | 1981 | 529026 | e-e-e-d(10)-k-k-k | 78 |
| 1968 | 1983 | 529027 | e-e-e-d(10)-k-k-k | 92 |
| 2409 | 2425 | 530038 | e-e-k-d(10)-k-e-k-e | 71 |
| 2409 | 2424 | 530358 | e-k-d(10)-k-e-k-e | 46 |
| 2410 | 2425 | 530106 | e-k-k-d(10)-k-k-e | 70 |
| 2410 | 2425 | 530153 | e-e-k-d(10)-k-k-e | 50 |
| 2410 | 2425 | 530203 | e-d-k-d(10)-k-k-e | 43 |
| 2410 | 2425 | 530253 | e-d-d-k-d(9)-k-k-e | 33 |
| 2410 | 2425 | 530303 | e-e-e-e-d(9)-k-k-e | 40 |
| 2670 | 2686 | 530039 | e-e-k-d(10)-k-e-k-e | 73 |
| 2670 | 2685 | 530359 | e-k-d(10)-k-e-k-e | 82 |
| 2671 | 2686 | 530107 | e-k-k-d(10)-k-k-e | 77 |
| 2671 | 2686 | 530154 | e-e-k-d(10)-k-k-e | 57 |
| 2671 | 2686 | 530204 | e-d-k-d(10)-k-k-e | 28 |
| 2671 | 2686 | 530254 | e-d-d-k-d(9)-k-k-e | 3 |
| 2671 | 2686 | 530304 | e-e-e-e-d(9)-k-k-e | 22 |
| 2703 | 2718 | 530429 | k-d(10)-k-e-k-e-e | 60 |
| 2704 | 2720 | 530065 | e-e-e-k-d(10)-k-e-k-e | 70 |
| 2704 | 2719 | 530379 | e-k-d(10)-k-e-k-e | 54 |
| 2705 | 2720 | 530127 | e-k-k-d(10)-k-k-e | 80 |
| 2705 | 2720 | 530174 | e-e-k-d(10)-k-k-e | 69 |
| 2705 | 2720 | 530224 | e-d-k-d(10)-k-k-e | 32 |
| 2705 | 2720 | 530274 | e-d-d-k-d(9)-k-k-e | 38 |
| 2705 | 2720 | 530324 | e-e-e-e-d(9)-k-k-e | 32 |
| 5000 | 5015 | 530410 | k-d(10)-k-e-k-e-e | 53 |
| 5001 | 5017 | 530040 | e-e-e-k-d(10)-k-e-k-e | 67 |
| 5001 | 5016 | 530360 | e-k-d(10)-k-e-k-e | 70 |
| 5002 | 5017 | 530108 | e-k-k-d(10)-k-k-e | 70 |
| 5002 | 5017 | 530155 | e-e-k-d(10)-k-k-e | 53 |
| 5002 | 5017 | 530205 | e-d-k-d(10)-k-k-e | 44 |
| 5002 | 5017 | 530255 | e-d-d-k-d(9)-k-k-e | 33 |
| 5002 | 5017 | 530305 | e-e-e-e-d(9)-k-k-e | 22 |
| 5699 | 5714 | 530411 | k-d(10)-k-e-k-e-e | 91 |
| 5700 | 5716 | 530041 | e-e-e-k-d(10)-k-e-k-e | 89 |
| 5700 | 5715 | 530361 | e-k-d(10)-k-e-k-e | 88 |

TABLE 117-continued

Inhibition of human Target-1 mRNA levels by chimeric antisense oligonucleotides targeted to Target-1 Genomic Sequence

| Human Start Site | Human Stop Site | ISIS No | Chemistry | % inhibition |
|---|---|---|---|---|
| 5701 | 5716 | 530109 | e-k-k-d(10)-k-k-e | 89 |
| 5701 | 5716 | 530156 | e-e-k-d(10)-k-k-e | 91 |
| 5701 | 5716 | 530206 | e-d-k-d(10)-k-k-e | 89 |
| 5701 | 5716 | 530256 | e-d-d-k-d(9)-k-k-e | 33 |
| 5701 | 5716 | 530306 | e-e-e-e-d(9)-k-k-e | 83 |
| 6475 | 6491 | 530066 | e-e-k-d(10)-k-e-k-e | 82 |
| 6475 | 6490 | 530386 | e-k-d(10)-k-e-k-e | 53 |
| 6476 | 6491 | 530131 | e-k-k-d(10)-k-k-e | 97 |
| 6476 | 6491 | 530181 | e-e-k-d(10)-k-k-e | 82 |
| 6476 | 6491 | 530231 | e-d-k-d(10)-k-k-e | 75 |
| 6476 | 6491 | 530281 | e-d-d-k-d(9)-k-k-e | 69 |
| 6476 | 6491 | 530331 | e-e-e-e-d(9)-k-k-e | 53 |
| 6846 | 6861 | 529039 | e-e-e-d(10)-k-k-k | 31 |
| 8079 | 8095 | 530042 | e-e-k-d(10)-k-e-k-e | 78 |
| 8079 | 8094 | 530362 | e-k-d(10)-k-e-k-e | 76 |
| 8080 | 8095 | 530110 | e-k-k-d(10)-k-k-e | 84 |
| 8080 | 8095 | 530157 | e-e-k-d(10)-k-k-e | 69 |
| 8080 | 8095 | 530207 | e-d-k-d(10)-k-k-e | 55 |
| 8080 | 8095 | 530257 | e-d-d-k-d(9)-k-k-e | 39 |
| 8080 | 8095 | 530307 | e-e-e-e-d(9)-k-k-e | 77 |
| 9123 | 9138 | 530413 | k-d(10)-k-e-k-e-e | 73 |
| 9862 | 9877 | 530414 | k-d(10)-k-e-k-e-e | 61 |
| 9863 | 9879 | 530044 | e-e-k-d(10)-k-e-k-e | 78 |
| 9863 | 9878 | 530364 | e-k-d(10)-k-e-k-e | 59 |
| 9864 | 9879 | 530112 | e-k-k-d(10)-k-k-e | 84 |
| 9864 | 9879 | 530159 | e-e-k-d(10)-k-k-e | 69 |
| 9864 | 9879 | 530209 | e-d-k-d(10)-k-k-e | 54 |
| 9864 | 9879 | 530259 | e-d-d-k-d(9)-k-k-e | 57 |
| 9864 | 9879 | 530309 | e-e-e-e-d(9)-k-k-e | 46 |
| 9864 | 9879 | 530415 | k-d(10)-k-e-k-e-e | 51 |
| 9865 | 9881 | 530045 | e-e-k-d(10)-k-e-k-e | 73 |
| 9865 | 9880 | 530365 | e-k-d(10)-k-e-k-e | 78 |
| 9866 | 9881 | 530113 | e-k-k-d(10)-k-k-e | 60 |
| 9866 | 9881 | 530160 | e-e-k-d(10)-k-k-e | 54 |
| 9866 | 9881 | 530210 | e-d-k-d(10)-k-k-e | 28 |
| 9866 | 9881 | 530260 | e-d-d-k-d(9)-k-k-e | 0 |
| 9866 | 9881 | 530310 | e-e-e-e-d(9)-k-k-e | 26 |
| 9873 | 9888 | 530416 | k-d(10)-k-e-k-e-e | 57 |
| 9874 | 9890 | 530046 | e-e-k-d(10)-k-e-k-e | 76 |
| 9874 | 9889 | 530366 | e-k-d(10)-k-e-k-e | 75 |
| 9874 | 9889 | 530417 | k-d(10)-k-e-k-e-e | 66 |
| 9875 | 9891 | 530047 | e-e-k-d(10)-k-e-k-e | 75 |
| 9875 | 9890 | 530114 | e-k-k-d(10)-k-k-e | 80 |
| 9875 | 9890 | 530161 | e-e-k-d(10)-k-k-e | 81 |
| 9875 | 9890 | 530211 | e-d-k-d(10)-k-k-e | 73 |
| 9875 | 9890 | 530261 | e-d-d-k-d(9)-k-k-e | 78 |
| 9875 | 9890 | 530311 | e-e-e-e-d(9)-k-k-e | 82 |
| 9875 | 9890 | 530367 | e-k-d(10)-k-e-k-e | 80 |
| 9876 | 9891 | 530115 | e-k-k-d(10)-k-k-e | 74 |
| 9876 | 9891 | 530162 | e-e-k-d(10)-k-k-e | 68 |
| 9876 | 9891 | 530212 | e-d-k-d(10)-k-k-e | 58 |
| 9876 | 9891 | 530262 | e-d-d-k-d(9)-k-k-e | 23 |
| 9876 | 9891 | 530312 | e-e-e-e-d(9)-k-k-e | 52 |
| 9876 | 9891 | 530418 | k-d(10)-k-e-k-e-e | 59 |
| 9877 | 9893 | 530048 | e-e-k-d(10)-k-e-k-e | 82 |
| 9877 | 9892 | 530368 | e-k-d(10)-k-e-k-e | 85 |
| 9878 | 9893 | 530116 | e-k-k-d(10)-k-k-e | 90 |
| 9878 | 9893 | 530163 | e-e-k-d(10)-k-k-e | 79 |
| 9878 | 9893 | 530213 | e-d-k-d(10)-k-k-e | 72 |
| 9878 | 9893 | 530263 | e-d-d-k-d(9)-k-k-e | 73 |
| 9878 | 9893 | 530313 | e-e-e-e-d(9)-k-k-e | 61 |
| 12345 | 12360 | 530414 | k-d(10)-k-e-k-e-e | 61 |
| 12346 | 12362 | 530044 | e-e-k-d(10)-k-e-k-e | 78 |
| 12346 | 12361 | 530364 | e-k-d(10)-k-e-k-e | 59 |
| 12347 | 12362 | 530112 | e-k-k-d(10)-k-k-e | 84 |
| 12347 | 12362 | 530159 | e-e-k-d(10)-k-k-e | 69 |
| 12347 | 12362 | 530209 | e-d-k-d(10)-k-k-e | 54 |
| 12347 | 12362 | 530259 | e-d-d-k-d(9)-k-k-e | 57 |
| 12347 | 12362 | 530309 | e-e-e-e-d(9)-k-k-e | 46 |
| 12347 | 12362 | 530415 | k-d(10)-k-e-k-e-e | 51 |
| 12348 | 12364 | 530045 | e-e-k-d(10)-k-e-k-e | 73 |
| 12348 | 12363 | 530365 | e-k-d(10)-k-e-k-e | 78 |
| 12349 | 12364 | 530113 | e-k-k-d(10)-k-k-e | 60 |
| 12349 | 12364 | 530160 | e-e-k-d(10)-k-k-e | 54 |
| 12349 | 12364 | 530210 | e-d-k-d(10)-k-k-e | 28 |
| 12349 | 12364 | 530260 | e-d-d-k-d(9)-k-k-e | 0 |
| 12349 | 12364 | 530310 | e-e-e-e-d(9)-k-k-e | 26 |
| 12356 | 12371 | 530416 | k-d(10)-k-e-k-e-e | 57 |
| 12357 | 12373 | 530046 | e-e-k-d(10)-k-e-k-e | 76 |
| 12357 | 12372 | 530366 | e-k-d(10)-k-e-k-e | 75 |
| 12357 | 12372 | 530417 | k-d(10)-k-e-k-e-e | 66 |
| 12358 | 12374 | 530047 | e-e-k-d(10)-k-e-k-e | 75 |
| 12358 | 12373 | 530114 | e-k-k-d(10)-k-k-e | 80 |
| 12358 | 12373 | 530161 | e-e-k-d(10)-k-k-e | 81 |
| 12358 | 12373 | 530211 | e-d-k-d(10)-k-k-e | 73 |
| 12358 | 12373 | 530261 | e-d-d-k-d(9)-k-k-e | 78 |
| 12358 | 12373 | 530311 | e-e-e-e-d(9)-k-k-e | 82 |
| 12358 | 12373 | 530367 | e-k-d(10)-k-e-k-e | 80 |
| 12359 | 12374 | 530115 | e-k-k-d(10)-k-k-e | 74 |
| 12359 | 12374 | 530162 | e-e-k-d(10)-k-k-e | 68 |
| 12359 | 12374 | 530212 | e-d-k-d(10)-k-k-e | 58 |
| 12359 | 12374 | 530262 | e-d-d-k-d(9)-k-k-e | 23 |
| 12359 | 12374 | 530312 | e-e-e-e-d(9)-k-k-e | 52 |
| 12359 | 12374 | 530418 | k-d(10)-k-e-k-e-e | 59 |
| 12360 | 12376 | 530048 | e-e-k-d(10)-k-e-k-e | 82 |
| 12360 | 12375 | 530368 | e-k-d(10)-k-e-k-e | 85 |
| 12361 | 12376 | 530116 | e-k-k-d(10)-k-k-e | 90 |
| 12361 | 12376 | 530163 | e-e-k-d(10)-k-k-e | 79 |
| 12361 | 12376 | 530213 | e-d-k-d(10)-k-k-e | 72 |
| 12361 | 12376 | 530263 | e-d-d-k-d(9)-k-k-e | 73 |
| 12361 | 12376 | 530313 | e-e-e-e-d(9)-k-k-e | 61 |
| 15469 | 15484 | 530132 | e-k-k-d(10)-k-k-e | 74 |
| 15469 | 15484 | 530182 | e-e-k-d(10)-k-k-e | 48 |
| 15469 | 15484 | 530232 | e-d-k-d(10)-k-k-e | 21 |
| 15469 | 15484 | 530282 | e-d-d-k-d(9)-k-k-e | 19 |
| 15469 | 15484 | 530332 | e-e-e-e-d(9)-k-k-e | 20 |
| 16863 | 16878 | 530419 | k-d(10)-k-e-k-e-e | 75 |
| 16864 | 16880 | 530049 | e-e-k-d(10)-k-e-k-e | 88 |
| 16864 | 16879 | 530369 | e-k-d(10)-k-e-k-e | 92 |
| 16865 | 16880 | 530117 | e-k-k-d(10)-k-k-e | 73 |
| 16865 | 16880 | 530164 | e-e-k-d(10)-k-k-e | 65 |
| 16865 | 16880 | 530214 | e-d-k-d(10)-k-k-e | 37 |
| 16865 | 16880 | 530264 | e-d-d-k-d(9)-k-k-e | 48 |
| 16865 | 16880 | 530314 | e-e-e-e-d(9)-k-k-e | 42 |
| 25105 | 25120 | 530717 | e-e-e-d(10)-k-k-k | 77 |
| 50692 | 50707 | 530423 | k-d(10)-k-e-k-e-e | 70 |
| 50693 | 50709 | 530053 | e-e-k-d(10)-k-e-k-e | 84 |
| 50693 | 50708 | 530373 | e-k-d(10)-k-e-k-e | 85 |
| 50694 | 50709 | 530121 | e-k-k-d(10)-k-k-e | 77 |
| 50694 | 50709 | 530168 | e-e-k-d(10)-k-k-e | 75 |
| 50694 | 50709 | 530218 | e-d-k-d(10)-k-k-e | 61 |
| 50694 | 50709 | 530268 | e-d-d-k-d(9)-k-k-e | 76 |
| 50694 | 50709 | 530318 | e-e-e-e-d(9)-k-k-e | 73 |
| 51905 | 51920 | 528400 | e-e-e-d(10)-k-k-k | 57 |
| 51910 | 51925 | 528403 | e-e-e-d(10)-k-k-k | 72 |
| 64959 | 64974 | 529082 | e-e-e-d(10)-k-k-k | 20 |
| 66136 | 66151 | 530425 | k-d(10)-k-e-k-e-e | 73 |
| 66137 | 66153 | 530054 | e-e-k-d(10)-k-e-k-e | 75 |
| 66137 | 66152 | 530375 | e-k-d(10)-k-e-k-e | 77 |
| 66138 | 66153 | 530123 | e-k-k-d(10)-k-k-e | 86 |
| 66138 | 66153 | 530170 | e-e-k-d(10)-k-k-e | 87 |
| 66138 | 66153 | 530220 | e-d-k-d(10)-k-k-e | 74 |
| 66138 | 66153 | 530270 | e-d-d-k-d(9)-k-k-e | 87 |
| 66138 | 66153 | 530320 | e-e-e-e-d(9)-k-k-e | 83 |
| 66184 | 66200 | 530059 | e-e-k-d(10)-k-e-k-e | 73 |
| 66184 | 66199 | 530376 | e-k-d(10)-k-e-k-e | 77 |
| 66185 | 66200 | 530124 | e-k-k-d(10)-k-k-e | 79 |
| 66185 | 66200 | 530171 | e-e-k-d(10)-k-k-e | 69 |
| 66185 | 66200 | 530221 | e-d-k-d(10)-k-k-e | 64 |
| 66185 | 66200 | 530271 | e-d-d-k-d(9)-k-k-e | 73 |
| 66185 | 66200 | 530321 | e-e-e-e-d(9)-k-k-e | 56 |
| 67067 | 67083 | 530060 | e-e-k-d(10)-k-e-k-e | 77 |
| 67067 | 67082 | 530377 | e-k-d(10)-k-e-k-e | 66 |
| 67068 | 67083 | 530125 | e-k-k-d(10)-k-k-e | 65 |
| 67068 | 67083 | 530172 | e-e-k-d(10)-k-k-e | 59 |
| 67068 | 67083 | 530222 | e-d-k-d(10)-k-k-e | 48 |
| 67068 | 67083 | 530272 | e-d-d-k-d(9)-k-k-e | 63 |
| 67068 | 67083 | 530322 | e-e-e-e-d(9)-k-k-e | 45 |

TABLE 117-continued

Inhibition of human Target-1 mRNA levels by chimeric antisense oligonucleotides targeted to Target-1 Genomic Sequence

| Human Start Site | Human Stop Site | ISIS No | Chemistry | % inhibition |
|---|---|---|---|---|
| 71616 | 71631 | 530120 | e-k-k-d(10)-k-k-e | 78 |
| 71616 | 71631 | 530167 | e-k-d-k(10)-k-e-k-e | 69 |
| 71616 | 71631 | 530217 | e-d-k-d(10)-k-k-e | 47 |
| 71616 | 71631 | 530267 | e-d-d-k-d(9)-k-k-e | 64 |
| 71616 | 71631 | 530317 | e-e-e-e-d(9)-k-k-e | 60 |
| 73868 | 73883 | 530126 | e-k-k-d(10)-k-k-e | 70 |
| 73868 | 73883 | 530173 | e-e-k-d(10)-k-k-e | 62 |
| 73868 | 73883 | 530223 | e-d-k-d(10)-k-k-e | 44 |
| 73868 | 73883 | 530273 | e-d-d-k-d(9)-k-k-e | 63 |
| 73868 | 73883 | 530323 | e-e-e-e-d(9)-k-k-e | 37 |
| 74199 | 74214 | 530513 | k-d(10)-k-e-k-e-e | 88 |
| 74200 | 74215 | 530507 | e-k-d(10)-k-e-k-e | 86 |
| 74200 | 74215 | 530514 | k-d(10)-k-e-k-e-e | 80 |
| 74201 | 74216 | 530430 | k-d(10)-k-e-k-e-e | 87 |
| 74201 | 74216 | 530468 | e-k-k-d(10)-k-k-e | 81 |
| 74201 | 74216 | 530476 | e-e-k-d(10)-k-k-e | 82 |
| 74201 | 74216 | 530484 | e-d-k-d(10)-k-k-e | 74 |
| 74201 | 74216 | 530492 | e-d-d-k-d(9)-k-k-e | 83 |
| 74201 | 74216 | 530500 | e-e-e-e-d(9)-k-k-e | 56 |
| 74201 | 74216 | 530508 | e-k-d(10)-k-e-k-e | 83 |
| 74202 | 74218 | 530062 | e-e-e-k-d(10)-k-e-k-e | 94 |
| 74202 | 74217 | 530380 | e-k-d(10)-k-e-k-e | 94 |
| 74202 | 74217 | 530469 | e-e-k-d(10)-k-k-e | 91 |
| 74202 | 74217 | 530477 | e-e-k-d(10)-k-k-e | 87 |
| 74202 | 74217 | 530485 | e-d-k-d(10)-k-k-e | 87 |
| 74202 | 74217 | 530493 | e-d-d-k-d(9)-k-k-e | 81 |
| 74202 | 74217 | 530501 | e-e-e-e-d(9)-k-k-e | 74 |
| 74202 | 74217 | 530515 | k-d(10)-k-e-k-e-e | 87 |
| 74203 | 74218 | 481464 | k-k-k-d(10)-k-k-k | 93 |
| 74203 | 74218 | 518349 | e-e-e-d(10)-k-k-k | 58 |
| 74203 | 74218 | 519637 | e-k-k-d(10)-k-k-e | 96 |
| 74203 | 74218 | 530175 | e-e-k-d(10)-k-k-e | 93 |
| 74203 | 74218 | 530225 | e-d-k-d(10)-k-k-e | 85 |
| 74203 | 74218 | 530275 | e-d-d-k-d(9)-k-k-e | 91 |
| 74203 | 74218 | 530325 | e-e-e-e-d(9)-k-k-e | 91 |
| 74204 | 74219 | 530470 | e-e-k-d(10)-k-k-e | 91 |
| 74204 | 74219 | 530478 | e-e-k-d(10)-k-k-e | 87 |
| 74204 | 74219 | 530486 | e-d-k-d(10)-k-k-e | 84 |
| 74204 | 74219 | 530494 | e-d-d-k-d(9)-k-k-e | 60 |
| 74204 | 74219 | 530502 | e-e-e-e-d(9)-k-k-e | 64 |
| 74204 | 74219 | 530509 | e-k-d(10)-k-e-k-e | 80 |
| 74205 | 74220 | 530471 | e-k-k-d(10)-k-k-e | 83 |
| 74205 | 74220 | 530479 | e-e-k-d(10)-k-k-e | 74 |
| 74205 | 74220 | 530487 | e-d-k-d(10)-k-k-e | 71 |
| 74205 | 74220 | 530495 | e-d-d-k-d(9)-k-k-e | 68 |
| 74205 | 74220 | 530503 | e-e-e-e-d(9)-k-k-e | 53 |
| 74648 | 74663 | 530128 | e-k-k-d(10)-k-k-e | 52 |
| 74648 | 74663 | 530176 | e-e-k-d(10)-k-k-e | 66 |
| 74648 | 74663 | 530226 | e-d-k-d(10)-k-k-e | 51 |
| 74648 | 74663 | 530276 | e-d-d-k-d(9)-k-k-e | 70 |
| 74648 | 74663 | 530326 | e-e-e-e-d(9)-k-k-e | 52 |
| 74734 | 74749 | 528866 | e-e-e-k-d(10)-k-k-k | 60 |
| 74735 | 74750 | 528867 | e-e-e-d(10)-k-k-k | 47 |
| 74772 | 74787 | 530086 | e-k-k-d(10)-k-k-e | 58 |
| 74772 | 74787 | 530133 | e-e-k-d(10)-k-k-e | 53 |
| 74772 | 74787 | 530183 | e-d-k-d(10)-k-k-e | 52 |
| 74772 | 74787 | 530233 | e-d-d-k-d(9)-k-k-e | 29 |
| 74772 | 74787 | 530283 | e-e-e-e-d(9)-k-k-e | 32 |
| 74782 | 74797 | 530390 | k-d(10)-k-e-k-e-e | 83 |
| 74783 | 74798 | 530340 | e-k-d(10)-k-e-k-e | 89 |
| 74784 | 74799 | 528869 | e-e-e-e-d(10)-k-k-k | 83 |
| 74784 | 74799 | 530088 | e-k-k-d(10)-k-k-e | 90 |
| 74784 | 74799 | 530135 | e-e-k-d(10)-k-k-e | 91 |
| 74784 | 74799 | 530185 | e-d-k-d(10)-k-k-e | 85 |
| 74784 | 74799 | 530235 | e-d-d-k-d(9)-k-k-e | 28 |
| 74784 | 74799 | 530285 | e-e-e-e-d(9)-k-k-e | 86 |
| 74784 | 74799 | 530391 | k-d(10)-k-e-k-e-e | 79 |
| 74785 | 74801 | 530021 | e-e-k-d(10)-k-e-k-e | 87 |
| 74785 | 74800 | 530341 | e-k-d(10)-k-e-k-e | 88 |
| 74786 | 74801 | 530089 | e-k-k-d(10)-k-k-e | 71 |
| 74786 | 74801 | 530136 | e-e-k-d(10)-k-k-e | 66 |
| 74786 | 74801 | 530186 | e-d-k-d(10)-k-k-e | 51 |
| 74786 | 74801 | 530236 | e-d-d-k-d(9)-k-k-e | 74 |
| 74786 | 74801 | 530286 | e-e-e-e-d(9)-k-k-e | 56 |
| 74902 | 74918 | 530022 | e-e-k-d(10)-k-e-k-e | 80 |
| 74902 | 74917 | 530342 | e-k-d(10)-k-e-k-e | 70 |
| 74902 | 74917 | 530393 | k-d(10)-k-e-k-e-e | 46 |
| 74903 | 74919 | 530023 | e-e-k-d(10)-k-e-k-e | 74 |
| 74903 | 74918 | 530090 | e-k-k-d(10)-k-k-e | 78 |
| 74903 | 74918 | 530137 | e-e-k-d(10)-k-k-e | 76 |
| 74903 | 74918 | 530187 | e-d-k-d(10)-k-k-e | 68 |
| 74903 | 74918 | 530237 | e-d-d-k-d(9)-k-k-e | 36 |
| 74903 | 74918 | 530287 | e-e-e-e-d(9)-k-k-e | 56 |
| 74903 | 74918 | 530343 | e-k-d(10)-k-e-k-e | 68 |
| 74903 | 74918 | 530394 | k-d(10)-k-e-k-e-e | 49 |
| 74904 | 74919 | 518343 | e-e-e-d(10)-k-k-k | 5 |
| 74904 | 74920 | 530024 | e-e-k-d(10)-k-e-k-e | 79 |
| 74904 | 74919 | 530091 | e-k-k-d(10)-k-k-e | 81 |
| 74904 | 74919 | 530138 | e-e-k-d(10)-k-k-e | 81 |
| 74904 | 74919 | 530188 | e-d-k-d(10)-k-k-e | 78 |
| 74904 | 74919 | 530238 | e-d-d-k-d(9)-k-k-e | 29 |
| 74904 | 74919 | 530288 | e-e-e-e-d(9)-k-k-e | 69 |
| 74904 | 74919 | 530344 | e-k-d(10)-k-e-k-e | 85 |
| 74905 | 74920 | 530092 | e-k-k-d(10)-k-k-e | 85 |
| 74905 | 74920 | 530139 | e-e-k-d(10)-k-k-e | 79 |
| 74905 | 74920 | 530189 | e-d-k-d(10)-k-k-e | 77 |
| 74905 | 74920 | 530239 | e-d-d-k-d(9)-k-k-e | 61 |
| 74905 | 74920 | 530289 | e-e-e-e-d(9)-k-k-e | 75 |
| 74907 | 74922 | 528880 | e-e-e-d(10)-k-k-k | 65 |
| 75209 | 75224 | 518344 | e-e-e-d(10)-k-k-k | 89 |
| 75421 | 75436 | 530395 | k-d(10)-k-e-k-e-e | 71 |
| 75422 | 75437 | 528936 | e-e-e-d(10)-k-k-k | 71 |
| 75422 | 75438 | 530025 | e-e-k-d(10)-k-e-k-e | 90 |
| 75422 | 75437 | 530345 | e-k-d(10)-k-e-k-e | 93 |
| 75422 | 75437 | 530396 | k-d(10)-k-e-k-e-e | 71 |
| 75423 | 75438 | 528937 | e-e-e-d(10)-k-k-k | 73 |
| 75423 | 75439 | 530026 | e-e-k-d(10)-k-e-k-e | 87 |
| 75423 | 75438 | 530093 | e-k-k-d(10)-k-k-e | 95 |
| 75423 | 75438 | 530140 | e-e-k-d(10)-k-k-e | 89 |
| 75423 | 75438 | 530190 | e-d-k-d(10)-k-k-e | 82 |
| 75423 | 75438 | 530240 | e-d-d-k-d(9)-k-k-e | 50 |
| 75423 | 75438 | 530290 | e-e-e-e-d(9)-k-k-e | 69 |
| 75423 | 75438 | 530346 | e-k-d(10)-k-e-k-e | 89 |
| 75424 | 75439 | 528938 | e-e-e-d(10)-k-k-k | 72 |
| 75424 | 75439 | 530094 | e-k-k-d(10)-k-k-e | 88 |
| 75424 | 75439 | 530141 | e-e-k-d(10)-k-k-e | 80 |
| 75424 | 75439 | 530191 | e-d-k-d(10)-k-k-e | 74 |
| 75424 | 75439 | 530241 | e-d-d-k-d(9)-k-k-e | 53 |
| 75424 | 75439 | 530291 | e-e-e-e-d(9)-k-k-e | 68 |
| 75429 | 75444 | 528942 | e-e-e-d(10)-k-k-k | 77 |
| 75492 | 75507 | 528944 | e-e-e-d(10)-k-k-k | 28 |
| 75507 | 75522 | 528945 | e-e-e-d(10)-k-k-k | 74 |
| 75626 | 75641 | 530096 | e-k-k-d(10)-k-k-e | 72 |
| 75626 | 75641 | 530143 | e-e-k-d(10)-k-k-e | 74 |
| 75626 | 75641 | 530193 | e-d-k-d(10)-k-k-e | 62 |
| 75626 | 75641 | 530243 | e-d-d-k-d(9)-k-k-e | 34 |
| 75626 | 75641 | 530293 | e-e-e-e-d(9)-k-k-e | 59 |
| 75676 | 75691 | 519638 | e-k-k-d(10)-k-k-e | 86 |
| 75676 | 75691 | 530177 | e-e-k-d(10)-k-k-e | 71 |
| 75676 | 75691 | 530227 | e-d-k-d(10)-k-k-e | 51 |
| 75676 | 75691 | 530277 | e-d-d-k-d(9)-k-k-e | 70 |
| 75676 | 75691 | 530327 | e-e-e-e-d(9)-k-k-e | 61 |
| 75677 | 75692 | 530466 | e-k-k-d(10)-k-k-e | 82 |
| 75677 | 75692 | 530474 | e-e-k-d(10)-k-k-e | 62 |
| 75677 | 75692 | 530482 | e-d-k-d(10)-k-k-e | 53 |
| 75677 | 75692 | 530490 | e-d-d-k-d(9)-k-k-e | 42 |
| 75677 | 75692 | 530498 | e-e-e-e-d(9)-k-k-e | 45 |
| 75677 | 75692 | 530506 | e-k-d(10)-k-e-k-e | 70 |
| 75726 | 75741 | 530433 | k-d(10)-k-e-k-e-e | 62 |
| 75727 | 75742 | 528958 | e-e-e-d(10)-k-k-k | 66 |
| 75727 | 75743 | 530056 | e-e-e-k-d(10)-k-e-k-e | 73 |
| 75727 | 75742 | 530383 | e-k-d(10)-k-e-k-e | 64 |
| 75728 | 75743 | 518345 | e-e-e-d(10)-k-k-k | 80 |
| 75728 | 75743 | 519636 | e-k-k-d(10)-k-k-e | 90 |
| 75728 | 75743 | 530178 | e-e-k-d(10)-k-k-e | 86 |
| 75728 | 75743 | 530228 | e-d-k-d(10)-k-k-e | 77 |
| 75728 | 75743 | 530278 | e-d-d-k-d(9)-k-k-e | 86 |
| 75728 | 75743 | 530328 | e-e-e-e-d(9)-k-k-e | 80 |

TABLE 117-continued

Inhibition of human Target-1 mRNA levels by chimeric antisense oligonucleotides targeted to Target-1 Genomic Sequence

| Human Start Site | Human Stop Site | ISIS No | Chemistry | % inhibition |
|---|---|---|---|---|
| 75729 | 75744 | 528959 | e-e-e-d(10)-k-k-k | 73 |
| 75808 | 75823 | 528973 | e-e-e-d(10)-k-k-k | 71 |
| 75969 | 75984 | 528995 | e-e-e-d(10)-k-k-k | 64 |
| 75969 | 75984 | 530129 | e-k-k-d(10)-k-k-e | 79 |
| 75969 | 75984 | 530179 | e-e-e-d(10)-k-k-e | 74 |
| 75969 | 75984 | 530229 | e-d-k-d(10)-k-k-e | 64 |
| 75969 | 75984 | 530279 | e-d-d-k-d(9)-k-k-e | 55 |
| 75969 | 75984 | 530329 | e-e-e-e-d(9)-k-k-e | 61 |
| 75999 | 76014 | 530402 | k-d(10)-k-e-k-e-e | 60 |
| 76000 | 76016 | 530032 | e-e-e-d(10)-k-e-k-e | 74 |
| 76000 | 76015 | 530099 | e-k-k-d(10)-k-k-e | 73 |
| 76000 | 76015 | 530146 | e-e-e-d(10)-k-k-e | 70 |
| 76000 | 76015 | 530196 | e-d-k-d(10)-k-k-e | 67 |
| 76000 | 76015 | 530246 | e-d-d-k-d(9)-k-k-e | 39 |
| 76000 | 76015 | 530296 | e-e-e-e-d(9)-k-k-e | 67 |
| 76000 | 76015 | 530352 | e-k-d(10)-k-e-k-e | 67 |
| 76001 | 76016 | 530100 | e-k-k-d(10)-k-k-e | 77 |
| 76001 | 76016 | 530147 | e-e-e-d(10)-k-k-e | 84 |
| 76001 | 76016 | 530197 | e-d-k-d(10)-k-k-e | 71 |
| 76001 | 76016 | 530247 | e-d-d-k-d(9)-k-k-e | 53 |
| 76001 | 76016 | 530297 | e-e-e-e-d(9)-k-k-e | 75 |
| 76001 | 76016 | 530403 | k-d(10)-k-e-k-e-e | 77 |
| 76002 | 76018 | 530033 | e-e-e-d(10)-k-e-k-e | 65 |
| 76002 | 76017 | 530353 | e-k-d(10)-k-e-k-e | 83 |
| 76003 | 76018 | 530101 | e-k-k-d(10)-k-k-e | 59 |
| 76003 | 76018 | 530148 | e-e-e-d(10)-k-k-e | 79 |
| 76003 | 76018 | 530198 | e-d-k-d(10)-k-k-e | 54 |
| 76003 | 76018 | 530248 | e-d-d-k-d(9)-k-k-e | 32 |
| 76003 | 76018 | 530298 | e-e-e-e-d(9)-k-k-e | 73 |
| 76014 | 76029 | 530404 | k-d(10)-k-e-k-e-e | 67 |
| 76015 | 76031 | 530034 | e-e-e-d(10)-k-e-k-e | 69 |
| 76015 | 76030 | 530354 | e-k-d(10)-k-e-k-e | 85 |
| 76015 | 76030 | 530405 | k-d(10)-k-e-k-e-e | 55 |
| 76016 | 76032 | 530035 | e-e-e-d(10)-k-e-k-e | 69 |
| 76016 | 76031 | 530102 | e-k-k-d(10)-k-k-e | 71 |
| 76016 | 76031 | 530149 | e-e-e-d(10)-k-k-e | 70 |
| 76016 | 76031 | 530199 | e-d-k-d(10)-k-k-e | 58 |
| 76016 | 76031 | 530249 | e-d-d-k-d(9)-k-k-e | 47 |
| 76016 | 76031 | 530299 | e-e-e-e-d(9)-k-k-e | 47 |
| 76016 | 76031 | 530355 | e-k-d(10)-k-e-k-e | 72 |
| 76017 | 76032 | 530103 | e-k-k-d(10)-k-k-e | 77 |
| 76017 | 76032 | 530150 | e-e-e-d(10)-k-k-e | 73 |
| 76017 | 76032 | 530200 | e-d-k-d(10)-k-k-e | 63 |
| 76017 | 76032 | 530250 | e-d-d-k-d(9)-k-k-e | 59 |
| 76017 | 76032 | 530300 | e-e-e-e-d(9)-k-k-e | 65 |
| 76029 | 76044 | 530435 | k-d(10)-k-e-k-e-e | 62 |
| 76030 | 76046 | 530057 | e-e-k-d(10)-k-e-k-e | 69 |
| 76030 | 76045 | 530385 | e-k-d(10)-k-e-k-e | 70 |
| 76031 | 76046 | 529005 | e-e-e-d(10)-k-k-k | 64 |
| 76031 | 76046 | 530130 | e-k-k-d(10)-k-k-e | 85 |
| 76031 | 76046 | 530180 | e-e-e-d(10)-k-k-e | 82 |
| 76031 | 76046 | 530230 | e-d-k-d(10)-k-k-e | 65 |
| 76031 | 76046 | 530280 | e-d-d-k-d(9)-k-k-e | 75 |
| 76031 | 76046 | 530330 | e-e-e-e-d(9)-k-k-e | 52 | e = 2'-MOE,
k = cEt,
d = 2'-deoxynucleoside

Example 71: Dose-Dependent Antisense Inhibition of Human Target-1 in HuVEC Cells Gapmers from the study described in Example 70 exhibiting in vitro inhibition of Target-1 were tested at various doses in HuVEC cells. Cells were plated at a density of 20,000 cells per well and transfected using electroporation with 39.1 nM, 156.3 nM, 625.0 nM, and 2,500.0 nM concentrations of antisense oligonucleotide, as specified in Table 118. After a treatment period of approximately 16 hours, RNA was isolated from the cells and Target-1 mRNA levels were measured by quantitative real-time PCR. Target-1 mRNA levels were adjusted according to total RNA content, as measured by RIBOGREEN®. Results are presented as percent inhibition of Target-1, relative to untreated control cells.

TABLE 118

Dose-dependent antisense inhibition of human Target-1 in HuVEC cells

| ISIS No | 39.1 nM | 156.3 nM | 625.0 nM | 2500.0 nM | IC$_{50}$ (µM) |
|---|---|---|---|---|---|
| 481464 | 6 | 51 | 84 | 94 | 0.2 |
| 518345 | 0 | 9 | 56 | 84 | 0.6 |
| 518349 | 16 | 3 | 47 | 83 | 0.6 |
| 519636 | 16 | 41 | 75 | 89 | 0.2 |
| 519637 | 24 | 43 | 84 | 94 | 0.2 |
| 519638 | 6 | 34 | 70 | 92 | 0.3 |
| 528403 | 0 | 4 | 39 | 77 | 0.9 |
| 528458 | 0 | 15 | 46 | 81 | 0.7 |
| 528475 | 1 | 10 | 51 | 76 | 0.7 |
| 528476 | 0 | 11 | 42 | 80 | 0.7 |
| 528869 | 25 | 19 | 67 | 86 | 0.3 |
| 528880 | 0 | 3 | 45 | 76 | 0.8 |
| 528937 | 0 | 1 | 49 | 82 | 0.8 |
| 528938 | 0 | 9 | 50 | 82 | 0.7 |
| 528942 | 0 | 20 | 59 | 88 | 0.5 |
| 528959 | 0 | 4 | 55 | 79 | 0.7 |
| 529022 | 0 | 0 | 52 | 81 | 0.8 |
| 529023 | 0 | 0 | 53 | 90 | 0.6 |
| 529024 | 0 | 0 | 47 | 80 | 0.8 |
| 529025 | 0 | 11 | 50 | 90 | 0.6 |
| 529026 | 0 | 31 | 73 | 96 | 0.4 |
| 529027 | 0 | 7 | 36 | 80 | 0.9 |
| 530021 | 6 | 30 | 69 | 92 | 0.3 |
| 530025 | 10 | 33 | 73 | 92 | 0.3 |
| 530026 | 3 | 18 | 52 | 80 | 0.6 |
| 530041 | 0 | 28 | 72 | 91 | 0.4 |
| 530048 | 0 | 22 | 53 | 83 | 0.5 |
| 530049 | 2 | 16 | 69 | 92 | 0.4 |
| 530053 | 0 | 16 | 66 | 90 | 0.5 |
| 530062 | 4 | 56 | 85 | 94 | 0.2 |
| 530066 | 0 | 12 | 46 | 84 | 0.7 |
| 530088 | 2 | 39 | 77 | 93 | 0.3 |
| 530091 | 3 | 12 | 59 | 84 | 0.5 |
| 530092 | 7 | 27 | 65 | 85 | 0.4 |
| 530093 | 7 | 46 | 79 | 96 | 0.2 |
| 530094 | 0 | 17 | 63 | 89 | 0.5 |
| 530109 | 9 | 30 | 72 | 94 | 0.3 |
| 530110 | 0 | 23 | 61 | 83 | 0.5 |
| 530112 | 0 | 13 | 42 | 90 | 0.6 |
| 530114 | 0 | 21 | 62 | 79 | 0.6 |
| 530116 | 22 | 40 | 71 | 92 | 0.2 |
| 530123 | 8 | 19 | 72 | 93 | 0.3 |
| 530130 | 0 | 33 | 64 | 89 | 0.4 |
| 530131 | 4 | 34 | 81 | 93 | 0.3 |
| 530135 | 22 | 38 | 79 | 94 | 0.2 |
| 530138 | 6 | 23 | 57 | 86 | 0.4 |
| 530140 | 4 | 22 | 62 | 91 | 0.4 |
| 530147 | 0 | 15 | 51 | 83 | 0.6 |
| 530156 | 7 | 41 | 81 | 96 | 0.2 |
| 530161 | 0 | 20 | 46 | 78 | 0.7 |
| 530170 | 0 | 29 | 67 | 90 | 0.4 |
| 530175 | 37 | 52 | 84 | 95 | 0.1 |
| 530178 | 8 | 24 | 70 | 86 | 0.4 |
| 530180 | 0 | 0 | 61 | 82 | 0.6 |
| 530181 | 0 | 27 | 52 | 86 | 0.5 |
| 530185 | 0 | 22 | 54 | 86 | 0.5 |
| 530190 | 17 | 17 | 60 | 87 | 0.4 |
| 530206 | 8 | 29 | 73 | 93 | 0.3 |
| 530225 | 0 | 27 | 67 | 91 | 0.4 |
| 530228 | 11 | 16 | 64 | 86 | 0.4 |
| 530261 | 5 | 25 | 57 | 91 | 0.4 |
| 530270 | 7 | 11 | 62 | 91 | 0.4 |
| 530275 | 14 | 34 | 73 | 91 | 0.3 |
| 530278 | 1 | 27 | 60 | 85 | 0.4 |
| 530285 | 5 | 20 | 61 | 82 | 0.5 |
| 530306 | 3 | 14 | 66 | 85 | 0.5 |
| 530311 | 6 | 27 | 59 | 86 | 0.4 |
| 530320 | 3 | 17 | 56 | 85 | 0.5 |
| 530325 | 5 | 35 | 70 | 92 | 0.3 |
| 530328 | 4 | 34 | 61 | 87 | 0.4 |

TABLE 118-continued

Dose-dependent antisense inhibition of human Target-1 in HuVEC cells

| ISIS No | 39.1 nM | 156.3 nM | 625.0 nM | 2500.0 nM | $IC_{50}$ (μM) |
|---|---|---|---|---|---|
| 530340 | 8 | 34 | 74 | 90 | 0.3 |
| 530341 | 2 | 23 | 77 | 89 | 0.4 |
| 530344 | 16 | 20 | 64 | 89 | 0.4 |
| 530345 | 15 | 35 | 77 | 94 | 0.2 |
| 530346 | 5 | 24 | 66 | 92 | 0.4 |
| 530353 | 7 | 25 | 57 | 83 | 0.5 |
| 530354 | 2 | 24 | 60 | 81 | 0.5 |
| 530359 | 0 | 4 | 44 | 89 | 0.7 |
| 530361 | 13 | 30 | 59 | 92 | 0.3 |
| 530365 | 0 | 0 | 45 | 88 | 0.7 |
| 530367 | 0 | 15 | 49 | 88 | 0.5 |
| 530368 | 0 | 27 | 64 | 89 | 0.4 |
| 530369 | 10 | 28 | 78 | 95 | 0.3 |
| 530373 | 13 | 29 | 64 | 92 | 0.3 |
| 530375 | 0 | 14 | 53 | 90 | 0.5 |
| 530380 | 8 | 40 | 80 | 94 | 0.2 |
| 530390 | 11 | 21 | 66 | 90 | 0.4 |
| 530391 | 20 | 7 | 49 | 86 | 0.5 |
| 530411 | 5 | 19 | 81 | 95 | 0.3 |
| 530430 | 0 | 8 | 53 | 91 | 0.6 |
| 530466 | 0 | 4 | 53 | 87 | 0.6 |
| 530468 | 4 | 17 | 65 | 90 | 0.4 |
| 530469 | 8 | 38 | 86 | 94 | 0.2 |
| 530470 | 5 | 39 | 78 | 91 | 0.3 |
| 530471 | 0 | 21 | 69 | 91 | 0.4 |
| 530476 | 7 | 9 | 32 | 89 | 0.7 |
| 530477 | 0 | 12 | 64 | 87 | 0.5 |
| 530478 | 0 | 14 | 59 | 90 | 0.5 |
| 530485 | 0 | 10 | 61 | 85 | 0.5 |
| 530486 | 0 | 17 | 64 | 80 | 0.5 |
| 530492 | 0 | 25 | 71 | 89 | 0.4 |
| 530493 | 4 | 23 | 58 | 88 | 0.4 |
| 530507 | 5 | 17 | 65 | 82 | 0.5 |
| 530508 | 0 | 14 | 56 | 89 | 0.5 |
| 530509 | 0 | 17 | 54 | 86 | 0.5 |
| 530513 | 6 | 24 | 74 | 91 | 0.3 |
| 530514 | 1 | 7 | 52 | 78 | 0.7 |
| 530515 | 0 | 19 | 73 | 89 | 0.4 |

Example 72: Antisense Inhibition of Human Target-1 in HuVEC Cells

Additional antisense oligonucleotides were designed targeting a Target-1 nucleic acid and were tested for their effects on Target-1 mRNA in vitro. Cultured HuVEC cells at a density of 20,000 cells per well were transfected using electroporation with 1,000 nM antisense oligonucleotide. After a treatment period of approximately 24 hours, RNA was isolated from the cells and Target-1 mRNA levels were measured by quantitative real-time PCR. Target-1 mRNA levels were adjusted according to total RNA content, as measured by RIBOGREEN®. Results are presented as percent inhibition of Target-1, relative to untreated control cells.

The chemistry column of Table 119 presents the sugar motif of each gapmer, where 'e' indicates a 2'-MOE nucleoside, 'k' indicates a constrained ethyl (cEt) nucleoside, and indicates a 2'-deoxynucleoside. The internucleoside linkages throughout each gapmer are phosphorothioate (P=S) linkages. All cytosine residues throughout each gapmer are 5'-methylcytosines.

"Human Target start site" indicates the 5'-most nucleoside to which the gapmer is targeted in the human gene sequence. "Human Target stop site" indicates the 3'-most nucleoside to which the gapmer is targeted in the human gene sequence. Each gapmer listed in Table 119 is targeted to human Target-1 mRNA. Each gapmer listed in Table 120 is targeted to human Target-1 genomic sequence, truncated from nucleotides 4185000 to 4264000).

TABLE 119

Inhibition of human Target-1 mRNA levels by chimeric antisense oligonucleotides targeted to Target-1 mRNA

| Human Start Site | Human Stop Site | ISIS No | Chemistry | % inhibition |
|---|---|---|---|---|
| 730 | 745 | 530011 | k-k-k-d(10)-e-e-e | 73 |
| 1901 | 1916 | 529974 | e-e-e-d(10)-k-k-k | 83 |
| 1901 | 1916 | 530012 | k-k-k-d(10)-e-e-e | 73 |
| 2206 | 2221 | 530015 | k-k-k-d(10)-e-e-e | 38 |
| 3016 | 3031 | 481464 | k-k-k-d(10)-k-k-k | 94 |
| 3461 | 3476 | 529975 | e-e-e-d(10)-k-k-k | 54 |
| 3461 | 3476 | 530013 | k-k-k-d(10)-e-e-e | 58 |
| 3584 | 3600 | 530018 | e-e-k-d(10)-k-e-k-e | 46 |
| 3585 | 3600 | 529944 | e-e-e-d(10)-k-k-k | 44 |
| 3585 | 3600 | 529977 | k-k-k-d(10)-e-e-e | 66 |
| 3592 | 3608 | 530019 | e-e-k-d(10)-k-e-k-e | 43 |
| 3593 | 3608 | 529945 | e-e-e-d(10)-k-k-k | 22 |
| 3593 | 3608 | 529978 | k-k-k-d(10)-e-e-e | 49 |
| 3596 | 3612 | 530020 | e-e-k-d(10)-k-e-k-e | 85 |
| 3597 | 3612 | 529979 | k-k-k-d(10)-e-e-e | 86 |
| 3599 | 3614 | 529946 | e-e-e-d(10)-k-k-k | 46 |
| 3599 | 3614 | 529980 | k-k-k-d(10)-e-e-e | 25 |
| 3716 | 3731 | 529947 | e-e-e-d(10)-k-k-k | 68 |
| 3716 | 3731 | 529981 | k-k-k-d(10)-e-e-e | 83 |
| 3718 | 3733 | 529948 | e-e-e-d(10)-k-k-k | 75 |
| 3718 | 3733 | 529982 | k-k-k-d(10)-e-e-e | 84 |
| 4236 | 4251 | 529983 | k-k-k-d(10)-e-e-e | 96 |
| 4237 | 4252 | 529984 | k-k-k-d(10)-e-e-e | 91 |
| 4437 | 4452 | 529949 | e-e-e-d(10)-k-k-k | 48 |
| 4437 | 4452 | 529985 | k-k-k-d(10)-e-e-e | 37 |
| 4439 | 4454 | 529950 | e-e-e-d(10)-k-k-k | 58 |
| 4439 | 4454 | 529986 | k-k-k-d(10)-e-e-e | 72 |
| 4646 | 4661 | 529987 | k-k-k-d(10)-e-e-e | 0 |
| 4664 | 4679 | 529951 | e-e-e-d(10)-k-k-k | 38 |
| 4664 | 4679 | 529988 | k-k-k-d(10)-e-e-e | 40 |
| 4782 | 4797 | 530016 | k-k-k-d(10)-e-e-e | 60 |
| 4813 | 4828 | 529952 | e-e-e-d(10)-k-k-k | 65 |
| 4813 | 4828 | 529989 | k-k-k-d(10)-e-e-e | 63 |
| 4814 | 4829 | 529953 | e-e-e-d(10)-k-k-k | 65 |
| 4814 | 4829 | 529990 | k-k-k-d(10)-e-e-e | 75 |
| 4816 | 4831 | 529954 | e-e-e-d(10)-k-k-k | 79 |
| 4816 | 4831 | 529991 | k-k-k-d(10)-e-e-e | 52 |
| 4829 | 4844 | 529955 | e-e-e-d(10)-k-k-k | 52 |
| 4829 | 4844 | 529992 | k-k-k-d(10)-e-e-e | 23 |
| 4830 | 4845 | 529956 | e-e-e-d(10)-k-k-k | 60 |
| 4830 | 4845 | 529993 | k-k-k-d(10)-e-e-e | 51 |
| 4844 | 4859 | 530014 | k-k-k-d(10)-e-e-e | 67 | e = 2'-MOE,
k = cEt,
d = 2'-deoxynucleoside

TABLE 120

Inhibition of human TARGET-1 mRNA levels by chimeric antisense oligonucleotides targeted to Target-1 Genomic Sequence

| Human Start Site | Human Stop Site | Sequence | Chemistry | % inhibition |
|---|---|---|---|---|
| 74203 | 74218 | 481464 | k-k-k-d(10)-k-k-k | 94 |
| 74772 | 74787 | 529944 | e-e-e-d(10)-k-k-k | 44 |
| 74780 | 74795 | 529945 | e-e-e-d(10)-k-k-k | 22 |
| 74786 | 74801 | 529946 | e-e-e-d(10)-k-k-k | 46 |
| 74903 | 74918 | 529947 | e-e-e-d(10)-k-k-k | 68 |
| 74905 | 74920 | 529948 | e-e-e-d(10)-k-k-k | 75 |
| 75624 | 75639 | 529949 | e-e-e-d(10)-k-k-k | 48 |
| 75626 | 75641 | 529950 | e-e-e-d(10)-k-k-k | 58 |
| 75851 | 75866 | 529951 | e-e-e-d(10)-k-k-k | 38 |
| 76000 | 76015 | 529952 | e-e-e-d(10)-k-k-k | 65 |
| 76001 | 76016 | 529953 | e-e-e-d(10)-k-k-k | 65 |
| 76003 | 76018 | 529954 | e-e-e-d(10)-k-k-k | 79 |
| 76016 | 76031 | 529955 | e-e-e-d(10)-k-k-k | 52 |
| 76017 | 76032 | 529956 | e-e-e-d(10)-k-k-k | 60 |
| 2340 | 2355 | 529957 | e-e-e-d(10)-k-k-k | 21 |
| 2385 | 2400 | 529958 | e-e-e-d(10)-k-k-k | 10 |
| 2410 | 2425 | 529959 | e-e-e-d(10)-k-k-k | 51 |

TABLE 120-continued

Inhibition of human TARGET-1 mRNA levels by chimeric antisense oligonucleotides targeted to Target-1 Genomic Sequence

| Human Start Site | Human Stop Site | Sequence | Chemistry | % inhibition |
|---|---|---|---|---|
| 2671 | 2686 | 529960 | e-e-e-d(10)-k-k-k | 30 |
| 5002 | 5017 | 529961 | e-e-e-d(10)-k-k-k | 52 |
| 5701 | 5716 | 529962 | e-e-e-d(10)-k-k-k | 91 |
| 8080 | 8095 | 529963 | e-e-e-d(10)-k-k-k | 55 |
| 9125 | 9140 | 529964 | e-e-e-d(10)-k-k-k | 18 |
| 11263 | 11278 | 529964 | e-e-e-d(10)-k-k-k | 18 |
| 9864 | 9879 | 529965 | e-e-e-d(10)-k-k-k | 52 |
| 12347 | 12362 | 529965 | e-e-e-d(10)-k-k-k | 52 |
| 9866 | 9881 | 529966 | e-e-e-d(10)-k-k-k | 51 |
| 12349 | 12364 | 529966 | e-e-e-d(10)-k-k-k | 51 |
| 9875 | 9890 | 529967 | e-e-e-d(10)-k-k-k | 80 |
| 12358 | 12373 | 529967 | e-e-e-d(10)-k-k-k | 80 |
| 9876 | 9891 | 529968 | e-e-e-d(10)-k-k-k | 56 |
| 12359 | 12374 | 529968 | e-e-e-d(10)-k-k-k | 56 |
| 9878 | 9893 | 529969 | e-e-e-d(10)-k-k-k | 69 |
| 12361 | 12376 | 529969 | e-e-e-d(10)-k-k-k | 69 |
| 16865 | 16880 | 529970 | e-e-e-d(10)-k-k-k | 41 |
| 26063 | 26078 | 529971 | e-e-e-d(10)-k-k-k | 32 |
| 48404 | 48419 | 529972 | e-e-e-d(10)-k-k-k | 30 |
| 71616 | 71631 | 529973 | e-e-e-d(10)-k-k-k | 49 |
| 66138 | 66153 | 529974 | e-e-e-d(10)-k-k-k | 83 |
| 74648 | 74663 | 529975 | e-e-e-d(10)-k-k-k | 54 |
| 2705 | 2720 | 529976 | e-e-e-d(10)-k-k-k | 25 |
| 74772 | 74787 | 529977 | k-k-k-d(10)-e-e-e | 66 |
| 74780 | 74795 | 529978 | k-k-k-d(10)-e-e-e | 49 |
| 74784 | 74799 | 529979 | k-k-k-d(10)-e-e-e | 86 |
| 74786 | 74801 | 529980 | k-k-k-d(10)-e-e-e | 25 |
| 74903 | 74918 | 529981 | k-k-k-d(10)-e-e-e | 83 |
| 74905 | 74920 | 529982 | k-k-k-d(10)-e-e-e | 84 |
| 75423 | 75438 | 529983 | k-k-k-d(10)-e-e-e | 96 |
| 75424 | 75439 | 529984 | k-k-k-d(10)-e-e-e | 91 |
| 75624 | 75639 | 529985 | k-k-k-d(10)-e-e-e | 37 |
| 75626 | 75641 | 529986 | k-k-k-d(10)-e-e-e | 72 |
| 75833 | 75848 | 529987 | k-k-k-d(10)-e-e-e | 0 |
| 75851 | 75866 | 529988 | k-k-k-d(10)-e-e-e | 40 |
| 76000 | 76015 | 529989 | k-k-k-d(10)-e-e-e | 63 |
| 76001 | 76016 | 529990 | k-k-k-d(10)-e-e-e | 75 |
| 76003 | 76018 | 529991 | k-k-k-d(10)-e-e-e | 52 |
| 76016 | 76031 | 529992 | k-k-k-d(10)-e-e-e | 23 |
| 76017 | 76032 | 529993 | k-k-k-d(10)-e-e-e | 51 |
| 2340 | 2355 | 529994 | k-k-k-d(10)-e-e-e | 44 |
| 2385 | 2400 | 529995 | k-k-k-d(10)-e-e-e | 0 |
| 2410 | 2425 | 529996 | k-k-k-d(10)-e-e-e | 65 |
| 2671 | 2686 | 529997 | k-k-k-d(10)-e-e-e | 44 |
| 5002 | 5017 | 529998 | k-k-k-d(10)-e-e-e | 35 |
| 5701 | 5716 | 529999 | k-k-k-d(10)-e-e-e | 91 |
| 8080 | 8095 | 530000 | k-k-k-d(10)-e-e-e | 80 |
| 9125 | 9140 | 530001 | k-k-k-d(10)-e-e-e | 21 |
| 11263 | 11278 | 530001 | k-k-k-d(10)-e-e-e | 21 |
| 9864 | 9879 | 530002 | k-k-k-d(10)-e-e-e | 74 |
| 12347 | 12362 | 530002 | k-k-k-d(10)-e-e-e | 74 |
| 9866 | 9881 | 530003 | k-k-k-d(10)-e-e-e | 67 |
| 12349 | 12364 | 530003 | k-k-k-d(10)-e-e-e | 67 |
| 9875 | 9890 | 530004 | k-k-k-d(10)-e-e-e | 83 |
| 12358 | 12373 | 530004 | k-k-k-d(10)-e-e-e | 83 |
| 9876 | 9891 | 530005 | k-k-k-d(10)-e-e-e | 77 |
| 12359 | 12374 | 530005 | k-k-k-d(10)-e-e-e | 77 |
| 9878 | 9893 | 530006 | k-k-k-d(10)-e-e-e | 89 |
| 12361 | 12376 | 530006 | k-k-k-d(10)-e-e-e | 89 |
| 16865 | 16880 | 530007 | k-k-k-d(10)-e-e-e | 21 |
| 26063 | 26078 | 530008 | k-k-k-d(10)-e-e-e | 58 |
| 48404 | 48419 | 530009 | k-k-k-d(10)-e-e-e | 59 |
| 71616 | 71631 | 530010 | k-k-k-d(10)-e-e-e | 75 |
| 50694 | 50709 | 530011 | k-k-k-d(10)-e-e-e | 73 |
| 66138 | 66153 | 530012 | k-k-k-d(10)-e-e-e | 73 |
| 74648 | 74663 | 530013 | k-k-k-d(10)-e-e-e | 58 |
| 76031 | 76046 | 530014 | k-k-k-d(10)-e-e-e | 67 |
| 67068 | 67083 | 530015 | k-k-k-d(10)-e-e-e | 38 |
| 75969 | 75984 | 530016 | k-k-k-d(10)-e-e-e | 60 |
| 2705 | 2720 | 530017 | k-k-k-d(10)-e-e-e | 46 |
| 74771 | 74787 | 530018 | e-e-k-d(10)-k-e-k-e | 46 |
| 74779 | 74795 | 530019 | e-e-k-d(10)-k-e-k-e | 43 |
| 74783 | 74799 | 530020 | e-e-k-d(10)-k-e-k-e | 85 | e = 2'-MOE,
k = cEt,
d = 2'-deoxynucleoside

Example 73: Dose-Dependent Antisense Inhibition of Human Target-1 in HuVEC Cells Gapmers from the study described in Example 72 exhibiting in vitro inhibition of Target-1 were tested at various doses in HuVEC cells. Cells were plated at a density of 20,000 cells per well and transfected using electroporation with 39.1 nM, 156.3 nM, 625.0 nM, and 2,500.0 nM concentrations of antisense oligonucleotide, as specified in Table 121. After a treatment period of approximately 16 hours, RNA was isolated from the cells and Target-1 mRNA levels were measured by quantitative real-time PCR. Target-1 mRNA levels were adjusted according to total RNA content, as measured by RIBOGREEN®. Results are presented as percent inhibition of Target-1, relative to untreated control cells.

TABLE 121

Dose-dependent antisense inhibition of human Target-1 in HuVEC cells

| ISIS No | 39.1 nM | 156.3 nM | 625.0 nM | 2500.0 nM | IC$_{50}$ (µM) |
|---|---|---|---|---|---|
| 481464 | 41 | 78 | 92 | 91 | 0.04 |
| 529962 | 30 | 51 | 86 | 95 | 0.12 |
| 529979 | 0 | 43 | 81 | 95 | 0.27 |
| 529982 | 0 | 0 | 70 | 90 | 0.56 |
| 529983 | 31 | 67 | 87 | 94 | 0.08 |
| 529984 | 17 | 44 | 83 | 97 | 0.19 |
| 529999 | 29 | 51 | 83 | 96 | 0.13 |
| 530006 | 18 | 38 | 77 | 94 | 0.22 |
| 530020 | 2 | 39 | 75 | 92 | 0.28 |

We claim:

1. A compound comprising:
   a modified oligonucleotide consisting of 19 or 20 linked nucleosides, wherein the modified oligonucleotide comprises:
   a 5'-wing comprising a BABBB motif, a BBABB motif, a BABAB motif, a BBAAB motif, a BAABB motif, or a BBBAB motif, wherein the 3'-most 5'-wing nucleoside is a bicyclic nucleoside;
   a 3'-wing comprising a BABBB motif, a BAABB motif, a BBAAB motif, a BABAB motif, or a BBABB motif, wherein the 5'-most 3'-wing nucleoside is a bicyclic nucleoside; and
   a gap between the 5'-wing and the 3'-wing consisting of 9 or 10 linked 2'-deoxynucleosides; and
   wherein each B is a bicyclic nucleoside and each A is a 2'-deoxynucleoside and the modified oligonucleotide does not comprise a non-bicyclic 2'-substituted nucleoside.

2. The compound of claim 1, wherein the gap consists of 9 linked 2'-deoxynucleosides.

3. The compound of claim 1, wherein the gap consists of 10 linked 2'-deoxynucleosides.

4. The compound of claim 1, wherein the 5' wing comprises a BABBB motif and the 3' wing comprises a BBABB motif.

5. The compound of claim 1, wherein the 5' wing comprises a BBABB motif and the 3' wing comprises a BBABB motif.

6. The compound of claim 1, wherein the 5' wing comprises a BBBAB motif and the 3' wing comprises a BABAB motif.

7. The compound of claim 1, wherein each bicyclic nucleoside is a locked nucleic acid (LNA) nucleoside.

8. The compound of claim 4, wherein each bicyclic nucleoside is a locked nucleic acid (LNA) nucleoside.

9. The compound of claim 5, wherein each bicyclic nucleoside is a locked nucleic acid (LNA) nucleoside.

10. The compound of claim 6, wherein each bicyclic nucleoside is a locked nucleic acid (LNA) nucleoside.

* * * * *

SEQUENCE LISTING

<160> NUMBER OF SEQ ID NOS: 45

<210> SEQ ID NO 1
<211> LENGTH: 19
<212> TYPE: DNA
<213> ORGANISM: Artificial Sequence
<220> FEATURE:
<223> OTHER INFORMATION: Synthetic oligonucleotide -continued

```
<400> SEQUENCE: 1
gtgctaccca acctttctg                                               19

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 2
cacagtgcta cccaacctt                                               19

<210> SEQ ID NO 3
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 3
cagtgctacc caacc                                                   15

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 4
atatcacagt gctacccaa                                               19

<210> SEQ ID NO 5
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 5
gatgctgact tgggccatt                                               19

<210> SEQ ID NO 6
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 6
gggatgctga cttgg                                                   15

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 7
tgccaaggga tgctgactt                                               19

<210> SEQ ID NO 8
<211> LENGTH: 19
```

```
<212> TYPE: DNA
<213> ORGANISM: Artificial Sequence
<220> FEATURE:
<223> OTHER INFORMATION: Synthetic oligonucleotide

<400> SEQUENCE: 8
aattgtcatc accagaaaa                                                    19

<210> SEQ ID NO 9
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 9
taaattgtca tcacc                                                        15

<210> SEQ ID NO 10
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 10
acagtagatg agggagcag                                                    19

<210> SEQ ID NO 11
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 11
acacagtaga tgagg                                                        15

<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 12
aagtgcacac agtagatga                                                    19

<210> SEQ ID NO 13
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 13
agctgcaacc tggcaacaa                                                    19

<210> SEQ ID NO 14
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 14
```
gcagctgcaa cctgg                                                    15

<210> SEQ ID NO 15
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 15
gcaagagcag ctgcaacct                                                19

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(16)
<223> OTHER INFORMATION: n = A,T,C or G

<400> SEQUENCE: 19
nnnnnnnnnn nnnnnn                                                   16

<210> SEQ ID NO 20
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(14)
<223> OTHER INFORMATION: n = A,T,C or G

<400> SEQUENCE: 20
nnnnnnnnnn nnnn                                                     14

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(20)
<223> OTHER INFORMATION: n = A,T,C or G

```
<400> SEQUENCE: 21
nnnnnnnnnn nnnnnnnnnn                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
ccttccctga aggttcctcc                                              20

<210> SEQ ID NO 23
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 23
atcatggctg cagctt                                                  16

<210> SEQ ID NO 24
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 24
atcatggctg cagctt                                                  16

<210> SEQ ID NO 25
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 25
tggctgcagc ttccga                                                  16

<210> SEQ ID NO 26
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 26
atggctgcag cttccg                                                  16

<210> SEQ ID NO 27
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 27
catggctgca gcttcc                                                  16

<210> SEQ ID NO 28
<211> LENGTH: 16
```

```
<212> TYPE: DNA
<213> ORGANISM: Artificial Sequence
<220> FEATURE:
<223> OTHER INFORMATION: Synthetic oligonucleotide

<400> SEQUENCE: 28
tcatggctgc agcttc                                                   16

<210> SEQ ID NO 29
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 29
catcatggct gcagct                                                   16

<210> SEQ ID NO 30
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 30
ccatcatggc tgcagc                                                   16

<210> SEQ ID NO 31
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 31
tccatcatgg ctgcag                                                   16

<210> SEQ ID NO 32
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 32
ttccatcatg gctgca                                                   16

<210> SEQ ID NO 33
<211> LENGTH: 19
<212> TYPE: DNA
<213> ORGANISM: Artificial Sequence
<220> FEATURE:
<223> OTHER INFORMATION: Primer

<400> SEQUENCE: 33
cttggtcatg ggccatcag                                                19

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
```
cggctaggag ttccgcagta                    20

<210> SEQ ID NO 35
<211> LENGTH: 22
<212> TYPE: DNA
<213> ORGANISM: Artificial Sequence
<220> FEATURE:
<223> OTHER INFORMATION: Probe

<400> SEQUENCE: 35
tgcgtggaac cttttcggct cc                 22

<210> SEQ ID NO 36
<211> LENGTH: 19
<212> TYPE: DNA
<213> ORGANISM: Artificial Sequence
<220> FEATURE:
<223> OTHER INFORMATION: Primer

<400> SEQUENCE: 36
ccaaaccttc ggacggaaa                     19

<210> SEQ ID NO 37
<211> LENGTH: 19
<212> TYPE: DNA
<213> ORGANISM: Artificial Sequence
<220> FEATURE:
<223> OTHER INFORMATION: Primer

<400> SEQUENCE: 37
tgaggcccac tcccatagg                     19

<210> SEQ ID NO 38
<211> LENGTH: 26
<212> TYPE: DNA
<213> ORGANISM: Artificial Sequence
<220> FEATURE:
<223> OTHER INFORMATION: Probe

<400> SEQUENCE: 38
cccatcatcc tgggctttcg gaaaat             26

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
gtgaagcgaa gtgcacacgg                    20

<210> SEQ ID NO 40
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 40
ggcatagcag caggatg                       17

```
<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
ccttccctga aggttcctcc                                                      20

<210> SEQ ID NO 42
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 42
cggtccttgg aggatgc                                                         17

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
atcctatcaa cacttccgga aact                                                 24

<210> SEQ ID NO 44
<211> LENGTH: 16
<212> TYPE: DNA
<213> ORGANISM: Artificial Sequence
<220> FEATURE:
<223> OTHER INFORMATION: Primer

<400> SEQUENCE: 44
cgacgcggcg attgag                                                          16

<210> SEQ ID NO 45
<211> LENGTH: 24
<212> TYPE: DNA
<213> ORGANISM: Artificial Sequence
<220> FEATURE:
<223> OTHER INFORMATION: Probe

<400> SEQUENCE: 45
aagaactccc tcgcctcgca gacg                                                 24
```